(12) United States Patent
Burke et al.

(10) Patent No.: US 12,084,411 B2
(45) Date of Patent: Sep. 10, 2024

(54) HINOKITIOL ANALOGUES, METHODS OF PREPARING AND PHARMACEUTICAL COMPOSITIONS THEREOF

(71) Applicant: The Board of Trustees of the University of Illinois, Urbana, IL (US)

(72) Inventors: Martin D. Burke, Champaign, IL (US); Anthony S. Grillo, Champaign, IL (US); Alexander G. Cioffi, Urbana, IL (US); Anna SantaMaria, Rockville, MD (US); Daniel Blair, Hull (GB); Andrew Blake, Urbana, IL (US)

(73) Assignee: The Board of Trustees of the University of Illinois, Urbana, IL (US)

( * ) Notice: Subject to any disclaimer, the term of this patent is extended or adjusted under 35 U.S.C. 154(b) by 57 days.

(21) Appl. No.: 17/046,608

(22) PCT Filed: Apr. 12, 2019

(86) PCT No.: PCT/US2019/027314
§ 371 (c)(1),
(2) Date: Oct. 9, 2020

(87) PCT Pub. No.: WO2019/200314
PCT Pub. Date: Oct. 17, 2019

(65) Prior Publication Data
US 2021/0163393 A1  Jun. 3, 2021

Related U.S. Application Data

(60) Provisional application No. 62/657,127, filed on Apr. 13, 2018.

(51) Int. Cl.
*C07C 45/68* (2006.01)
*A61K 45/06* (2006.01)
*C07C 61/22* (2006.01)

(52) U.S. Cl.
CPC .............. *C07C 45/68* (2013.01); *A61K 45/06* (2013.01); *C07C 61/22* (2013.01)

(58) Field of Classification Search
CPC .......... C07C 45/68; C07C 61/22; C07C 61/26
See application file for complete search history.

(56) References Cited

U.S. PATENT DOCUMENTS

| | | |
|---|---|---|
| 4,110,468 A | 8/1978 | Bagli et al. |
| 4,152,457 A | 5/1979 | Bagli et al. |
| 4,183,955 A | 1/1980 | Bagli et al. |
| 4,950,686 A | 8/1990 | Kondo et al. |
| 5,003,077 A | 3/1991 | Hioki et al. |
| 2004/0082550 A1 | 4/2004 | Kagechika |
| 2010/0152301 A1 | 6/2010 | Pommier et al. |
| 2015/0166448 A1 | 6/2015 | Wright et al. |

FOREIGN PATENT DOCUMENTS

| | | |
|---|---|---|
| EP | 1357104 A1 | 10/2003 |
| EP | 2864311 A1 | 4/2015 |
| JP | H02 237964 A | 9/1990 |
| JP | 2004/238291 A | 8/2004 |
| JP | 2008/158060 A | 7/2008 |
| JP | 2013/237618 A | 11/2013 |
| JP | 2015/526396 A | 9/2015 |
| JP | 2018/504392 A | 2/2018 |
| WO | WO-2001/089504 A1 | 11/2001 |
| WO | WO-2013/192554 A1 | 12/2013 |
| WO | WO-2016/112381 A1 | 7/2016 |
| WO | WO-2017/156194 A1 | 9/2017 |
| WO | WO-2017/184752 A1 | 10/2017 |
| WO | WO-2019/200314 A2 | 10/2019 |

OTHER PUBLICATIONS

Li et al. Photochemical Reactions of Dialkylboryltropolonate Compexes. Tetrahedron Letters,vol. 30, No. 33, pp. 4395-4398. (Year: 1989).*
Oblak et al. The furan route to tropolones: probing the antiproliferative effects of B-thujaplicin analogs. Organic & Biomolecular Chemistry, vol. 10, 8597-8604. (Year: 2012).*
Doering et al., "Synthesis of Substituted Tropolones," Journal of the American Chemical Society, 75(2): 297-303 (1953).
Extended European Search Report for EP Application No. 19784841.9 dated Feb. 25, 2022.
Lee et al., "Hinokitiol activates the hypoxia-inducible factor (HIF) pathway through inhibition of HIF hydroxylases," Biochemical and Biophysical Research Communications, 396(2): 370-375 (2010).
Li et al., "Novel α-substituted tropolones promote potent and selective caspase-dependent leukemia cell apoptosis," Pharmacological Research, 113: 438-448 (2016).
Mori et al., "meta-Photoaddition reactions of 2-chloro-, 2,5-dichloro-, and 2-halo-5-isopropyl-tropones with 9,10-dicyanoanthracene," Tetrahedron, 60(40): 8783-8790 (2004).
Ononye et al., "Tropolones as Lead-Like Natural Products: The Development of Potent and Selective Histone Deaetylase Inhibitors," ACS Medicinal Chemistry Letters, 4(8): 757-761 (2013).
Piettre et al., "Monoaryl- and bisaryldihydroxytropolones as potent inhibitors of inositol monophosphatase," Journal of Medicinal Chemistry, 40(26): 4208-4221 (1997).
Whitman et al., "The role of ClpX in erythropoietic protoporphyria," Hematology, Transfusion and Cell Therapy, 40(2): 182-188 (2018).
International Search Report and Written Opinion for International Application No. PCT/US19/27314 dated Oct. 2, 2019.
Kato et al., "One pot synthesis of substituted tropones from 7,7-Dihalo-2,3-(ore 3,4-)epoxybicydo[ 4.1.0]heptane derivatives," Bulletin of the Chemical Society of Japan, 63(1):64-73 (1990).

(Continued)

*Primary Examiner* — Sikarl A Witherspoon
(74) *Attorney, Agent, or Firm* — Foley Hoag LLP; Dana M. Gordon; Benjamin A. Vaughan

(57) ABSTRACT

Disclosed are analogues of hinokitiol, methods for preparing them, and pharmaceutical compositions thereof. Also disclosed are methods for their use in treating iron-related diseases.

25 Claims, 89 Drawing Sheets
Specification includes a Sequence Listing.

(56) References Cited

OTHER PUBLICATIONS

Lindsay et al., "Pyrolysis of 7,7-dibromobicyclo [4.1.0] heptane and derivatives: A general 1,3,5-cycloheptatriene synthesis," Tetrahedron, 21(7):1673-1680 (1965).
Ononye, "Towards the development of tropolone natural product derivatives as novel, potent anticancer therapeutics that selectively target histone deacetylase (HDAC) enzymes," Dissertation, University of Connecticut: 100 pages (2013).
Smith, "The mechanistic path of the 4-methyl-alphatropolone methyl ether to methyl 1-methyl-4-oxo-2-cyclopentenylacetate conversion," Dissertation, Iowa State University: 99 pages (1961).
Tansakui, "Nitroxides: Profluorescent sensors and functionalized alkoxyamine initiators for nitroxide mediated radical polymerization," Dissertation, University of California Santa Cruz: 103 pages (2012).
CAS Registry No. 1004-72-4, Entered STN: Nov. 16, 1984.
CAS Registry No. 130663-67-1, Entered STN: Nov. 30, 1990.
CAS Registry No. 1824438-51-8, Entered STN: Dec. 7, 2015.
CAS Registry No. 20856-84-2, Entered STN: Nov. 16, 1984.
CAS Registry No. 50904-27-3, Entered STN: Nov. 16, 1984.
CAS Registry No. 6754-42-3, Entered STN: Nov. 16, 1984.
Grillo et al., "Restored iron transport by a small molecule promotes absorption and hemoglobinization in animals" Science, 356 (6338): 608-616 (2017).
Liu et al., "Synthesis of Naturally Occurring Tropones and Tropolones" Tetrahedron, vol. 70, No. 49, p. 9281-9305 (2014).
PubChem CID 13661167.
Qian et al., "Hantzsch reaction of 3-(2-Bromoacetyl)tropolone. Synthesis of 3-(-Thiazolyl)tropolones" J.Heterocyclic, vol. 26 (601): 601-604 (1989).

* cited by examiner

R = OH, hinokitiol
R = H, C2deOHino fet3Δftr1Δ

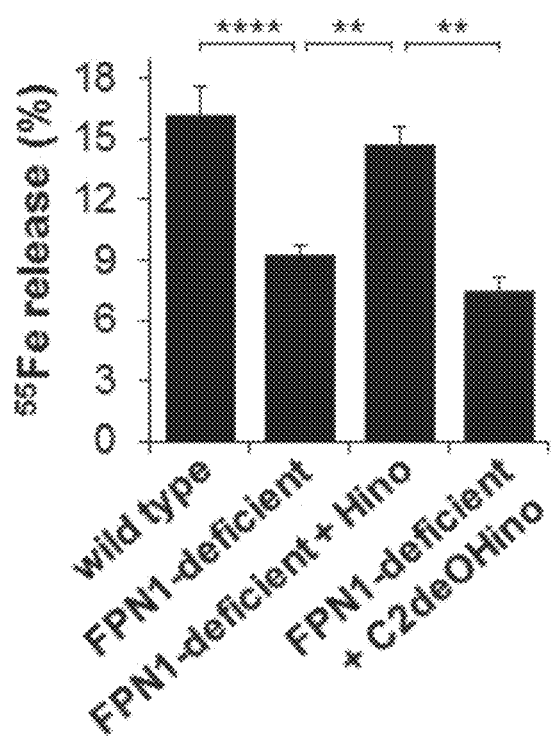
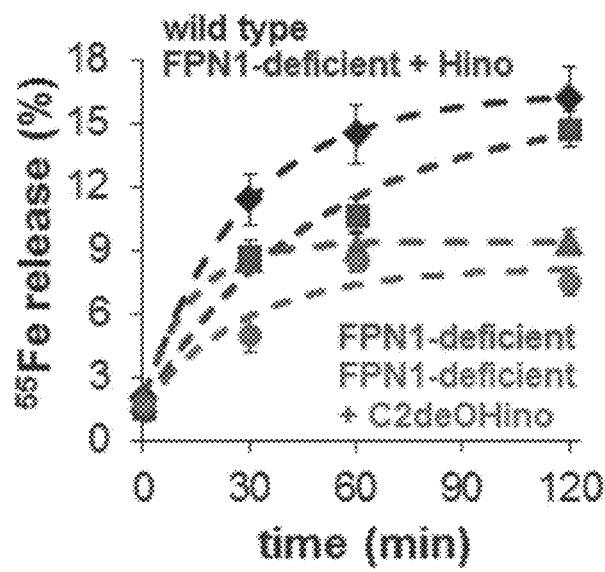
Fig. 3J
Fig. 3K

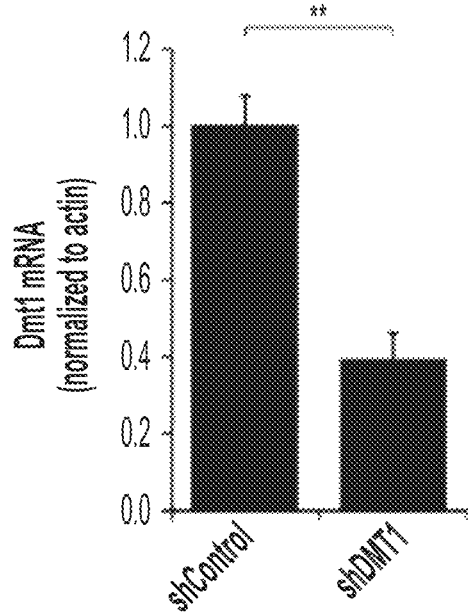
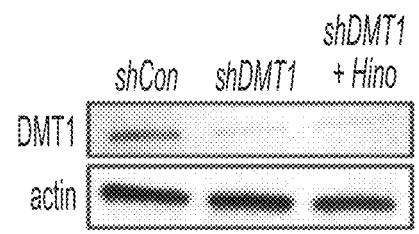
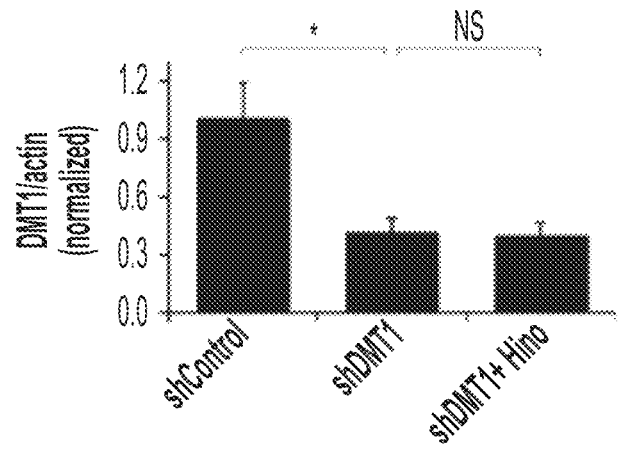
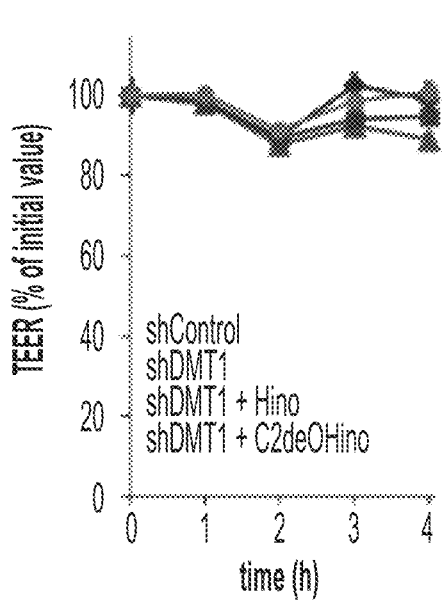
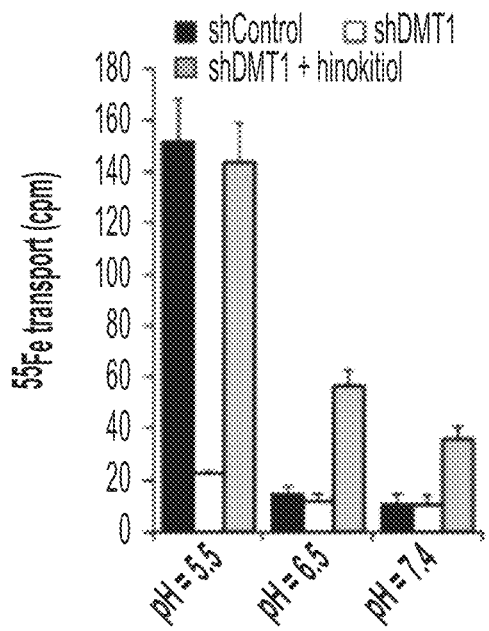
Fig. 12A
Fig. 12B
Fig. 12C
Fig. 12D
Fig. 12E Calcein Green (cytosol)
↑ Iron = ↓ Flourescence
↓ Iron = ↑ Flourescence RPA (mitochondria)
↑ Iron = ↓ Flourescence
↓ Iron = ↑ Flourescence ↑ Iron = ↑ Flourescence
↓ Iron = ↓ Flourescence

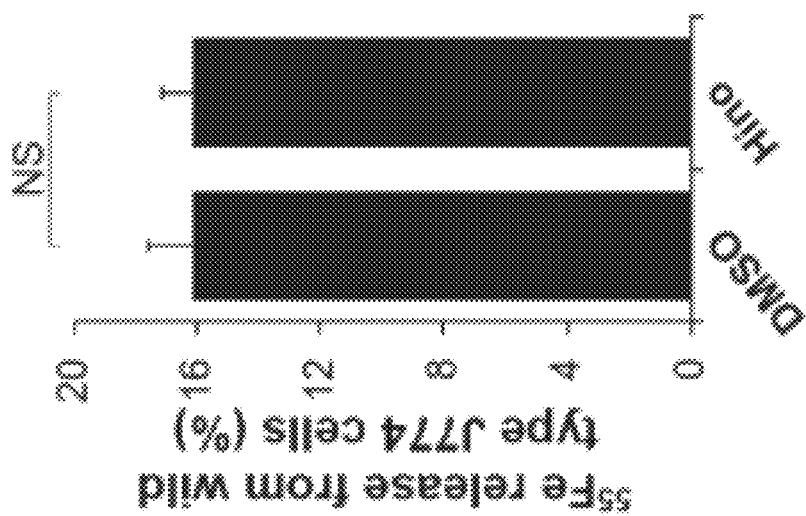
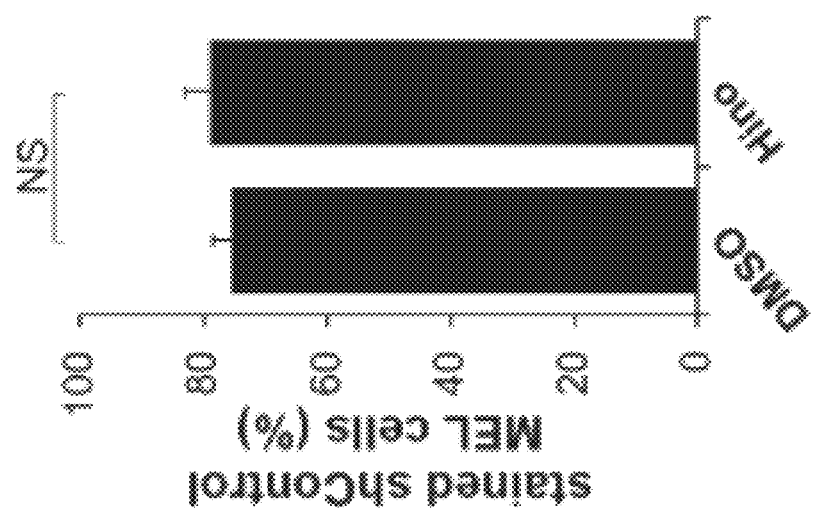
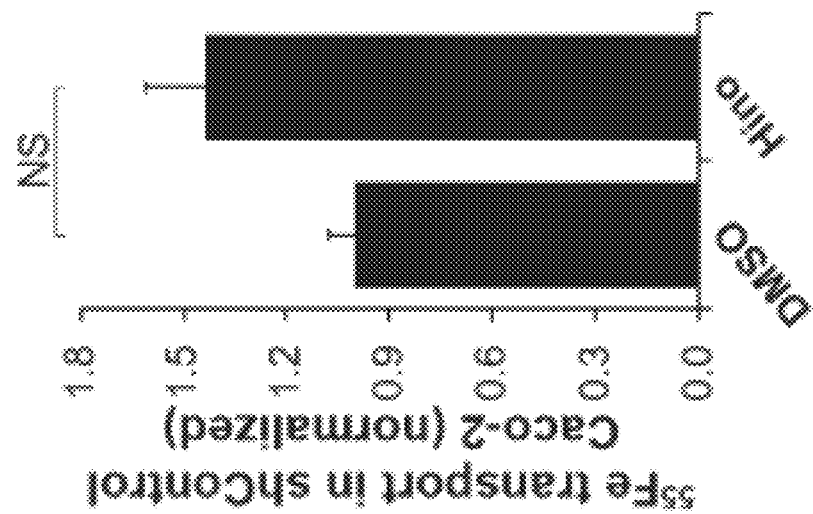
Fig. 23A
Fig. 23B
Fig. 23C

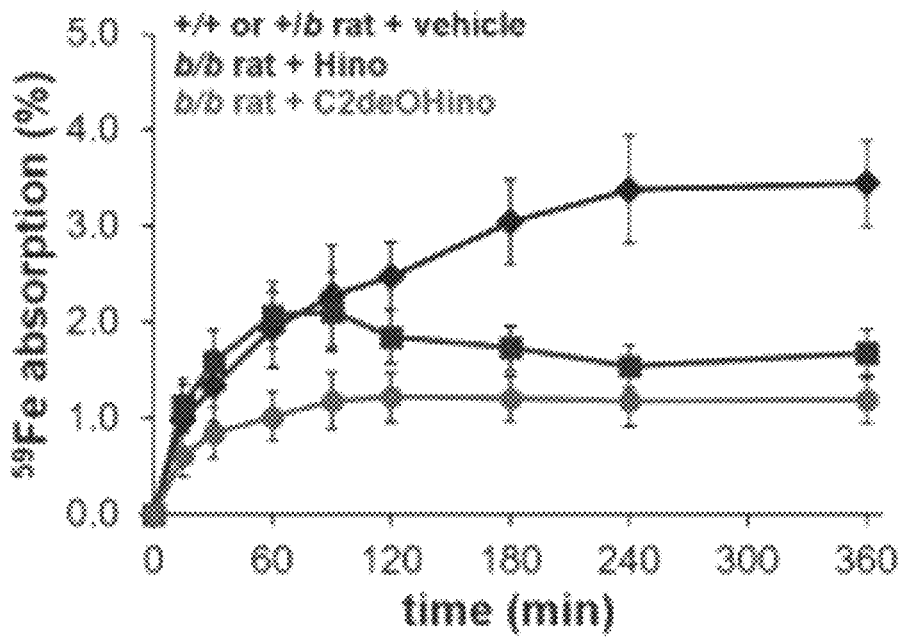
Fig. 24A
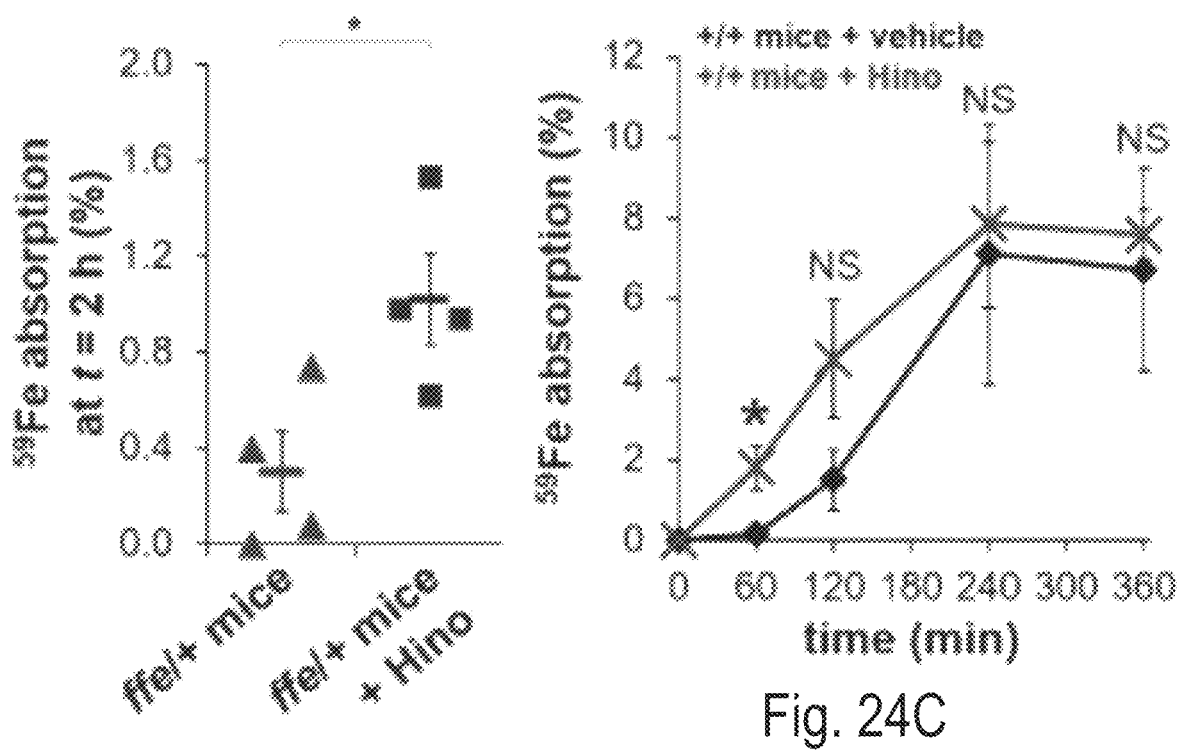
Fig. 24B
Fig. 24C

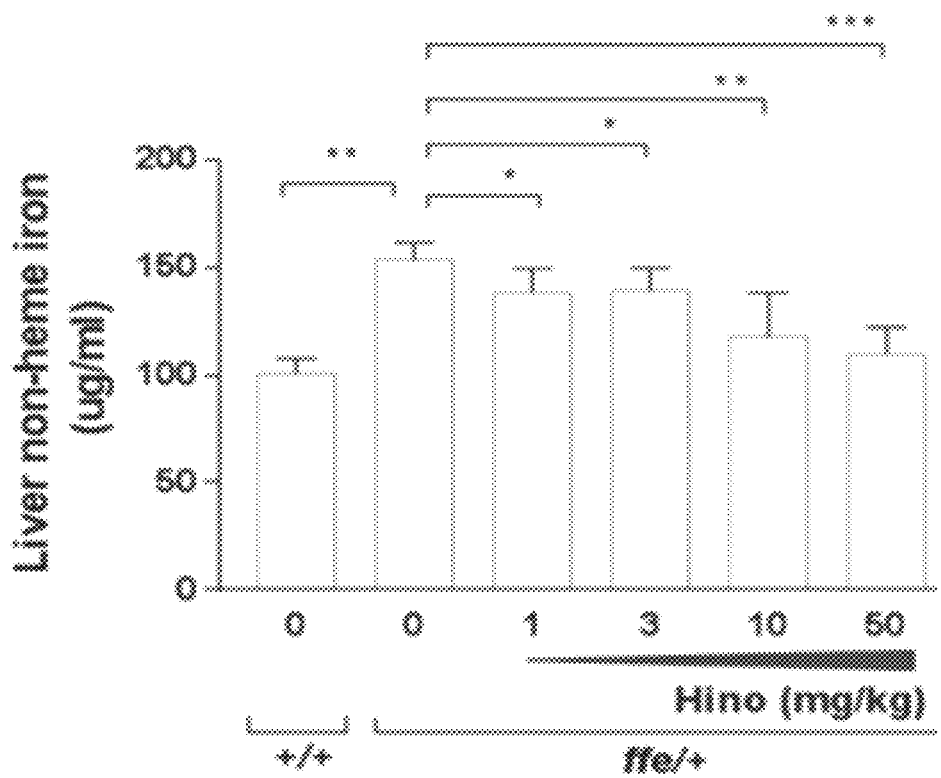
Fig. 26A
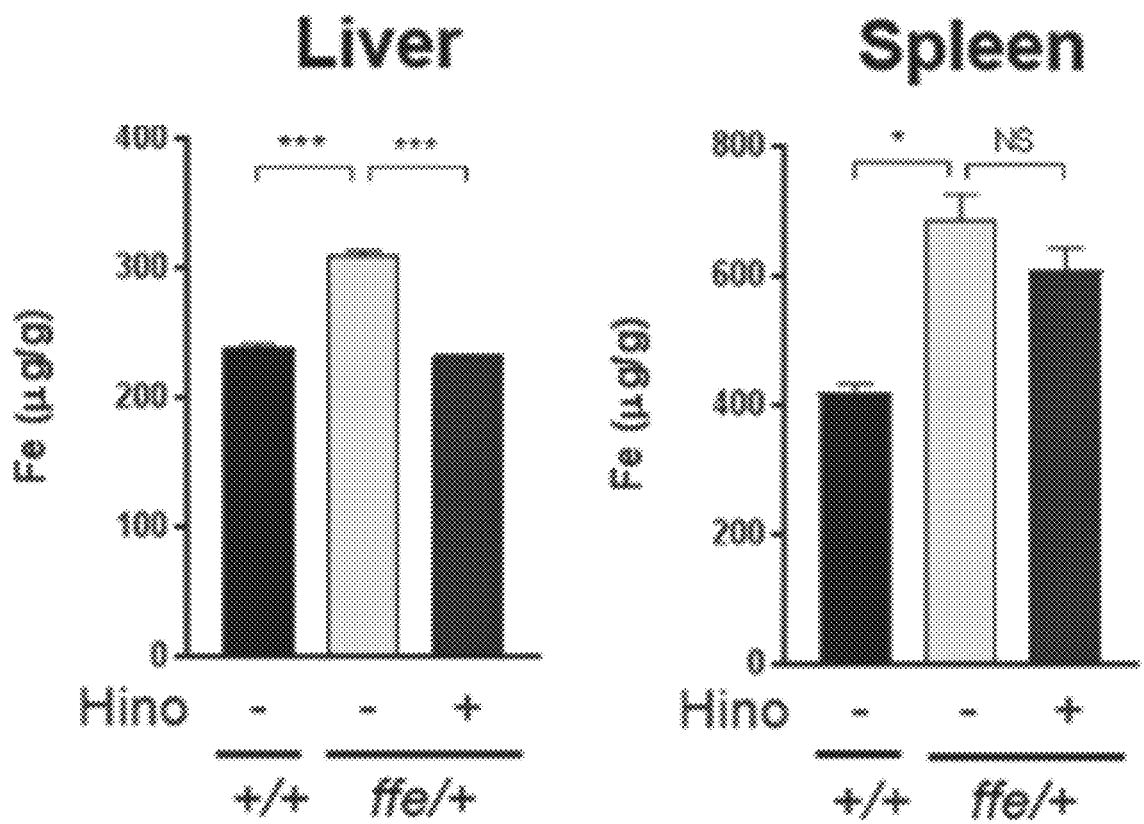
Fig. 26B
Fig. 26C

HINOKITIOL ANALOGUES, METHODS OF PREPARING AND PHARMACEUTICAL COMPOSITIONS THEREOF

RELATED APPLICATIONS

This application is a US National Stage application under 35 USC § 371 of International Application No. PCT/US2019/027314, filed Apr. 12, 2019; which claims the benefit of priority to U.S. Provisional Application No. 62/657,127, filed Apr. 13, 2018.

STATEMENT OF GOVERNMENT SUPPORT

This invention was made with Government support under Grant No. GM118185 awarded by National Institutes of Health. The Government has certain rights in the invention.

SEQUENCE LISTING

The instant application contains a Sequence Listing which has been submitted electronically in ASCII format and is hereby incorporated by reference in its entirety. Said ASCII copy, created on Oct. 9, 2020, is named UIX-03001_SL.txt and is 3,614 bytes in size.

BACKGROUND OF THE INVENTION

Iron homeostasis is critical for the normal function of the body. Because iron is central to hemoglobin production, deficient levels of iron result in iron-deficient anemia. Iron overload can also upset the balance of iron by inappropriately increasing intestinal iron absorption. This increase often results in the deposition of iron in the liver, pancreas, heart, pituitary, and other organs, leading to tissue damage and impairment of normal function of those organs.

Current treatment options for iron-related disorders include the administration of erythropoetic agents, such as epoetin alpha, epoetin beta, and darbepoetin. Other treatments options include oral or parental iron therapy and/or blood transfusions. Iron therapies however have limited efficacy and are usually not recommended for some patients. In addition, blood transfusions have the ongoing issue of multi-organ failure and increased mortality in critical care patients. Accordingly, there exists a need for a new method of treatment for iron-related diseases that is highly specific, well-tolerated, and can serve as a useful therapy for those subjects that do not respond to epoetin and its related analogs in a sufficient manner.

SUMMARY OF THE INVENTION

The present disclosure provides analogues of hinokitiol, methods for preparing the same, and pharmaceutical compounds thereof for use in treating iron-related diseases.

Accordingly, in one aspect, provided herein, is a method of preparing 6-bromo-2-methoxycyclohepta-2,4,6-trien-1-one or a salt thereof:

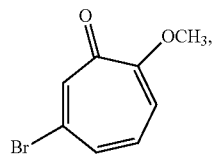

comprising the step of combining a Bronsted base and 7,7-dibromo-3-methoxybicyclo[4.1.0]hept-3-en-2-one or a salt thereof:

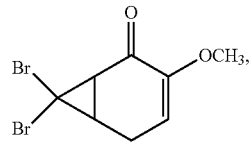 [SMILES: COC1=CCC2C(C1=O)C2(Br)Br]

thereby forming 6-bromo-2-methoxycyclohepta-2,4,6-trien-1-one or a salt thereof.

In another aspect, provided herein is a method of preparing a compound of the following structural formula or a salt thereof:

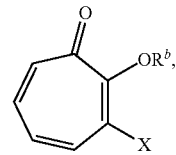

comprising reacting a compound of the following structural formula or a salt thereof:

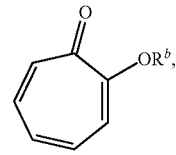

with a halogenating agent, thereby forming the compound, wherein $R^b$ is H or methyl, and X is halogen.

In yet another aspect, provided herein is a method of preparing 4-bromo-2-hydroxycyclohepta-2,4,6-trien-1-one or a salt thereof:

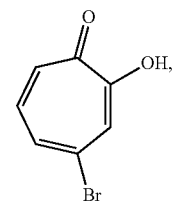

comprising combining 7,7-dibromobicyclo[4.1.0]heptane-2,3-diol or a salt thereof:

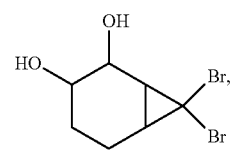

and an oxidizing agent, thereby forming 4-bromo-2-hydroxycyclohepta-2,4,6-trien-1-one or a salt thereof.

In still another aspect, provided herein is a method of preparing 5-bromo-2-hydroxycyclohepta-2,4,6-trien-1-one or a salt thereof:

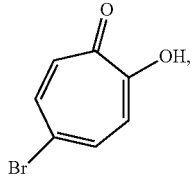

comprising combining 7,7-dibromobicyclo[4.1.0]heptane-3,4-diol or a salt thereof:

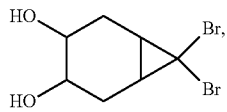

with an oxidizing agent, thereby forming 5-bromo-2-hydroxycyclohepta-2,4,6-trien-1-one or a salt thereof.

In another aspect, provided herein is a method of preparing a compound of the following structural formula or a salt thereof:

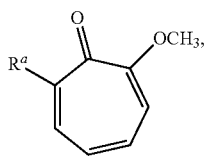

comprising reacting a compound of the following structural formula or a salt thereof:

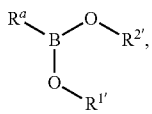

with 2-bromo-7-methoxycyclohepta-2,4,6-trien-1-one or a salt thereof:

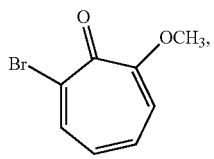

thereby providing the compound of structural formula or a salt thereof:

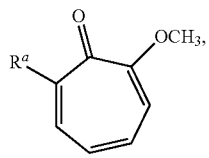

wherein $R^a$ is $C_{1-20}$-alkyl, $C_{2-20}$-alkenyl, $C_{2-20}$-alkynyl, $C_{3-9}$-cycloalkyl, aryl, or heteroaryl, each of which is unsubstituted or substituted with a substituent selected from the group consisting of halo, $NO_2$, CN, $C_{1-6}$-alkyl, $C_{1-6}$-haloalkyl, and $C_{1-6}$-alkoxy;

$R^{1'}$ and $R^{2'}$ are each, independently hydrogen or $C_{1-4}$-alkyl; or $R^{1'}$ and $R^{2'}$, together with atoms to which they are attached, form a ring having 2 to 4 carbon atoms, each of which is independently optionally substituted with $C_{1-3}$-alkyl or C=O; and B is a boron atom having $sp^3$ hybridization.

In yet another aspect, provided herein is a method of preparing a compound of structural formula or a salt thereof:

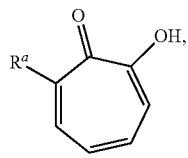

comprising combining a compound having structural formula or a salt thereof:

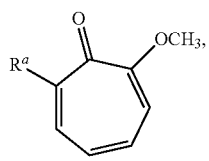

with a demethylating agent; thereby providing the compound of structural formula:

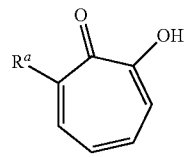

or a salt thereof; wherein $R^a$ is $C_{1-20}$-alkyl, $C_{2-20}$-alkenyl, $C_{2-20}$-alkynyl, $C_{3-9}$-cycloalkyl, aryl, or heteroaryl, each of which is unsubstituted or substituted with a substituent selected from the group consisting of halo, $NO_2$, CN, $C_{1-6}$-alkyl, $C_{1-6}$-haloalkyl, and $C_{1-4}$-alkylkoxy.

In still another aspect, provided herein is a method of preparing a compound of structural formula:

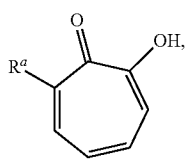

or a salt thereof; comprising:
(1) reacting a compound of structural formula:

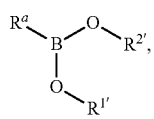

or a salt thereof; with a compound of structural formula:

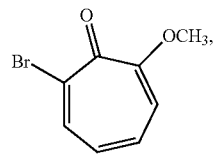

or a salt thereof; thereby providing a compound having structural formula:

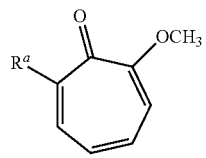

or a salt thereof; and
(2) contacting the compound having structural formula:

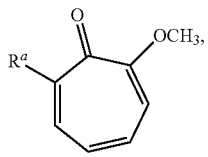

or a salt thereof; with a demethylating agent; thereby providing the compound of structural formula:

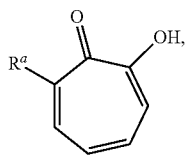

or a salt thereof; wherein
$C_{1-20}$-alkyl, $C_{2-20}$-alkenyl, $C_{2-20}$-alkynyl, $C_{3-9}$-cycloalkyl, aryl, or heteroaryl, each of which is unsubstituted or substituted with a substituent selected from the group consisting of halo, $NO_2$, CN, $C_{1-6}$-alkyl, $C_{1-6}$-haloalkyl, and $C_{1-6}$-alkoxy;

$R^{1'}$ and $R^{2'}$ are each, independently hydrogen or $C_{1-6}$-alkyl; or
$R^{1'}$ and $R^{2'}$, together with atoms to which they are attached, form a ring having 2 to 4 carbon atoms, each of which is optionally and independently substituted with $C_{1-3}$-alkyl or C=O; and
B is a boron atom having $sp^3$ hybridization.

In another aspect, provided herein is a method of preparing a compound of structural formula:

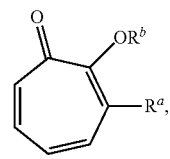

or a salt thereof; comprising reacting a compound of structural formula:

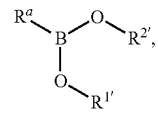

or a salt thereof; with a compound of structural formula:

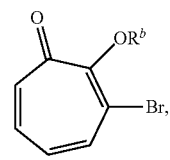

or a salt thereof; thereby providing the compound of structural formula:

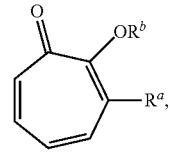

or a salt thereof; wherein
$R^a$ is $C_{1-20}$-alkyl, $C_{2-20}$-alkenyl, $C_{2-20}$-alkynyl, $C_{3-9}$-cycloalkyl, aryl, or heteroaryl, each of which is unsubstituted or substituted with a substituent selected from the group consisting of halo, $NO_2$, CN, $C_{1-6}$-alkyl, $C_{1-6}$-haloalkyl, and $C_{1-6}$-alkoxy;
$R^b$ is hydrogen or methyl;
$R^{1'}$ and $R^{2'}$ are each, independently hydrogen or $C_{1-6}$-alkyl; or
$R^{1'}$ and $R^{2'}$, together with atoms to which they are attached, form a ring having 2 to 4 carbon atoms, each of which is optionally and independently substituted with $C_{1-3}$-alkyl or C=O; and
B is a boron atom having $sp^3$ hybridization.

In yet another aspect, provided herein is a method of preparing a compound of structural formula:

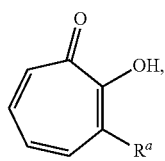

or a salt thereof; comprising combining a compound having structural formula:

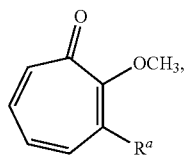

or a salt thereof; with a demethylating agent; thereby providing the compound of structural formula:

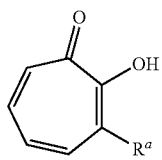

or a salt thereof; wherein $R^a$ is $C_{1-20}$-alkyl, $C_{2-20}$-alkenyl, $C_{2-20}$-alkynyl, $C_{3-9}$-cycloalkyl, aryl, or heteroaryl, each of which is unsubstituted or substituted with a substituent selected from the group consisting of halo, $NO_2$, CN, $C_{1-6}$-alkyl, $C_{1-6}$-haloalkyl, and $C_{1-6}$-alkoxy.

In still another aspect, provided herein is a method of preparing a compound of structural formula:

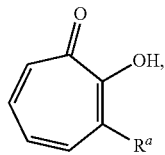

or a salt thereof; comprising:

(1) reacting 2-methoxycyclohepta-2,4,6-trien-1-one:

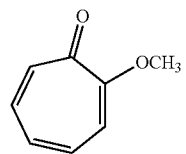

or a salt thereof, with a brominating agent, thereby forming 3-bromo-2-methoxycyclohepta-2,4,6-trien-1-one:

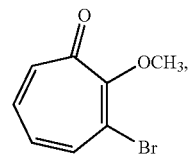 [SMILES: COc1c(Br)ccccc1=O]

or a salt thereof, (2) reacting a compound of structural formula:

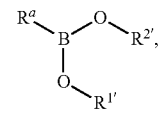

or a salt thereof; with 3-bromo-2-methoxycyclohepta-2,4,6-trien-1-one:

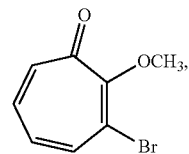 [SMILES: COc1c(Br)ccccc1=O]

or a salt thereof, thereby forming a compound having structural formula:

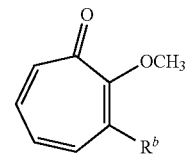

or a salt thereof; and (3) contacting the compound having structural formula:

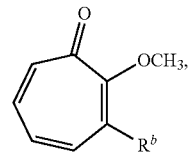

or a salt thereof; with a demethylating agent; thereby providing the compound of structural formula:

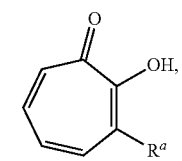

or a salt thereof; wherein $R^a$ is $C_{1-20}$-alkyl, $C_{2-20}$-alkenyl, $C_{2-20}$-alkynyl, $C_{3-9}$-cycloalkyl, aryl, or heteroaryl, each of which is unsubstituted or substituted with a substituent selected from the group consisting of halo, NO$_2$, CN, C$_{1-6}$-alkyl, C$_{1-6}$-haloalkyl, and C$_{1-6}$-alkoxy;

R$^{1'}$ and R$^{2'}$ are each, independently hydrogen or C$_{1-6}$-alkyl; or

R$^{1'}$ and R$^{2'}$, together with atoms to which they are attached, form a ring having 2 to 4 carbon atoms, each of which is optionally and independently substituted with C$_{1-3}$-alkyl or C=O; and B is a boron atom having sp$^3$ hybridization.

In another aspect, provided herein is a method of preparing a compound of structural formula:

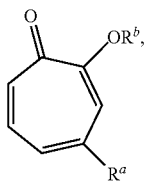

or a salt thereof; comprising reacting a compound of structural formula:

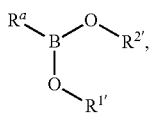

or a salt thereof; with a compound of structural formula:

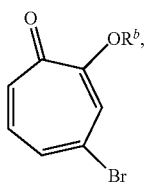

or a salt thereof; thereby providing the compound of structural formula:

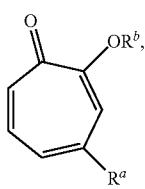

or a salt thereof; wherein

R$^a$ is C$_{1-20}$-alkyl, C$_{2-20}$-alkenyl, C$_{2-20}$-alkynyl, C$_{3-9}$-cycloalkyl, aryl, or heteroaryl, each of which is unsubstituted or substituted with a substituent selected from the group consisting of halo, NO$_2$, CN, C$_{1-6}$-alkyl, C$_{1-6}$-haloalkyl, and C$_{1-6}$-alkoxy;

R$^b$ is hydrogen or methyl;

R$^{1'}$ and R$^{2'}$ are each, independently hydrogen or C$_{1-6}$-alkyl; or

R$^{1'}$ and R$^{2'}$, together with atoms to which they are attached, form a ring having 2 to 4 carbon atoms, each of which is optionally and independently substituted with C$_{1-3}$-alkyl or C=O; and B is a boron atom having sp$^3$ hybridization.

In yet another embodiment, provided herein is a method of preparing a compound of structural formula:

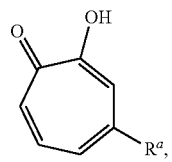

or a salt thereof; comprising combining a compound having structural formula:

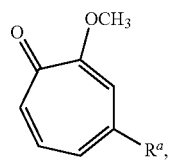

or a salt thereof; with a demethylating agent; thereby providing the compound of structural formula:

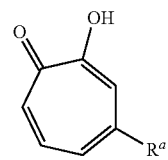

or a salt thereof; wherein

R$^a$ is C$_{1-20}$-alkyl, C$_{2-20}$-alkenyl, C$_{2-20}$-alkynyl, C$_{3-9}$-cycloalkyl, aryl, or heteroaryl, each of which is unsubstituted or substituted with a substituent selected from the group consisting of halo, NO$_2$, CN, C$_{1-6}$-alkyl, C$_{1-4}$-haloalkyl, and C$_{1-6}$-alkoxy.

In still another aspect, provided is a method of preparing a compound of structural formula:

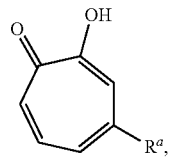

or a salt thereof; comprising:
(1) contacting 7,7-dibromobicyclo[4.1.0]heptane-2,3-diol:

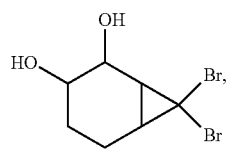 [SMILES: OC1CCC2C(C1O)C2(Br)Br]

or a salt thereof, with an oxidizing agent, thereby forming 4-bromo-2-hydroxycyclohepta-2,4,6-trien-1-one:

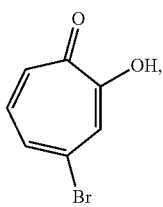

or a salt thereof, (2) reacting a compound of structural formula:

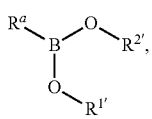

or a salt thereof; with 4-bromo-2-hydroxycyclohepta-2,4,6-trien-1-one:

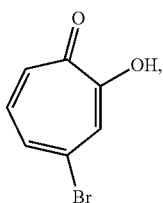

or a salt thereof, thereby forming a compound having structural formula:

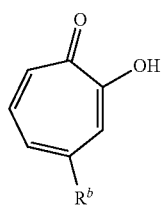

or a salt thereof; wherein $R^a$ is $C_{1-20}$-alkyl, $C_{2-20}$-alkenyl, $C_{2-20}$-alkynyl, $C_{3-9}$-cycloalkyl, aryl, or heteroaryl, each of which is unsubstituted or substituted with a substituent selected from the group consisting of halo, $NO_2$, CN, $C_{1-6}$-alkyl, $C_{1-6}$-haloalkyl, and $C_{1-6}$-alkoxy;

$R^{1'}$ and $R^{2'}$ are each, independently hydrogen or $C_{1-6}$-alkyl; or $R^{1'}$ and $R^{2'}$, together with atoms to which they are attached, form a ring having 2 to 4 carbon atoms, each of which is optionally and independently substituted with $C_{1-3}$-alkyl or C=O; and B is a boron atom having sp³ hybridization.

In another aspect, provided herein is a method of preparing a compound of structural formula:

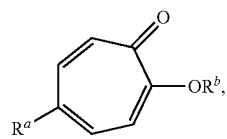

or a salt thereof; comprising reacting a compound of structural formula:

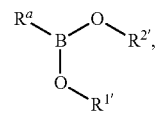

or a salt thereof; with a compound of structural formula:

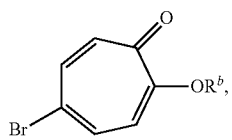

or a salt thereof; thereby providing the compound of structural formula:

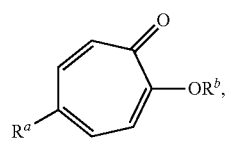

or a salt thereof; wherein $R^a$ is $C_{1-20}$-alkyl, $C_{2-20}$-alkenyl, $C_{2-20}$-alkynyl, $C_{3-9}$-cycloalkyl, aryl, or heteroaryl, each of which is unsubstituted or substituted with a substituent selected from the group consisting of halo, $NO_2$, CN, $C_{1-6}$-alkyl, $C_{1-6}$-haloalkyl, and $C_{1-6}$-alkoxy;

$R^b$ is hydrogen or methyl;

$R^{1'}$ and $R^{2'}$ are each, independently hydrogen or $C_{1-6}$-alkyl; or $R^{1'}$ and $R^{2'}$, together with atoms to which they are attached, form a ring having 2 to 4 carbon atoms, each of which is optionally and independently substituted with $C_{1-3}$-alkyl or C=O; and B is a boron atom having sp³ hybridization.

In yet another embodiment, provided herein is a method of preparing a compound of structural formula:

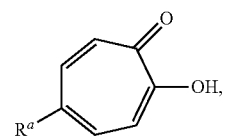

or a salt thereof; comprising combining a compound having structural formula:

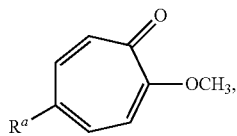

or a salt thereof; with a demethylating agent; thereby providing the compound of structural formula:

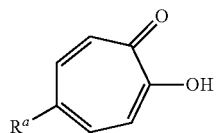

or a salt thereof; wherein $R^a$ is $C_{1-20}$-alkyl, $C_{2-20}$-alkenyl, $C_{2-20}$-alkynyl, $C_{3-9}$-cycloalkyl, aryl, or heteroaryl, each of which is unsubstituted or substituted with a substituent selected from the group consisting of halo, $NO_2$, CN, $C_{1-6}$-alkyl, $C_{1-6}$-haloalkyl, and $C_{1-6}$-alkoxy.

In still another aspect, provided herein is method of preparing a compound of structural formula:

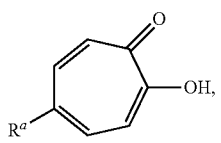

or a salt thereof; comprising:

(1) contacting 7,7-dibromobicyclo[4.1.0]heptane-3,4-diol:

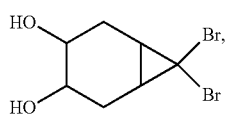

or a salt thereof, with an oxidizing agent, thereby forming 5-bromo-2-hydroxycyclohepta-2,4,6-trien-1-one:

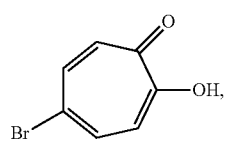

or a salt thereof; and (2) reacting a compound of structural formula:

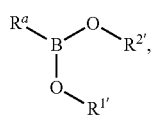

or a salt thereof; with 5-bromo-2-hydroxycyclohepta-2,4,6-trien-1-one:

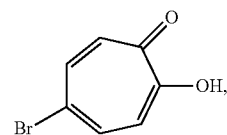

or a salt thereof, thereby forming a compound having structural formula:

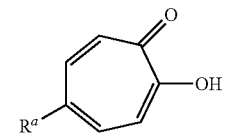

or a salt thereof; wherein $R^a$ is $C_{1-20}$-alkyl, $C_{2-20}$-alkenyl, $C_{2-20}$-alkynyl, $C_{3-9}$-cycloalkyl, aryl, or heteroaryl, each of which is unsubstituted or substituted with a substituent selected from the group consisting of halo, $NO_2$, CN, $C_{1-6}$-alkyl, $C_{1-6}$-haloalkyl, and $C_{1-6}$-alkoxy;

$R^{1'}$ and $R^{2'}$ are each, independently hydrogen or $C_{1-6}$-alkyl; or $R^{1'}$ and $R^{2'}$, together with atoms to which they are attached, form a ring having 2 to 4 carbon atoms, each of which is optionally and independently substituted with $C_{1-3}$-alkyl or C=O; and B is a boron atom having $sp^3$ hybridization.

In another aspect, provided herein is a method of preparing a compound of structural formula:

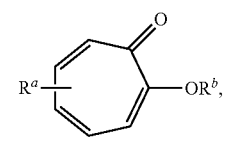

or a salt thereof; comprising reacting a compound of structural formula:

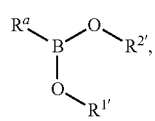

or a salt thereof; with a compound of structural formula:

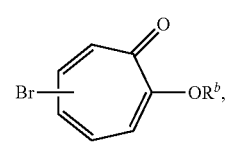

or a salt thereof; thereby providing the compound of structural formula:

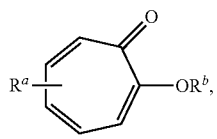

or a salt thereof; wherein
  $R^a$ is $C_{1-20}$-alkyl, $C_{2-20}$-alkenyl, $C_{2-20}$-alkynyl, $C_{3-9}$-cycloalkyl, aryl, or heteroaryl, each of which is unsubstituted or substituted with a substituent selected from the group consisting of halo, $NO_2$, CN, $C_{1-6}$-alkyl, $C_{1-6}$-haloalkyl, and $C_{1-6}$-alkoxy;
  $R^b$ is hydrogen or methyl;
  $R^{1'}$ and $R^{2'}$ are each, independently hydrogen or $C_{1-6}$-alkyl; or
  $R^{1'}$ and $R^{2'}$, together with atoms to which they are attached, form a ring having 2 to 4 carbon atoms, each of which is optionally and independently substituted with $C_{1-3}$-alkyl or C=O; and
  B is a boron atom having $sp^3$ hybridization.

In yet another aspect, provided herein is a method of preparing a compound of structural formula:

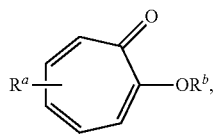

or a salt thereof; comprising reacting a compound of structural formula:

or a salt thereof; with a compound of structural formula:

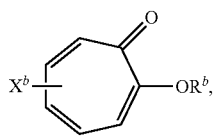

or a salt thereof; thereby providing the compound of structural formula:

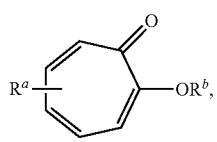

or a salt thereof; wherein
  $R^a$ is $C_{1-20}$-alkyl, $C_{2-20}$-alkenyl, $C_{2-20}$-alkynyl, $C_{3-9}$-cycloalkyl, aryl, or heteroaryl, each of which is unsubstituted or substituted with a substituent selected from the group consisting of halo, $NO_2$, CN, $C_{1-6}$-alkyl, $C_{1-6}$-haloalkyl, and $C_{1-6}$-alkoxy;
  $R^b$ is hydrogen or methyl;

$X^a$ is

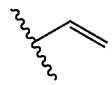

or $-Sn(C_{1-6}$-alkyl); and
  $X^b$ is halo or pseudohalo.

In still another aspect, provided herein is a method of preparing a compound of structural formula:

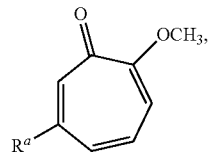

or a salt thereof; comprising reacting a compound of structural formula:

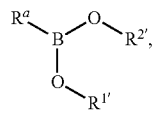

or a salt thereof; with 3-bromo-7-methoxycyclohepta-2,4,6-trien-1-one:

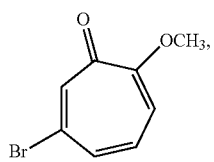

or a salt thereof; thereby providing the compound of structural formula:

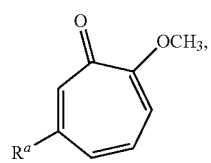

or a salt thereof; wherein
  $R^a$ is $C_{1-20}$-alkyl, $C_{2-20}$-alkenyl, $C_{2-20}$-alkynyl, $C_{3-9}$-cycloalkyl, aryl, or heteroaryl, each of which is unsubstituted or substituted with a substituent selected from the group consisting of halo, $NO_2$, CN, $C_{1-6}$-alkyl, $C_{1-6}$-haloalkyl, and $C_{1-6}$-alkoxy;
  $R^{1'}$ and $R^{2'}$ are each, independently hydrogen or $C_{1-6}$-alkyl; or
  $R^{1'}$ and $R^{2'}$, together with atoms to which they are attached, form a ring having 2 to 4 carbon atoms, each of which is optionally and independently substituted with $C_{1-3}$-alkyl or C=O; and
  B is a boron atom having $sp^3$ hybridization.

In another aspect, provided herein is a method of preparing a compound of structural formula:

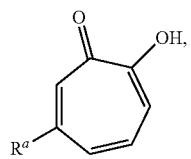

or a salt thereof; comprising combining a compound having structural formula:

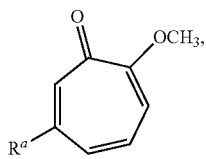

or a salt thereof; with a demethylating agent; thereby providing the compound of structural formula:

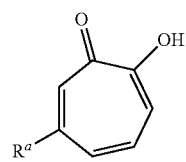

or a salt thereof; wherein
R$^a$ is C$_{1-20}$-alkyl, C$_{2-20}$-alkenyl, C$_{2-20}$-alkynyl, C$_{3-9}$-cycloalkyl, aryl, or heteroaryl, each of which is unsubstituted or substituted with a substituent selected from the group consisting of halo, NO$_2$, CN, C$_{1-6}$-alkyl, C$_{1-6}$-haloalkyl, and C$_{1-6}$-alkoxy.

In yet another aspect, provided herein is a method of preparing a compound of structural formula:

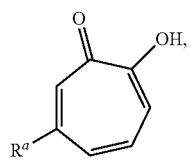

or a salt thereof; comprising:
(1) contacting 7,7-dibromo-3-methoxybicyclo[4.1.0]hept-3-en-2-one:

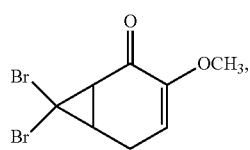

or a salt thereof; with a base; thereby forming 6-bromo-2-methoxycyclohepta-2,4,6-trien-1-one:

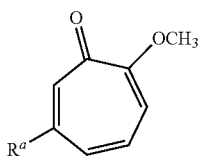

or a salt thereof;
(2) reacting a compound of structural formula:

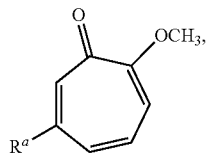

or a salt thereof; with 6-bromo-2-methoxycyclohepta-2,4,6-trien-1-one, or a salt thereof; thereby providing a compound having structural formula:

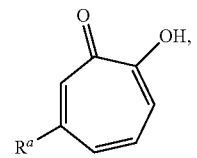

or a salt thereof; and
(3) contacting the compound having structural formula:

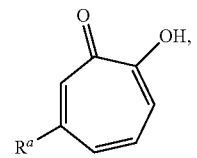

or a salt thereof; with a demethylating agent; thereby providing the compound of structural formula:

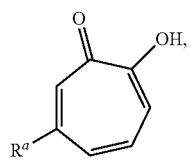

or a salt thereof; wherein C$_{1-20}$-alkyl, C$_{2-20}$-alkenyl, C$_{2-20}$-alkynyl, C$_{3-9}$-cycloalkyl, aryl, or heteroaryl, each of which is unsubstituted or substituted with a substituent selected from the group consisting of halo, NO$_2$, CN, C$_{1-6}$-alkyl, C$_{1-6}$-haloalkyl, and C$_{1-6}$-alkoxy;
R$^{1'}$ and R$^{2'}$ are each, independently hydrogen or C$_{1-4}$-alkyl; or
R$^{1'}$ and R$^{2'}$, together with atoms to which they are attached, form a ring having 2 to 4 carbon atoms, each of which is optionally and independently substituted with C$_{1-3}$-alkyl or C=O; and
B is a boron atom having sp$^3$ hybridization.

Also provided herein are compounds, which are analogues of the natural product hinokitiol. Exemplary compounds of the invention include:

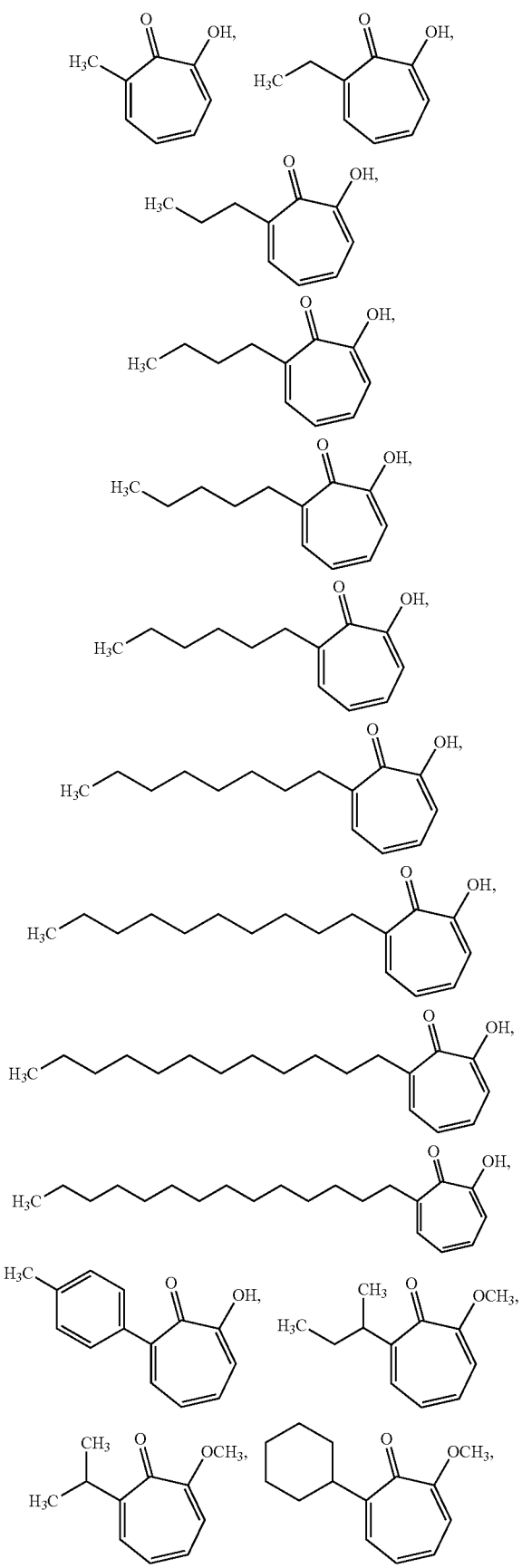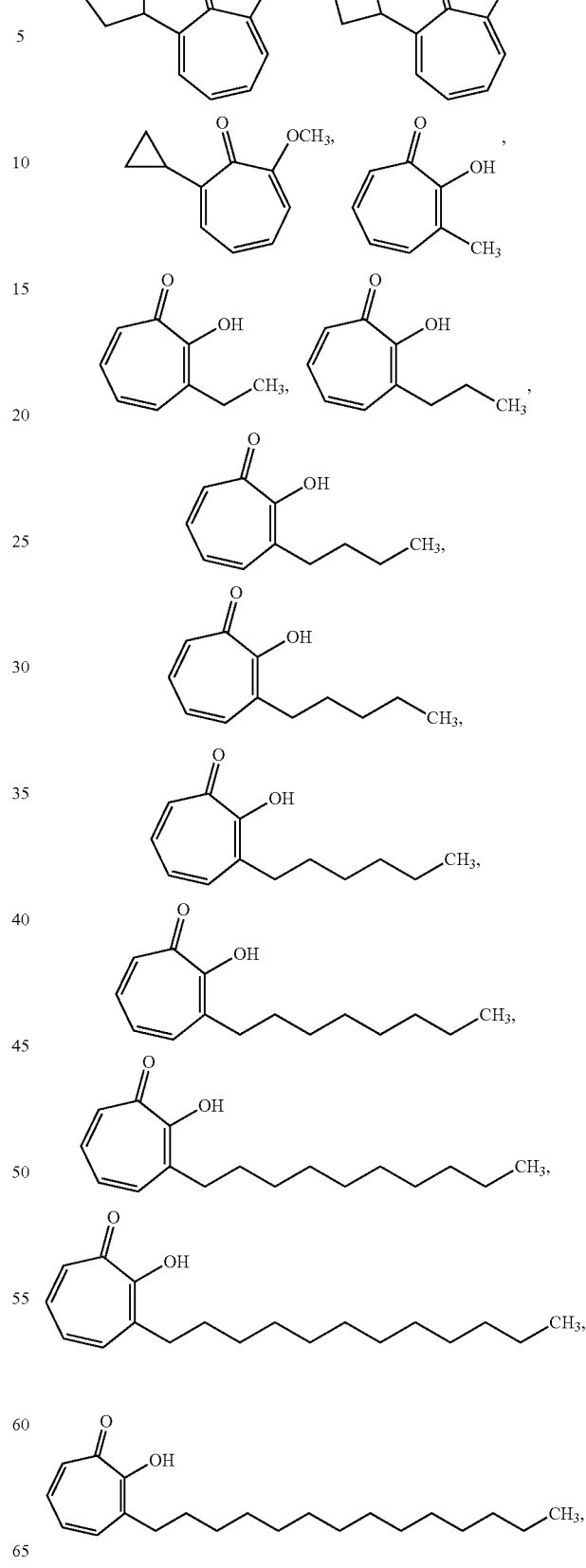

-continued
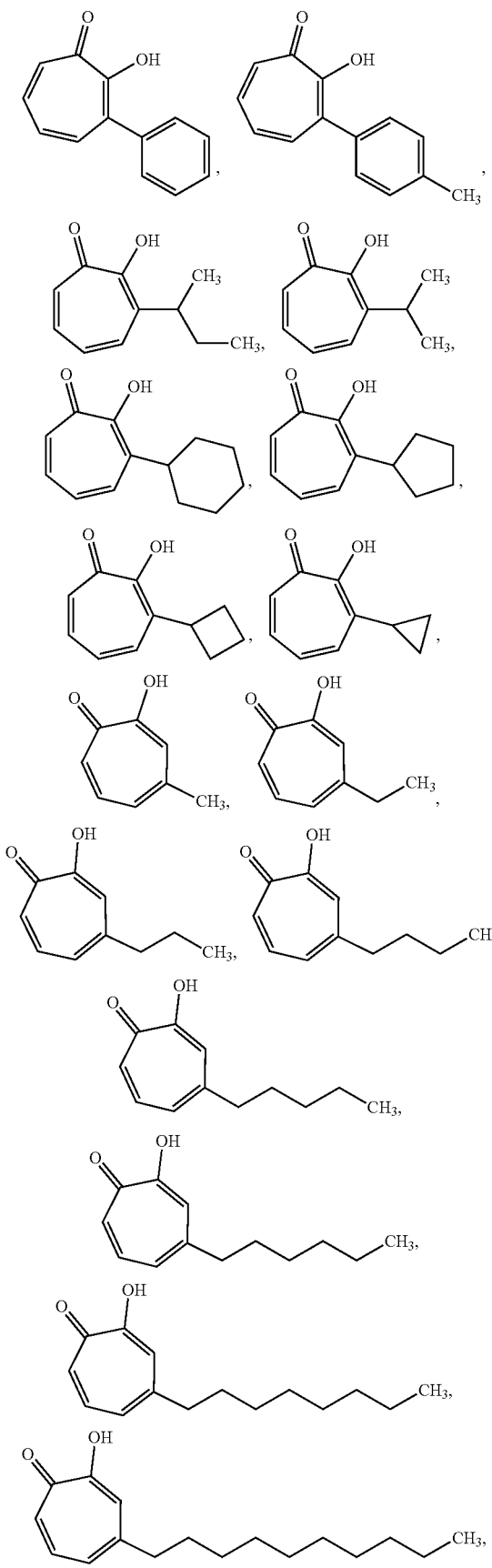
-continued
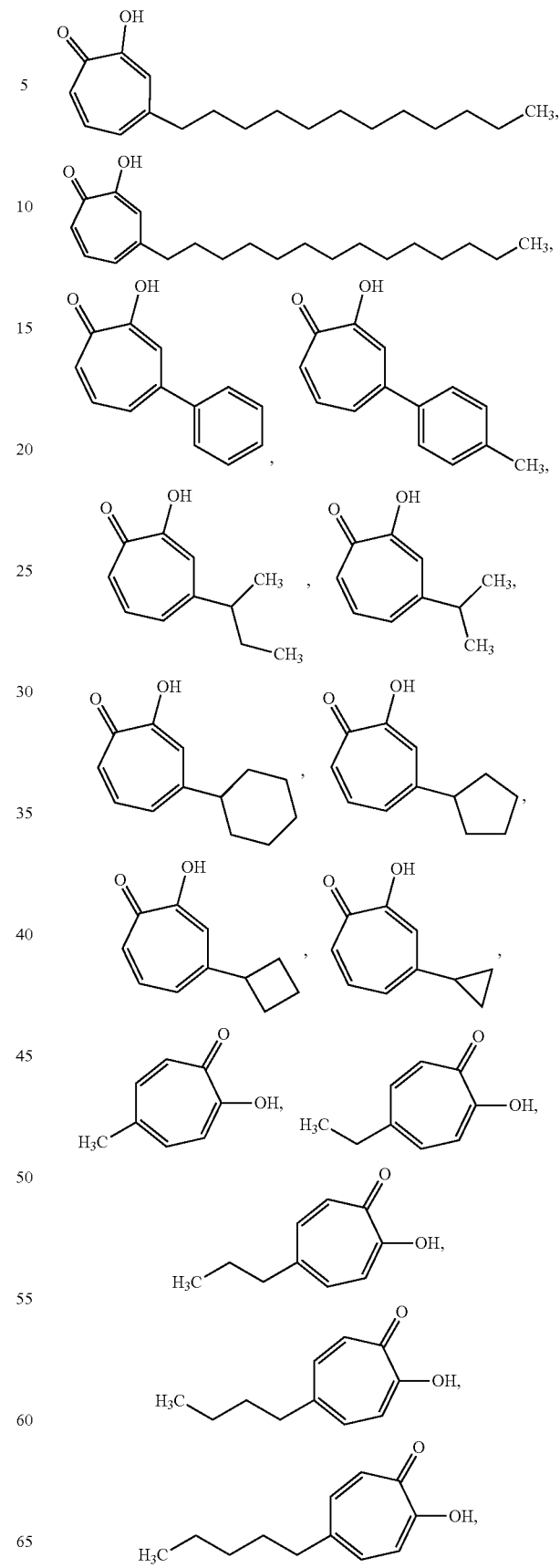

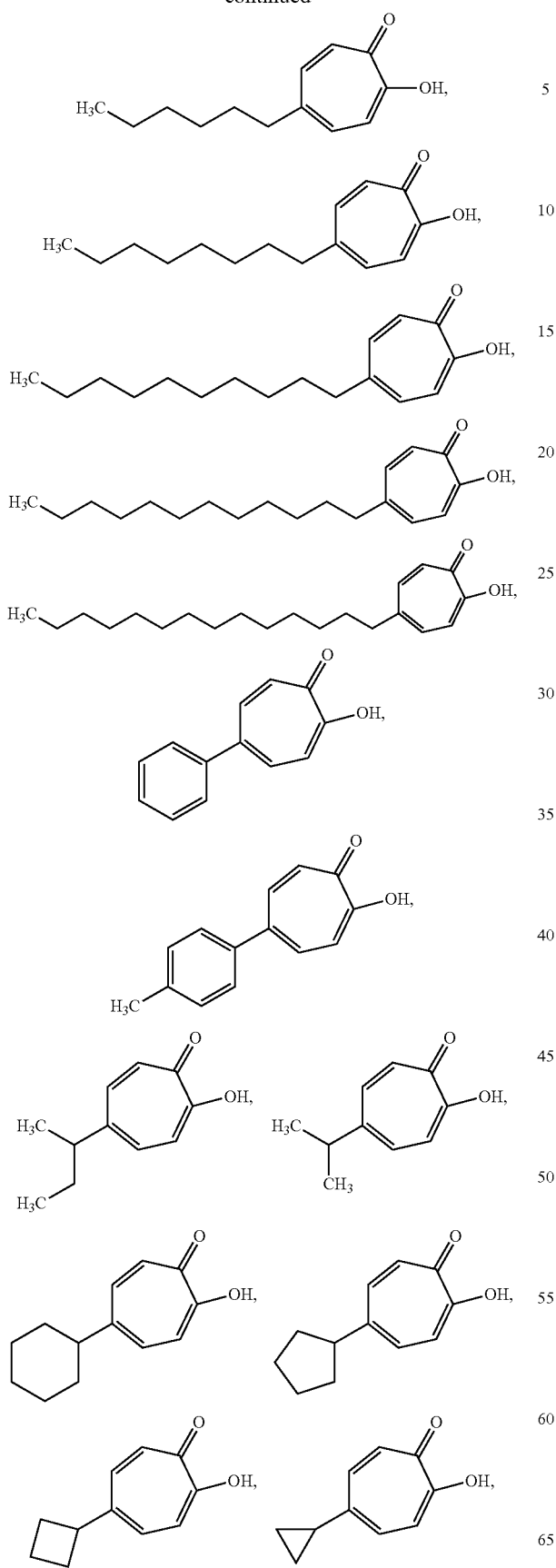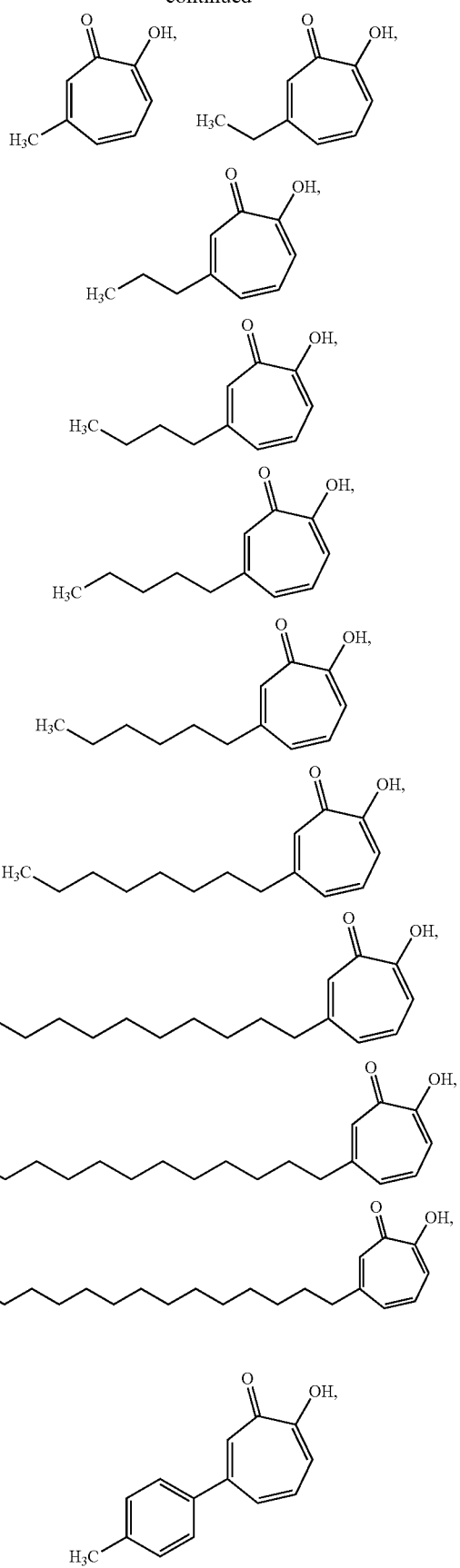

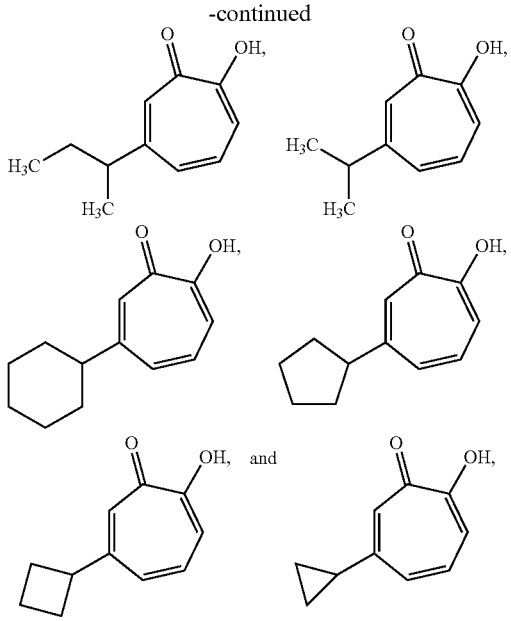

or a salt thereof.

In some embodiments, the compounds disclosed herein are provided as a pharmaceutical composition.

The compounds and pharmaceutical compositions disclosed herein may be used to treat any iron-related disorder, including, but not limited to, iron deficiency, AI, and iron overload. Other examples of disorders caused by too much iron include cirrhosis, liver cancer, osteoarthritis, osteopenia, osteomalacia, diabetes, irregular heart beat, heart attack, hypothyroidism, infertility, impotence, depression, hypogonadism, and bronze or ashen gray skin miscoloration. Examples of other iron-related disorders that may be diagnosed and treated according to the present invention include, e.g., hemochromatosis, juvenile hemochromatosis, acquired iron overload, sickle cell anemia, thalassemia, African siderosis, porphyria cutaena tarda, iron deficiency anemia, Friedreich Ataxia, ferroportin disease, hyperferritinemia, atransferrinemia, and sideroblastic anemia. Iron-related disorders further include, e.g., heart failure, haemolytic anaemia, and neurological disorders.

Also provided herein are methods of treating a disease or condition characterized by a deficiency of or a defect in an iron transporter, comprising administering to a subject in need thereof a therapeutically effective amount of tropolone or a compound disclosed herein, thereby treating the disease or condition. In some such embodiments, the disease or condition characterized by a deficiency of or defect in an iron transporter is hypochromic, microcytic anemia.

In other embodiments, provided herein is a method of increasing transepithelial iron transport, comprising administering to a subject in need thereof an effective amount of tropolone or a compound disclosed herein.

In yet other embodiments, provided herein is a method of increasing physiology, comprising administering to a subject in need thereof an effective amount of tropolone or a compound disclosed herein.

In still other embodiments, provided herein is a method of increasing hemoglobinization, comprising administering to a subject in need thereof an effective amount of tropolone or a compound disclosed herein.

In other embodiments, provided herein is a method of increasing iron release, comprising administering to a subject in need thereof an effective amount of tropolone or a compound disclosed herein.

Also provided herein is method of increasing transepithelial iron transport, physiology, or hemoglobinization in a cell in vitro, comprising contacting the cell with an effective amount of the compound disclosed herein.

In other embodiments, provided herein is a method of increasing transepithelial iron transport, physiology, or hemoglobinization in an organ ex vivo, comprising contacting the organ with an effective amount of the compound disclosed herein.

BRIEF DESCRIPTION OF THE DRAWINGS

FIGS. 3A-3K show hinokitiol restores mammalian cell physiology. (A) $^{55}$Fe uptake into DMT1-deficient Caco-2 monolayers and (B) transepithelial transport (apical to basolateral) indicated hinokitiol (500 nM) restored normal iron absorption. N=3. (C) Hinokitiol-promoted $^{55}$Fe transport occurs on times commensurate with dwell times in the gut. N=3. (D) Cell pellets from shControl and hinokitiol-treated (1 μM) DMT1-deficient MEL cells appear pink, characteristic of hemoglobin, while DMT1-deficient cell pellets do not. (E) ImageJ quantification of MEL cells stained brown with o-dianisidine. Dotted line represents shControl levels. N=6-48. (F)[15]Fe incorporation into heme in hinokitiol-rescued DMT1-deficient MEL cells. Dotted line represents shControl levels. N=3-23. (G) Hinokitiol increases the number of o-dianisidine stained Mfrn1-deficient MEL cells. Dotted line represents DS19 levels. N=21-48. (H) Hinokitiol (1 μM) restores $^{55}$Fe transepithelial transport across FPN1-deficient Caco-2 monolayers (I) without affecting iron uptake. N=12. (J) Hinokitiol (5 μM) promotes the release of $^{55}$Fe from hepcidin-treated FPN1-deficient J774 macrophages (t=2 hours). N=6-20. (K) Time-dependent release of $^{55}$Fe from wild type and FPN1-deficient J774 macrophages treated with or without hinokitiol and C$_2$deOHino. N=6-20. (A, B, E-J) NS, not significant;  P≤0.01; * P≤0.001; **** P≤0.0001; Graphs depict means±SEM.

FIG. 10A-I show hinokitiol competitively bound 10-fold more $Cu^{II}$ than $Fe^{II}$ and transported $Cu^{II}$ 80-fold faster than $Fe^{II}$ in liposomes, yet the low accessibility of copper likely leads to high iron selectivity in vivo. FIG. 10J shows that upon treatment of fet3Δftr1Δ yeast with hinokitiol intracellular iron levels increased relative to vehicle-treated controls, while levels of manganese, cobalt, nickel, zinc, and copper were unchanged.

FIGS. 12A-12G show Hinokitiol promotes uptake and transport in DMT1-deficient Caco-2 cells. (A) Dmt1 mRNA levels, quantified via qRT-PCR, are reduced in shDMT1 Caco-2 monolayers as compared to the shControl cell monolayers. N=9. (B and C) Quantitative densitometric analysis of western blots indicated decreased DMT1 protein levels in shDMT1 Caco-2 monolayers. Hinokitiol (500 nM) treatment did not induce DMT1 expression. N=13-14. (D) Transepithelial electrical resistance (TEER) values of Caco-2 monolayers treated with DMSO, hinokitiol (500 nM), or C$_2$deOHino (500 nM) remain consistent over the course of the experiment. N=3. (E) Hinokitiol (500 nM) promotes transport in shDMT1 Caco-2 monolayers at a range of pHs found throughout the duodenum. N=3. (F and G) In contrast to hinokitiol, the iron chelators deferiprone, PIH, SIH, and deferoxamine do not simultaneously restore (F) uptake into or (G) transcellular transport across DMT1-deficient Caco-2 monolayers under identical conditions (pH=5.5 apical, pH=7.4 basolateral). Dotted line represents shControl levels. While a slight increase in transport was observed in SIH treated cells, reduced uptake was observed, consistent with paracellular, and not transcellular, iron transport. Concentrations used for each small molecule were 0, 0.01, 0.1, 1, and 10 μM. N=3. (A, C-G) NS, not significant; * P≤0.05; Graphs depict means±SEM.

FIGS. 23A-23F show hinokitiol has minor effects in normal systems. (A) Transepithelial iron transport in shControl Caco-2 monolayers treated with DMSO or hinokitiol (500 nM). N=3. (B) Relative shControl MEL cell populations positively stained with o-dianisidine after DMSO induction in the presence or absence of hinokitiol (1 µM). N =12-48. (C) Iron release from wild type J774 macrophages in the presence or absence of hinokitiol (5 µM). N=6-18. (D) Changes in Caco-2 transport relative to DMSO control upon hinokitiol addition to DMT1-deficient and shControl monolayers. N=3. (E) Changes in o-dianisidine staining relative to DMSO control upon hinokitiol addition to Mfrn1-deficient and shControl MEL cells induced for differentiation. N=6-48. (F) Changes in iron release relative to DMSO control upon hinokitiol addition to FPN1-deficient and wild type J774 cells. N=6-20. (A-F) NS, not significant;  P≤0.01; ** P≤0.0001; Graphs depict means±SEM.

FIGS. 24A-24E show studies in animals missing iron transporting proteins. (A) Time-dependent gut iron absorption in Belgrade (b/b) and healthy (+/+ or +/b) rats treated with vehicle, hinokitiol (1.5 mg/kg), or C$_2$deOHino (1.5 mg/kg). N=4-7. (B) Increased rates of gut absorption in hinokitiol-treated (1.5 mg/kg) FPN1-deficient flatiron mice was observed after 2 hours relative to vehicle-treated mice. N=4. (C) Time-dependent gut absorption of $^{59}$Fe in wild type (+/+) mice in the presence or absence of hinokitiol (1.5 mg/kg). N=6-8. (D) Morpholino-mediated knockdown of steady-state Dmt1 mRNA in Tg(globinLCR:eGFP) fish as determined by semi-quantitative RT-PCR with β-actin as a loading control. (E) Hinokitiol (1 µM) and C$_2$deOHino (1 µM) do not promote hemoglobinization in Alas2-deficient sauternes zebrafish from a heterozygous cross of +/sau fish 72 hpf after 48 hours of small molecule treatment. (A-C) NS, not significant; * P≤0.05; Graphs depict means ±SEM. (E) Graph depicts weighted mean±SEM.

FIGS. 26A-26E show the results of acute injection of Hinokitiol in flatiron mice. Wild-type (+/+) and I (ffe/+) mice were administered hinokitiol by IP injection and were sacrificed after 4 h to measure iron content. (A) presents means f SEM (n=48/group). (B)-(E) present means±SEM (n=2/group). * P≤0.05,  P≤0.005, and * P≤0.001.

DETAILED DESCRIPTION OF THE INVENTION

Figure 1A:
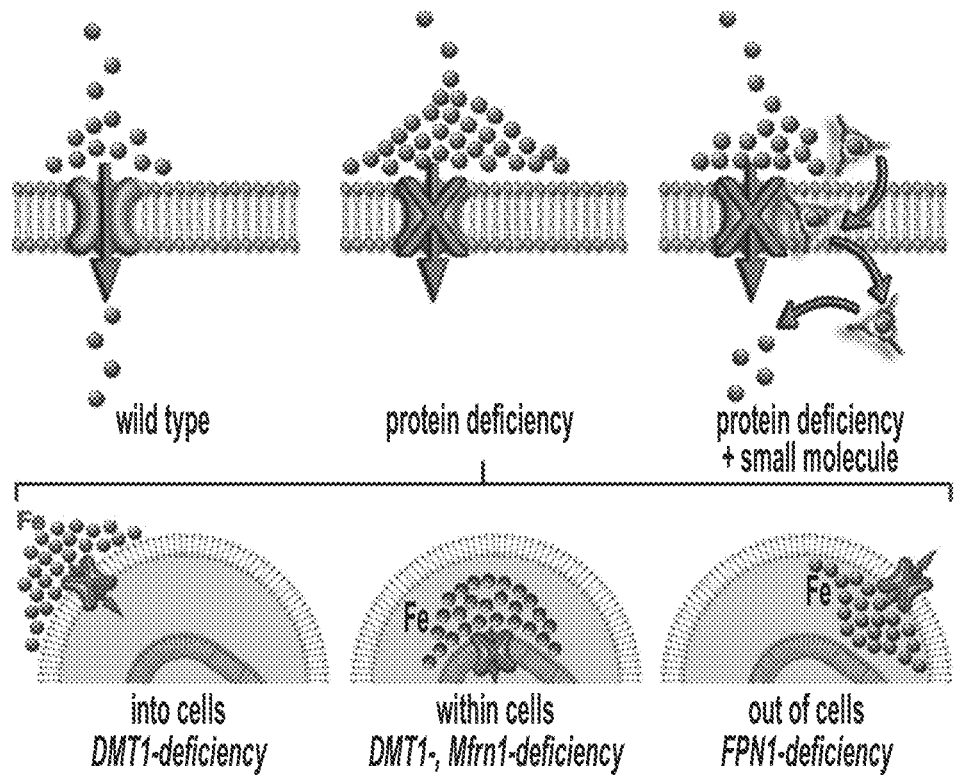
FIGS. 1A-1G show restoring physiology to iron transporter-deficient organisms. (A) A small molecule that autonomously performs transmembrane iron transport is hypothesized to harness local ion gradients of the labile iron pool that selectively accumulate in the setting of missing protein iron transporters. Brown spheres represent labile iron, which includes both ionic iron and iron weakly bound to small molecules such as citrate. (B) Structures of hinokitiol (Hino) and the transport-inactive derivative C2-deoxy hinokitiol (C2deOHino). (C) Disc diffusion with hinokitiol of fet3Δftr1Δ cells streaked on a low iron SD-agar plate containing 10 μM $FeCl_3$ restored yeast cell growth at intermediate concentrations of small molecule. (D) In the absence of hinokitiol, reduced fet3Δftr1Δ yeast cell growth was observed on low iron SD-agar plates containing 10 μM $FeCl_3$ by serial 10-fold dilution plating (from $OD_{600}$=1.0). Under identical conditions, restored cell growth was observed on the same low iron SD-agar plates containing 10 μM hinokitiol. (E) Yeast cell growth in liquid SD media containing 10 μM $FeCl_3$ in the absence or presence of 10 μM hinokitiol. N=3. (F) Hinokitiol restored growth of fet3Δftr1Δ yeast while C2deOHino did not. N=3. (G) Hinokitiol increases $^{55}$Fe influx into fet3Δftr1Δ yeast while C2deOHino does not. N=3. (E-G) NS, not significant; **** P≤0.0001; Graphs depict means±SEM.

Multiple human diseases ensue from a hereditary or acquired deficiency of iron-transporting protein function that diminishes transmembrane iron flux in distinct sites and directions. Whilst other iron-transport proteins remain active, labile iron gradients build up across the corresponding protein-deficient membranes. Certain chemical compounds can harness such gradients to restore iron transport into, within, and/or out of cells (see, e.g., Example 1) and thus may be useful in the treatment of conditions associated with deficiencies in passive ion-transport proteins, such as anemias, cystic fibrosis, and arrhythmias, as well as neurological, skeletal muscle, endocrine, and renal disorders.

The same compound promotes gut iron absorption in DMT1-deficient rats and ferroportin-deficient mice, as well as hemoglobinization in DMT1- and mitoferrin-deficient zebrafish. These findings illuminate a general mechanistic framework for small molecule-mediated site- and direction-selective restoration of iron transport. They also suggest small molecules that partially mimic the function of missing protein transporters of iron, and possibly other ions, may have potential in treating human diseases. Accordingly, provided herein, are compounds (namely analogues of hinokitiol), methods for preparing the same, and pharmaceutical compounds thereof for use in treating iron-related diseases.

Definitions

As used herein the term "physiological conditions" refers to temperature, pH, ionic strength, viscosity, and like biochemical parameters which are compatible with a viable organism, and/or which typically exist intracellularly in a viable mammalian cell.

The term "prodrug" as used herein encompasses compounds that, under physiological conditions, are converted into therapeutically active agents. A common method for making a prodrug is to include selected moieties that are hydrolyzed under physiological conditions to reveal the desired molecule. In other embodiments, the prodrug is converted by an enzymatic activity of the host animal.

The phrase "pharmaceutically acceptable excipient" or "pharmaceutically acceptable carrier" as used herein means a pharmaceutically acceptable material, composition or vehicle, such as a liquid or solid filler, diluent, excipient, solvent or encapsulating material, involved in carrying or transporting the subject chemical from one organ or portion of the body, to another organ or portion of the body. Each carrier must be "acceptable" in the sense of being compatible with the other ingredients of the formulation, not injurious to the patient, and substantially non-pyrogenic. Some examples of materials which can serve as pharmaceutically acceptable carriers include: (1) sugars, such as lactose, glucose, and sucrose; (2) starches, such as corn starch and potato starch; (3) cellulose, and its derivatives, such as sodium carboxymethyl cellulose, ethyl cellulose, and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil, and soybean oil; (10) glycols, such as propylene glycol; (11) polyols, such as glycerin, sorbitol, mannitol, and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations. In certain embodiments, pharmaceutical compositions of the present invention are non-pyrogenic, i.e., do not induce significant temperature elevations when administered to a patient.

The term "pharmaceutically acceptable salts" refers to the relatively non-toxic, inorganic and organic acid addition salts of the compounds of the invention. These salts can be prepared in situ during the final isolation and purification of the compound(s), or by separately reacting the purified compound(s) in its free base form with a suitable organic or inorganic acid, and isolating the salt thus formed. Representative salts include the hydrobromide, hydrochloride, sulfate, bisulfate, phosphate, nitrate, acetate, valerate, oleate, palmitate, stearate, laurate, benzoate, lactate, phosphate, tosylate, citrate, maleate, fumarate, succinate, tartrate, naphthylate, mesylate, glucoheptonate, lactobionate, and laurylsulphonate salts, and the like. See, for example, Berge et al. (1977) "Pharmaceutical Salts", J. Pharm. Sci. 66:1-19.

In other cases, the compounds useful in the methods of the present invention may contain one or more acidic functional groups and, thus, are capable of forming pharmaceutically acceptable salts with pharmaceutically acceptable bases. The term "pharmaceutically acceptable salts" in these instances refers to the relatively non-toxic inorganic and organic base addition salts of a compound of the invention. These salts can likewise be prepared in situ during the final isolation and purification of the compound(s), or by separately reacting the purified compound(s) in its free acid form with a suitable base, such as the hydroxide, carbonate, or bicarbonate of a pharmaceutically acceptable metal cation, with ammonia, or with a pharmaceutically acceptable organic primary, secondary, or tertiary amine. Representative alkali or alkaline earth salts include the lithium, sodium, potassium, calcium, magnesium, and aluminum salts, and the like. Representative organic amines useful for the formation of base addition salts include ethylamine, diethylamine, ethylenediamine, ethanolamine, diethanolamine, piperazine, and the like (see, for example, Berge et al., supra).

A "therapeutically effective amount" of a compound with respect to use in treatment, refers to an amount of the compound in a preparation which, when administered as part of a desired dosage regimen (to a mammal, preferably a human) alleviates a symptom, ameliorates a condition, or slows the onset of disease conditions according to clinically acceptable standards for the disorder or condition to be treated or the cosmetic purpose, e.g., at a reasonable benefit/risk ratio applicable to any medical treatment.

The term "prophylactic or therapeutic" treatment is art-recognized and includes administration to the host of one or more of the subject compositions. If it is administered prior to clinical manifestation of the unwanted condition (e.g., disease or other unwanted state of the host animal) then the treatment is prophylactic, (i.e., it protects the host against developing the unwanted condition), whereas if it is administered after manifestation of the unwanted condition, the treatment is therapeutic, (i.e., it is intended to diminish, ameliorate, or stabilize the existing unwanted condition or side effects thereof).

The pharmacophores used in the present invention are effective for the usual purposes for which the corresponding drugs are effective, and, in certain embodiments, have superior efficacy because of the ability, inherent in the azido-sugar targeting moiety, to transport the drug to the desired cell where it is of particular benefit.

The preferred therapeutic agents for use in the present embodiments are cytotoxic drugs, such as those which are used for cancer therapy. Such drugs include, in general, alkylating agents, antimetabolites, anti-tumor antibiotics such as anthracyclines, topoisomerase inhibitors, mitotic inhibitors, and corticosteroids.

One skilled in the art may make chemical modifications to the desired compound in order to make reactions of that compound more convenient for purposes of preparing conjugates of the invention.

Certain compounds of the present invention may exist in particular geometric or stereoisomeric forms. The present invention contemplates all such compounds, including cis- and trans-isomers, R- and S-enantiomers, diastereomers, (D)-isomers, (L)-isomers, the racemic mixtures thereof, and other mixtures thereof, as falling within the scope of the invention. Additional asymmetric carbon atoms may be present in a substituent such as an alkyl group. All such isomers, as well as mixtures thereof, are intended to be included in this invention.

If, for instance, a particular enantiomer of a compound of the present invention is desired, it may be prepared by asymmetric synthesis or by derivation with a chiral auxiliary, where the resulting diastereomeric mixture is separated and the auxiliary group cleaved to provide the pure desired enantiomer. Alternatively, where the molecule contains a basic functional group, such as amino, or an acidic functional group, such as carboxyl, diastereomeric salts are formed with an appropriate optically-active acid or base, followed by resolution of the diastereomers thus formed by fractional crystallization or chromatographic means well known in the art, and subsequent recovery of the pure enantiomer.

An aliphatic chain comprises the classes of alkyl, alkenyl and alkynyl defined below. A straight aliphatic chain is limited to unbranched carbon chain moieties. As used herein, the term "aliphatic group" refers to a straight chain, branched-chain, or cyclic aliphatic hydrocarbon group and includes saturated and unsaturated aliphatic groups, such as an alkyl group, an alkenyl group, or an alkynyl group.

"Alkyl" refers to a fully saturated cyclic or acyclic, branched or unbranched carbon chain moiety having the number of carbon atoms specified, or up to 30 carbon atoms if no specification is made. For example, alkyl of 1 to 8 carbon atoms refers to moieties such as methyl, ethyl, propyl, butyl, pentyl, hexyl, heptyl, and octyl, and those moieties that are positional isomers of these moieties. Alkyl of 10 to 30 carbon atoms includes decyl, undecyl, dodecyl, tridecyl, tetradecyl, pentadecyl, hexadecyl, heptadecyl, octadecyl, nonadecyl, eicosyl, heneicosyl, docosyl, tricosyl and tetracosyl. In certain embodiments, a straight chain or branched chain alkyl has 30 or fewer carbon atoms in its backbone (e.g., $C_1$-$C_{30}$ for straight chains, C3-C30 for branched chains), and more preferably 20 or fewer.

Unless the number of carbons is otherwise specified, "lower alkyl," as used herein, means an alkyl group, as defined above, but having from one to ten carbons, more preferably from one to six carbon atoms in its backbone structure such as methyl, ethyl, n-propyl, isopropyl, n-butyl, isobutyl, sec-butyl, and tert-butyl. Likewise, "lower alkenyl" and "lower alkynyl" have similar chain lengths. Throughout the application, preferred alkyl groups are lower alkyls. In certain embodiments, a substituent designated herein as alkyl is a lower alkyl.

"Cycloalkyl" means mono- or bicyclic or bridged saturated or unsaturated (i.e., containing one or more double bonds in a non-aromatic configuration) carbocyclic rings, each having from 3 to 12 carbon atoms. Likewise, preferred cycloalkyls have from 5-12 carbon atoms in their ring structure, and more preferably have 6-10 carbons in the ring structure.

"Alkenyl" refers to any cyclic or acyclic, branched or unbranched unsaturated carbon chain moiety having the number of carbon atoms specified, or up to 26 carbon atoms if no limitation on the number of carbon atoms is specified; and having one or more double bonds in the moiety. Alkenyl of 6 to 26 carbon atoms is exemplified by hexenyl, heptenyl, octenyl, nonenyl, decenyl, undecenyl, dodenyl, tridecenyl, tetradecenyl, pentadecenyl, hexadecenyl, heptadecenyl, octadecenyl, nonadecenyl, eicosenyl, heneicosoenyl, docosenyl, tricosenyl, and tetracosenyl, in their various isomeric forms, where the unsaturated bond(s) can be located anywhere in the moiety and can have either the (Z) or the (E) configuration about the double bond(s).

"Alkynyl" refers to hydrocarbyl moieties of the scope of alkenyl, but having one or more triple bonds in the moiety.

The terms "alkoxyl" or "alkoxy" as used herein refers to an alkyl group, as defined below, having an oxygen moiety attached thereto. Representative alkoxyl groups include methoxy, ethoxy, propoxy, tert-butoxy, and the like. An "ether" is two hydrocarbons covalently linked by an oxygen. Accordingly, the substituent of an alkyl that renders that alkyl an ether is or resembles an alkoxyl, such as can be represented by one of —O-alkyl, —O— alkenyl, —O-alkynyl, —O—$(CH_2)_m$-$R^1$, where $R_1$ represents an alkenyl, aryl, cycloalkyl, a cycloalkenyl, a heterocyclyl, or a polycyclyl; and m is an integer having a value of 0 to about 10.

The term "aryl" as used herein includes 3- to 12-membered substituted or unsubstituted single-ring aromatic groups in which each atom of the ring is carbon (i.e., carbocyclic aryl) or where one or more atoms are heteroatoms (i.e., heteroaryl). Preferably, aryl groups include 5- to 12-membered rings, more preferably 6- to 10-membered rings. In certain embodiments, aryl includes ($C_6$-$C_{10}$)aryl. The term "aryl" also includes polycyclic ring systems having two or more cyclic rings in which two or more carbons are common to two adjoining rings wherein at least one of the rings is aromatic, e.g., the other cyclic rings can be cycloalkyls, cycloalkenyls, cycloalkynyls, aryls, heteroaryls, and/or heterocyclyls. Carbocyclic aryl groups include benzene, naphthalene, phenanthrene, phenol, aniline, and the like.

Heteroaryl groups include substituted or unsubstituted aromatic 3- to 12-membered ring structures, more preferably 5- to 12-membered rings, more preferably 6- to 10-membered rings, whose ring structures include one to four heteroatoms. In certain embodiments, heteroaryl includes ($C_2$-$C_9$)heteroaryl. Heteroaryl groups include, for example, pyrrole, furan, thiophene, imidazole, oxazole, thiazole, triazole, pyrazole, pyridine, pyrazine, pyridazine and pyrimidine, and the like.

The term "haloalkyl" means at least one halogen, as defined herein, appended to the parent molecular moiety through an alkyl group, as defined herein. Representative examples of haloalkyl include, but are not limited to, chloromethyl, 2-fluoroethyl, trifluoromethyl, pentafluoroethyl, and 2-chloro-3-fluoropentyl.

As used herein, the term "substituted" is contemplated to include all permissible substituents of organic compounds. In a broad aspect, the permissible substituents include acyclic and cyclic, branched and unbranched, carbocyclic and heterocyclic, aromatic and nonaromatic substituents of organic compounds. Illustrative substituents include, for example, those described herein above. The permissible substituents can be one or more and the same or different for appropriate organic compounds. For purposes of this invention, the heteroatoms such as nitrogen may have hydrogen substituents and/or any permissible substituents of organic compounds described herein which satisfy the valences of the heteroatoms. This invention is not intended to be limited in any manner by the permissible substituents of organic compounds. It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, etc.

For purposes of this invention, the chemical elements are identified in accordance with the Periodic Table of the Elements, CAS version, Handbook of Chemistry and Physics, 67th ed., 1986-87, inside cover.

Compounds of the Invention

The famed Japanese chemist Tetsuo Nozoe first isolated the tropolone monoterpenoid hinokitiol from the wood of the Taiwanese ninoki tree (*Chamaecyparis taiwanensis*) in 1936.

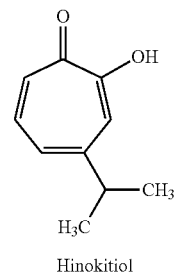

Hinokitiol

Since then, it has been found in other trees of the Cupressaceae family, although not in the Japanese hinoki. The present invention relates, in part, to a significant medical use for hinokitiol, namely overcoming irregular iron transport in animals.

Included in the present disclosure are analogues of hinokitiol, specifically compounds having a structure according to Formula (I):

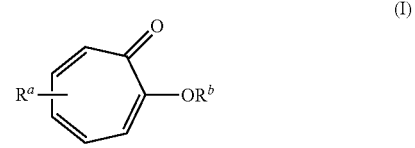

(I)

or a salt thereof; wherein $R^a$ is $C_{1-20}$-alkyl, $C_{2-20}$-alkenyl, $C_{2-20}$-alkynyl, $C_{3-9}$-cycloalkyl, aryl, or heteroaryl, each of which is unsubstituted or substituted with a substituent selected from the group consisting of halo, $NO_2$, CN, $C_{1-6}$-alkyl, $C_{1-6}$-haloalkyl, and $C_{1-6}$-alkoxy; and $R^b$ is hydrogen or methyl; provided the compound is not hinokitiol.

For example, in some embodiments, the compound of Formula (I) is selected from the group consisting of:

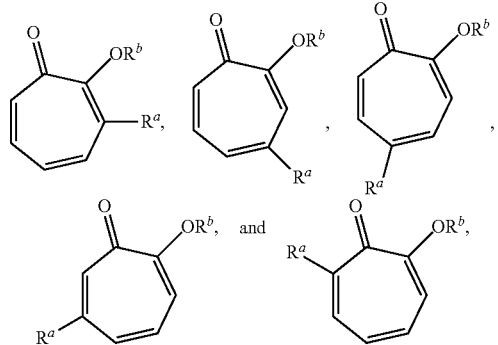

wherein $R^a$ is $C_{1-4}$-alkyl, $C_{2-4}$-alkenyl, $C_{2-4}$-alkynyl, or $C_{3-4}$-cycloalkyl; provided the compound is not hinokitiol. In some such embodiments, $R^a$ is selected from the group consisting of:

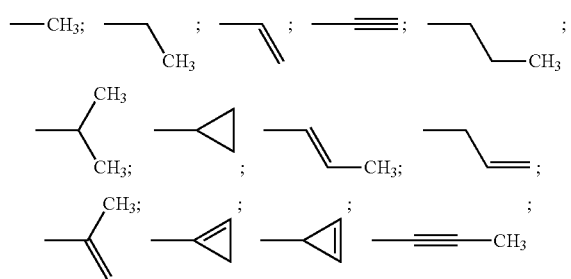
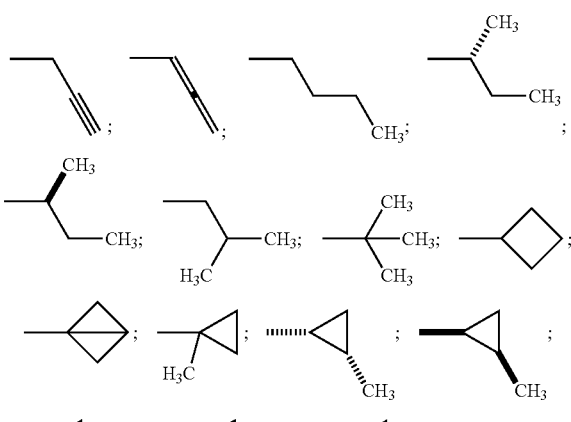
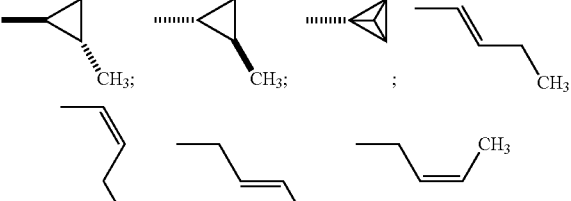
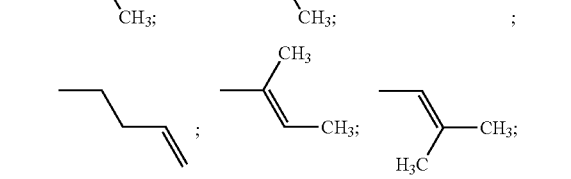
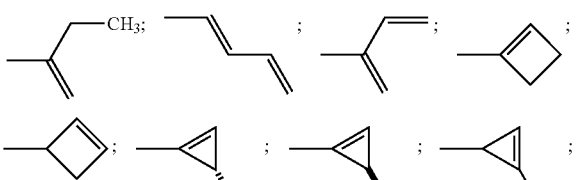
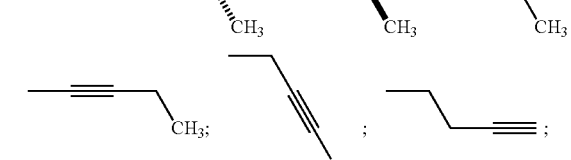
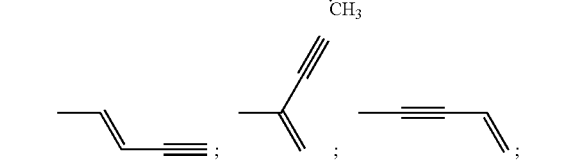
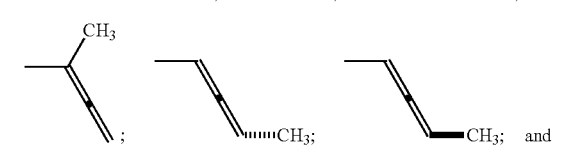

-continued

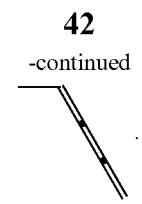

In some embodiments, provided herein are compounds having a structure according to Formula (II):

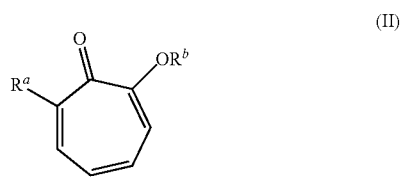

(II)

or a salt thereof.

In certain embodiments, provided herein are compounds having a structure according to Formula (IIa) or (IIb):

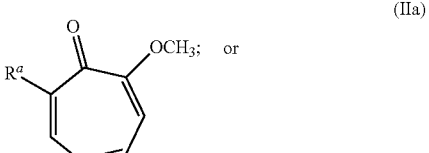

(IIa)

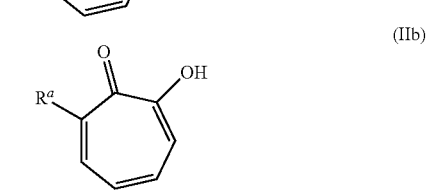

(IIb)

or a salt thereof.

In other embodiments, provided herein are compounds having a structure according to Formula (III):

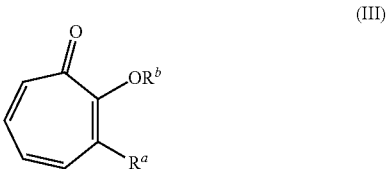

(III)

or a salt thereof.

In certain embodiments, provided herein are compounds having a structure according to Formula (IIIa) or (IIIb):

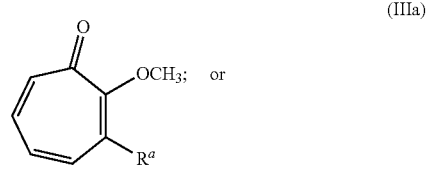

(IIIa)

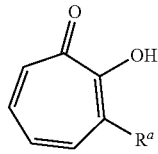
(IIIb)
or a salt thereof.
In some embodiments, $R^a$ is selected from the group consisting of:
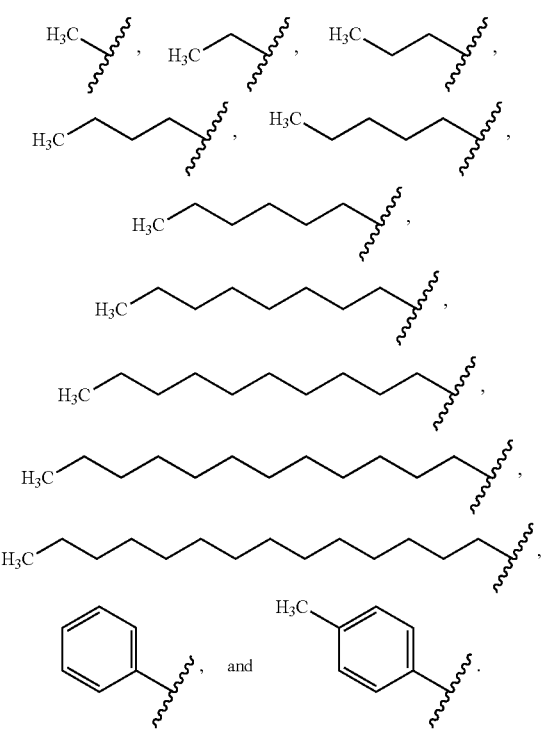
In other embodiments, $R^a$ is selected from the group consisting of
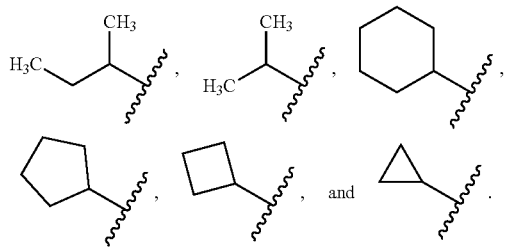
In some embodiments, the compound is selected from:
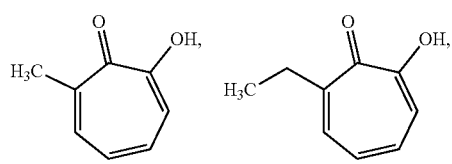
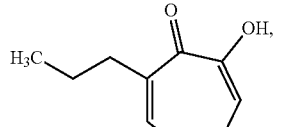
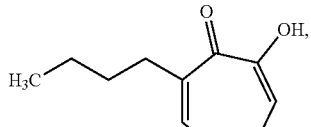
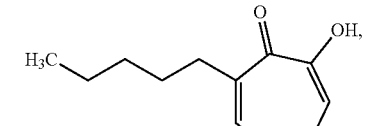
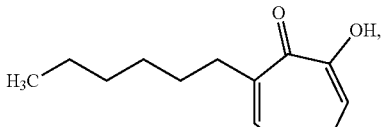
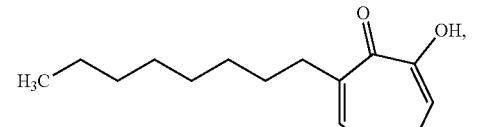
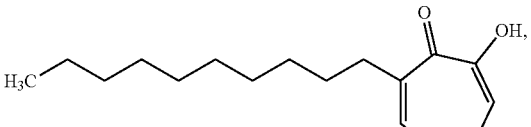
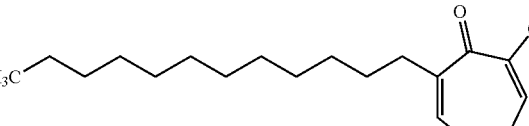
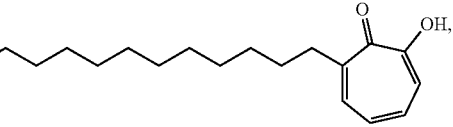
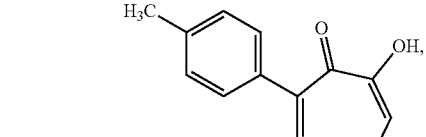
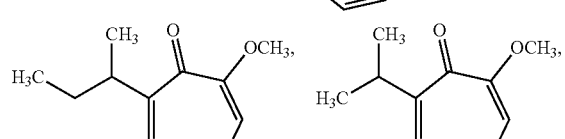
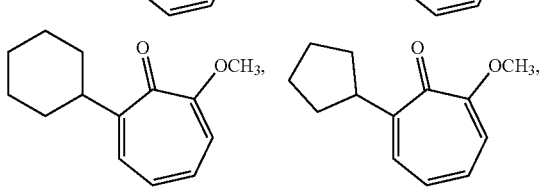

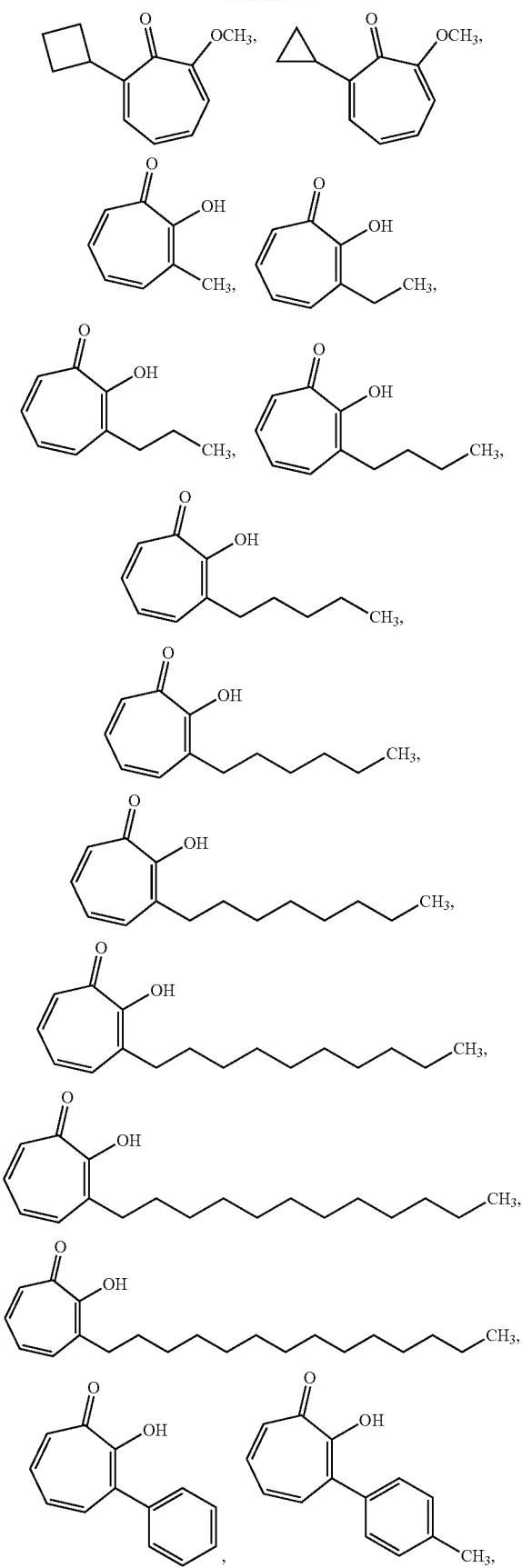
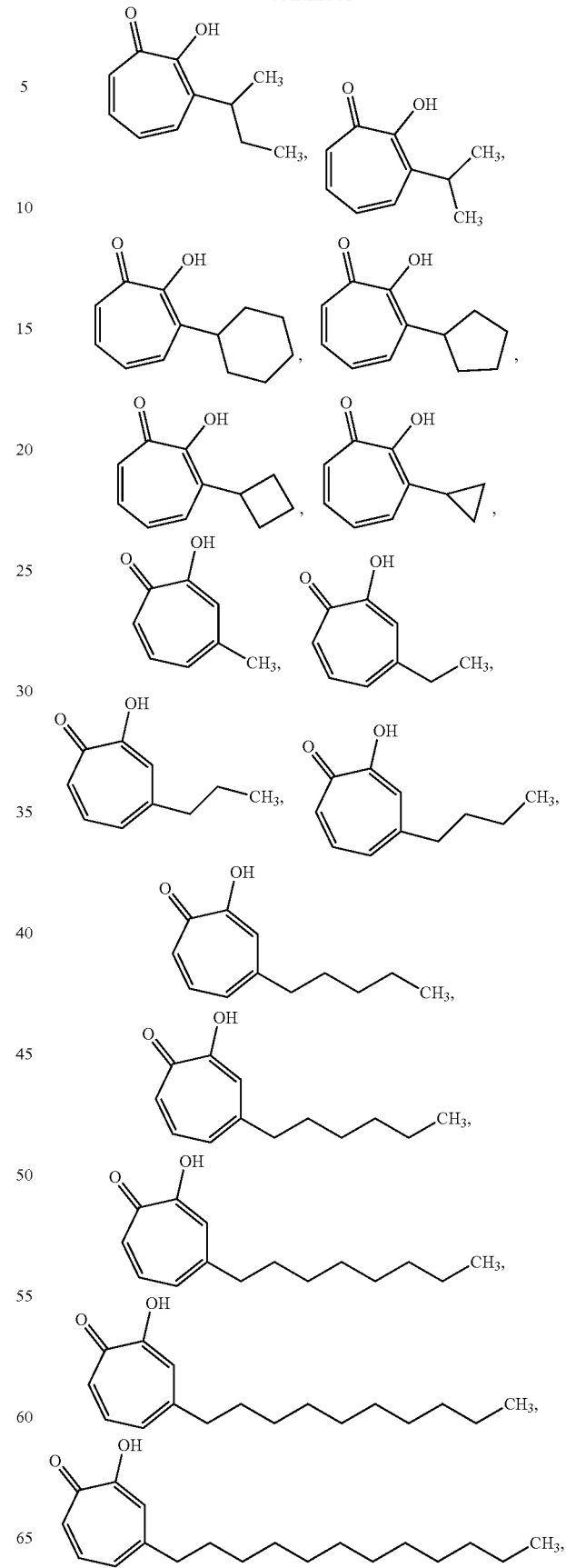

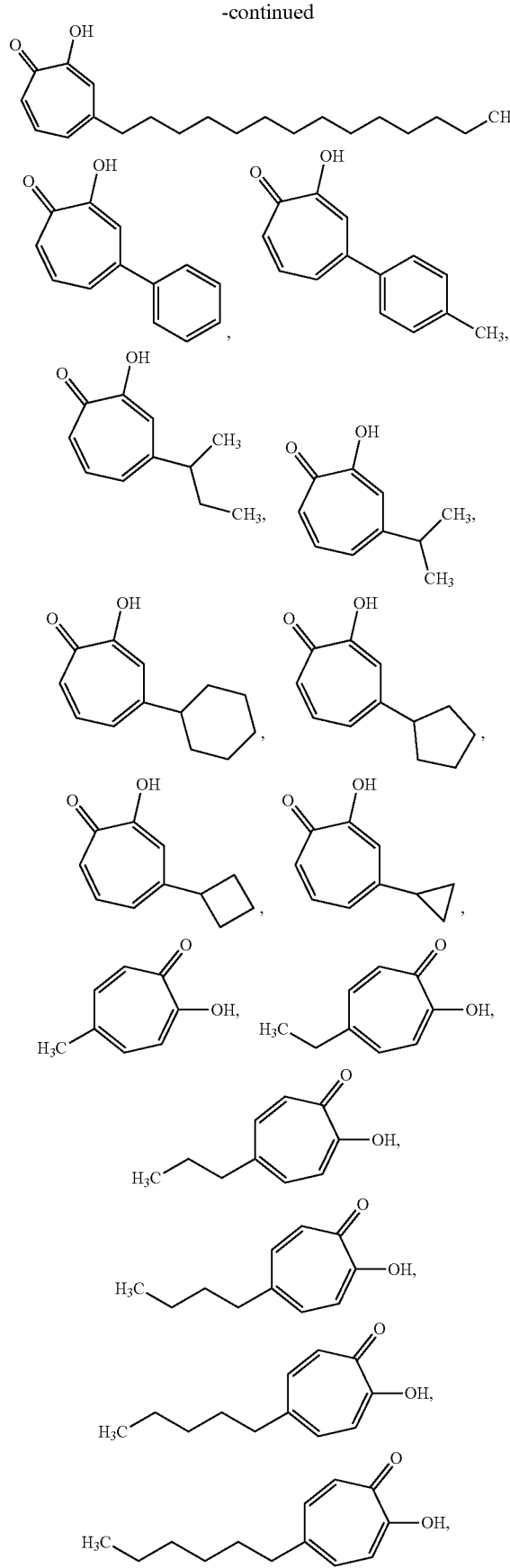
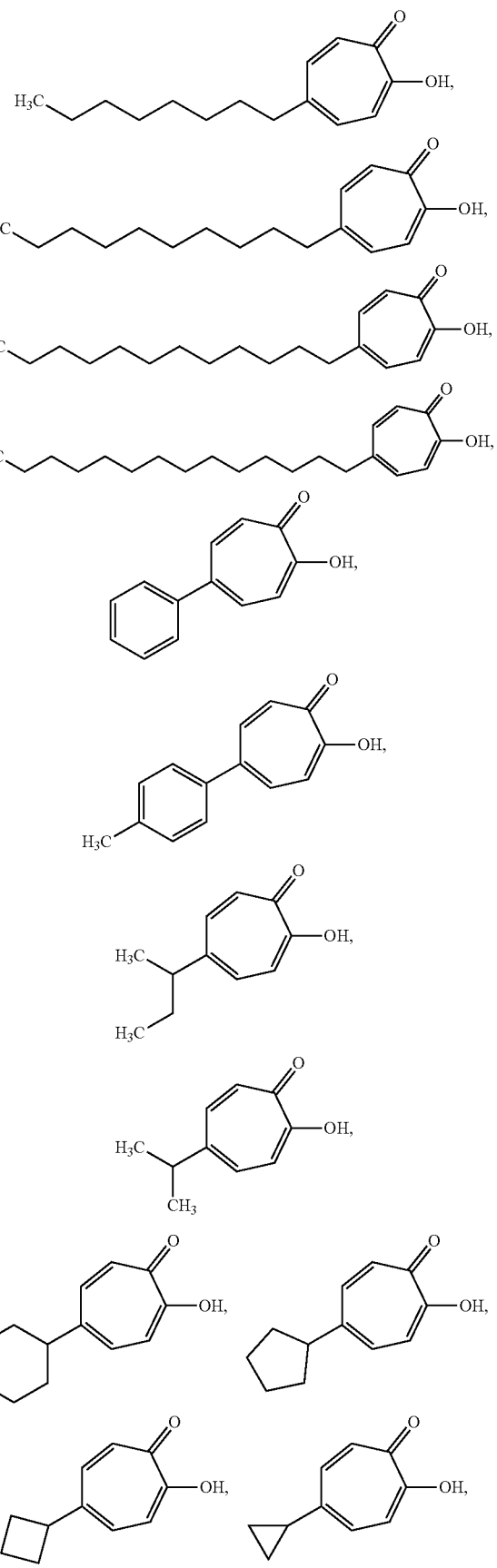

-continued
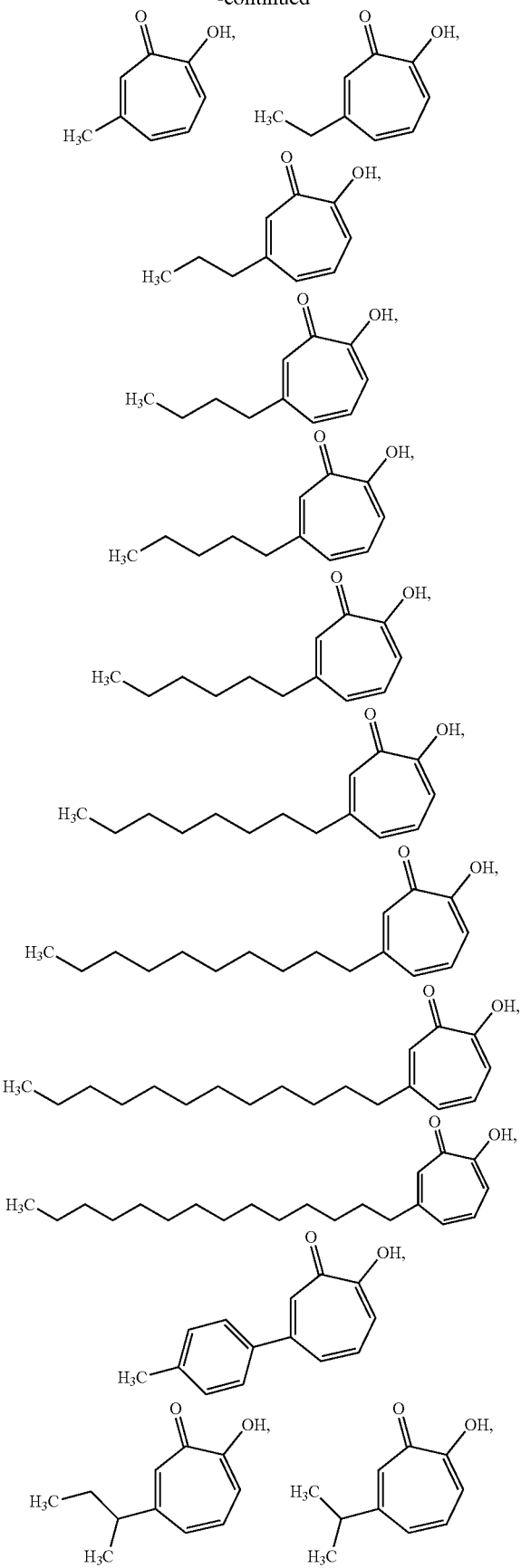
-continued
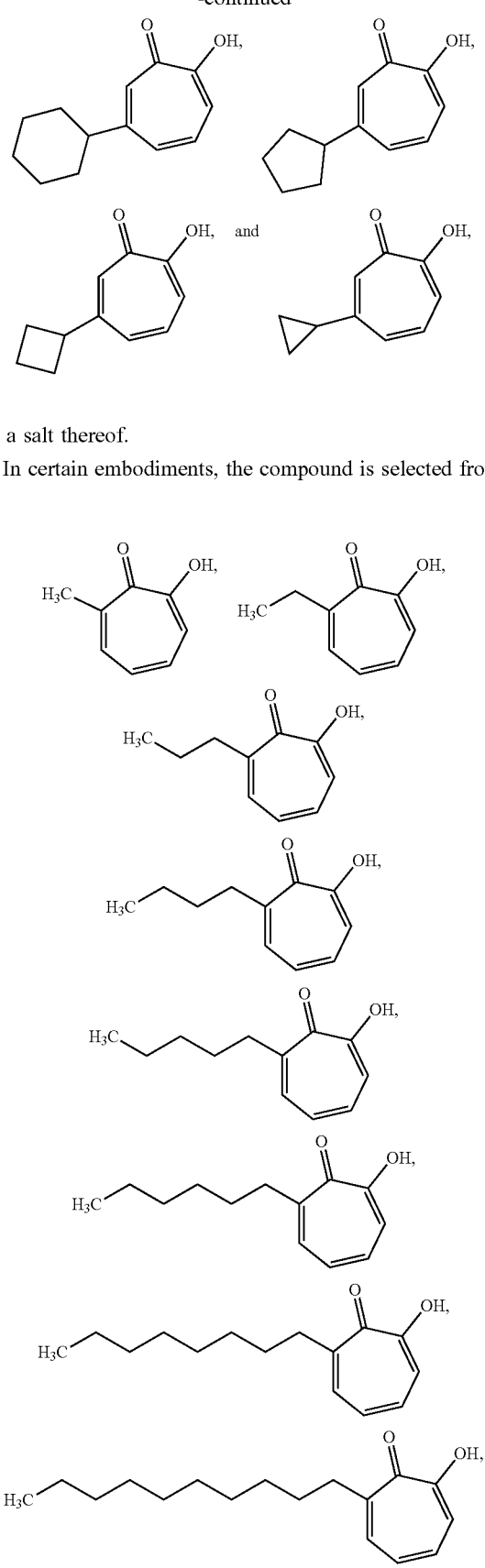
or a salt thereof.
In certain embodiments, the compound is selected from:

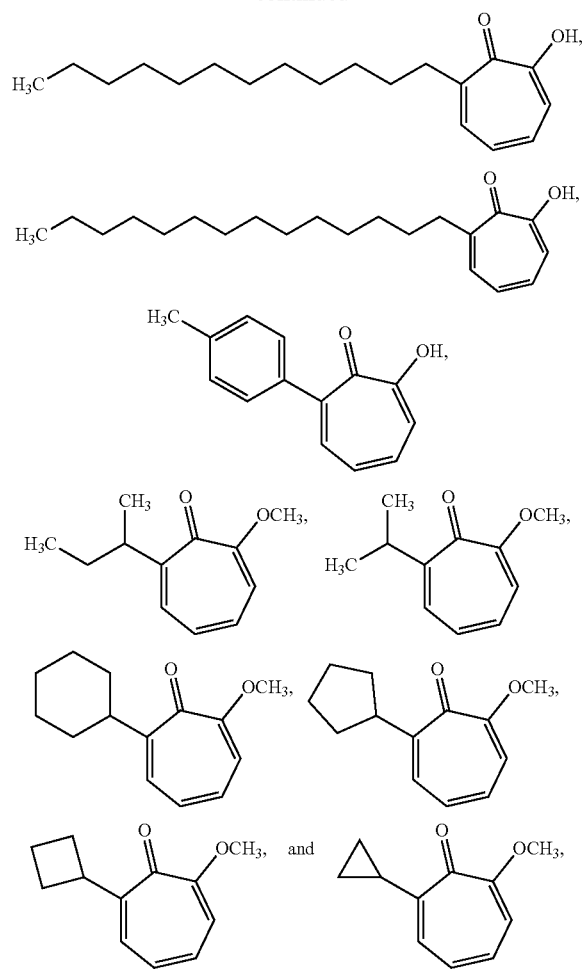
or a salt thereof.
In certain other embodiments, the compound is selected from:
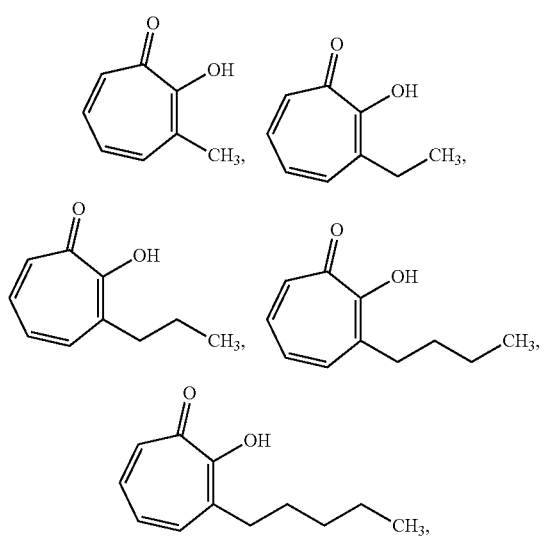
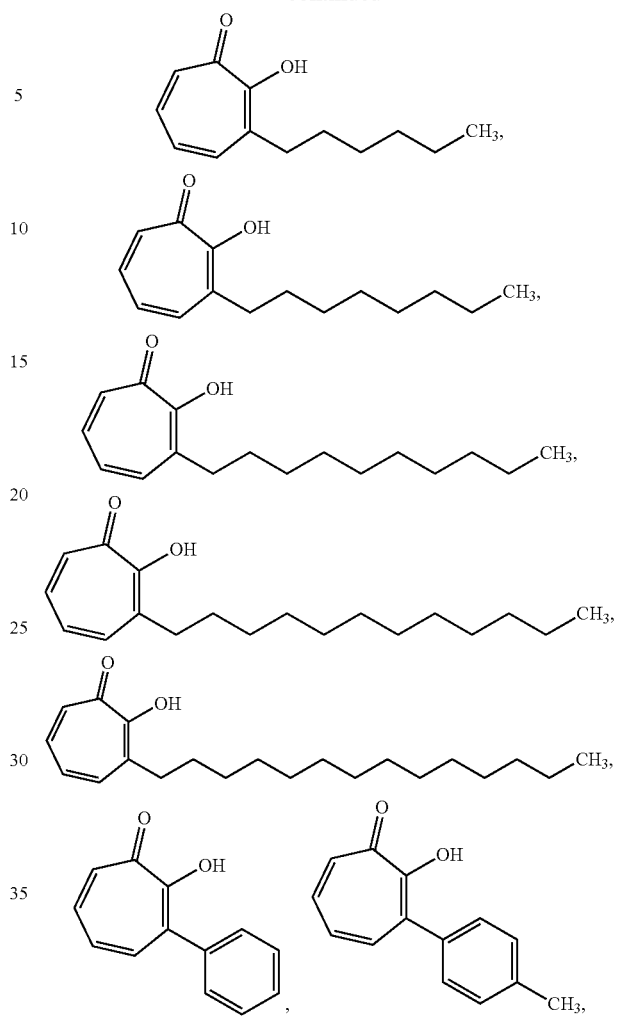
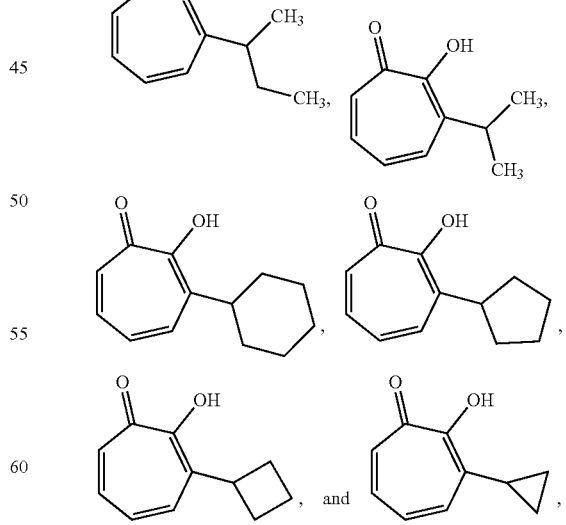
or a salt thereof.
In certain other embodiments the compound is selected from:

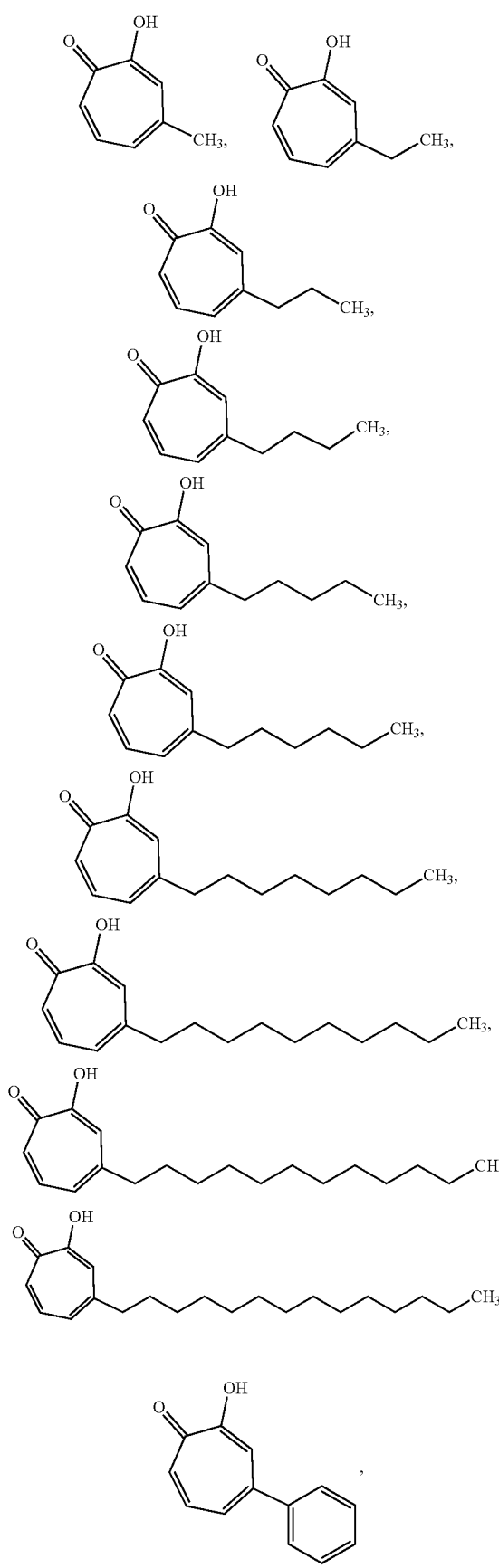
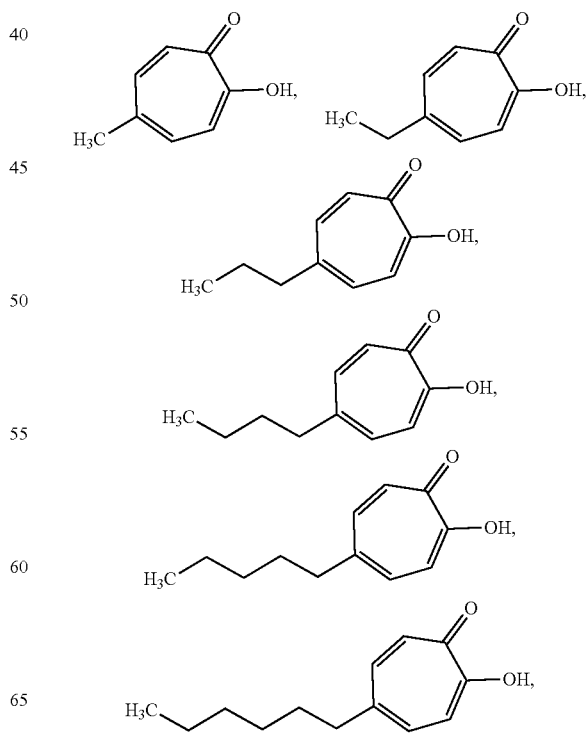
or a salt thereof.
In certain other embodiments, the compound is selected from:

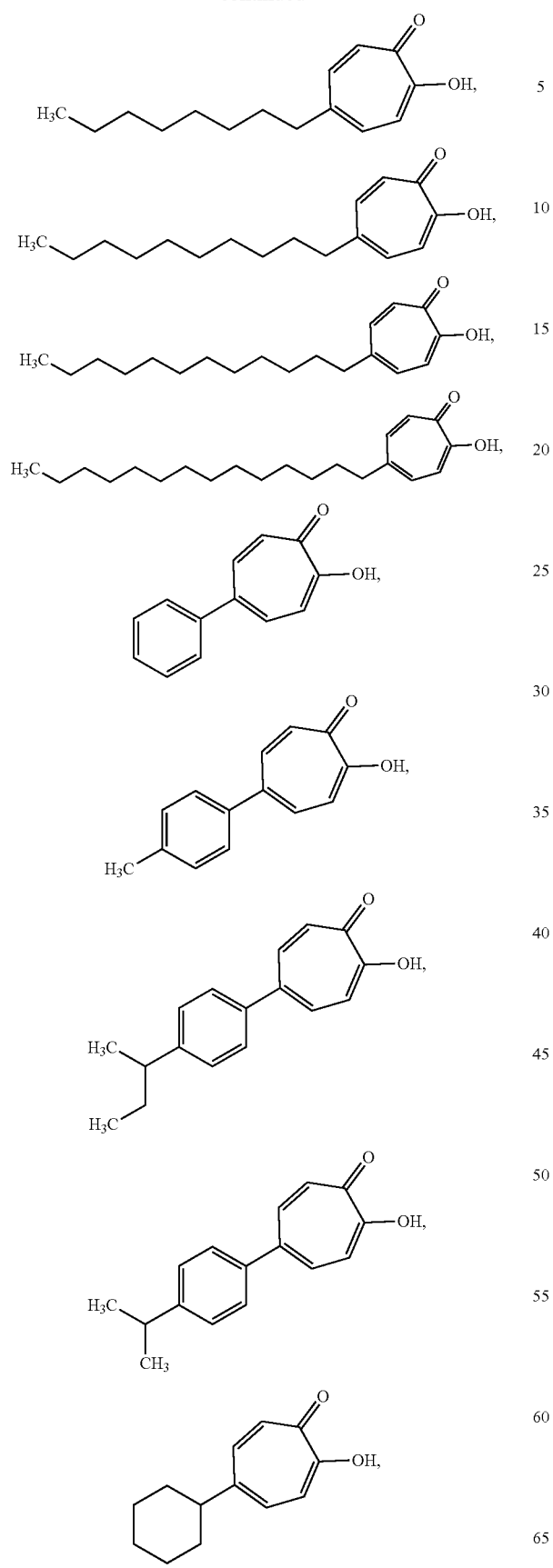
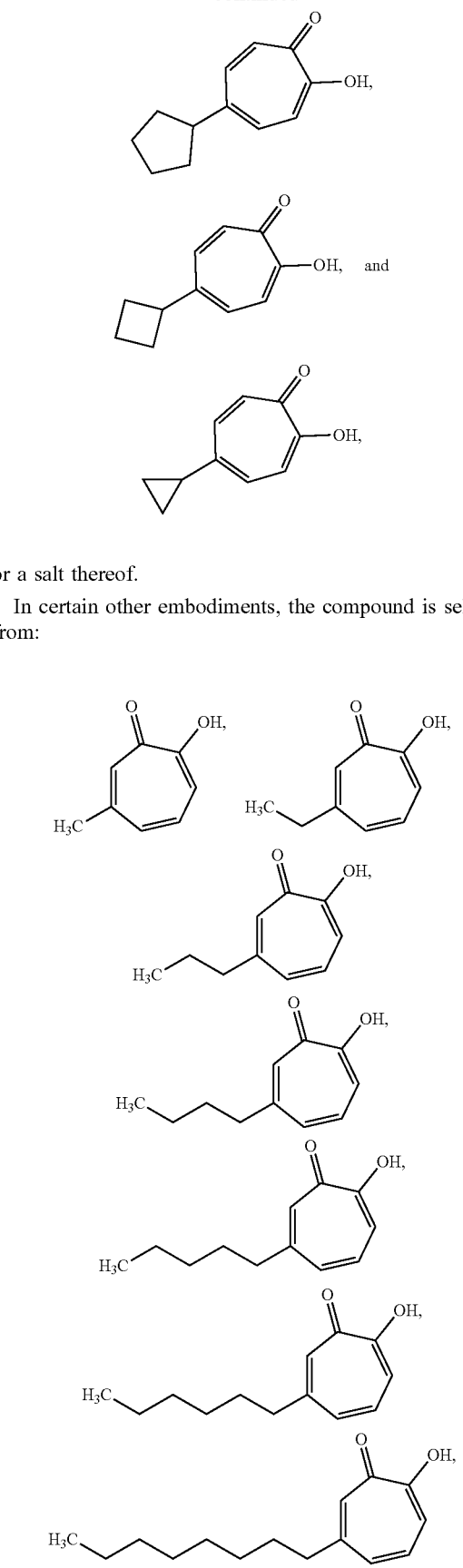
or a salt thereof.
In certain other embodiments, the compound is selected from:

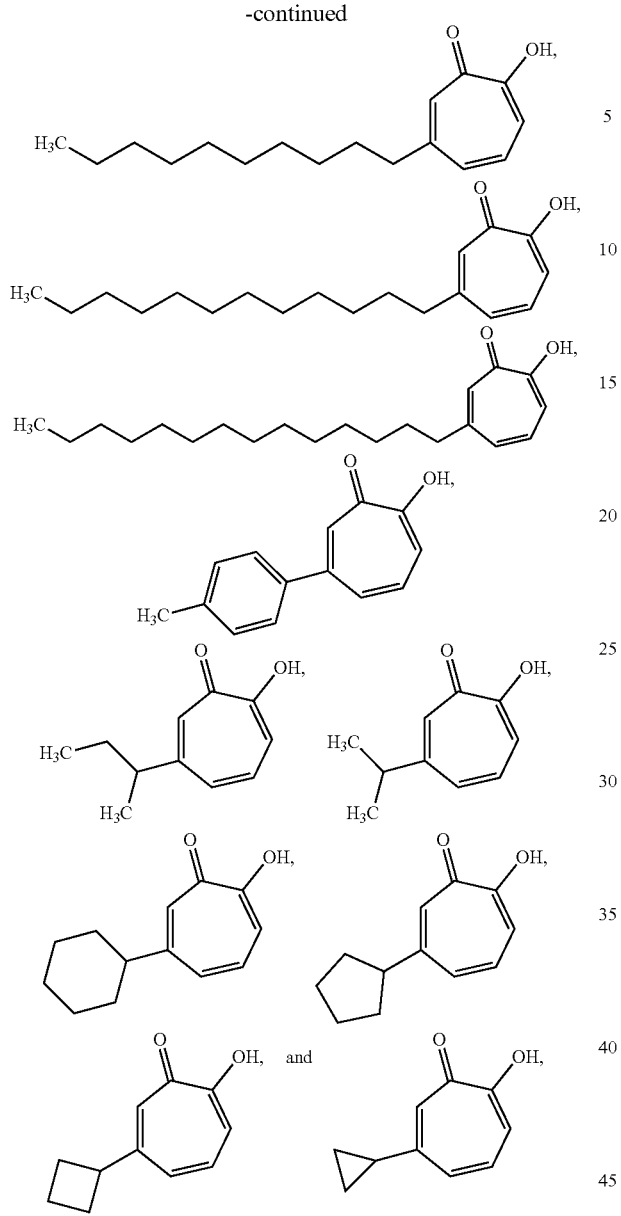
or a salt thereof.
Also provided herein are compounds selected from the group consisting of:
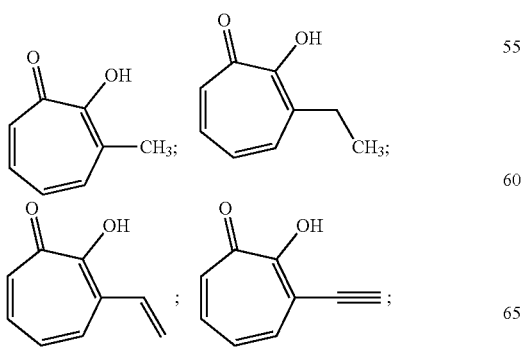
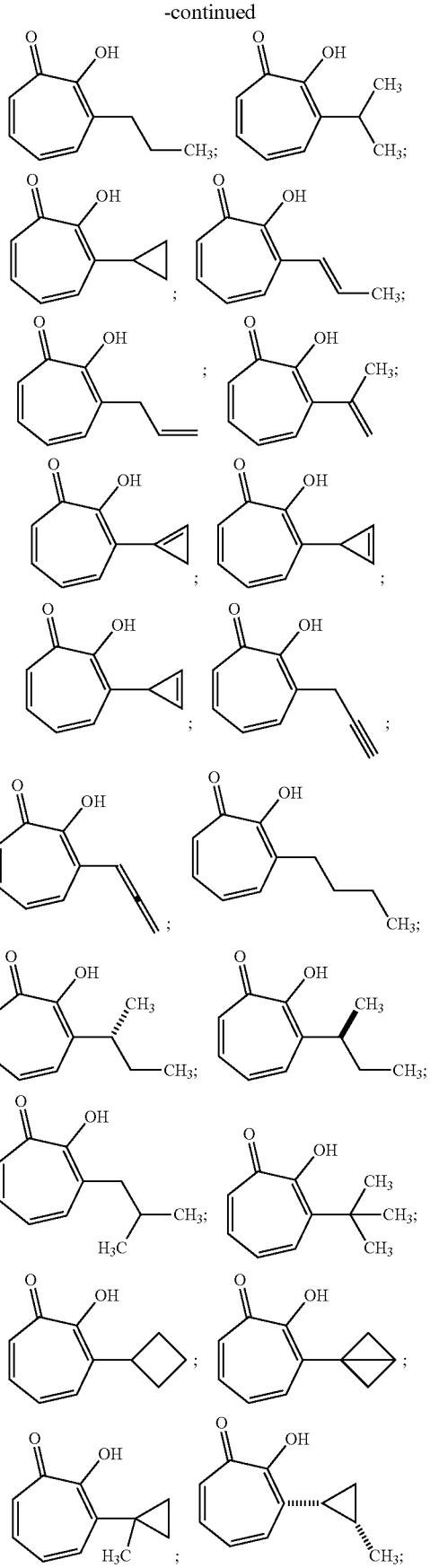

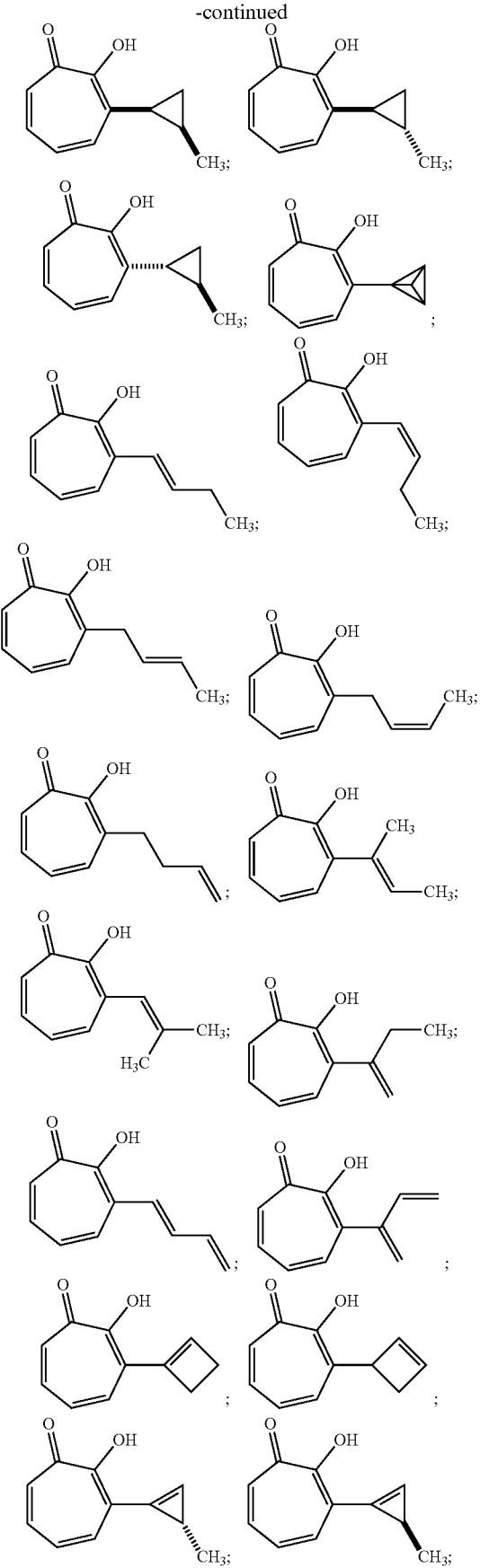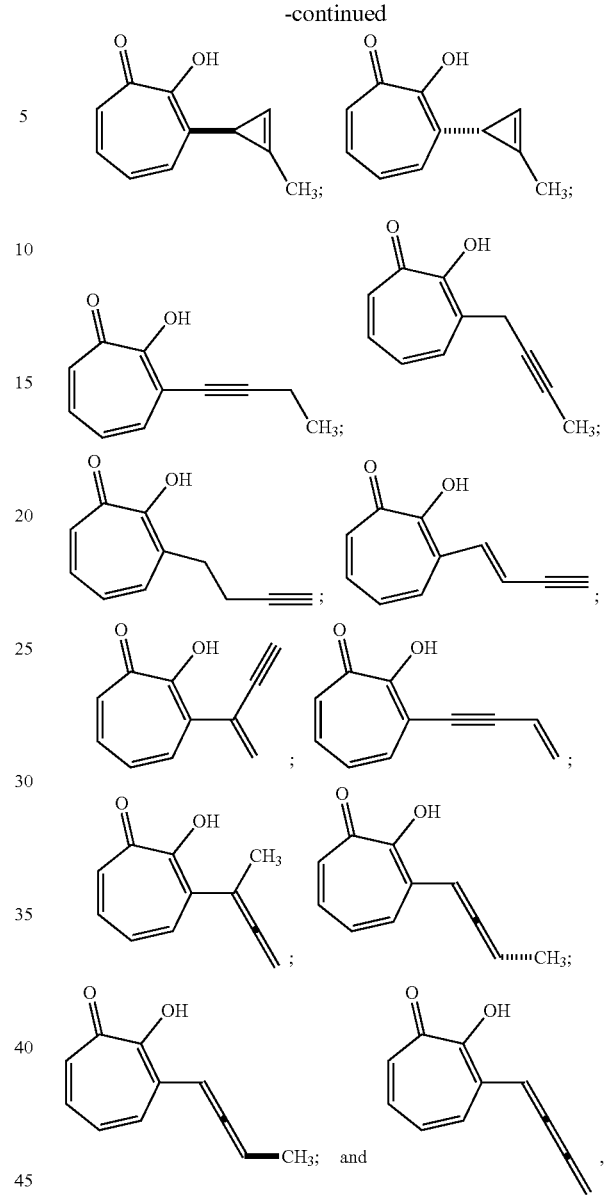
and salts thereof.
Also provided herein are compounds selected from the group consisting of:
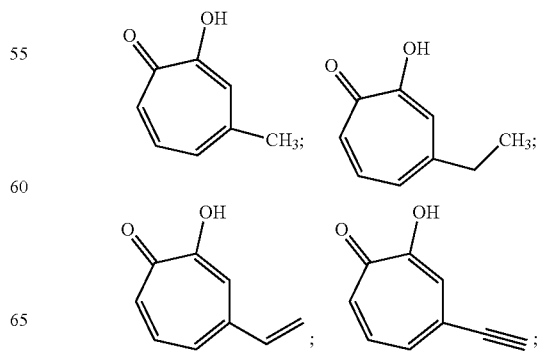

-continued
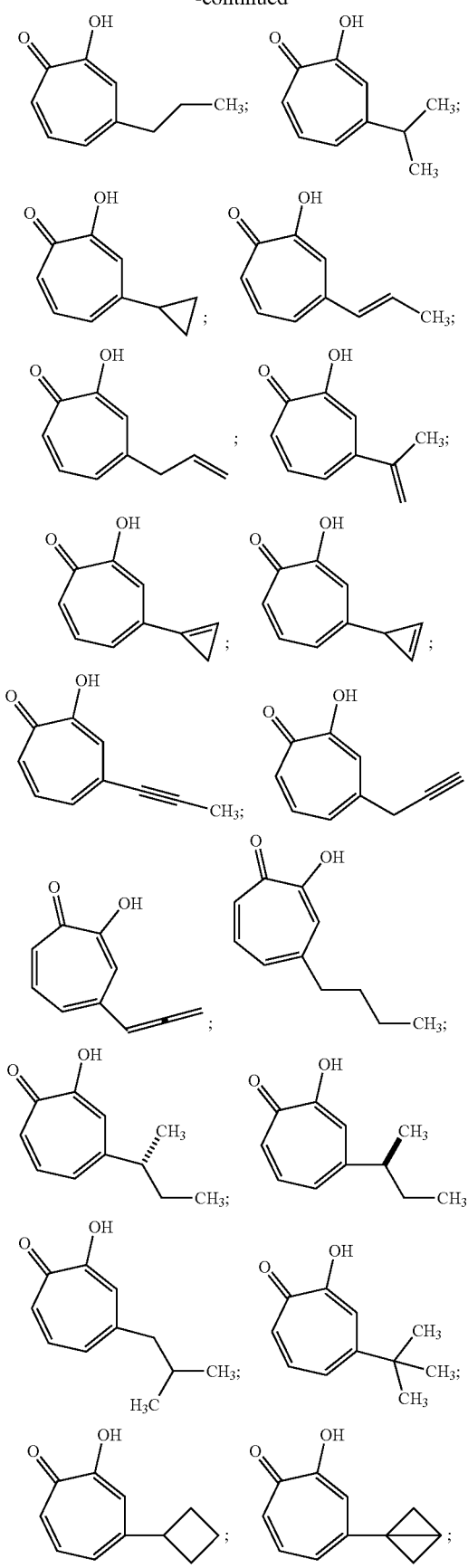
-continued
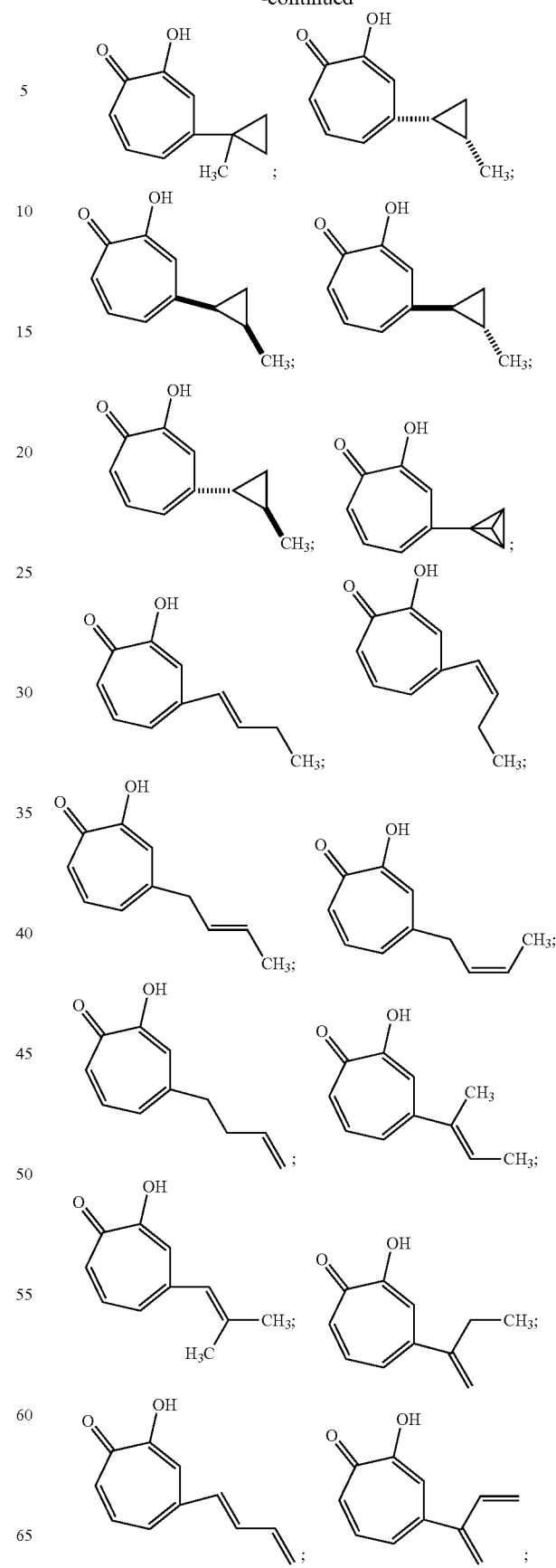

-continued
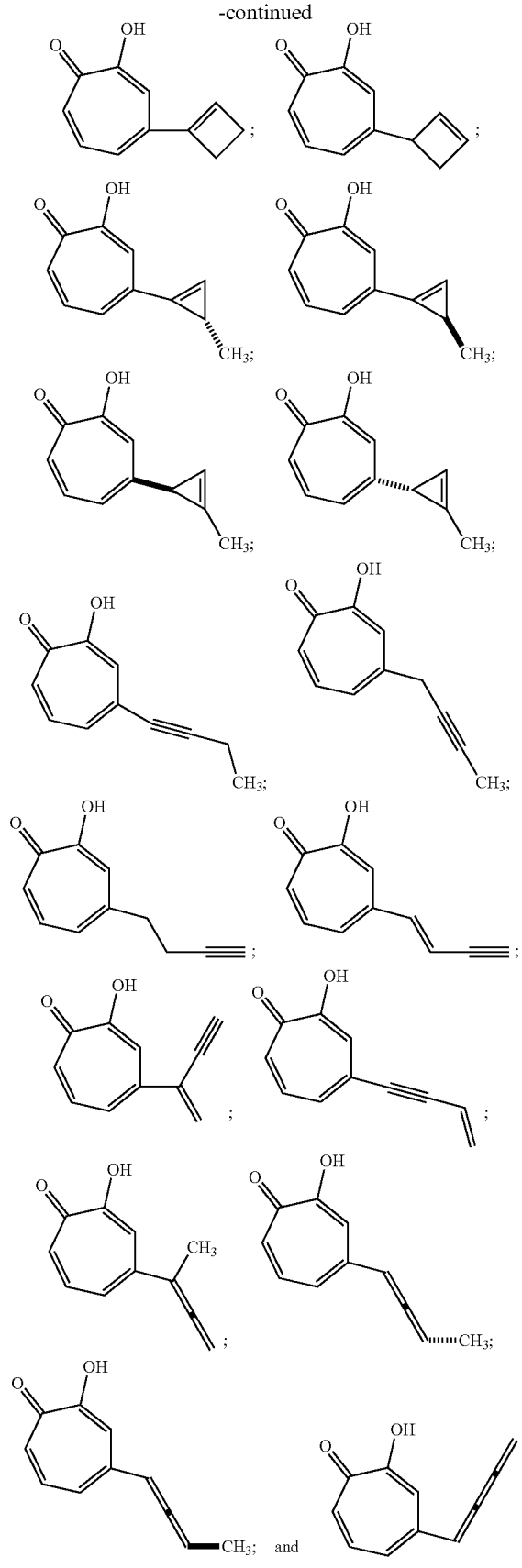
and salts thereof.
Also provided herein are compounds selected from the group consisting of:
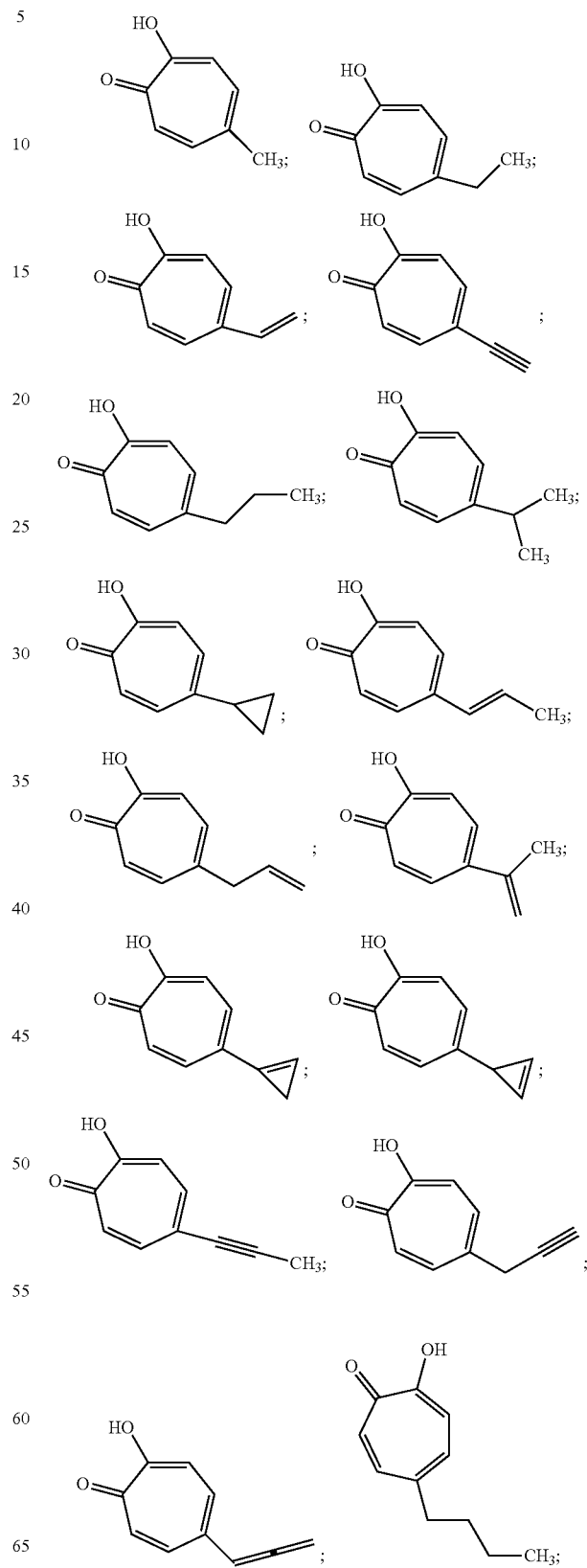

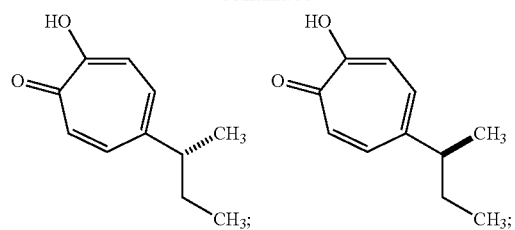
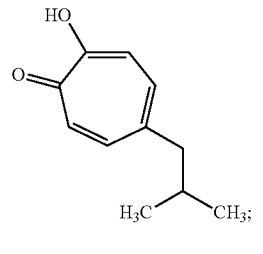
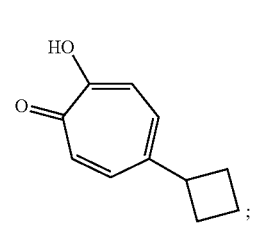
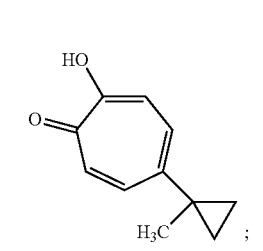
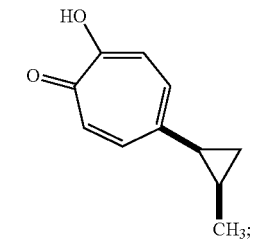
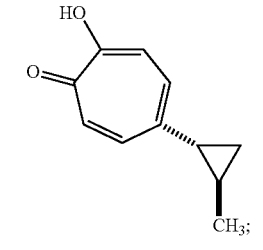
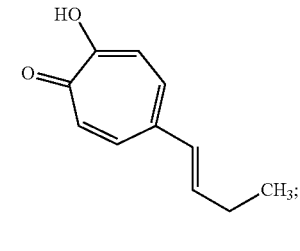
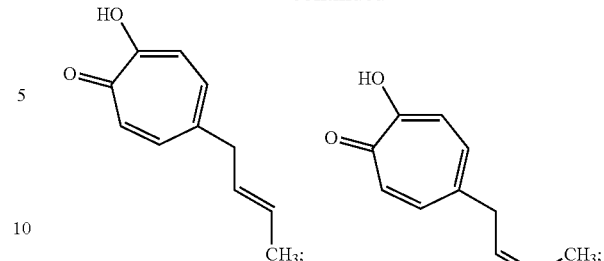
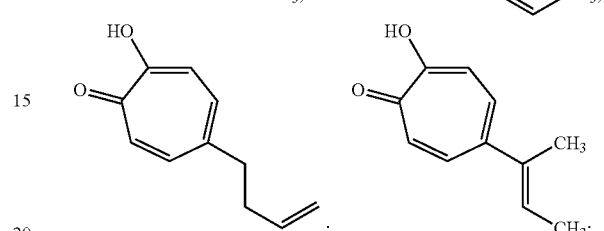
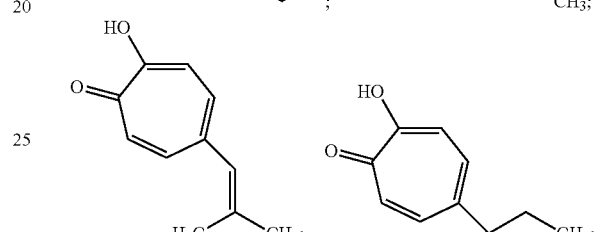
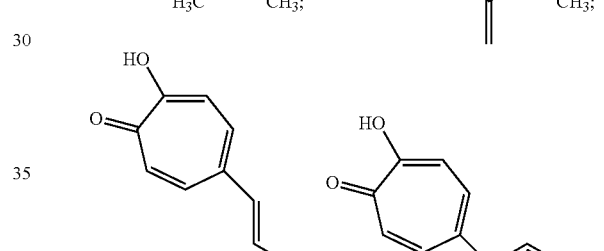
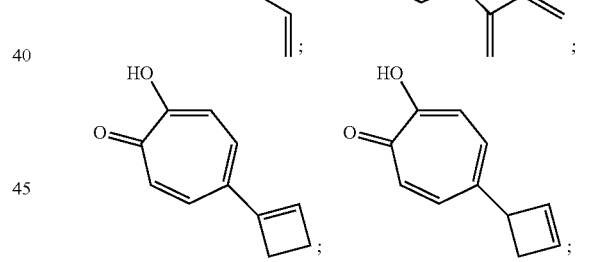
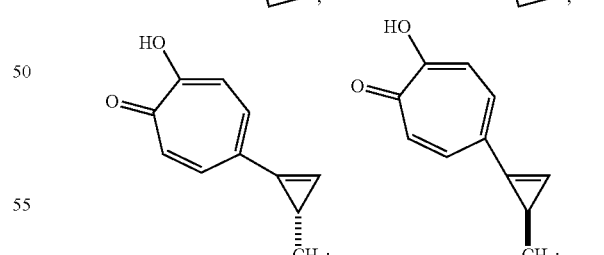
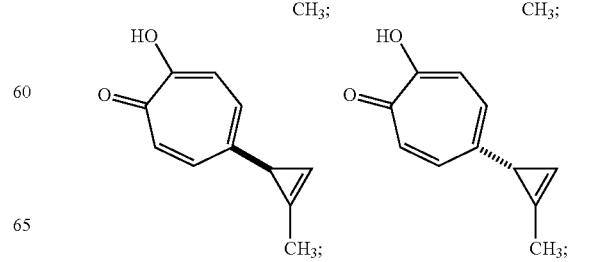

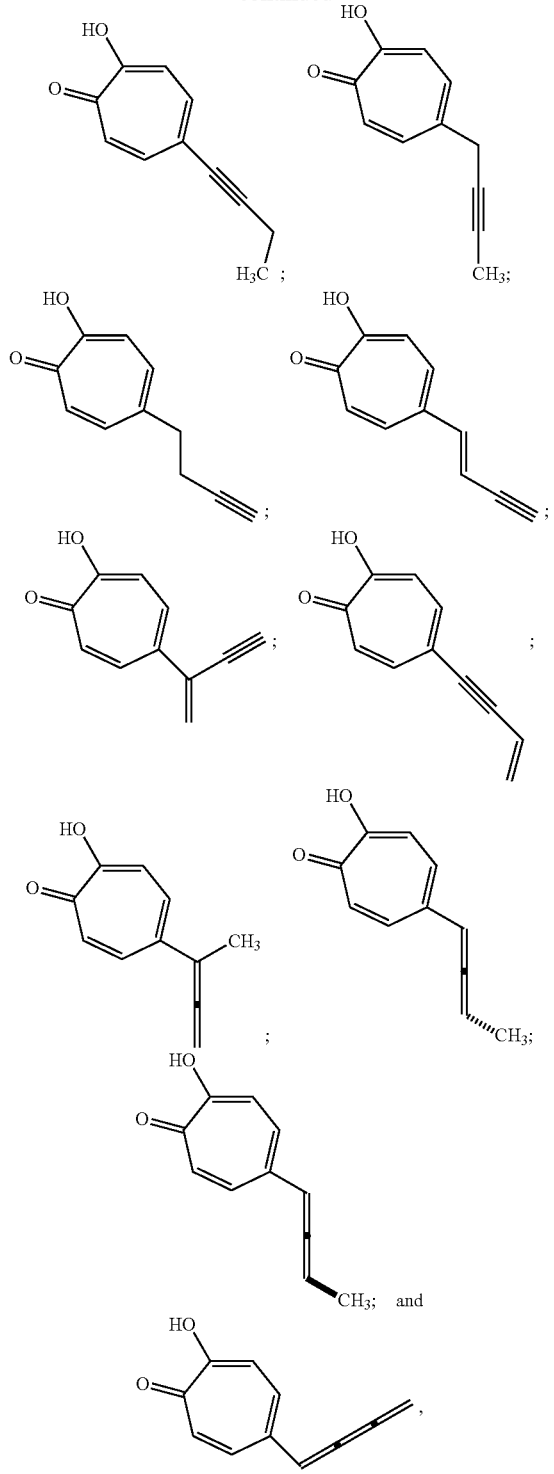

and salts thereof.

Methods of Preparing Compounds of the Inventions

Included in the present disclosure are methods of preparing compounds of the invention (i.e., compounds having a structure according to Formula (I)), described below.

Method A Provided herein is a method of preparing 6-bromo-2-methoxycyclohepta-2,4,6-trien-1-one or a salt thereof:

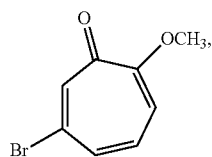

comprising the step of combining a Bronsted base and 7,7-dibromo-3-methoxybicyclo[4.1.0]hept-3-en-2-one or a salt thereof:

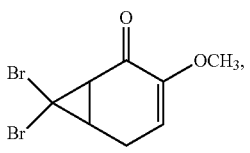 [SMILES: COC1=CCC2C(C1=O)C2(Br)Br]

thereby forming 6-bromo-2-methoxycyclohepta-2,4,6-trien-1-one or a salt thereof.

In some embodiments, the base is an inorganic base, such as a carbonate. Exemplary carbonates include, but are not limited to, potassium carbonate, sodium carbonate, cesium carbonate, calcium carbonate, and combinations thereof.

In some embodiments, the method further comprises the step of preparing 7,7-dibromo-3-methoxybicyclo[4.1.0] hept-3-en-2-one or a salt thereof:

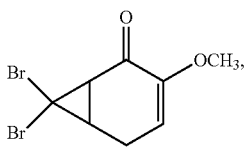 [SMILES: COC1=CCC2C(C1=O)C2(Br)Br]

combining a methylating agent and 7,7-dibromo-3-hydroxybicyclo[4.1.0]hept-3-en-2-one or a salt thereof to form a mixture:

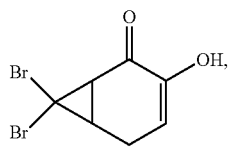 [SMILES: O=C1C(O)=CCC2C1C2(Br)Br]

thereby forming 6-bromo-2-methoxycyclohepta-2,4,6-trien-1-one or a salt thereof.

In some embodiments, the methylating agent is methyl iodide.

In some embodiments, the method further comprises adding an inorganic base. In some such embodiments, the inorganic base is a carbonate. Exemplary carbonates include potassium carbonate, sodium carbonate, cesium carbonate, calcium carbonate, and combinations thereof.

In some embodiments, the method further comprises heating the mixture at a temperature of greater than about 80° C. (e.g., at about 90° C.).

In some embodiments, the method further comprises further comprising the step of preparing 7,7-dibromo-3-hydroxybicyclo[4.1.0]hept-3-en-2-one or a salt thereof:

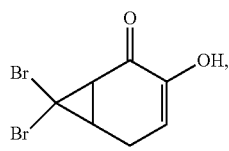

comprising combining an oxidizing agent and 7,7-dibromobicyclo[4.1.0]heptane-2,3-diol or a salt thereof:

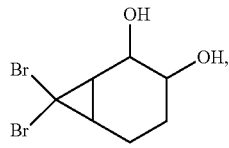 [SMILES: OC1CCC2C(C1O)C2(Br)Br]

thereby forming 7,7-dibromo-3-hydroxybicyclo[4.1.0]hept-3-en-2-one or a salt thereof.

In some embodiments, the oxidizing agent comprises potassium dichromate, pyridinium chlorochromate, Dess-Martin periodinane, oxalyl chloride, dimethylsulfoxide, aluminum alkoxide (e.g., aluminum isopropoxide), trimethylaluminum, potassium tert-butoxide, silver carbonate, or a mixture of any of them. In some such embodiments, the oxidizing agent further comprises dimethylsulfoxide and one or more additional reagents selected from the group consisting of a carbodiimide, trifluoroacetic anhydride, oxalyl chloride, and sulfur trioxide pyridine complex.

In some embodiments, 7,7-dibromobicyclo[4.1.0]heptane-2,3-diol is contacted with a basic amine after being contacted with the oxidizing agent. In some such embodiments, the basic amine is a tertiary amine, such as triethylamine.

In some embodiments, 7,7-dibromobicyclo[4.1.0]heptane-2,3-diol is contacted with the oxidizing agent at a temperature of less than about 5° C. In some such embodiments, 7,7-dibromobicyclo[4.1.0]heptane-2,3-diol is first contacted with the oxidizing agent at a temperature of about −78° C. In certain embodiments of the method, the temperature is subsequently warmed to about 0° C.

In some embodiments, the method does not afford 4-bromo-2-methoxycyclohepta-2,4,6-trien-1-one or a salt thereof:

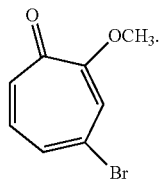 [SMILES: COc1cc(Br)cccc1=O]

Method B

Also provided herein is a method of preparing a compound of the following structural formula or a salt thereof:

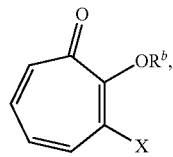

comprising reacting a compound of the following structural formula or a salt thereof:

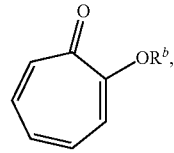

with a halogenating agent, thereby forming the compound, wherein $R^b$ is H or methyl, and X is halogen.

In some embodiments, the halogenating agent is a brominating agent. In some such embodiments, the brominating agent is N-bromosuccinimide (NBS) or hydrobromic acid.

Method C

Also provided herein is a method of preparing 4-bromo-2-hydroxycyclohepta-2,4,6-trien-1-one or a salt thereof:

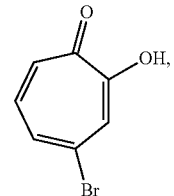

comprising combining 7,7-dibromobicyclo[4.1.0]heptane-2,3-diol or a salt thereof:

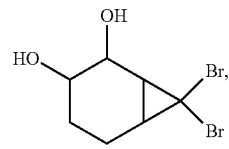 [SMILES: OC1CCC2C(C1O)C2(Br)Br]

and an oxidizing agent, thereby forming 4-bromo-2-hydroxycyclohepta-2,4,6-trien-1-one or a salt thereof.

In some embodiments, the method further comprises combining 7,7-dibromobicyclo[4.1.0] heptane-2,3-diol and the oxidizing agent with a base. In some such embodiments, base is an amine. In certain embodiments, the amine is a tertiary amine, such as triethylamine.

In some embodiments, 7,7-dibromobicyclo[4.1.0]heptane-2,3-diol is first contacted with the oxidizing agent at a temperature of about −78° C. In certain embodiments of the method, the temperature is subsequently warmed to about 0° C.

Method D

Also provided herein is a method of preparing 5-bromo-2-hydroxycyclohepta-2,4,6-trien-1-one or a salt thereof:

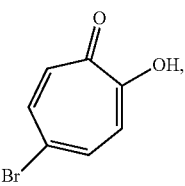

comprising combining 7,7-dibromobicyclo[4.1.0]heptane-3,4-diol or a salt thereof:

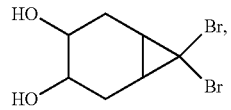

with an oxidizing agent, thereby forming 5-bromo-2-hydroxycyclohepta-2,4,6-trien-1-one or a salt thereof.

In some embodiments, 7,7-dibromobicyclo[4.1.0]heptane-3,4-diol is first contacted with the oxidizing agent at a temperature of about −78° C. In certain embodiments of the method, the temperature is subsequently warmed to about 0° C. In some embodiments, the oxidizing agent comprises one or more of potassium dichromate, pyridinium chlorochromate, Dess-Martin periodinane, oxalyl chloride, dimethylsulfoxide, aluminum alkoxide (e.g., aluminum isopropoxide), trimethylaluminum, potassium tert-butoxide, or silver carbonate. In other embodiments, the oxidizing agent comprises dimethylsulfoxide and one or more additional reagents selected from the group consisting of a carbodiimide, trifluoroacetic anhydride, oxalyl chloride, and sulfur trioxide pyridine complex.

In some embodiments, the method further comprises combining 7,7-dibromobicyclo[4.1.0] heptane-3,4-diol and the oxidizing agent with a base. In some such embodiments, the base is an amine base. In certain embodiments, the base is a tertiary amine base, such as triethylamine.

Method E

Also provided herein is a method of preparing a compound of the following structural formula or a salt thereof:

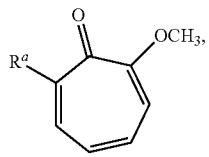

comprising reacting a compound of the following structural formula or a salt thereof:

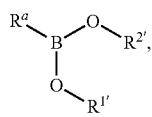

with 2-bromo-7-methoxycyclohepta-2,4,6-trien-1-one or a salt thereof:

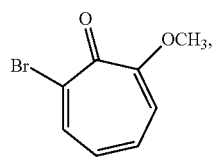

thereby providing the compound of structural formula or a salt thereof:

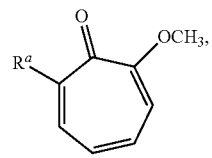

wherein $R^a$ is $C_{1-20}$-alkyl, $C_{2-20}$-alkenyl, $C_{2-20}$-alkynyl, $C_{3-9}$-cycloalkyl, aryl, or heteroaryl, each of which is unsubstituted or substituted with a substituent selected from the group consisting of halo, $NO_2$, CN, $C_{1-6}$-alkyl, $C_{1-6}$-haloalkyl, and $C_{1-6}$-alkoxy;

$R^{1'}$ and $R^{2'}$ are each, independently hydrogen or $C_{1-6}$-alkyl; or $R^{1'}$ and $R^{2'}$, together with atoms to which they are attached, form a ring having 2 to 4 carbon atoms, each of which is independently optionally substituted with $C_{1-3}$-alkyl or C=O; and B is a boron atom having $sp^3$ hybridization.

In some embodiments, $R^{1'}$ and $R^{2'}$ are both hydrogen.

In some embodiments $R^a$ is selected from the group consisting of:

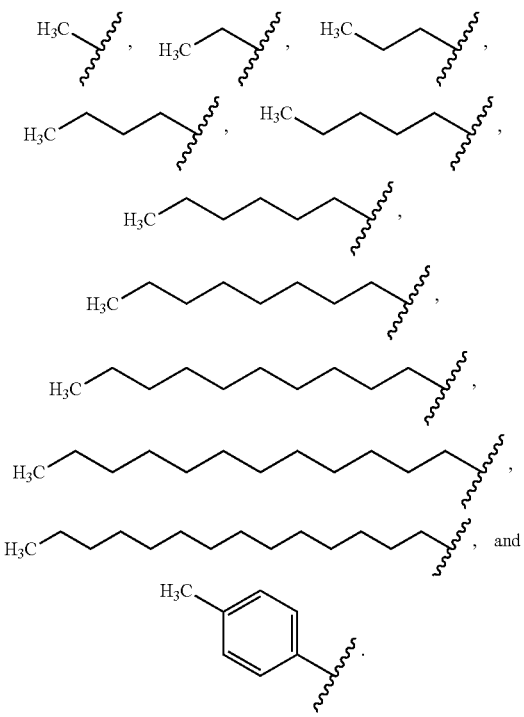

In some such embodiments, the compound of structural formula or salt thereof:

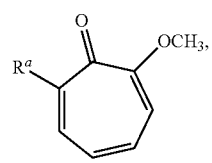

is selected from the group consisting of:

[structures of 2-methoxy-7-alkyl-tropone series with alkyl = methyl, ethyl, propyl, butyl, pentyl, hexyl, heptyl, octyl, nonyl, decyl, undecyl, and 4-methylphenyl]

In other embodiments, $R^a$ is selected from the group consisting of

[structures: sec-butyl, isopropyl, cyclohexyl, cyclopentyl, cyclobutyl, and cyclopropyl]

In some such embodiments, the compound of structural formula or salt thereof:

[structure with $R^a$ group on 2-methoxytropone]

is selected from the group consisting of:

[structures: sec-butyl-, isopropyl-, cyclohexyl-, cyclopentyl-, cyclobutyl-, and cyclopropyl-substituted 2-methoxytropones]

In some embodiments, $R^a$ is selected from the group consisting of:

—$CH_3$; $CH_3$ (ethyl); vinyl; ethynyl; propyl;

isopropyl with two $CH_3$; cyclopropyl; propenyl with $CH_3$; allyl;

isopropenyl with $CH_3$; methylenecyclopropyl; cyclopropenyl; propynyl —$CH_3$;

butynyl; butadienyl; butyl —$CH_3$; sec-butyl with $CH_3$;

75
-continued
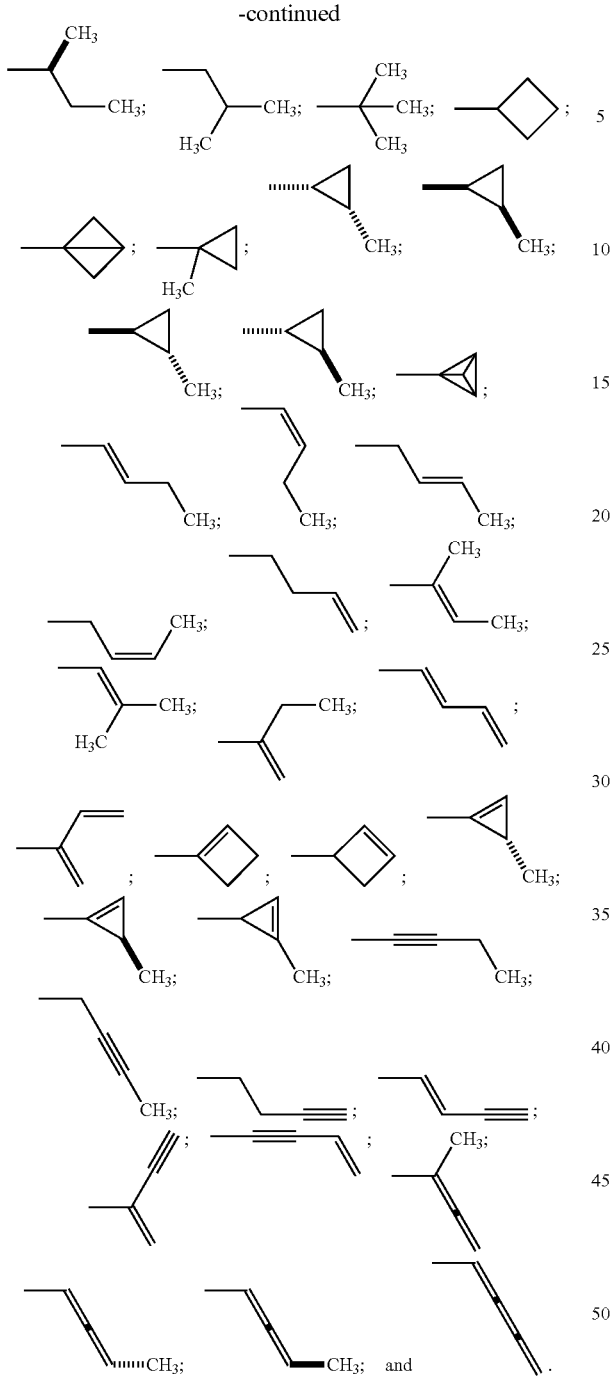
In some such embodiments, the compound of structural formula or salt thereof:
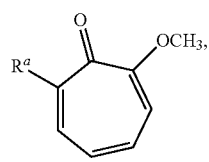
76
is selected from the group consisting of:
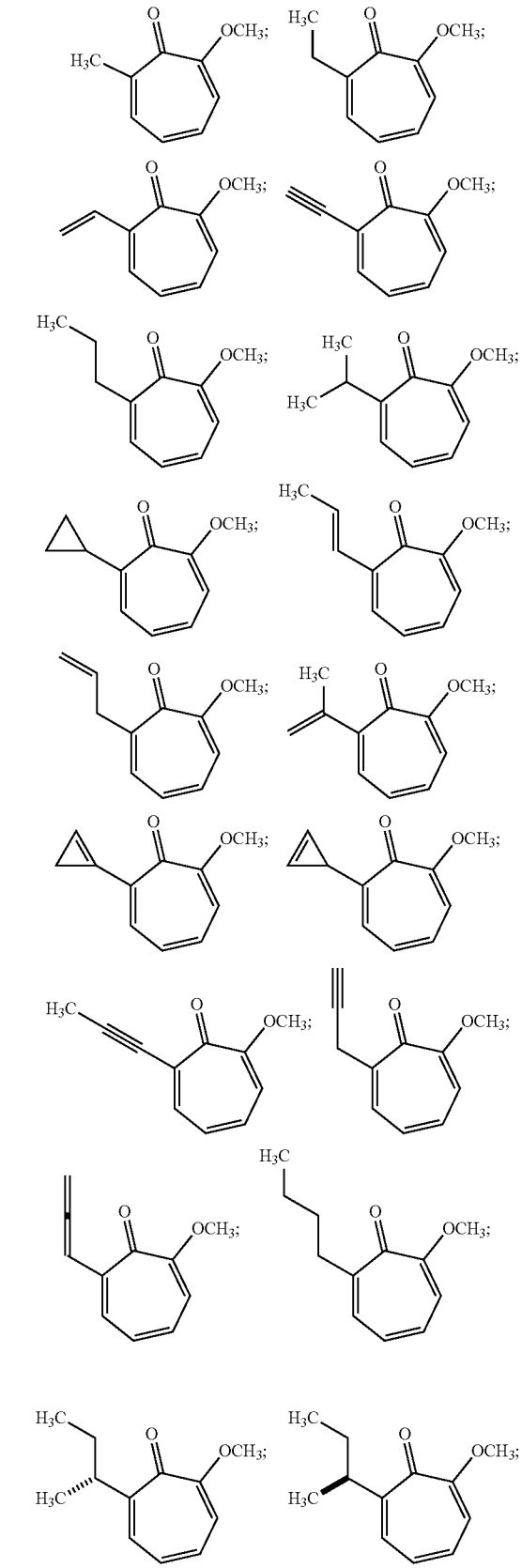

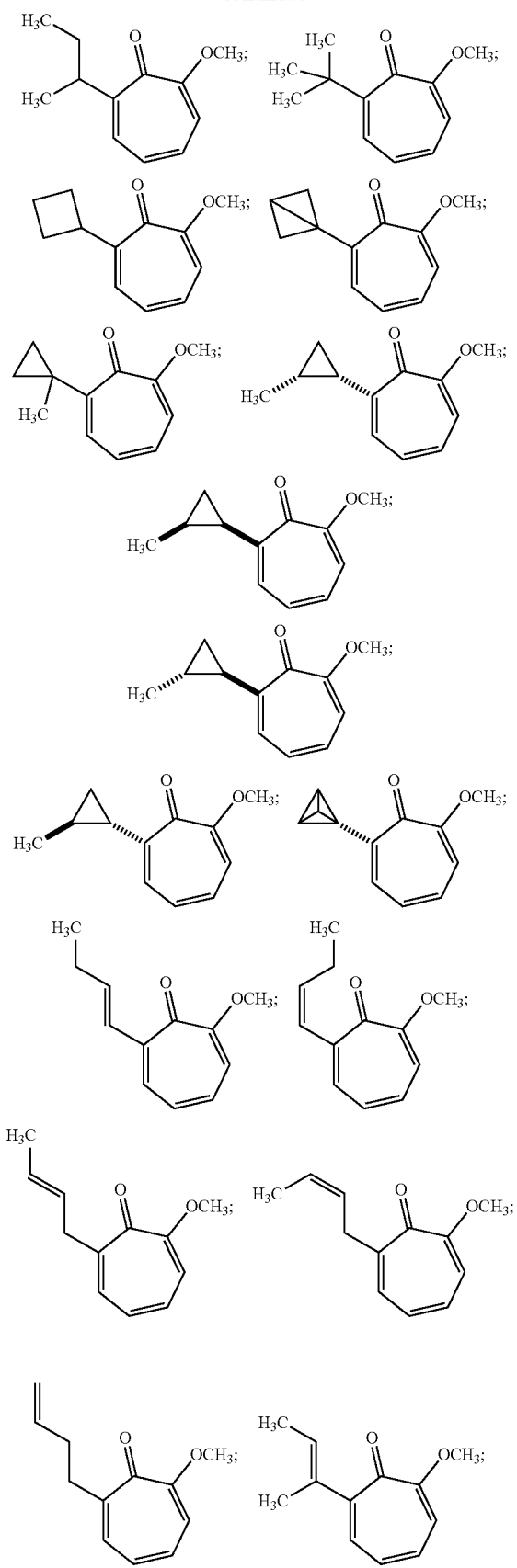
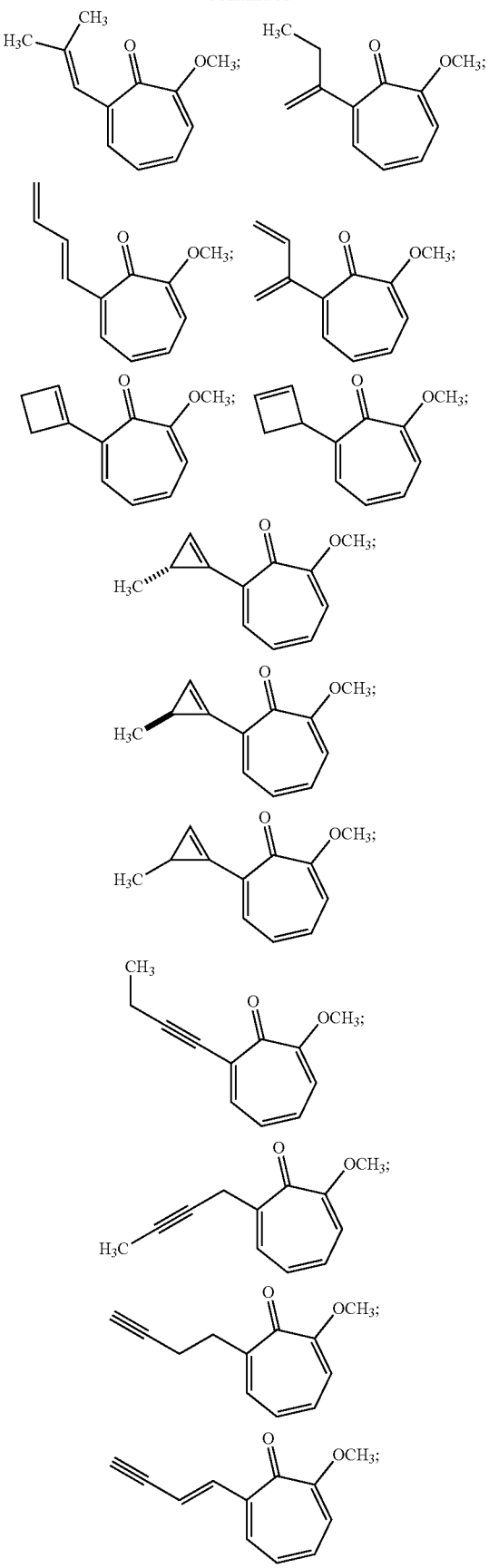

-continued

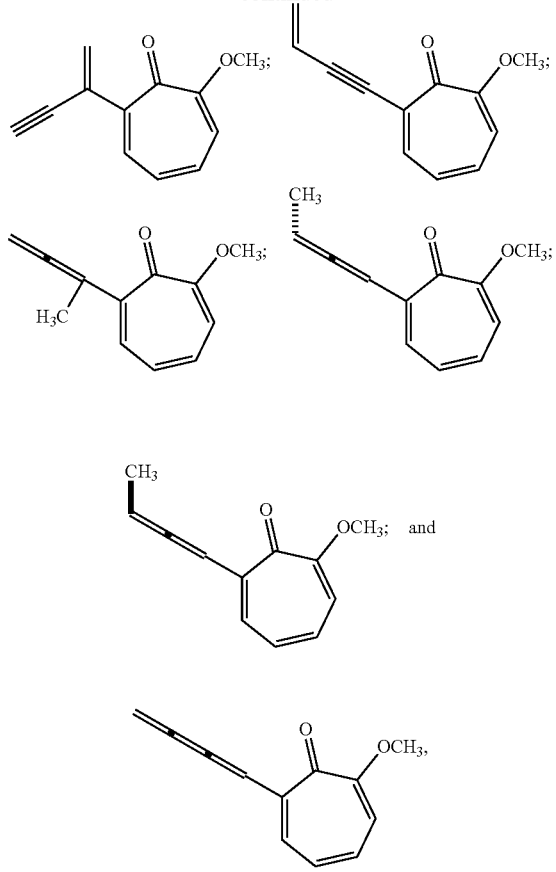

or a salt thereof.

In some embodiments, the method further comprises contacting the reacting compounds with a metal catalyst. In some such embodiments, the metal catalyst is a palladium catalyst or a palladium nanomaterial-based catalyst. In certain embodiments, the metal catalyst is an organopalladium catalyst. For example, in particular embodiments, the metal catalyst is selected from the group consisting of tetrakis(triphenylphosphine)palladium(O), palladium chloride, and palladium(II) acetate.

In some embodiments, the reaction with comprising the metal catalyst further comprises a promoter. In some such embodiments, the promoter is thallium (I) ethoxide or silver oxide. In preferred embodiments, the promoter is silver oxide.

Method F

Also provided herein is a method of preparing a compound of structural formula or a salt thereof:

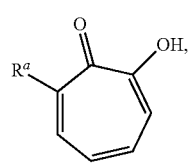

comprising combining a compound having structural formula or a salt thereof:

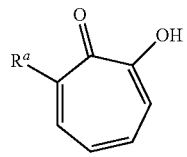

with a demethylating agent; thereby providing the compound of structural formula:

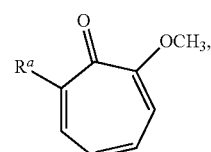

or a salt thereof; wherein $R^a$ is $C_{1-20}$-alkyl, $C_{2-20}$-alkenyl, $C_{2-20}$-alkynyl, $C_{3-9}$-cycloalkyl, aryl, or heteroaryl, each of which is unsubstituted or substituted with a substituent selected from the group consisting of halo, $NO_2$, CN, $C_{1-6}$-alkyl, $C_{1-6}$-haloalkyl, and $C_{1-6}$-alkoxy.

In some embodiments, the demethylating agent is an acid. In some such embodiments, the demethylating agent is a mineral acid, an organic acid, or a combination thereof. In certain embodiments, the demethylating agent is hydrochloric acid, hydrobromic acid, sulfuric acid, acetic acid, or a combination thereof. In preferred embodiments, the demethylating agent is hydrobromic or hydrochloric acid in acetic acid. Alternatively, the demethylating agent is sulfuric acid.

In some embodiments, the compound having structural formula:

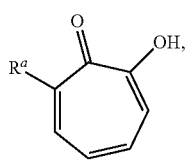

or a salt thereof; is contacted with a demethylating agent and heated to boiling; thereby providing the compound of structural formula:

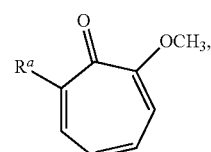

or salt thereof.

In some embodiments, the compound of structural formula:

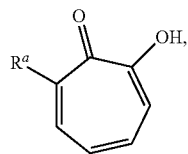
or salt thereof, is selected from:
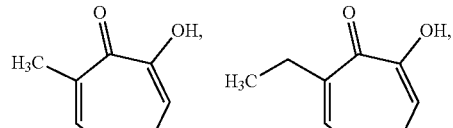
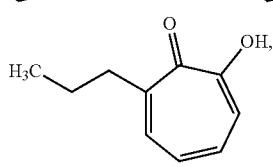
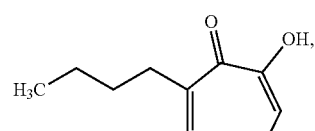
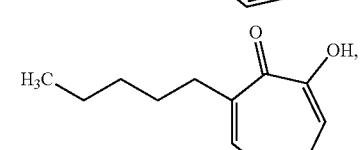
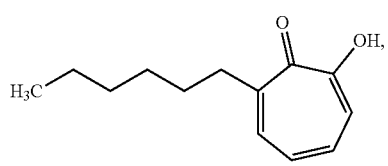
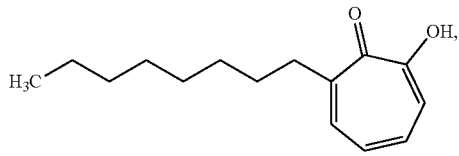
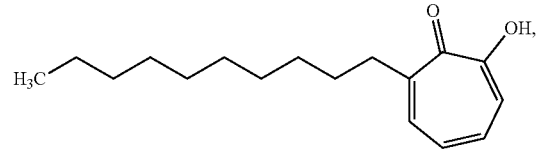
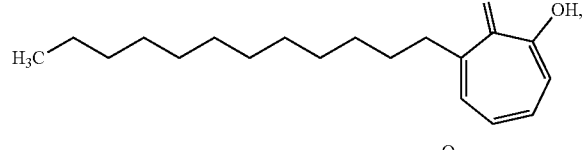
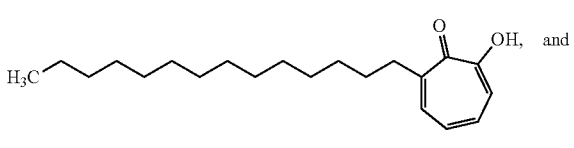
-continued
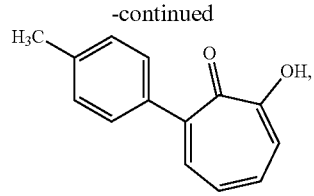
or a salt thereof.
In some embodiments, the compound of structural formula:
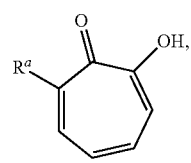
or salt thereof, is selected from the group consisting of:
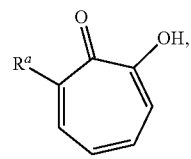
or a salt thereof.
In some embodiments, the compound of structural formula:
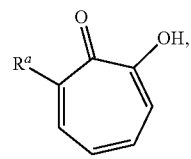
or salt thereof, is selected from the group consisting of:
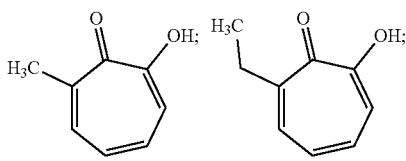

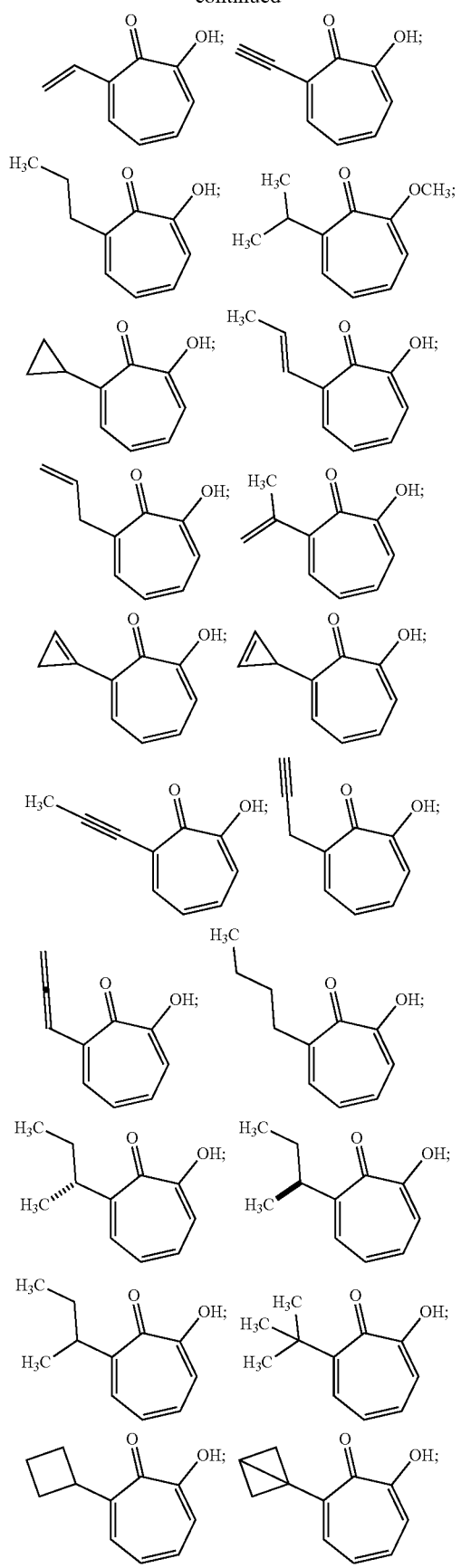
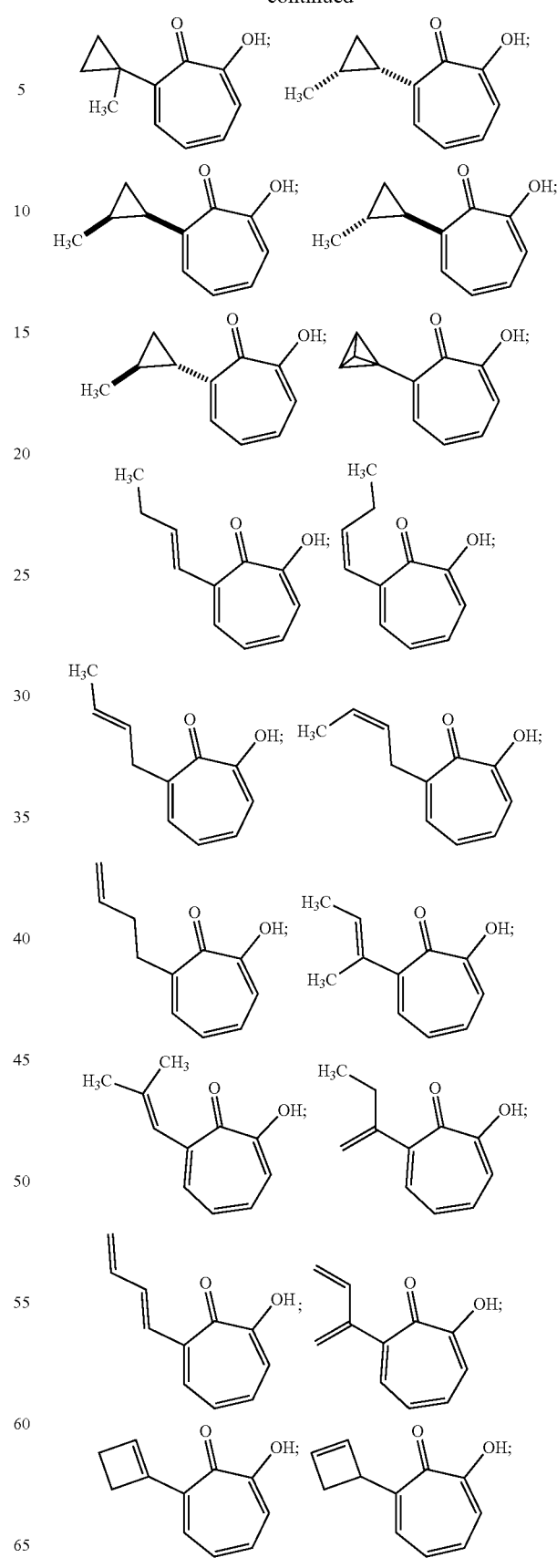

-continued

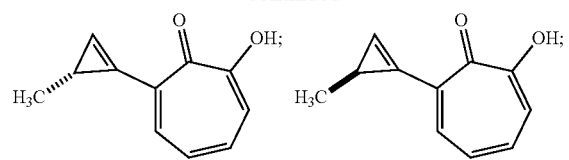

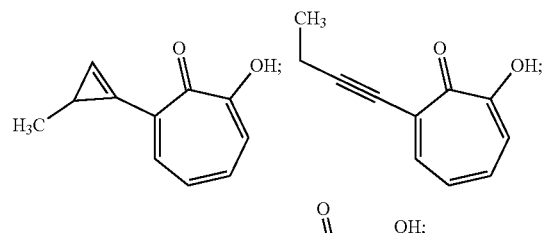

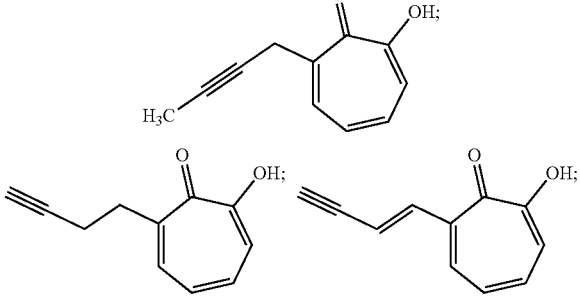

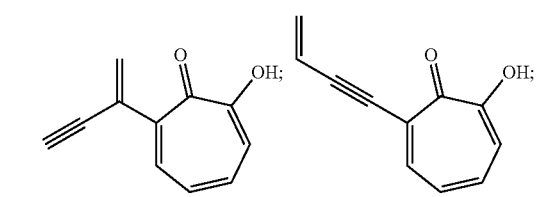

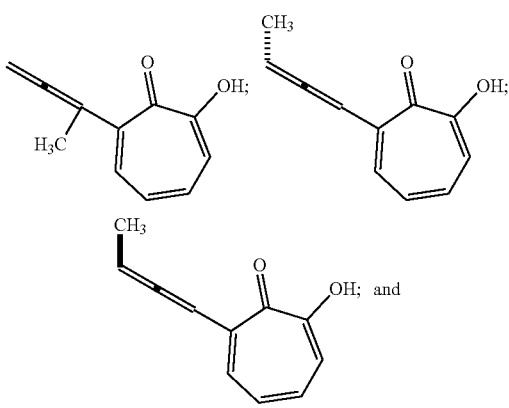

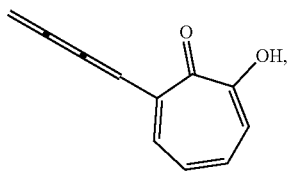

or a salt thereof.

Method G

Also provided herein is a method of preparing a compound of structural formula:

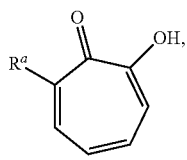

or a salt thereof; comprising:
(1) reacting a compound of structural formula:

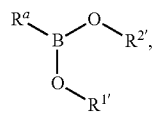

or a salt thereof; with a compound of structural formula:

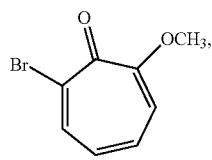 [SMILES: COc1ccccc(Br)c1=O]

or a salt thereof; thereby providing a compound having structural formula:

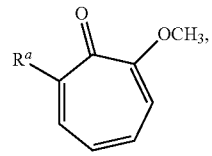

or a salt thereof; and
(2) contacting the compound having structural formula:

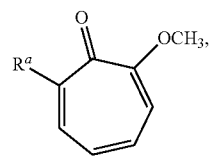

or a salt thereof; with a demethylating agent; thereby providing the compound of structural formula:

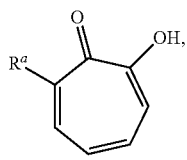

or a salt thereof; wherein
$C_{1-20}$-alkyl, $C_{2-20}$-alkenyl, $C_{3-9}$-cycloalkyl, aryl, or heteroaryl, each of which is unsubstituted or substituted with a substituent selected from the group consisting of halo, $NO_2$, CN, $C_{1-6}$-alkyl, $C_{1-6}$-haloalkyl, and $C_{1-6}$-alkoxy;

R$^{1'}$ and R$^{2'}$ are each, independently hydrogen or C$_{1-6}$-alkyl; or

R$^{1'}$ and R$^{2'}$, together with atoms to which they are attached, form a ring having 2 to 4 carbon atoms, each of which is optionally and independently substituted with C$_{1-3}$-alkyl or C=O; and B is a boron atom having sp$^3$ hybridization.

In some embodiments, R$^{1'}$ and R$^{2'}$ are both hydrogen.

In some embodiments, step (1) of the method further comprises contacting the reacting compounds with a metal catalyst. In some such embodiments, the metal catalyst is a palladium catalyst or a palladium nanomaterial-based catalyst. In certain embodiments, the metal catalyst is an organopalladium catalyst. In particular embodiments, the metal catalyst is selected from the group consisting of tetrakis(triphenylphosphine)palladium(0), palladium chloride, and palladium(II) acetate.

In some embodiments, the reaction with comprising the metal catalyst further comprises a promoter. In some such embodiments, the promoter is thallium (I) ethoxide or silver oxide. In preferred embodiments, the promoter is silver oxide.

In some embodiments, the demethylating agent is an acid. In some such embodiments, the demethylating agent is a mineral acid, an organic acid, or a combination thereof. In certain embodiments, the demethylating agent is hydrochloric acid, hydrobromic acid, sulfuric acid, acetic acid, or a combination thereof. In preferred embodiments, the demethylating agent is hydrobromic or hydrochloric acid in acetic acid. Alternatively, the demethylating agent is sulfuric acid.

In some embodiments, R$^a$ is selected from the group consisting of:

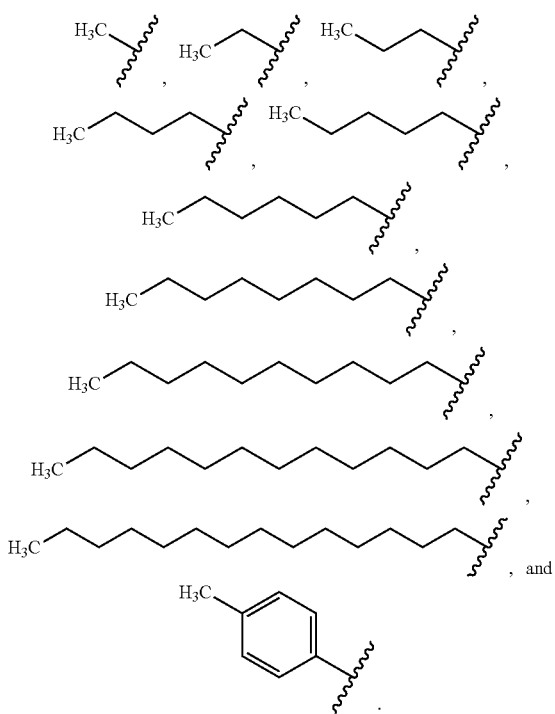

In some such embodiments, the compound of structural formula:

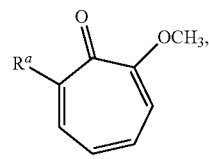

or salt thereof, is selected from the group consisting of:

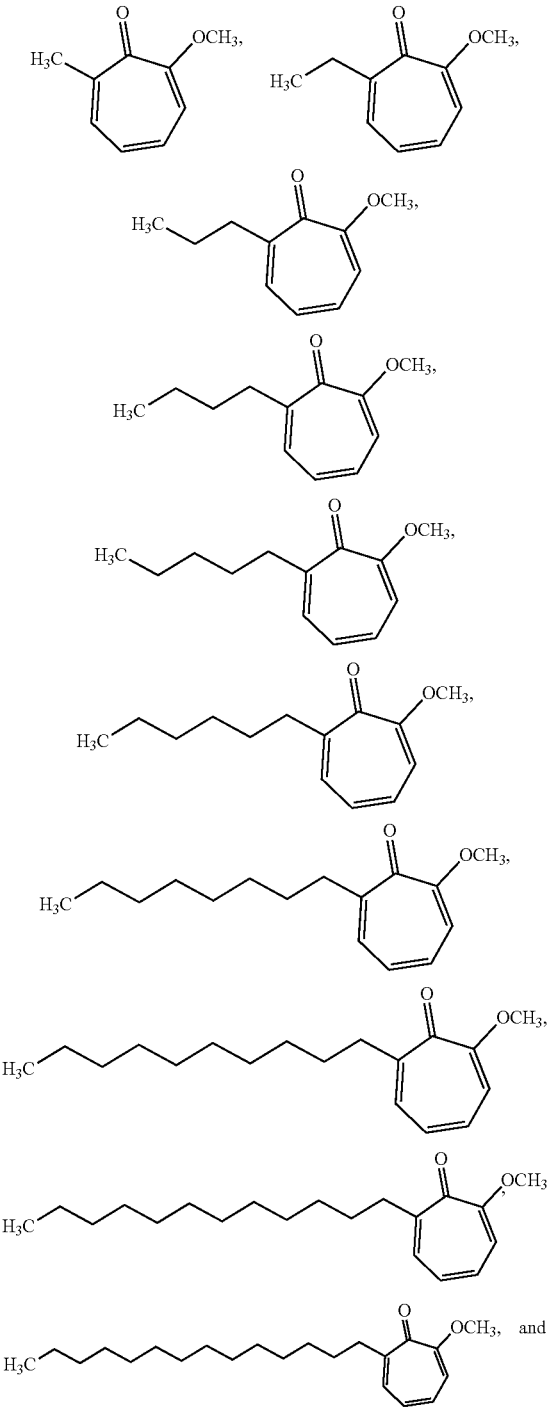

-continued
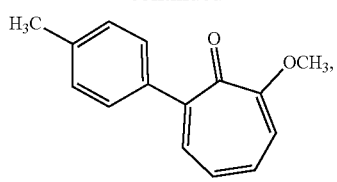
or a salt thereof.
In some embodiments, the compound of structural formula:
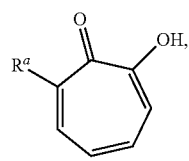
or salt thereof, is selected from:
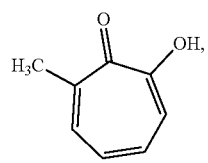 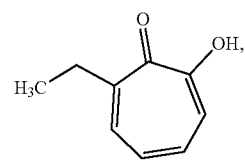
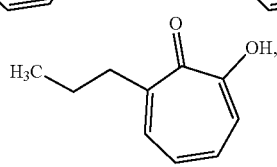
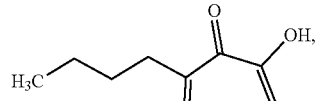
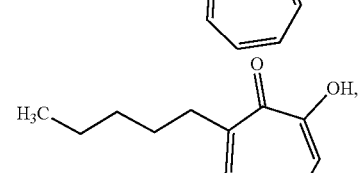
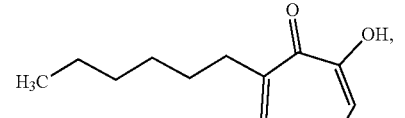
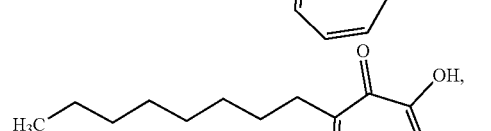
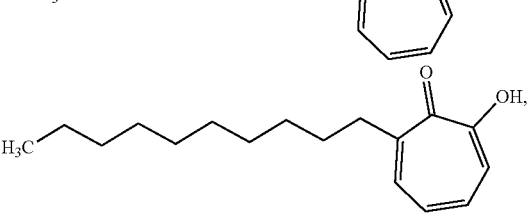
-continued
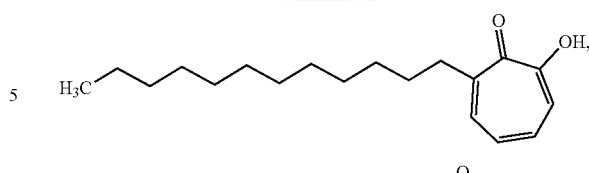
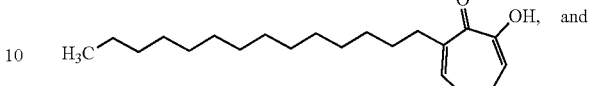
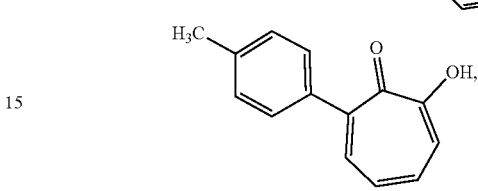
or a salt thereof.
In other embodiments, $R^a$ is selected from the group consisting of
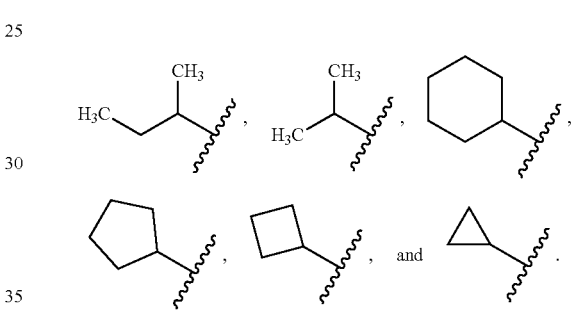
In some such embodiments, the compound of structural formula:
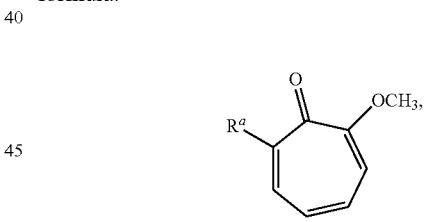
or salt thereof, is selected from the group consisting of:
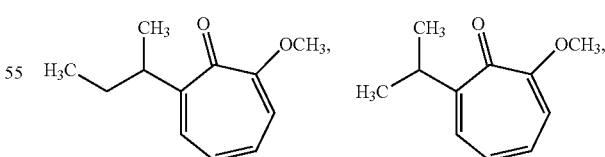
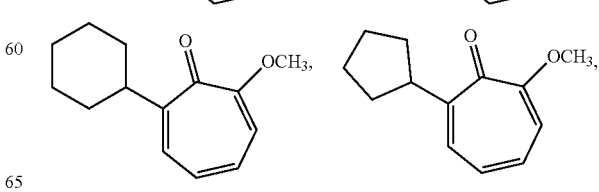

-continued
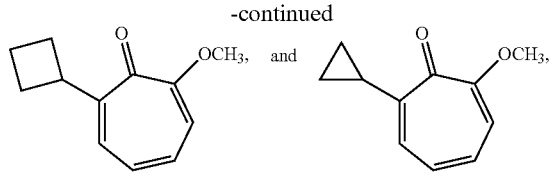
or a salt thereof.
In some embodiments, the compound of structural formula:
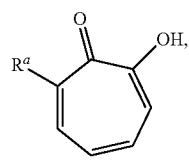
or salt thereof, is selected from the group consisting of:
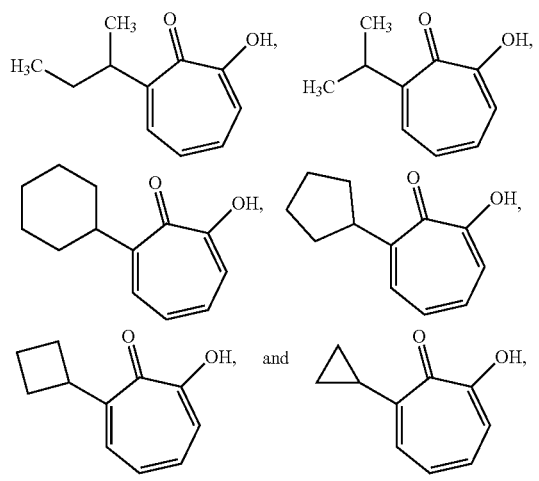
or a salt thereof.
In yet other embodiments, $R^a$ is selected from the group consisting of:
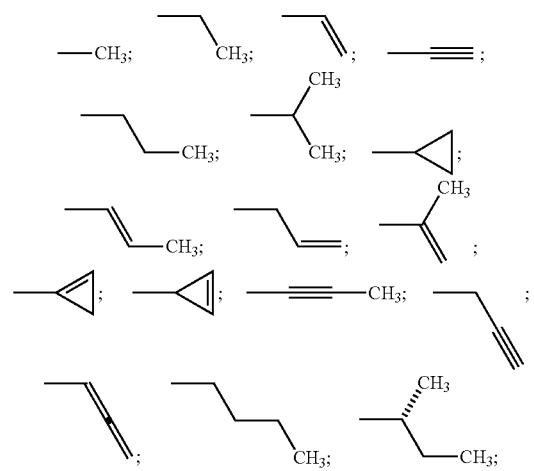
-continued
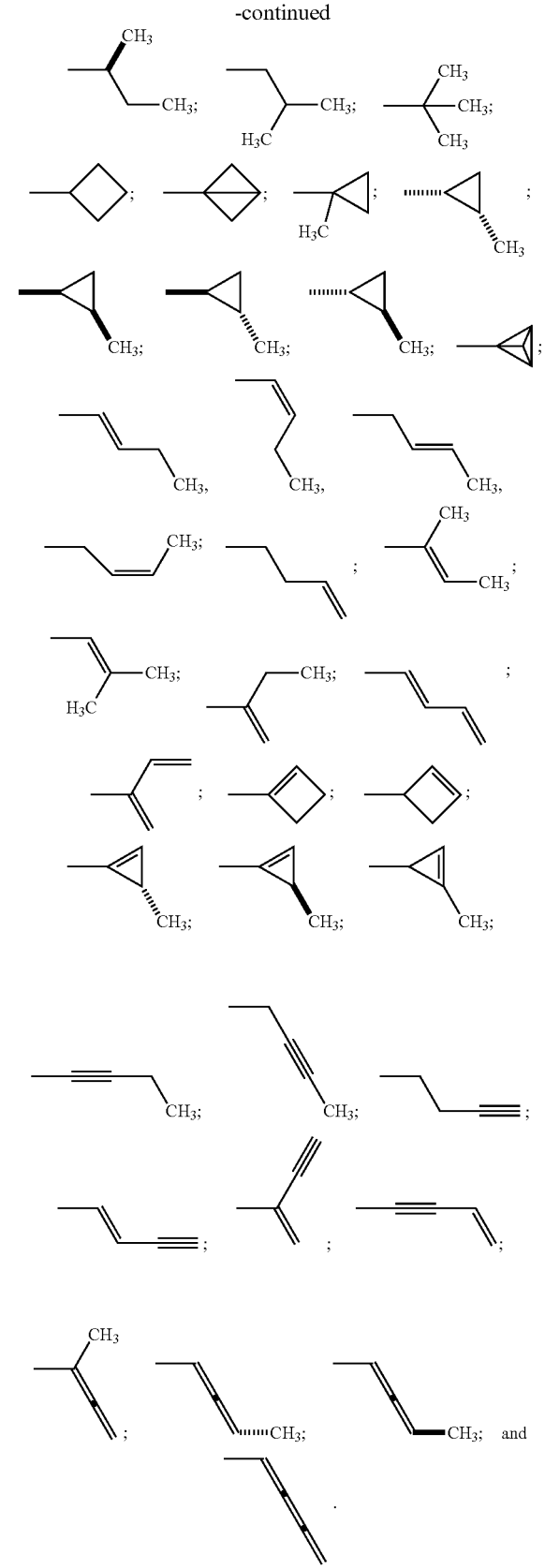
In some such embodiments, the compound of structural formula:

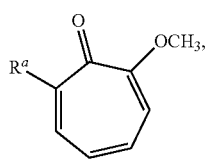
or salt thereof, is selected from the group consisting of:
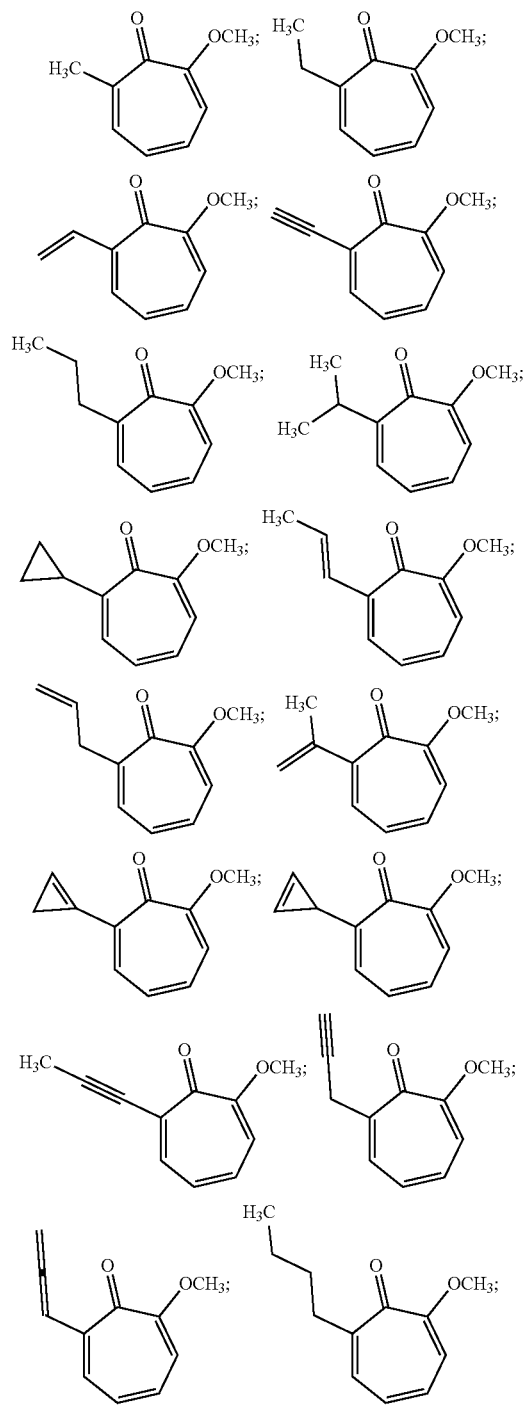
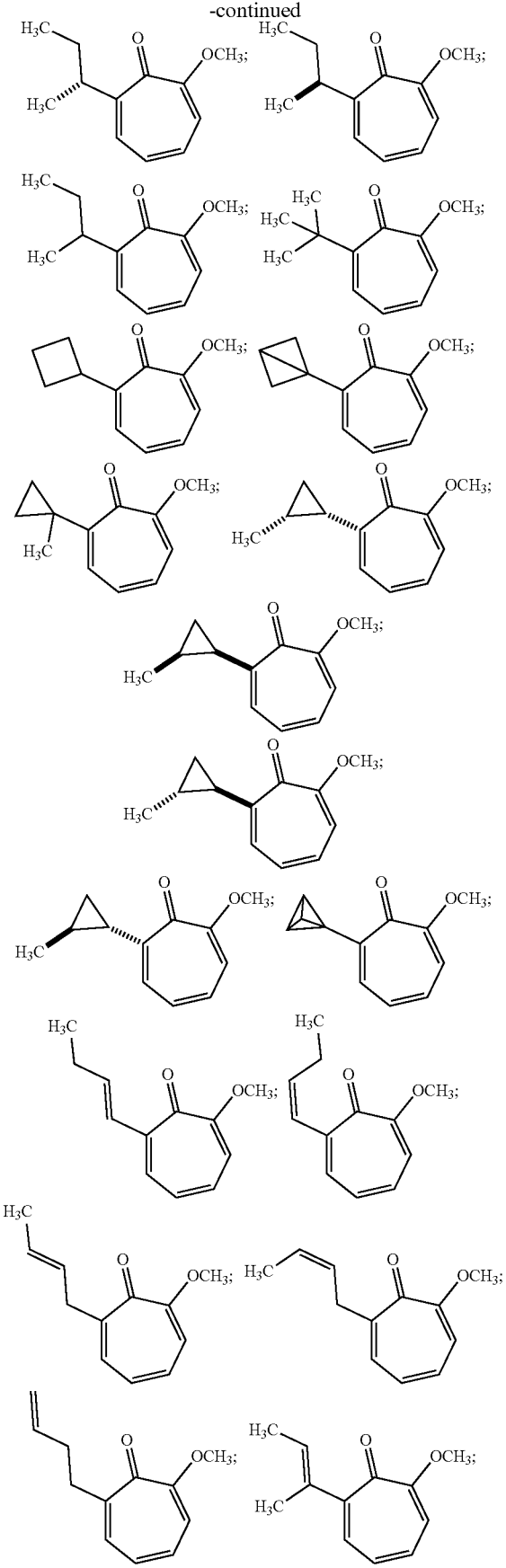

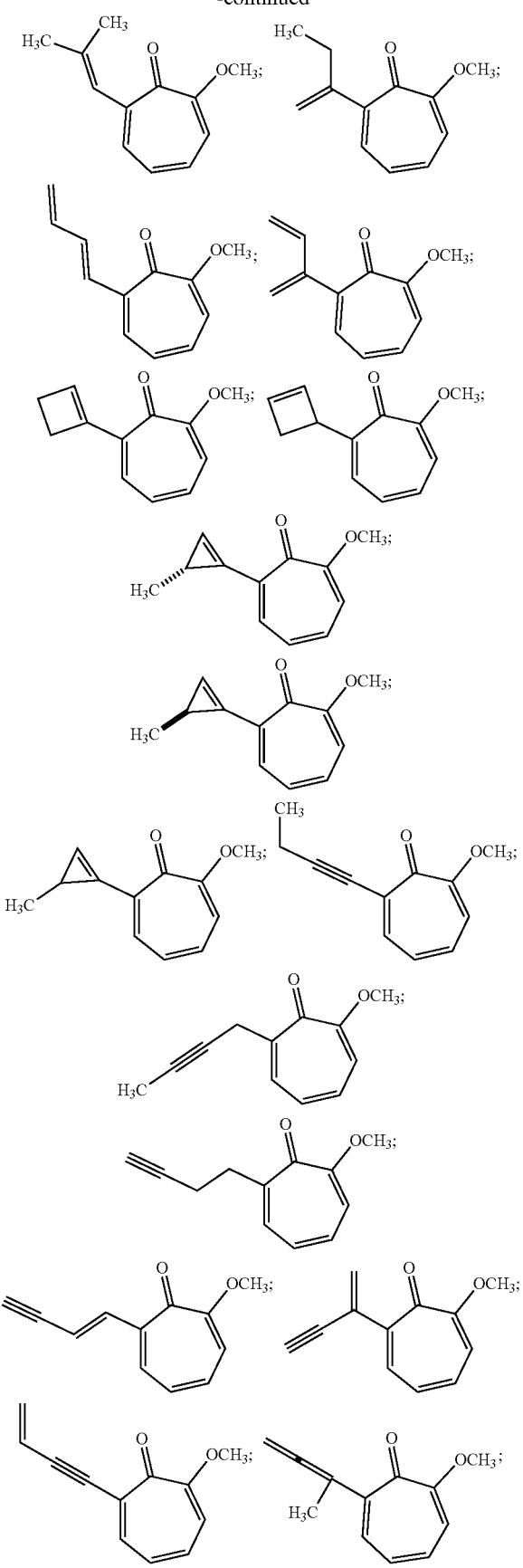
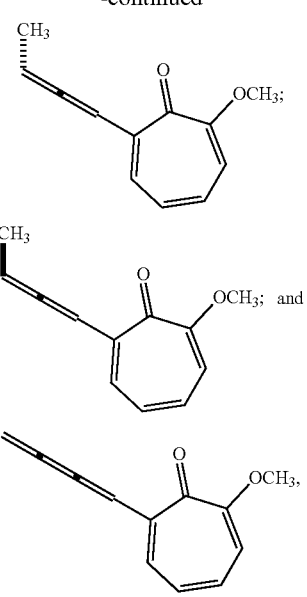
or a salt thereof.
In some embodiments, the compound of the structural formula:
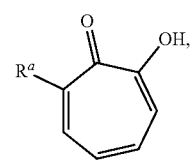
or salt thereof, is selected from the group consisting of:
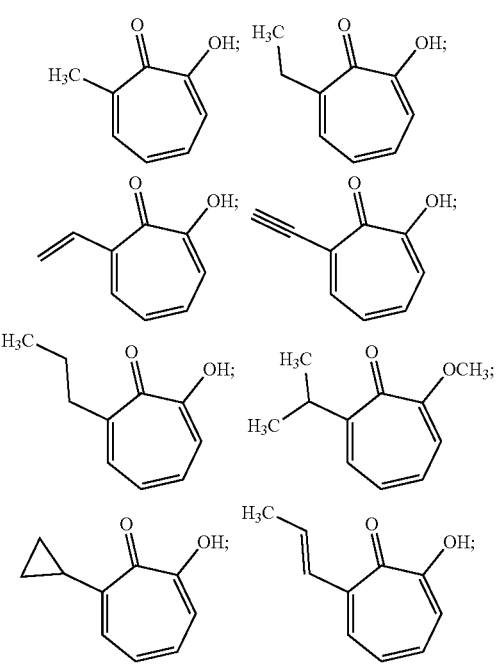

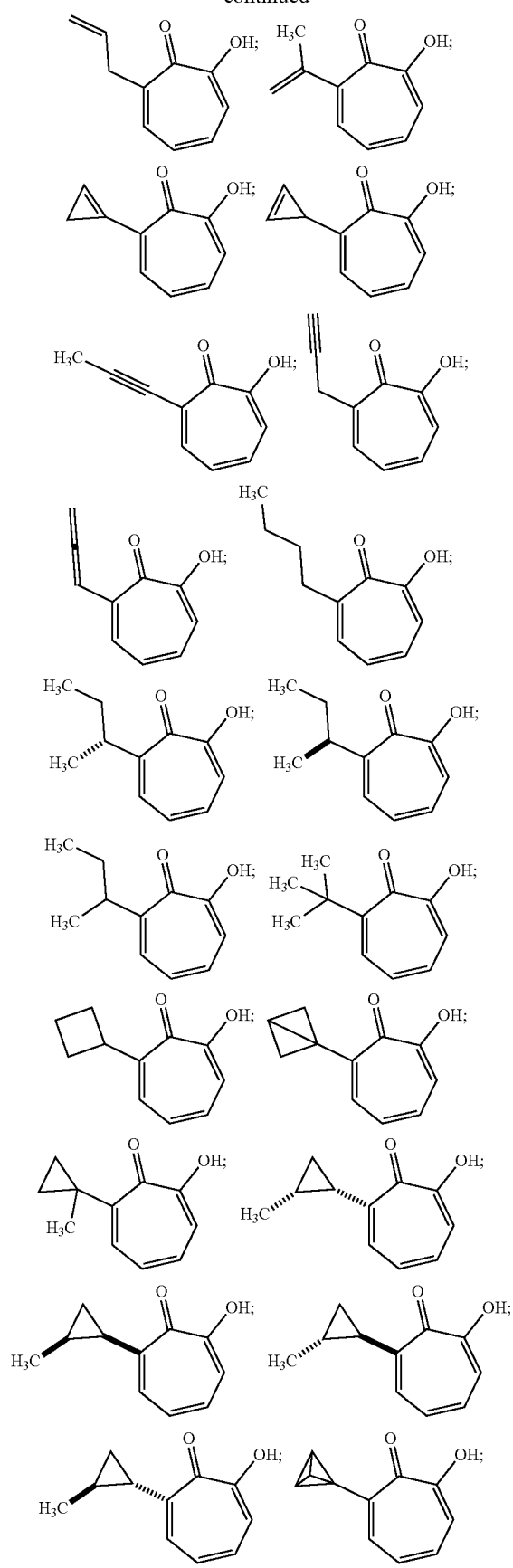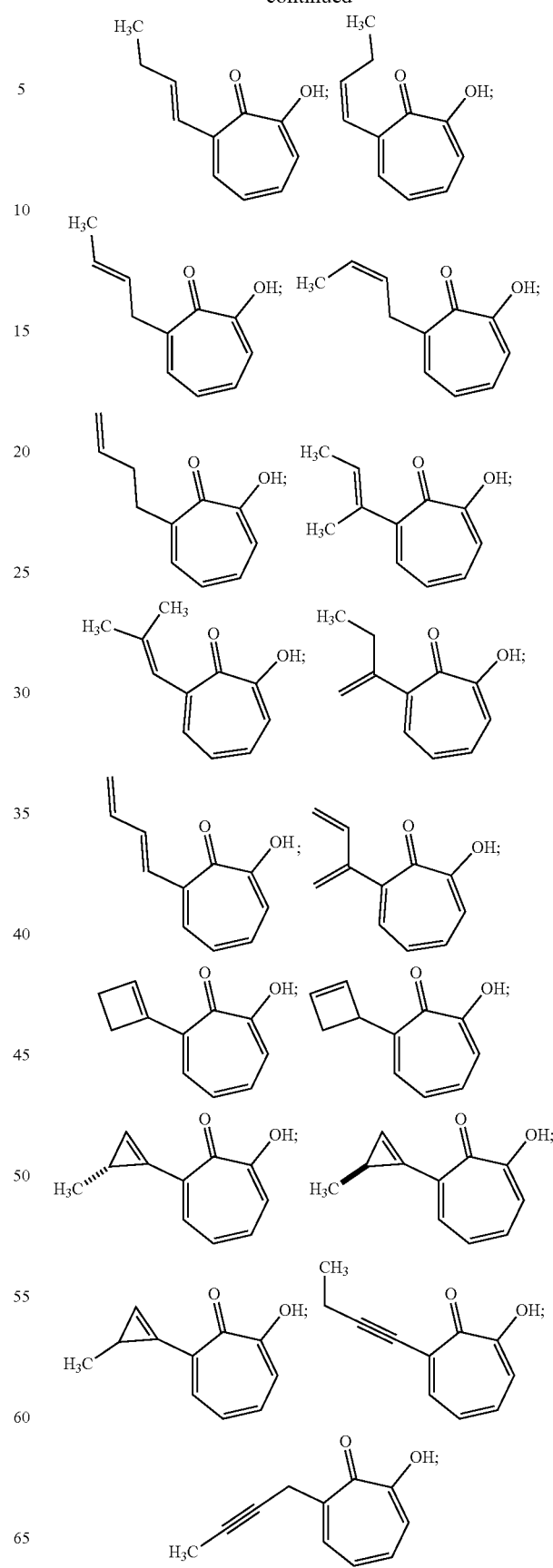

-continued

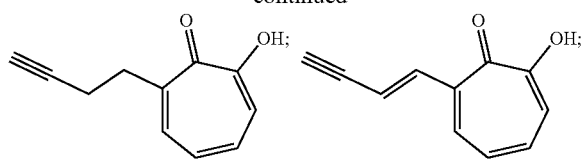

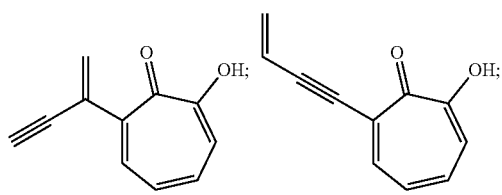

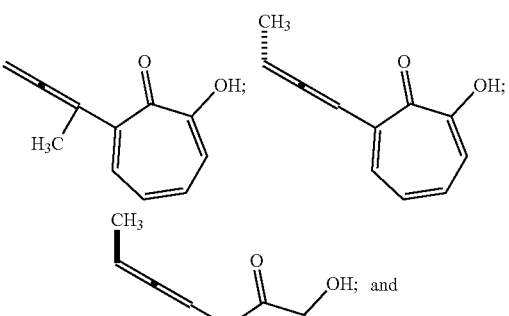

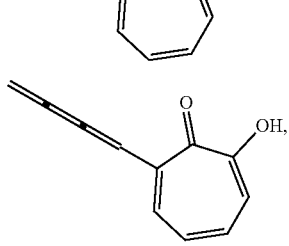

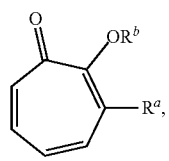

or a salt thereof.

Method H

Also provided herein is a method of preparing a compound of structural formula:

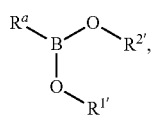

or a salt thereof; comprising reacting a compound of structural formula:

$$R^a\text{-B}(O\text{-}R^{2'})(O\text{-}R^{1'})$$

or a salt thereof; with a compound of structural formula:

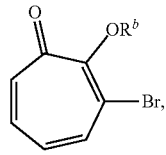

or a salt thereof; thereby providing the compound of structural formula:

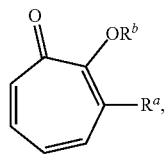

or a salt thereof; wherein
- $R^a$ is $C_{1\text{-}20}$-alkyl, $C_{2\text{-}20}$-alkenyl, $C_{2\text{-}20}$-alkynyl, $C_{3\text{-}9}$-cycloalkyl, aryl, or heteroaryl, each of which is unsubstituted or substituted with a substituent selected from the group consisting of halo, $NO_2$, CN, $C_{1\text{-}6}$-alkyl, $C_{1\text{-}6}$-haloalkyl, and $C_{1\text{-}6}$-alkoxy;
- $R^b$ is hydrogen or methyl;
- $R^{1'}$ and $R^{2'}$ are each, independently hydrogen or $C_{1\text{-}6}$-alkyl; or
- $R^{1'}$ and $R^{2'}$, together with atoms to which they are attached, form a ring having 2 to 4 carbon atoms, each of which is optionally and independently substituted with $C_{1\text{-}3}$-alkyl or C=O; and
- B is a boron atom having $sp^3$ hybridization.

In some embodiments, the method further comprises contacting the reacting compounds with a metal catalyst. In some such embodiments, the metal catalyst is a palladium catalyst or a palladium nanomaterial-based catalyst. In certain embodiments, the metal catalyst is an organopalladium catalyst. In particular embodiments, the metal catalyst is selected from the group consisting of tetrakis(triphenylphosphine)palladium(0), palladium chloride, and palladium(II) acetate.

In some embodiments, the reaction with comprising the metal catalyst further comprises a promoter. In some such embodiments, the promoter is thallium (I) ethoxide or silver oxide. In preferred embodiments, the promoter is silver oxide.

In some embodiments, $R^{1'}$ and $R^{2'}$ are both hydrogen.

In some embodiments, $R^a$ is $C_{1\text{-}4}$-alkyl, $C_{2\text{-}4}$-alkenyl, $C_{2\text{-}4}$-alkynyl, or $C_{3\text{-}4}$-cycloalkyl. In some such embodiments, $R^a$ is selected from the group consisting of:

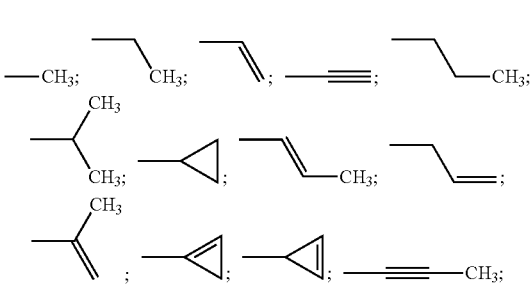

101
-continued
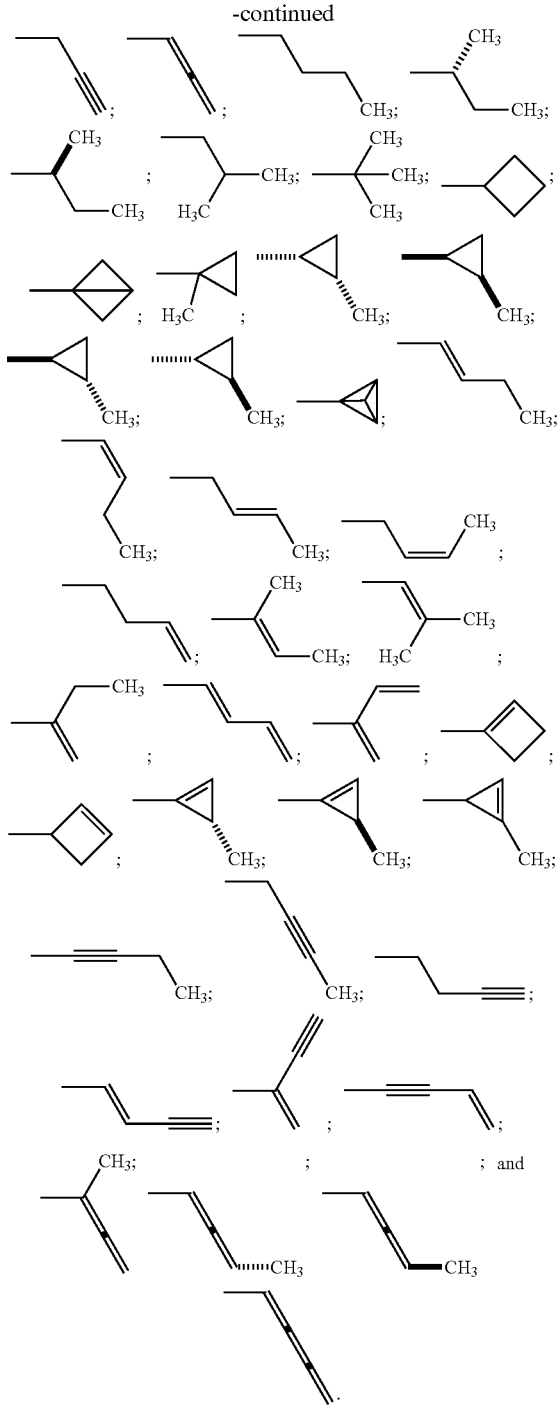
In some such embodiments, the compound of structural formula or salt thereof:
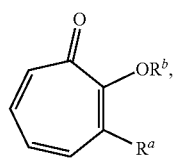
102
is selected from the group consisting of:
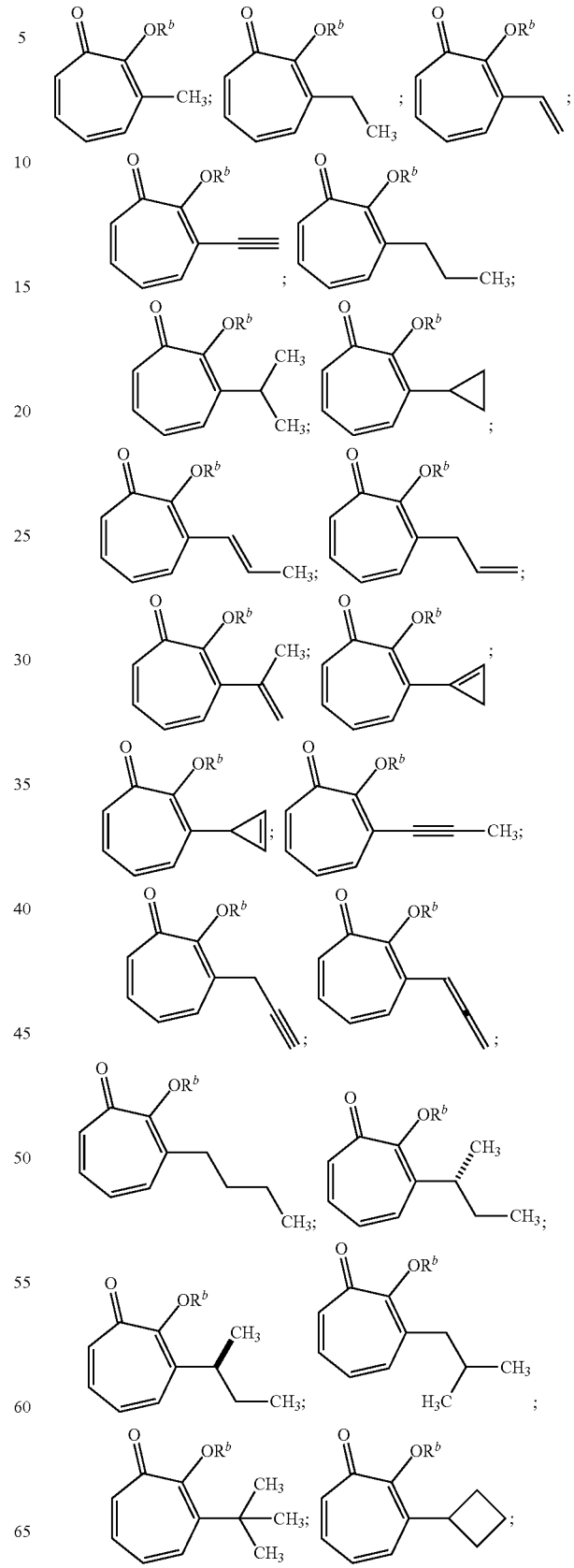

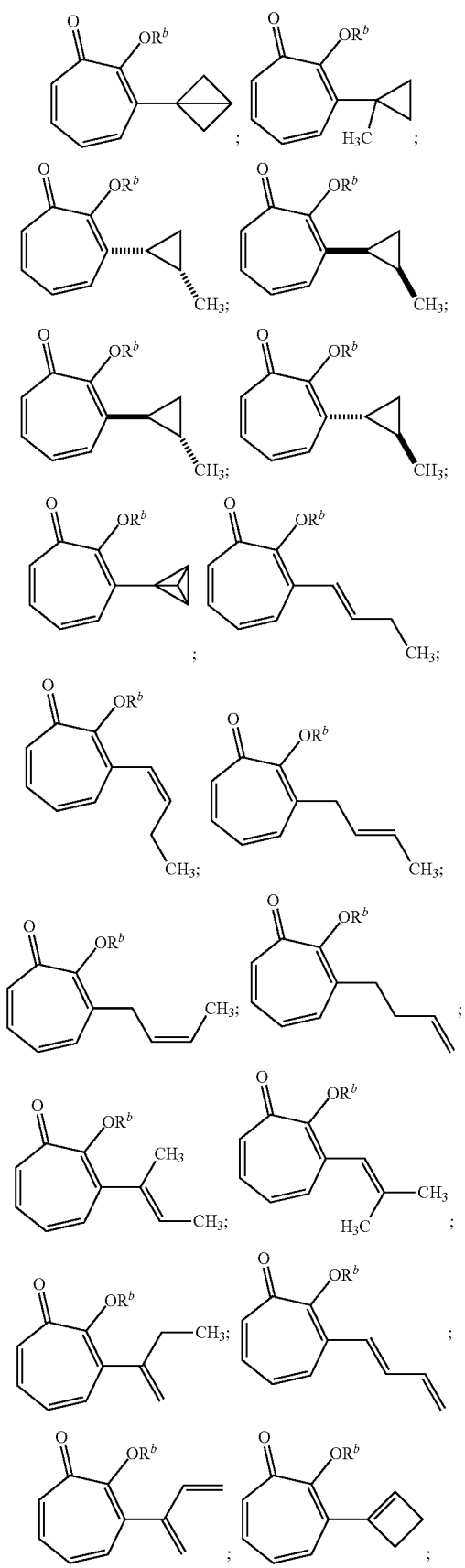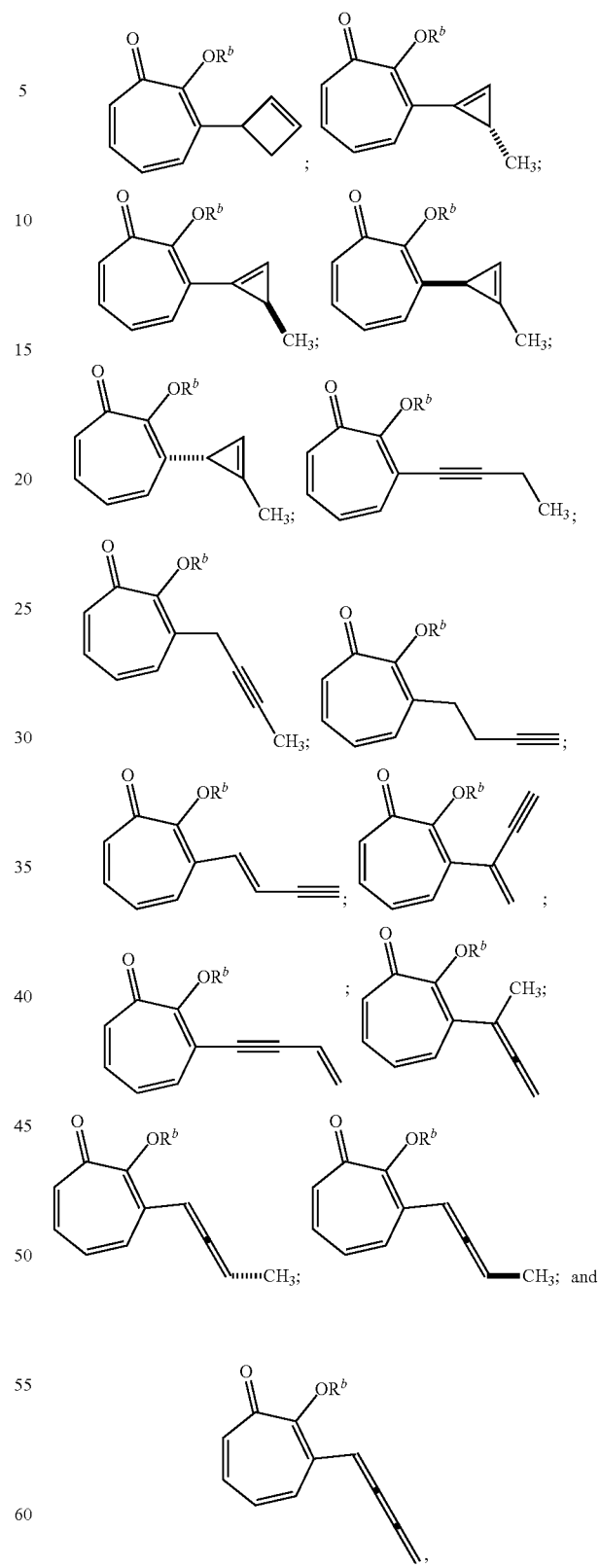
or a salt thereof.
In some other embodiments, $R^a$ is selected from the group consisting of:

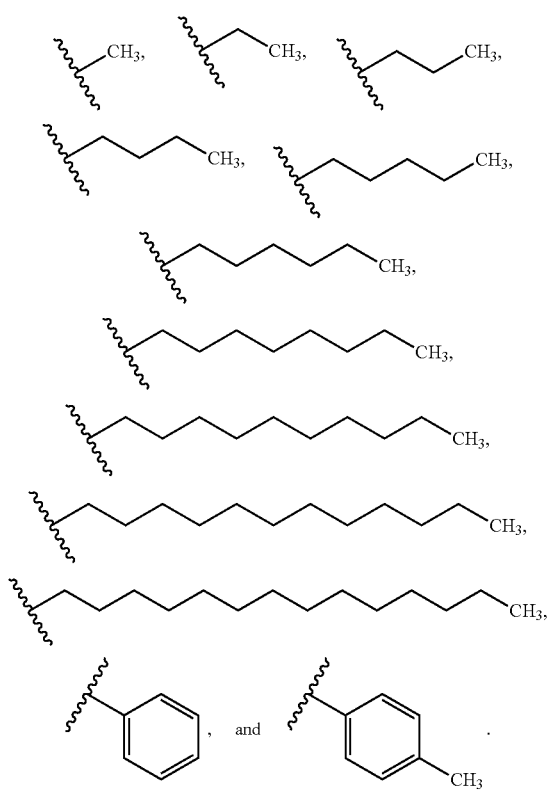
, and 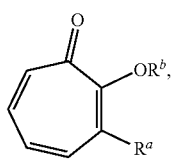 .
In some such embodiments, the compound of structural formula:
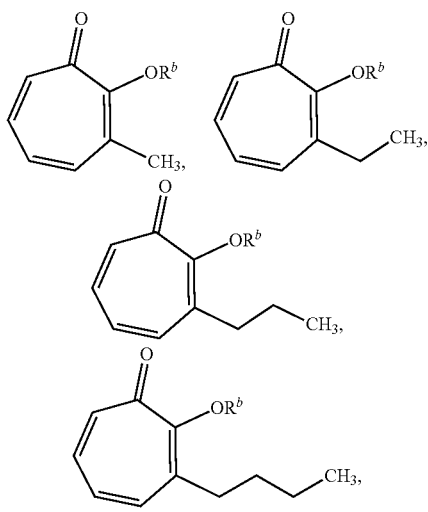
or salt thereof, is selected from the group consisting of:
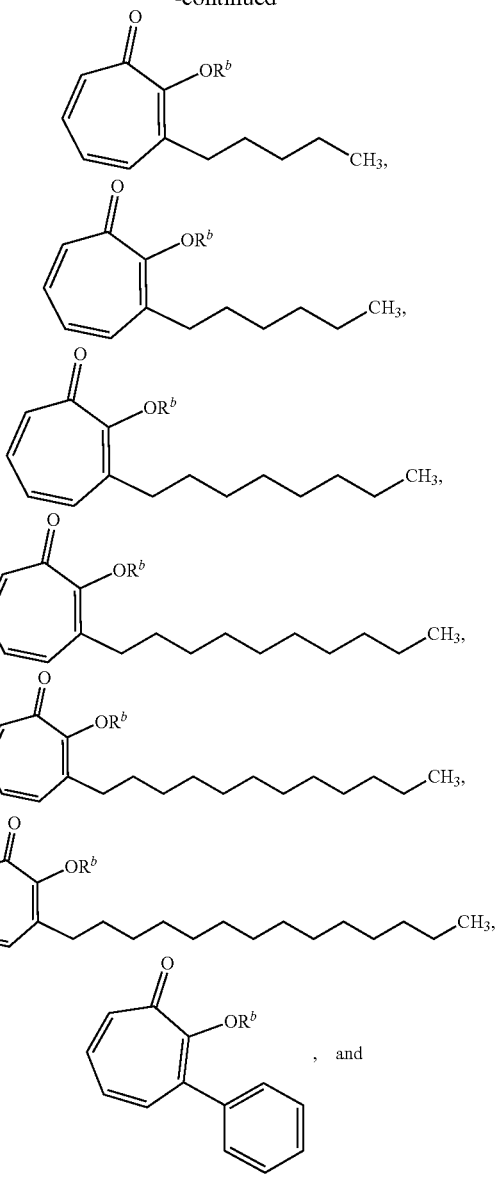
or a salt thereof.
In other embodiments, $R^a$ is selected from the group consisting of
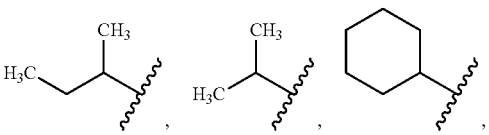

-continued
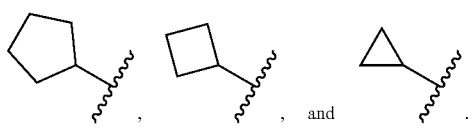
In some such embodiments, the compound of structural formula:
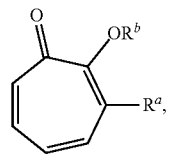
or salt thereof, is selected from the group consisting of:
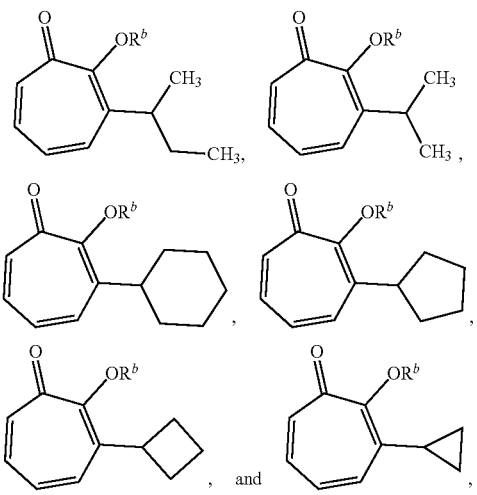
or a salt thereof.
In yet other embodiments, $R^a$ is selected from the group consisting of:
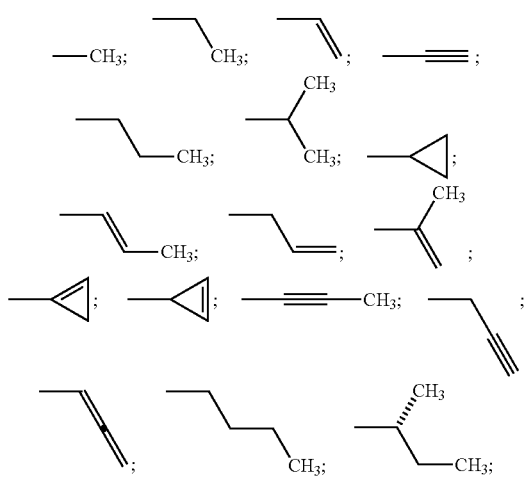
-continued
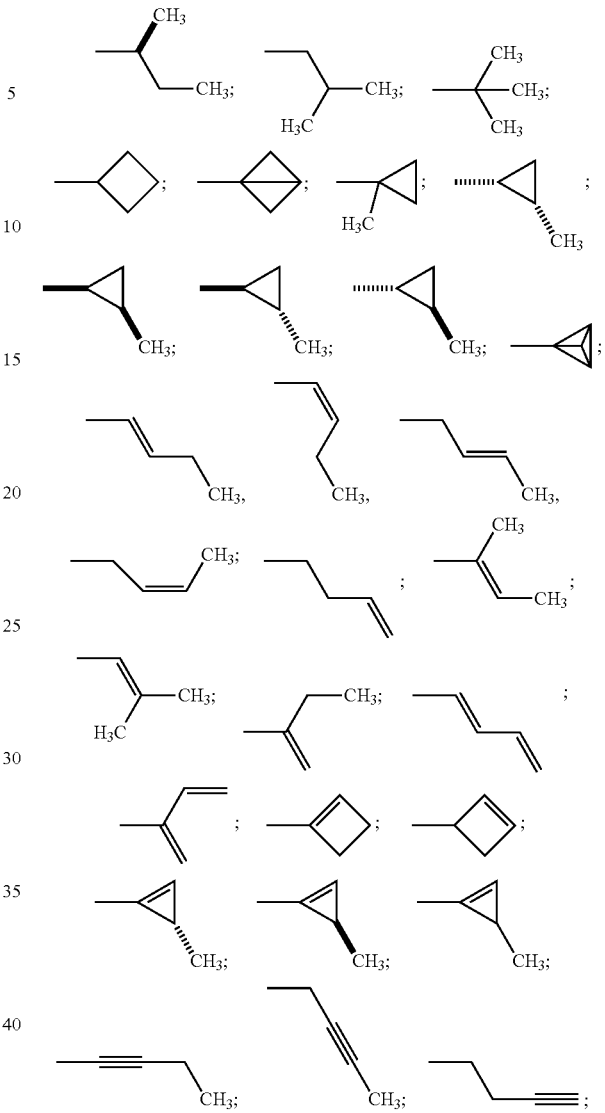
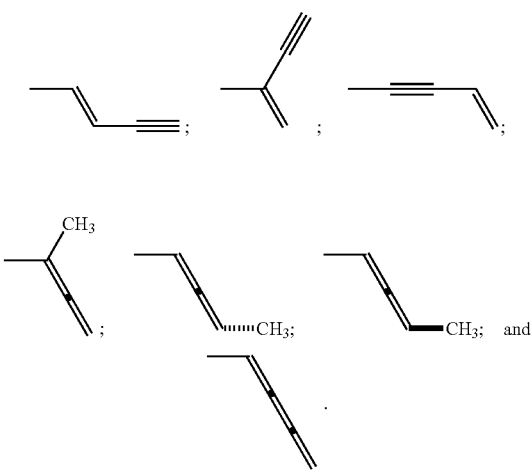
In some such embodiments, the compound of structural formula:

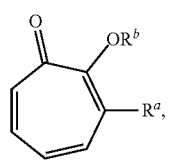
or salt thereof, is selected from the group consisting of:
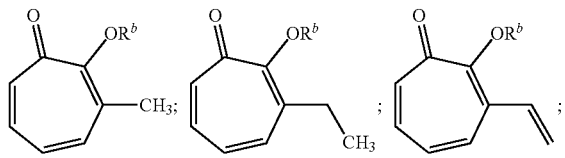
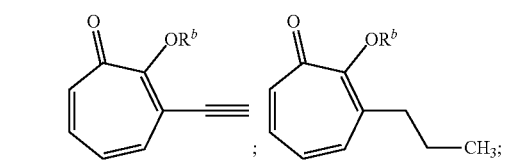
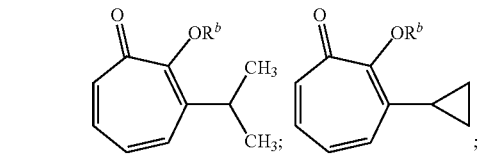
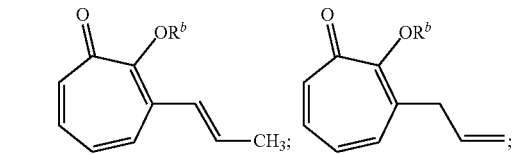
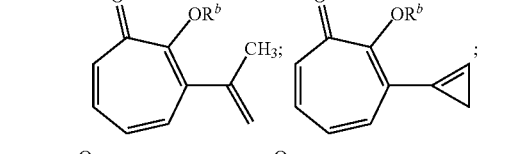
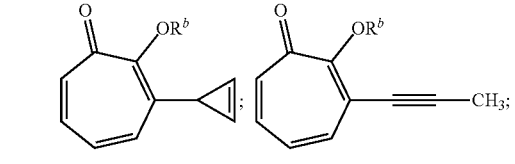
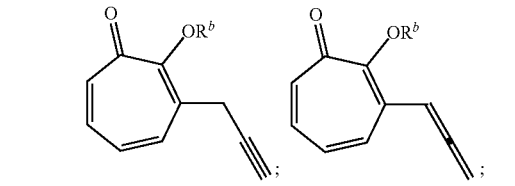
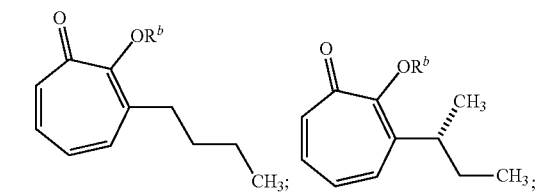
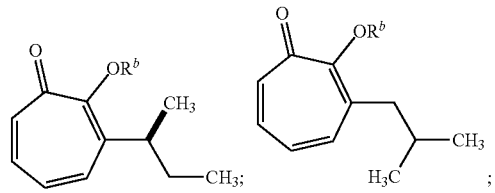
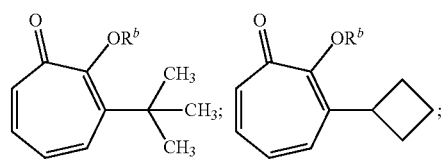
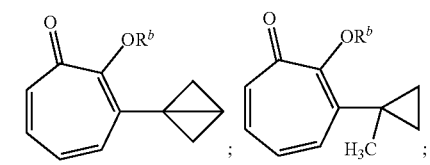
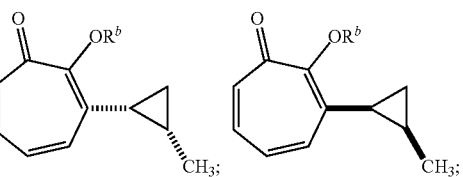
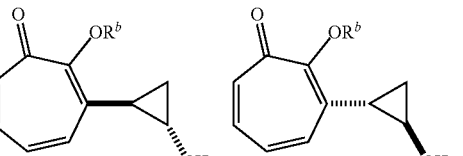
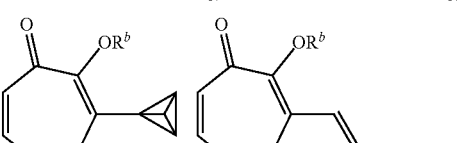
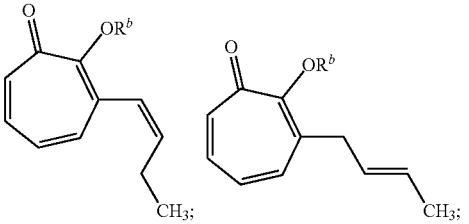
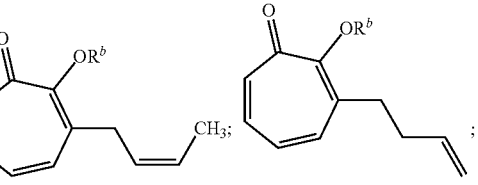
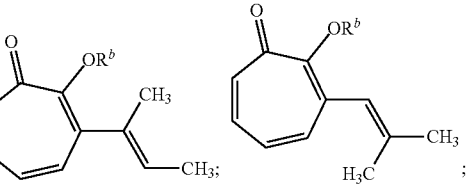

-continued

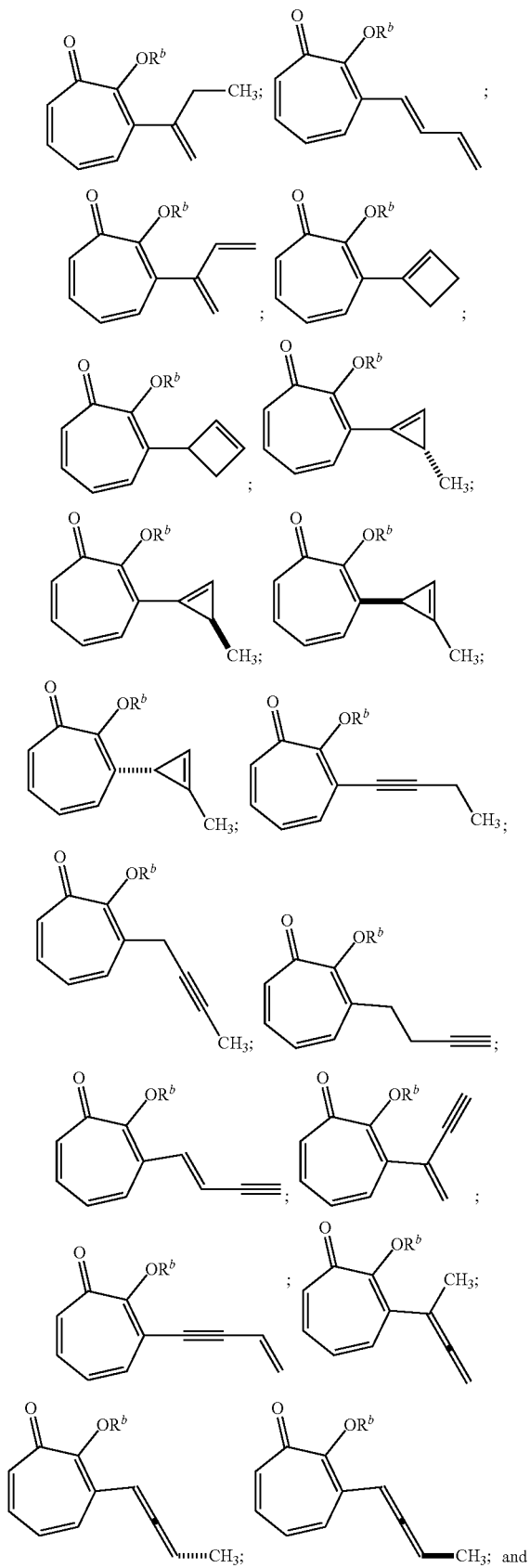

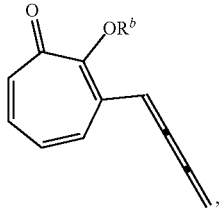

or a salt thereof.

Method I

Also provided herein is a method of preparing a compound of structural formula:

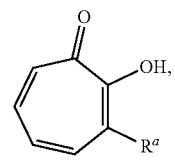

or a salt thereof; comprising combining a compound having structural formula:

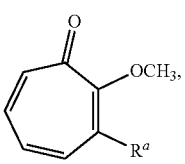

or a salt thereof; with a demethylating agent; thereby providing the compound of structural formula:

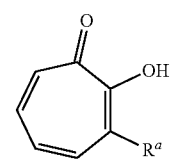

or a salt thereof; wherein $R^a$ is $C_{1-20}$-alkyl, $C_{2-20}$-alkenyl, $C_{2-20}$-alkynyl, $C_{3-9}$-cycloalkyl, aryl, or heteroaryl, each of which is unsubstituted or substituted with a substituent selected from the group consisting of halo, $NO_2$, CN, $C_{1-6}$-alkyl, $C_{1-4}$-haloalkyl, and $C_{1-6}$-alkoxy.

In some embodiments, the demethylating agent is an acid. In some such embodiments, the demethylating agent is a mineral acid, an organic acid, or a combination thereof. In certain embodiments, the demethylating agent is hydrochloric acid, hydrobromic acid, sulfuric acid, acetic acid, or a combination thereof. In preferred embodiments, the demethylating agent is hydrobromic or hydrochloric acid in acetic acid. Alternatively, the demethylating agent is sulfuric acid.

In some embodiments, the compound having structural formula:

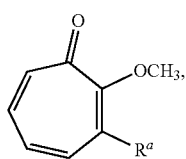

or a salt thereof; is contacted with a demethylating agent and heated to boiling; thereby providing the compound of structural formula:

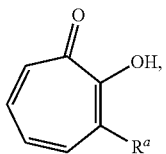

or salt thereof.

In some embodiments, the compound of structural formula:

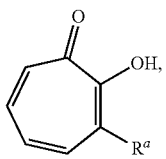

or salt thereof, is selected from:

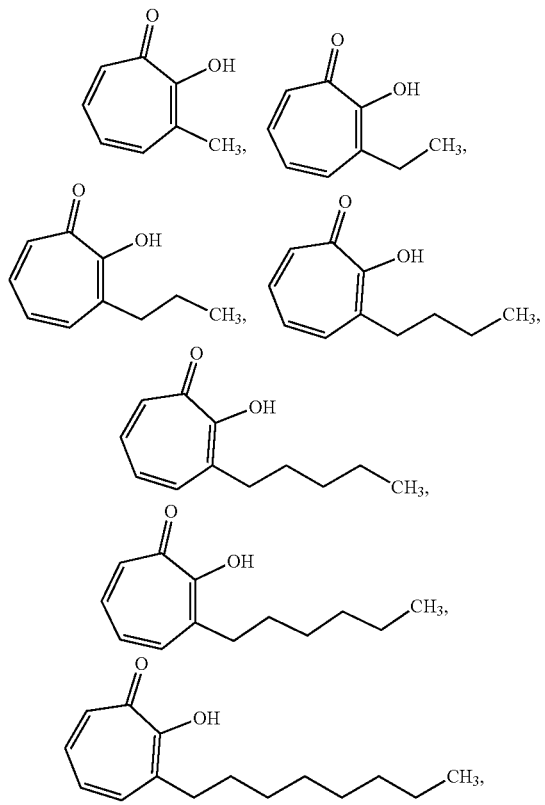

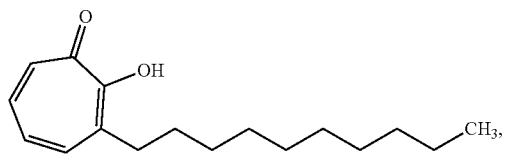

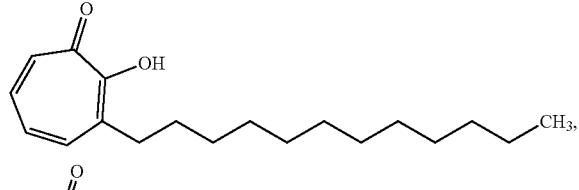

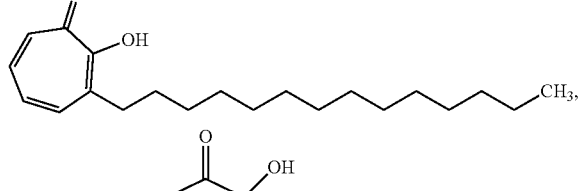

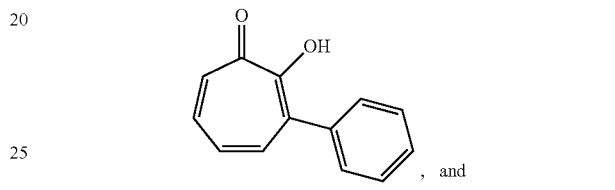

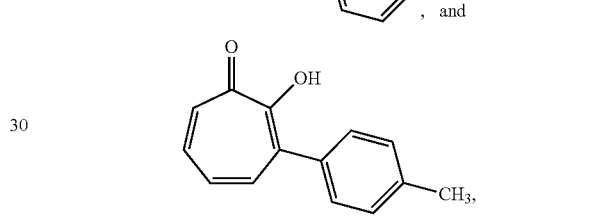, and

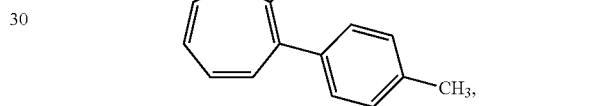

or a salt thereof.

In other embodiments, the compound of structural formula:

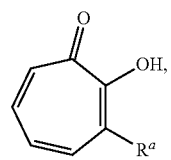

or salt thereof, is selected from the group consisting of:

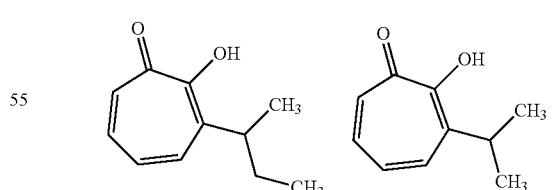

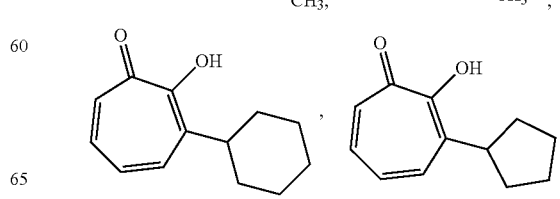

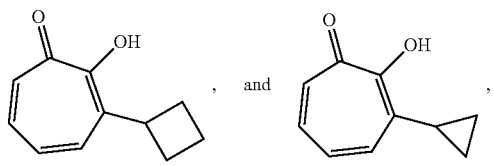
or a salt thereof.
In yet other embodiments, the compound of structural formula:
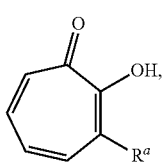
or salt thereof, is selected from the group consisting of:
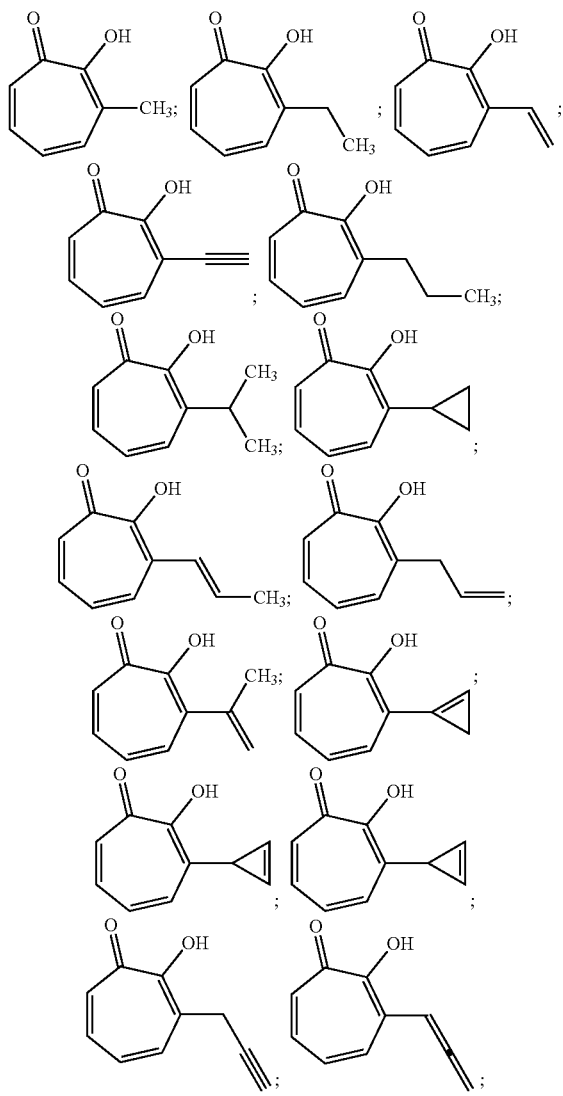
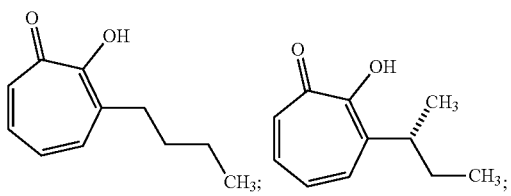
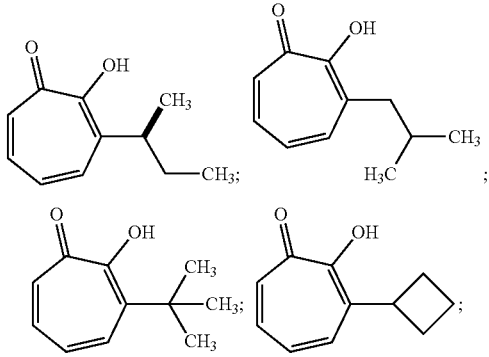
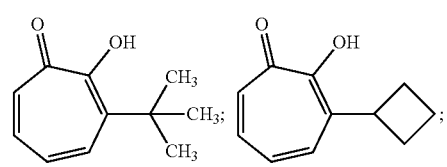
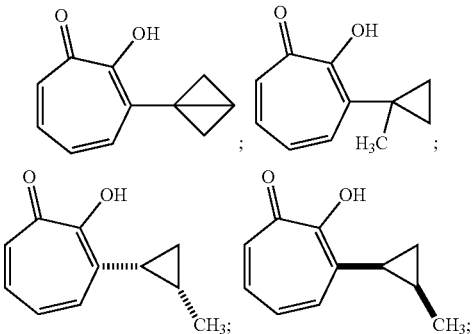
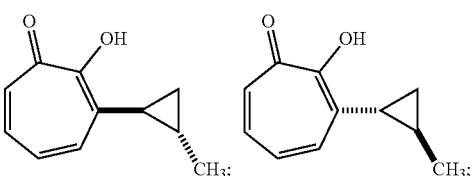
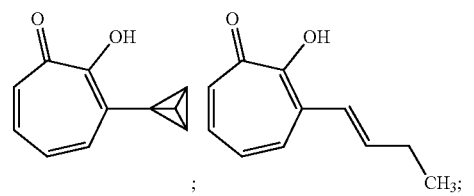
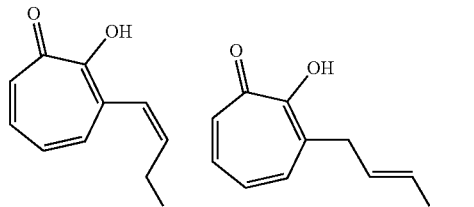
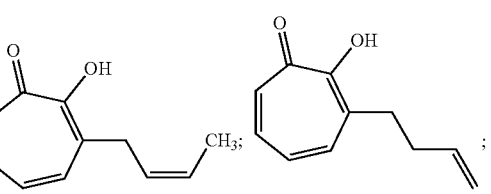

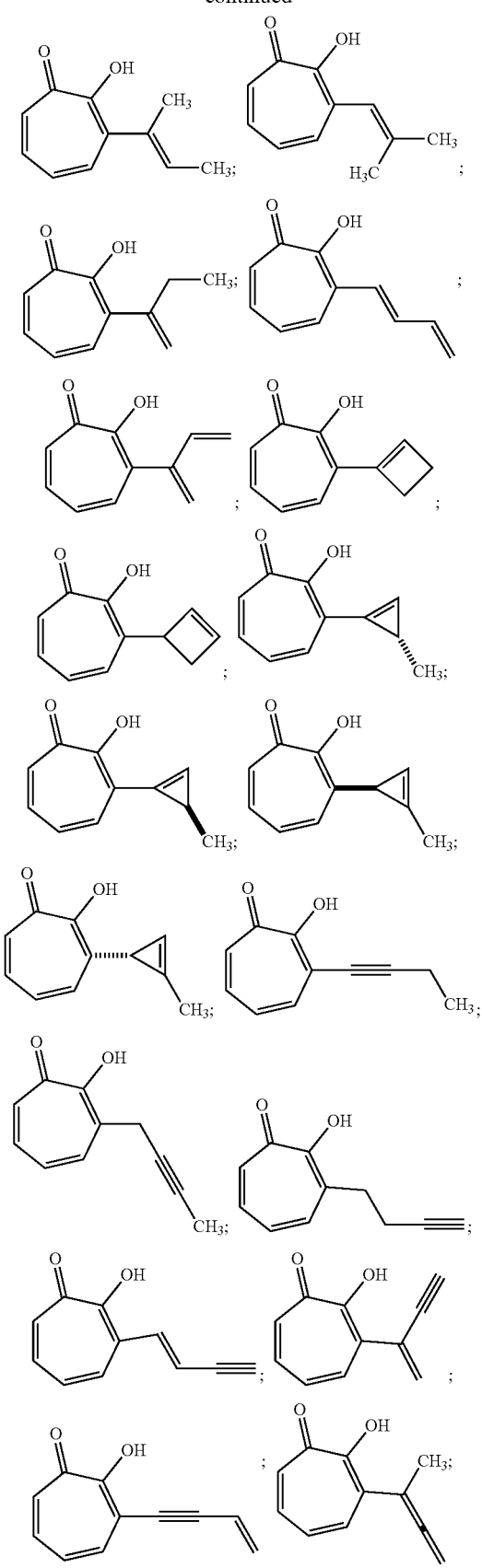

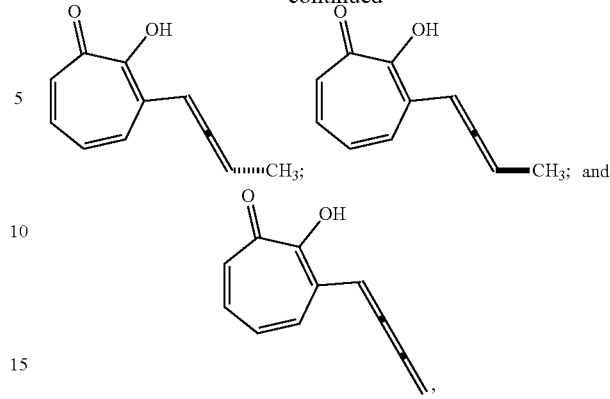

or a salt thereof.

Method J

Also provided herein is a method of preparing a compound of structural formula:

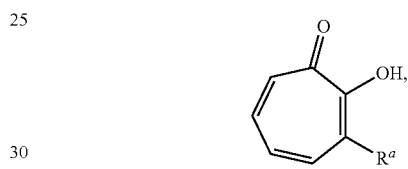

or a salt thereof; comprising:

(1) reacting 2-methoxycyclohepta-2,4,6-trien-1-one:

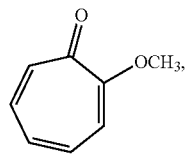

or a salt thereof, with a brominating agent, thereby forming 3-bromo-2-methoxycyclohepta-2,4,6-trien-1-one:

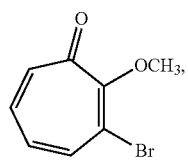 [SMILES: COc1c(Br)ccccc1=O]

or a salt thereof, (2) reacting a compound of structural formula:

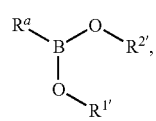

or a salt thereof; with 3-bromo-2-methoxycyclohepta-2,4,6-trien-1-one:

or a salt thereof, thereby forming a compound having structural formula:

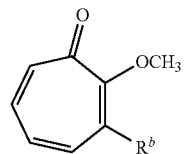

or a salt thereof; and
(3) contacting the compound having structural formula:

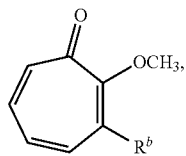

or a salt thereof; with a demethylating agent; thereby providing the compound of structural formula:

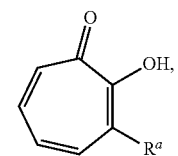

or a salt thereof; wherein
$R^a$ is $C_{1-20}$-alkyl, $C_{2-20}$-alkenyl, $C_{2-20}$-alkenyl, $C_{3-9}$-cycloalkyl, aryl, or heteroaryl, each of which is unsubstituted or substituted with a substituent selected from the group consisting of halo, $NO_2$, CN, $C_{1-6}$-alkyl, $C_{1-6}$-haloalkyl, and $C_{1-6}$-alkoxy;
$R^{1'}$ and $R^{2'}$ are each, independently hydrogen or $C_{1-6}$-alkyl; or
$R^{1'}$ and $R^{2'}$, together with atoms to which they are attached, form a ring having 2 to 4 carbon atoms, each of which is optionally and independently substituted with $C_{1-3}$-alkyl or C=O; and
B is a boron atom having $sp^3$ hybridization.

In some embodiments, step (2) of the method further comprises contacting the reacting compounds with a metal catalyst. In some such embodiments, the metal catalyst is a palladium catalyst or a palladium nanomaterial-based catalyst. In certain embodiments, the metal catalyst is an organopalladium catalyst. In particular embodiments, the metal catalyst is selected from the group consisting of tetrakis(triphenylphosphine)palladium(0), palladium chloride, and palladium(II) acetate.

In some embodiments, the reaction with comprising the metal catalyst further comprises a promoter. In some such embodiments, the promoter is thallium (I) ethoxide or silver oxide. In preferred embodiments, the promoter is silver oxide.

In some embodiments, the demethylating agent is an acid. In some such embodiments, the demethylating agent is a mineral acid, an organic acid, or a combination thereof. In certain embodiments, the demethylating agent is hydrochloric acid, hydrobromic acid, sulfuric acid, acetic acid, or a combination thereof. In preferred embodiments, the demethylating agent is hydrobromic or hydrochloric acid in acetic acid. Alternatively, the demethylating agent is sulfuric acid.

In some embodiments, $R^{1'}$ and $R^{2'}$ are both hydrogen.

In some embodiments, $R^a$ is $C_{1-4}$-alkyl, $C_{2-4}$-alkenyl, $C_{2-4}$-alkynyl, or $C_{3-4}$-cycloalkyl.

In some such embodiments, $R^a$ is selected from the group consisting of:

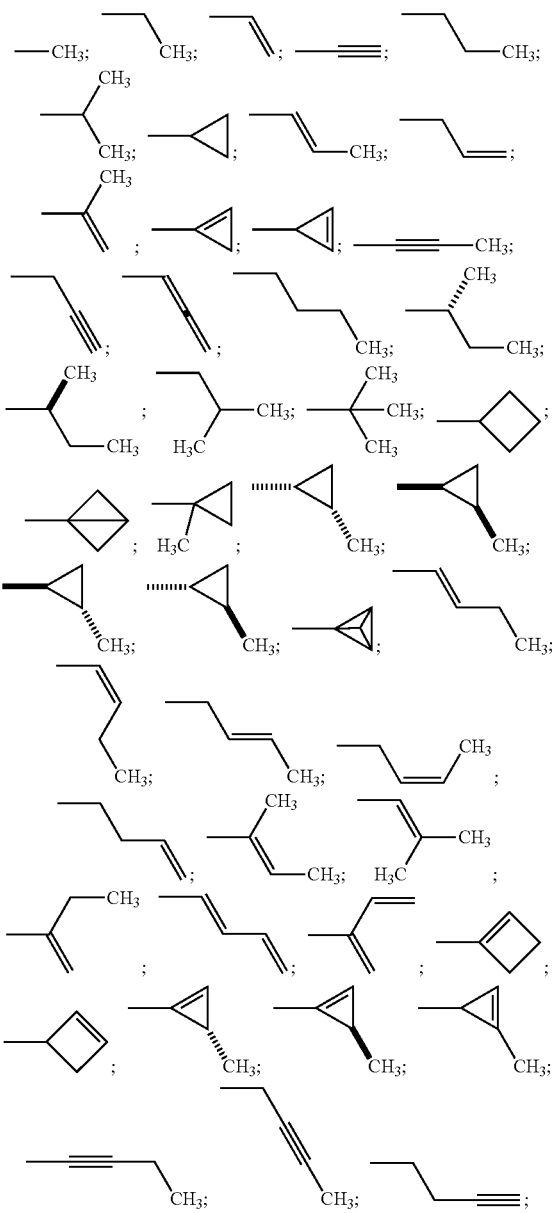

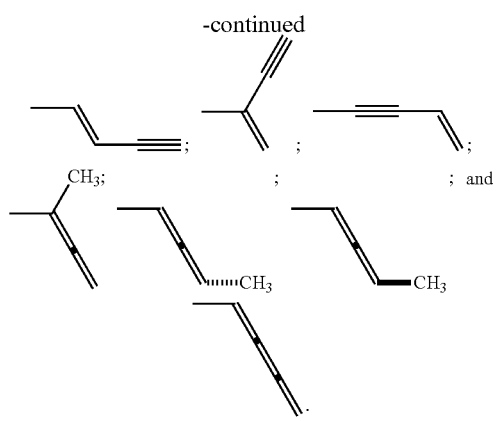
In some such embodiments, the compound of structural formula or salt thereof:
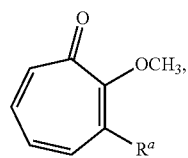
is selected from the group consisting of:
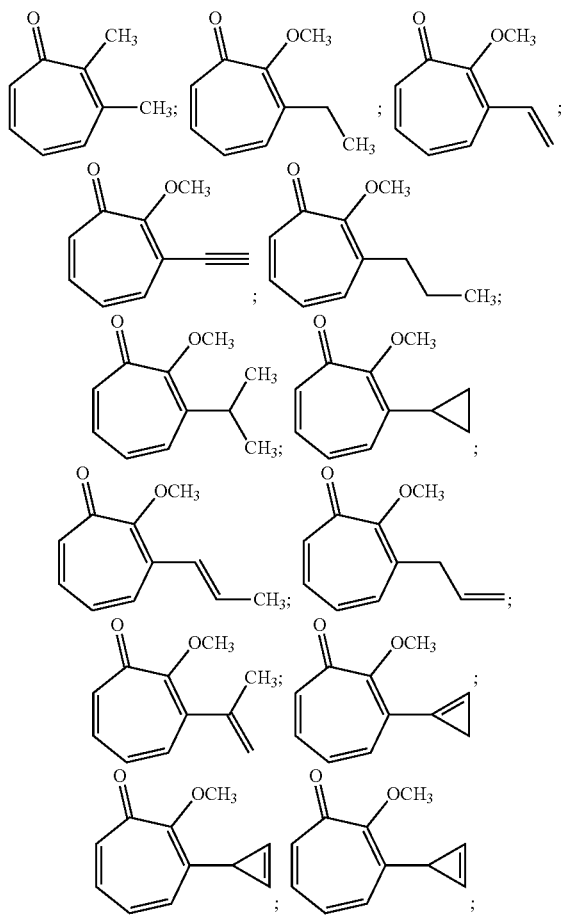
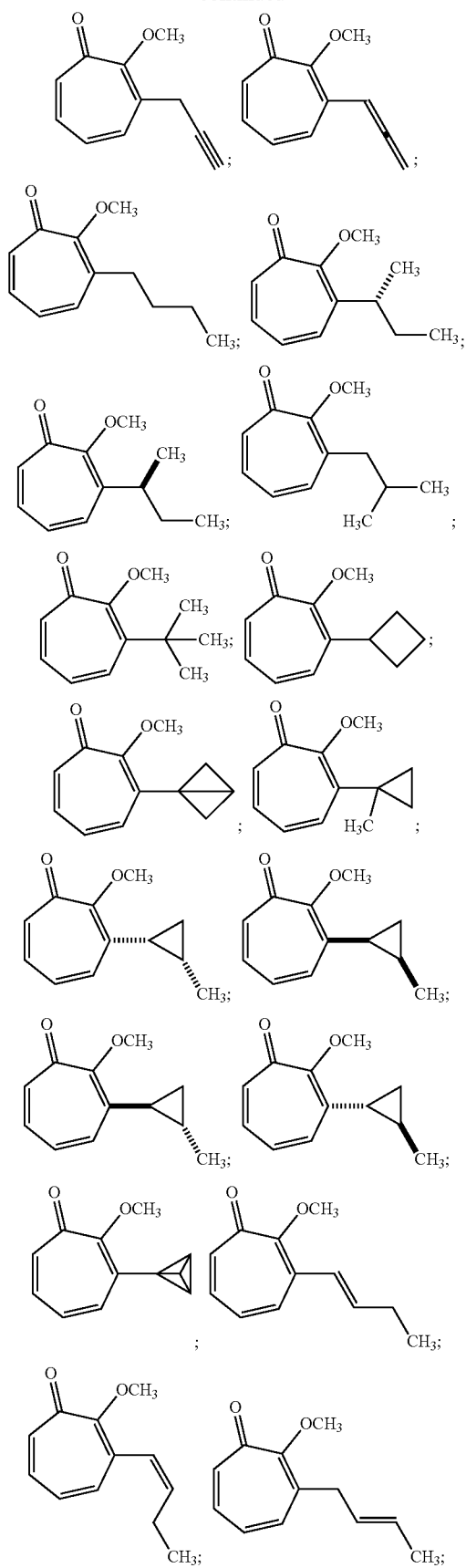

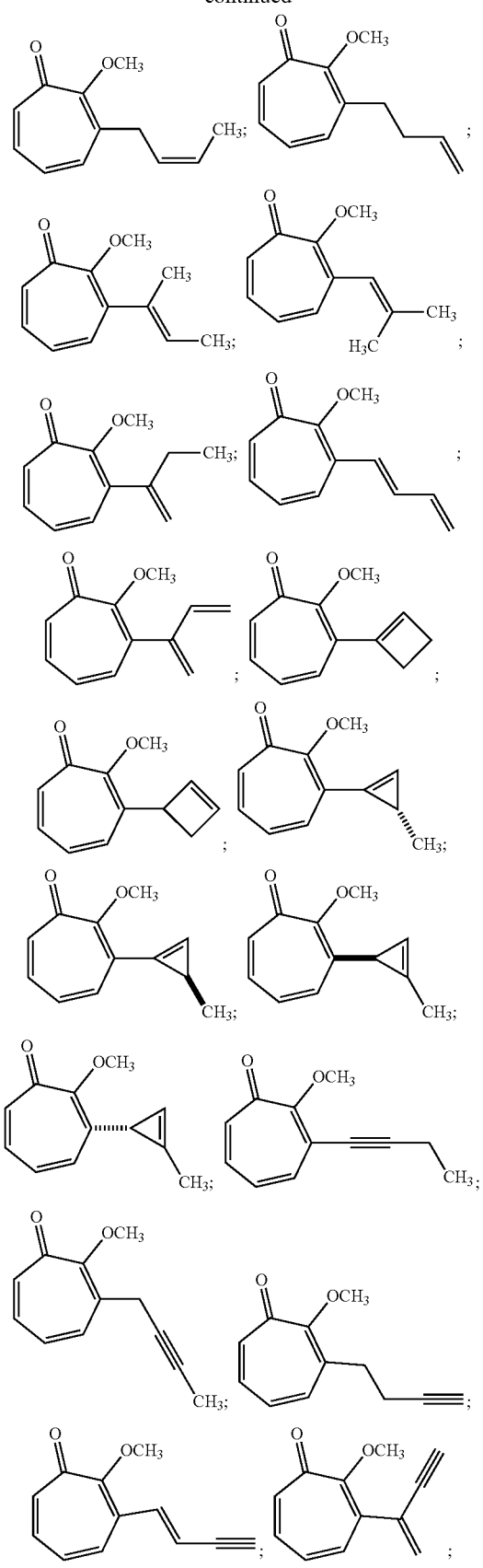
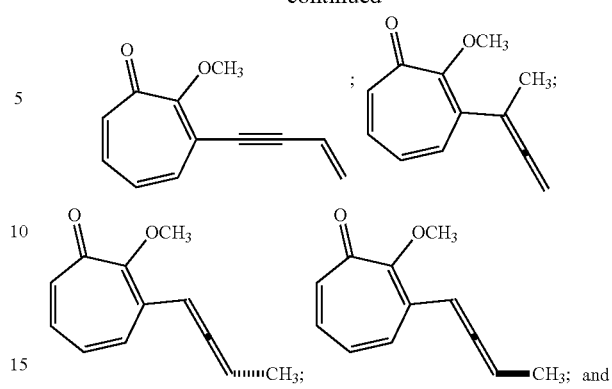
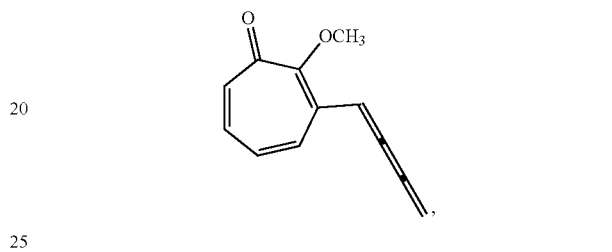
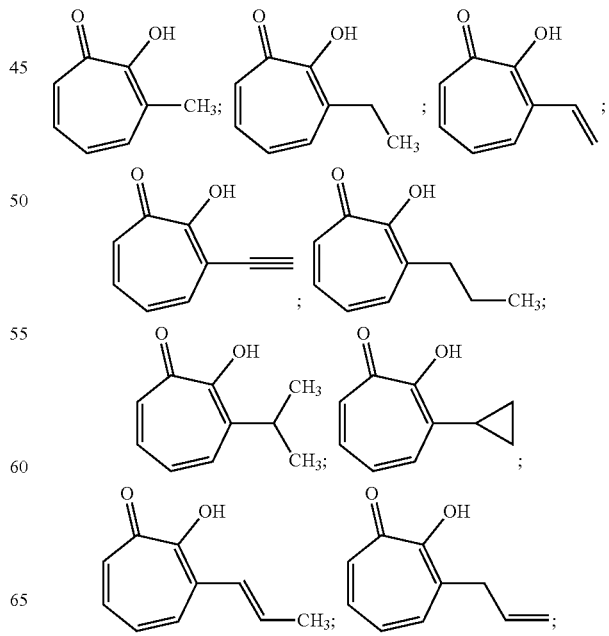
or a salt thereof.
In some embodiments, the compound of structural formula:
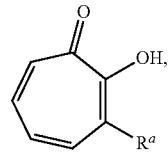
or salt thereof, is selected from:

125
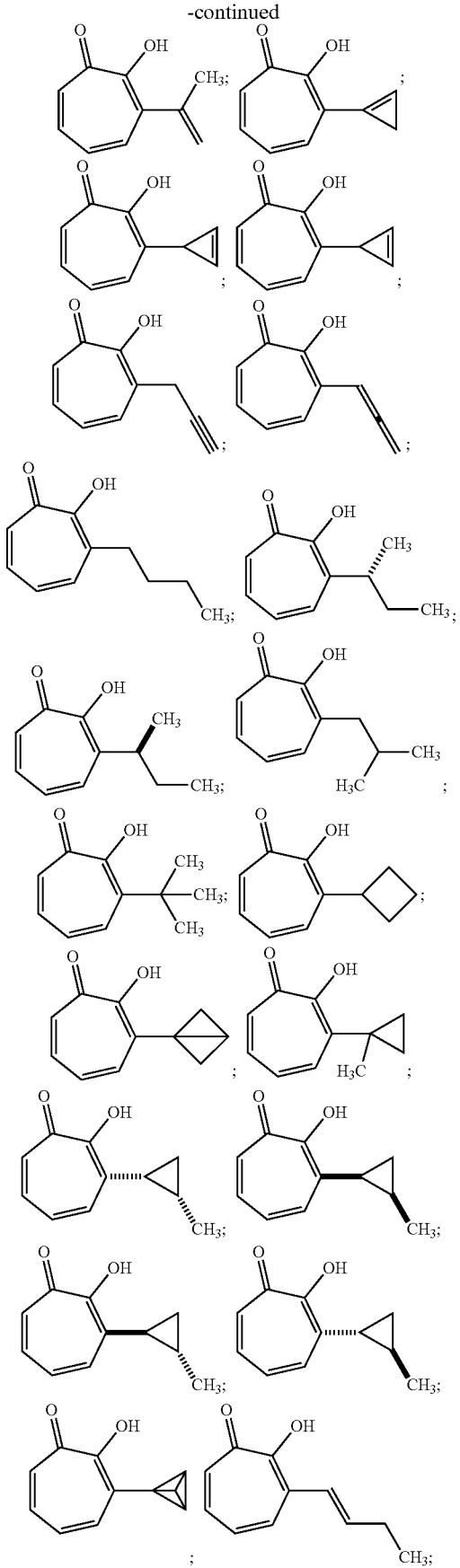
126
-continued
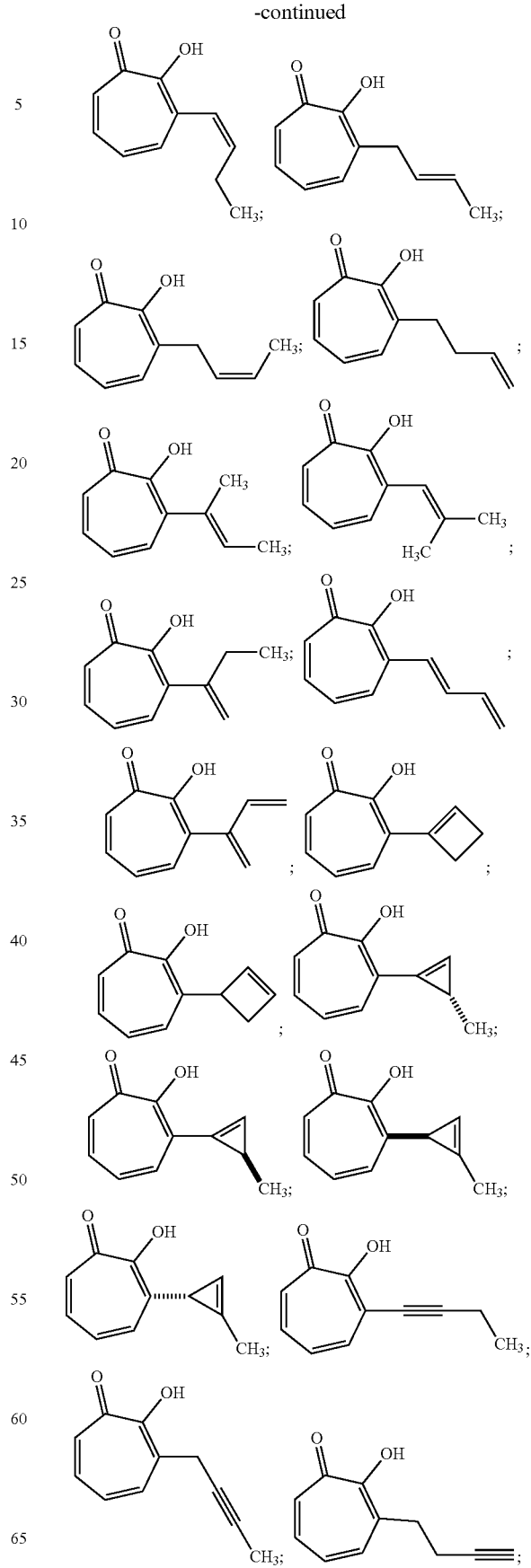

-continued
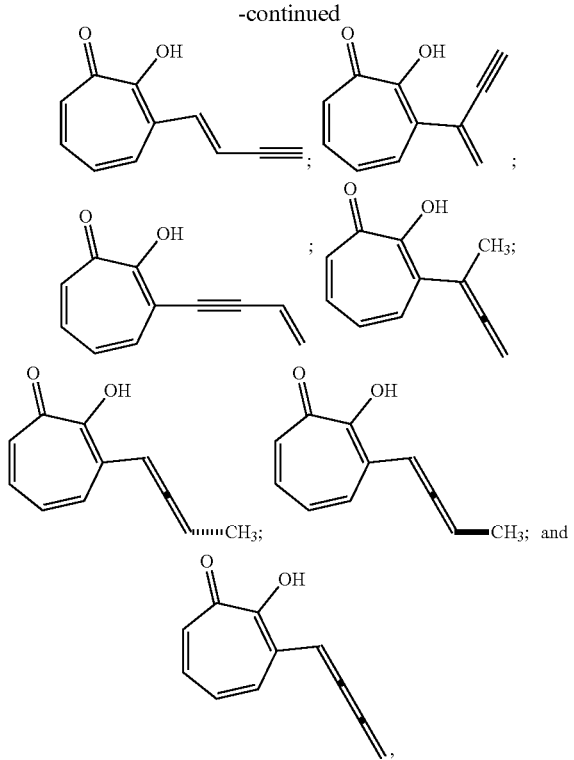
or a salt thereof.
In some other embodiments, $R^a$ is selected from the group consisting of:
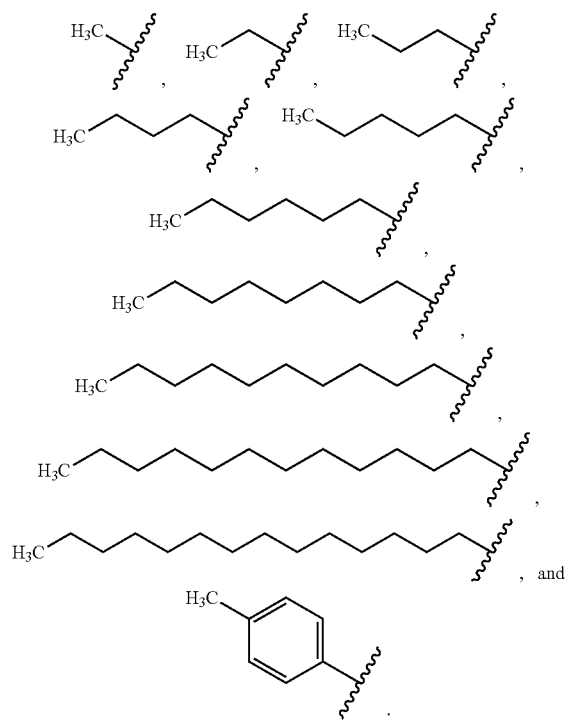
In some such embodiments, the compound of structural formula:
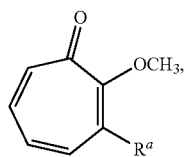
or salt thereof, is selected from the group consisting of:
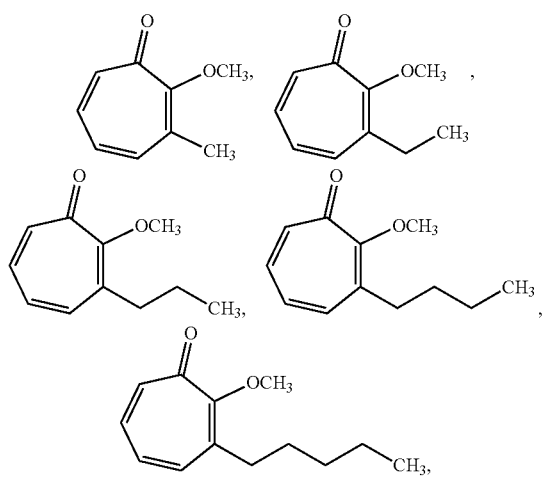
or a salt thereof.

In some embodiments, the compound of structural formula:

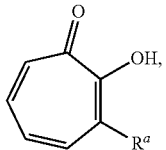

or salt thereof, is selected from:

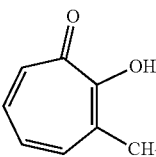 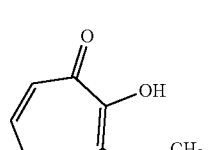

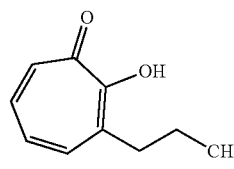 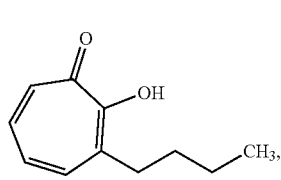

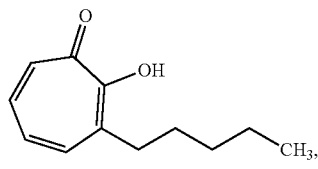

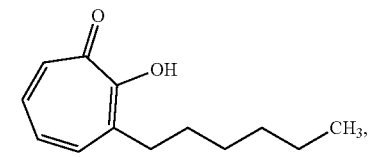

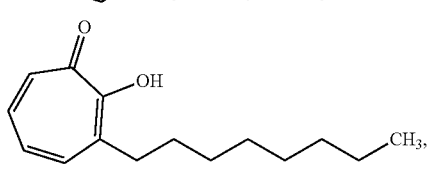

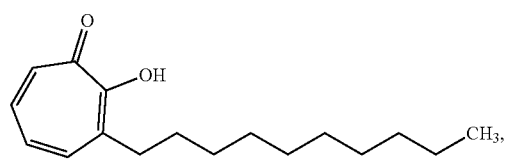

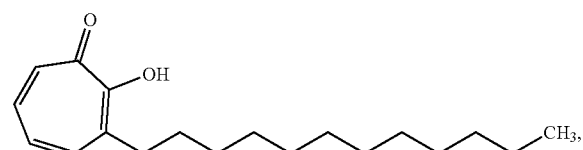

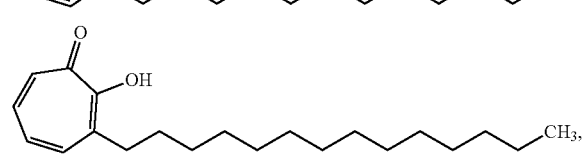

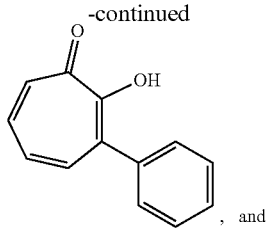, and

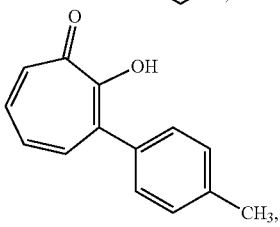

or a salt thereof.

In other embodiments, $R^a$ is selected from the group consisting of

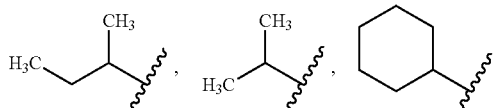

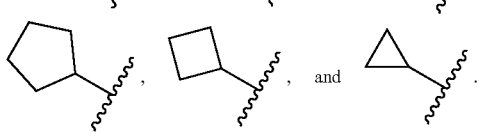

In some such embodiments, the compound of structural formula:

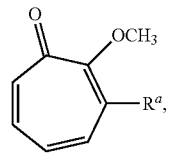

or salt thereof, is selected from the group consisting of:

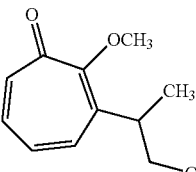 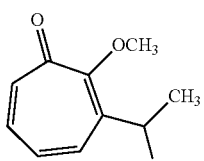

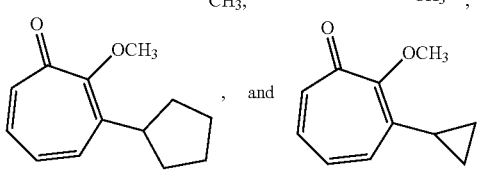

or a salt thereof.

In some embodiments, the compound of structural formula:

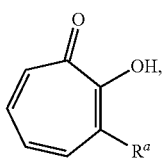

or salt thereof, is selected from the group consisting of:

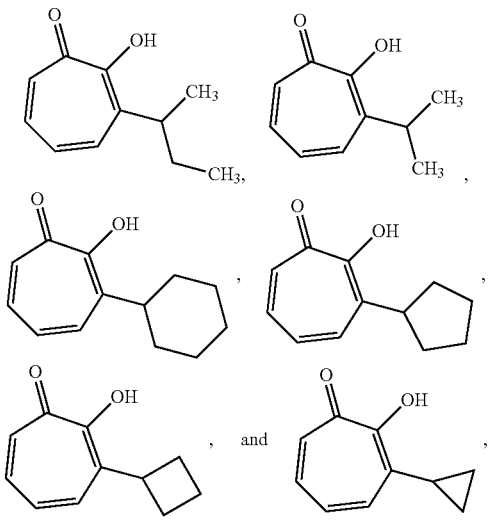

or a salt thereof.

Method K

Also provided herein is a method of preparing a compound of structural formula:

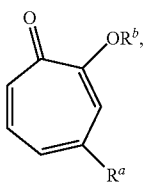

or a salt thereof; comprising reacting a compound of structural formula:

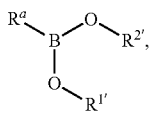

or a salt thereof; with a compound of structural formula:

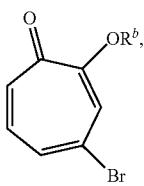

or a salt thereof; thereby providing the compound of structural formula:

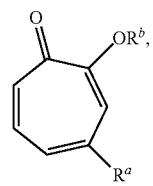

or a salt thereof; wherein $R^a$ is $C_{1-20}$-alkyl, $C_{2-20}$-alkenyl, $C_{2-20}$-alkynyl, $C_{3-9}$-cycloalkyl, aryl, or heteroaryl, each of which is unsubstituted or substituted with a substituent selected from the group consisting of halo, $NO_2$, CN, $C_{1-6}$-alkyl, $C_{1-6}$-haloalkyl, and $C_{1-6}$-alkoxy;

$R^b$ is hydrogen or methyl;

$R^{1'}$ and $R^{2'}$ are each, independently hydrogen or $C_{1-6}$-alkyl; or $R^{1'}$ and $R^{2'}$, together with atoms to which they are attached, form a ring having 2 to 4 carbon atoms, each of which is optionally and independently substituted with $C_{1-3}$-alkyl or C=O; and B is a boron atom having $sp^3$ hybridization.

In some embodiments, the method further comprises contacting the compounds with a metal catalyst. In some such embodiments, the metal catalyst is a palladium catalyst or a palladium nanomaterial-based catalyst. In certain embodiments, the metal catalyst is an organopalladium catalyst. In particular embodiments, the metal catalyst is selected from the group consisting of tetrakis(triphenylphosphine)palladium(0), palladium chloride, and palladium(II) acetate.

In some embodiments, the reaction with comprising the metal catalyst further comprises a promoter. In some such embodiments, the promoter is thallium (I) ethoxide or silver oxide. In preferred embodiments, the promoter is silver oxide.

In some embodiments, $R^{1'}$ and $R^{2'}$ are both hydrogen.

In some embodiments, $R^a$ is $C_{1-4}$-alkyl, $C_{2-4}$-alkenyl, $C_{2-4}$-alkynyl, or $C_{3-4}$-cycloalkyl. In some such embodiments, $R^a$ is selected from the group consisting of:

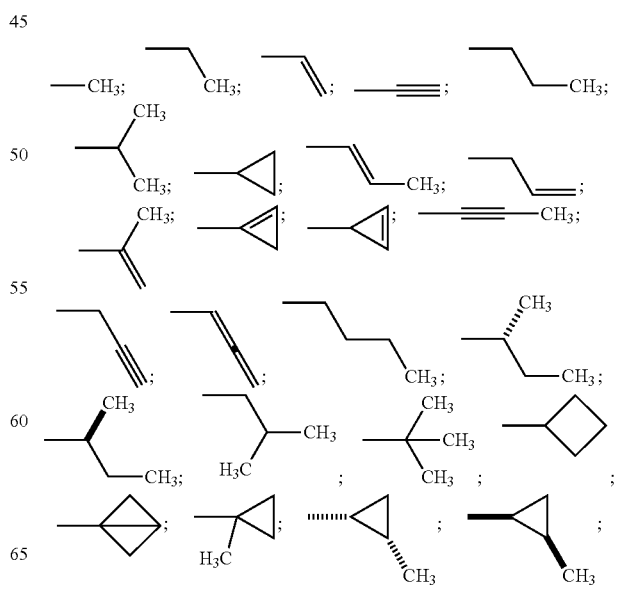

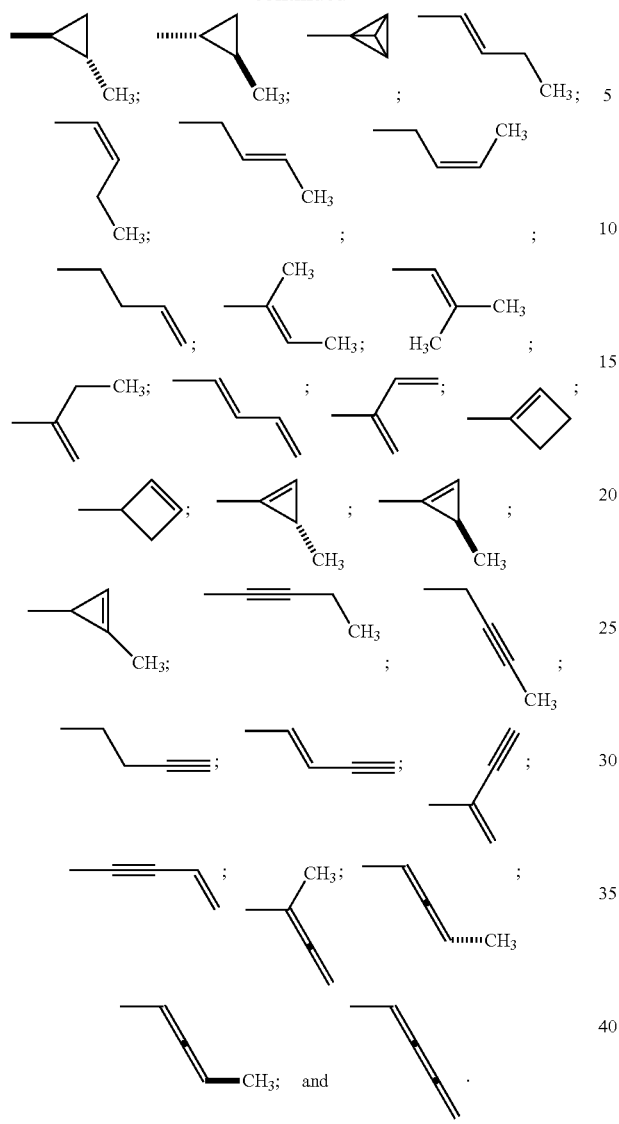
In some such embodiments, the
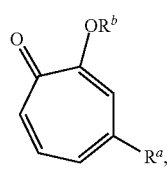
or salt thereof, is selected from the group consisting of:
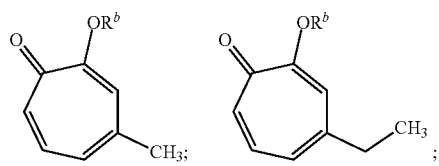
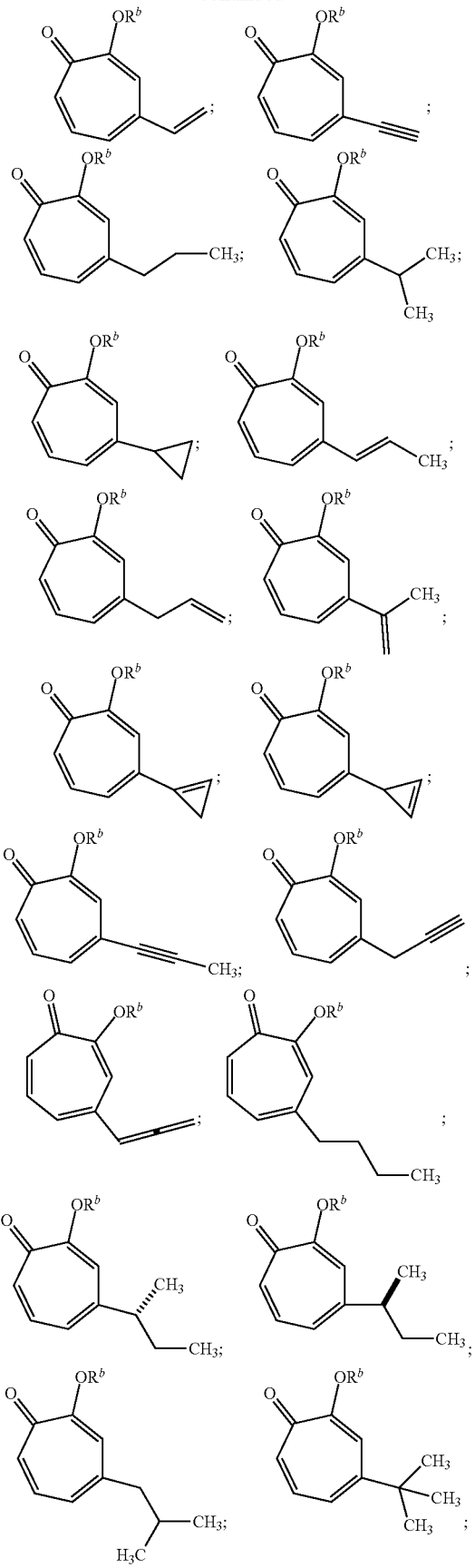

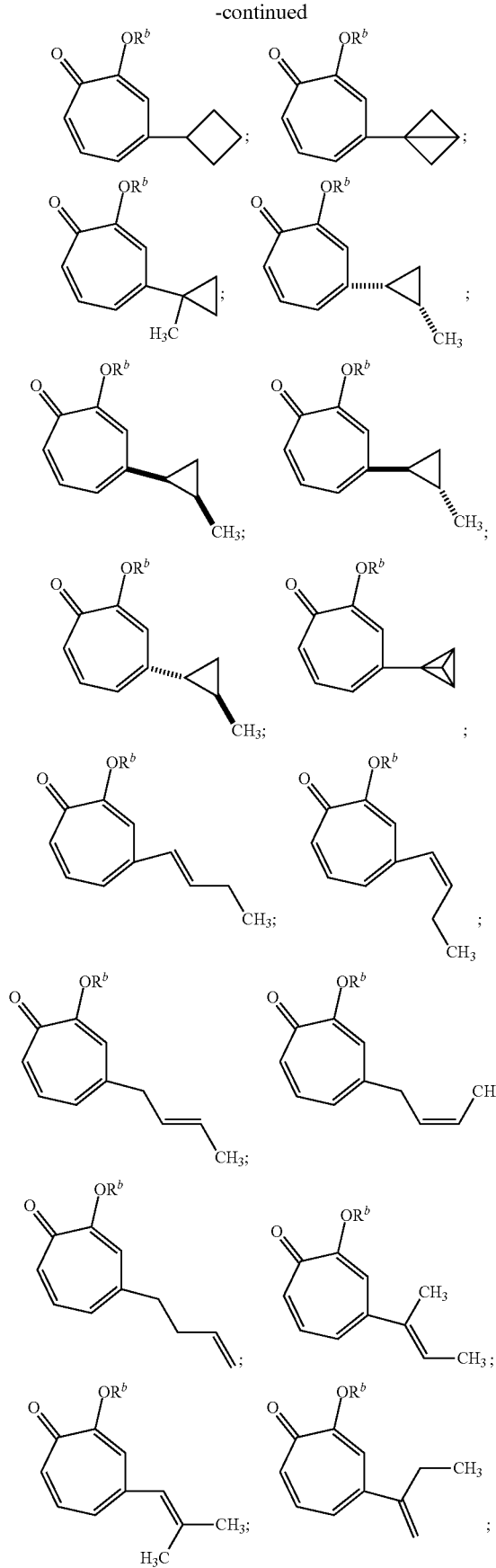
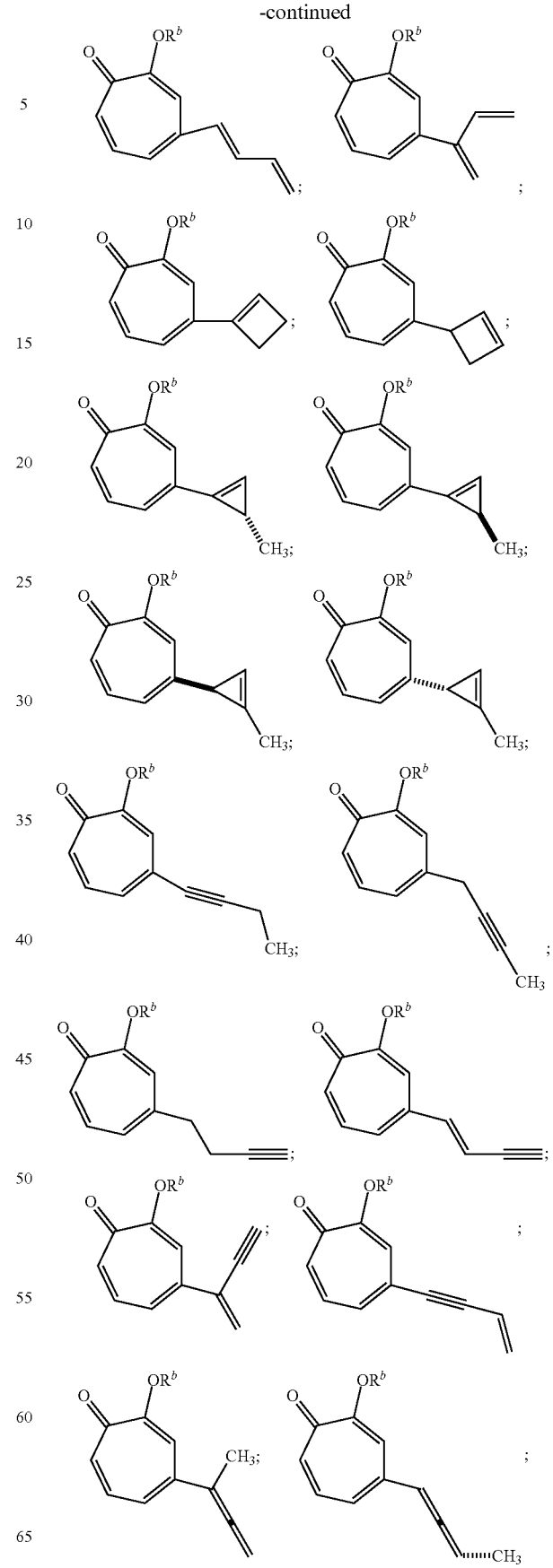

-continued
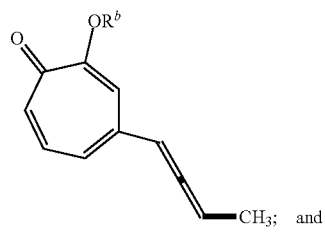 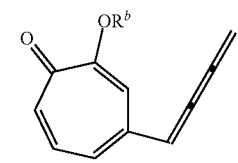
or a salt thereof.
In some other embodiments, $R^a$ is selected from the group consisting of:
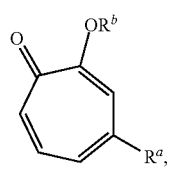
In some such embodiments, the compound of structural formula:
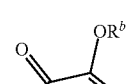
or salt thereof, is selected from the group consisting of:
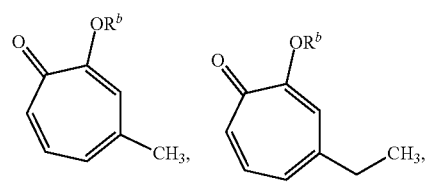
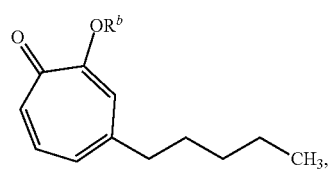
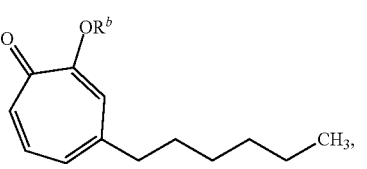
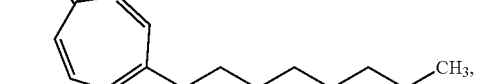
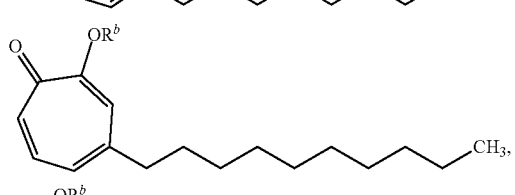
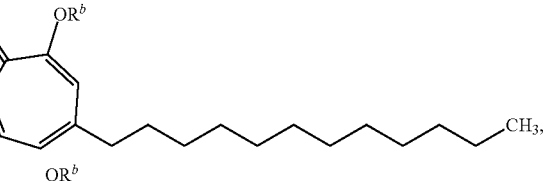
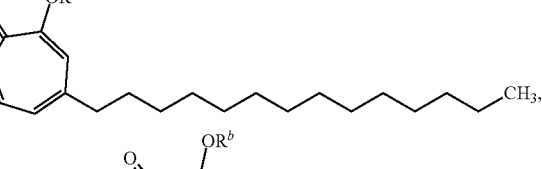
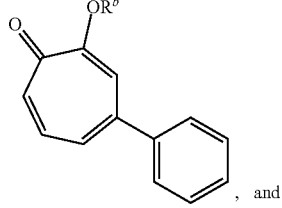

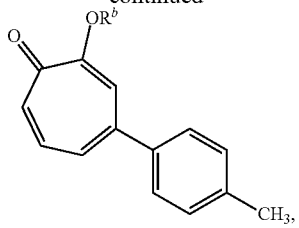

or a salt thereof.

In other embodiments, $R^a$ is selected from the group consisting of

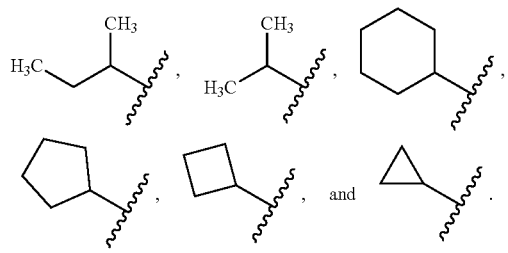

In some such embodiments, the compound of structural formula:

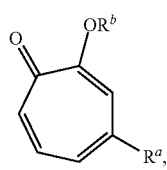

or salt thereof, is selected from the group consisting of:

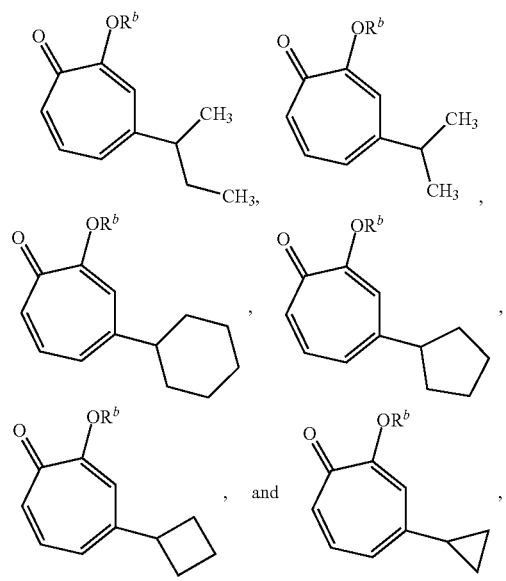

or a salt thereof.

Method L

Also provided herein is a method of preparing a compound of structural formula:

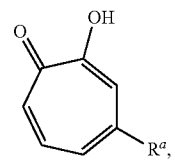

or a salt thereof; comprising combining a compound having structural formula:

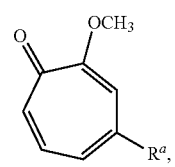

or a salt thereof; with a demethylating agent; thereby providing the compound of structural formula:

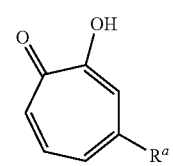

or a salt thereof; wherein $R^a$ is $C_{1-20}$-alkyl, $C_{2-20}$-alkenyl, $C_{2-20}$-alkynyl, $C_{3-9}$-cycloalkyl, aryl, or heteroaryl, each of which is unsubstituted or substituted with a substituent selected from the group consisting of halo, $NO_2$, CN, $C_{1-6}$-alkyl, $C_{1-6}$-haloalkyl, and $C_{1-6}$-alkoxy.

In some embodiments, the demethylating agent is an acid. In some such embodiments, the demethylating agent is a mineral acid, an organic acid, or a combination thereof. In certain embodiments, the demethylating agent is hydrochloric acid, hydrobromic acid, sulfuric acid, acetic acid, or a combination thereof. In preferred embodiments, the demethylating agent is hydrobromic or hydrochloric acid in acetic acid. Alternatively, the demethylating agent is sulfuric acid.

In some embodiments, the compound having structural formula:

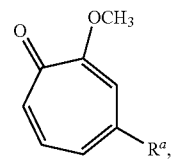

or a salt thereof; is contacted with a demethylating agent and heated to boiling; thereby providing the compound of structural formula:

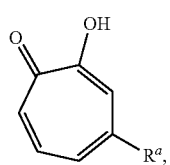
or salt thereof.
In some embodiments, the compound of structural formula:
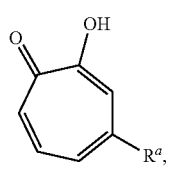
or salt thereof, selected from:
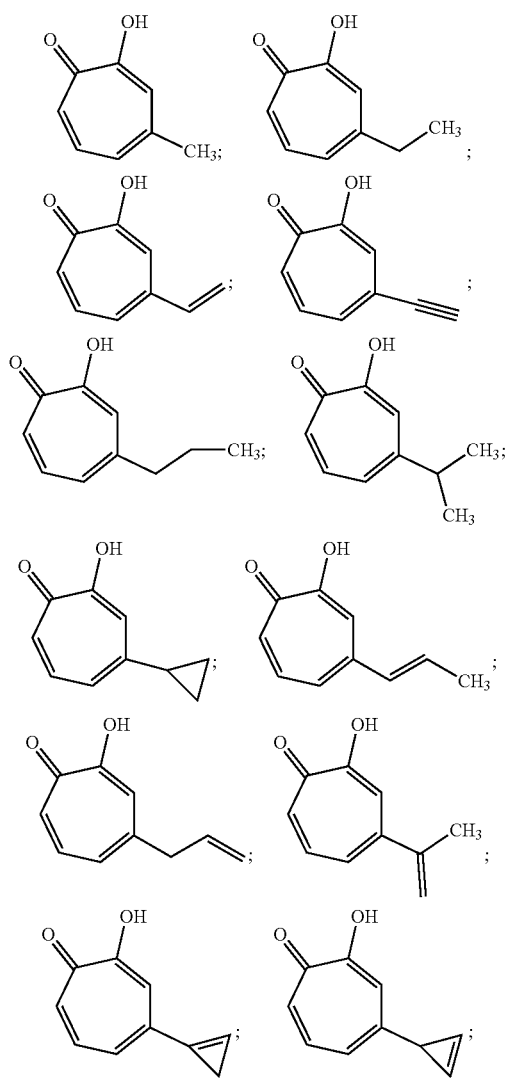
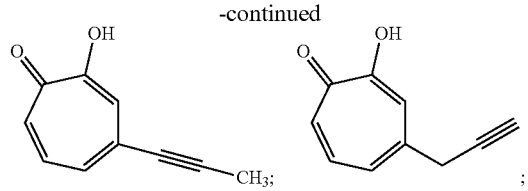
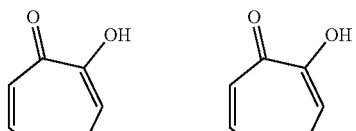
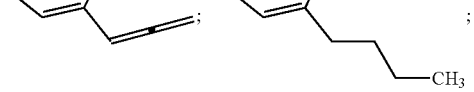
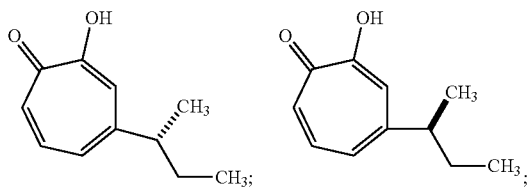
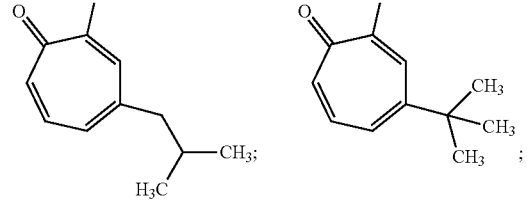
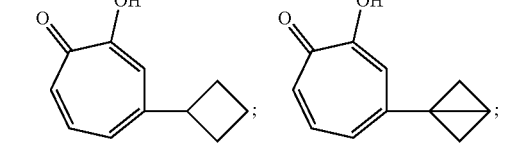
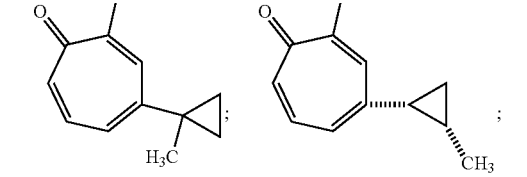
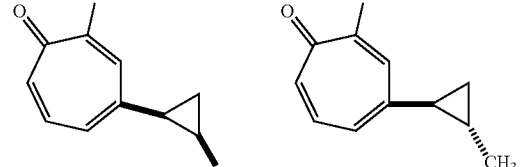
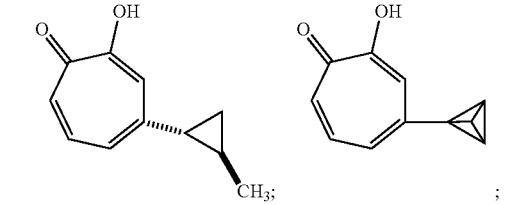

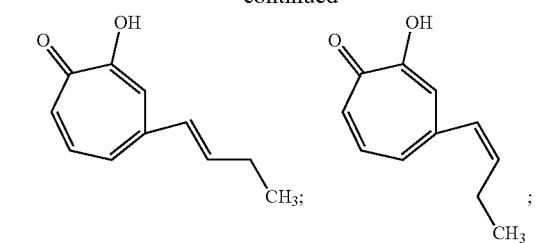
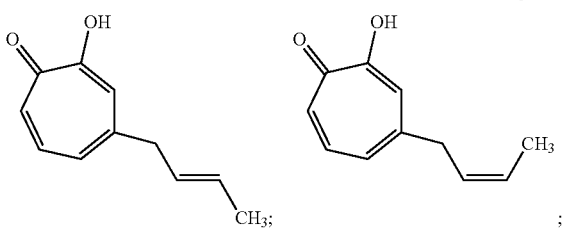
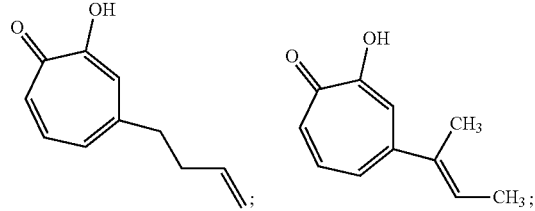
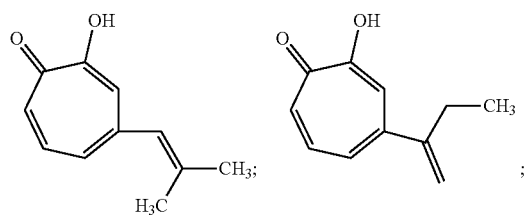
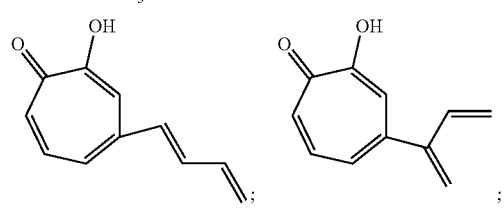
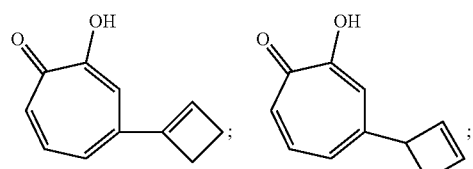
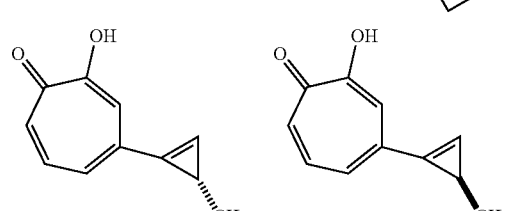
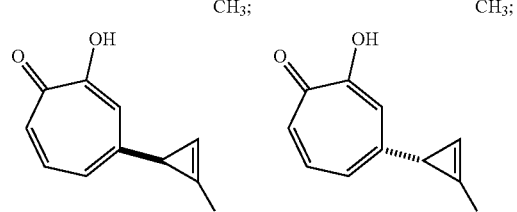
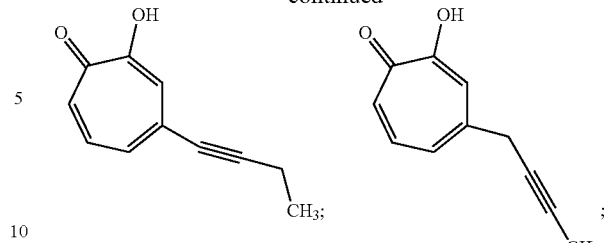
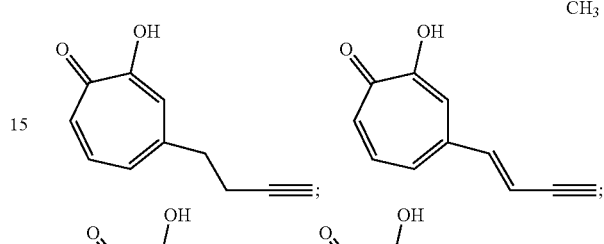
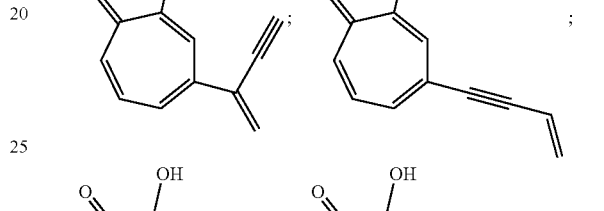
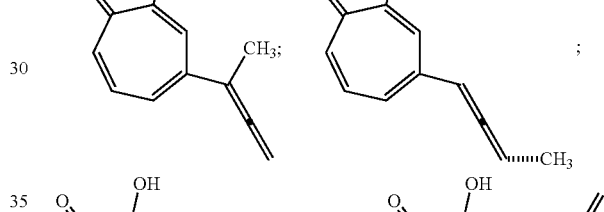
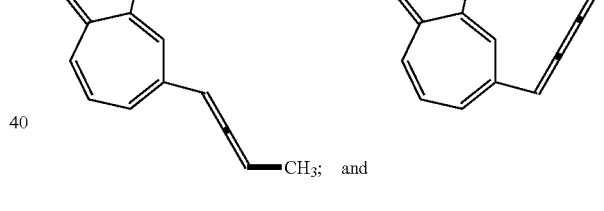
or a salt thereof.
In some other embodiments, the compound of structural formula:
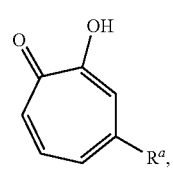
or salt thereof, is selected from:
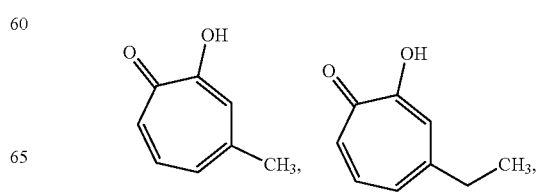

-continued

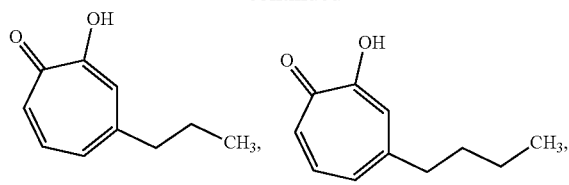

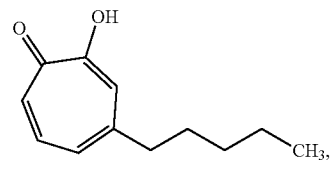

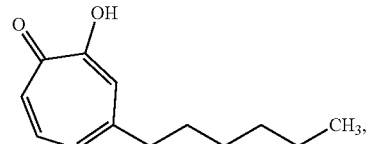

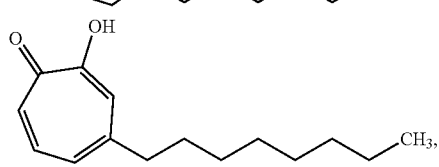

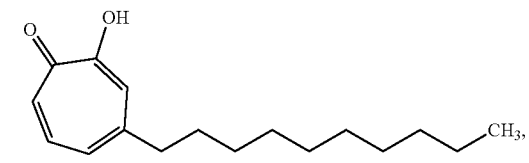

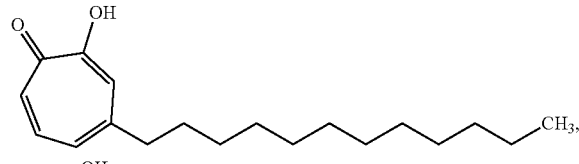

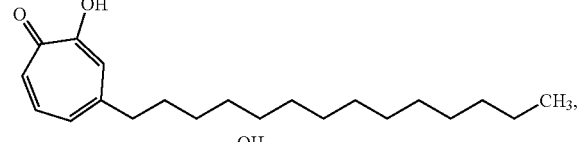

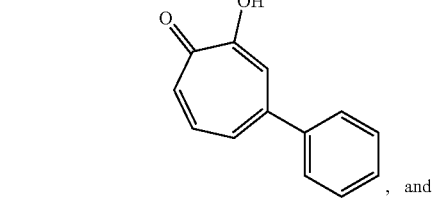, and

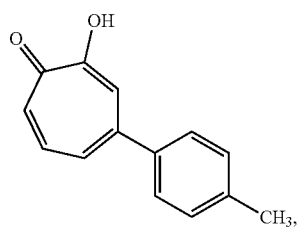

or a salt thereof.

In other embodiments, the compound of structural formula:

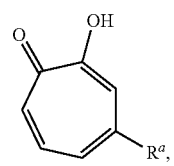

or salt thereof, is selected from the group consisting of:

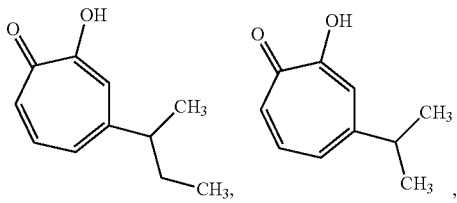

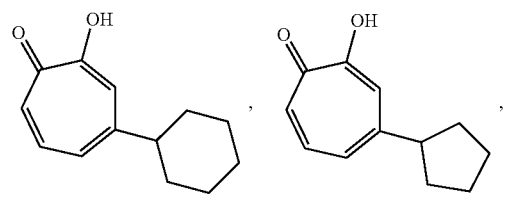

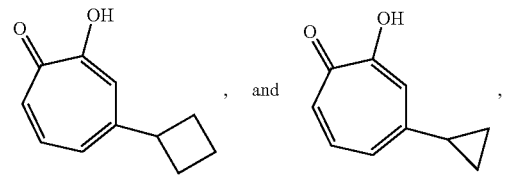, and or a salt thereof.

Method M

Also provided herein is a method of preparing a compound of structural formula:

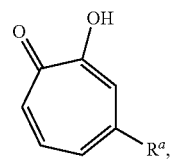

or a salt thereof; comprising:

(1) contacting 7,7-dibromobicyclo[4.1.0]heptane-2,3-diol:

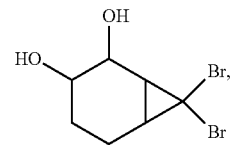 [SMILES: OC1CCC2C(C1O)C2(Br)Br]

or a salt thereof, with an oxidizing agent, thereby forming 4-bromo-2-hydroxycyclohepta-2,4,6-trien-1-one:

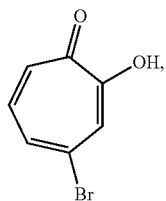

or a salt thereof, (2) reacting a compound of structural formula:

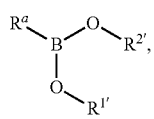

or a salt thereof; with 4-bromo-2-hydroxycyclohepta-2,4,6-trien-1-one:

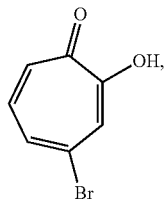

or a salt thereof, thereby forming a compound having structural formula:

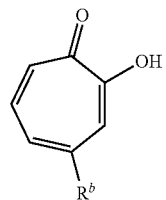

or a salt thereof; wherein
- $R^a$ is $C_{1-20}$-alkyl, $C_{2-20}$-alkenyl, $C_{2-20}$-alkynyl, $C_{3-9}$-cycloalkyl, aryl, or heteroaryl, each of which is unsubstituted or substituted with a substituent selected from the group consisting of halo, $NO_2$, CN, $C_{1-6}$-alkyl, $C_{1-6}$-haloalkyl, and $C_{1-6}$-alkoxy;
- $R^{1'}$ and $R^{2'}$ are each, independently hydrogen or $C_{1-6}$-alkyl; or
- $R^{1'}$ and $R^{2'}$, together with atoms to which they are attached, form a ring having 2 to 4 carbon atoms, each of which is optionally and independently substituted with $C_{1-3}$-alkyl or C=O; and
- B is a boron atom having $sp^3$ hybridization.

In some embodiments, in step (1) of the method, 7,7-dibromobicyclo[4.1.0]heptane-2,3-diol is first contacted with the oxidizing agent at a temperature of about −78° C. In certain embodiments of the method, the temperature is subsequently warmed to about 0° C. In some embodiments, the oxidizing agent comprises one or more of potassium dichromate, pyridinium chlorochromate, Dess-Martin periodinane, oxalyl chloride, dimethylsulfoxide, aluminum alkoxide (e.g., aluminum isopropoxide), trimethylaluminum, potassium tert-butoxide, or silver carbonate. In other embodiments, the oxidizing agent comprises dimethylsulfoxide and one or more additional reagents selected from the group consisting of a carbodiimide, trifluoroacetic anhydride, oxalyl chloride, and sulfur trioxide pyridine complex.

In some embodiments, step (1) of the method further comprises contacting 7,7-dibromobicyclo[4.1.0]heptane-2,3-diol and the oxidizing agent with a base. In some such embodiments, the base is an amine base. In certain embodiments, the base is a tertiary amine base, such as triethylamine.

In some embodiments, step (2) of the method further comprises contacting the compounds with a metal catalyst. In some such embodiments, the metal catalyst is a palladium catalyst or a palladium nanomaterial-based catalyst. In certain embodiments, the metal catalyst is an organopalladium catalyst. In particular embodiments, the metal catalyst is selected from the group consisting of tetrakis(triphenylphosphine)palladium(0), palladium chloride, and palladium(II) acetate.

In some embodiments, the reaction with comprising the metal catalyst further comprises a promoter. In some such embodiments, the promoter is thallium (I) ethoxide or silver oxide. In preferred embodiments, the promoter is silver oxide.

In some embodiments, $R^a$ is $C_{1-4}$-alkyl, $C_2$-alkenyl, $C_{2-4}$-alkynyl, or $C_{3-4}$-cycloalkyl. In some such embodiments, $R^a$ is selected from the group consisting of:

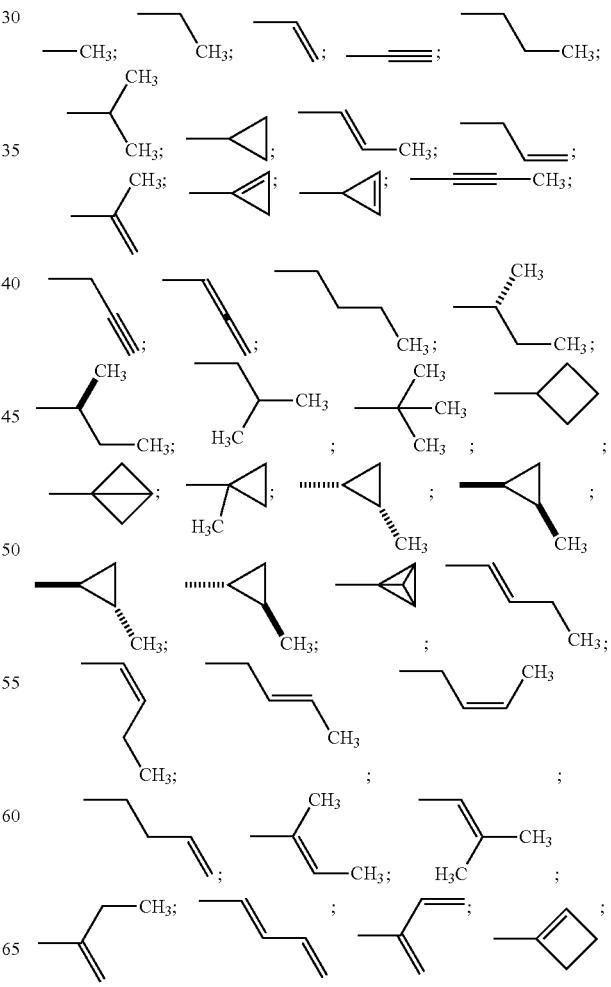

-continued
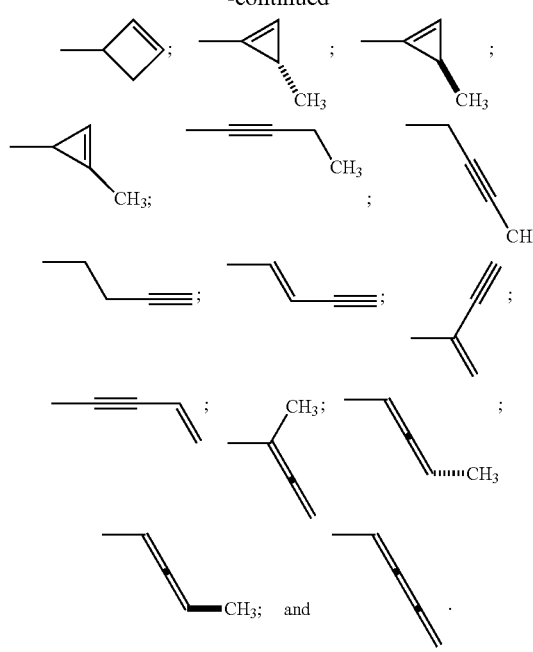
Accordingly, the compound of structural formula:
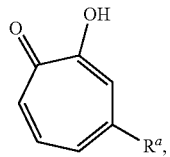
or salt thereof, is selected from:
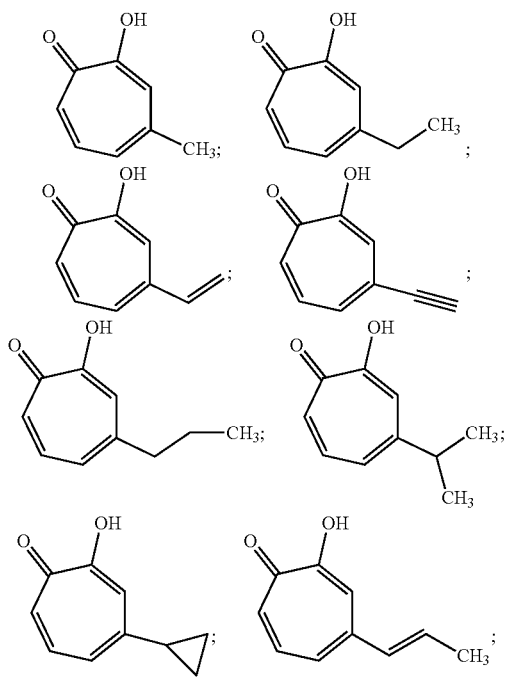
-continued
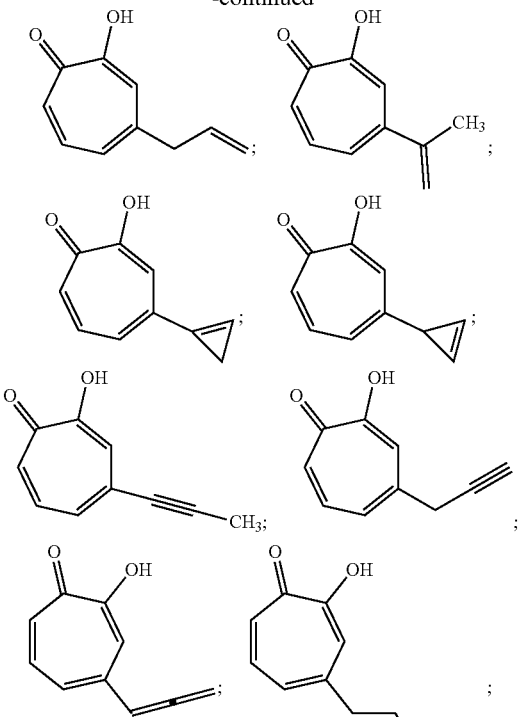

-continued
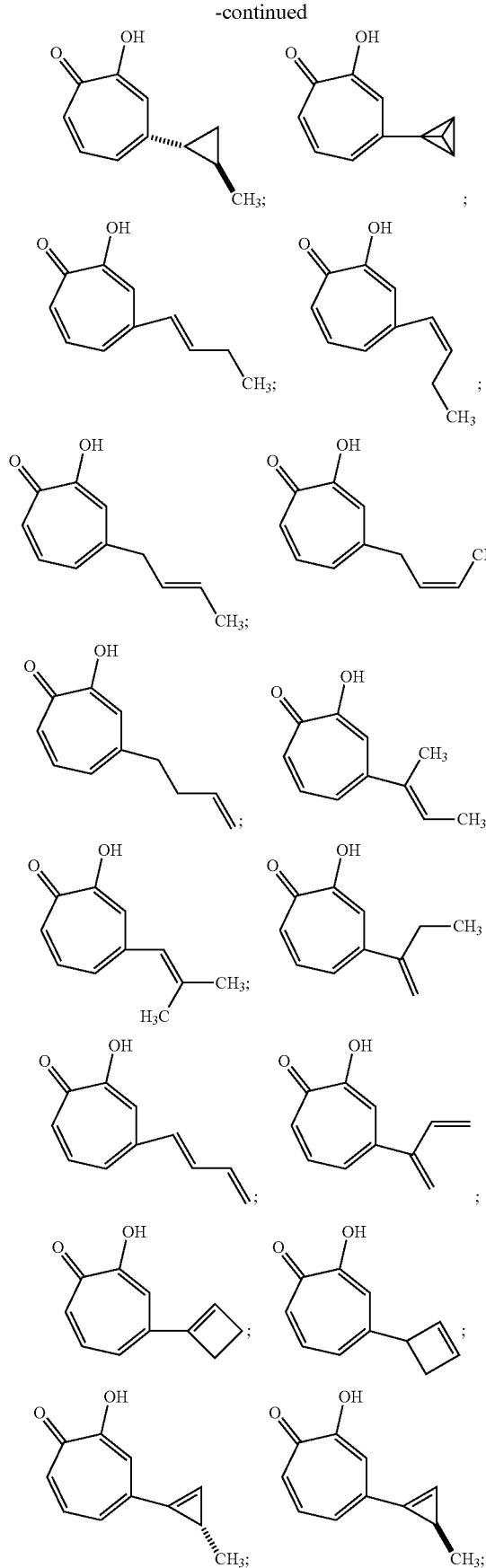
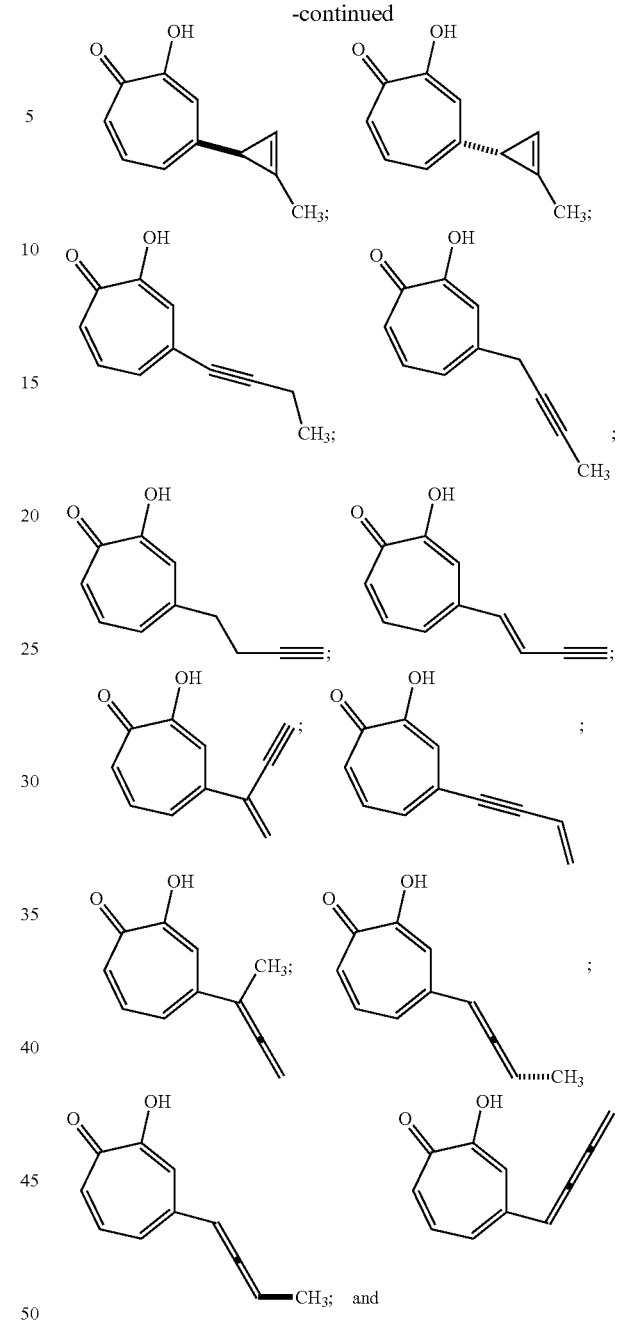
or a salt thereof.
In some other embodiments, $R^a$ is selected from the group consisting of:
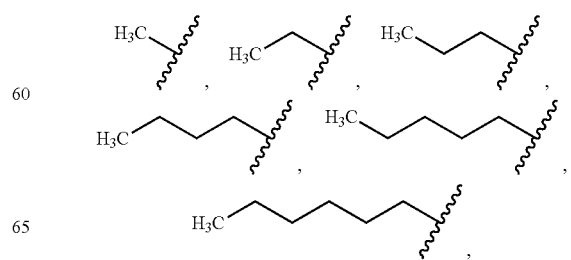

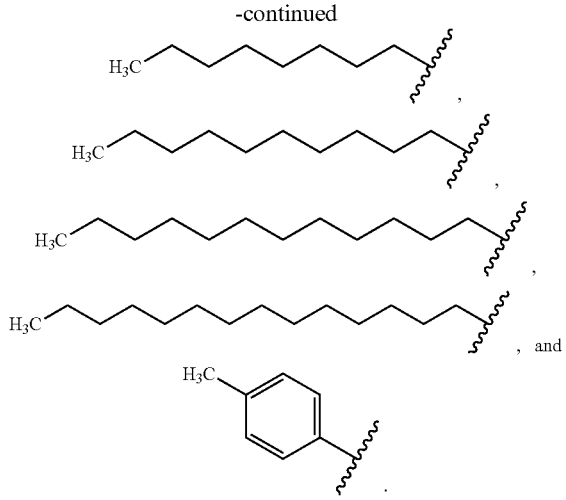
In some such embodiments, the compound of structural formula:
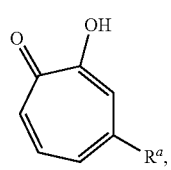
or salt thereof, is selected from:
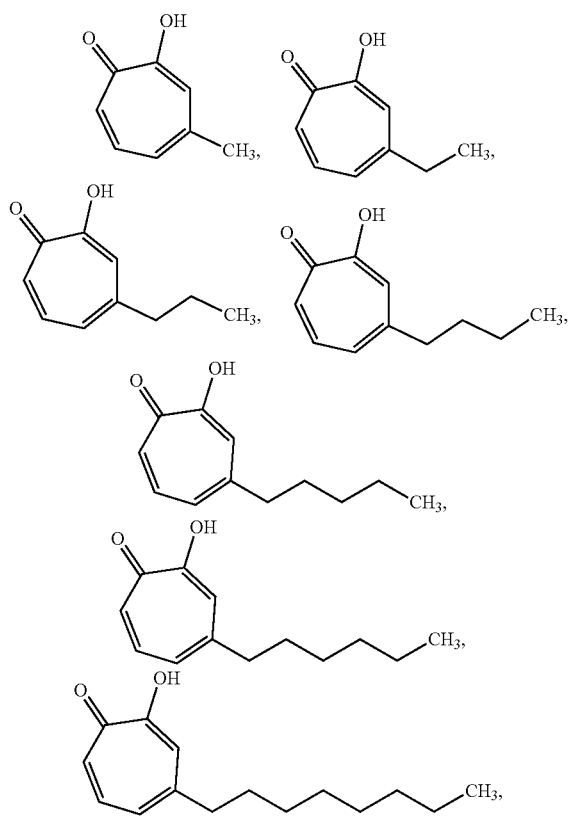
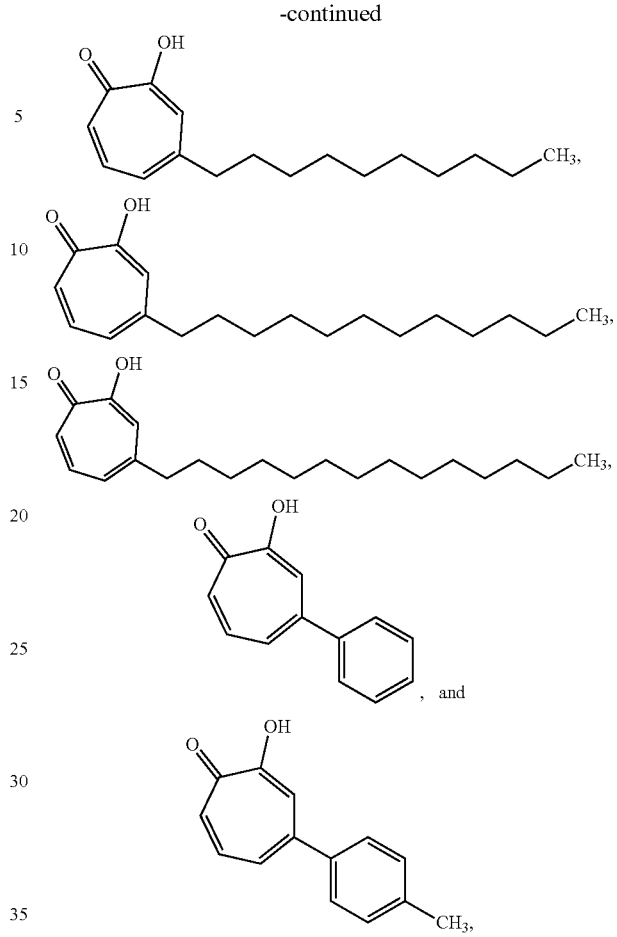
or a salt thereof.
In other embodiments, $R^a$ is selected from the group consisting of
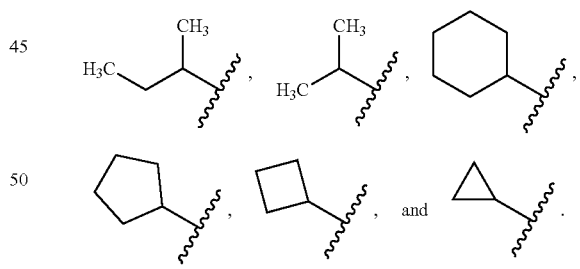
In some such embodiments, the compound of structural formula:
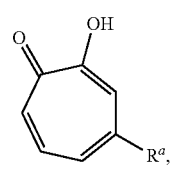

or salt thereof, is selected from the group consisting of:

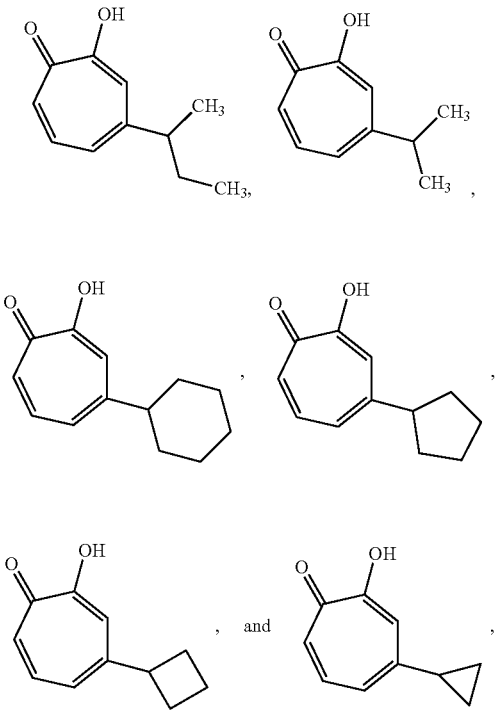

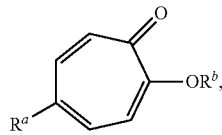

, and

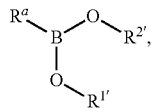

, or a salt thereof.

Method N

Also provided herein is a method of preparing a compound of structural formula:

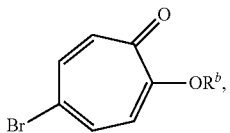

or a salt thereof; comprising reacting a compound of structural formula:

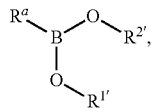

or a salt thereof; with a compound of structural formula:

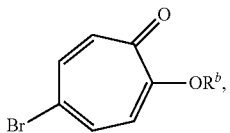

or a salt thereof; thereby providing the compound of structural formula:

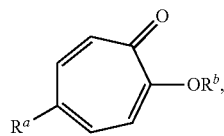

or a salt thereof; wherein $R^a$ is $C_{1-20}$-alkyl, $C_{2-20}$-alkenyl, $C_{2-20}$-alkynyl, $C_{3-9}$-cycloalkyl, aryl, or heteroaryl, each of which is unsubstituted or substituted with a substituent selected from the group consisting of halo, $NO_2$, CN, $C_{1-6}$-alkyl, $C_{1-6}$-haloalkyl, and $C_{1-6}$-alkoxy;

$R^b$ is hydrogen or methyl;

$R^{1'}$ and $R^{2'}$ are each, independently hydrogen or $C_{1-6}$-alkyl; or $R^{1'}$ and $R^{2'}$, together with atoms to which they are attached, form a ring having 2 to 4 carbon atoms, each of which is optionally and independently substituted with $C_{1-3}$-alkyl or C=O; and B is a boron atom having $sp^3$ hybridization.

In some embodiments, the method further comprises contacting the compounds with a metal catalyst. In some such embodiments, the metal catalyst is a palladium catalyst or a palladium nanomaterial-based catalyst. In certain embodiments, the metal catalyst is an organopalladium catalyst. In particular embodiments, the metal catalyst is selected from the group consisting of tetrakis(triphenylphosphine)palladium(0), palladium chloride, and palladium(II) acetate.

In some embodiments, the reaction with comprising the metal catalyst further comprises a promoter. In some such embodiments, the promoter is thallium (I) ethoxide or silver oxide. In preferred embodiments, the promoter is silver oxide.

In some embodiments, $R^{1'}$ and $R^{2'}$ are both hydrogen.

In some embodiments, $R^a$ is $C_{1-4}$-alkyl, $C_{2-4}$-alkenyl, $C_{2-4}$-alkynyl, or $C_{3-4}$-cycloalkyl. In some such embodiments, $R^a$ is selected from the group consisting of:

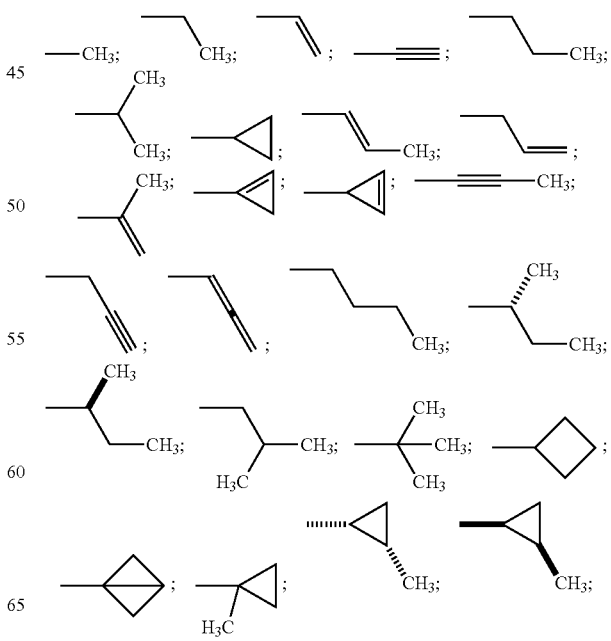

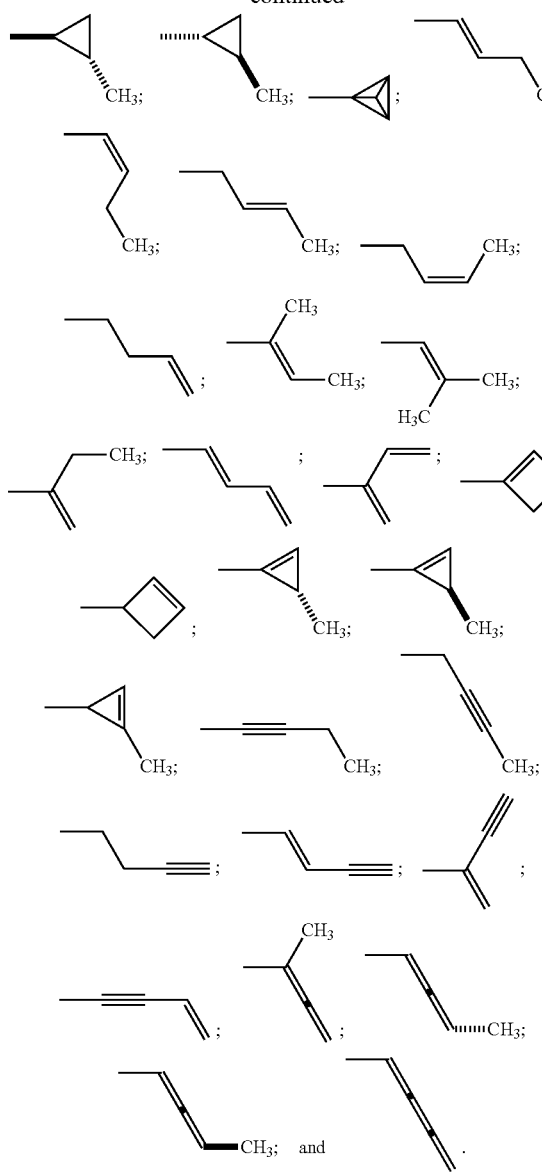
Accordingly, the compound of structural
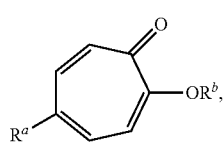
or salt thereof, is selected from the group consisting of:
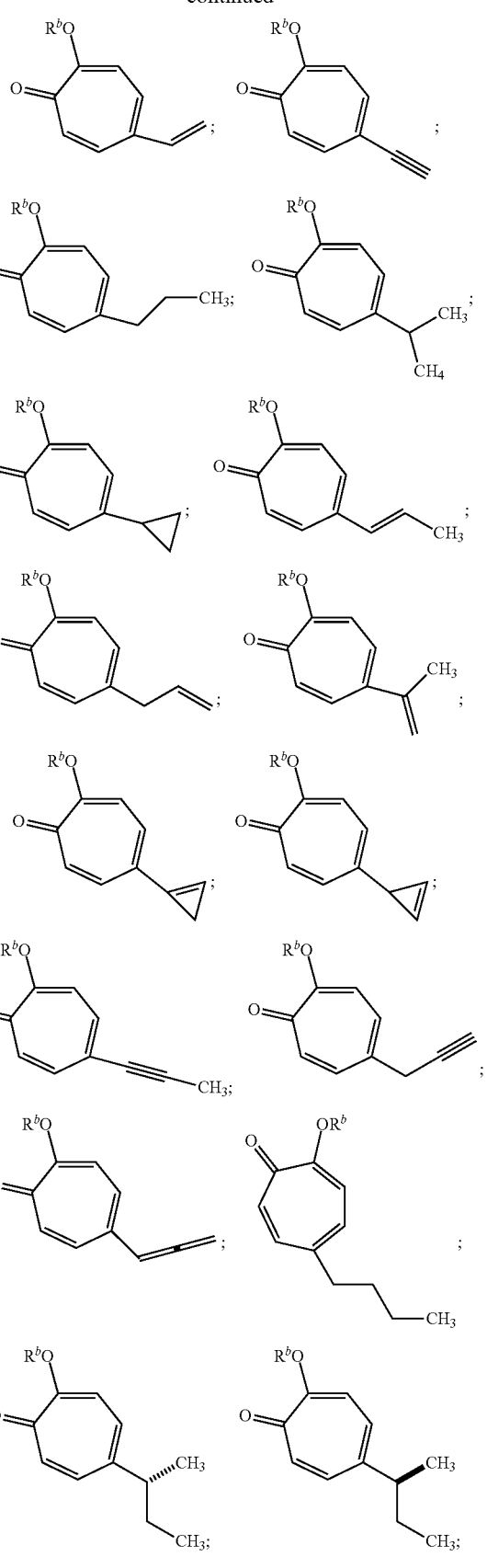

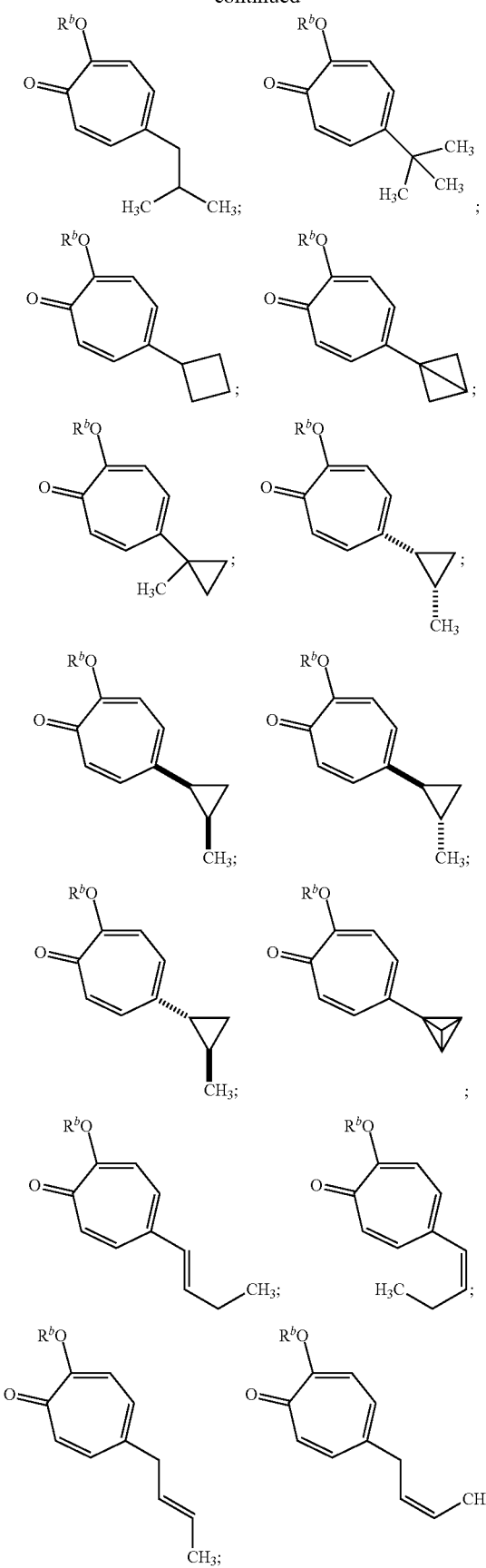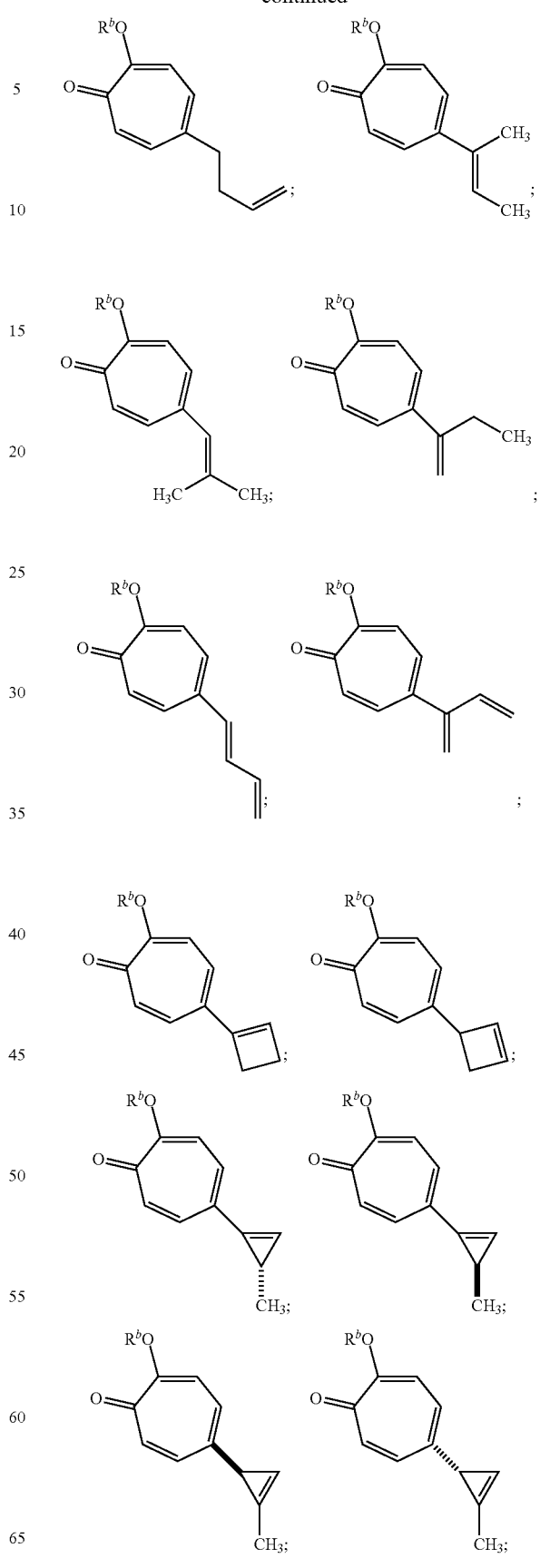

161
-continued
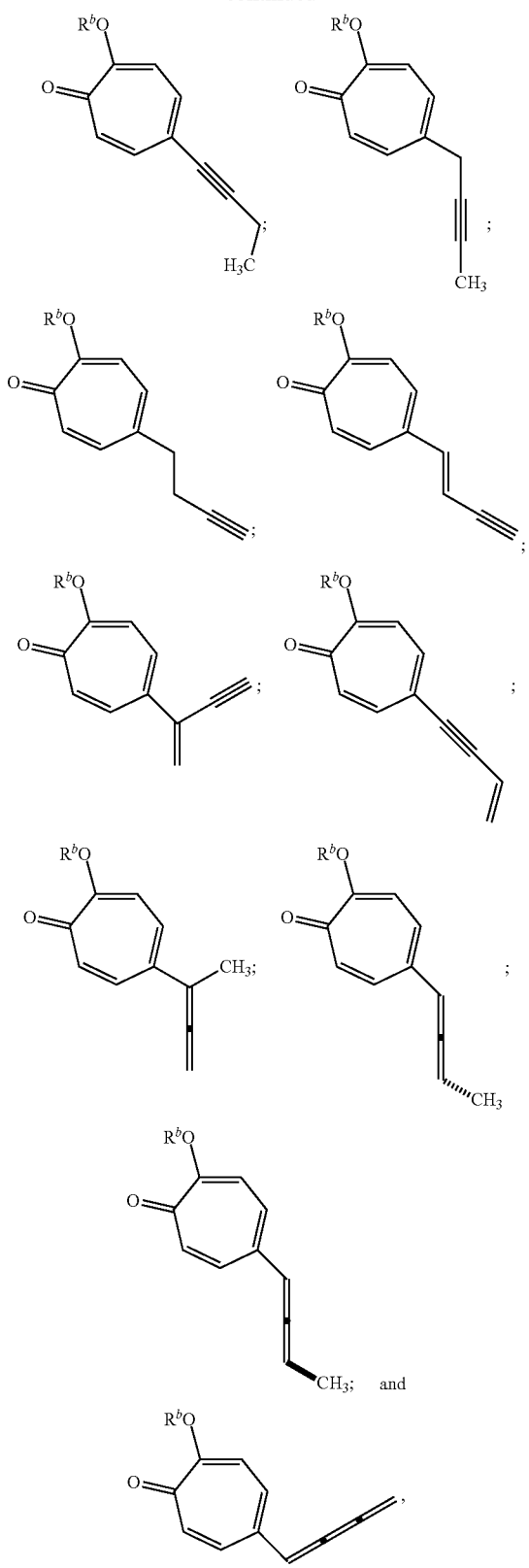
or a salt thereof.
In some embodiments, $R^a$ is selected from the group consisting of:
162
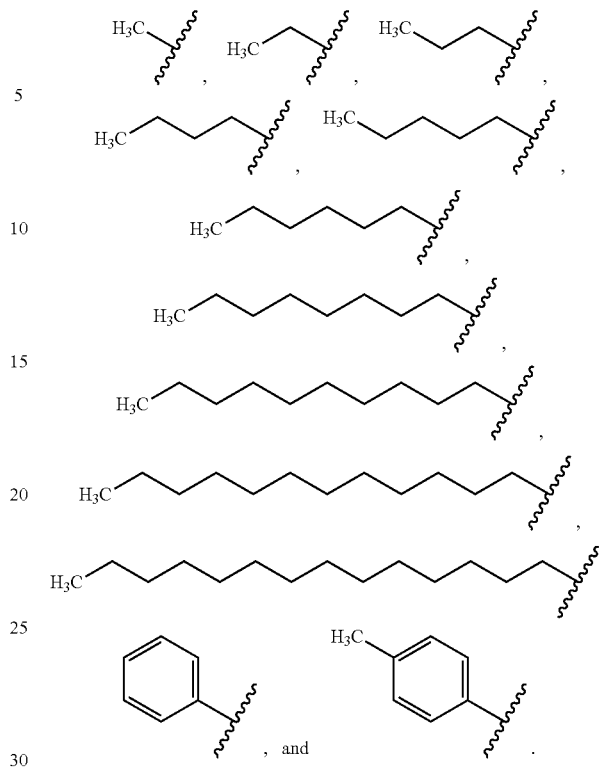
, and
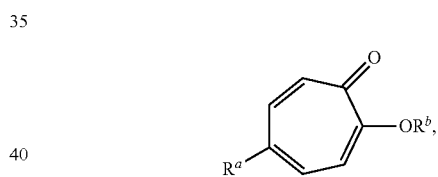
.
In some such embodiments, the compound of structural formula:
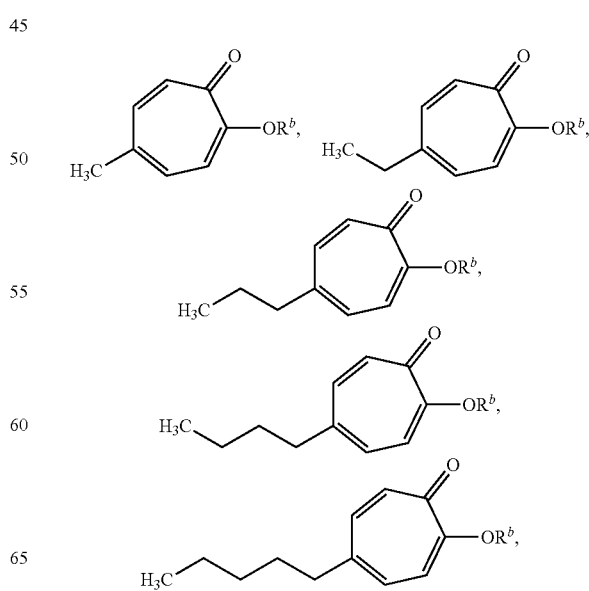
or salt thereof, is selected from the group consisting of:

-continued

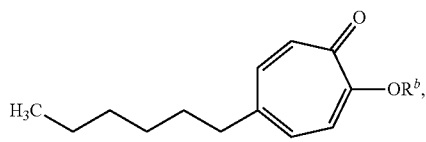

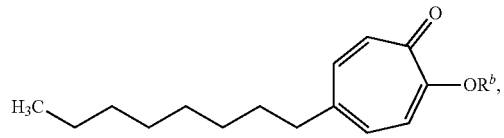

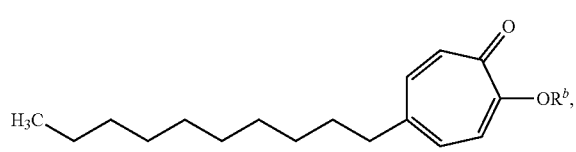

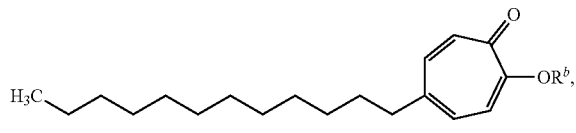

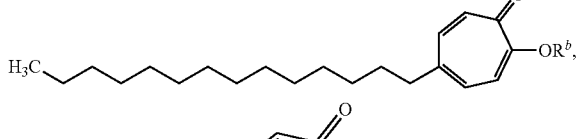

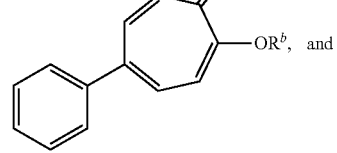

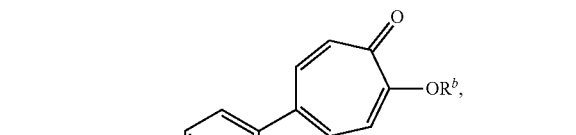

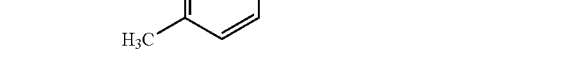

or a salt thereof.

In other embodiments, $R^a$ is selected from the group consisting of

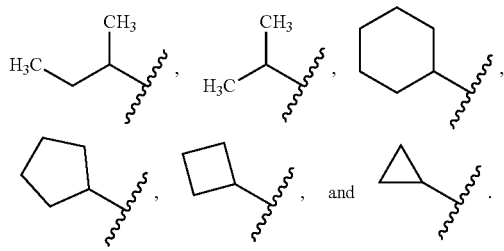

In some such embodiments, the compound of structural formula:

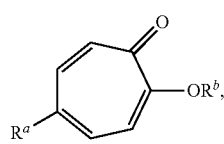

or salt thereof, is selected from the group consisting of:

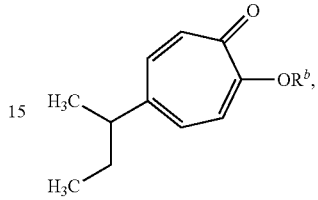

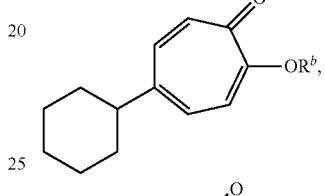

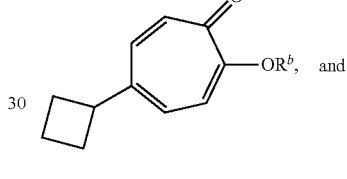

or a salt thereof.

Method O

Also provided herein is a method of preparing a compound of structural formula:

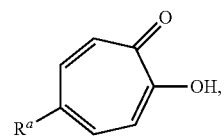

or a salt thereof; comprising combining a compound having structural formula:

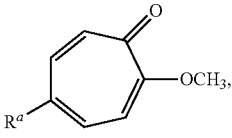

or a salt thereof; with a demethylating agent; thereby providing the compound of structural formula:

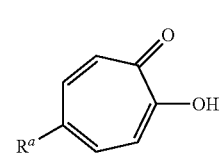

or a salt thereof; wherein $R^a$ is $C_{1-20}$-alkyl, $C_{2-20}$-alkenyl, $C_{2-20}$-alkynyl, $C_{3-9}$-cycloalkyl, aryl, or heteroaryl, each of which is unsubstituted or substituted with a substituent selected from the group consisting of halo, $NO_2$, CN, $C_{1-6}$-alkyl, $C_{1-6}$-haloalkyl, and $C_{1-6}$-alkoxy.

In some embodiments, the demethylating agent is an acid. In some such embodiments, the demethylating agent is a mineral acid, an organic acid, or a combination thereof. In certain embodiments, the demethylating agent is hydrochloric acid, hydrobromic acid, sulfuric acid, acetic acid, or a combination thereof. In preferred embodiments, the demethylating agent is hydrobromic or hydrochloric acid in acetic acid. Alternatively, the demethylating agent is sulfuric acid.

In some embodiments, the compound having structural formula:

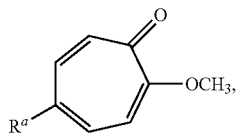

or a salt thereof; is contacted with a demethylating agent and heated to boiling; thereby providing the compound of structural formula:

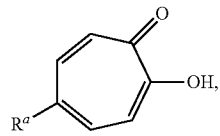

or salt thereof.

In some embodiments, the compound of structural formula:

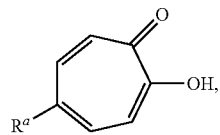

or salt thereof, is selected from the group consisting of:

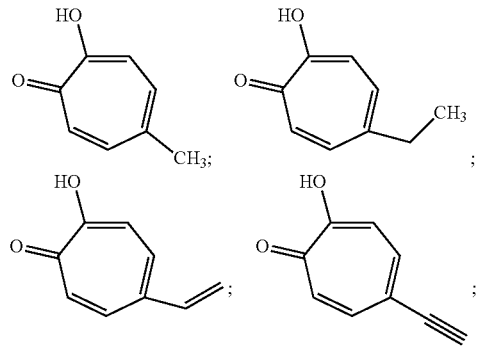

-continued

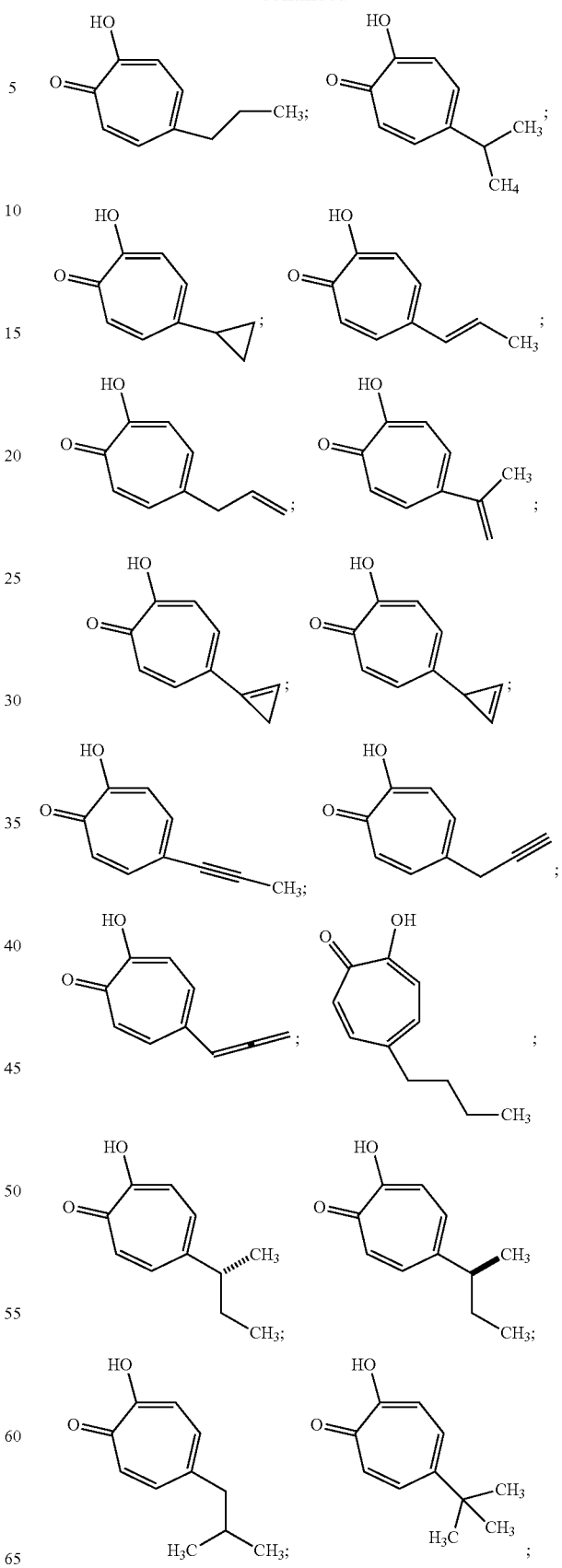

167
-continued
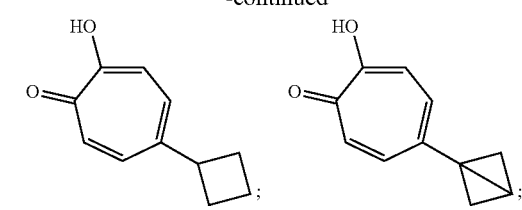
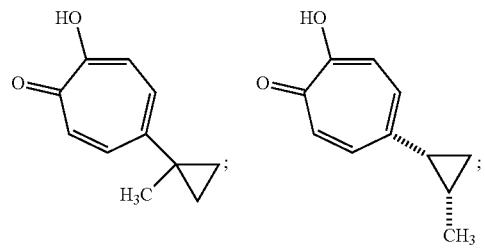
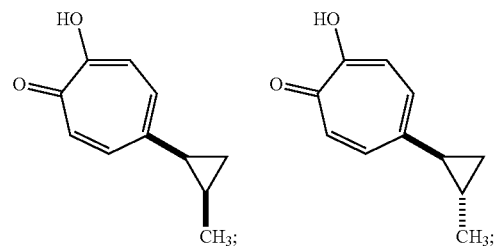
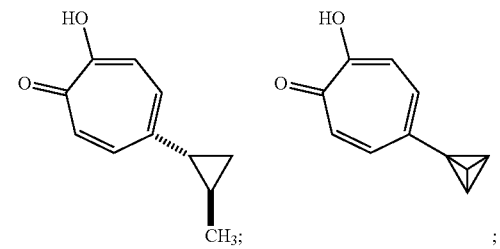
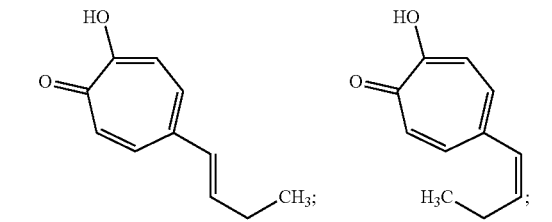
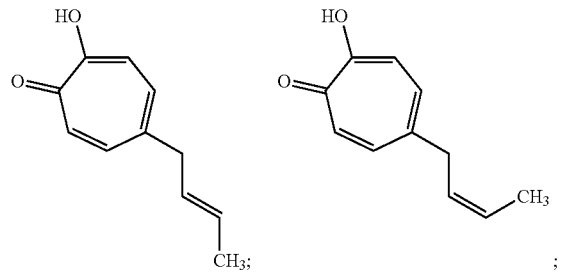
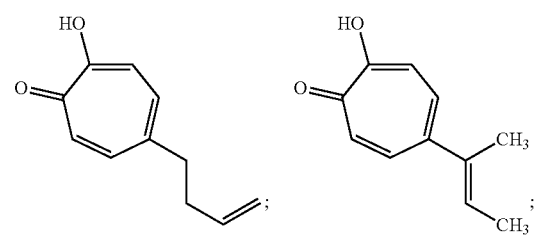
168
-continued
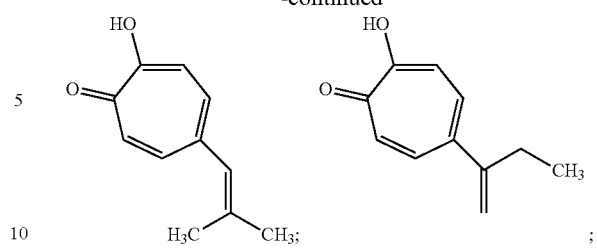
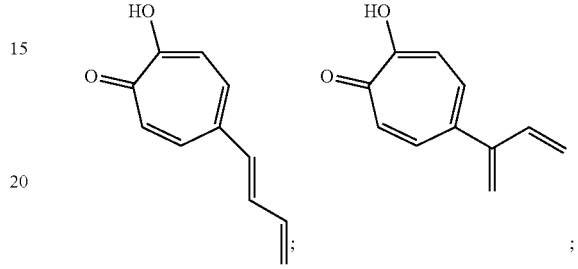
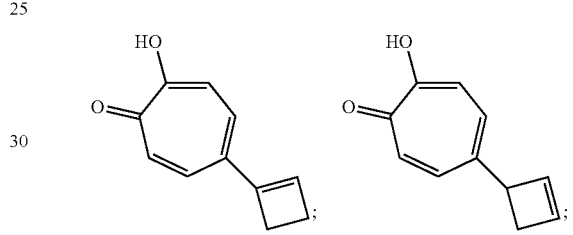
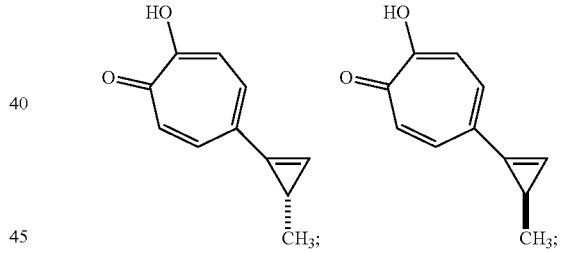
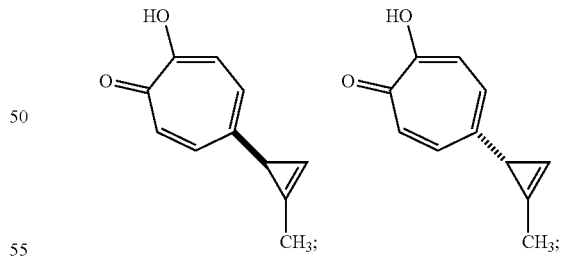
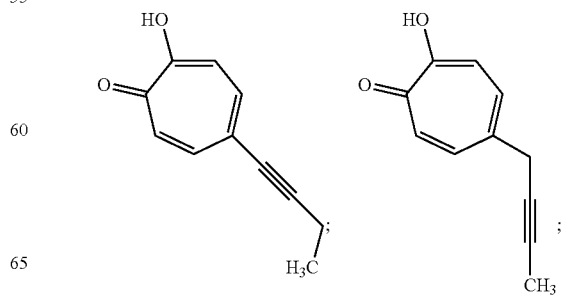

-continued
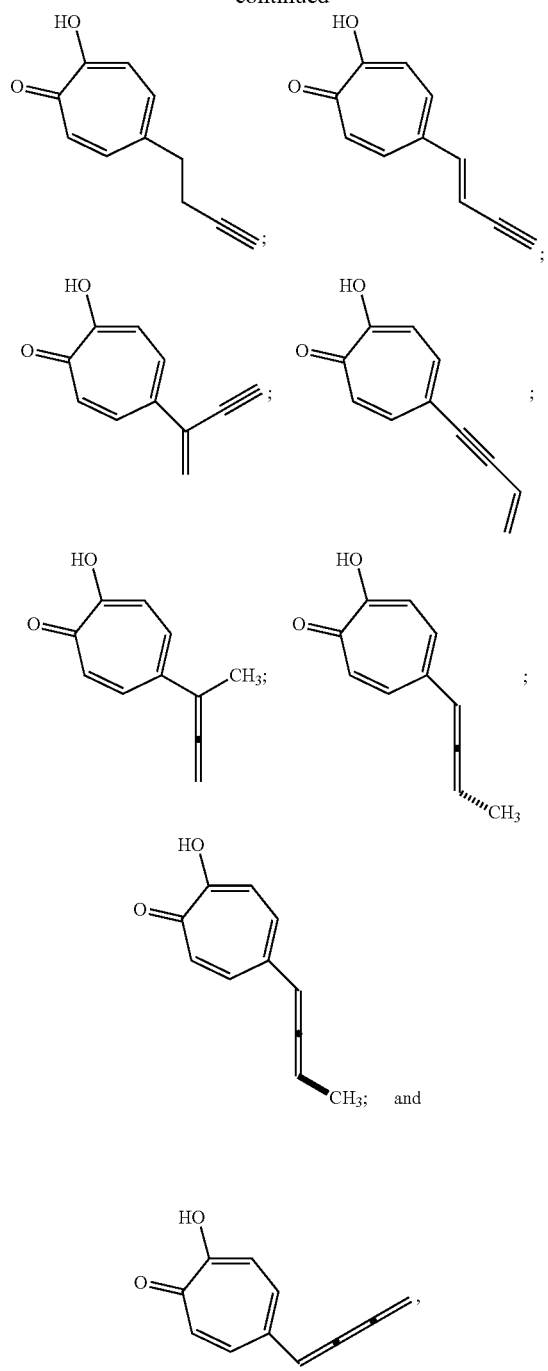
or a salt thereof.
In some other embodiments, the compound of structural formula:
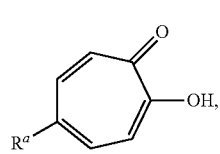
or salt thereof, is selected from the group consisting of:
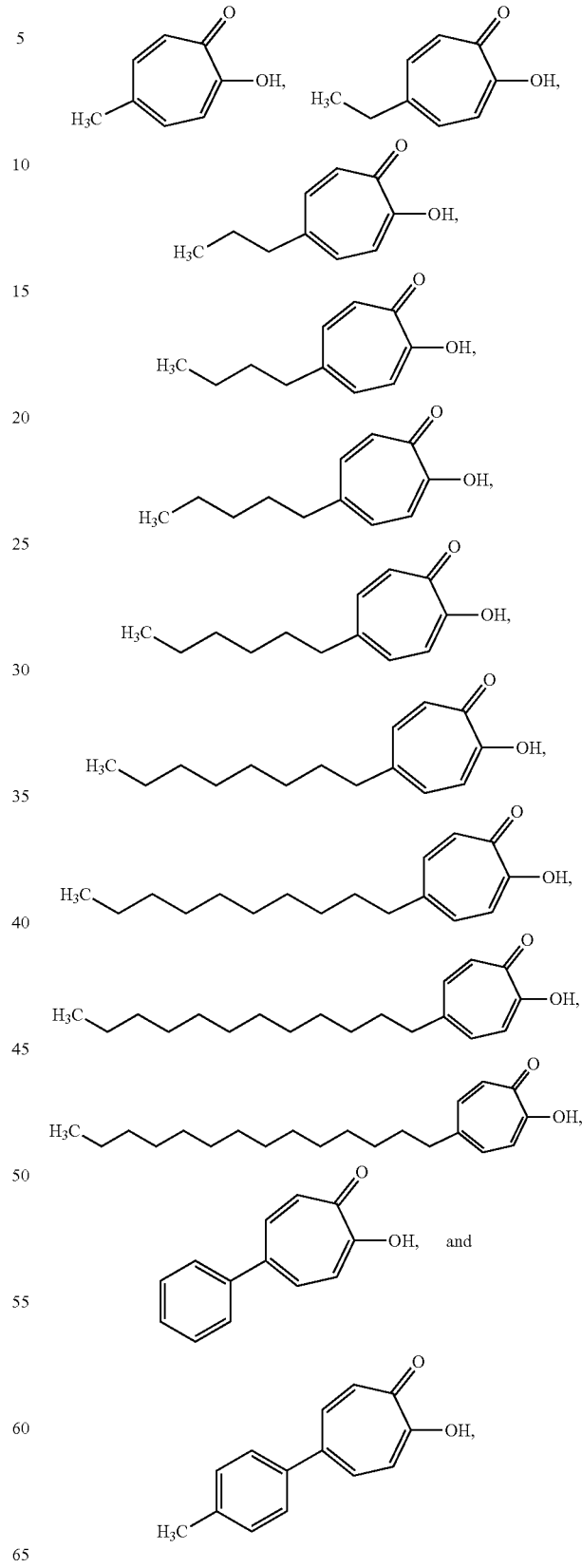
or a salt thereof.

In other embodiments, the compound of structural formula:

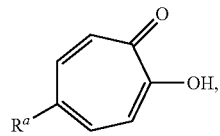

or salt thereof, is selected from the group consisting of:

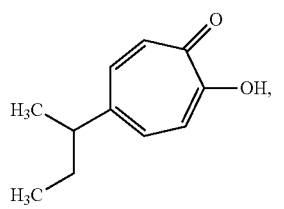 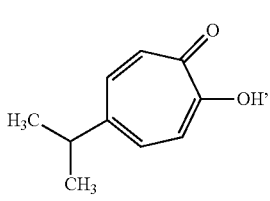

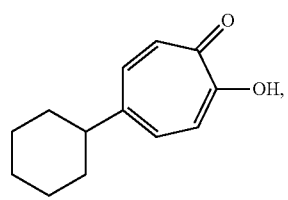 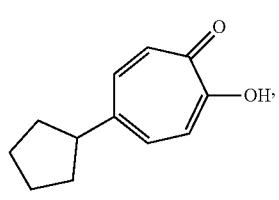

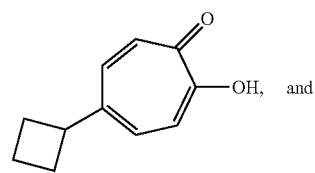 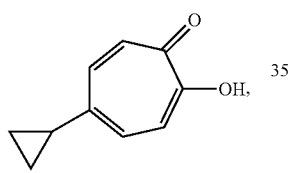

or a salt thereof.

Method P

Also provided herein is a method of preparing a compound of structural formula:

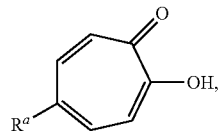

or a salt thereof; comprising:
(1) contacting 7,7-dibromobicyclo[4.1.0]heptane-3,4-diol:

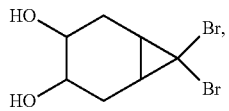

or a salt thereof, with an oxidizing agent, thereby forming 5-bromo-2-hydroxycyclohepta-2,4,6-trien-1-one:

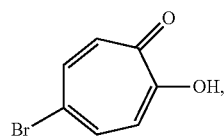

or a salt thereof; and
(2) reacting a compound of structural formula:

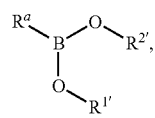

or a salt thereof; with 5-bromo-2-hydroxycyclohepta-2,4,6-trien-1-one:

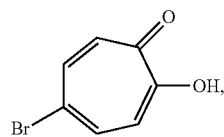

or a salt thereof, thereby forming a compound having structural formula:

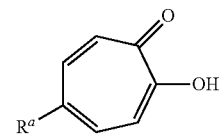

or a salt thereof; wherein
$R^a$ is $C_{1-20}$-alkyl, $C_{2-20}$-alkenyl, $C_{2-20}$-alkynyl, $C_{3-9}$-cycloalkyl, aryl, or heteroaryl, each of which is unsubstituted or substituted with a substituent selected from the group consisting of halo, $NO_2$, CN, $C_{1-6}$-alkyl, $C_{1-6}$-haloalkyl, and $C_{1-6}$-alkoxy;
$R^{1'}$ and $R^{2'}$ are each, independently hydrogen or $C_{1-6}$-alkyl; or
$R^{1'}$ and $R^{2'}$, together with atoms to which they are attached, form a ring having 2 to 4 carbon atoms, each of which is optionally and independently substituted with $C_{1-3}$-alkyl or C=O; and
B is a boron atom having $sp^3$ hybridization.

In some embodiments, step (1) of the method further comprises contacting 7,7-dibromobicyclo[4.1.0]heptane-3,4-diol and the oxidizing agent with a base. In some such embodiments, the base is an amine base. In certain embodiments, the base is a tertiary amine base, such as triethylamine.

In some embodiments, step (2) of the method further comprises contacting the compounds with a metal catalyst. In some such embodiments, the metal catalyst is a palladium catalyst or a palladium nanomaterial-based catalyst. In certain embodiments, the metal catalyst is an organopalladium catalyst. For example, in particular embodiments, the metal catalyst is selected from the group consisting of tetrakis(triphenylphosphine)palladium(0), palladium chloride, and palladium(II) acetate.

In some embodiments, the reaction with comprising the metal catalyst further comprises a promoter. In some such embodiments, the promoter is thallium (I) ethoxide or silver oxide. In preferred embodiments, the promoter is silver oxide.

In some embodiments, $R^a$ is $C_{1-4}$-alkyl, $C_{2-4}$-alkenyl, $C_{2-4}$-alkynyl or $C_{3-4}$-cycloalkyl. In some such embodiments, $R^a$ is selected from the group consisting of:

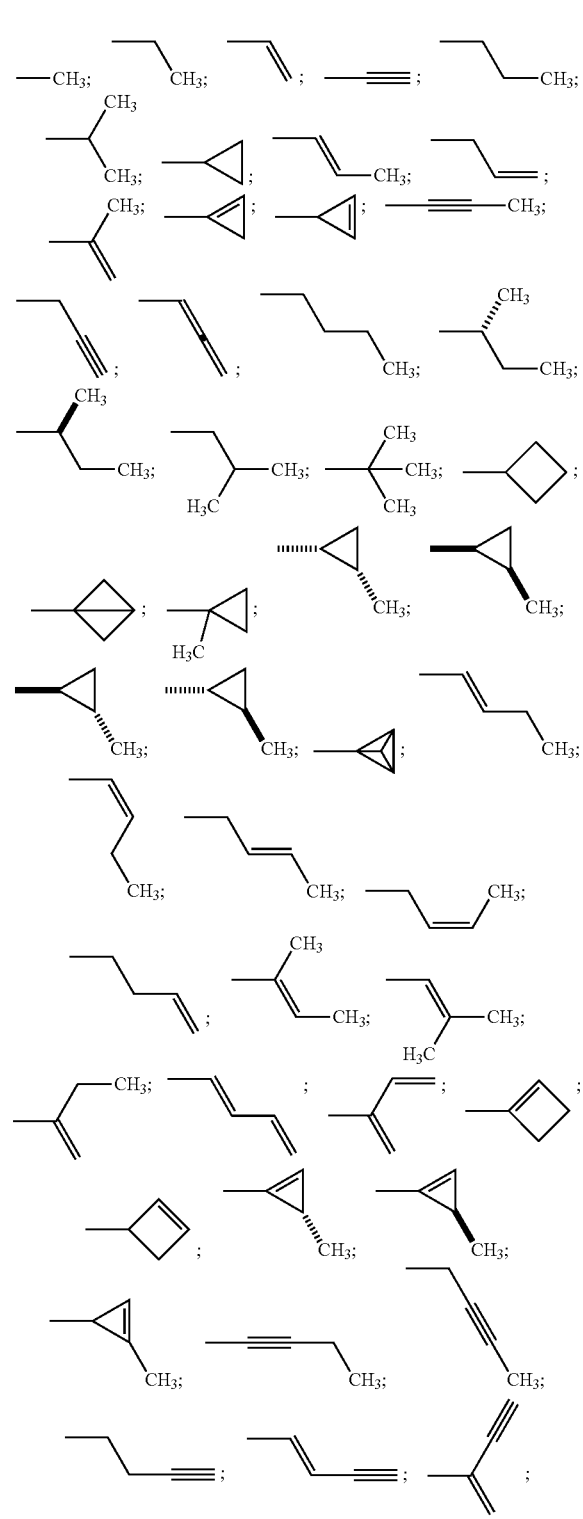

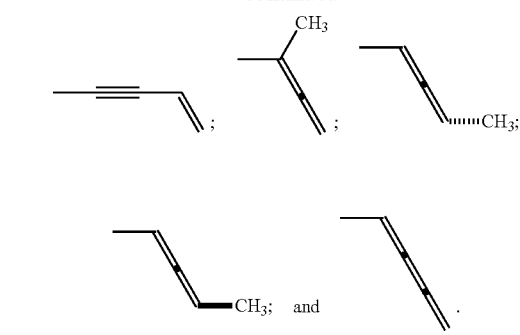

Accordingly, in some embodiments, the compound of structural formula:

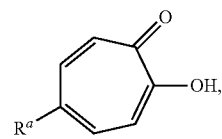

or salt thereof, is selected from the group consisting of:

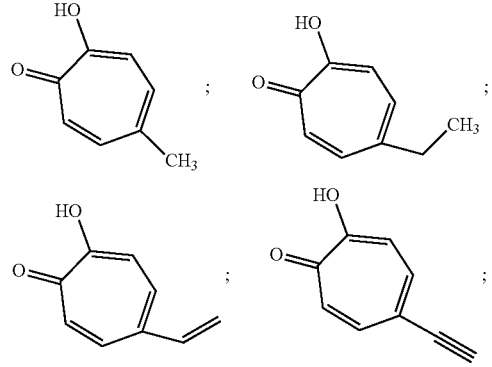
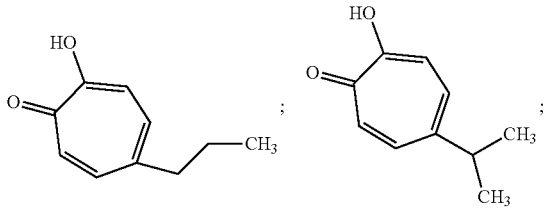
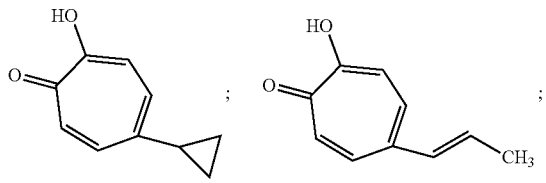
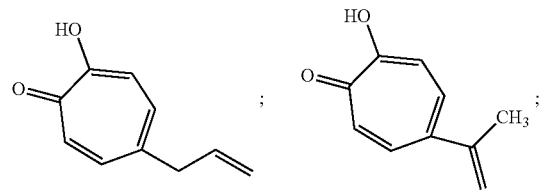

-continued
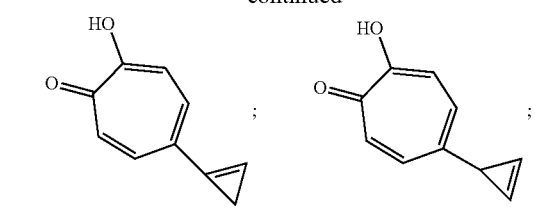
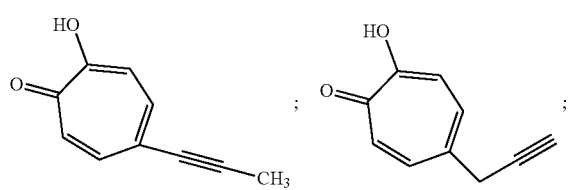
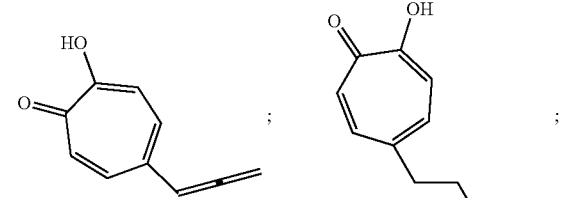
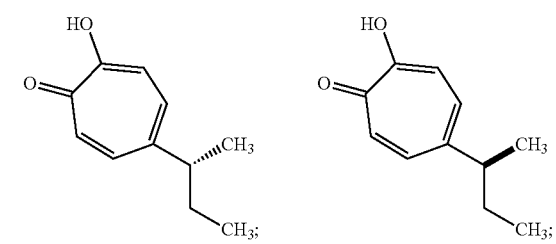
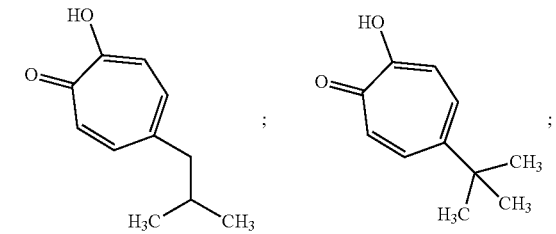
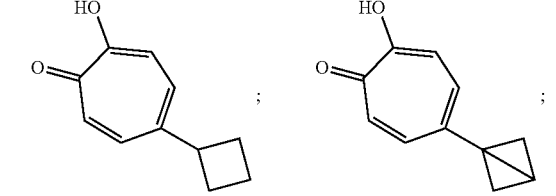
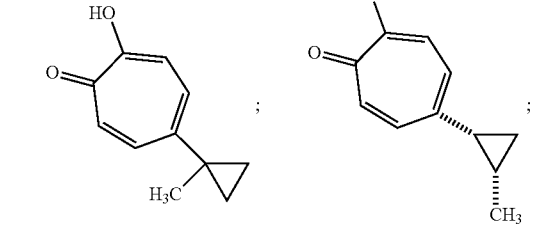
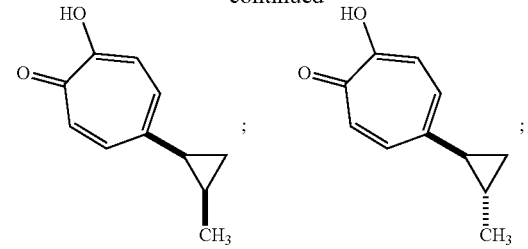
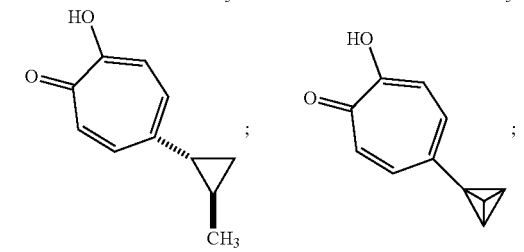
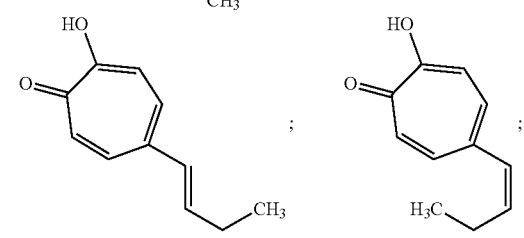
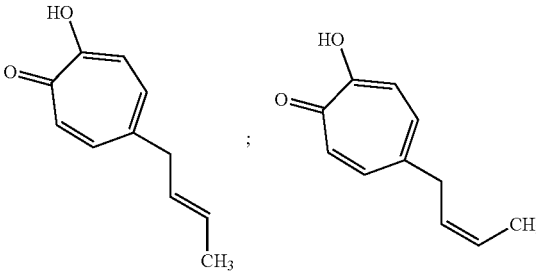
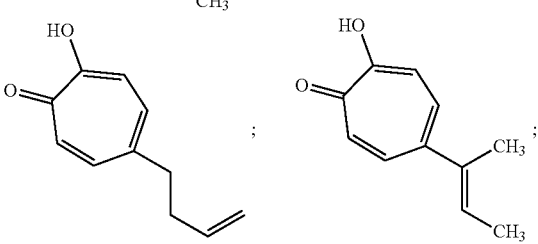
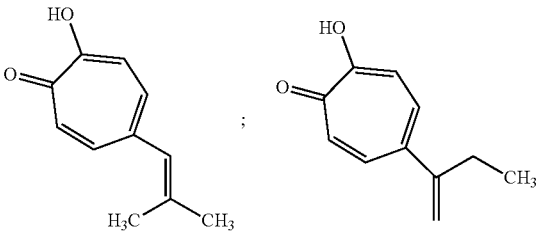
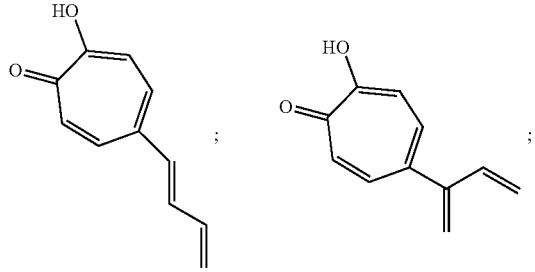

-continued
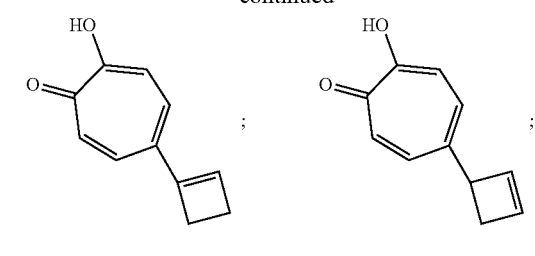
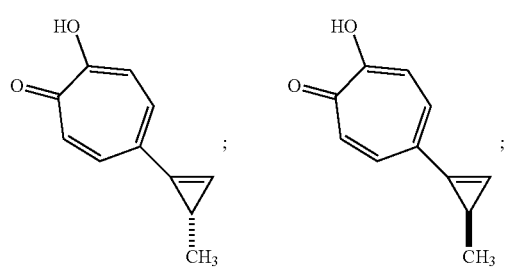
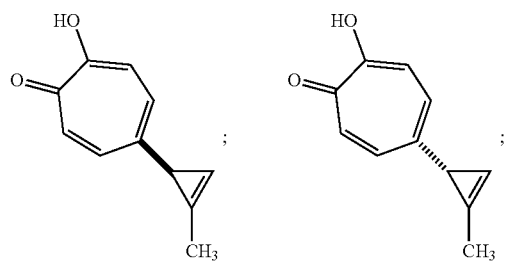
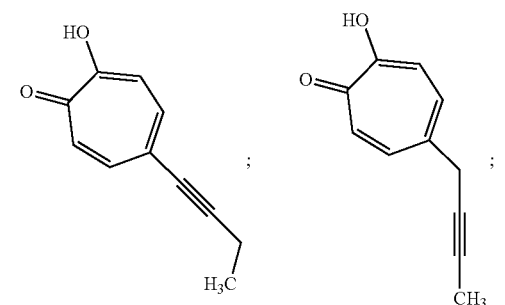
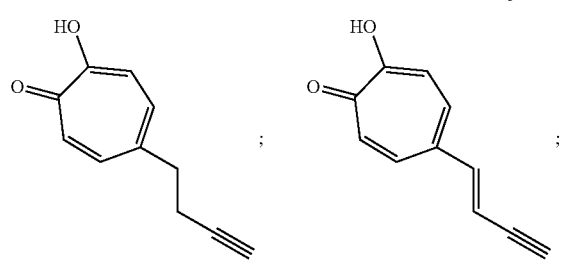
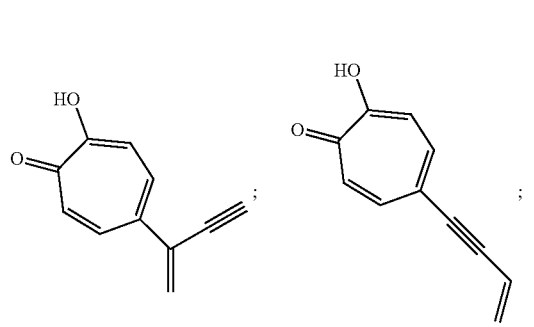
-continued
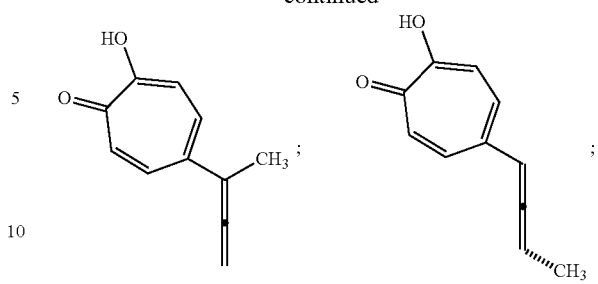
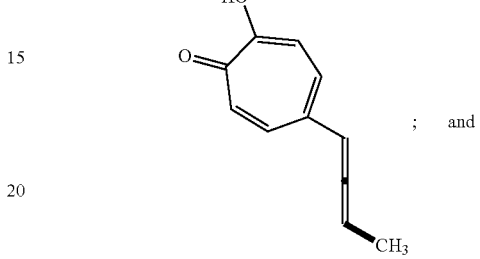
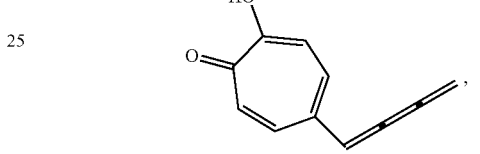
or a salt thereof.
In some other embodiments, $R^a$ is selected from the group consisting of:
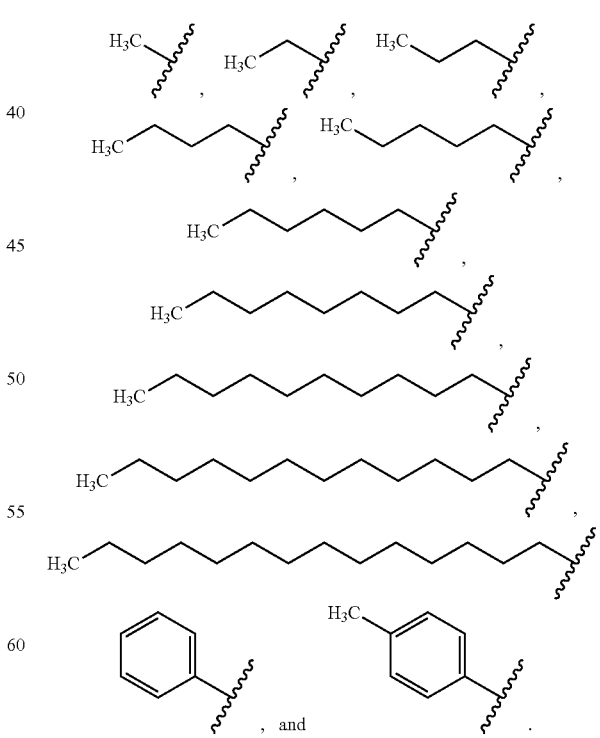
, and
In some such embodiments, the compound of structural formula:

179

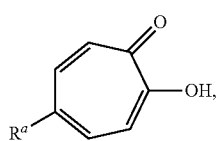

or salt thereof, is selected from the group consisting of:

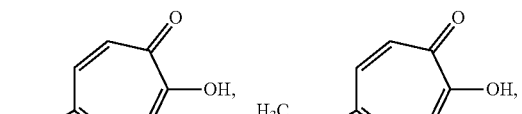

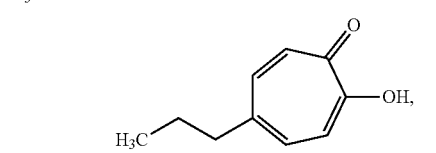

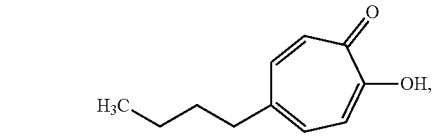

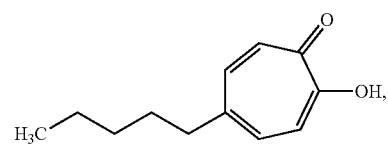

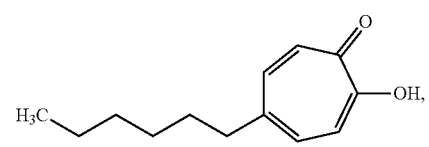

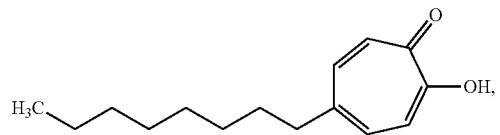

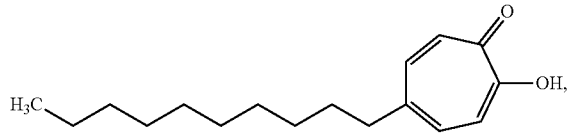

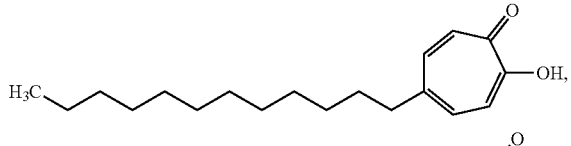

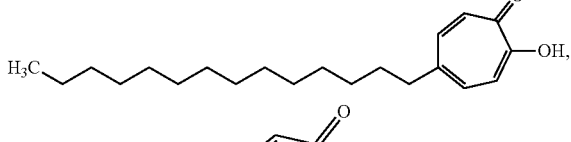

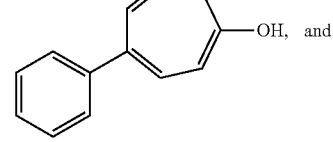

180

-continued

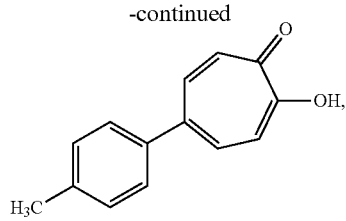

or a salt thereof.

In other embodiments, $R^a$ is selected from the group consisting of

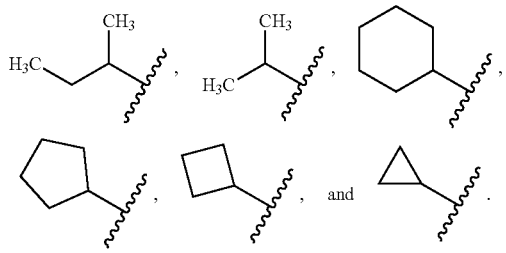

In some such embodiments, the compound of structural formula:

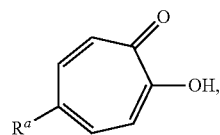

or salt thereof, is selected from the group consisting of:

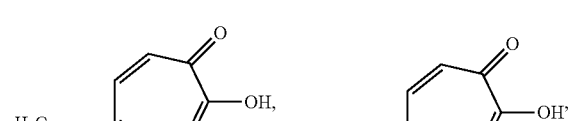

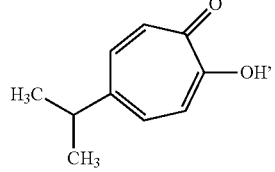

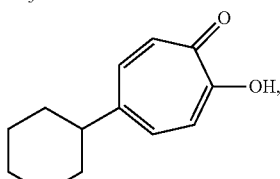

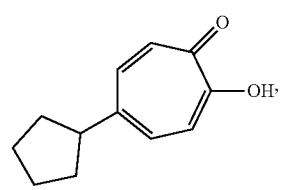

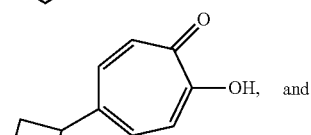 and 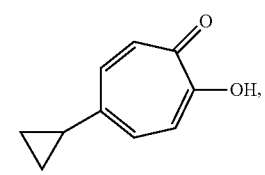

or a salt thereof.

Method Q

Also provided herein is a method of preparing a compound of structural formula:

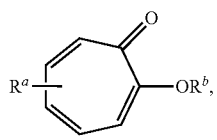

or a salt thereof; comprising reacting a compound of structural formula:

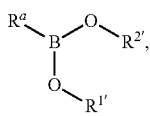

or a salt thereof; with a compound of structural formula:

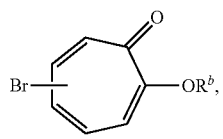

or a salt thereof; thereby providing the compound of structural formula:

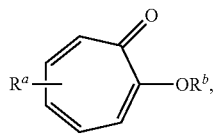

or a salt thereof; wherein
- $R^a$ is $C_{1-20}$-alkyl, $C_{2-20}$-alkenyl, $C_{2-20}$-alkynyl, $C_{3-9}$-cycloalkyl, aryl, or heteroaryl, each of which is unsubstituted or substituted with a substituent selected from the group consisting of halo, $NO_2$, CN, $C_{1-6}$-alkyl, $C_{1-6}$-haloalkyl, and $C_{1-6}$-alkoxy;
- $R^b$ is hydrogen or methyl;
- $R^{1'}$ and $R^{2'}$ are each, independently hydrogen or $C_{1-6}$-alkyl; or
- $R^{1'}$ and $R^{2'}$, together with atoms to which they are attached, form a ring having 2 to 4 carbon atoms, each of which is optionally and independently substituted with $C_{1-3}$-alkyl or C=O; and
- B is a boron atom having sp$^3$ hybridization.

In some embodiments, $R^{1'}$ and $R^{2'}$ are both hydrogen.

In some embodiments, the method further comprises contacting the compounds with a metal catalyst. In some such embodiments, the metal catalyst is a palladium catalyst or a palladium nanomaterial-based catalyst. In certain embodiments, the metal catalyst is an organopalladium catalyst. For example, in particular embodiments, the metal catalyst is selected from the group consisting of tetrakis(triphenylphosphine)palladium(0), palladium chloride, and palladium(II) acetate.

In some embodiments, the reaction with comprising the metal catalyst further comprises a promoter. In some such embodiments, the promoter is thallium (I) ethoxide or silver oxide. In preferred embodiments, the promoter is silver oxide.

Method R

Also provided herein is a method of preparing a compound of structural formula:

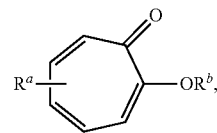

or a salt thereof; comprising reacting a compound of structural formula:

or a salt thereof; with a compound of structural formula:

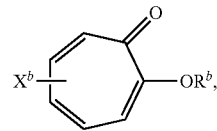

or a salt thereof; thereby providing the compound of structural formula:

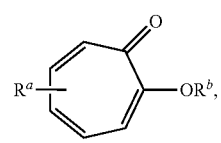

or a salt thereof; wherein
- $R^a$ is $C_{1-20}$-alkyl, aryl, or heteroaryl, each of which is unsubstituted or substituted with a substituent selected from the group consisting of halo, $NO_2$, CN, $C_{1-6}$-alkyl, $C_{1-6}$-haloalkyl, and $C_{1-6}$-alkoxy;
- $R^b$ is hydrogen or methyl;
- $X^a$ is

or $-Sn(C_{1-6}\text{-alkyl})$; and
- $X^b$ is halo or pseudohalo.

In some embodiments, $X^b$ is chloro, bromo, iodo, triflate, mesylate, or phosphonate.

In some embodiments, $R^a$ is

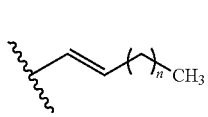 or 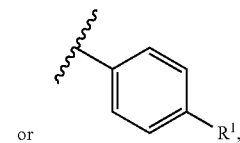

wherein n is an integer from 1 to 20, and $R^1$ is hydrogen, halo, $NO_2$, CN, $C_{1-6}$-alkyl, $C_{1-6}$-haloalkyl, or $C_{1-6}$-alkoxy.

In some embodiments, the compound of structural formula:

or a salt thereof; is reacted with the compound of structural formula:

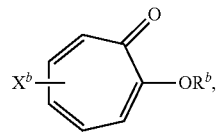

or a salt thereof, in the presence of a metal catalyst.

In some embodiments, the metal catalyst is a palladium catalyst or a palladium nanomaterial-based catalyst. In certain embodiments, the metal catalyst is an organopalladium catalyst. For example, in particular embodiments, the metal catalyst is selected from the group consisting of tetrakis(triphenylphosphine)palladium(0), palladium chloride, and palladium(II) acetate.

Method S

Also provided herein is a method of preparing a compound of structural formula:

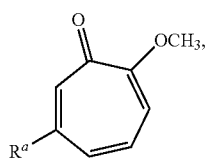

or a salt thereof; comprising reacting a compound of structural formula:

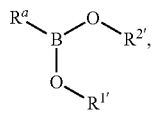

or a salt thereof; with 3-bromo-7-methoxycyclohepta-2,4,6-trien-1-one:

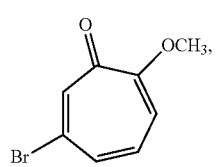

or a salt thereof; thereby providing the compound of structural formula:

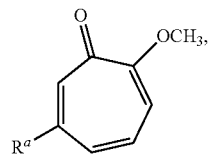

or a salt thereof; wherein $R^a$ is $C_{1-20}$-alkyl, $C_{2-20}$-alkenyl, $C_{3-9}$-cycloalkyl, aryl, or heteroaryl, each of which is unsubstituted or substituted with a substituent selected from the group consisting of halo, $NO_2$, CN, $C_{1-6}$-alkyl, $C_{1-6}$-haloalkyl, and $C_{1-4}$-alkoxy;

$R^{1'}$ and $R^{2'}$ are each, independently hydrogen or $C_{1-6}$-alkyl; or $R^{1'}$ and $R^{2'}$, together with atoms to which they are attached, form a ring having 2 to 4 carbon atoms, each of which is optionally and independently substituted with $C_{1-3}$-alkyl or C=O; and B is a boron atom having sp$^3$ hybridization.

In some embodiments, the method further comprises contacting the reacting compounds with a metal catalyst. In some such embodiments, the metal catalyst is a palladium catalyst or a palladium nanomaterial-based catalyst. In certain embodiments, the metal catalyst is an organopalladium catalyst. For example, in particular embodiments, the metal catalyst is selected from the group consisting of tetrakis(triphenylphosphine)palladium(0), palladium chloride, and palladium(II) acetate.

In some embodiments, the reaction with comprising the metal catalyst further comprises a promoter. In some such embodiments, the promoter is thallium (I) ethoxide or silver oxide. In preferred embodiments, the promoter is silver oxide.

In some embodiments, $R^{1'}$ and $R^{2'}$ are both hydrogen.

In some embodiments, $R^a$ is selected from the group consisting of:

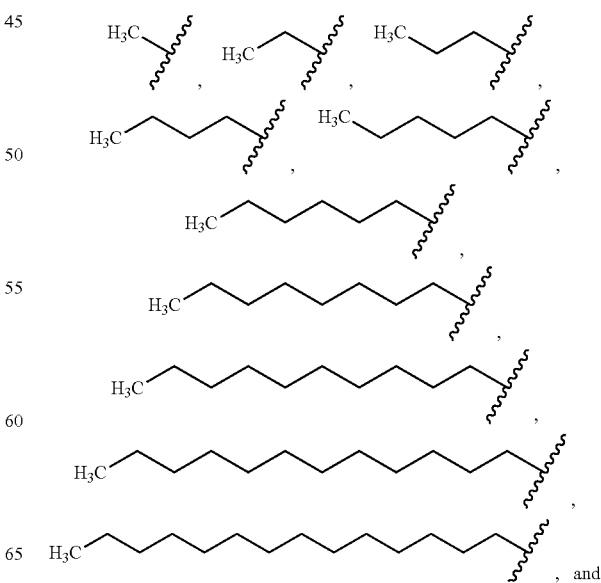

, and

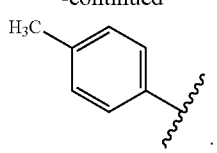
In some such embodiments, the compound of structural formula:
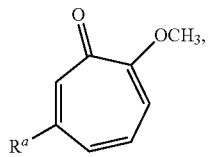
or salt thereof, is selected from the group consisting of:
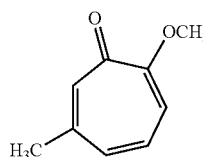 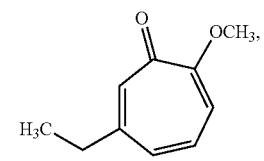
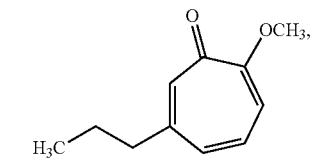
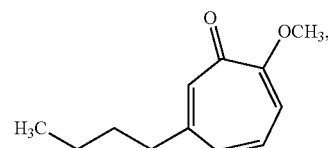
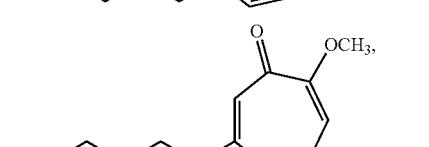
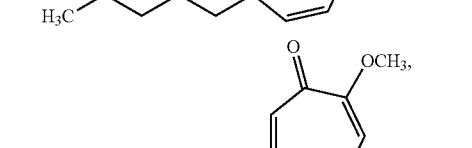
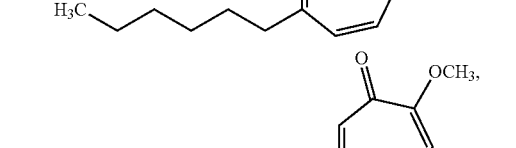
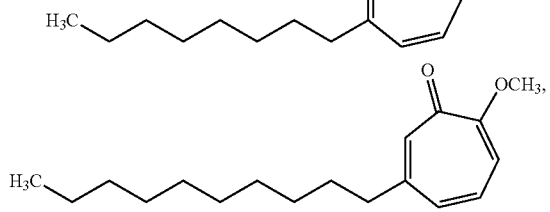
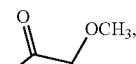
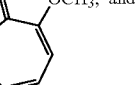
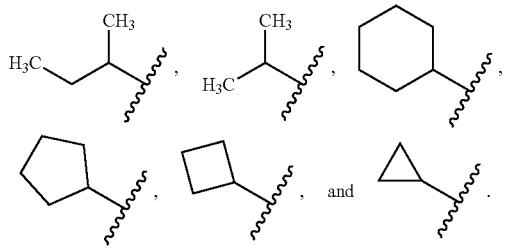
or a salt thereof.
In other embodiments, $R^a$ is selected from the group consisting of
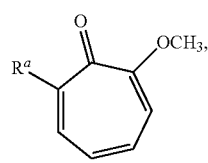
In some such embodiments, the compound of structural formula:
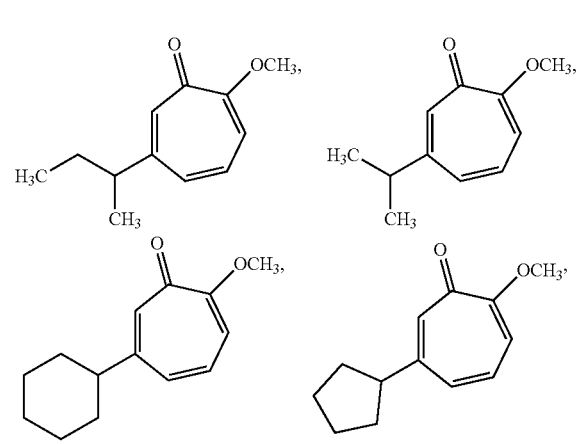
or salt thereof, is selected from the group consisting of:

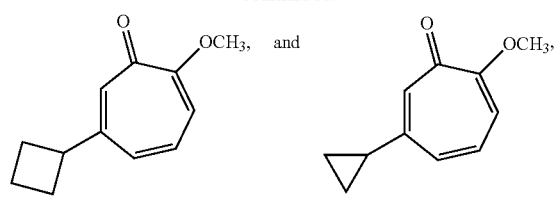
or a salt thereof.
In some embodiments, $R^a$ is selected from the group consisting of:
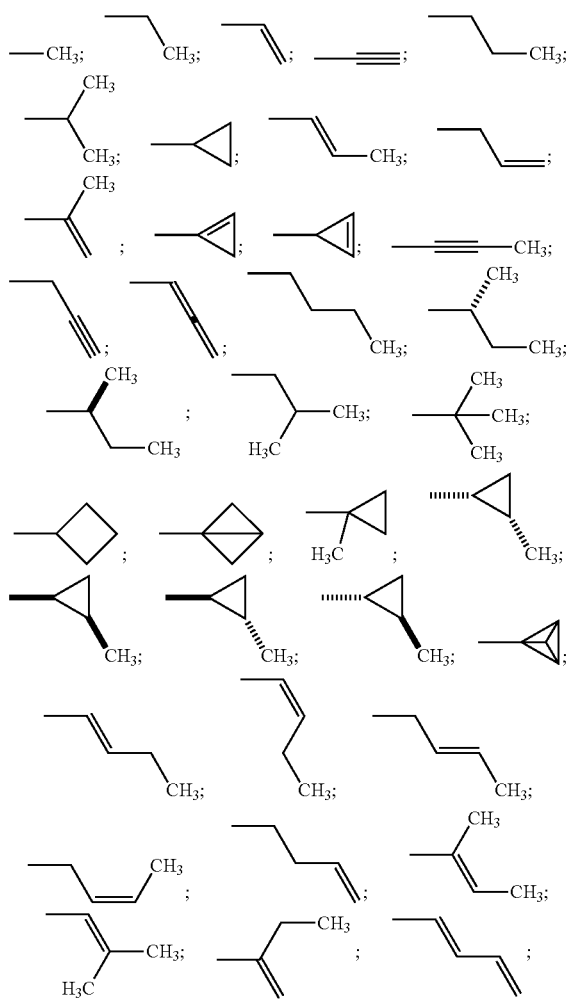
In some such embodiments, the compound of structural formula:
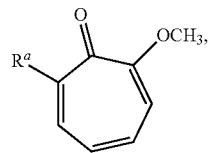
or salt thereof, is selected from the group consisting of:
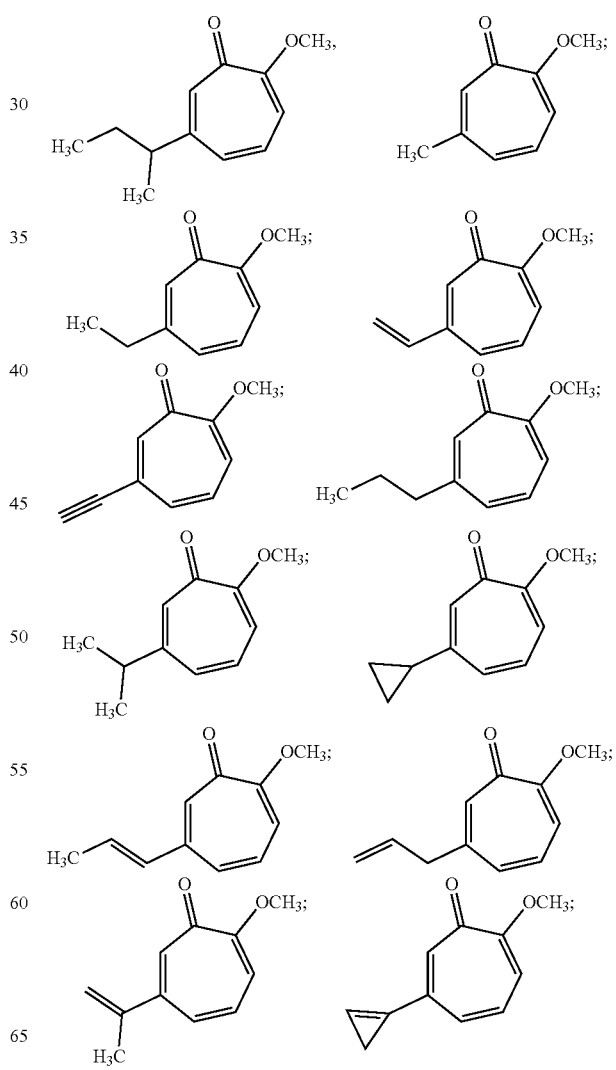

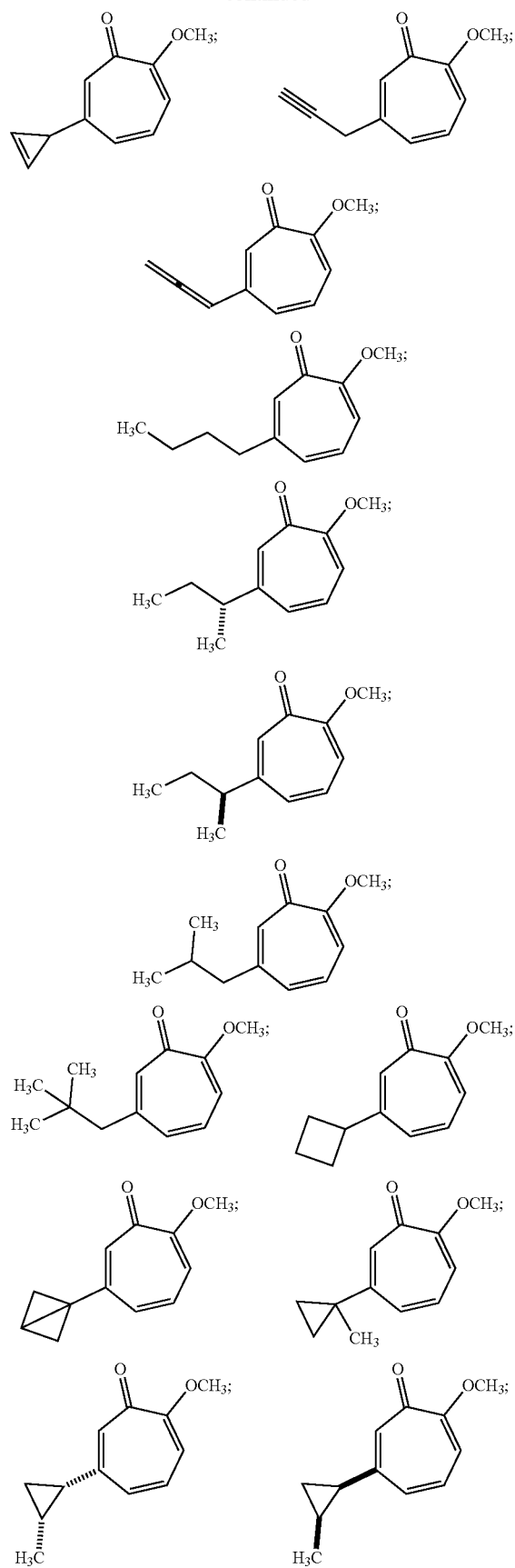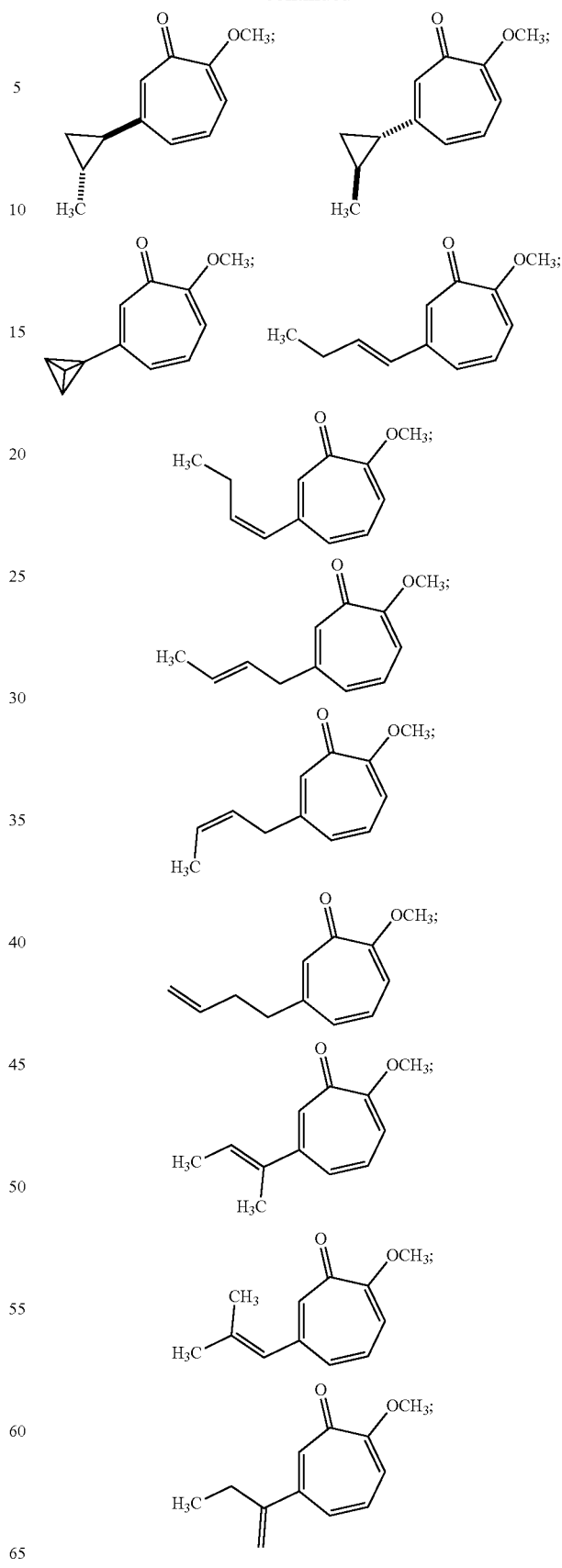

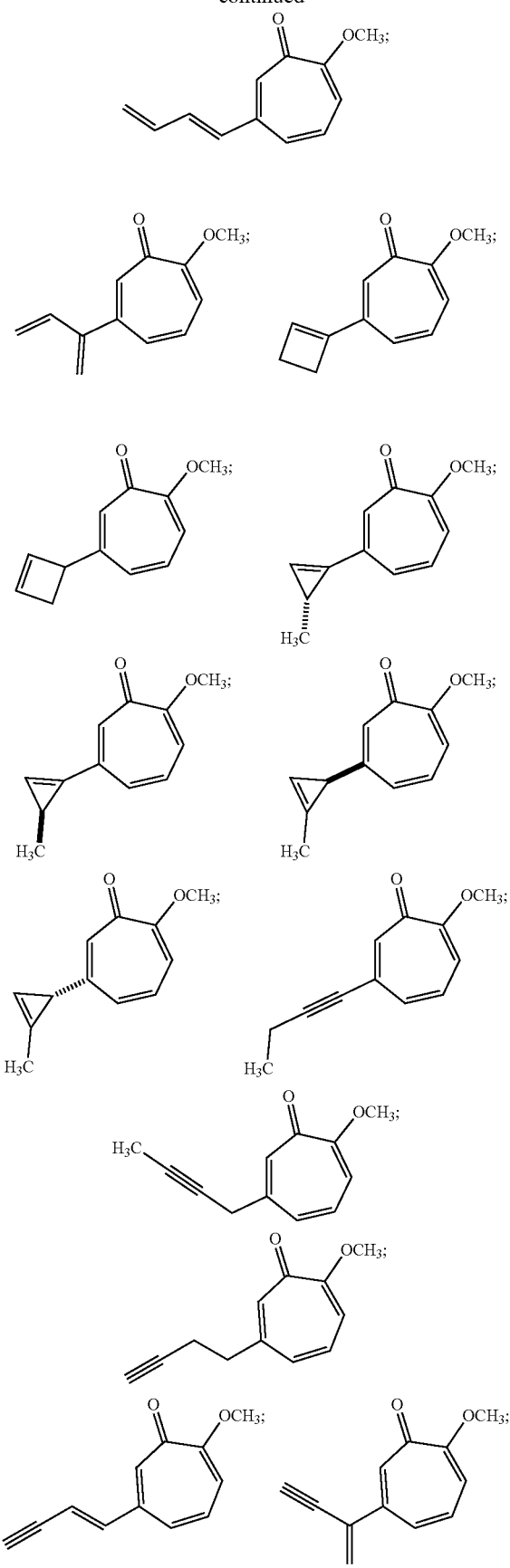

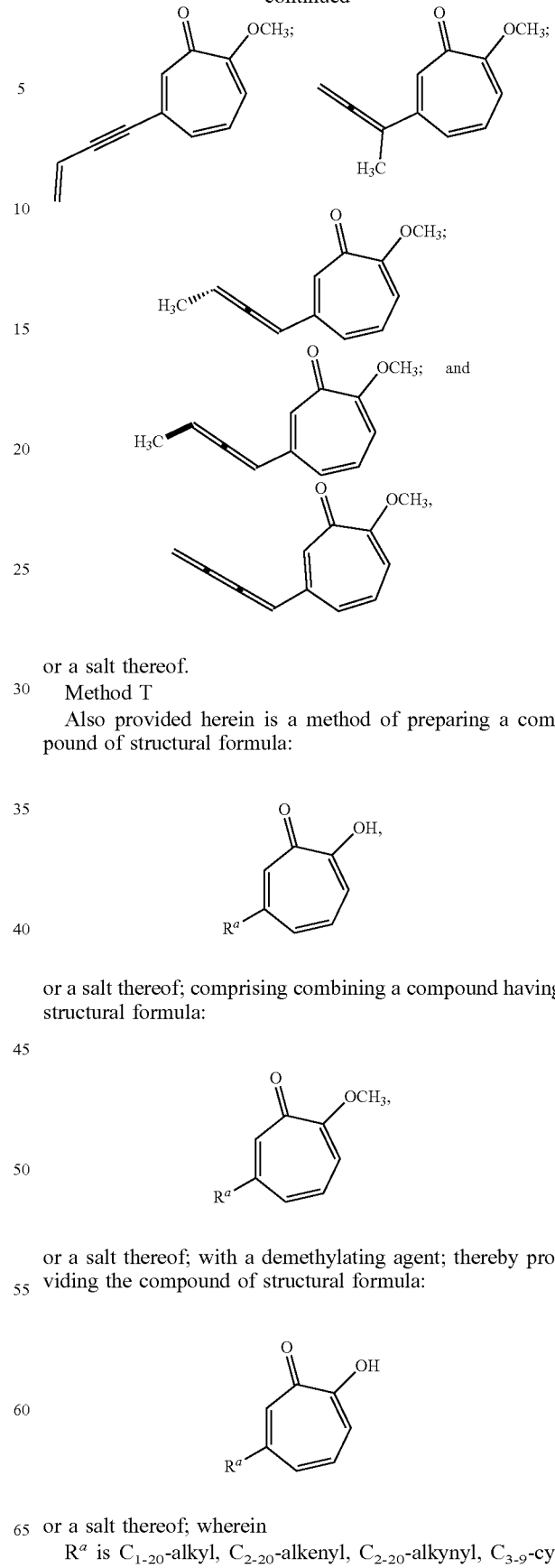

or a salt thereof.

Method T

Also provided herein is a method of preparing a compound of structural formula:

or a salt thereof; comprising combining a compound having structural formula:

or a salt thereof; with a demethylating agent; thereby providing the compound of structural formula:

or a salt thereof; wherein $R^a$ is $C_{1-20}$-alkyl, $C_{2-20}$-alkenyl, $C_{2-20}$-alkynyl, $C_{3-9}$-cycloalkyl, aryl, or heteroaryl, each of which is unsubstituted or substituted with a substituent selected from the group consisting of halo, $NO_2$, CN, $C_{1-6}$-alkyl, $C_{1-6}$-haloalkyl, and $C_{1-6}$-alkoxy.

In some embodiments, the demethylating agent is an acid. In some such embodiments, the demethylating agent is a mineral acid, an organic acid, or a combination thereof. In certain embodiments, the demethylating agent is hydrochloric acid, hydrobromic acid, sulfuric acid, acetic acid, or a combination thereof. In preferred embodiments, the demethylating agent is hydrobromic or hydrochloric acid in acetic acid. Alternatively, the demethylating agent is sulfuric acid.

In some embodiments, the compound having structural formula:

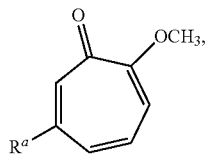

or a salt thereof; is contacted with a demethylating agent and heated to boiling; thereby providing the compound of structural formula:

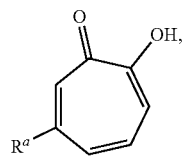

or salt thereof.

In some embodiments, the compound of structural formula:

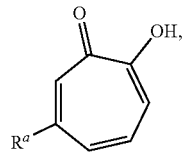

or salt thereof, is selected from:

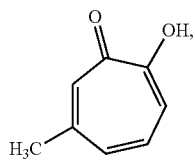 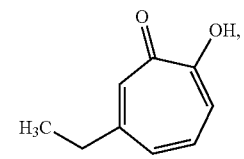

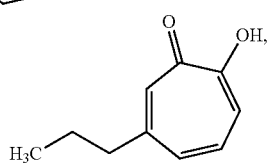

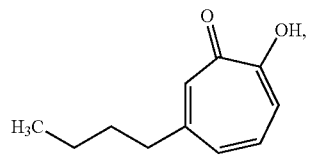

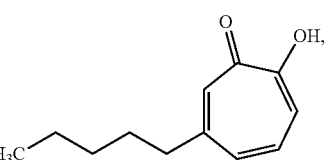

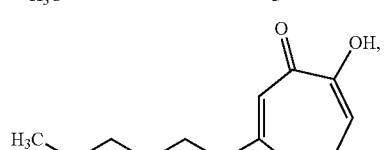

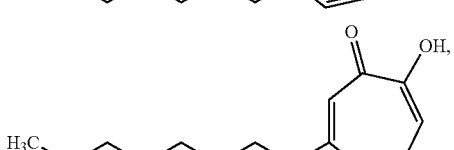

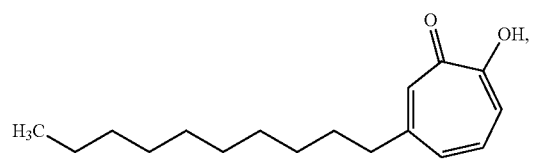

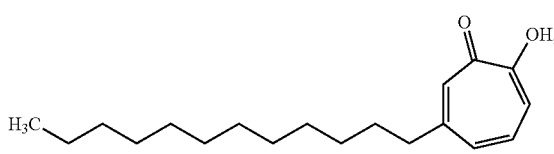

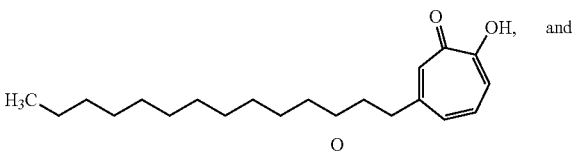

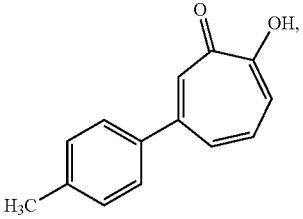

or a salt thereof.

In other embodiments, the compound of structural formula:

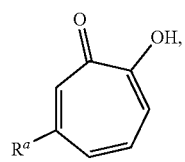

or salt thereof, is selected from the group consisting of:
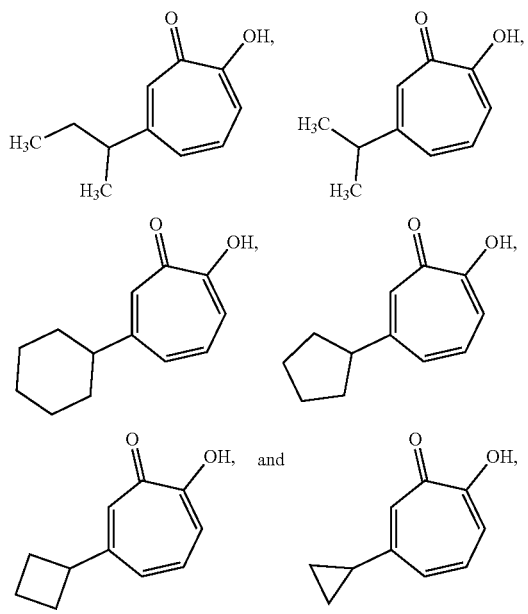
or a salt thereof.
In yet other embodiments, the compound of structural formula:
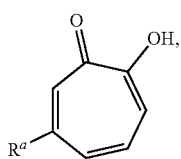
or salt thereof, is selected from the group consisting of:
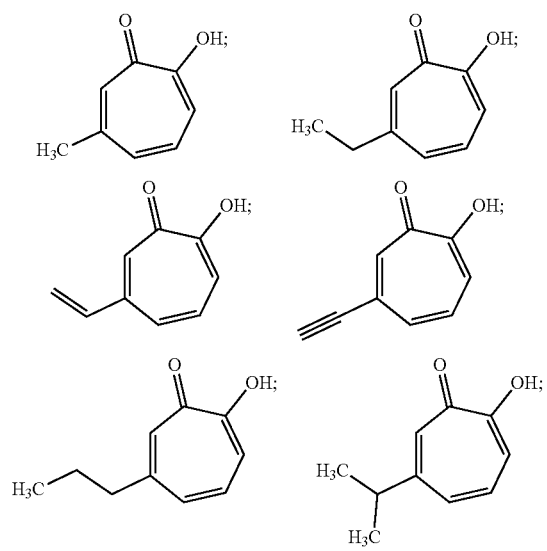
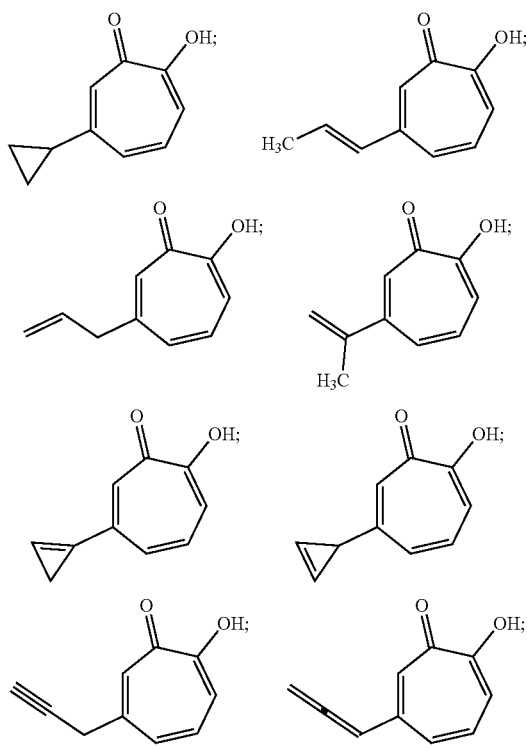
-continued
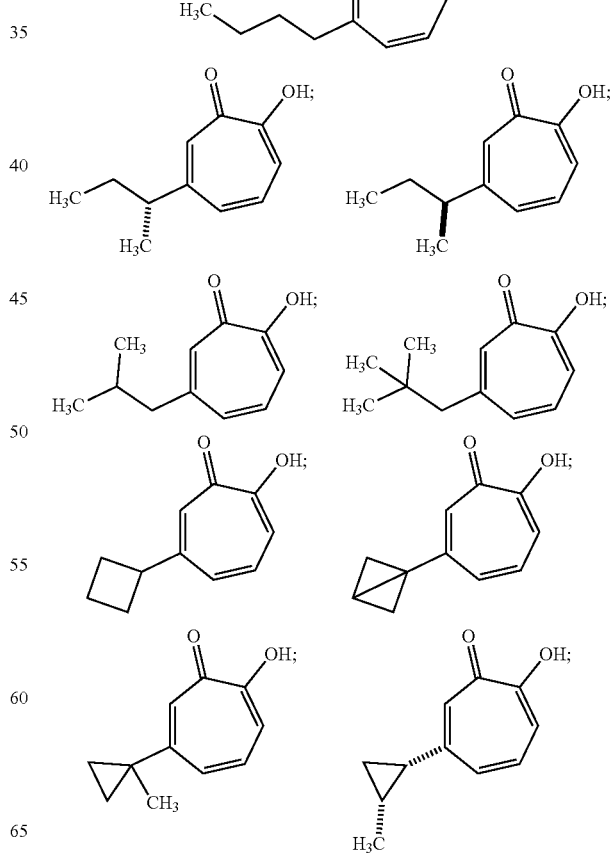

-continued
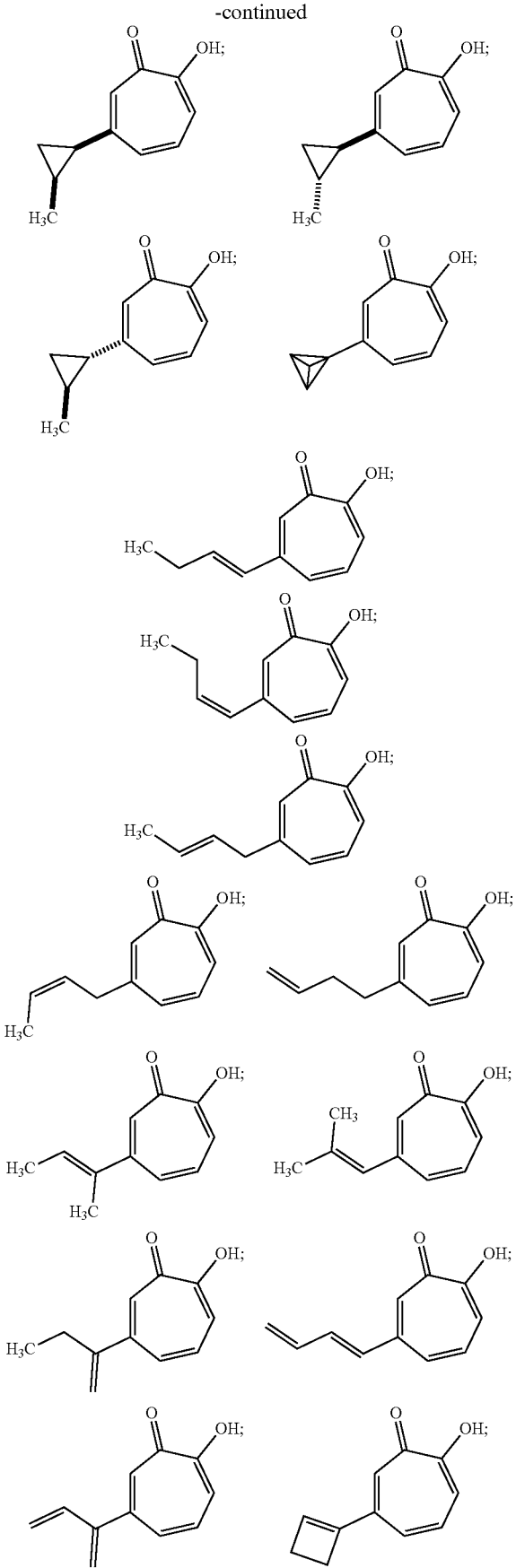
-continued
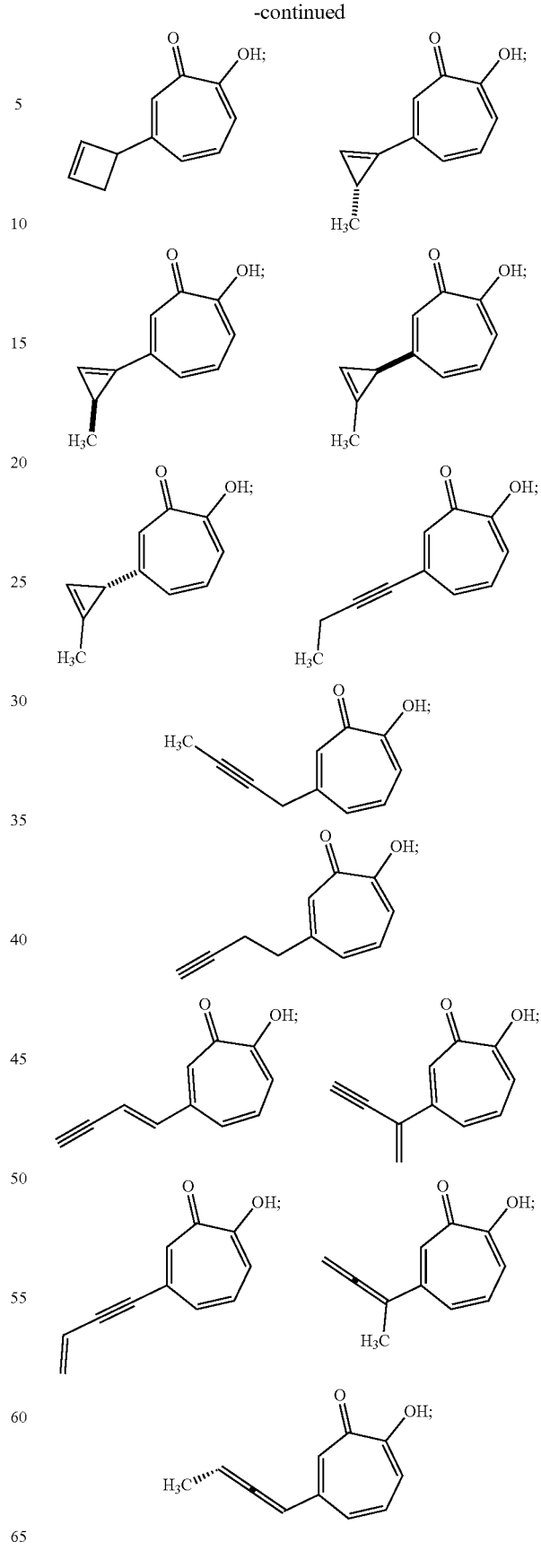

-continued

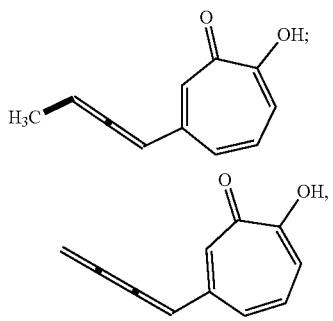

and

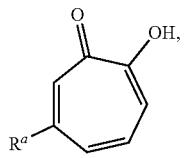

or a salt thereof.

Method U

Also provided herein is a method of preparing a compound of structural formula:

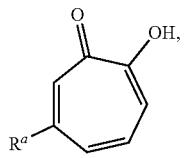

or a salt thereof; comprising:

(1) contacting 7,7-dibromo-3-methoxybicyclo[4.1.0]hept-3-en-2-one:

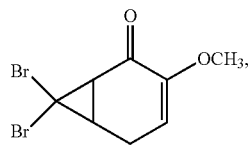

or a salt thereof; with a base; thereby forming 6-bromo-2-methoxycyclohepta-2,4,6-trien-1-one:

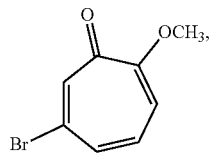

or a salt thereof;

(2) reacting a compound of structural formula:

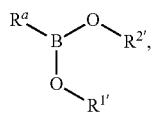

or a salt thereof; with 6-bromo-2-methoxycyclohepta-2,4,6-trien-1-one, or a salt thereof; thereby providing a compound having structural formula:

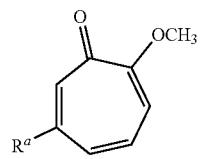

or a salt thereof; and (3) contacting the compound having structural formula:

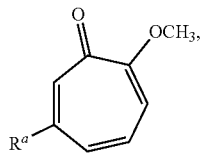

or a salt thereof; with a demethylating agent; thereby providing the compound of structural formula:

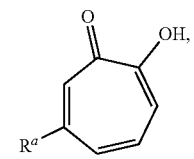

or a salt thereof; wherein $C_{1-20}$-alkyl, $C_{2-20}$-alkenyl, $C_{2-20}$-alkynyl, $C_{3-9}$-cycloalkyl, aryl, or heteroaryl, each of which is unsubstituted or substituted with a substituent selected from the group consisting of halo, $NO_2$, CN, $C_{1-6}$-alkyl, $C_{1-6}$-haloalkyl, and $C_{1-4}$-alkoxy;

$R^{1'}$ and $R^{2'}$ are each, independently hydrogen or $C_{1-6}$-alkyl; or $R^{1'}$ and $R^{2'}$, together with atoms to which they are attached, form a ring having 2 to 4 carbon atoms, each of which is optionally and independently substituted with $C_{1-3}$-alkyl or C=O; and B is a boron atom having $sp^3$ hybridization.

In some embodiments, in step (1) of the method, 7,7-dibromo-3-methoxybicyclo[4.1.0]hept-3-en-2-one is first contacted with the oxidizing agent at a temperature of about −78° C. In certain embodiments of the method, the temperature is subsequently warmed to about 0° C. In some embodiments, the oxidizing agent comprises one or more of potassium dichromate, pyridinium chlorochromate, Dess-Martin periodinane, oxalyl chloride, dimethylsulfoxide, aluminum alkoxide (e.g., aluminum isopropoxide), trimethylaluminum, potassium tert-butoxide, or silver carbonate. In other embodiments, the oxidizing agent comprises dimethylsulfoxide and one or more additional reagents selected from the group consisting of a carbodiimide, trifluoroacetic anhydride, oxalyl chloride, and sulfur trioxide pyridine complex.

In some embodiments, step (1) of the method further comprises contacting 7,7-dibromo-3-methoxybicyclo[4.1.0]hept-3-en-2-one and the oxidizing agent with a base. In some such embodiments, the base is an amine base. In certain embodiments, the base is a tertiary amine base, such as triethylamine.

In some embodiments, step (2) of the method further comprises contacting the compounds with a metal catalyst. In some such embodiments, the metal catalyst is a palladium catalyst or a palladium nanomaterial-based catalyst. In certain embodiments, the metal catalyst is an organopalladium catalyst. For example, in particular embodiments, the metal catalyst is selected from the group consisting of tetrakis(triphenylphosphine)palladium(0), palladium chloride, and palladium(II) acetate.

In some embodiments, the reaction with comprising the metal catalyst further comprises a promoter. In some such embodiments, the promoter is thallium (I) ethoxide or silver oxide. In preferred embodiments, the promoter is silver oxide.

In some embodiments, $R^1$ and $R^{2'}$ are both hydrogen.

In some embodiments, the demethylating agent is an acid. In some such embodiments, the demethylating agent is a mineral acid, an organic acid, or a combination thereof. In certain embodiments, the demethylating agent is hydrochloric acid, hydrobromic acid, sulfuric acid, acetic acid, or a combination thereof. In preferred embodiments, the demethylating agent is hydrobromic or hydrochloric acid in acetic acid. Alternatively, the demethylating agent is sulfuric acid.

In some embodiments, $R^a$ is $C_{1-4}$-alkyl, $C_{2-4}$-alkenyl, $C_{2-4}$-alkynyl, or $C_{3-4}$-cycloalkyl.

In some such embodiments, $R^a$ is selected from the group consisting of:

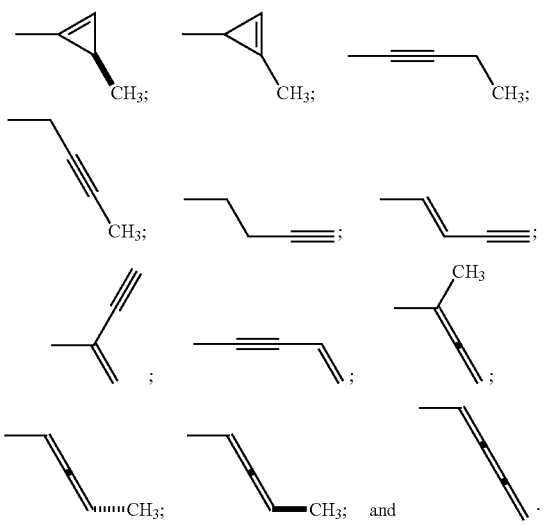

In some such embodiments, the compound of structural formula:

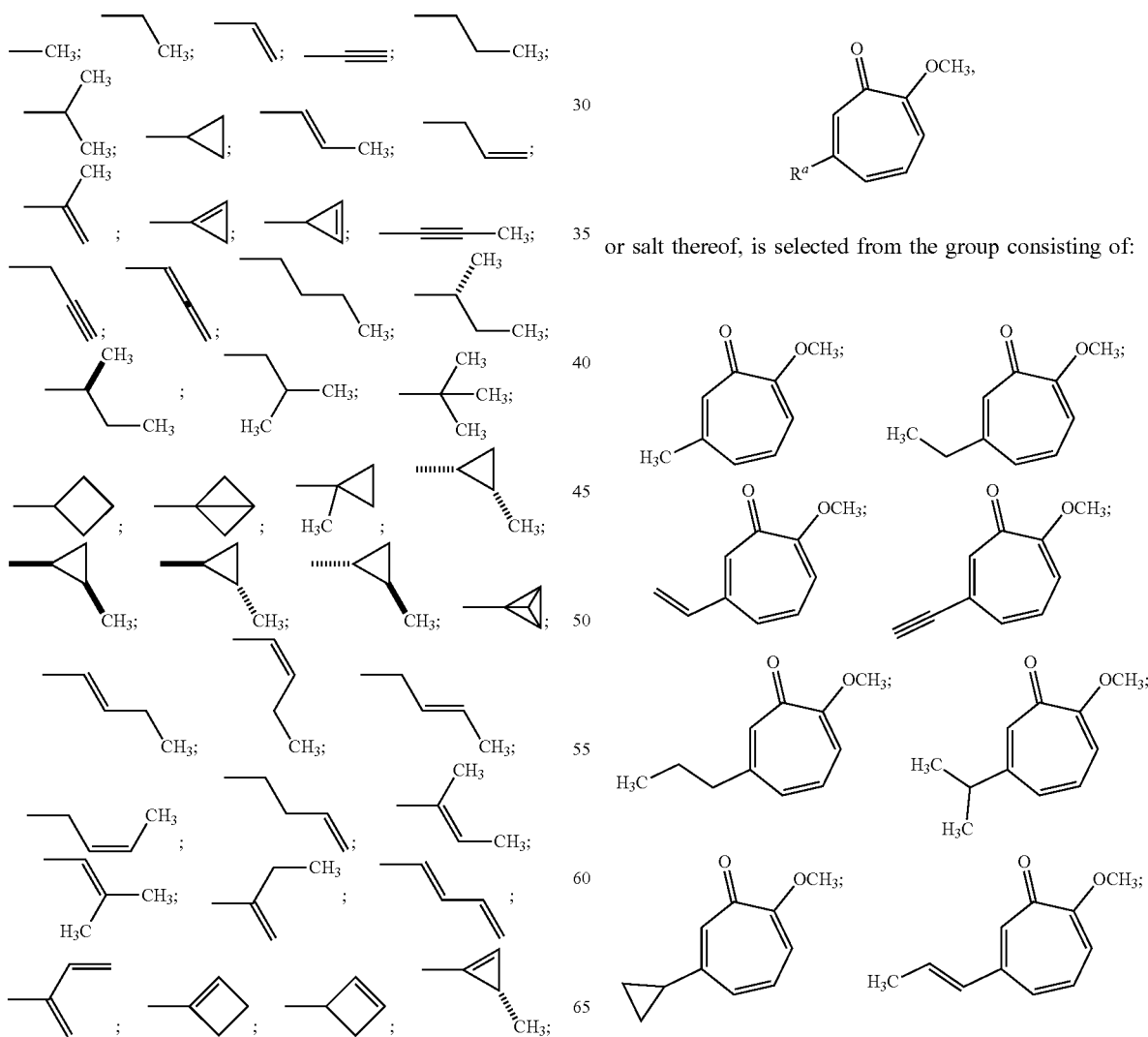

or salt thereof, is selected from the group consisting of:

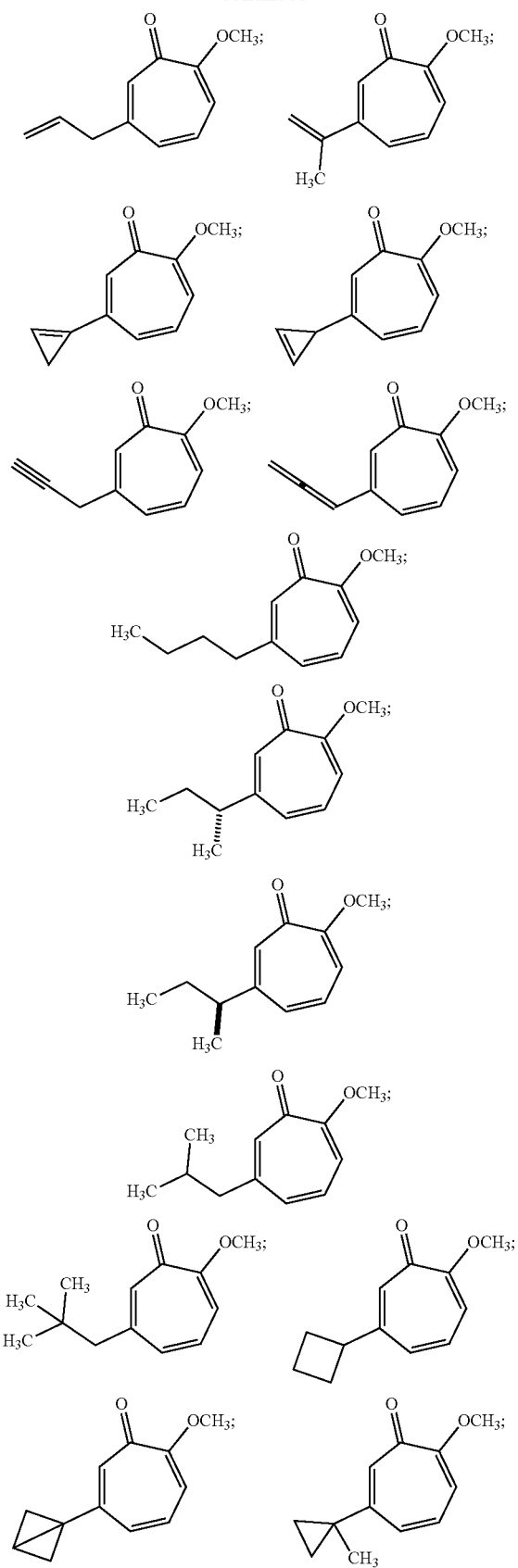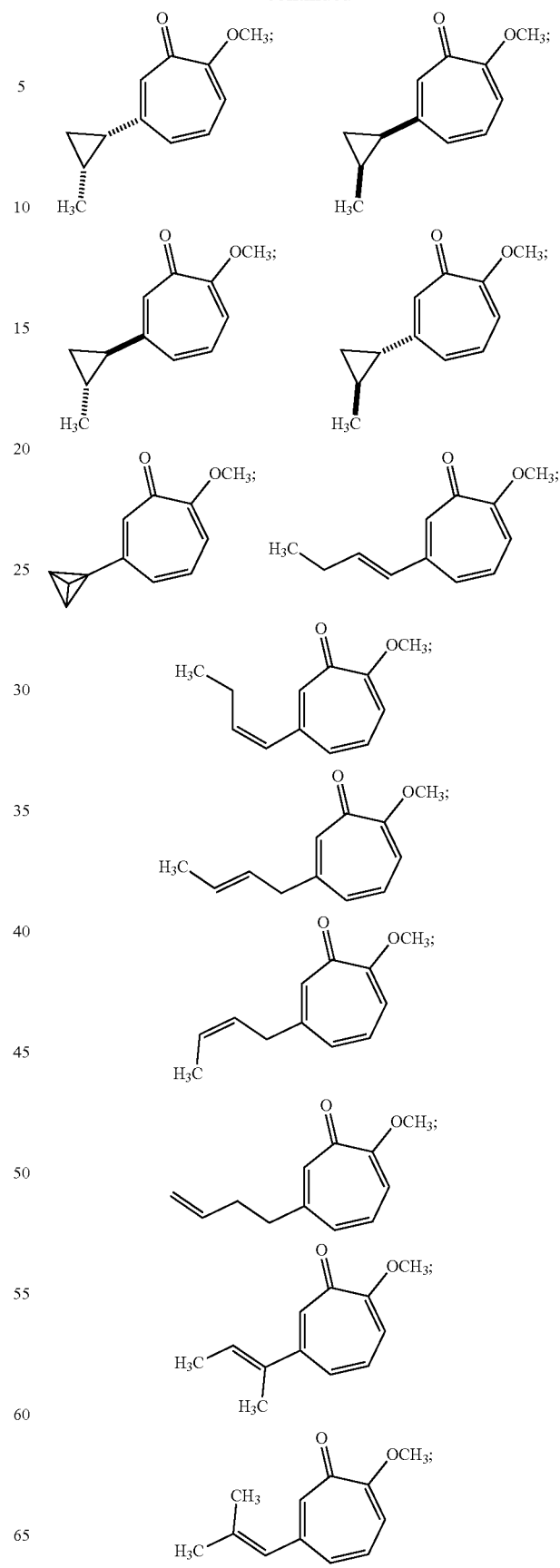

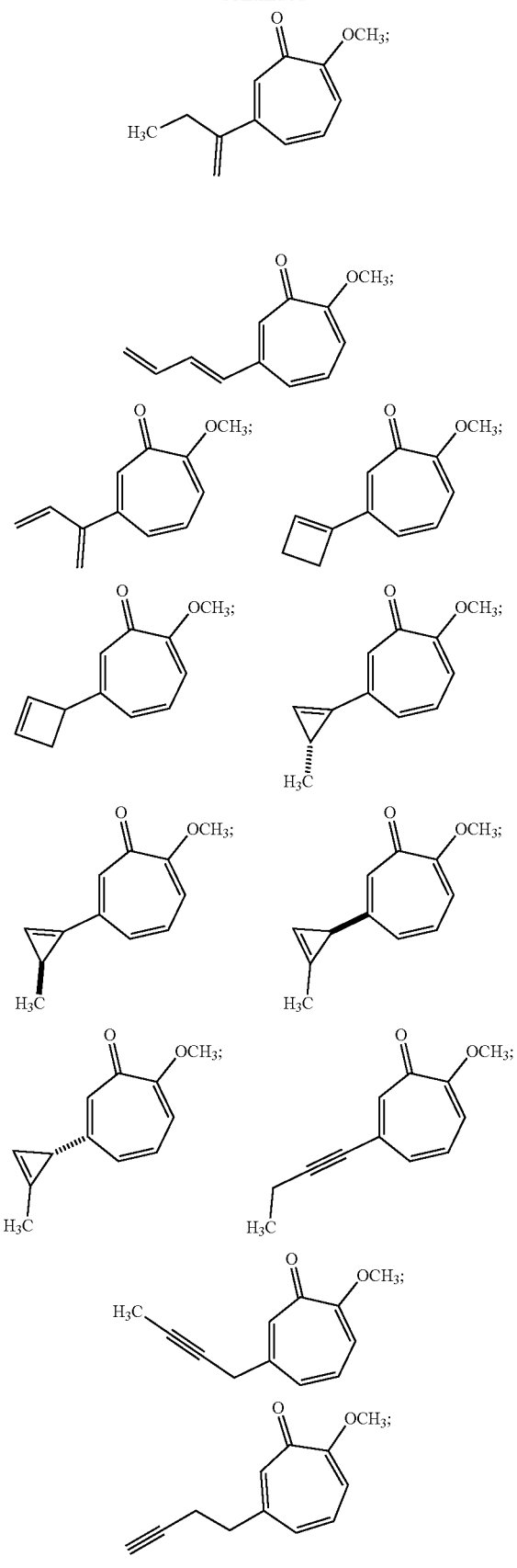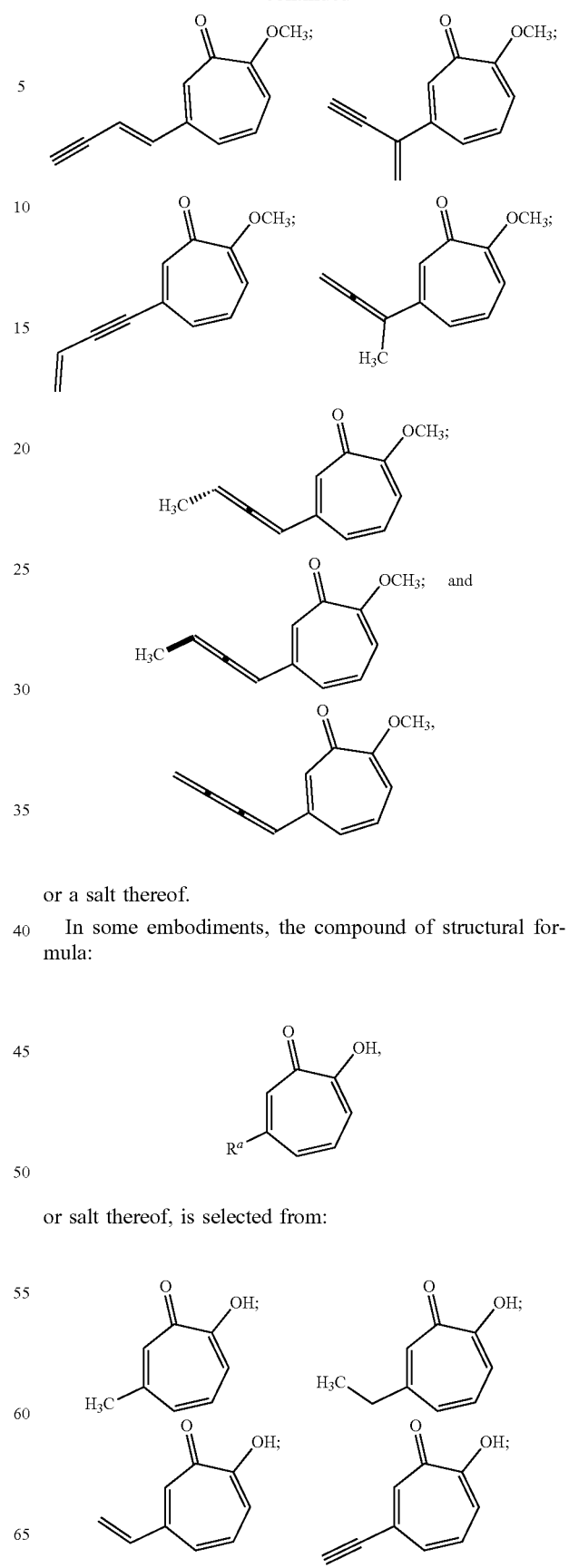
or a salt thereof.
In some embodiments, the compound of structural formula:
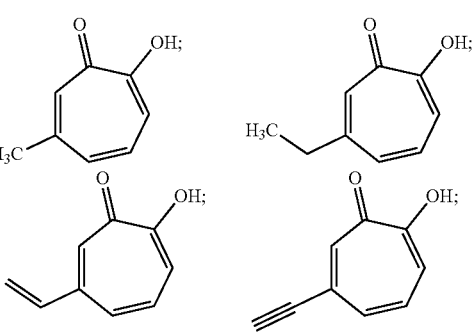
or salt thereof, is selected from:

-continued
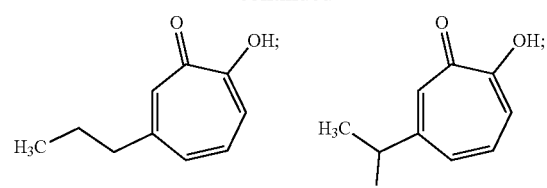
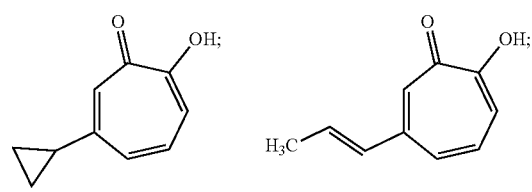
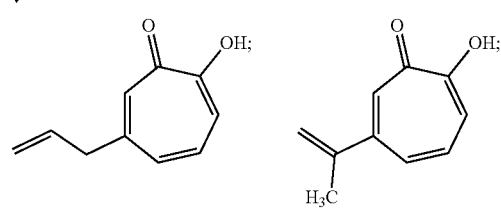
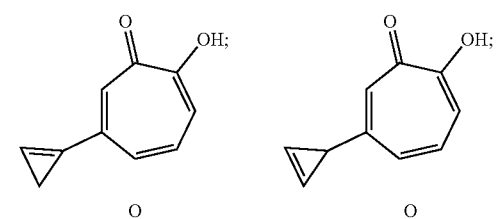
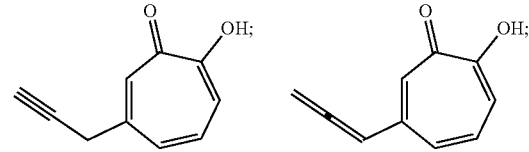
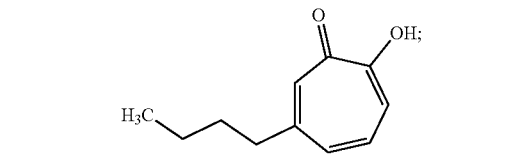
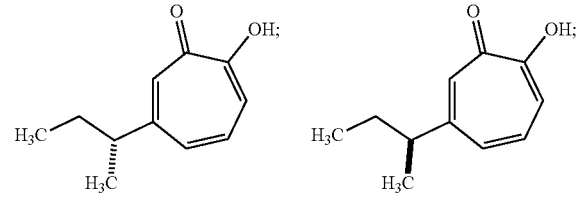
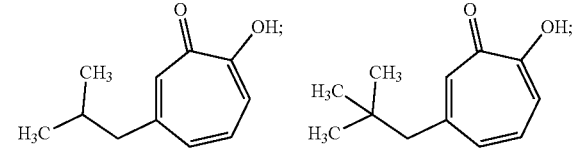
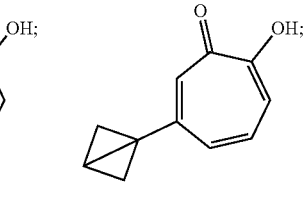
-continued
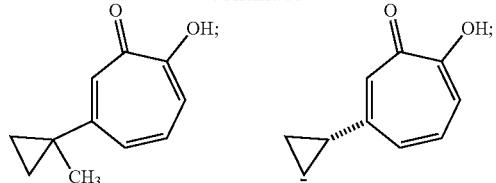
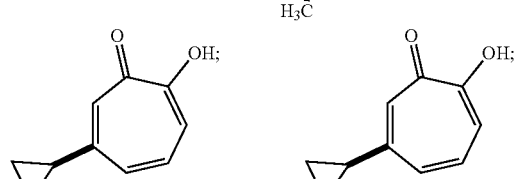
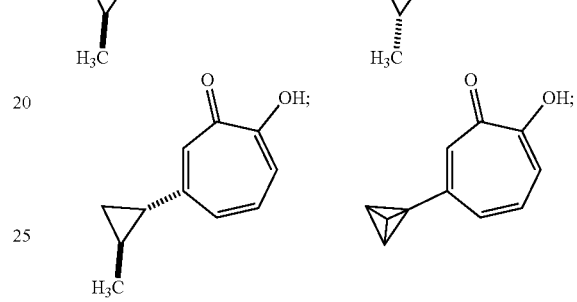
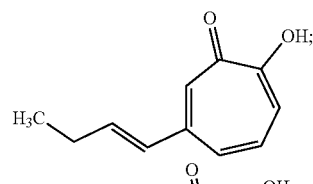
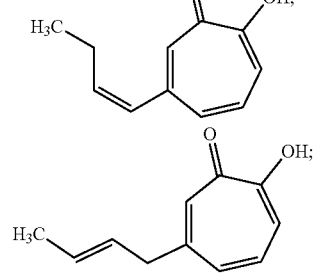
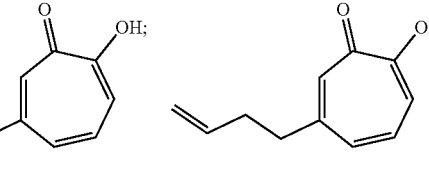
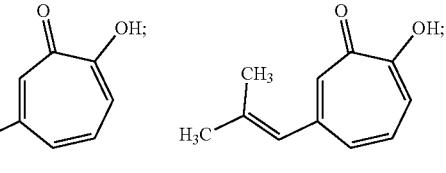
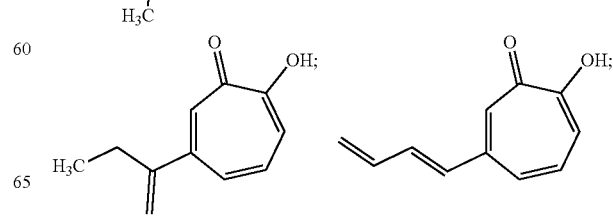

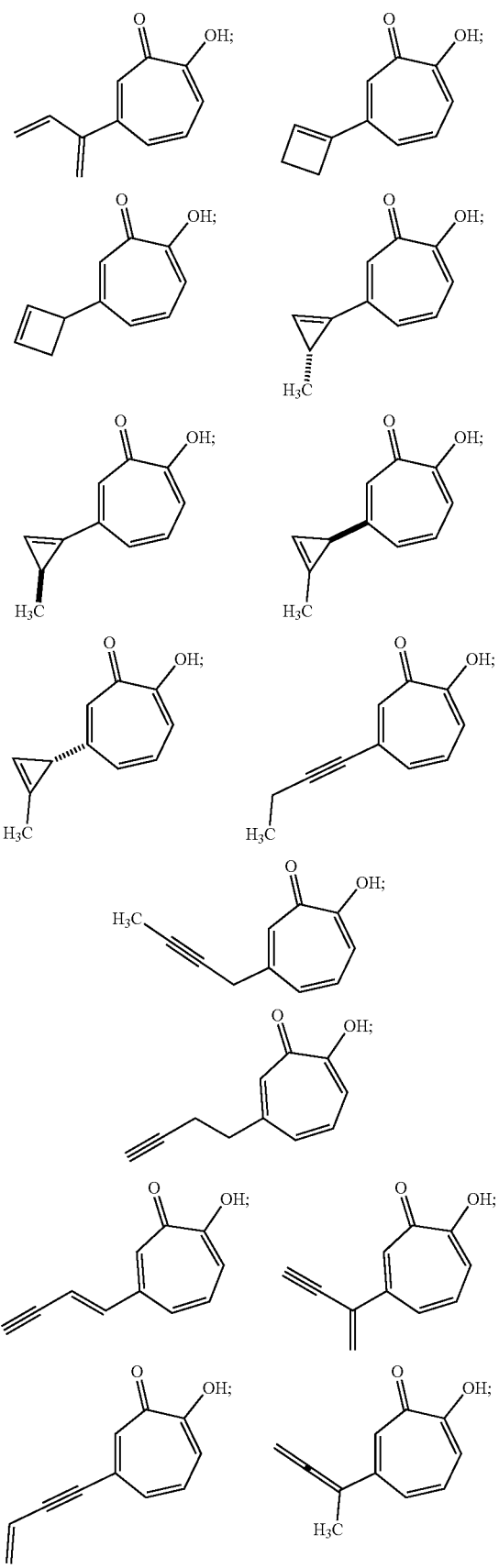
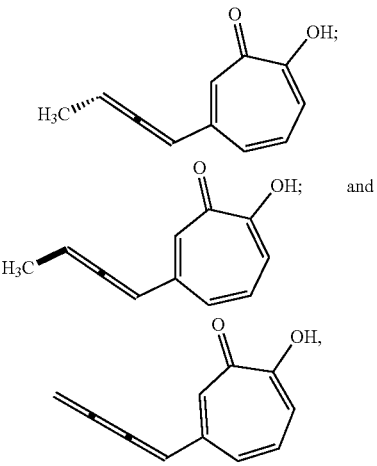
or a salt thereof.
In some other embodiments, $R^a$ is selected from the group consisting of:
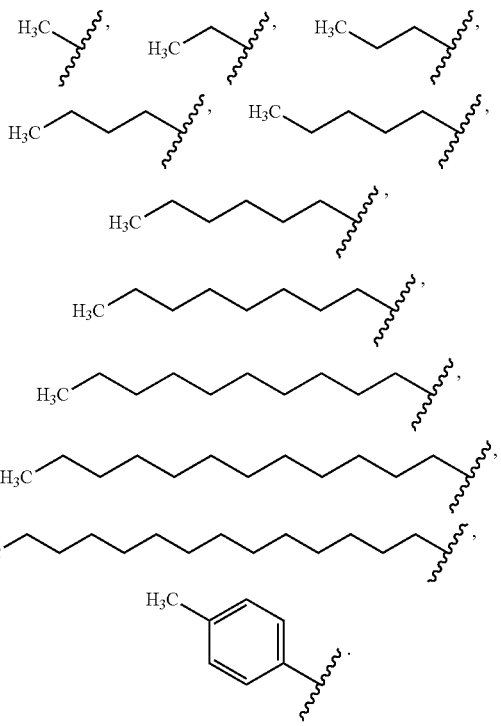
In some such embodiments, the compound of structural formula:
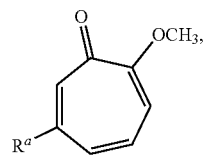

or salt thereof, is selected from the group consisting of:
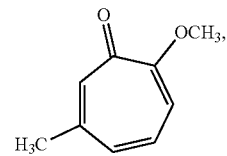
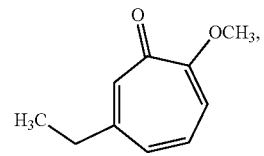
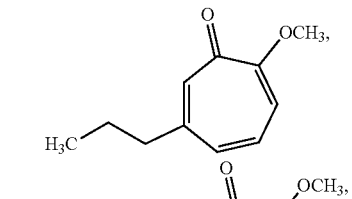
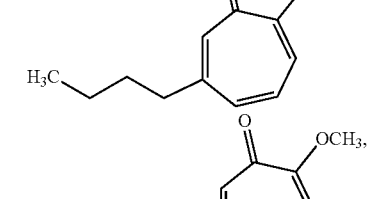
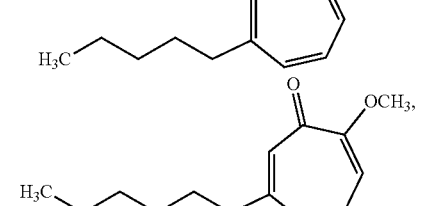
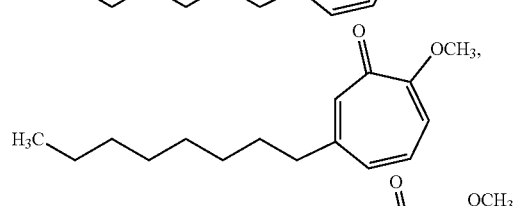
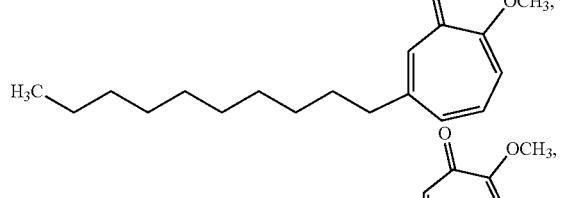
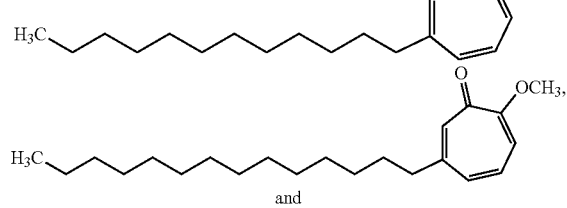
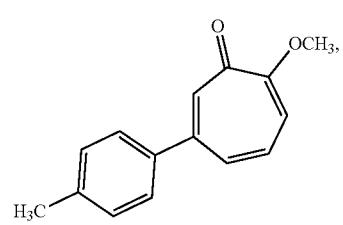
and
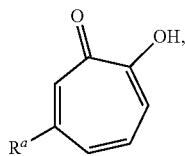
or a salt thereof.
In some embodiments, the compound of structural formula:
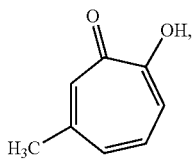
or salt thereof, is selected from:
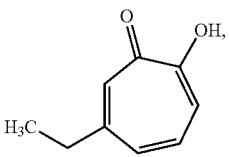
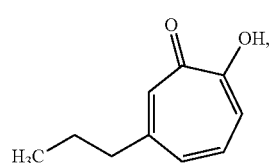
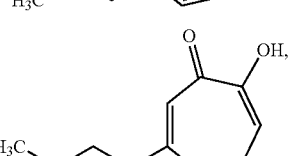
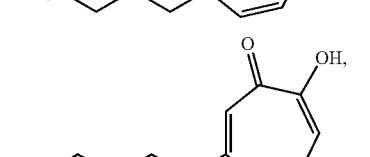
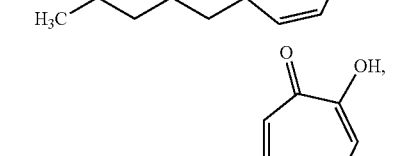
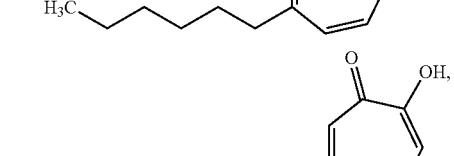
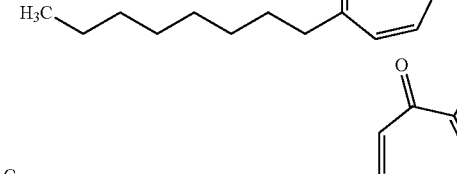
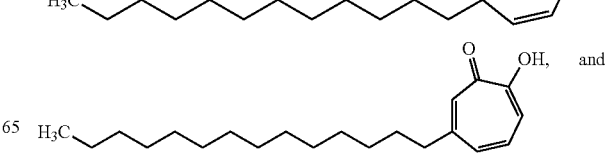
and

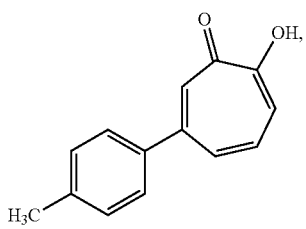

or a salt thereof.

In other embodiments, $R^a$ is selected from the group consisting of

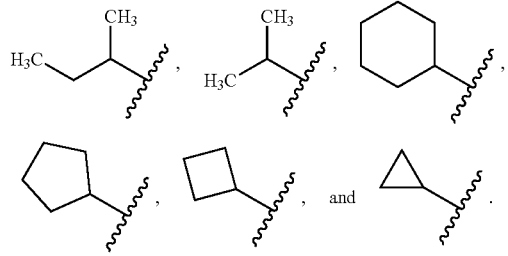

In some such embodiments, compound of structural formula:

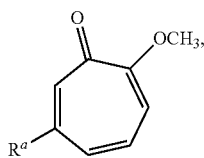

or salt thereof, is selected from the group consisting of:

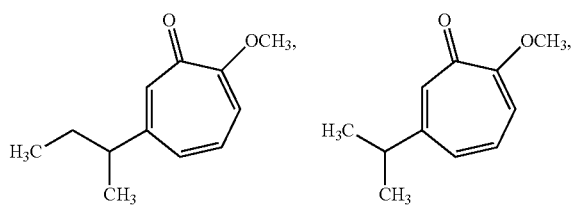

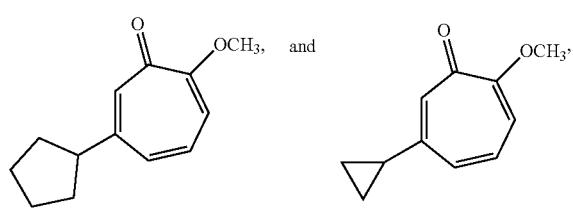

or a salt thereof.

In some embodiments, the compound of structural formula:

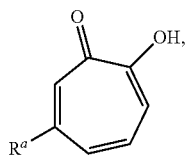

or salt thereof, is selected from the group consisting of:

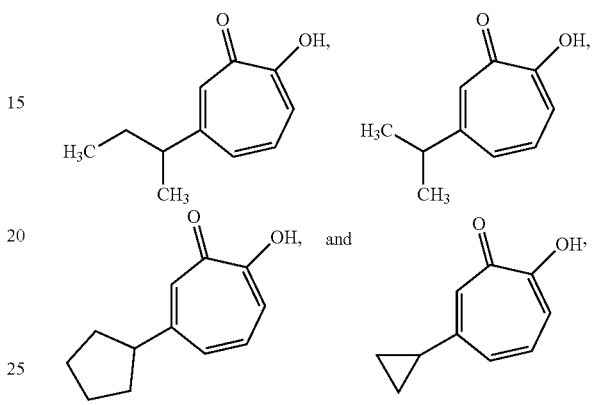

or a salt thereof.

Methods of Treatment

In any subject, an assessment may be made as to whether the subject has an iron metabolism-related disorder using routine techniques known in the art (e.g., such an assessment can include one or more blood tests to determine hemoglobin level, red blood count, reticulocyte count, serum ferritin, serum iron, saturated serum transferrin, serum hepcidin, serum RGMc, etc.). The assessment may be made as to whether the subject has an iron-related disorder related to iron deficiency or iron overload and, thus, may indicate an appropriate course of therapy, such as preventative therapy, maintenance therapy, or modulative therapy. As a reference, a haematologist may use the following reference numbers to indicate that the patient has normal levels of the corresponding parameter. See Table A.

TABLE A

| Serum Iron in Micrograms per Deciliter (Rows 1-4) | |
|---|---|
| 1. Men | 65 to 176 |
| 2. Women | 50 to 170 |
| 3. Newborn | 100 to 250 |
| 4. Child | 50 to 120 |
| 5. Total Binding Capacity ("TIBC") | 240 to 450 |
| 6. Transferrin Saturation | 20% to 50% |

Accordingly, provided herein is a method of treating, preventing, modulating, or attenuating a disease of iron metabolism. The compounds disclosed herein may be administered to a subject in need thereof. The compounds disclosed herein may be administered to the subject in a therapeutically effective amount, wherein said amount can be readily determined by one skilled in the art.

The disease or disorder of iron metabolism may be any disease or disorder in which iron homeostasis is perturbed in the subject. This homeostasis relies on the proper regulation of adequate plasma iron levels. Iron circulates in plasma bound to transferrin, which is a vehicle for iron delivery into cells. Plasma transferrin is normally about 30% saturated with iron. Accordingly, transferrin saturation must be maintained at appropriate physiological levels in response to a variety of signals from pathways involved in iron consumption.

The subject may have, or be at risk of, a disease or disorder such as fatigue, joint pain, bone or joint disease (osteoarthritis, osteoporosis), rheumatoid arthritis, inflammatory bowel disease, shortness of breath, irregular heart beat, liver trouble, diabetes, infertility, impotence, depression, mood or mental disorders, poor cognitive skills or neurodegenerative diseases, ACD, iron-refractory iron-deficiency anemia, anemia of chronic kidney disease, resistance to erythropoiesis-stimulating agents, aplastic anemia, divalent metal transporter 1 (DMT1), myelodysplastic syndromes, sideroblastic anemia, hypoplastic anemias, paroxysmal nocturnal hemoglobinuria, von Willebrand disease, hemophilia hereditary hemorrhagic telangiectasia, red cell enzymopathies: glucose-6 phosphate dehydrogenase (G6PD) or pyruvate kinase deficiency (PKD), atransferrinemia or hypotransferrinemia, aceruloplasminemia or hypoceruloplasminia, CDAII: (congenital dyserythropoietic anemia), which is also called:HEMPAS (hereditary erythroblastic multi-nuclearity with positive acidified serum lysis test). In preferred embodiments, the subject is deficient in divalent metal transporter 1 (DMT1).

The disease of iron metabolism may be one in which there is too little iron in the body. For example, a subject may be diagnosed with an iron deficiency if serum iron is found to be below 60 µg/dl, below 55 µg/dl, below 50 µg/dl, below 45 µg/dl, or below 40 µg/dl. A subject may be diagnosed with an iron deficiency if his/her total iron binding capacity ("TIBC") is lower than 50%, 45%, 40%, 35%, 30%, 25%, 20%, 15%, or 10%. A subject may be diagnosed with an iron deficiency if he/she has increased ferritin levels as compared to a subject that does not have an iron deficiency. A subject may be diagnosed with an iron deficiency if he/she has a hemoglobin level of lower than 15.5, 15, 14.5, 14, 13.5, 13, 12.5, 12, 11.5, 11, 10.5, 10, 9.5, 9, 8.5, 8, 7.5, 7, 6.5, or 6 g/dl. A transferrin saturation of less than 25%, less than 20%, less than 19%, 18%, 17%, 16%, 15%, 14%, 13%, 12%, 11%, 10%, 9%, 8%, or 7% may be indicative of iron deficiency. A subject may be diagnosed as having an iron deficiency based on one or more factors as set forth above.

Iron deficiency at critical times of growth and development can result in premature births, low birth weight babies, delayed growth and development, and delayed normal infant activity and movement; iron deficiency can result in poor memory or poor cognitive skills (mental function) resulting in poor performance in school, work, the military or in recreation. Lower IQs have been linked to iron deficiency occurring during critical periods of growth.

Iron Deficiency Anemia ("IDA") is a condition where a subject has inadequate amounts of iron to meet body demands. IDA results from a decrease in the amount of red cells in the blood, which is related to the subject having too little iron. IDA may be caused by a diet insufficient in iron or from blood loss. IDA is the most common form of anemia. About 20% of women, 50% of pregnant women, and 3% of men are iron-deficient.

Iron refractory iron anemia ("IRIDA") afflicted subjects suffer from microcytic anemia and do not respond to oral therapy and are partially refractory to parenteral iron, because of inappropriately high hepcidin levels. IRIDA is caused by a mutation in the matriptase-2 gene (TMPRSS6), which encodes a serine protease that negatively regulates hepcidin expression by cleaving membrane-bound RGMc.

Accordingly, the compounds disclosed herein may be used to treat any iron-related disorder, including, but not limited to, iron deficiency, AI, and iron overload. Other examples of disorders caused by too much iron include cirrhosis, liver cancer, osteoarthritis, osteopenia, osteomalacia, diabetes, irregular heart beat, heart attack, hypothyroidism, infertility, impotence, depression, hypogonadism, and bronze or ashen gray skin miscoloration. Examples of other iron-related disorders that may be diagnosed and treated according to the present invention include, e.g., hemochromatosis, juvenile hemochromatosis, acquired iron overload, sickle cell anemia, thalassemia, African siderosis, porphyria cutaena tarda, iron deficiency anemia, Friedreich Ataxia, ferroportin disease, hyperferritinemia, atransferrinemia, and sideroblastic anemia. Iron-related disorders further include, e.g., heart failure, haemolytic anaemia, and neurological disorders.

In some embodiments, provided herein is a method to of treating a disease or condition characterized by a deficiency of or a defect in an iron transporter, comprising administering to a subject in need thereof a therapeutically effective amount of tropolone or a compound disclosed herein, thereby treating the disease or condition. In some such embodiments, the disease or condition characterized by a deficiency of or defect in an iron transporter is hypochromic, microcytic anemia.

In other embodiments, provided herein is a method of increasing transepithelial iron transport, comprising administering to a subject in need thereof an effective amount of tropolone or a compound disclosed herein.

In yet other embodiments, provided herein is a method of increasing physiology, comprising administering to a subject in need thereof an effective amount of tropolone or a compound disclosed herein.

In still other embodiments, provided herein is a method of increasing hemoglobinization, comprising administering to a subject in need thereof an effective amount of tropolone or a compound disclosed herein.

In other embodiments, provided herein is a method of increasing iron release, comprising administering to a subject in need thereof an effective amount of tropolone or a compound disclosed herein.

In some embodiments, the methods further comprising administering an effective amount of one or more additional compounds selected from the group consisting of amphotericin B (AmB), calcimycin, nonactin, deferiprone, purpurogallin, and maltol.

Also provided herein is method of increasing transepithelial iron transport, physiology, or hemoglobinization in a cell in vitro, comprising contacting the cell with an effective amount of the compound disclosed herein. In some such embodiments, the method further comprises contacting the cell with an effective amount of one or more compounds selected from the group consisting of amphotericin B (AmB), calcimycin, nonactin, deferiprone, purpurogallin, and maltol, and any combination thereof.

In other embodiments, provided herein is a method of increasing transepithelial iron transport, physiology, or hemoglobinization in an organ ex vivo, comprising contacting the organ with an effective amount of the compound disclosed herein. In some such embodiments, the method further comprises contacting the organ with an effective amount of one or more compounds selected from the group consisting of amphotericin B (AmB), calcimycin, nonactin, deferiprone, purpurogallin, and maltol, and any combination thereof.

Pharmaceutical Compositions

Also provided are pharmaceutical compositions comprising a compound of the invention, or a pharmaceutically acceptable salt thereof, and a pharmaceutically acceptable excipient or carrier. Also provided is a method for making such pharmaceutical compositions. The method comprises placing a compound of the invention, or a pharmaceutically acceptable salt thereof, in a pharmaceutically acceptable excipient or carrier.

Compounds of the invention and pharmaceutical compositions of the invention are useful for the treatment of cancer in a subject. In certain embodiments, a therapeutically effective amount of a compound of the invention, or a pharmaceutically acceptable salt thereof, is administered to a subject in need thereof, thereby treating cancer.

As used herein, "inhibit" or "inhibiting" means reduce by an objectively measureable amount or degree compared to control. In one embodiment, inhibit or inhibiting means reduce by at least a statistically significant amount compared to control. In one embodiment, inhibit or inhibiting means reduce by at least 5 percent compared to control. In various individual embodiments, inhibit or inhibiting means reduce by at least 10, 15, 20, 25, 30, 33, 40, 50, 60, 67, 70, 75, 80, 90, or 95 percent (%) compared to control.

As used herein, the terms "treat" and "treating" refer to performing an intervention that results in (a) preventing a condition or disease from occurring in a subject that may be at risk of developing or predisposed to having the condition or disease but has not yet been diagnosed as having it; (b) inhibiting a condition or disease, e.g., slowing or arresting its development; or (c) relieving or ameliorating a condition or disease, e.g., causing regression of the condition or disease. In one embodiment the terms "treating" and "treat" refer to performing an intervention that results in (a) inhibiting a condition or disease, e.g., slowing or arresting its development; or (b) relieving or ameliorating a condition or disease, e.g., causing regression of the condition or disease.

As used herein, a "subject" refers to a living mammal. In various embodiments a subject is a non-human mammal, including, without limitation, a mouse, rat, hamster, guinea pig, rabbit, sheep, goat, cat, dog, pig, horse, cow, or non-human primate. In certain embodiments a subject is a human.

In certain embodiments, the subject is a human.

As used herein, "administering" has its usual meaning and encompasses administering by any suitable route of administration, including, without limitation, intravenous, intramuscular, intraperitoneal, intrathecal, intraocular (e.g., intravitreal), subcutaneous, direct injection (for example, into a tumor), mucosal, inhalation, oral, and topical.

In one embodiment, the administration is intravenous.

In one embodiment, the administration is oral.

As used herein, the phrase "effective amount" refers to any amount that is sufficient to achieve a desired biological effect.

Compounds of the invention can be combined with other therapeutic agents, or may be used in combination with other compounds of the invention. The compound of the invention and other therapeutic agent may be administered simultaneously or sequentially. When the other therapeutic agents are administered simultaneously, they can be administered in the same or separate formulations, but they are administered substantially at the same time. The other therapeutic agents are administered sequentially with one another and with compound of the invention, when the administration of the other therapeutic agents and the compound of the invention is temporally separated. The separation in time between the administration of these compounds may be a matter of minutes or it may be longer.

Examples of other therapeutic agents include antibiotics, anti-viral agents, anti-inflammatory agents, immunosuppressive agents, antiarrhythmic agents, beta blockers, analgesics, and anti-cancer agents.

As stated above, an "effective amount" refers to any amount that is sufficient to achieve a desired biological effect. Combined with the teachings provided herein, by choosing among the various active compounds and weighing factors such as potency, relative bioavailability, patient body weight, severity of adverse side-effects and preferred mode of administration, an effective prophylactic or therapeutic treatment regimen can be planned which does not cause substantial unwanted toxicity and yet is effective to treat the particular subject. The effective amount for any particular application can vary depending on such factors as the disease or condition being treated, the particular compound of the invention being administered, the size of the subject, or the severity of the disease or condition. One of ordinary skill in the art can empirically determine the effective amount of a particular compound of the invention and/or other therapeutic agent without necessitating undue experimentation. It is sometimes preferred that a maximum dose be used, that is, the highest safe dose according to some medical judgment. Multiple doses per day may be contemplated to achieve appropriate systemic levels of compounds. Appropriate systemic levels can be determined by, for example, measurement of the patient's peak or sustained plasma level of the drug. "Dose" and "dosage" are used interchangeably herein.

Generally, daily oral doses of active compounds will be, for human subjects, from about 0.01 milligrams/kg per day to 1000 milligrams/kg per day. It is expected that oral doses in the range of 0.5 to 50 milligrams/kg, in one or several administrations per day, will yield the desired results. Dosage may be adjusted appropriately to achieve desired drug levels, local or systemic, depending upon the mode of administration. For example, it is expected that intravenous administration would be from one order to several orders of magnitude lower dose per day. In the event that the response in a subject is insufficient at such doses, even higher doses (or effective higher doses by a different, more localized delivery route) may be employed to the extent that patient tolerance permits. Multiple doses per day are contemplated to achieve appropriate systemic levels of compounds.

In one embodiment, intravenous administration of a compound of the invention may typically be from 0.1 mg/kg/day to 20 mg/kg/day.

For any compound described herein the therapeutically effective amount can be initially determined from animal models. A therapeutically effective dose can also be determined from human data for compounds of the invention which have been tested in humans and for compounds which are known to exhibit similar pharmacological activities, such as other related active agents. Higher doses may be required for parenteral administration. The applied dose can be adjusted based on the relative bioavailability and potency of the administered compound. Adjusting the dose to achieve maximal efficacy based on the methods described above and other methods as are well-known in the art is well within the capabilities of the ordinarily skilled artisan.

The formulations of the invention may be administered in pharmaceutically acceptable solutions, which may routinely contain pharmaceutically acceptable concentrations of salt, buffering agents, preservatives, compatible carriers, adjuvants, and optionally other therapeutic ingredients.

For use in therapy, an effective amount of the compound of the invention can be administered to a subject by any mode that delivers the compound of the invention to the desired location or surface. Administering the pharmaceutical composition of the present invention may be accomplished by any means known to the skilled artisan. Routes of administration include but are not limited to oral, intravenous, intramuscular, intraperitoneal, subcutaneous, direct injection (for example, into a tumor or abscess), mucosal, inhalation, and topical.

For intravenous and other parenteral routes of administration, the compound can be formulated as a lyophilized preparation with desoxycholic acid, as a lyophilized preparation of liposome-intercalated or -encapsulated active compound, as a lipid complex in aqueous suspension, or as a cholesteryl sulfate complex. Lyophilized formulations are generally reconstituted in suitable aqueous solution, e.g., in sterile water or saline, shortly prior to administration.

For oral administration, the compounds (i.e., compounds of the invention, and other therapeutic agents) can be formulated readily by combining the active compound(s) with pharmaceutically acceptable carriers well known in the art. Such carriers enable the compounds of the invention to be formulated as tablets, pills, dragees, capsules, liquids, gels, syrups, slurries, suspensions and the like, for oral ingestion by a subject to be treated. Pharmaceutical preparations for oral use can be obtained as solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate. Optionally the oral formulations may also be formulated in saline or buffers, e.g., EDTA for neutralizing internal acid conditions or may be administered without any carriers.

Also specifically contemplated are oral dosage forms of the above component or components. The component or components may be chemically modified so that oral delivery of the derivative is efficacious. Generally, the chemical modification contemplated is the attachment of at least one moiety to the component molecule itself, where said moiety permits (a) inhibition of acid hydrolysis; and (b) uptake into the blood stream from the stomach or intestine. Also desired is the increase in overall stability of the component or components and increase in circulation time in the body. Examples of such moieties include: polyethylene glycol, copolymers of ethylene glycol and propylene glycol, carboxymethyl cellulose, dextran, polyvinyl alcohol, polyvinyl pyrrolidone and polyproline. Abuchowski and Davis, "Soluble Polymer-Enzyme Adducts", In: Enzymes as Drugs, Hocenberg and Roberts, eds., Wiley-Interscience, New York, N.Y., pp. 367-383 (1981); Newmark et al., *J Appl Biochem* 4:185-9 (1982). Other polymers that could be used are poly-1,3-dioxolane and poly-1,3,6-tioxocane. Preferred for pharmaceutical usage, as indicated above, are polyethylene glycol moieties.

For the component (or derivative) the location of release may be the stomach, the small intestine (the duodenum, the jejunum, or the ileum), or the large intestine. One skilled in the art has available formulations which will not dissolve in the stomach, yet will release the material in the duodenum or elsewhere in the intestine. Preferably, the release will avoid the deleterious effects of the stomach environment, either by protection of the compound of the invention (or derivative) or by release of the biologically active material beyond the stomach environment, such as in the intestine.

To ensure full gastric resistance a coating impermeable to at least pH 5.0 is essential. Examples of the more common inert ingredients that are used as enteric coatings are cellulose acetate trimellitate (CAT), hydroxypropylmethylcellulose phthalate (HPMCP), HPMCP 50, HPMCP 55, polyvinyl acetate phthalate (PVAP), Eudragit L30D, Aquateric, cellulose acetate phthalate (CAP), Eudragit L, Eudragit S, and shellac. These coatings may be used as mixed films.

A coating or mixture of coatings can also be used on tablets, which are not intended for protection against the stomach. This can include sugar coatings, or coatings which make the tablet easier to swallow. Capsules may consist of a hard shell (such as gelatin) for delivery of dry therapeutic (e.g., powder); for liquid forms, a soft gelatin shell may be used. The shell material of cachets could be thick starch or other edible paper. For pills, lozenges, molded tablets or tablet triturates, moist massing techniques can be used.

The therapeutic can be included in the formulation as fine multi-particulates in the form of granules or pellets of particle size about 1 mm. The formulation of the material for capsule administration could also be as a powder, lightly compressed plugs or even as tablets. The therapeutic could be prepared by compression.

Colorants and flavoring agents may all be included. For example, the compound of the invention (or derivative) may be formulated (such as by liposome or microsphere encapsulation) and then further contained within an edible product, such as a refrigerated beverage containing colorants and flavoring agents.

One may dilute or increase the volume of the therapeutic with an inert material. These diluents could include carbohydrates, especially mannitol, a-lactose, anhydrous lactose, cellulose, sucrose, modified dextrans and starch. Certain inorganic salts may be also be used as fillers including calcium triphosphate, magnesium carbonate and sodium chloride. Some commercially available diluents are Fast-Flo, Emdex, STA-Rx 1500, Emcompress and Avicell.

Disintegrants may be included in the formulation of the therapeutic into a solid dosage form. Materials used as disintegrates include but are not limited to starch, including the commercial disintegrant based on starch, Explotab. Sodium starch glycolate, Amberlite, sodium carboxymethylcellulose, ultramylopectin, sodium alginate, gelatin, orange peel, acid carboxymethyl cellulose, natural sponge and bentonite may all be used. Another form of the disintegrants are the insoluble cationic exchange resins. Powdered gums may be used as disintegrants and as binders and these can include powdered gums such as agar, Karaya or tragacanth. Alginic acid and its sodium salt are also useful as disintegrants.

Binders may be used to hold the therapeutic agent together to form a hard tablet and include materials from natural products such as acacia, tragacanth, starch and gelatin. Others include methyl cellulose (MC), ethyl cellulose (EC) and carboxymethyl cellulose (CMC). Polyvinyl pyrrolidone (PVP) and hydroxypropylmethyl cellulose (HPMC) could both be used in alcoholic solutions to granulate the therapeutic.

An anti-frictional agent may be included in the formulation of the therapeutic to prevent sticking during the formulation process. Lubricants may be used as a layer between the therapeutic and the die wall, and these can include but are not limited to; stearic acid including its magnesium and calcium salts, polytetrafluoroethylene (PTFE), liquid paraffin, vegetable oils and waxes. Soluble lubricants may also be used such as sodium lauryl sulfate, magnesium lauryl sulfate, polyethylene glycol of various molecular weights, Carbowax 4000 and 6000.

Glidants that might improve the flow properties of the drug during formulation and to aid rearrangement during compression might be added. The glidants may include starch, talc, pyrogenic silica and hydrated silicoaluminate.

To aid dissolution of the therapeutic into the aqueous environment a surfactant might be added as a wetting agent. Surfactants may include anionic detergents such as sodium lauryl sulfate, dioctyl sodium sulfosuccinate and dioctyl sodium sulfonate. Cationic detergents which can be used and can include benzalkonium chloride and benzethonium chloride. Potential non-ionic detergents that could be included in the formulation as surfactants include lauromacrogol 400, polyoxyl 40 stearate, polyoxyethylene hydrogenated castor oil 10, 50 and 60, glycerol monostearate, polysorbate 40, 60, 65 and 80, sucrose fatty acid ester, methyl cellulose and carboxymethyl cellulose. These surfactants could be present in the formulation of the compound of the invention or derivative either alone or as a mixture in different ratios.

Pharmaceutical preparations which can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. Microspheres formulated for oral administration may also be used. Such microspheres have been well defined in the art. All formulations for oral administration should be in dosages suitable for such administration.

For buccal administration, the compositions may take the form of tablets or lozenges formulated in conventional manner.

For administration by inhalation, the compounds for use according to the present invention may be conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of e.g., gelatin for use in an inhaler or insufflator may be formulated containing a powder mix of the compound and a suitable powder base such as lactose or starch.

Also contemplated herein is pulmonary delivery of the compounds of the invention (or derivatives thereof). The compound of the invention (or derivative) is delivered to the lungs of a mammal while inhaling and traverses across the lung epithelial lining to the blood stream. Other reports of inhaled molecules include Adjei et al., *Pharm Res* 7:565-569 (1990); Adjei et al., *Int J Pharmaceutics* 63:135-144 (1990) (leuprolide acetate); Braquet et al., *J Cardiovasc Pharmacol* 13(suppl. 5):143-146 (1989) (endothelin-1); Hubbard et al., *Annal Int Med* 3:206-212 (1989) (al-antitrypsin); Smith et al., 1989, *J Clin Invest* 84:1145-1146 (a-l-proteinase); Oswein et al., 1990, "Aerosolization of Proteins", Proceedings of Symposium on Respiratory Drug Delivery II, Keystone, Colorado, March, (recombinant human growth hormone); Debs et al., 1988, *J Immunol* 140:3482-3488 (interferon-gamma and tumor necrosis factor alpha) and Platz et al., U.S. Pat. No. 5,284,656 (granulocyte colony stimulating factor). A method and composition for pulmonary delivery of drugs for systemic effect is described in U.S. Pat. No. 5,451,569, issued Sep. 19, 1995 to Wong, et al.

Contemplated for use in the practice of this invention are a wide range of mechanical devices designed for pulmonary delivery of therapeutic products, including but not limited to nebulizers, metered dose inhalers, and powder inhalers, all of which are familiar to those skilled in the art.

Some specific examples of commercially available devices suitable for the practice of this invention are the Ultravent nebulizer, manufactured by Mallinckrodt, Inc., St. Louis, Mo.; the Acorn II nebulizer, manufactured by Marquest Medical Products, Englewood, Colo.; the Ventolin metered dose inhaler, manufactured by Glaxo Inc., Research Triangle Park, North Carolina; and the Spinhaler powder inhaler, manufactured by Fisons Corp., Bedford, Mass.

All such devices require the use of formulations suitable for the dispensing of compound of the invention (or derivative). Typically, each formulation is specific to the type of device employed and may involve the use of an appropriate propellant material, in addition to the usual diluents, adjuvants and/or carriers useful in therapy. Also, the use of liposomes, microcapsules or microspheres, inclusion complexes, or other types of carriers is contemplated. Chemically modified compound of the invention may also be prepared in different formulations depending on the type of chemical modification or the type of device employed.

Formulations suitable for use with a nebulizer, either jet or ultrasonic, will typically comprise compound of the invention (or derivative) dissolved in water at a concentration of about 0.1 to 25 mg of biologically active compound of the invention per mL of solution. The formulation may also include a buffer and a simple sugar (e.g., for compound of the invention stabilization and regulation of osmotic pressure). The nebulizer formulation may also contain a surfactant, to reduce or prevent surface induced aggregation of the compound of the invention caused by atomization of the solution in forming the aerosol.

Formulations for use with a metered-dose inhaler device will generally comprise a finely divided powder containing the compound of the invention (or derivative) suspended in a propellant with the aid of a surfactant. The propellant may be any conventional material employed for this purpose, such as a chlorofluorocarbon, a hydrochlorofluorocarbon, a hydrofluorocarbon, or a hydrocarbon, including trichlorofluoromethane, dichlorodifluoromethane, dichlorotetrafluoroethanol, and 1,1,1,2-tetrafluoroethane, or combinations thereof. Suitable surfactants include sorbitan trioleate and soya lecithin. Oleic acid may also be useful as a surfactant.

Formulations for dispensing from a powder inhaler device will comprise a finely divided dry powder containing compound of the invention (or derivative) and may also include a bulking agent, such as lactose, sorbitol, sucrose, or mannitol in amounts which facilitate dispersal of the powder from the device, e.g., 50 to 90% by weight of the formulation. The compound of the invention (or derivative) should advantageously be prepared in particulate form with an average particle size of less than 10 micrometers (µm), most preferably 0.5 to 5 µm, for most effective delivery to the deep lung.

Nasal delivery of a pharmaceutical composition of the present invention is also contemplated. Nasal delivery allows the passage of a pharmaceutical composition of the present invention to the blood stream directly after administering the therapeutic product to the nose, without the necessity for deposition of the product in the lung. Formulations for nasal delivery include those with dextran or cyclodextran.

For nasal administration, a useful device is a small, hard bottle to which a metered dose sprayer is attached. In one embodiment, the metered dose is delivered by drawing the pharmaceutical composition of the present invention solution into a chamber of defined volume, which chamber has an aperture dimensioned to aerosolize and aerosol formulation by forming a spray when a liquid in the chamber is compressed. The chamber is compressed to administer the pharmaceutical composition of the present invention. In a specific embodiment, the chamber is a piston arrangement. Such devices are commercially available.

Alternatively, a plastic squeeze bottle with an aperture or opening dimensioned to aerosolize an aerosol formulation by forming a spray when squeezed is used. The opening is usually found in the top of the bottle, and the top is generally tapered to partially fit in the nasal passages for efficient administration of the aerosol formulation. Preferably, the nasal inhaler will provide a metered amount of the aerosol formulation, for administration of a measured dose of the drug.

The compounds, when it is desirable to deliver them systemically, may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions, or emulsions in oily or aqueous vehicles, and may contain formulatory agents such as suspending, stabilizing and/or dispersing agents.

Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethylcellulose, sorbitol, or dextran. Optionally, the suspension may also contain suitable stabilizers or agents which increase the solubility of the compounds to allow for the preparation of highly concentrated solutions.

Alternatively, the active compounds may be in powder form for constitution with a suitable vehicle, e.g., sterile pyrogen-free water, before use.

The compounds may also be formulated in rectal or vaginal compositions such as suppositories or retention enemas, e.g., containing conventional suppository bases such as cocoa butter or other glycerides.

In addition to the formulations described above, the compounds may also be formulated as a depot preparation. Such long acting formulations may be formulated with suitable polymeric or hydrophobic materials (for example as an emulsion in an acceptable oil) or ion exchange resins, or as sparingly soluble derivatives, for example, as a sparingly soluble salt.

The pharmaceutical compositions also may comprise suitable solid or gel phase carriers or excipients. Examples of such carriers or excipients include but are not limited to calcium carbonate, calcium phosphate, various sugars, starches, cellulose derivatives, gelatin, and polymers such as polyethylene glycols.

Suitable liquid or solid pharmaceutical preparation forms are, for example, aqueous or saline solutions for inhalation, microencapsulated, encochleated, coated onto microscopic gold particles, contained in liposomes, nebulized, aerosols, pellets for implantation into the skin, or dried onto a sharp object to be scratched into the skin. The pharmaceutical compositions also include granules, powders, tablets, coated tablets, (micro)capsules, suppositories, syrups, emulsions, suspensions, creams, drops or preparations with protracted release of active compounds, in whose preparation excipients and additives and/or auxiliaries such as disintegrants, binders, coating agents, swelling agents, lubricants, flavorings, sweeteners or solubilizers are customarily used as described above. The pharmaceutical compositions are suitable for use in a variety of drug delivery systems. For a brief review of methods for drug delivery, see Langer R, Science 249:1527-33 (1990), which is incorporated herein by reference.

The compounds of the invention and optionally other therapeutics may be administered per se (neat) or in the form of a pharmaceutically acceptable salt. When used in medicine the salts should be pharmaceutically acceptable, but non-pharmaceutically acceptable salts may conveniently be used to prepare pharmaceutically acceptable salts thereof. Such salts include, but are not limited to, those prepared from the following acids: hydrochloric, hydrobromic, sulphuric, nitric, phosphoric, maleic, acetic, salicylic, p-toluene sulphonic, tartaric, citric, methane sulphonic, formic, malonic, succinic, naphthalene-2-sulphonic, and benzene sulphonic. Also, such salts can be prepared as alkaline metal or alkaline earth salts, such as sodium, potassium or calcium salts of the carboxylic acid group.

Suitable buffering agents include: acetic acid and a salt (1-2% w/v); citric acid and a salt (1-3% w/v); boric acid and a salt (0.5-2.5% w/v); and phosphoric acid and a salt (0.8-2% w/v). Suitable preservatives include benzalkonium chloride (0.003-0.03% w/v); chlorobutanol (0.3-0.9% w/v); parabens (0.01-0.25% w/v) and thimerosal (0.004-0.02% w/v).

Pharmaceutical compositions of the invention contain an effective amount of a compound of the invention and optionally therapeutic agents included in a pharmaceutically acceptable carrier. The term "pharmaceutically acceptable carrier" means one or more compatible solid or liquid filler, diluents or encapsulating substances which are suitable for administration to a human or other vertebrate animal. The term "carrier" denotes an organic or inorganic ingredient, natural or synthetic, with which the active ingredient is combined to facilitate the application. The components of the pharmaceutical compositions also are capable of being commingled with the compounds of the present invention, and with each other, in a manner such that there is no interaction which would substantially impair the desired pharmaceutical efficiency.

The therapeutic agent(s), including specifically but not limited to the compound of the invention, may be provided in particles. Particles as used herein means nanoparticles or microparticles (or in some instances larger particles) which can consist in whole or in part of the compound of the invention or the other therapeutic agent(s) as described herein. The particles may contain the therapeutic agent(s) in a core surrounded by a coating, including, but not limited to, an enteric coating. The therapeutic agent(s) also may be dispersed throughout the particles. The therapeutic agent(s) also may be adsorbed into the particles. The particles may be of any order release kinetics, including zero-order release, first-order release, second-order release, delayed release, sustained release, immediate release, and any combination thereof, etc. The particle may include, in addition to the therapeutic agent(s), any of those materials routinely used in the art of pharmacy and medicine, including, but not limited to, erodible, nonerodible, biodegradable, or nonbiodegradable material or combinations thereof. The particles may be microcapsules which contain the compound of the invention in a solution or in a semi-solid state. The particles may be of virtually any shape.

Both non-biodegradable and biodegradable polymeric materials can be used in the manufacture of particles for delivering the therapeutic agent(s). Such polymers may be natural or synthetic polymers. The polymer is selected based on the period of time over which release is desired. Bioadhesive polymers of particular interest include bioerodible hydrogels described in Sawhney H S et al. (1993) *Macromolecules* 26:581-7, the teachings of which are incorporated herein. These include polyhyaluronic acids, casein, gelatin, glutin, polyanhydrides, polyacrylic acid, alginate, chitosan, poly(methyl methacrylates), poly(ethyl methacrylates), poly (butylmethacrylate), poly(isobutyl methacrylate), poly(hexylmethacrylate), poly(isodecyl methacrylate), poly(lauryl methacrylate), poly(phenyl methacrylate), poly(methyl acrylate), poly(isopropyl acrylate), poly(isobutyl acrylate), and poly(octadecyl acrylate).

The therapeutic agent(s) may be contained in controlled release systems. The term "controlled release" is intended to refer to any drug-containing formulation in which the manner and profile of drug release from the formulation are controlled. This refers to immediate as well as non-immediate release formulations, with non-immediate release formulations including but not limited to sustained release and delayed release formulations. The term "sustained release" (also referred to as "extended release") is used in its conventional sense to refer to a drug formulation that provides for gradual release of a drug over an extended period of time, and that preferably, although not necessarily, results in substantially constant blood levels of a drug over an extended time period. The term "delayed release" is used in its conventional sense to refer to a drug formulation in which there is a time delay between administration of the formulation and the release of the drug there from. "Delayed release" may or may not involve gradual release of drug over an extended period of time, and thus may or may not be "sustained release."

Use of a long-term sustained release implant may be particularly suitable for treatment of chronic conditions. "Long-term" release, as used herein, means that the implant is constructed and arranged to deliver therapeutic levels of the active ingredient for at least 7 days, and preferably 30-60 days. Long-term sustained release implants are well-known to those of ordinary skill in the art and include some of the release systems described above.

It will be understood by one of ordinary skill in the relevant arts that other suitable modifications and adaptations to the compositions and methods described herein are readily apparent from the description of the invention contained herein in view of information known to the ordinarily skilled artisan, and may be made without departing from the scope of the invention or any embodiment thereof.

EXEMPLIFICATION

The invention now being generally described, it will be more readily understood by reference to the following examples that are included merely for purposes of illustration of certain aspects and embodiments of the present invention, and are not intended to limit the invention.

Example 1: Restored Iron Transport by Small Molecule Promotes Absorption and Hemoglobinization in Animals Summary This example shows that a small molecule natural product, hinokitiol, can harness such gradients to restore iron transport into, within, and/or out of cells. The same compound promotes gut iron absorption in DMT1-deficient rats and ferroportin-deficient mice, as well as hemoglobinization in DMT1- and mitoferrin-deficient zebrafish. These findings illuminate a general mechanistic framework for small molecule-mediated site- and direction-selective restoration of iron transport. They also suggest small molecules that partially mimic the function of missing protein transporters of iron, and possibly other ions, may have potential in treating human diseases.

Site- and direction-selective transmembrane ion transport is achieved in most living systems via the concerted functions of active ion-transport proteins that generate localized electrochemical gradients and the passive ion-transport proteins that use them (1). Deficiencies of passive ion-transport proteins cause many human diseases including anemias, cystic fibrosis, arrhythmias, and neurological, skeletal muscle, endocrine, and renal disorders (2-5). Because the corresponding active ion-transport proteins typically remain functional, there may be a build-up of ion gradients upstream of the membranes that normally host these missing proteins. Noting the capacity for these robust networks to achieve ion-selective transport despite the unselective nature of many ion-transport proteins (1, 2), it was hypothesized that small molecules capable of autonomously performing ion transport could leverage such gradients to restore transmembrane ion flux in a site- and direction-selective manner (FIG. 1A).

Iron homeostasis is maintained by dynamic networks of active and passive iron-transport proteins and their regulators which permit essential use while minimizing toxicity of this redox-active metal (2). No known regulatory mechanisms of iron excretion exist (6), and thus systemic iron levels are primarily controlled through rigorous regulation of dietary iron absorption (2, 6). Deficiencies or dysfunction of proteins involved in iron transport, homeostasis, or metabolism often impede the movement of iron into, within, and/or out of cells (FIG. 1A), and are associated with more than twenty-five Mendelian diseases (Table S1) (6-9). It was questioned whether a small molecule iron transporter could leverage transmembrane gradients of the labile iron pool (2) that selectively build up in such situations to restore the movement of iron into, within, and/or out of cells, and thereby enable its use in endogenous iron-dependent physiological processes (FIG. 1A).

Three disease-relevant iron transporter deficiencies that disrupt iron movement in different directions, cellular locations, and tissues were specifically chosen for this study (2, 6). Deficiencies of divalent metal transporter 1 (DMT1, aka Nramp2, DCT1, SLC11A2) reduce apical iron uptake into duodenal enterocytes and prevent endosomal iron release in red blood cell progenitors (2, 6). Mitoferrin (Mfrn1, aka SLC25A37) deficiencies in the inner mitochondrial membrane impair iron import into the mitochondrial matrix (10, 11). Ferroportin (FPN1, aka IReg1, MTP1, SLC40A1) deficiencies reduce iron efflux from gut epithelium and from reticuloendothelial macrophages (12-15).

Previous reports suggest high doses of hydrophilic iron chelators, such as deferiprone and pyridoxal isonicotinoyl hydrazone (PIH), as well as more lipophilic derivatives such as salicylaldehyde isonicotinoyl hydrazone (SIH), may bind and relocate excess iron (16, 17). However, the corresponding complexes of many of these chelators show limited membrane permeation and may require the action of co-localized proteins to achieve iron mobilization (18, 19). We alternatively sought to identify a lipophilic small molecule that can autonomously perform transmembrane iron transport to promote physiology in cells and animals missing each of the aforementioned proteins.

Small Molecule-Mediated Functional Complementation in Yeast

Figure 7A:
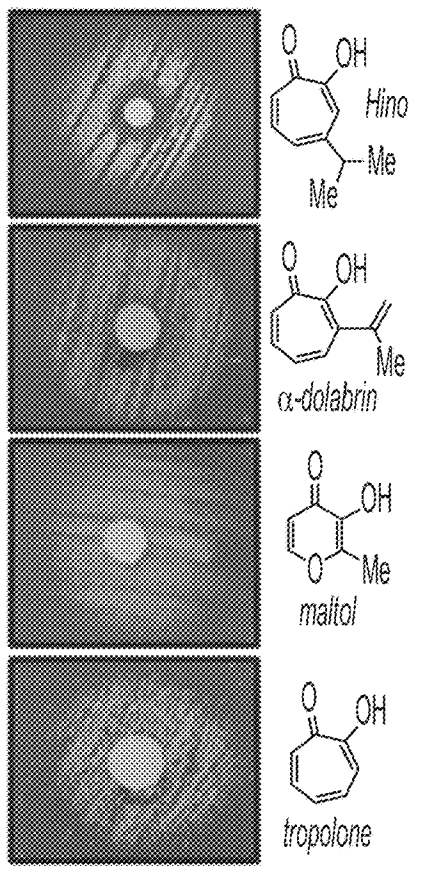
FIGS. 7A-C show small molecule-mediated growth is general to lipophilic carriers. (A) Hinokitiol and other lipophilic a-hydroxy ketones restore growth to fet3Δftr1Δ yeast streaked onto low iron SD-agar plates containing 10 μM FeCl$_3$ while (B) other iron chelators and (C) small molecule transporters of other ions do not restore growth under identical conditions.
Figure 7B:
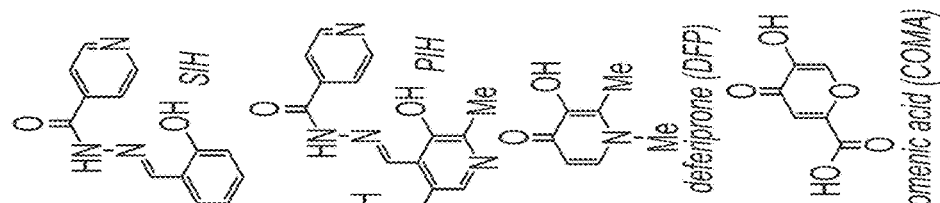
Figure 7C:
Figure 8A:
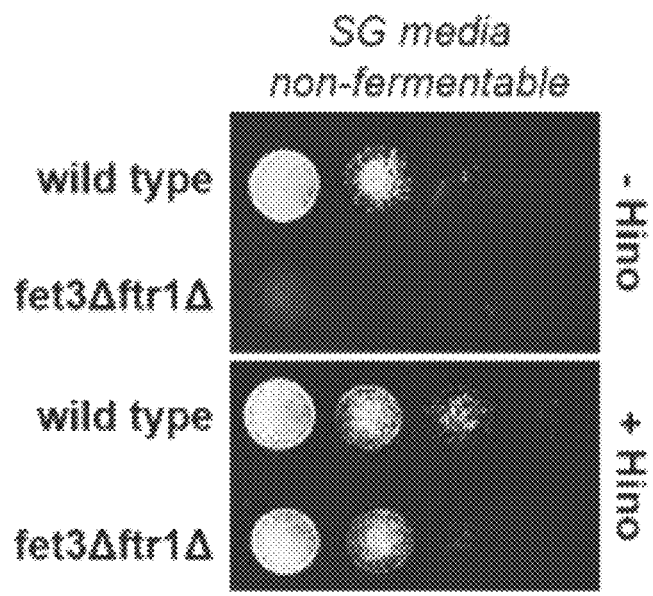
FIGS. 8A-8I show hinokitiol restores growth to iron-deficient yeast. (A) 10-fold serial dilution plating (from OD600=1.0) of iron-deficient yeast (fet3Δftr1Δ) on low iron SG-agar plates containing 10 μM FeCl$_3$ in the absence or presence of hinokitiol (10 μM). (B) Hinokitiol (10 μM) also restores growth to iron-deficient yeast missing all known siderophore protein transporters (fet3Δarn1-4Δ) on low iron SD-agar plates containing 10 μM FeCl$_3$. (C) Growth restoration to fet3Δftr1Δ yeast can be sustained for >100 days with continued reliance on hinokitiol. N=8. (D and E) Doubling times of hinokitiol-treated fet3Δftr1Δ yeast are similar to wild type yeast. N=3. (F) The transport inactive derivative, C$_2$-deoxy hinokitiol (C$_2$deOHino), was synthesized on multi-gram scale in two steps from hinokitiol. (G) Hinokitiol-promoted growth restoration of fet3Δftr1Δ yeast is dependent on iron levels in the media. N=3. (H) Increased environmental iron levels broaden the rescue window where hinokitiol-promoted growth is observed before toxicity alternatively occurs. No growth was observed for fet3Δftr1Δ yeast in the absence of hinokitiol at any tested iron concentration. N=3. (I) Octanol/water partition coefficients of the iron complexes of other iron chelators that do or do not restore growth to fet3Δftr1Δ yeast. N=3. (C-E, G) NS, not significant; Graphs depict means±SEM. (H, I) Graphs depict means of three independent experiments.
Figure 8B:
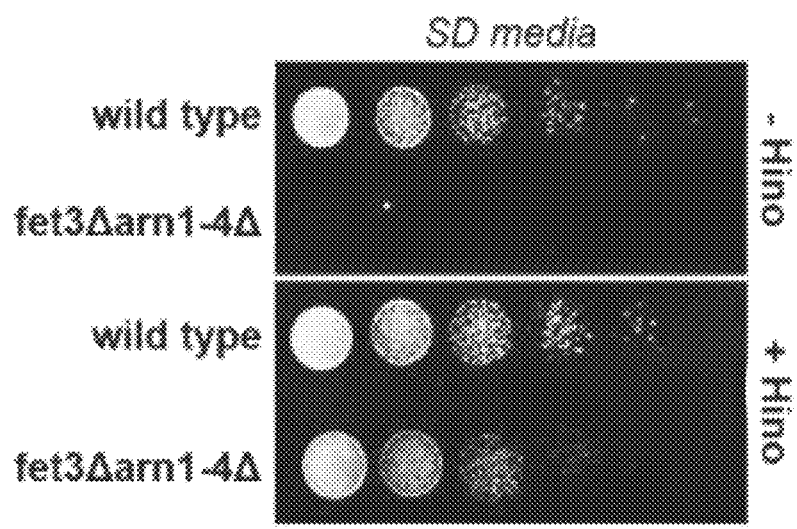

To find such a molecule, a modified functional complementation experiment (20) was designed, in which candidate compounds known or predicted to bind iron were tested for their capacity to restore growth to a strain of Saccharomyces cerevisiae missing the iron transporting complex FetFtr1 (fet3Δftr1Δ) (21). Deferiprone, PIH, and SIH showed no growth rescue (FIG. 7B). In contrast, the natural product hinokitiol (Hino, β-thujaplicin, FIG. 1B), originally isolated by Nozoe from essential oil of the Chamaecyparis taiwanensis (Taiwan Hinoki) tree (22), was highly effective (FIG. 1C-E and FIG. 8A). This natural product has previously been characterized as a potent chelator of iron and other metals (23-26) that exerts a range of other biological activities (25-31). Hinokitiol restored growth to iron transporter-deficient yeast under fermentative and respiratory conditions (FIG. 1D and FIG. 8A) and independent of known siderophore transporters (FIG. 8B) (21, 32). Hinokitiol sustainably restores growth to wild type levels with similar doubling times (FIG. 1E and FIG. 8C-E).

Figure 1B:
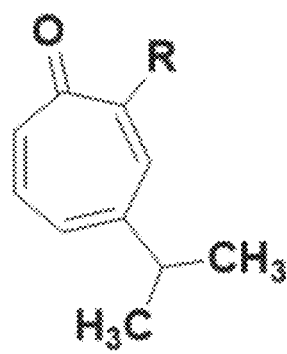
Figure 8C:
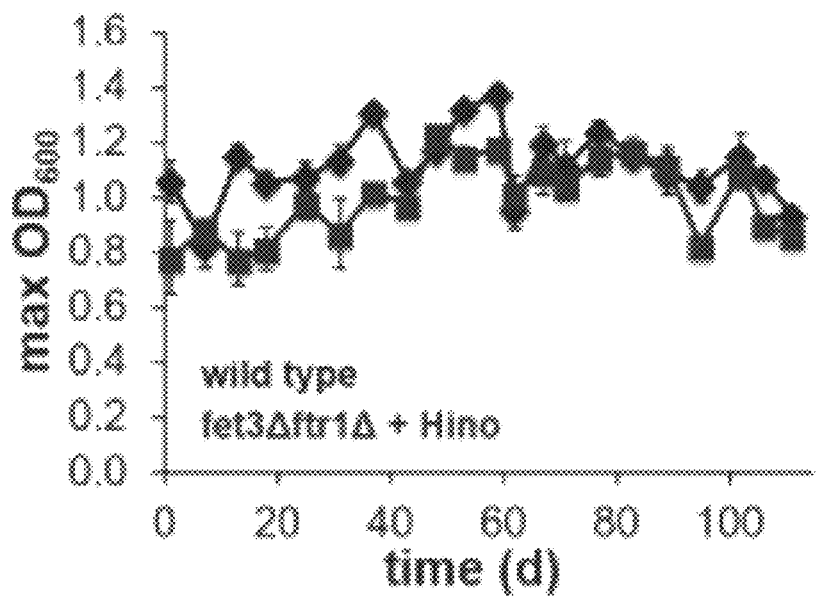
Figure 8D:
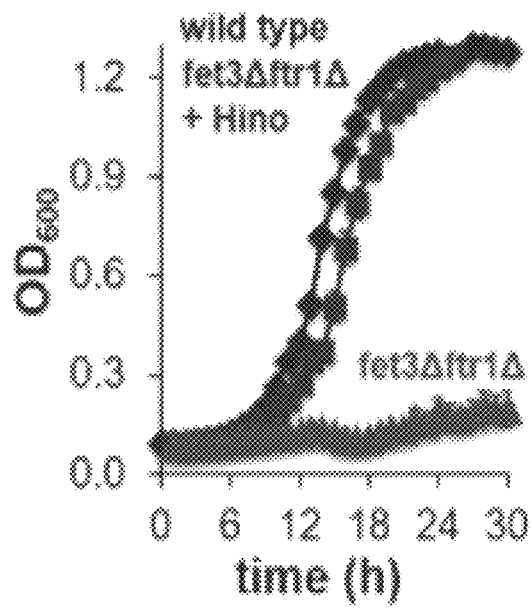
Figure 8E:
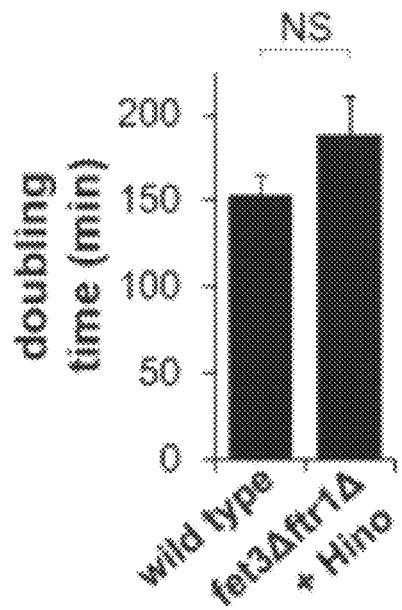
Figure 8F:
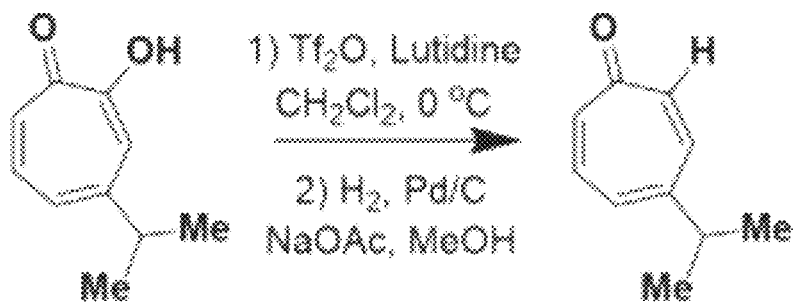
Figure 8G:
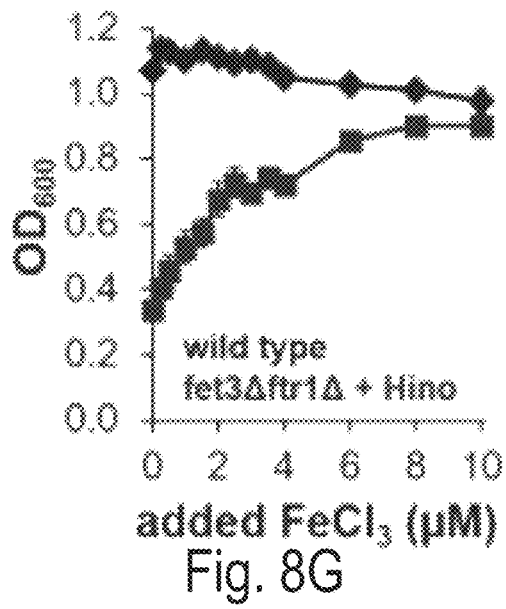
Figure 8H:
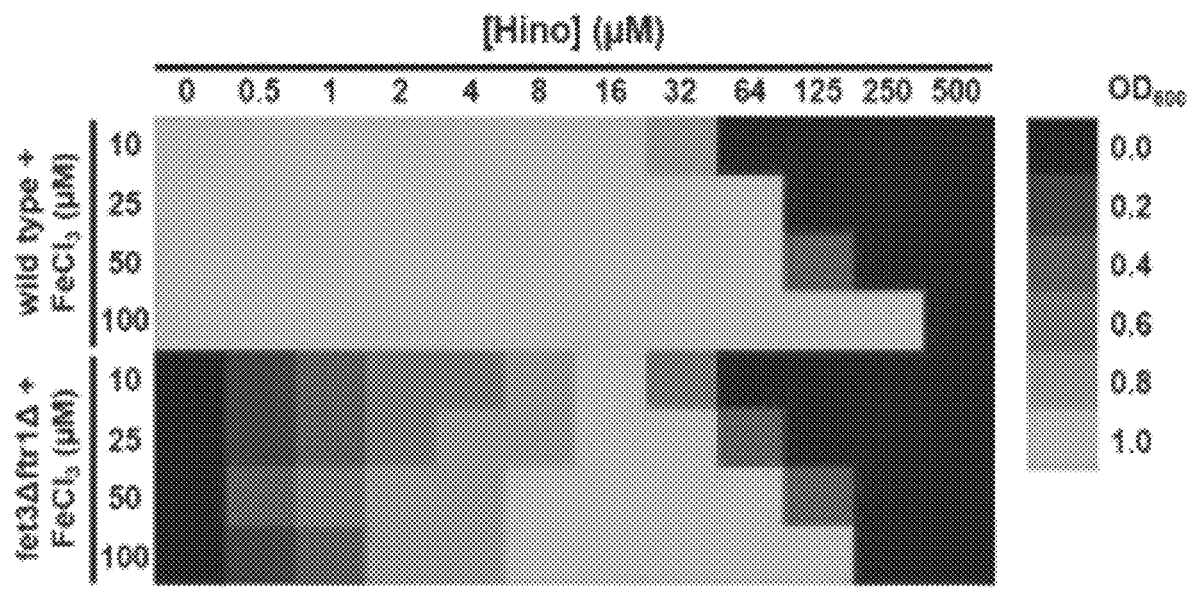
Figure 8I:
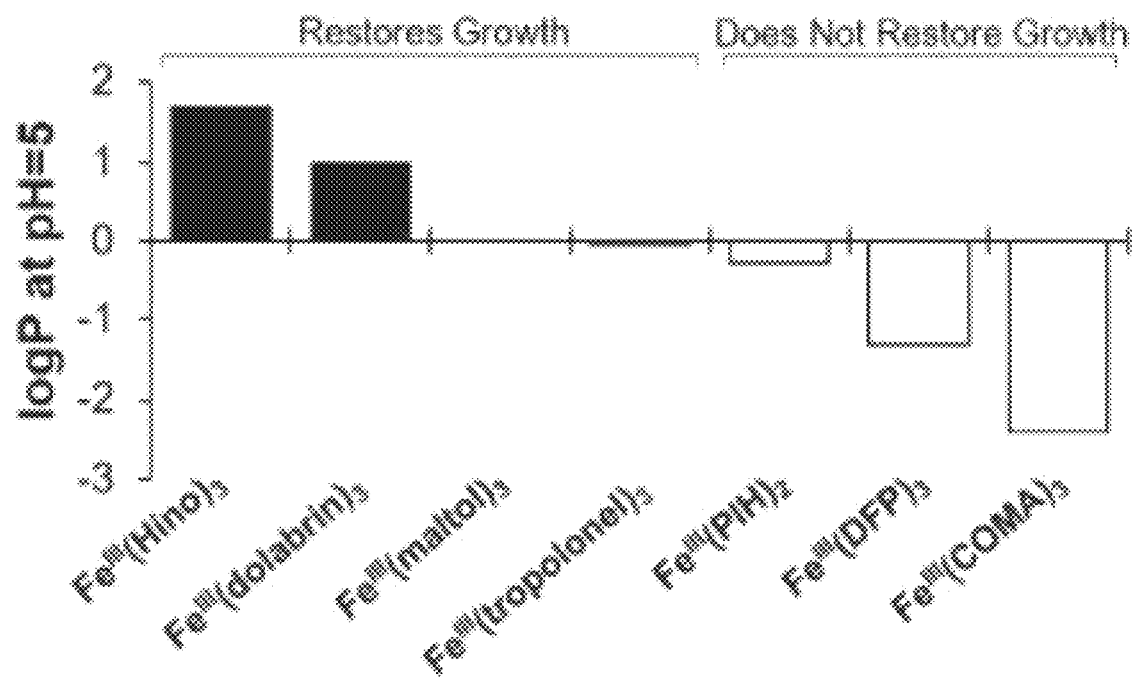
Figure 9A:
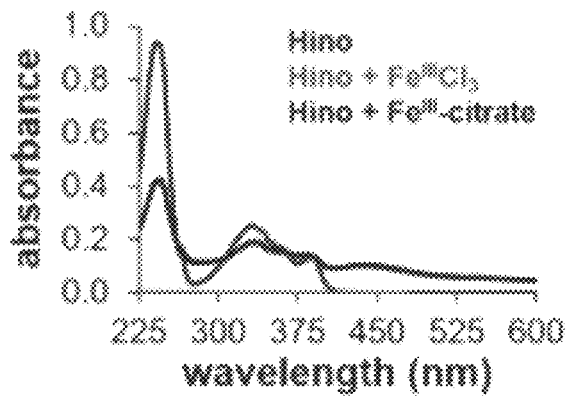
FIGS. 9A-9P show biophysical studies on the binding of iron and hinokitiol. (A) Hinokitiol binds iron (III) using a source of ionic iron (III) and iron (III) weakly bound to small molecules. (B) C2deOHino does not bind iron. (C) Hinokitiol similarly forms a complex with iron (II). (D) The iron is quantitatively bound to hinokitiol in solution at pH=7.0 as determined by iron content in the organic layer after extraction of hinokitiol-bound iron by ICP-MS. N=3. (E) UV-Vis spectra of ferrozine bound to iron (II) with increasing doses of the competitive chelator hinokitiol. High doses of hinokitiol largely remove iron from ferrozine. (F) Hinokitiol strongly binds iron (II) relative to deferiprone as determined by the $EC_{50}$ values obtained from a ferrozine competition study. N=3. (G) UV-Vis spectra of hinokitiol bound to iron (III) with increasing doses of the competitive chelator EDTA. High doses of EDTA largely remove iron from hinokitiol. (H) Hinokitiol strongly binds iron (III) relative to deferiprone as determined by the EC50 values obtained from an EDTA competition study. N=3. (1) Transferrin (100 μM) saturated with iron is not denatured after extraction with ethyl acetate. (J and K) Hinokitiol removes iron from (J) transferrin (1 nM) and (K) ferritin (2.5 ng ferritin/mL) in a dose-dependent fashion using $^{55}$Fe as a radiotracer. N=3. (L) Increased absorbance of the peak at 387 nm for hinokitiol increases with increasing pH. A clear isobestic point is observed (365 nm), indicating speciation between the protonated and deprotonated forms of hinokitiol. pKa was calculated through logistic fitting of the plot of Abs387/Abs240 vs. pH on OriginPro (R2=0.996). (M) Stoichiometric ionic $^{55}$Fe was added to a solution containing a pre-formed $^{56}$Fe-hinokitiol complex in 10 mM Mes/Tris buffer at pH=7.0. Equilibrium between the $^{55}$Fe-hinokitiol complex and the $^{56}$Fe-hinokitiol complex was achieved within one hour. N=3. (N and O) Titration studies with iron and hinokitiol support that a 3:1 Hino:Fe complex is predominantly formed in 10 mM Mes/Tris buffer at pH=7.0 as indicated by saturation of the (N) λmax and the (O) absorbance at 420 nm at 3:1 Hino:Fe ratios. Increased amounts of iron led to no changes in the UV-Vis spectra. (P) X-ray crystal structure of a second C1-symmetric Fe(Hino)$_3$ complex. (D, F, H, J, K, M) NS, not significant; Graphs depict means±SEM.

Synthetic removal of the C-2 oxygen atom by hydrogenolysis yielded $C_2$-deoxy hinokitiol ($C_2$deOHino, FIG. 1B and FIG. 8F). In contrast to hinokitiol, $C_2$deOHino cannot bind or transport iron and thus served as a negative control (FIG. 9A, B). Hinokitiol dose-dependently restores yeast growth whereas $C_2$deOHino does not (FIG. 1F). Hinokitiol, but not $C_2$deOHino, also restores iron influx (FIG. 1G) and hinokitiol-mediated growth is iron-dependent (FIG. 8G, H). Growth restoration was similarly observed with other lipophilic a-hydroxy ketones, but not with hydrophilic a-hydroxy ketones nor small molecules that transport other ions (FIG. 7A-C and FIG. 8I).

Characterization of Iron Binding and Transport with Hinokitiol

Figure 2A:
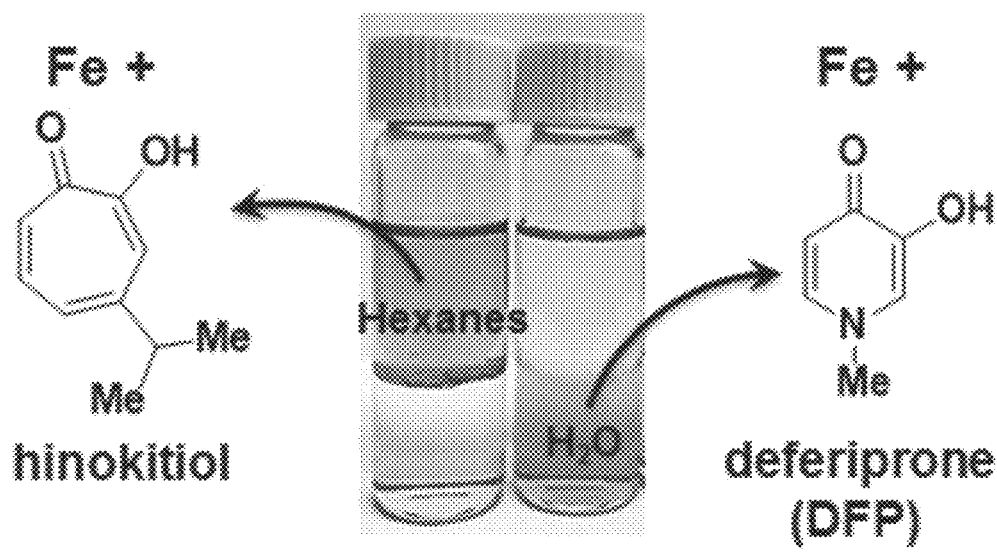
FIGS. 2A-2F show the physical characteristics of hinokitiol binding and transport. (A) Opposite to water soluble chelators, such as deferiprone, the hinokitiol-iron complex partitions into non-polar solvents. (B) UV-Vis titration study of hinokitiol with increasing $FeCl_3$ indicates hinokitiol binds iron. Arrows indicate changes in UV spectrum with increasing iron from 0:1 Fe:Hino to 6:1 Fe:Hino. (C and D) In contrast to water-soluble iron chelators and C2deOHino, hinokitiol autonomously promotes the efflux of (C) ferrous and (D) ferric iron from model POPC liposomes. N=3. (E) X-ray crystal structure of a C1-symmetric Fe(Hino)$_3$ complex. (F) Cyclic voltammogram of the iron-hinokitiol complex in 0.1 M Tris buffer in 1:1 MeOH:$H_2O$ at pH=7.2 using 500 μM Hino and 100 μM Fe(NO$_3$)$_3$ with a 100 mV/s scan rate. (C, D) Graphs depict representative runs of three independent experiments. (F) Graph depicts a representative run of four independent experiments.

Biophysical experiments were performed to better understand the capacity for hinokitiol to bind and transport ferrous and ferric iron across lipid membranes. This natural product rapidly binds iron to form a hinokitiol:iron complex, as evidenced by an immediate change in color and UV-Vis spectra upon addition of ferric or ferrous iron (FIG. 2A, B and FIG. 9A, C). Unlike water-soluble iron chelators (17), hinokitiol:iron complexes predominantly partition into nonpolar solvents over water (FIG. 2A and FIG. 8I). For example, >95% of hinokitiol:iron complexes partition into octanol over water, whereas deferiprone:iron complexes alternatively exhibit >95% partitioning into water (FIG. 8I). This was consistent with quantitative extraction of hinokitiol:iron complexes from the aqueous to the organic layer as determined via ICP-MS analysis (FIG. 9D).

Hinokitiol strongly binds ferrous and ferric iron, with a $K_A=5.1\times10^{15}$ for ferrous iron and $K_A=5.8\times10^{25}$ for ferric iron, the latter of which is more than an order of magnitude stronger than deferiprone (FIG. 9E-H and table 2). Consistent with its high affinity, hinokitiol removes iron from iron-citrate complexes that compose the labile iron pool (FIG. 9A). In buffered solution, competition experiments indicate hinokitiol can also remove iron from iron-binding proteins transferrin and ferritin, but only when hinokitiol is used in >1,000-fold excess relative to transferrin and >1,000,000-fold excess relative to ferritin (FIG. 9I-K). Hinokitiol has a pKa=7.33 suggesting both the neutral and anionic states are accessible under physiological conditions (FIG. 9L). Moreover, $^{56}Fe$ bound to hinokitiol readily exchanges with $^{55}Fe$ in solution, with >20% exchange observed within 10 minutes (FIG. 9M). Thus, the binding of iron by hinokitiol under physiological conditions is expected to be highly dynamic, which may allow for the facile release of iron from hinokitiol complexes to iron-binding proteins and its subsequent use in iron-related physiological processes.

Figure 2B:
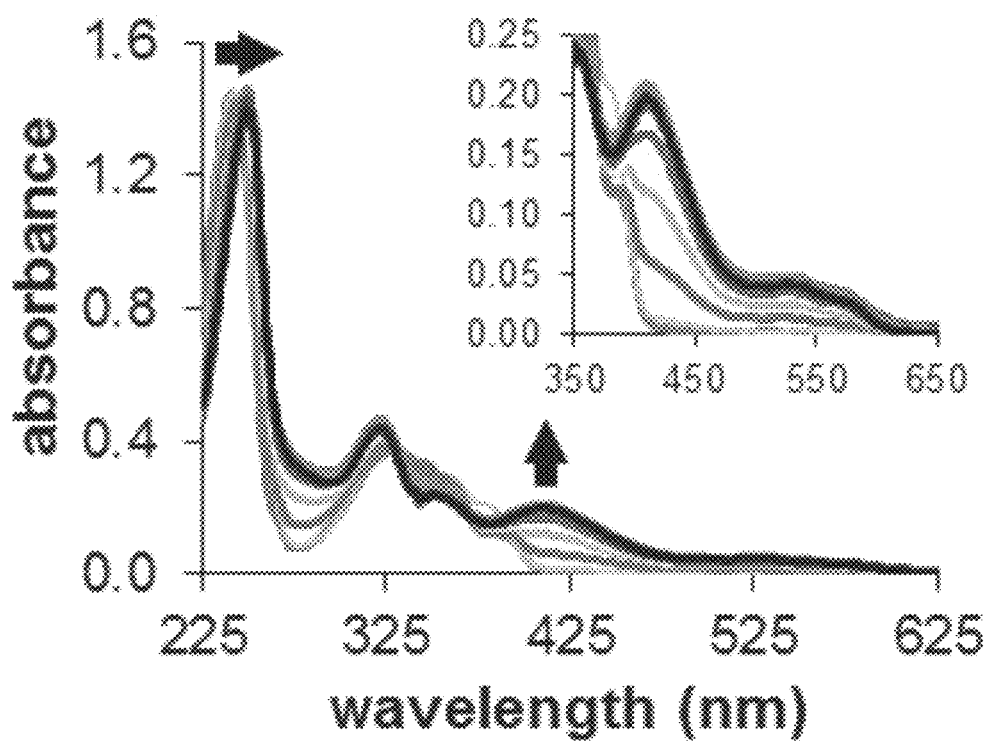
Figure 2C:
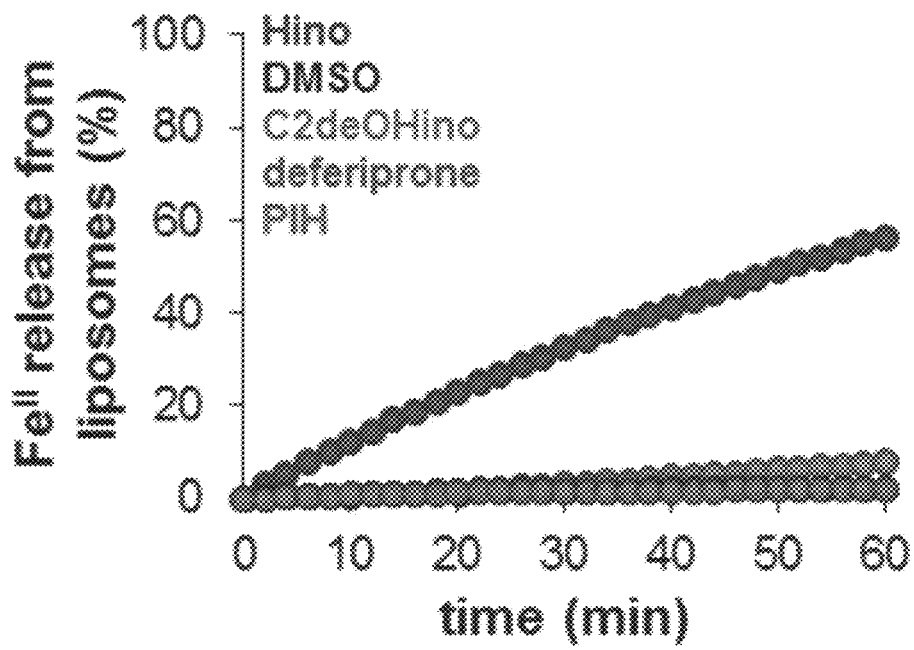
Figure 2D:
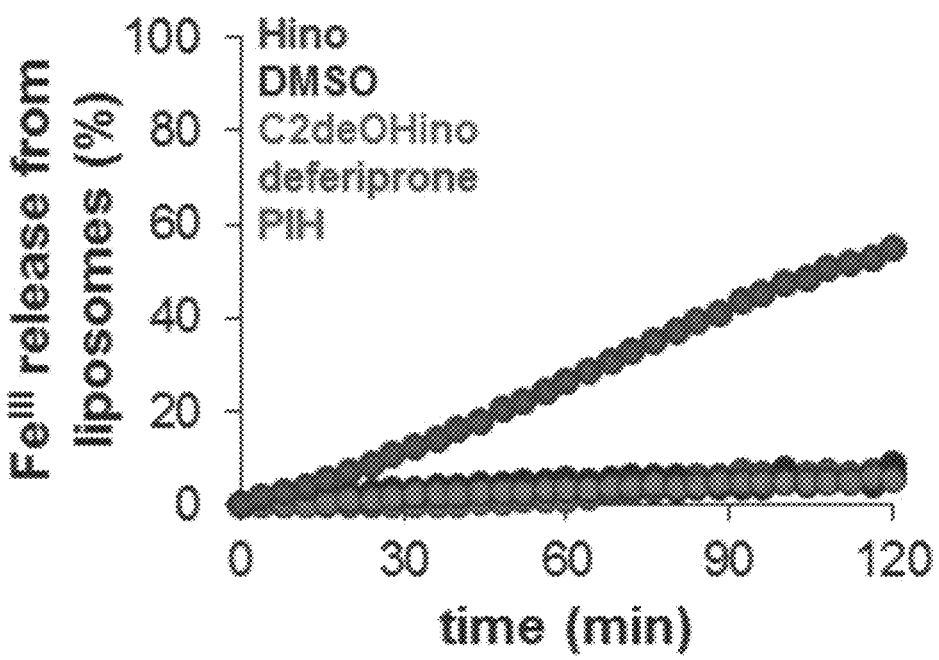
Figure 2E:
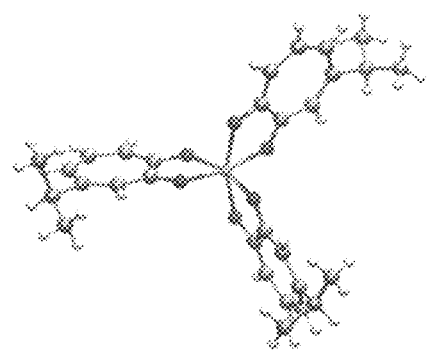
Figure 2F:
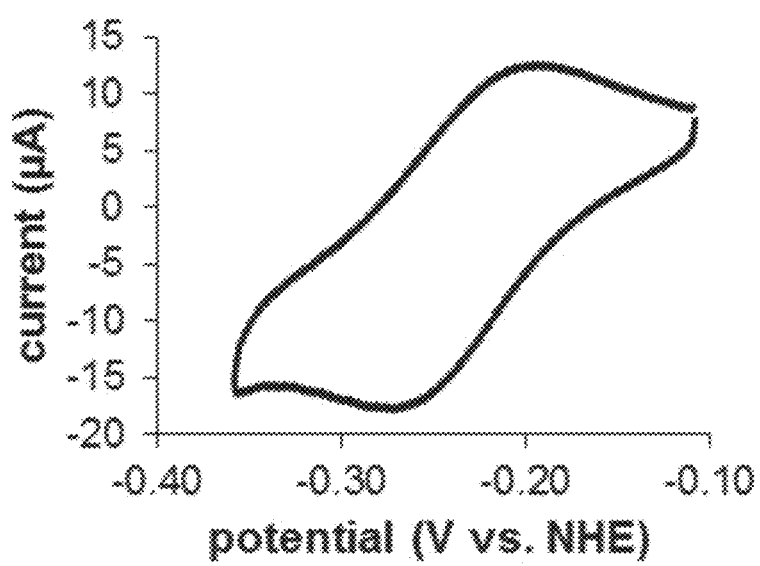

Hinokitiol autonomously transports both ferrous and ferric iron across model liposomal membranes whereas $C_2$deOHino, deferiprone, and PIH show minimal transport (FIG. 2C, D). Although the transport-active complex remains to be identified, speciation studies are consistent with the predominant formation of a 3:1 Hino:$Fe^{III}$ complex in aqueous buffer (FIG. 9N, O). X-ray crystallography of tris(hinacolato) iron (III) revealed a pair of $C_1$-symmetric complexes, each composed of a lipophilic outer shell encasing a hydrophilic and iron-binding central core (FIG. 2E and FIG. 9P).

Figure 10A:
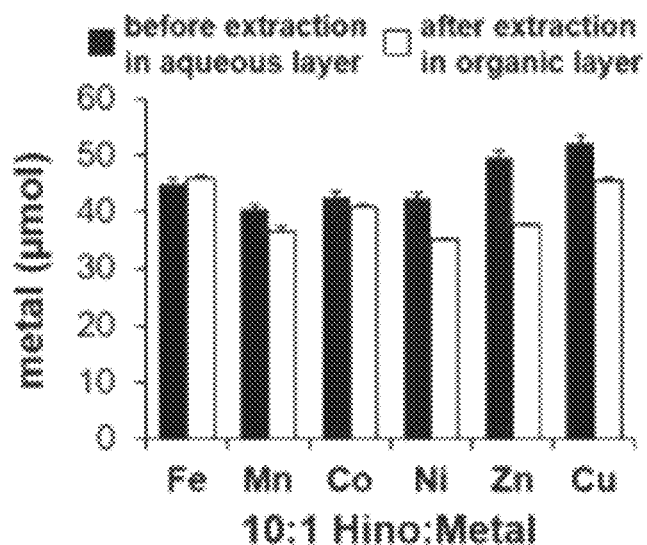
FIGS. 10A-10J show that hinokitiol is a broad-spectrum metallophore capable of binding and transporting multiple divalent metals.
Figure 10B:
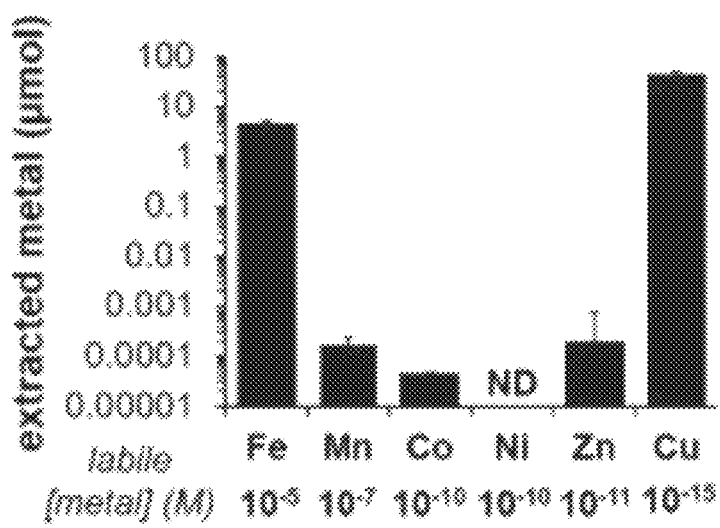
Figure 10C:
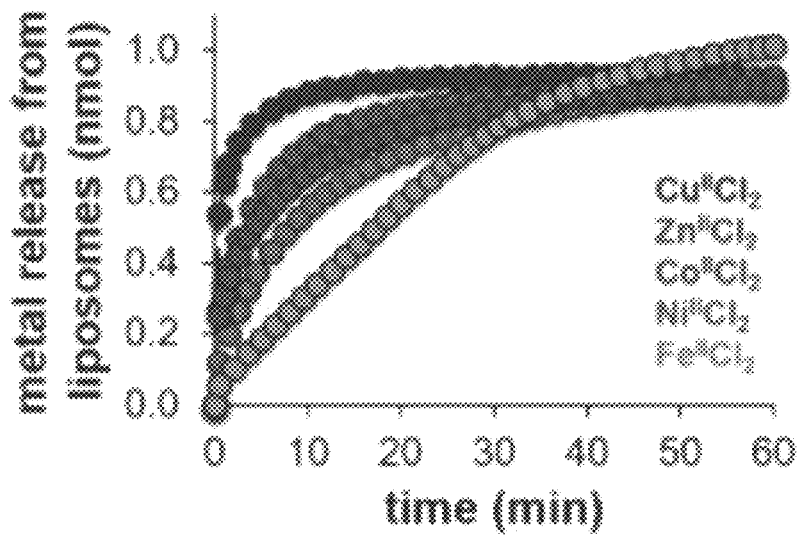
Figure 10D:
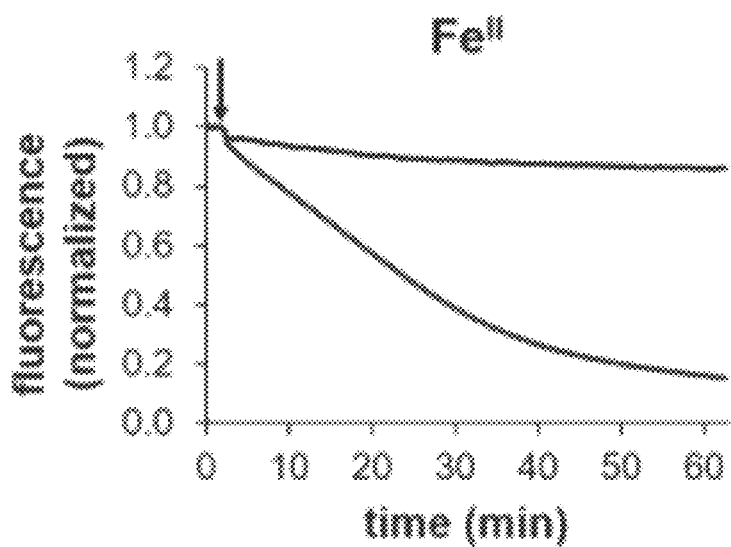
Figure 10E:
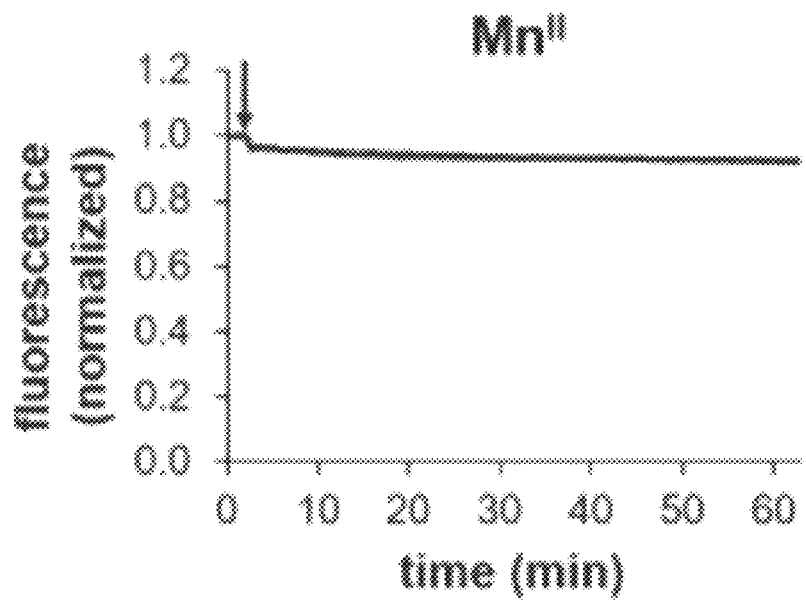
Figure 10F:
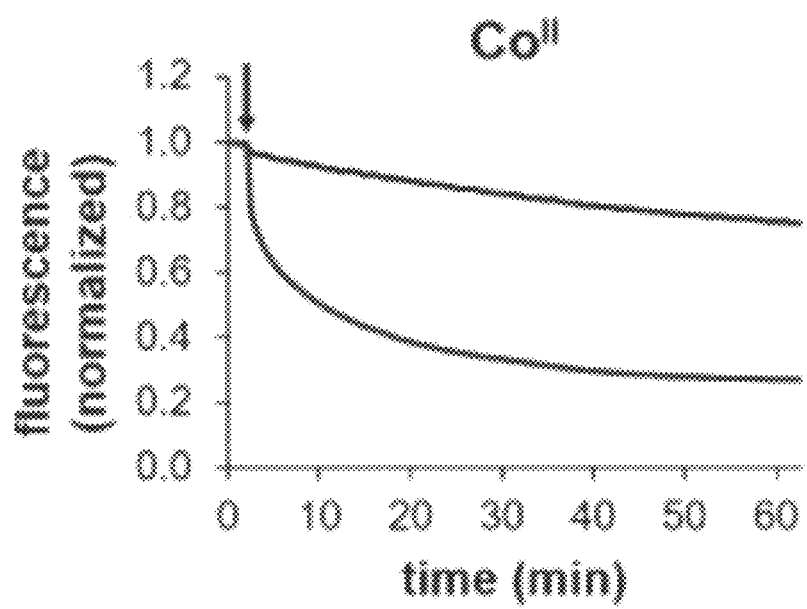
Figure 10G:
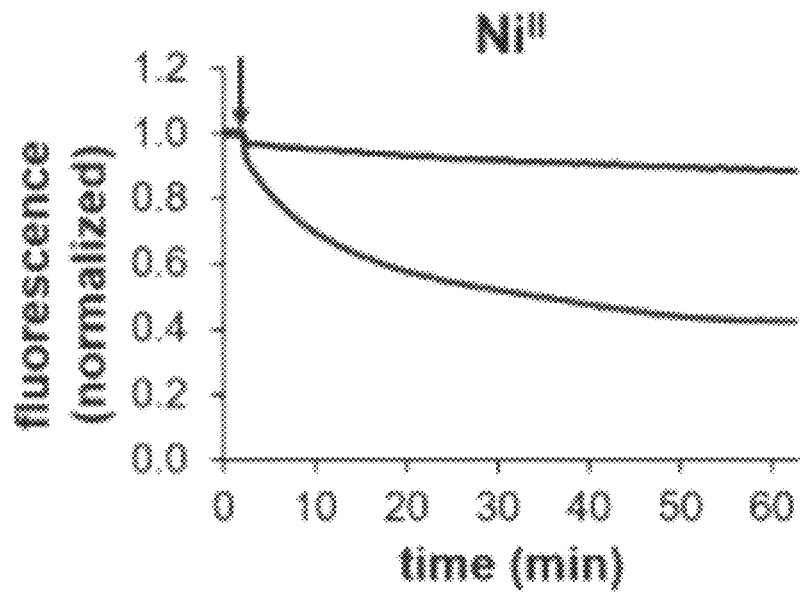
Figure 10H:
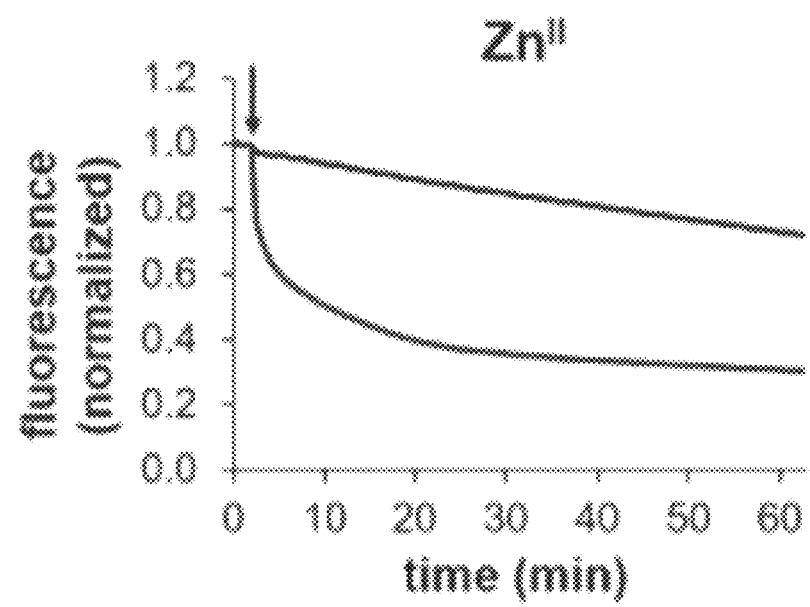
Figure 10I:
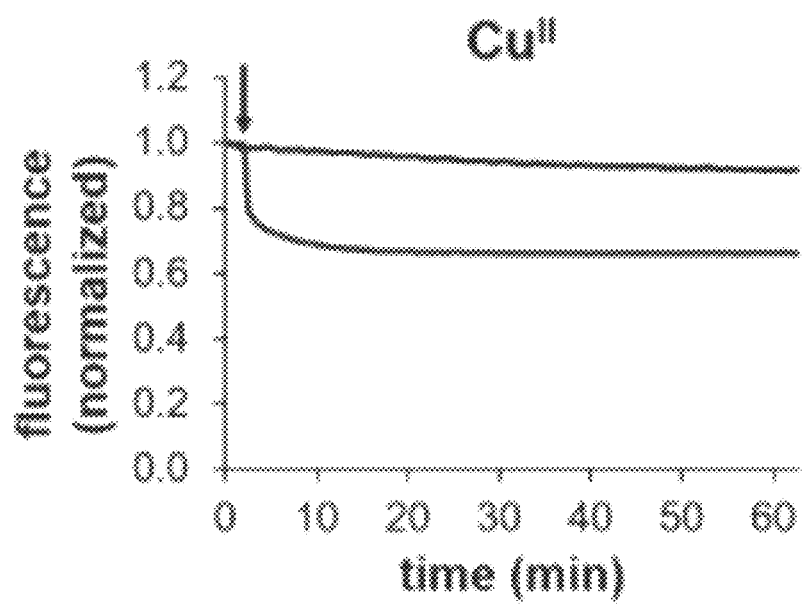
Figure 10J:
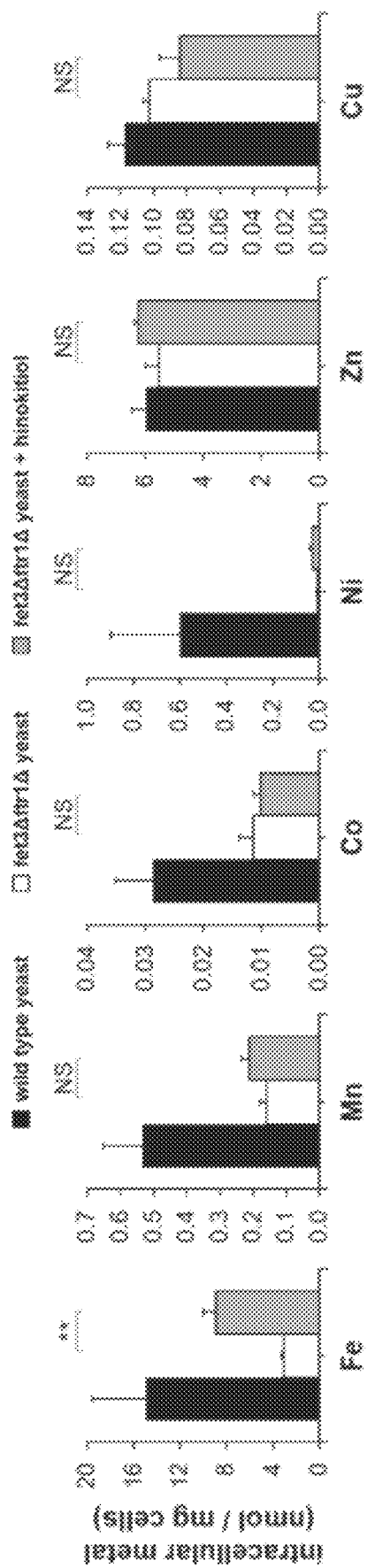

Hinokitiol is a broad spectrum metallophore capable of binding and transporting multiple divalent metals (FIG. 10A-I, and table S3). Hinokitiol competitively bound 10-fold more $Cu^{II}$ than $Fe^{II}$ and transported $Cu^{II}$ 80-fold faster than $Fe^{II}$ in liposomes, yet the low accessibility of copper likely leads to high iron selectivity in vivo. Specifically, the cytosolic labile copper pool is ten billion times lower than iron (Table S3) (33-35). This is attributed to robust networks of transporters, chaperones, storage proteins, efflux proteins, and regulators that bind $Cu^{II}$ with exceptional affinities and selectivities (35). For example, the transcriptional activator Mac1, which is essential in regulating yeast copper homeostasis, binds copper with a $K_D$ of $9.7\times10^{20}$ M (35). Upon treatment of fet3Δftr1Δ yeast with hinokitiol, intracellular iron levels increased relative to vehicle-treated controls, while levels of manganese, cobalt, nickel, zinc, and copper were unchanged (FIG. 10J).

Figure 11A:
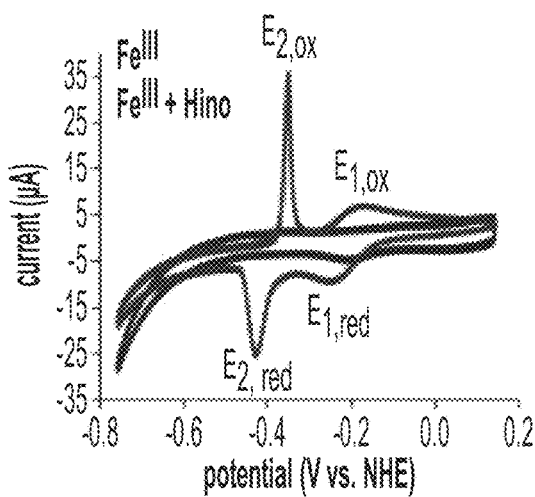
FIGS. 11A-11L show electrochemical studies of hinokitiol-iron complexes. Unless indicated otherwise, all CVs were obtained with a 100 mV/s scan rate with a Hg electrode and Ag/AgCl reference and graphite auxiliary using a 0.1 M Tris buffer in 1:1 MeOH:H2O at pH=7.2 and 100 μM Fe(NO$_3$)$_3$ and 500 μM hinokitiol. (A) Cyclic voltammograms (CVs) of iron and an iron-hinokitiol complex. Two different redox waves are present in the voltammogram for hinokitiol. N=4. (B) CVs obtained at different scan rates under identical conditions for E1. N=1. (C) Diffusion controlled linear behavior was observed vs. the square root of scan rate for E1. The number of electrons obtained utilizing the Randles-Sevcik equation (see Reference 85) were 1.1 for the electrochemical reduction process and 0.9 for the oxidation process indicating this redox pair is the one electron reduction of FeIII(Hino)$_3$ complex. N=1. (D) CVs obtained at different scan rates under identical conditions for E2. N=1. (E) Non-linear behavior was observed vs. the square root of scan rate for E2. This is consistent with a surface confined electrodeposition process at more negative potentials, which is not pertinent to the electrochemical characterization of iron-hinokitiol complexes in biological systems. N=1. (F) Effect of the Hino:Fe ratio on E01. Representative traces of three independent experiments. (G) Decreasing the concentration of MeOH decreased E01. N=1. (H) Extrapolation of the obtained E01 vs. MeOH concentration estimates the redox potential of Fe(Hino)$_3$ in aqueous solutions to be as low as −361 mV vs. NHE. N=1. (I) Effect of pH on the redox potential of Fe(Hino)$_3$. N=1-2. (J) The Fe(Hino)$_3$ redox potential decreases with increasing pH. N=1. (K) In a strongly reducing ascorbate (62.5 mM) buffer, iron (III) is instantaneously reduced to iron (II) as determined by the absorbance of a ferrozine-FeII complex at 562 nm. Preformed FeIII(Hino)$_3$ significantly attenuated the rate of reduction, however, iron (II) was primarily present after one hour using the same ascorbate buffer. (L) Quantification of the rate of iron (III) reduction over time in the same strongly reducing ascorbate buffer. N=3. Graph depicts means±SEM.
Figure 11B:
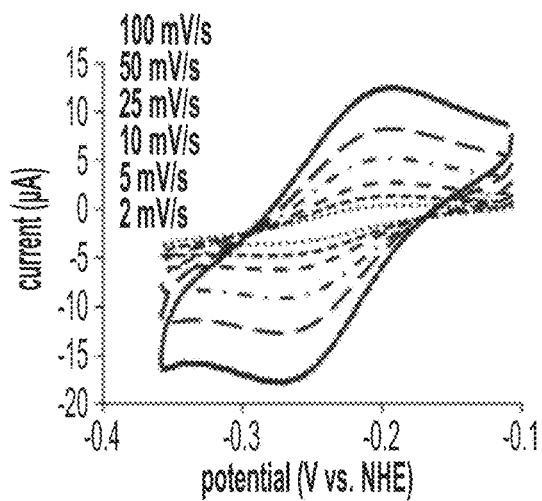
Figure 11C:
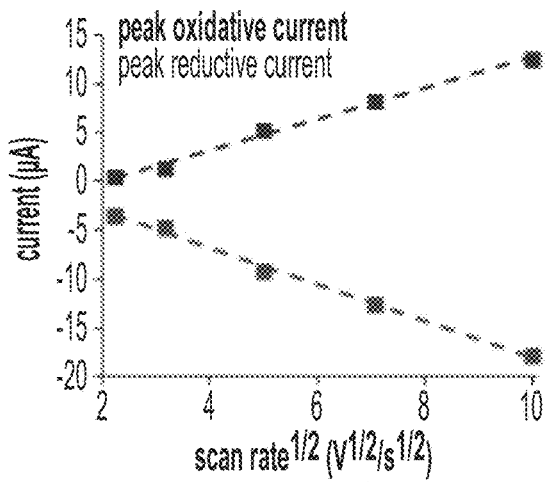
Figure 11D:
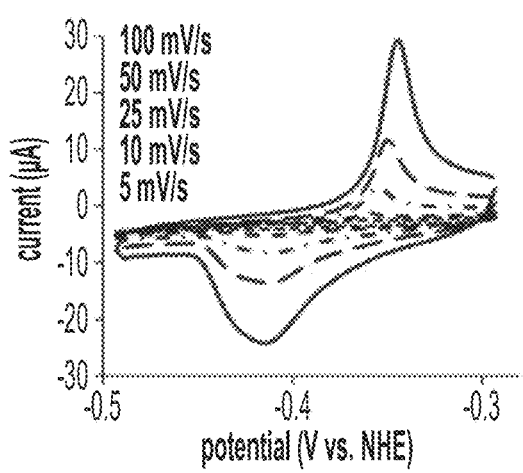
Figure 11E:
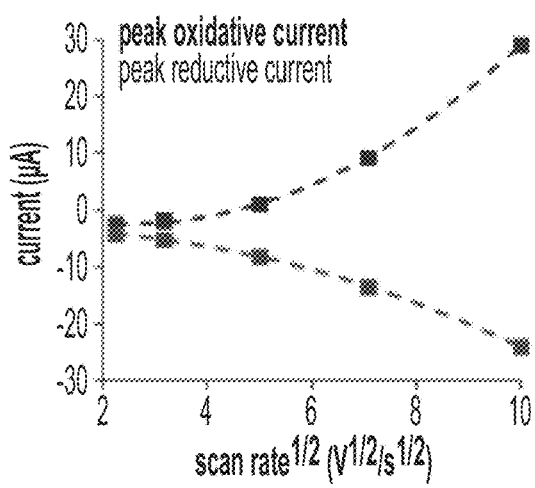
Figure 11F:
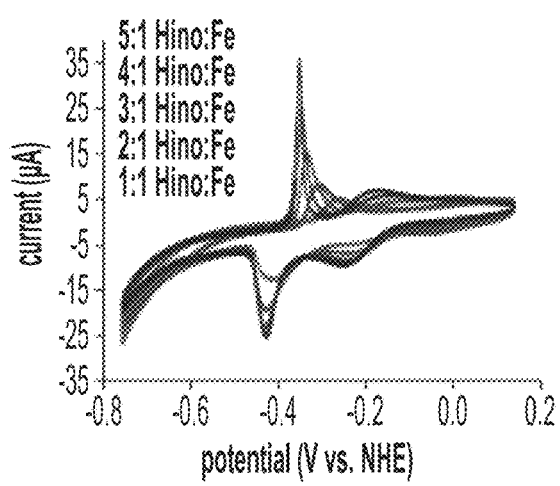
Figure 11G:
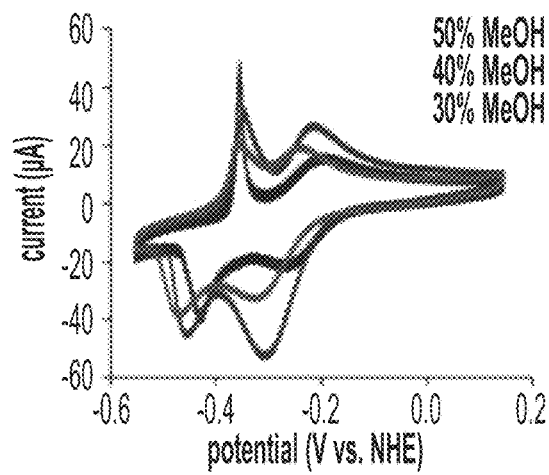
Figure 11H:
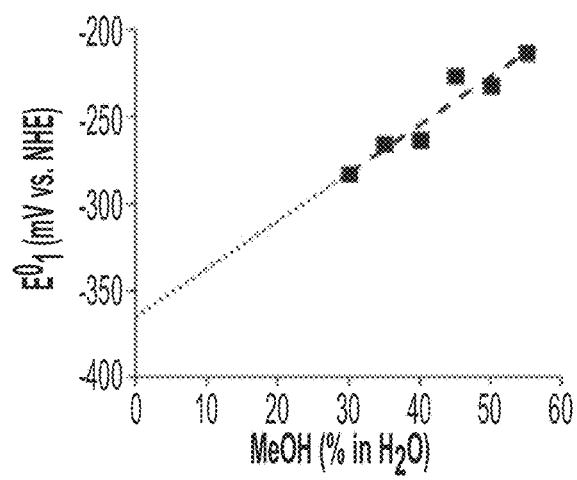
Figure 11I:
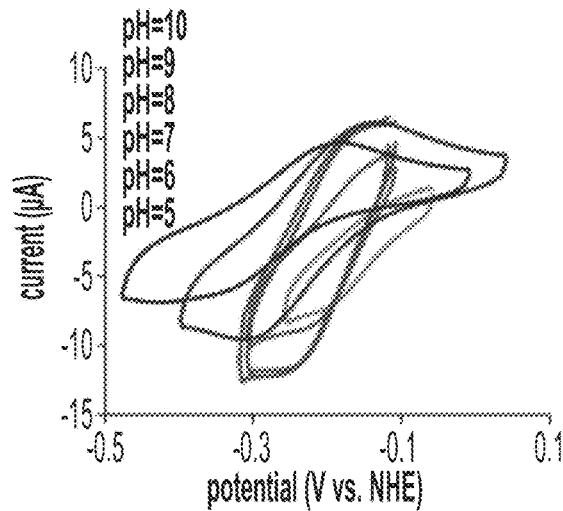
Figure 11J:
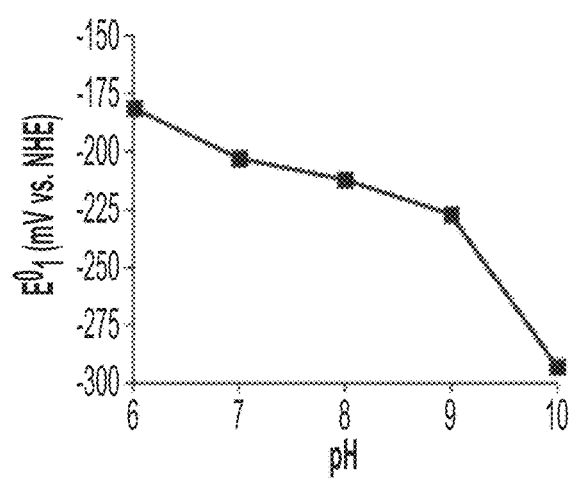
Figure 11K:
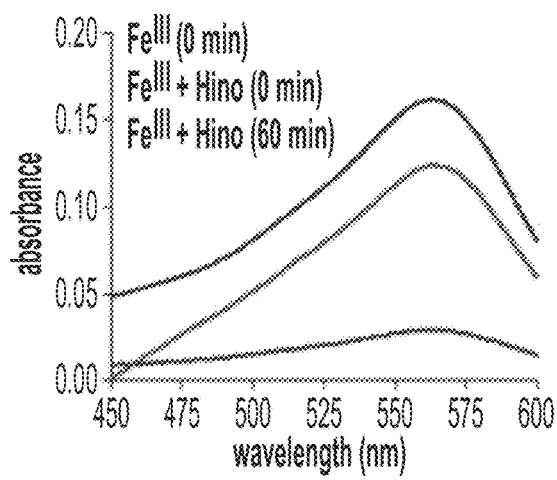
Figure 11L:
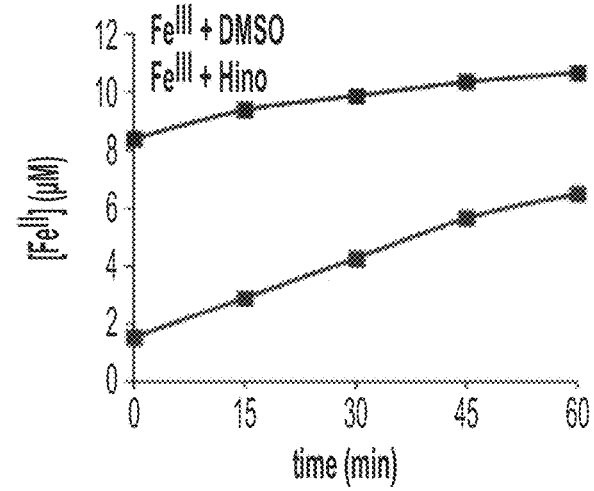

The redox potential of Fe(Hino)₃ in aqueous systems is estimated to be as low as −361 mV, compared to +770 mV for free iron (FIG. 2F, FIG. 11A-J, and table S2, 4-6). Consistent with this, in a reducing environment the reduction of iron (III) is slowed in the presence of hinokitiol, but still nearly quantitative in less than two hours (FIG. 11K, L). Moreover, the redox potential increases with decreasing pH and decreasing hinokitiol concentrations (FIG. 11F, I, J and table S4, 5). Collectively, these data suggest that both ferric and ferrous iron should be readily accessible in the presence of hinokitiol under physiological conditions.

Restored Iron Transport Promotes Absorption and Hemoglobinization in Cells

Figure 3A:
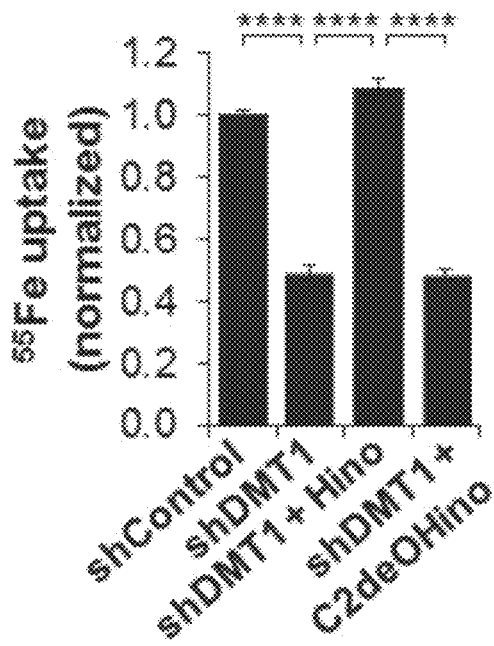
Figure 12F:
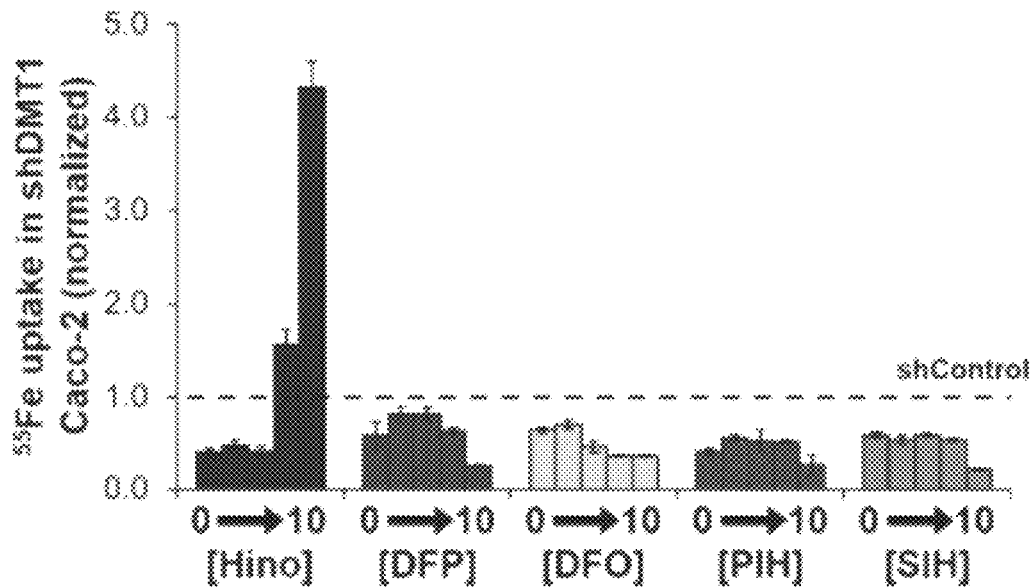
Figure 12G:
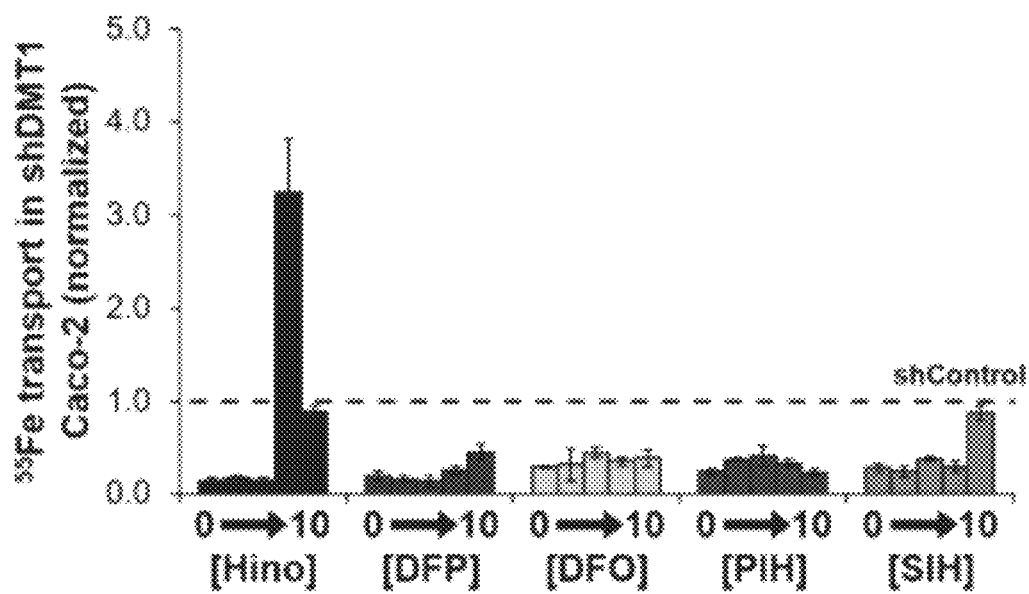

It was thus postulated whether hinokitiol could promote iron movement into, within, and/or out of mammalian cells deficient in DMT1, Mfrn1, or FPN1. Iron uptake and transepithelial transport in differentiated DMT1-deficient Caco-2 gut epithelia monolayers (FIG. S1A) (36, 37) established through stable shRNA transfection (FIG. 12A-C) were first studied. Relative to wild type controls, DMT1-deficient monolayers showed reduced iron uptake into cells and reduced transepithelial iron transport to the basolateral fluid after apical addition of $^{55}FeC_3$ (FIG. 3A, B). Apical addition of hinokitiol (500 nM) restored uptake and transport (FIG. 3A, B) in a timeframe commensurate with dwell times in the gut (FIG. 3C). Hinokitiol did not disrupt monolayer integrity (FIG. 12D), caused no observable toxicity (table S7), and did not affect basal DMT1 expression (FIG. 12B, C). Hinokitiol-mediated transport occurs across a range of pHs found throughout the duodenum, and increases with decreasing pH (FIG. 12E). Whereas hinokitiol promotes uptake and transport over a wide range of concentrations, $C_2$deOHino and sub-toxic concentrations of iron chelators deferiprone, deferoxamine, PIH, and SIH did not promote both uptake and transport (FIG. 12F, G and table S7). High concentrations of these more hydrophilic iron chelators alternatively decreased iron uptake into DMT1-deficient monolayers (FIG. 12F).

Figure 13A:
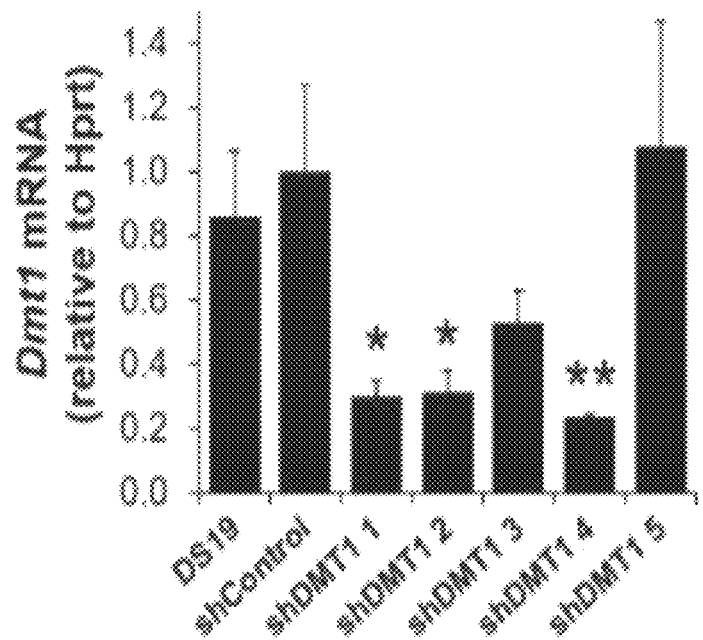
FIGS. 13A-13L show hinokitiol promotes differentiation in DMT1-deficient MEL cells. (A) Dmt1 mRNA (N=12-16) and (B) DMT1 protein levels are reduced in shDMT1 MEL cells (Clones 1, 2, and 4) relative to shControl after DMSO induction for terminal differentiation. N=13. (C) Representative western blot image of DMT1 protein levels in differentiated MEL cells. (D and E) Hinokitiol (1 μM for three days) visually restores differentiation as evidenced by staining hemoglobinized cells brown with o-dianisidine. (F) Hinokitiol (1 μM) restores iron uptake into differentiated shDMT1 MEL cells while C$_2$deOHino (1 µM) does not. N=6-25. (G and H) Hinokitiol (1 µM) restores differentiation of shDMT1 4 cells in a (G) time- and (H) dose-dependent manner. N=3-27. (I) Quantification of hemoglobin levels in DMT1-deficient MEL cells treated with small molecule (1 µM). N=3. (J) Representative western blot image of globin levels in differentiated MEL cells treated with DMSO, hinokitiol (1 µM), or C$_2$deOHino (1 µM). (K) Three days of hinokitiol (1 µM) treatment to induced shDMT1 MEL cells did not decrease MEL cell counts. N=3-15. (L) No differentiation is observed in hinokitiol (1 µM) treated MEL cells without DMSO induction. N=4-6. Scale bar=100 µm (E) (A, B, F-I, K, L) NS, not significant; * P≤0.05;  P≤0.01; * P≤0.001; **** P≤0.0001; Graphs depict means±SEM.
Figure 13B:
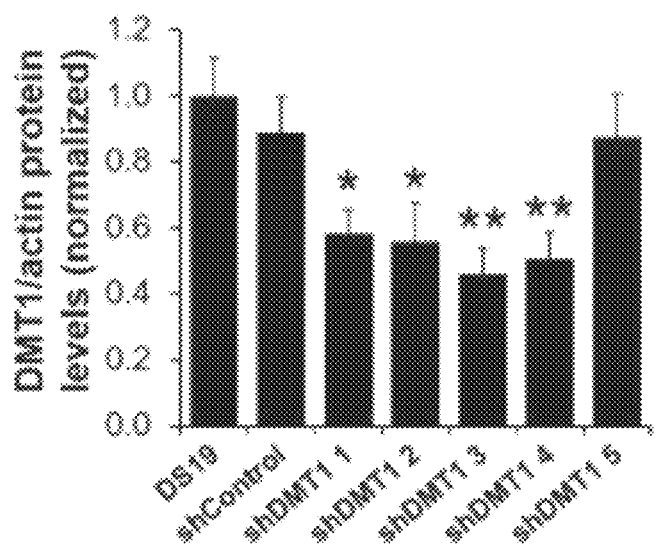
Figure 13C:
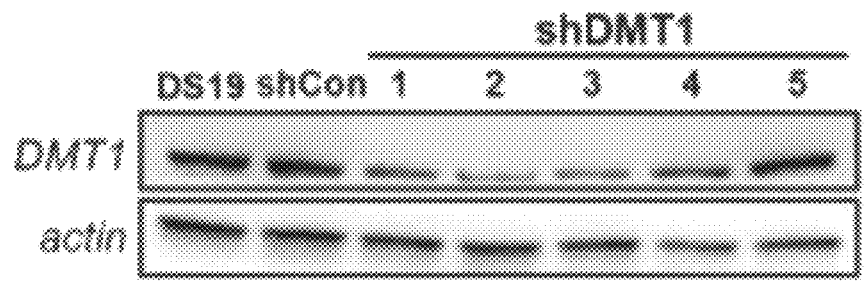
Figure 13D:
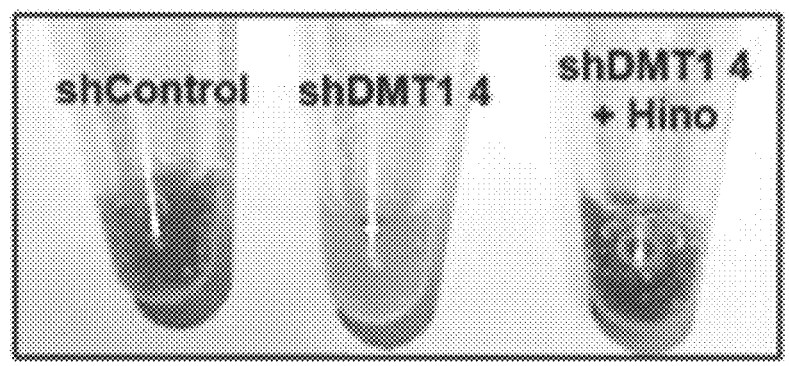
Figure 13E:
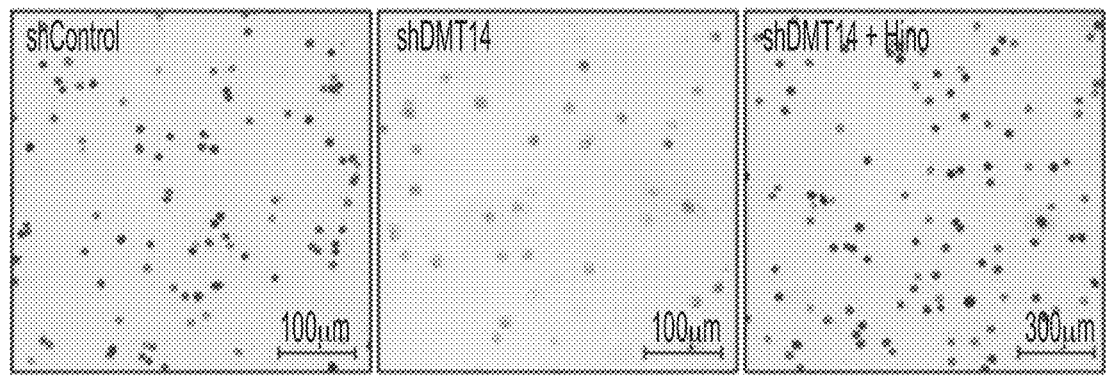
Figure 13F:
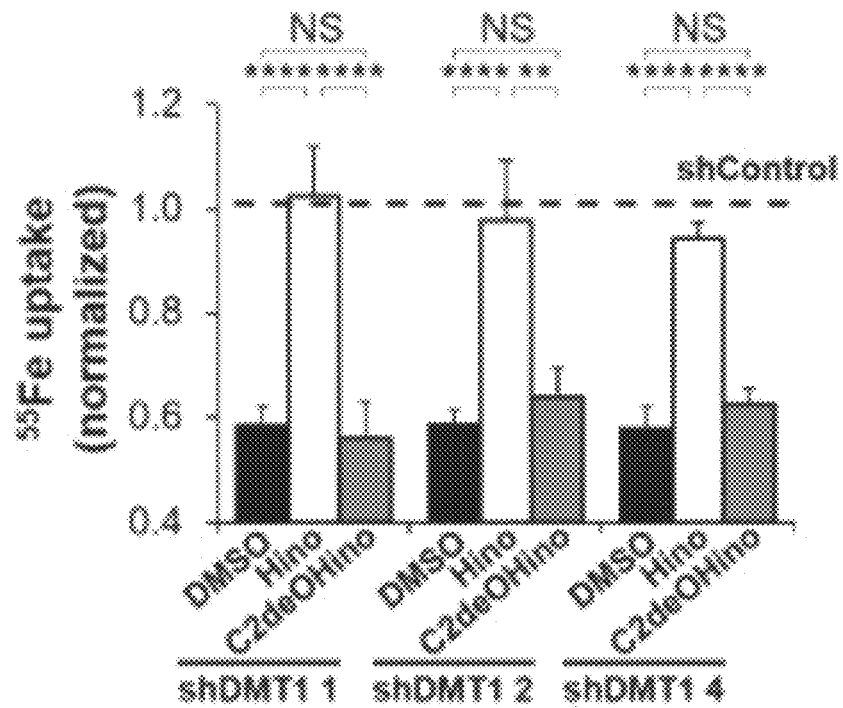
Figure 13G:
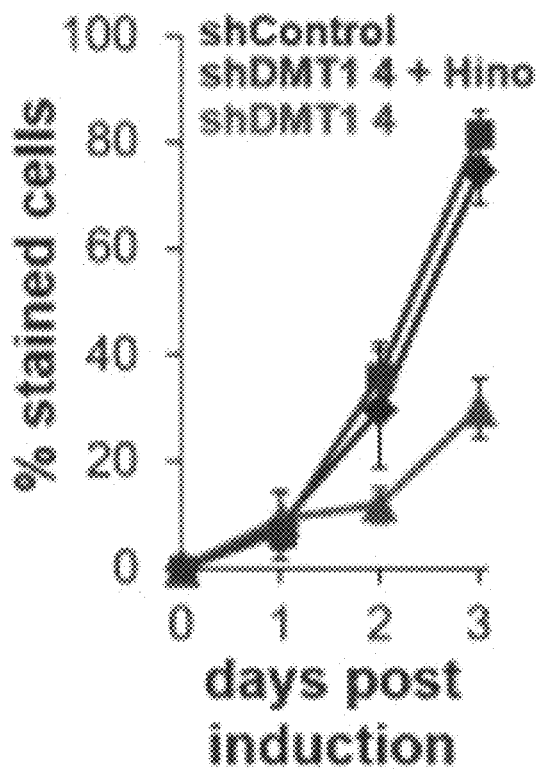

If DMT1 is missing, depleted, or hypomorphic, intracellular iron (II) efflux from endosomes of erythroid precursors is precluded, thus preventing hemoglobinization (FIG. S1B) (2, 6, 38). DMSO-induced differentiation and hemoglobinization was tested for in DS19 murine erythroleukemia (MEL) cells (39), as well as in shRNA-transfected DMT1-deficient MEL cells (FIG. 13A-C), in the absence or presence of hinokitiol. Control cells differentiated normally after three days as indicated by the characteristic pink color of hemoglobin in cell pellets (FIG. 3D) and brown staining of hemoglobinized cells with o-dianisidine (FIG. 13D, E). Reduced hemoglobinization was observed in DMT1-deficient cells (FIG. 3D-F, and FIG. 13D-F). Three days of hinokitiol treatment (1 µM) restored $^{55}Fe$ uptake (FIG. 13F), $^{55}Fe$-heme incorporation (FIG. 3F), and hemoglobinization (FIG. 3D and FIG. 13D-J) without observable toxicity (FIG. 13K and table S7) whereas $C_2$deOHino had no effect (FIG. 3E, F and FIG. 13F, I, J). As expected, no differentiation was observed in the absence of DMSO with or without hinokitiol treatment (FIG. 13L).

Figure 14A:
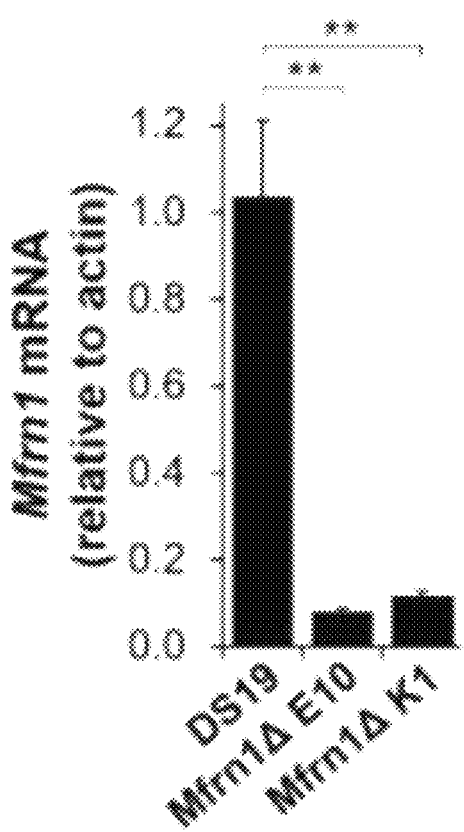
FIGS. 14A-14M show hinokitiol restores physiology in other iron transporter-deficient systems in vitro. (A) Mfrn1 mRNA levels are reduced in CRISPR derived Mfrn1 knockdown MEL cells relative to wild type cells after induction for terminal differentiation. N=3. (B and C) Hinokitiol (1 µM) restores normal (B) iron uptake and (C) iron incorporation into heme in Mfrn1-deficient MEL cells using $^{55}$Fe radiotracer. N=5-25. (D-F) As expected, hinokitiol (1 µM) cannot restore (D) differentiation (quantified via ImageJ analysis after o-dianisidine staining), (E) iron uptake, or (F) iron heme incorporation in DMSO-induced TMEM14CΔ MEL cells, which are missing a protein involved in porphyrin biosynthesis. N=8-25. (G and H) Quercetin incubation for eighteen hours knocks down FPN1 protein levels in Caco-2 cells; hinokitiol (1 µM) does not increase FPN1 levels. N=8. (I and J) Hepcidin reduces FPN1 levels in J774 macrophages; hinokitiol (5 µM) does not increase FPN1 levels. N=20. (K) Hinokitiol (1 µM) restores transepithelial iron transport across FPN1-deficient Caco-2 monolayers at rates commensurate with wild type monolayers. N=3. (L) Wild type and quercetin-treated FPN1-deficient monolayers in the absence or presence of hinokitiol (1 µM) or C$_2$deOHino (1 µM) remain intact for the duration of the experiments as evident by their consistent TransEpithelial Electrical Resistance (TEER) values. N=3. (M) Hinokitiol promotes iron release in FPN1-deficient J774 cells in a dose-dependent manner after 2 hours. N=6-20. (A-F, H, J-M) NS, not significant; * P≤0.05;  P≤0.01; * P≤0.001; **** P ≤0.0001; Graphs depict means±SEM.

Having observed hinokitiol-mediated transport of iron into and within DMT1-deficient cells, it was then postulated whether the same small molecule could also substitute for other iron-transport proteins. Mfrn1 in the inner mitochondrial membrane imports iron into the mitochondrial matrix for hemoglobinization (FIG. S1C) (2, 10). Mfrn1-deficient MEL cells developed through CRISPR-Cas9-mediated knockout (FIG. 14A) exhibited reduced hemoglobinization by o-dianisidine staining (FIG. 3G), $^{55}Fe$ uptake (FIG. 14B), and $^{55}Fe$-heme incorporation (FIG. 14C) after DMSO induction. Hinokitiol (1 µM) restored hemoglobinization whereas $C_2$deOHino showed no effect (FIG. 3G and FIG. 14B, C), suggesting hinokitiol-mediated mitochondrial delivery of iron. As expected, hinokitiol did not promote hemoglobinization to MEL cells alternatively deficient in a protein involved in porphyrin biosynthesis (TMEM14CA) (FIG. 14D-F).

Figure 14B:
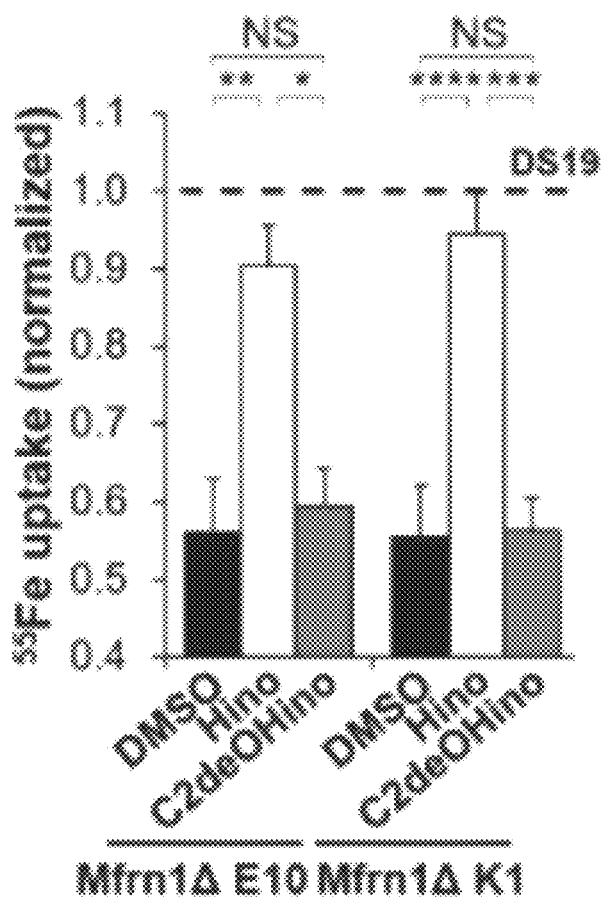
Figure 14C:
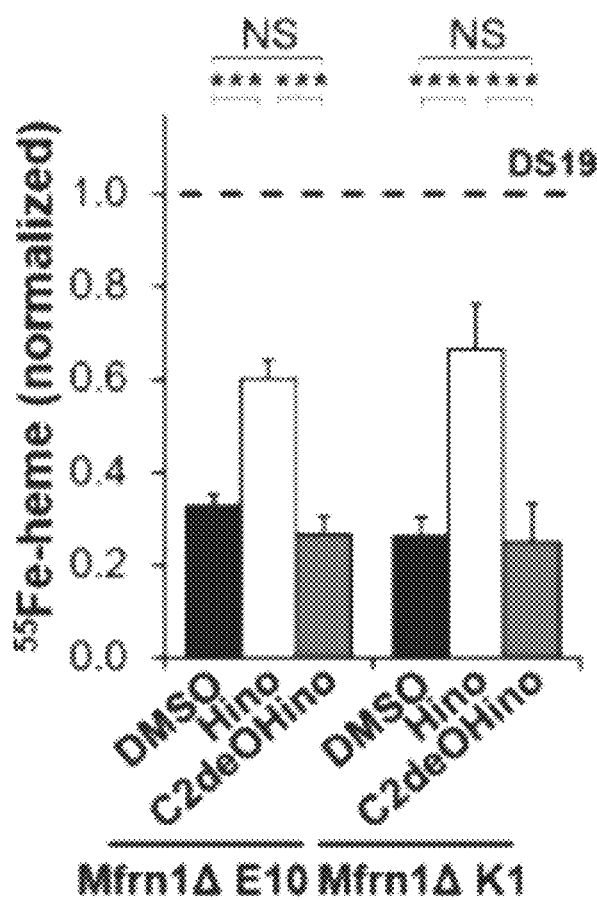
Figure 14D:
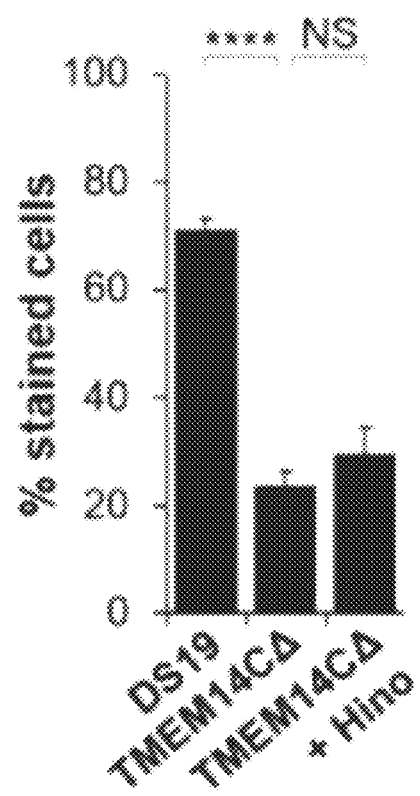
Figure 14E:
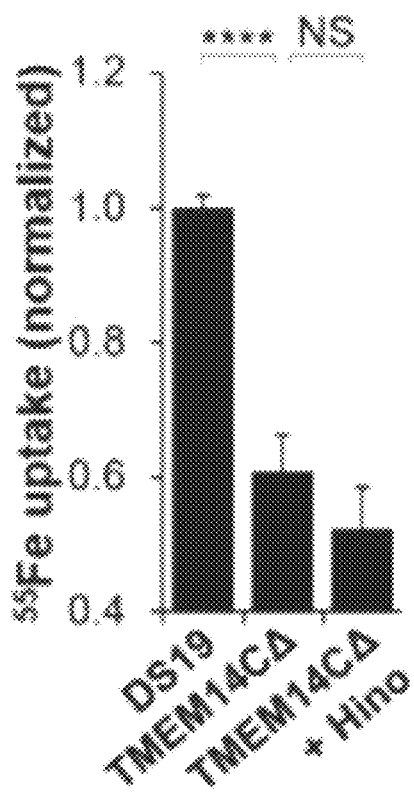
Figure 14F:
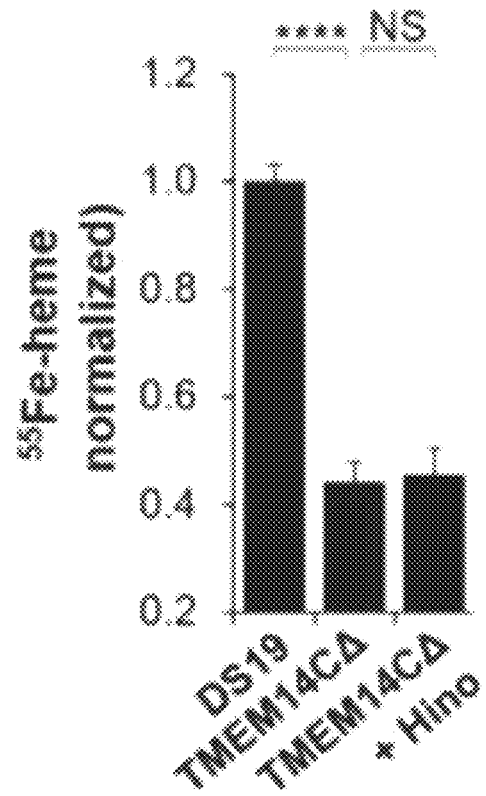
Figure 14G:
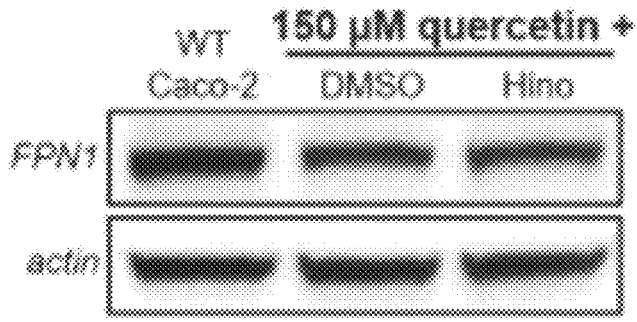
Figure 14H:
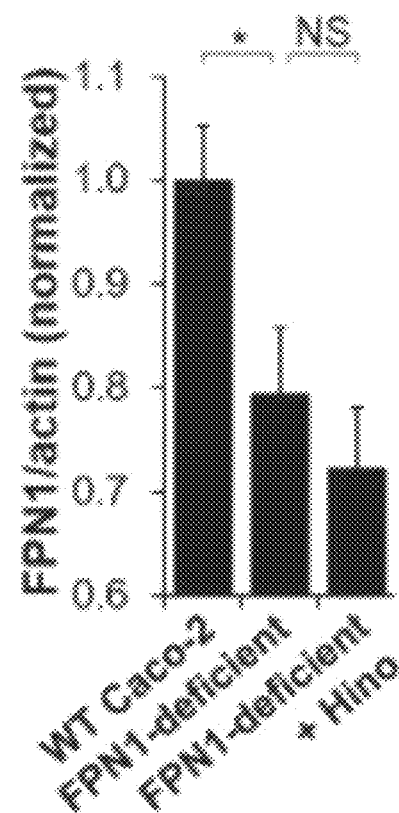

FPN1 deficiencies reduce iron efflux across the basolateral membrane of gut epithelia (FIG. S1D) and from reticuloendothelial macrophages (FIG. S1E) that recycle iron from senescent erythrocytes (13, 14). Quercetin (40) and hepcidin (41) were used to transiently decrease FPN1 levels in differentiated Caco-2 epithelia monolayers and J774 macrophages (41), respectively (FIG. 14G-J). Hinokitiol (1 µM) restored transepithelial iron transport in FPN1-deficient Caco-2 monolayers (FIG. 3H and FIG. 14K) without affecting iron uptake (FIG. 3I) nor disrupting monolayer integrity (FIG. 14L). Hinokitiol also time- and dose-dependently restored iron release from FPN1-deficient J774 macrophages without observable toxicity (FIG. 3J, K, FIG. 14M, and table S7).

Site- and Direction-Selective Build-Up and Release of Iron Gradients

Figure 4A:
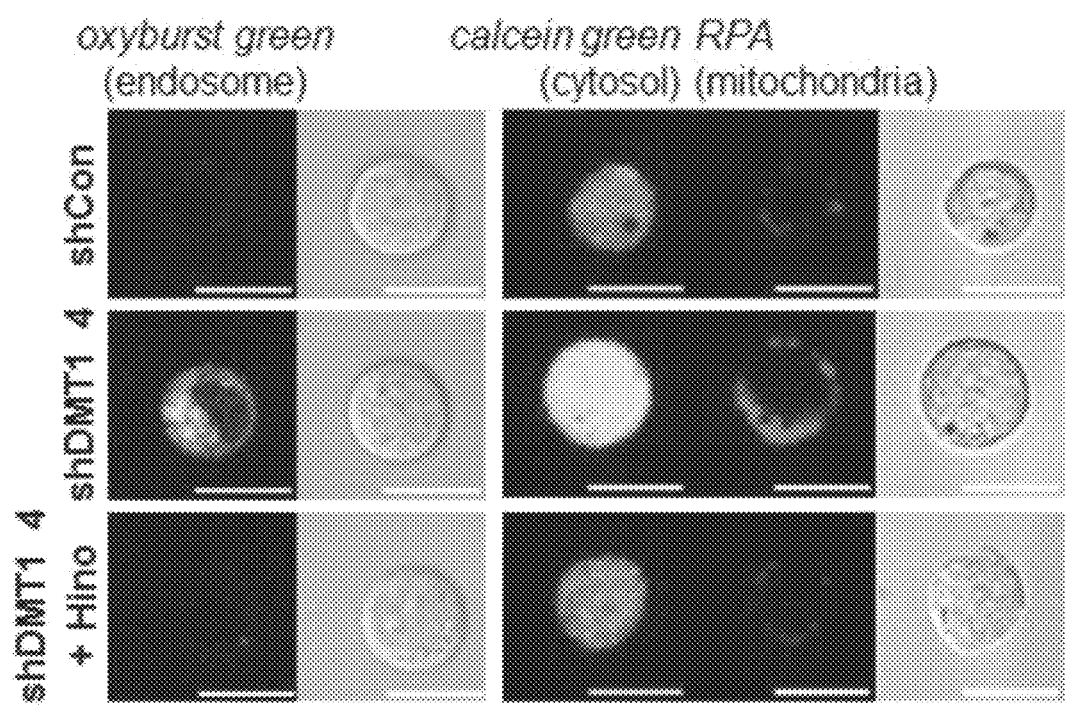
FIGS. 4A-4I show hinokitiol leverages built-up iron gradients. (A) Representative fluorescence images of differentiated shControl and DMT1-deficient MEL cells in the absence or presence of hinokitiol (1 μM) using oxyburst green, calcein green, and RPA to detect relative endosomal, cytosolic, and mitochondrial iron levels, respectively. A build-up of labile iron was observed in endosomes of DMT1-deficient cells, which was released after hinokitiol treatment. (B and C) A build-up of intracellular labile iron is observed in FPN1-deficient J774 macrophages treated with 200 μM FeSO$_4$ by quenching of calcein green fluorescence. N=3. (D) Iron (III) uptake into J774 macrophages with 50 μM FeCl$_3$ similarly revealed a build-up of total intracellular iron in FPN1-deficient cells after 4 hours using $^{55}$Fe as a radiotracer. N=8. (E) Increased extracellular iron (III) levels increased rates of iron uptake into J774 macrophages when treated with hinokitiol (1 μM) using $^{55}$Fe as a radiotracer. N=3. (F and G) Increased intraliposomal (F) ferrous iron and (G) ferric iron leads to increased rates of iron efflux in the presence of hinokitiol (10 μM). No efflux was observed in the absence of hinokitiol. N=3. (H) Fluorescence imaging of cytosolic iron with calcein green using artificially created iron gradients in J774 macrophages in opposite directions. Cells were loaded with FeSO$_4$ (200 μM), rinsed, then hinokitiol (100 PM) was added at t=5 min. An increase in fluorescence was observed, consistent with decreased intracellular labile iron. The gradient was then reversed in these same cells by addition of 100 μM FeCl$_3$ to the media at t=12 min. Fluorescence quenching was observed, consistent with iron uptake. (I) Representative ImageJ quantification of calcein green fluorescence in iron-loaded J774 cells with addition of DMSO, hinokitiol, or C$_2$deOHino at t=5 min and FeCl$_3$ at t=12 minutes. Scale bar=10 μm (A), 20 μm (B, H). (C-E)  P≤0.01; ** P≤0.0001; Graphs depict means±SEM. (F, G) Graphs depict means of three independent experiments. (I) Representative graph from six independent experiments.

A mechanistic hypothesis that hinokitiol promotes site- and direction-selective iron movement by harnessing built-up transmembrane iron gradients in transporter-deficient systems (FIG. 1A) was then probed. Compartmentalized iron was first visualized in DMT1-deficient MEL cells with fluorescent dyes (FIG. 15A-C) (42, 43). An oxyburst green-BSA conjugate localized to endosomes fluoresces upon iron-mediated oxidation (FIG. 15C), and fluorescence emissions from the turn-off probes calcein green (FIG. 15A) and RPA (FIG. 15B) in the cytosol and mitochondria, respectively, are quenched upon iron binding. Relatively low endosomal, high cytosolic, and high mitochondrial iron levels were observed in induced shControl MEL cells (FIG. 4A and FIG. 16A, B, E, H). Two-fold increases in iron-promoted oxyburst green fluorescence in DMT1-deficient MEL cells were observed (FIG. 4A and FIG. 16A, B) along with reduced cytosolic and mitochondrial iron (FIG. 4A and FIG. 16A, E, H). Hinokitiol treatment decreased oxyburst green fluorescence 2.1-fold and concomitantly quenched calcein green and RPA fluorescence (FIG. 4A and FIG. 16A-J). Without being bound by any one particular theory, these data support hinokitiol-mediated release of built-up pools of endosomal iron into the cytosol and subsequent mitochondrial uptake.

Figure 4B:
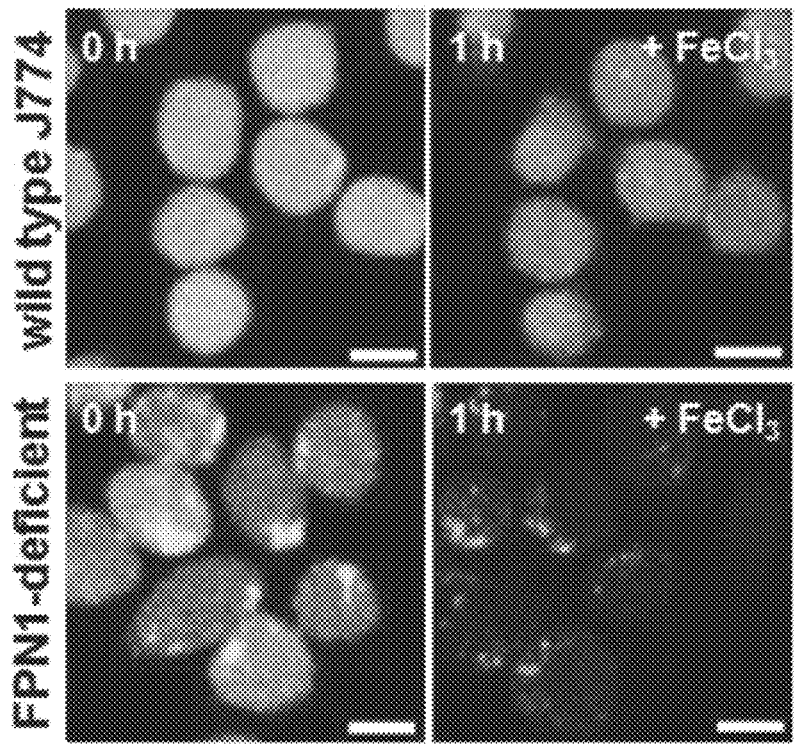
Figure 4C:
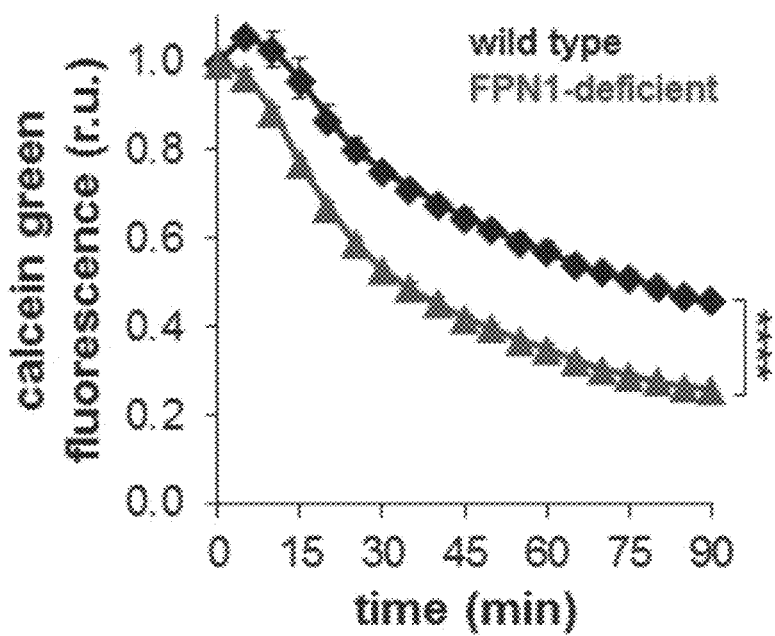
Figure 4D:
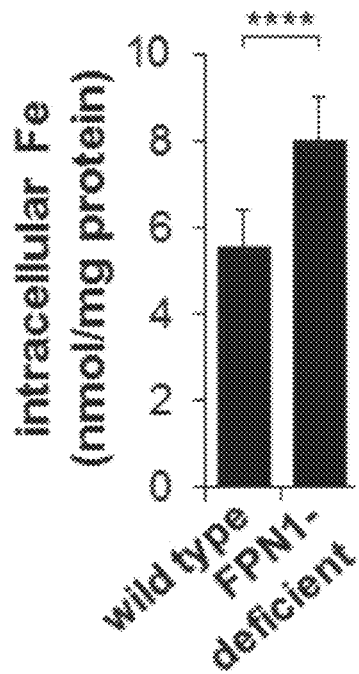
Figure 4E:
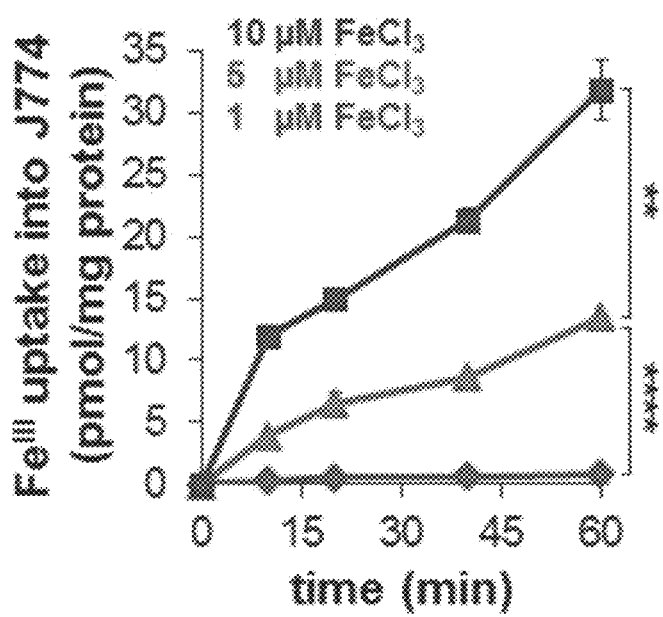
Figure 17A:
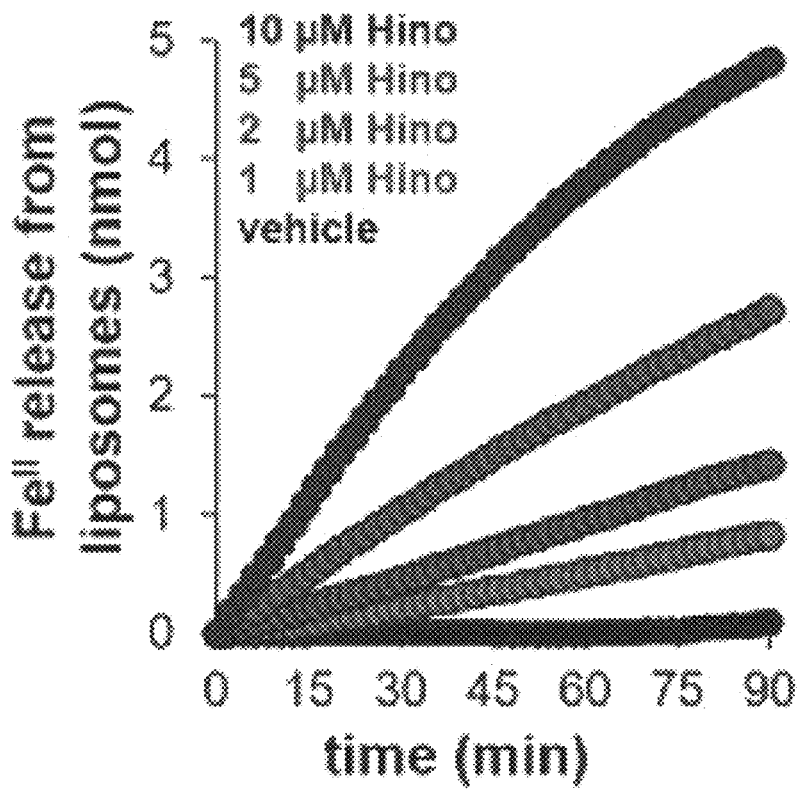
FIGS. 17A-17E show hinokitiol transport as a function of the iron gradient. (A and B) Hinokitiol increases the release of (A) ferrous and (B) ferric iron from POPC liposomes in a dose-dependent fashion with a constant concentration of iron (30 mM). N=3. (C and D) The rate of iron release from hinokitiol-treated (10 µM) POPC liposomes also increases as a function of the amount of (C) ferrous and (D) ferric iron inside of the liposomes. N=3. (E) Simplified schematic for hinokitiol-promoted direction-selective iron transport across membranes of J774 macrophages using artificial gradients. FeSO$_4$ (200 µM) is first loaded into J774 cells, the extracellular fluid is replaced with a low iron media (<500 nM), then hinokitiol (100 µM) is added at t=5 min. Hinokitiol releases iron to the extracellular fluid. The gradient is then reversed by addition of extracellular FeCl$_3$ (100 µM) at t=12 min. Hinokitiol alternatively promotes the uptake of iron into J774 macrophages, consistent with direction-selective transport depending on the direction of the pre-formed iron gradients. (A, B) Representative graphs from three independent experiments. (C, D) Graphs depict means SEM.
Figure 17B:
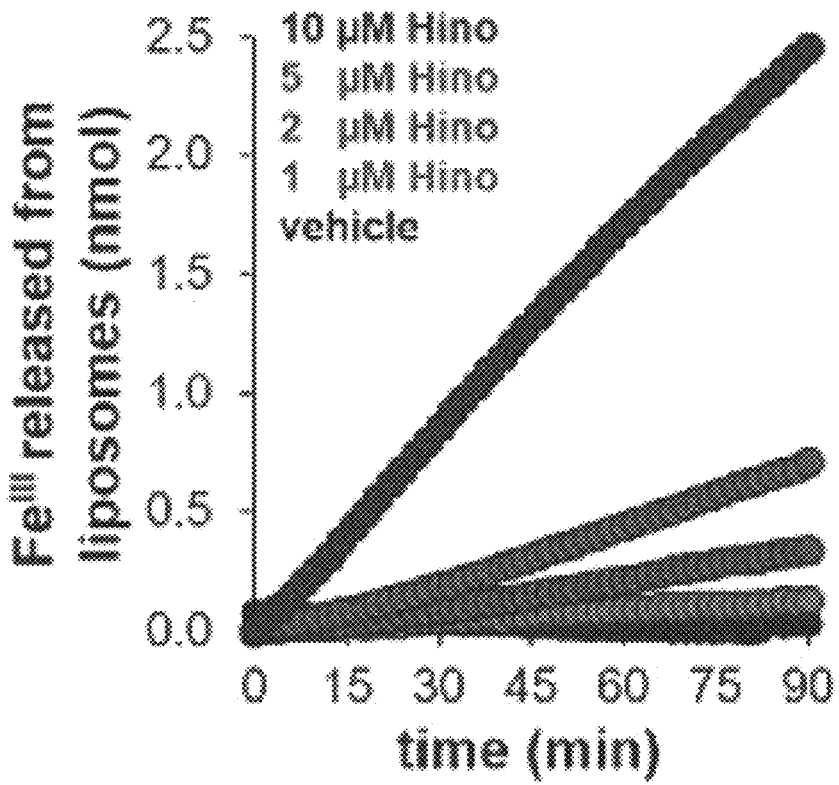
Figure 17C:
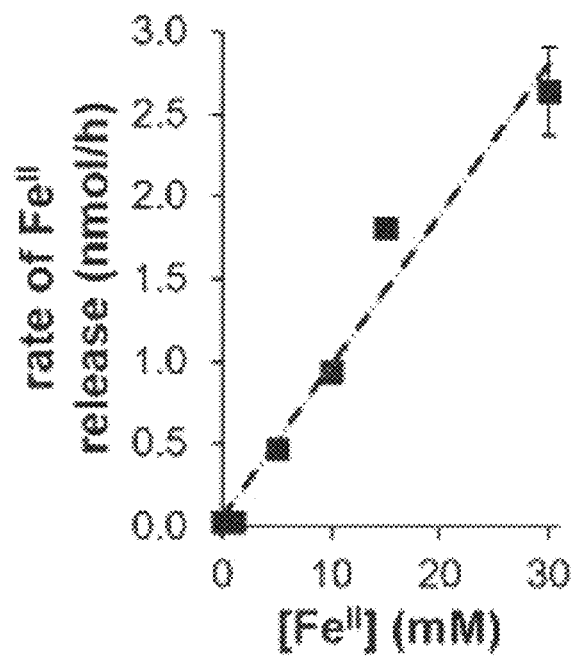
Figure 17D:
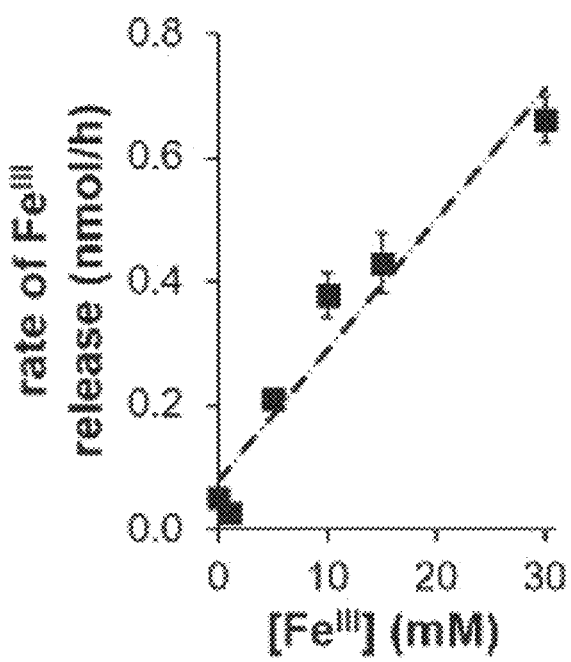
Figure 17E:
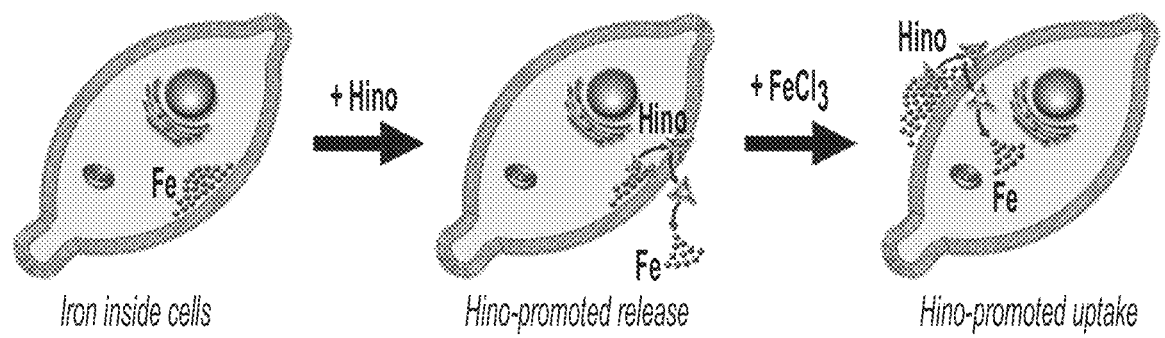

Calcein green and $^{55}Fe$ studies also revealed a build-up of labile iron in FPN1-deficient J774 macrophages relative to wild type cells (FIG. 4B-D). Hinokitiol direction-selectively promotes both iron influx (FIG. 4E) and efflux (FIG. 3J and FIG. 14M) from J774 macrophages depending on the presence of high extracellular or intracellular iron, respectively. Further, hinokitiol-mediated iron (II) and iron (III) efflux from liposomes and iron (III) uptake into J774 macrophages is directly proportional to the transmembrane iron gradients (FIG. 4E-G and FIG. 17A-D). Finally, we loaded iron into J774 macrophages, rinsed the cells to remove extracellular iron, and stained with calcein green (FIG. 17E). Hinokitiol addition (t=5 min) rapidly increased calcein green fluorescence whereas vehicle and $C_2$deOHino had no effect (FIG. 41H, I, FIG. 18A-C, and Movie S1). The gradient was then reversed in these same cells via external addition of $FeC_3$ (t=12 min) (FIG. 17E). DMSO or $C_2$deOHino treated cells had no effect (FIG. 4i and FIG. 18A, C), whereas quenching of calcein green fluorescence was observed with hinokitiol treatment (FIG. 4H, I, FIG. 18B). These results are consistent with initial hinokitiol-mediated release of iron from J774 macrophages when intracellular iron levels are high, followed by hinokitiol-mediated uptake of iron into these macrophages when this transmembrane gradient is reversed by addition of extracellular iron (FIG. 17E).

Mechanisms for Maintaining Iron Homeostasis

Figure 19A:
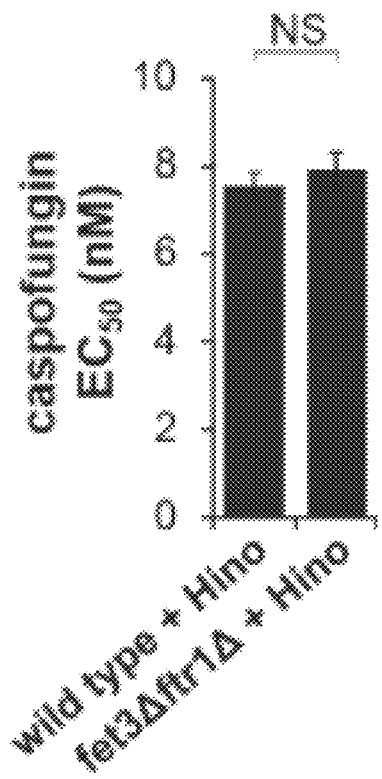
FIGS. 19A-19Q show endogenous proteins involved in iron uptake and transport. (A) As expected, wild type and fet3Δftr1Δ yeast grown in the presence of hinokitiol (10 µM) are equisensitive to an inhibitor of cell wall biosynthesis, caspofungin, which is off-pathway of iron uptake. N=3. (B and C) Inhibition of the proton-motive force generating pumps, (B) Pma1 with ebselen and (C) V-ATPase with bafilomycin, lead to increased sensitivity of hinokitiol-rescued fet3Δftr1Δ yeast relative to hinokitiol-treated wild type yeast. This suggests these proteins play a role in hinokitiol-mediated restoration of yeast cell growth. N=3. (D-K) Western blot or ELISA quantification of protein levels of iron-related proteins in shDMT1 Caco-2 monolayers indicate other proteins respond via transcriptional and translational feedback mechanisms to changes in cellular iron status. Importantly, (E) decreased ferritin and (I) increased FPN1 levels were observed, presumably creating an environment favorable for small molecule-mediated iron transport. N=3-16. (L) $^{55}$Fe incorporation into immunoprecipitated ferritin is also decreased in DMT1-deficient Caco-2 monolayers relative to shControl. N=14. (M) Hinokitiol-promoted (500 nM) uptake into shDMT1 monolayers is unidirectional. Apical addition of $^{55}$FeCl$_3$ and hinokitiol (500 nM) led to significant levels of iron inside of cells, while basolateral addition of the same concentrations of $^{55}$FeCl$_3$ and hinokitiol led to no uptake. N=3. (N and O) Quercetin (250 µM) treatment for 18 hours decreased FPN1 levels in shDMT1 Caco-2 monolayers by western blotting analysis. N=16. (P) Quercetin-mediated knockdown of FPN1 in Caco-2 monolayers did not affect iron uptake into these cells in the presence and absence of hinokitiol (1 µM). N=3. (Q) Quantification of relative iron transport vs. uptake in Caco-2 monolayers supports hinokitiol restores normal iron homeostasis in these cells. N=3. (A-M, O-Q) NS, not significant; * P≤0.05; ** P≤0.01; 'K'K'K'K P<0.0001; Graphs depict means±SEM.
Figure 19B:
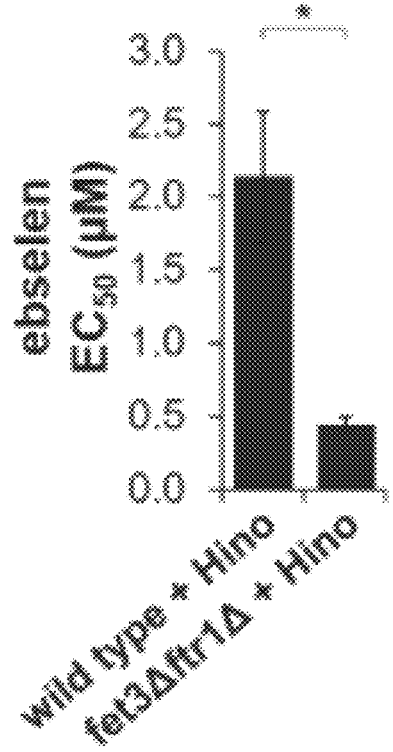
Figure 19C:
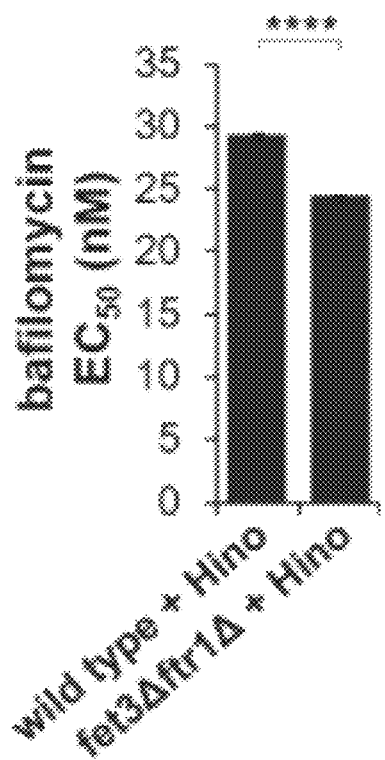
Figure 19D:
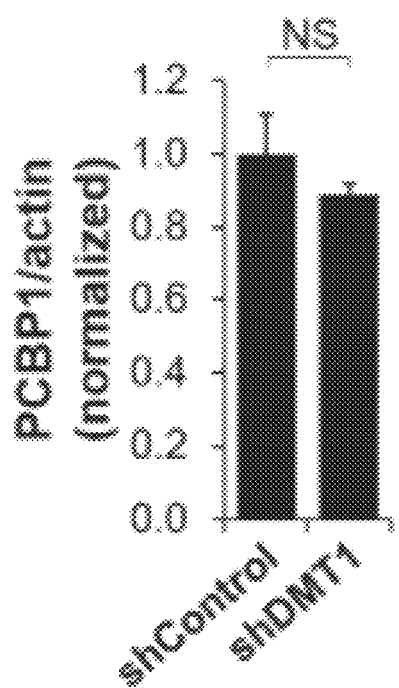

It was next postulated whether endogenous networks of other ion-transport proteins and regulators (2) in iron transporter-deficient cells can collaborate with the small molecule, hinokitiol, to help promote restoration of site- and direction-selective iron transport while still maintaining iron homeostasis. In yeast, the intracellular movement and storage of iron is dependent on a proton gradient known as the proton motive force, which is generated by the ATP-dependent active ion-transport proteins Pmal and V-ATPase in the plasma and vacuolar membranes, respectively (21, 35). Consistent with the dependence of hinokitiol-mediated iron transport on this proton motive force, hinokitiol-rescued fet3Δftr1Δ yeast are exceptionally sensitive to chemical inhibition of Pma1 and V-ATPase, but not to off-pathway inhibitors (FIG. 19A-C).

Figure 20A:
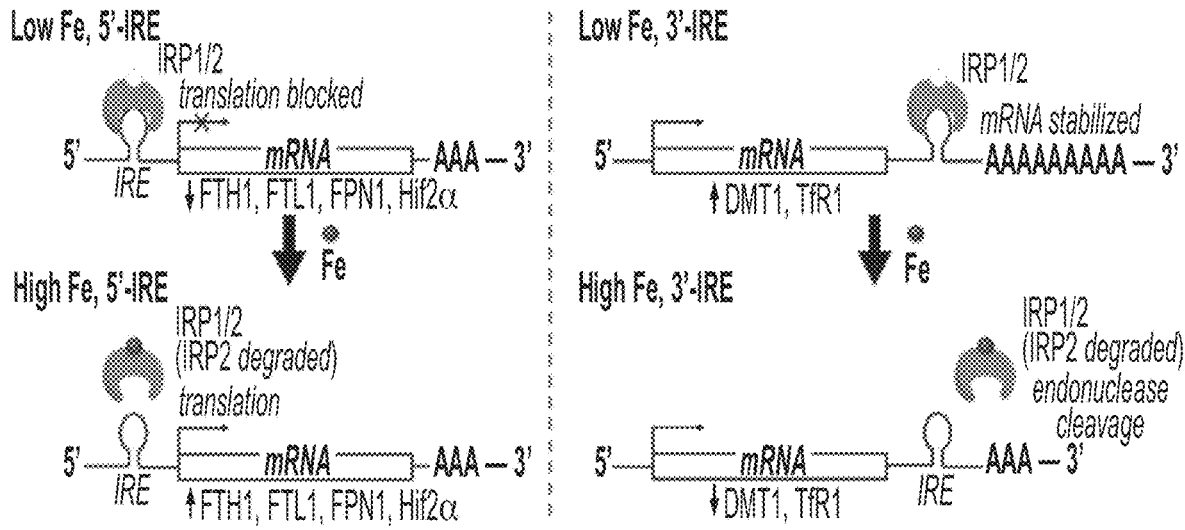
FIGS. 20A and 20B show simplified schematics for translational and transcriptional regulation of iron-related proteins. (A) Translational regulation in duodenal enterocytes is mediated through iron response elements (IREs) located on the 5' or 3' ends of mRNA of several iron-related proteins. In the absence of iron, iron response proteins (IRP1 and IRP2) bind to the 5'- or 3'-IRE to block translation or stabilize mRNA, respectively. Upon iron binding, IRP1/2 dissociate from IRE (and IRP2 is degraded) and translation occurs (5'-IRE) or mRNA degrades (3'-IRE) to allow for iron-sensitive regulation of proteins involved in iron uptake and transport. (B) Transcriptional regulation of FPN1 via Hif2α occurs to evade translational repression of FPN1. Hif2α activates Fpn1 transcription under iron-deplete conditions, however, in the presence of iron and O2, Hif2α is degraded, thus decreasing FPN1 protein levels.
Figure 20B:
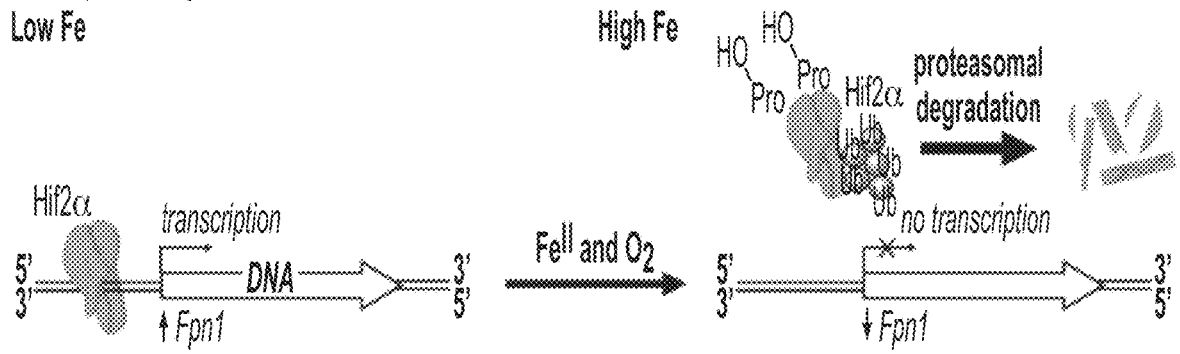

In intestinal epithelia, iron-transport proteins are transcriptionally and translationally regulated to maintain systemic iron levels while avoiding overload (2, 44). Specifically, levels of the apical H+/Fe$^{2+}$ symporter DMT1, heavy (FTH1) and light (FTL1) chains of ferritin responsible for sequestering excess iron, basolateral efflux protein FPN1, and transferrin receptor 1 (TfR1) are translationally regulated through short hairpin iron response elements (IREs) located at the 5'- and 3'-untranslated regions of the corresponding mRNA transcripts (FIG. 20A) (2). Iron-sensing iron response proteins (IRP1 and IRP2) bind to these IREs to block translation (5'-IRE, Fth1, Ftl1, Fpn1) or stabilize mRNA (3'-IRE, Dmt1, TfR1) under iron starvation (FIG. 20A). Upon iron stimulation and binding, IRPs dissociate from the mRNAs, reversing their described effects. Transcriptional regulation is achieved through the transcriptional activator, hypoxia-inducible factor 2-alpha (Hif2α), which is degraded after O$_2$ and iron-mediated proline hydroxylation (FIG. 20B) (2). Hif2α activates transcription of Fpn1 to evade IRE-mediated translational repression under iron deprivation (2).

Consistent with these homeostatic mechanisms, an anemic state (45) is initially observed in DMT1-deficient Caco-2 monolayers, with decreased levels of ferritin and increased levels of FPN1 (FIG. 5A and FIG. 19D-L), thus providing a favorable cellular environment for small molecule-mediated iron transport. Providing support for functional collaboration with these endogenous proteins, hinokitiol-mediated iron uptake and transport across DMT1-deficient Caco-2 monolayers is unidirectional (FIG. 5B and FIG. 19M). Apical treatment with this low dose of hinokitiol (500 nM) allows for $^{55}$Fe incorporation into ferritin (FIG. 5C), possibly mediated by the high affinity iron chaperone Poly (rC)-binding protein 1 (PCBP1) (2). Finally, quercetin-mediated knockdown of FPN1 (40) antagonizes hinokitiol-mediated transmembrane transport without affecting apical uptake (FIG. 5D and FIG. 19N-P).

Figure 5A:
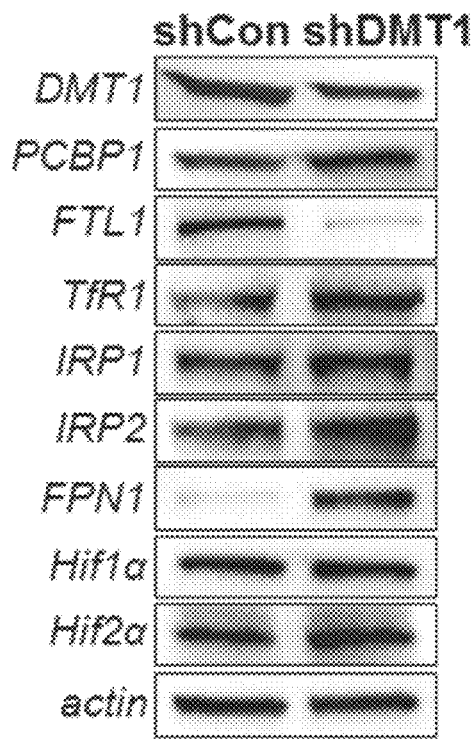
FIG. 5A-5J show the endogenous network is involved in hinokitiol-mediated Caco-2 transport. (A) Representative western blot images of proteins involved in iron absorption and regulation indicate an anemic state is observed in shDMT1 Caco-2 monolayers to promote maximal iron absorption. (B) Unidirectional hinokitiol-mediated transport in shDMT1 Caco-2 monolayers by apical or basolateral addition of hinokitiol (500 nM) and $^{55}$Fe radiotracer. N=3. (C) Determination of $^{55}$Fe levels in immunoprecipitated ferritin in Caco-2 monolayers. N=3. (D) Knockdown of FPN1 in shDMT1 Caco-2 monolayers with quercetin abrogates hinokitiol-mediated transport. N=3. (E) Rates of Caco-2 transport with varying concentrations of iron treated with DMSO or hinokitiol (500 nM) after 4 hours. The rates of transport level off with increasing iron concentrations. N=3. (F) Increased doses of hinokitiol increase uptake into shDMT1 Caco-2 monolayers apically treated with 25 μM FeCl$_3$; however, a bimodal effect is observed in transepithelial iron transport at 5 μM hinokitiol. N=3. (G) Representative western blot images of proteins involved in iron absorption and regulation after treatment with increasing hinokitiol and 25 μM FeCl$_3$. Bimodal effects were similarly observed in protein levels involved in iron absorption and regulation. (H) Intermediate concentrations of hinokitiol lead to significant calcein green quenching in shDMT1 monolayers treated with 25 μM FeCl$_3$ after 1 hour, consistent with increased labile iron. This effect was reversed at high doses of hinokitiol. (I and J) ImageJ quantification of calcein green fluorescence in these monolayers. N=3-6. Scale bar=20 m (H). (B-F, I, J) NS, not significant; **** P≤0.0001; Graphs depict means±SEM.
Figure 5B:
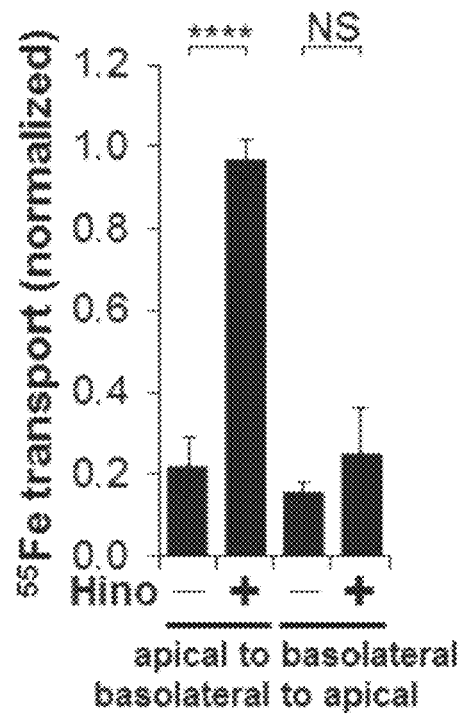
Figure 5C:
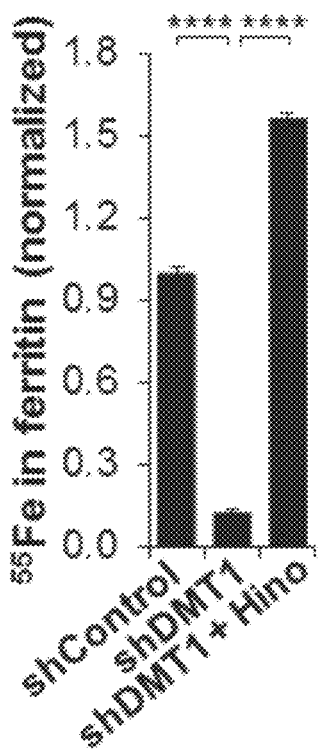
Figure 5D:
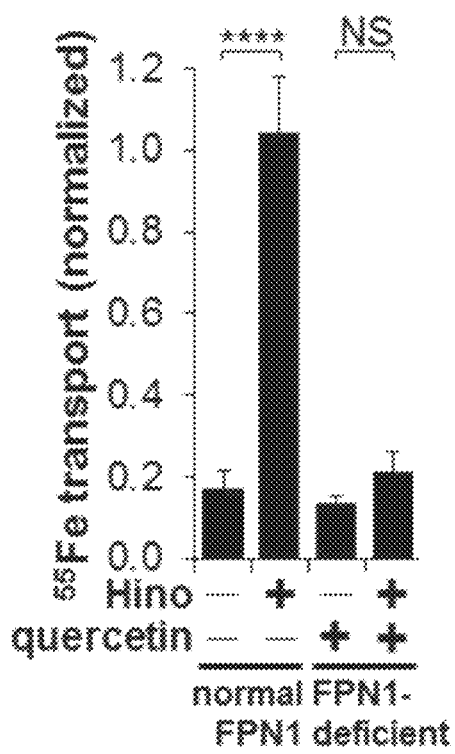
Figure 5E:
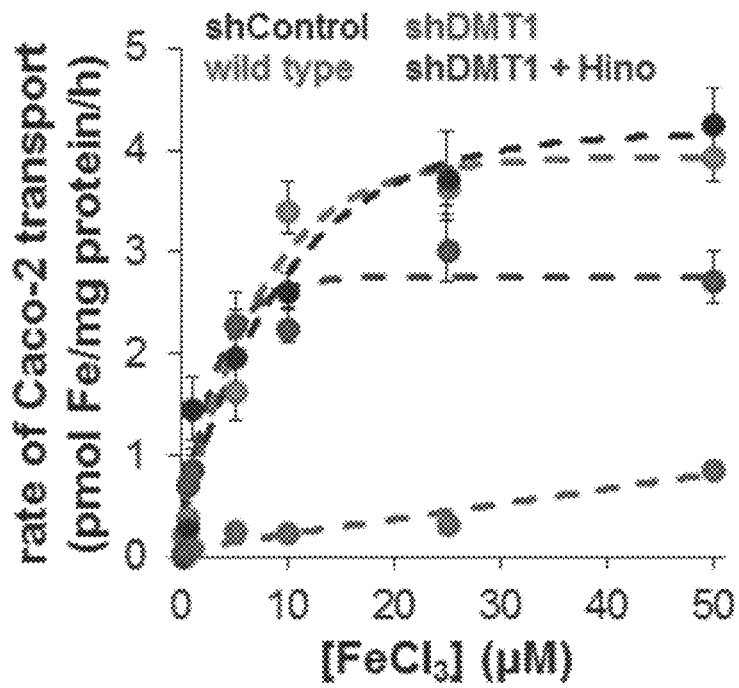
Figure 5F:
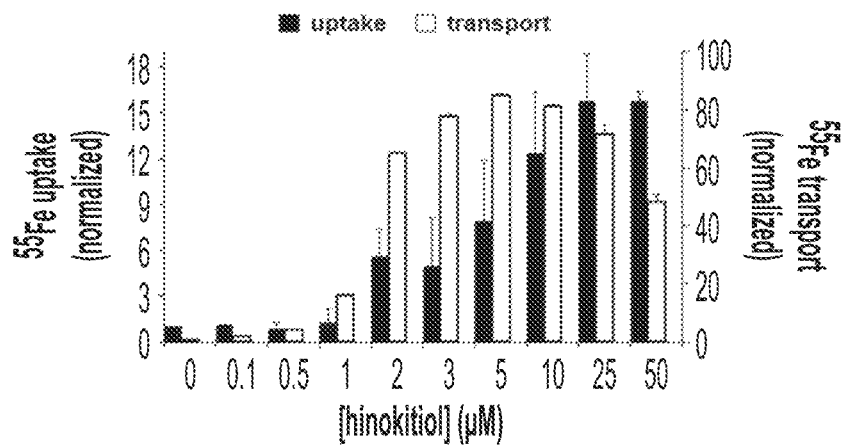
Figure 5G:
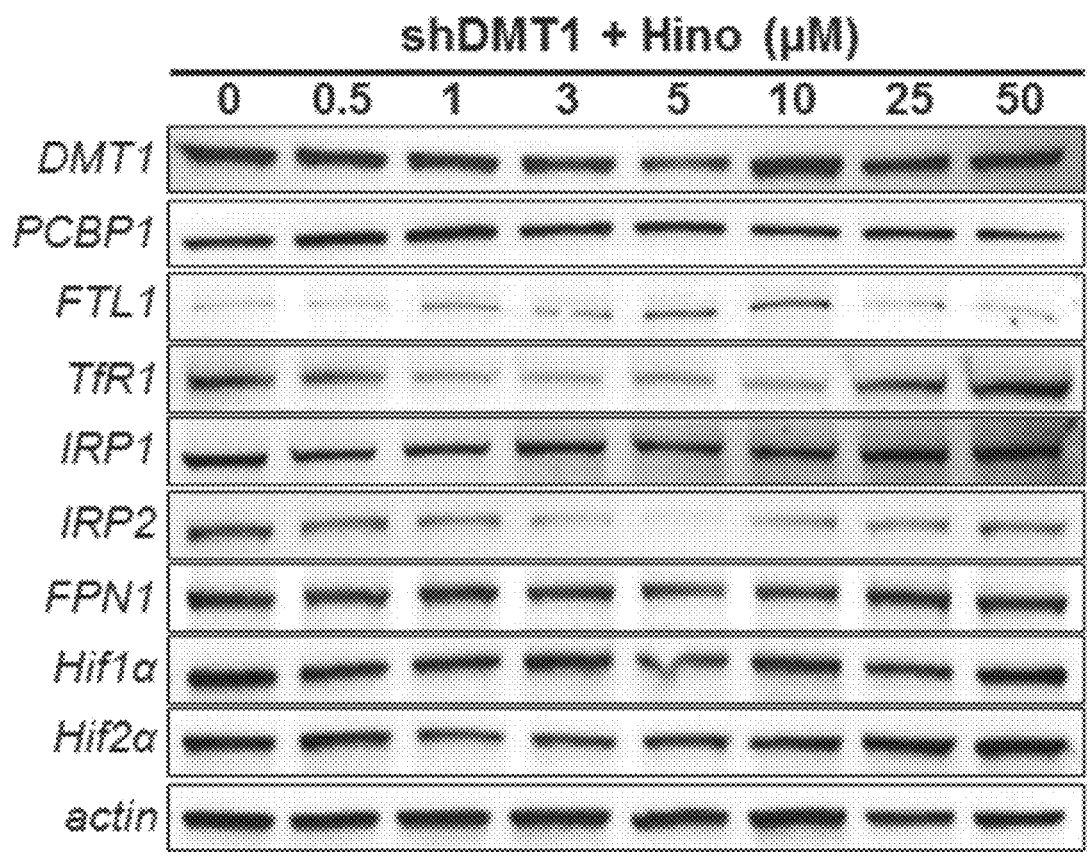
Figure 5H:
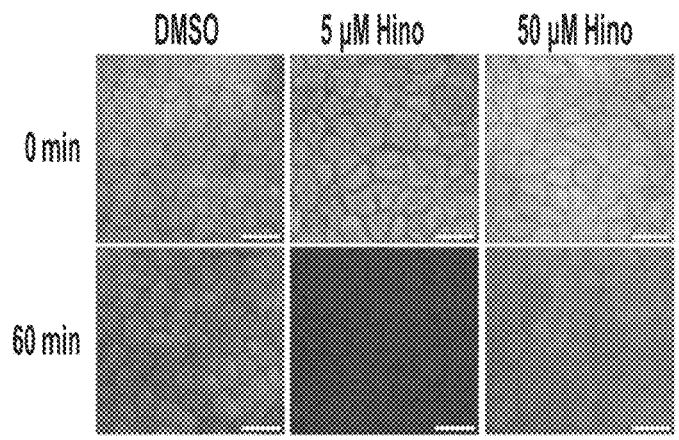
Figure 5I:
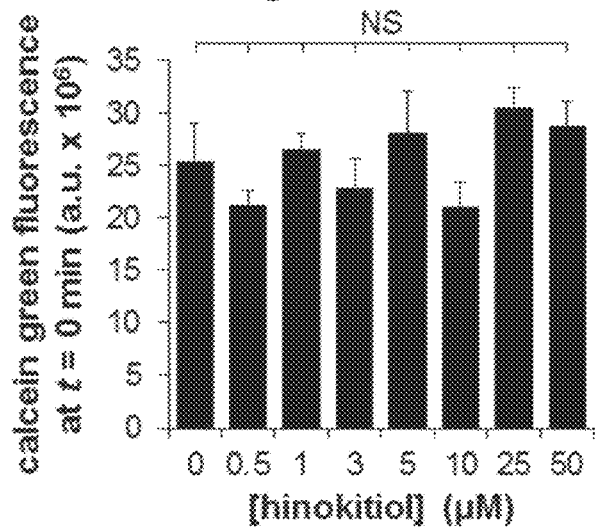
Figure 5J:
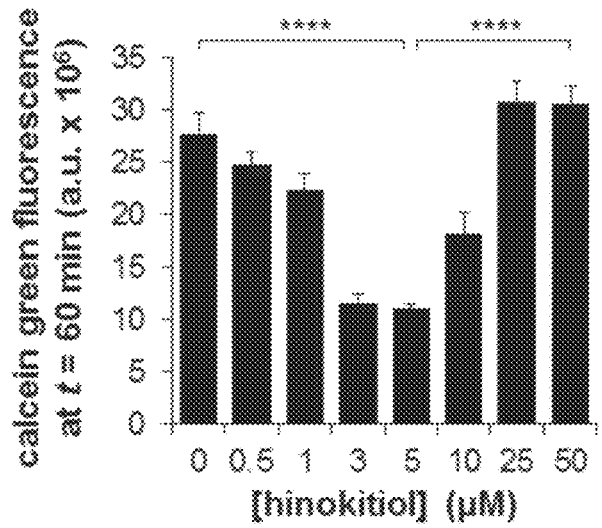
Figure 21:
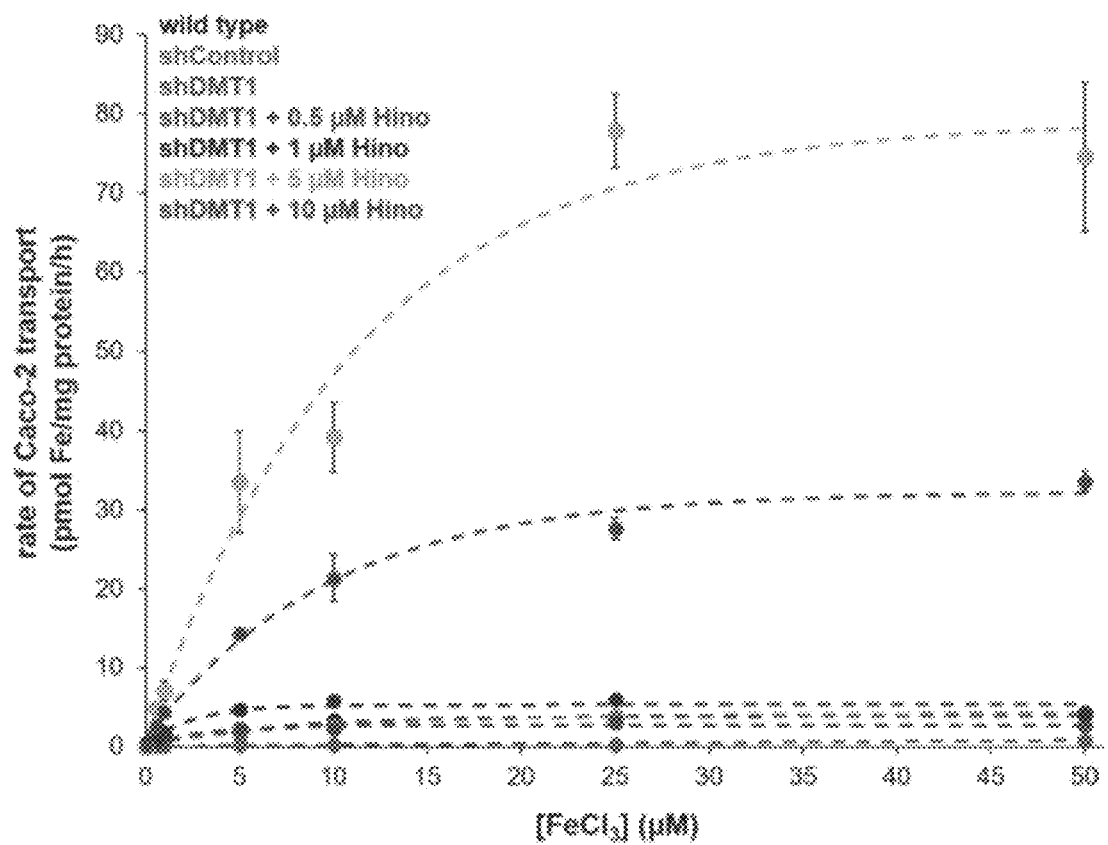
FIG. 21 shows rates of Caco-2 transport with increasing hinokitiol and iron. The rates of the transepithelial transport of iron across differentiated shDMT1 Caco-2 monolayers over a wide range of hinokitiol concentrations increases with increasing iron. The rates of iron transport level off at high concentrations of iron, consistent with homeostatic regulation of iron uptake and transport to maintain normal homeostasis and prevent iron-related toxicity. N =3. Graph depicts means±SEM.

Moreover, increased rates of transepithelial transport in DMT1-deficient monolayers were observed with increased concentrations of apical FeCl$_3$, but these effects level off at higher concentrations of iron (FIG. 5E). Further, a similar leveling of transmembrane transport is observed when the same monolayers are treated with a persistent iron gradient (25 μM FeCl$_3$) and increasing concentrations of hinokitiol (FIG. 5F). This phenomenon was observed over a wide range of hinokitiol and iron concentrations (FIG. 21). It was then asked how the endogenous system responds to the hinokitiol-mediated changes in cellular iron status in the presence of a persistent iron gradient. Consistent with IRP-mediated translational regulation, decreased IRP2, increased ferritin subunits (5'-IREs), and decreased TfR1 (3'-IRE) protein levels were observed as a function of hinokitiol concentrations up to 5 μM in the presence of a persistent iron gradient (FIG. 5G and FIG. 22A-E). The transcription factors Hif1α a and Hif2α similarly decreased along with decreased Fpn1 mRNA and protein levels (FIG. 5G and FIG. 22F-I). As expected, IRE-independent expression of the cytosolic iron chaperone PCBP1 and Hif2α-independent Fth1 mRNA levels did not change, and no changes in FPN1 were observed upon the addition of hinokitiol in the absence of iron (FIG. 5G and FIG. 22K-N). A modest reversal of these effects was observed with higher concentrations of hinokitiol (FIG. 5G and FIG. 22A-J). Visualization of cytosolic iron with calcein green indicated that incubation of DMT1-deficient Caco-2 monolayers with increasing hinokitiol led to increased labile iron up to 5 μM (FIG. 5H-J). Further increases in hinokitiol prevented fluorescence quenching, possibly due to competitive intracellular chelation of labile iron with high doses of this strongly binding metallophore (FIG. 5H-J). These results collectively support the conclusion that the endogenous homeostatic networks can collaborate with the small molecule hinokitiol to help promote iron transport while maintaining its homeostasis and preventing ferritoxicity.

Based on this mechanistic framework, it was hypothesized hinokitiol would have relatively minimal effects in wild type cells. The capacity for the same concentrations of hinokitiol to perturb transepithelial iron transport, hemoglobinization, and iron release in normal Caco-2 monolayers, MEL cells, and J774 cells, respectively, (FIG. 23A-F) were tested. In contrast to hinokitiol-promoted increases in transepithelial iron transport (FIG. 3B), hemoglobinization (FIG. 3G), and iron release (FIG. 3J) observed in the corresponding protein-deficient systems, negligible effects were observed in hinokitiol-treated wild type systems under identical conditions (FIG. 23A-F). Collectively, these results are consistent with hinokitiol restoring site- and direction-selective iron transport by harnessing gradients that selectively build up across lipid membranes missing specific iron transporter proteins.

Restored Gut Iron Absorption and Peripheral Hemoglobinization in Animals

Figure 6A:
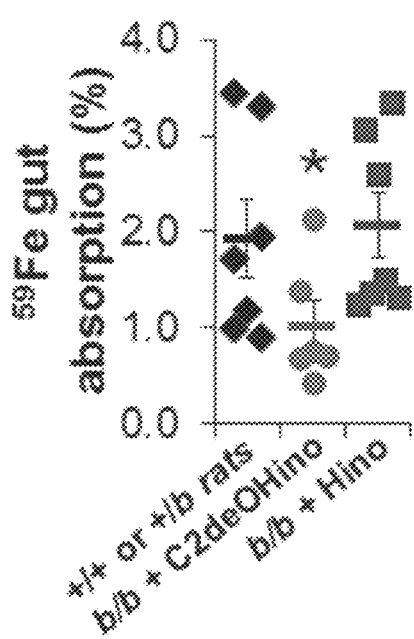
FIG. 6A-6H show hinokitiol restores physiology in iron transporter-deficient animals. (A and B) Oral gavage of 1.5 mg/kg hinokitiol promotes the gut absorption of $^{59}$Fe into (A) DMT1-deficient Belgrade (b/b) rats and (B) FPN1-deficient Flatiron (ffe/+) mice after 1 hour. N=4-7. (C) Hinokitiol treatment (1 μM) to the water to embryos at 24 hpf and incubation for an additional forty-eight hours increases the number of GFP-positive erythroids by FACS analysis in DMT1-deficient morphant zebrafish using a transgenic fish containing GFP-tagged erythroids. N=7-17. (D) Hinokitiol decreases the number of anemic fish from a heterozygous cross of +/cdy fish as determined by o-dianisidine staining, while C$_2$deOHino does not. (E) Hinokitiol (1 μM) increases the number of GFP-positive erythrocytes in Mfrn1-deficient morphant zebrafish. N=12-13. (F) Hinokitiol increases the number of non-anemic embryos from a heterozygous cross of +/frs fish. (G) Embryos from a heterozygous cross of +/frs fish were genotyped by restriction enzyme digestion with BsrI. Lanes 4 and 5 correspond to frs/frs fish treated with hinokitiol for forty-eight hours. (H) Hinokitiol-treated frs/frs fish stain brown with o-dianisidine while anemic frs/frs fish do not, indicating increased hemoglobin levels after hinokitiol treatment. (A-F) NS, not significant; * P≤0.05;  P≤0.01; * P≤0.001; Graphs depict (A-C, E) means±SEM or (D, F) weighted means±SEM.
Figure 6B:
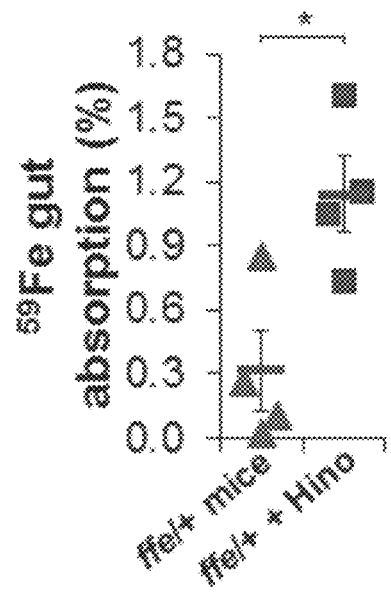

It was then asked whether hinokitiol could restore gut iron absorption and hemoglobinization in animal models of these iron transporter deficiencies. DMT1- and FPN1-deficiencies in duodenal enterocytes reduce rates of iron absorption in the gut by disrupting apical iron uptake into cells and basolateral efflux into the blood, respectively (2, 6, 12-15). Gut iron absorption in DMT1-deficient Belgrade (b/b) rats (6) and FPN1-deficient Flatiron (ffe/+) mice (14, 15) upon administration of a single dose of $^{59}$Fe and 1.5 mg/kg hinokitiol via oral gavage was tested. Higher doses of hinokitiol are reported to be non-toxic in rats upon chronic oral administration for two years (46). Similar to the reduced iron absorption previously reported in b/b rats (47), a 2-fold reduction in $^{59}$Fe absorption was observed in C$_2$deOHino-treated b/b rats relative to sibling controls (+/+ or +/b) (FIG. 6A and FIG. 24A). Treatment of b/b rats with hinokitiol increased $^{55}$Fe absorption back to control levels after one hour (FIG. 6A and FIG. 24A). Consistent with our previous results (15), ffe/+ mice also absorbed iron at low rates (FIG. 6B). Hinokitiol increased $^{59}$Fe absorption in ffe/+ mice after both one and two hours (FIG. 6B and FIG. 24B). A statistically significant increase in the rate of $^{55}$Fe absorption was observed in hinokitiol-treated wild type mice after one hour, but not after two hours (FIG. 24C).

Figure 6C:
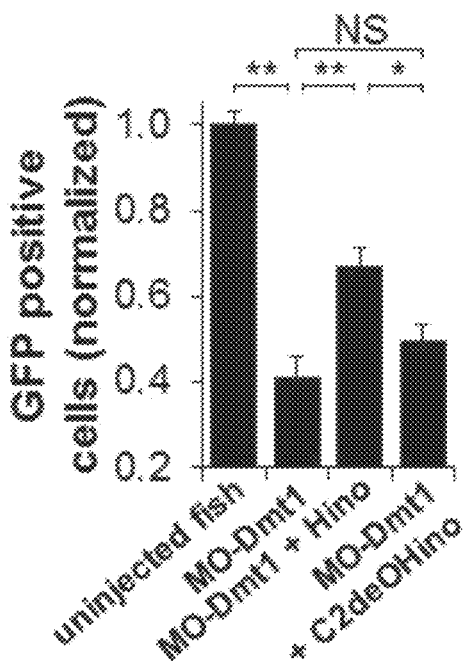
Figure 6D:
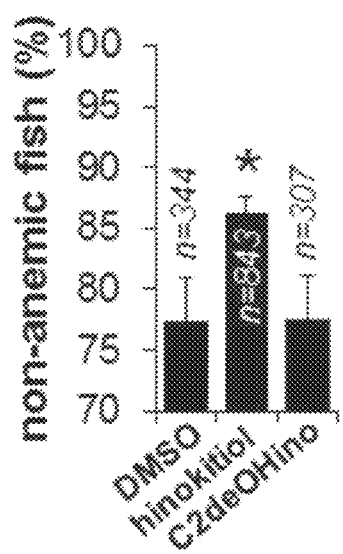

It has been previously shown restoration of hemoglobinization in Mfrn1-deficient zebrafish, via ectopic expression of Mfrn1 protein with complementary RNA (10). *Danio rerio* is well established as a powerful model organism in the study of hematopoiesis (48), and was employed to alternatively test whether chronic treatment with a small molecule iron transporter could restore hemoglobinization in DMT1- and Mfrn1-deficiencies (10, 49). We first performed morpholino-mediated transient knockdown of DMT1 in a Tg(globinLCR:eGFP) zebrafish strain expressing GFP-tagged erythrocytes (50). Injection of a designed anti-sense morpholino targeting the exon 4/intron 4 junction of pre-mature Dmt1 mRNA reduced steady-state Dmt1 levels (FIG. 24D) and decreased the number of GFP-positive erythroid cells by FACS analysis (FIG. 6C). Addition of hinokitiol to the water twenty-four hours post fertilization (hpf) and incubation for an additional two days promoted hemoglobinization in these DMT1-deficient morphant zebrafish without observable toxicity, whereas $C_2$deOHino had no effect (FIG. 6C). We further tested whether hinokitiol could similarly restore hemoglobinization in genetically mutated Chardonnay (cdy$^{fe216}$) zebrafish, which contain a nonsense mutation leading to truncated DMT1 and thereby exhibit severe hypochromic, microcytic anemia (49). A heterozygous cross of +/cdy fish led to a Mendelian distribution of ~75% healthy (+/+ and +/cdy) and ~25% anemic (cdy/cdy) embryos in each clutch after o-dianisidine staining 72 hpf (FIG. 6D). Hinokitiol treatment for two days increased the number of fish exhibiting high hemoglobin levels, whereas $C_2$deOHino had no effect (FIG. 6D).

Figure 6E:
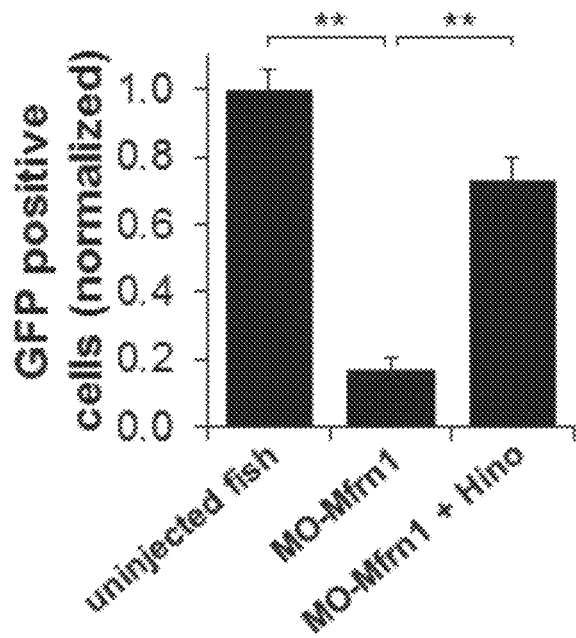
Figure 6F:
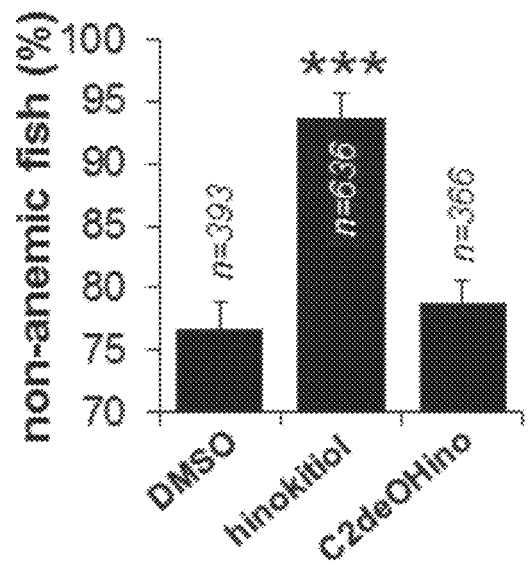

Hemoglobinization in Mfrn1-deficient morphant Tg(globinLCR:eGFP) zebrafish (10, 50) was also tested. Forty-eight hours of hinokitiol treatment again restored hemoglobinization and the number of GFP-positive erythrocytes in these morphants (FIG. 6E). Finally, hinokitiol was test to see if it could restore hemoglobinization in genetically mutated Frascati (frs$^{tq223}$) zebrafish, which contain a missense mutation leading to an inactive Mfrn1 mitochondrial protein and profound anemia during embryogenesis (10, 11). Hinokitiol treatment of embryos collected from a heterozygous cross of +/frs fish rescued the anemic phenotype (FIG. 6F). Genotyped (FIG. 6G) healthy larvae (+/+ and +/frs) exhibit brown staining with o-dianisidine, whereas untreated frs/frs fish do not (FIG. 6H). Hinokitiol treatment restored brown staining to frs/frs fish (FIG. 6H). As expected, hinokitiol did not rescue sauternes (sau$^{th223}$) zebrafish (51) deficient in the initial enzyme involved in porphyrin biosynthesis (Alas2) (FIG. 24E), indicating the specificity of rescue to defects in iron transport.

Outlook

Thus, a small molecule can restore site- and direction-selective iron transport in different cells deficient in three distinct iron-transport proteins, and the same compound can promote dietary gut iron absorption or peripheral hemoglobinization in corresponding animal models. Mechanistic studies support the role of transmembrane ion gradients that build up in the setting of missing iron transporters, enabling hinokitiol to restore site- and direction-selective transmembrane iron transport. Further, endogenous protein-based homeostatic mechanisms interface with this imperfect small molecule to promote iron-related physiological processes without disrupting other cellular processes.

Like hinokitiol, many ion-transport proteins are imperfectly selective. However, the relative abundance of different ions contributes to increased selectivity in living systems. For example, protein chloride channels are largely unselective for chloride versus bromide and iodide, but the low natural abundance of the latter halogens favors chloride selectivity in vivo (1, 52). Differential ion accessibility further enhances the in vivo selectivity observed for many imperfect ion-transport proteins (33-35). Like hinokitiol, DMT1 and FPN1 transport $Co^{2+}$, $Mn^{2+}$, $Zn^{2+}$, and/or $Cu^2$ (6, 13, 15). However, high affinity metalloproteins markedly decrease the labile pool of these other metals, leading to higher accessibility and thus selective binding and transport of iron in vivo (33-35).

These findings also provide a conceptual framework and proof-of-concept demonstration to support the pursuit of small molecule surrogates for missing or dysfunctional iron-transport proteins that underlie many human diseases. It has recently been recognized that acquired deficiencies of FPN1 underlie the anemia of chronic inflammation (AI) that frequently occurs in patients suffering from many common diseases, including rheumatoid arthritis, systemic lupus erythematosus, and inflammatory bowel disease (9). Further, this approach may have potential in promoting the rapid excretion of excess iron that builds up in tissues (e.g., liver or brain) in many diverse iron overload disorders.

Materials and Methods

Cell Lines and Growth Conditions

Wild type (DEY1457) and isogenic fet3Δftr1Δ S. cerevisiae were obtained from D. Kosman (53). Wild type (YPH499) and isogenic fet3Δarn1-4Δ S. cerevisiae were obtained from C. Philpott (54). Yeast were maintained on standard YPD media containing 10 g/L yeast extract, 20 g/L peptone, and 20 g/L dextrose without (liquid media) or with (solid media) 20 g/L agar. Unless otherwise indicated, growth-restoration assays in yeast used a low iron SD media consisting of 1.91 g/L iron-free YNB-FeCl3 (ForMedium CYN 1201), 0.79 g/L Complete Supplement Mixture (Sunrise Science Products 1001-010), 5 g/L ammonium sulfate (Sigma A4418), 20 g/L dextrose, 10 μM FeCl$_3$ (Sigma 451649), and 10 μM hinokitiol (β-Thujaplicin, Sigma 469521) in 50 mM MES/Tris buffer at pH=7.0 without (liquid media) or with (solid media) 20 g/L agar. Dextrose, hinokitiol, and FeCl$_3$ were added after autoclave sterilization from a filter-sterilized 40% w/v dextrose solution in water, from a freshly prepared sterile 10 mM hinokitiol stock in DMSO, and from a freshly prepared 10 mM FeCl$_3$ stock in sterile water, respectively. Non-fermentable growth restoration used the same synthetic medium except for the use of 30 g/L glycerol instead of dextrose.

Human Caco-2 cells (HTB-37) and mouse macrophages (J774A.1) were obtained from ATCC and cultured with DMEM (Gibco 10313-021) containing 10% HI FBS (Gibco 16000-036), 4 mM glutamine (Lonza BE17-605E), 100 μg/mL PEN-STREP (Lonza DE17-602E), and 1% MEM NEAA (Fisher 11140-050). Transfected Caco-2 cell lines were maintained on this media containing 800 mg/L G418 (Santa Cruz sc-29065B). Friend mouse erythroleukemia cells (MEL, DS19 subclone) were obtained from Arthur Skoultchi (Albert Einstein College of Medicine, Bronx, NY) and cultured with DMEM containing 10% HI FBS, 2 mM glutamine, 100 μg/mL PEN-STREP, and 1% MEM NEAA. Transfected shControl and shDMT1 MEL cell lines were maintained on this media containing 1 g/L G418.

Caco-2 cells (passage 18-50) were grown in T75 flasks to ≥90% confluency before trypsinization with 0.25% trypsin-EDTA (Fisher 25200-056) and passaging at 10:1 dilution in Caco-2 media without (wild type) or with G418 (transfected). Monolayers were grown by seeding Caco-2 cells (passage 20-50) onto 0.4 μm PET cell culture inserts (Fisher 08-771) in 6-well companion plates (Fisher 08-771-24) at $2 \times 10^5$ cells/well and allowed to fully differentiate for 21-28 days before experiments were performed with changing of media every 3-4 days.

MEL cells were grown in suspension in T25 flasks until $\sim 1 \times 10^6$ cells/mL and re-seeding into a new T25 flask at $1 \times 10^5$ cells/mL in MEL Complete media with or without G418. Every month of culturing, new backstocks of MEL cells were used.

J774 cells (passage 20-80) were grown in T25 flasks to 90% confluency before scraping and reseeding at 5:1 dilution in J774 Complete media. Media was changed every 1-2 days.

Animals and Animal Care

The studies performed were in strict accordance with the guidance and recommendations outlined in the Guide for the Care and Use of Laboratory Animals of the National Institutes of Health.

The protocols used for studies in healthy (+/+) and Flatiron (ffe/+) mice were approved by the Harvard Medical Animal Care and Use Committee. Breeding, diets, and genotyping of flatiron mice were performed as previously described (55).

All zebrafish experiments were performed in accordance with the Institutional Animal Care and Use Committee regulations. The following wild type AB strains and zebrafish mutant strains were used: frascati ($frs^1q^{223}$) (10), chardonnay ($cdy^{te216}$) (49), and sauternes ($sau^{th223}$) (51).

The protocols for studies in Belgrade (+/+, +/b, or b/b) rats were approved by the Division of Laboratory Animal Medicine (DLAM) and the Northeastern University-Institutional Animal Care and Use Committee (NU-IACUC). Breeders of heterozygous (+/b) and homozygous (b/b) Belgrade rats (Fischer F344 background) were kindly provided by Dr. Michael Garrick (SUNY Buffalo) and maintained on a 12:12-hr light/dark cycle and given water and facility chow ad libitum. Prior to $^{55}$Fe gut iron absorption experiments, a variety of preliminary studies were performed on cohorts of Belgrade rats (ranging from 3-5 months old) during which the rats were treated with vehicle or various compounds for <15 weeks in iron-supplemented diet containing 500 mg/kg iron (TD.02385, Harlan Teklad, Madison, WI). All rats were allowed to be drug-free and continued to receive iron-supplemented diet for at least one week before $^{59}$Fe gut absorption experiments were performed.

Statistics

All data depicts the means or weighted mean±SEM with a minimum of 3 biological replicates unless otherwise noted. Statistical analysis represents P values obtained from student t-test or one- or two-way analysis of variance (ANOVA) with post-hoc TUKEY test where appropriate. NS, not significant; * $P≤0.05$;  $P≤0.01$; * $P≤0.001$; **** $P<0.0001$ unless otherwise noted.

Figure 1C:
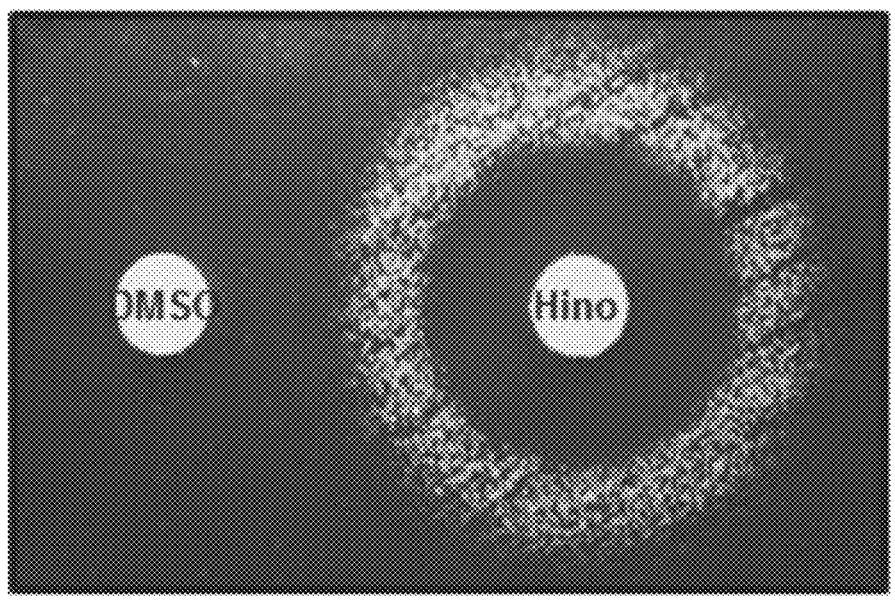
Figure 1D:
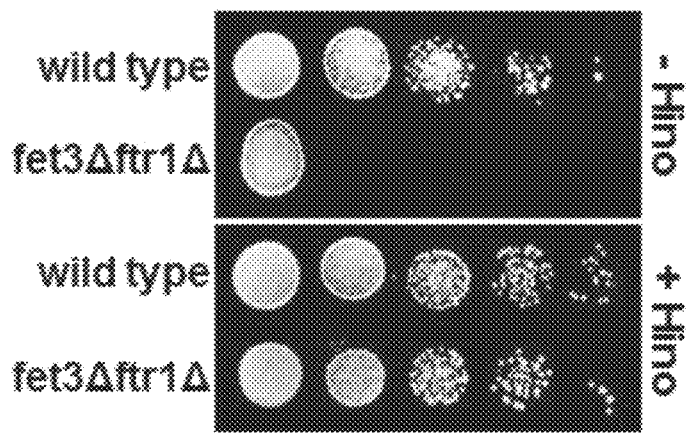

Growth Rescue of Iron-Deficient Yeast with Small Molecules on Agar Plates (FIG. 1C, D, FIG. 7A-C, and FIG. 8A, B)

Growth rescue in yeast was performed similar to previously reported (20) on low iron SD-agar plates in 50 mM MES/Tris buffer at pH=7.0 containing 2% agarose gel, 10 μM FeCl$_3$, and 10 μM hinokitiol (from 40X stock in DMSO). Wild type and fet3Δftr1Δ or fet3Δarn1-4Δ controls treated with vehicle (DMSO) were performed under identical conditions using the same low iron SD media containing 10 μM FeCl$_3$ in the absence of hinokitiol. Yeast were grown overnight in YPD media and diluted to an optical density at 600 nM (OD600) of 1.0 in low iron SD media before 10-fold serial dilution and inoculation of these yeast suspensions (10 μL per dot) onto the low iron SD-agar plates described above containing either DMSO vehicle or hinokitiol (10 μM from 40X DMSO stock).

For disc diffusion assays, yeast were grown overnight in YPD media and diluted to an OD600=0.1 in low iron SD media and streaked onto low iron SD-agar plates containing 10 μM FeCl$_3$. Disc diffusion assays were performed using ≥10 mM stock solutions (in DMSO) of hinokitiol, tropolone (Sigma T89702), α-dolabrin (Specs Compound Handling AN-584/43416897), maltol (Sigma H43407), deferiprone (DFP, Sigma 379409), pyridoxal isonicotinoyl hydrazone (PIH, Santa Cruz sc-204192), salicylaldehyde isonicotinoyl hydrazone (SIH, see synthesis and characterization below), comenic acid (COMA, kindly donated by Obiter Research, LLC), amphotericin B (AK Scientific L970), nonactin (Sigma N2286), calcimycin (Sigma C$_{7522}$), or prodigiosin (Santa Cruz sc-202298) (10 μL per paper disc) on low iron SD-agar plates containing 10 μM FeCl3 streaked with the appropriate yeast strain (from OD600=0.1 in low iron SD media). Growth restoration under non-fermentable conditions was performed using 3% glycerol instead of 2% dextrose. Images were taken 48-72 hours after inoculation and incubation at 30° C. unless otherwise noted.

Figure 1E:
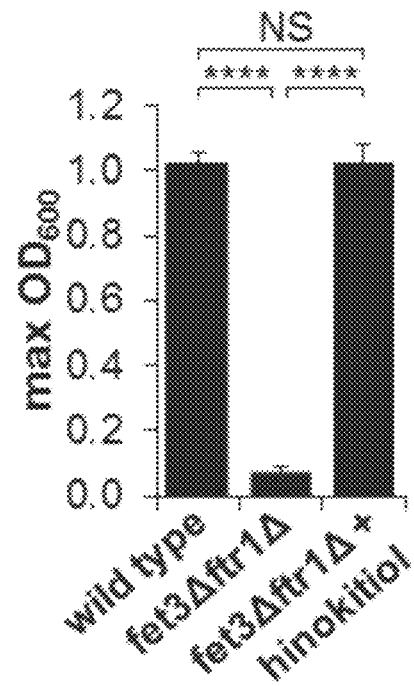
Figure 1F:
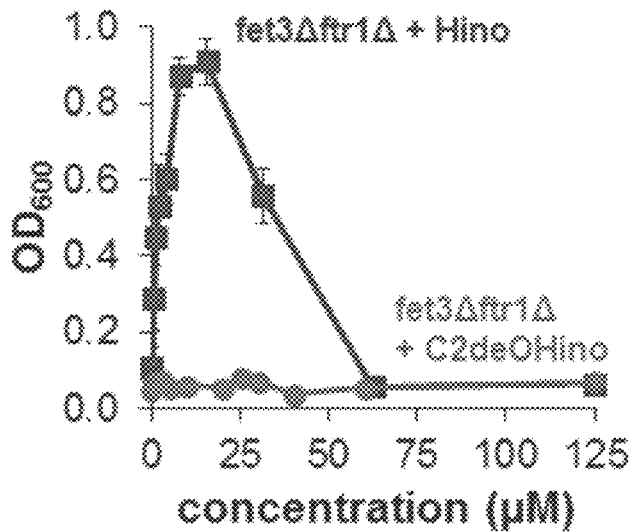

Growth Rescue of fet34ftr1Δ Yeast with Small Molecules in Liquid Media (FIG. 1E, F and FIG. S3G, H)

Growth rescue in yeast was performed similar to previously reported (20) using 10 μM hinokitiol in low iron SD liquid media containing 10 μM FeCl$_3$ in a 96-well plate unless otherwise noted. Wild type and fet3Δftr1Δ controls treated with vehicle (DMSO) were performed under identical conditions using the same low iron SD media containing 10 μM FeCl$_3$ in the absence of hinokitiol. Yeast were grown overnight in YPD media and diluted at an OD600 of 0.1 in SD media, diluted 10-fold, and incubated at 30° C. with continuous shaking (200 rpm). The OD600 was obtained 24-48 hours after inoculation unless otherwise noted.

Small molecule dose-response (FIG. 1F) with hinokitiol and C$_2$-deoxy hinokitiol (C$_2$deOHino, see synthesis below) was determined by addition of the small molecule (40X stock solution in DMSO) to give the indicated final concentrations.

Iron dose-response studies (FIG. 8G) were performed in the same low iron SD media without FeCl$_3$ containing 10 μM hinokitiol (from a 40X stock solution in DMSO). FeCl$_3$ (40X stock solution in water) was added to the give the indicated final concentrations up to 10 μM FeCl$_3$.

For dose-dependent hinokitiol-promoted rescue at increasing dosages of FeCl$_3$ (FIG. 8H), SD media was made containing either 10, 25, 50, or 100 μM FeCl$_3$ from a 10 mM FeCl$_3$ stock before adding hinokitiol (40X stock solution in DMSO) to give the indicated final concentrations.

Sustainability Assay (FIG. 8C)

Sustainable hinokitiol-promoted growth restoration of fet3Δftr1Δ yeast was performed similar to previously reported (20) by inoculation of hinokitiol-rescued yeast from low iron SD-agar plates containing 10 μM hinokitiol and 10 μM FeCl$_3$ into low iron SD liquid media containing 10 μM hinokitiol and 10 μM FeCl$_3$, then streaking of the yeast suspension (diluted to OD600 of 0.1) onto agar plates. This process was repeated for >100 days. Continued reliance of fet3Δftr1Δ yeast growth on hinokitiol was observed, as removal of hinokitiol from the SD-agar plates led to no fet3Δftr1Δ yeast cell growth.

Doubling Time of Fet3ΔFtr1Δ Yeast Treated with Hinokitiol (FIG. 13D, E)

Doubling times of wild type and hinokitiol-rescued fet3Δftr1Δ yeast were determined similar to previously reported (20) by tracking the OD600 every hour over 48 hours in the same low iron SD media containing 10 μM FeCl$_3$ and DMSO or 10 μM hinokitiol (from 40X stock in DMSO) and applying the equation Td=(t2-t1)×[log(2)/log (q2/q1)] during exponential phase.

Chemical Inhibition of Yeast Cell Growth with Inhibitors of Pma1, V-ATPase (FIG. 19A-C)

Chemical inhibition of hinokitiol-treated wild type and hinokitiol-rescued fet3Δftr1Δ yeast cell growth was performed as previously reported (20) in low iron SD media containing 10 μM FeCl$_3$ and 10 μM hinokitiol. Increasing dosages of caspofungin (Sigma SML0425), ebselen (Sigma 70530), or bafilomycin B1 (Santa Cruz sc-202072) (40X stocks in DMSO) were added to a yeast suspension (10-fold dilution from OD600=0.1) to give the indicated final dose. EC50 values were calculated from fitting of yeast growth curves using GraphPad PRISM.

Figure 1G:
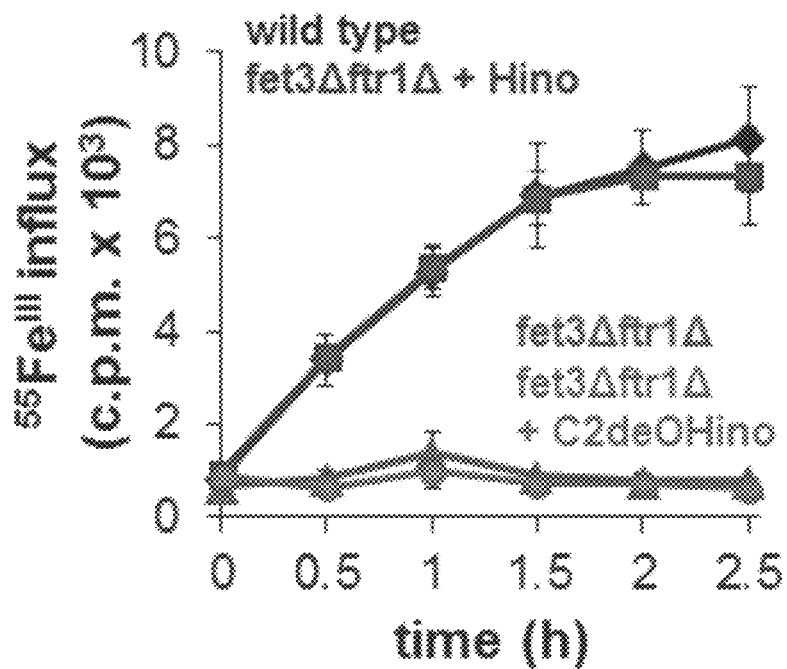

$Fe^{3+}$ Uptake Assay in Yeast (FIG. 1G)

Iron (III) uptake into wild type and fet3Δftr1Δ yeast was adapted from Kosman and coworkers (56). Overnight yeast cultures were repeatedly centrifuged and rinsed with water. The cell pellet was resuspended in MilliQ water, and diluted in SD media without $FeCl_3$. The cells were incubated at 30° C. for 3 hours, centrifuged and rinsed with water twice. The cells were then suspended to $3\times10^7$ cells/mL in SD media containing 50 mM sodium citrate and 2% glucose. Hinokitiol or $C_2$deOHino (from 40X stocks in DMSO) was added to a final concentration of 100 μM before $^{55}FeCl_3$ (1.1 ρCi) was added to the yeast suspensions. The suspension was continuously homogenized before aliquots were taken and diluted with 10 mL of room temperature water. Cells were then collected via vacuum filtration through a 0.45 μm nitrocellulose filter (Millipore HAWP), and rinsed with room temperature water (×5 of 100 mL). The filters were then transferred to a scintillation vial containing 3 mL of scintillation cocktail for measuring radioactivity using a liquid scintillation counter. Hinokitiol showed a dose-dependent increase in $^{55}Fe$ uptake from 5 to 100 μM while $C_2$deOHino showed no uptake up to 100 μM.

Lipophilicity Determination for Small Molecule Iron Chelates (FIG. 2A and FIG. 81)

Octanol-water partition coefficients were obtained as previously reported (57, 58) with 100 μM small molecule and 33 μM $FeCl_3$ (50 μM $FeCl_3$ for PIH as it forms a 2:1 complex) using equal volumes of equilibrated pH=5 water and octanol. Concentrations of small molecule in water were determined via UV-Vis spectroscopy compared to known initial standards.

Hexane-water partition was obtained similar to above with 500 μM small molecule and 50 μM $FeCl_3$ using equal volumes of 50 mM Mes-Tris buffer at pH=$^7$0.0 and hexanes.

Determination of the pKa of Hinokitiol (FIG. 9L)

The pKa of hinokitiol was determined by spectrophotometric titration with varying pH. Hinokitiol (100 μM) was dissolved in a 0.1 M KCl solution in H2O and acidified to pH=3.0 (using 0.1 M HCl). The UV-Vis spectrum was repeatedly obtained upon sequential titration of 0.1 M KOH to obtain a range of pHs (3.0, 3.4, 3.9, 4.2, 4.6, 4.9, 6.0, 6.4, 7.0, 7.2, 7.6, 8.4, 9.3, 9.7, 10.4, 10.9, 11.7, 12.0). A clear isobestic point was observed at 365 nm, and a new λmax was observed with decreasing pH at 387 nm. The pKa was then determined via plotting the Abs387/Abs240 vs. pH and logistic fitting on OriginPro ($R^2$=0.996) to calculate the point of inflection (pKa=7.33).

Figure 9B:
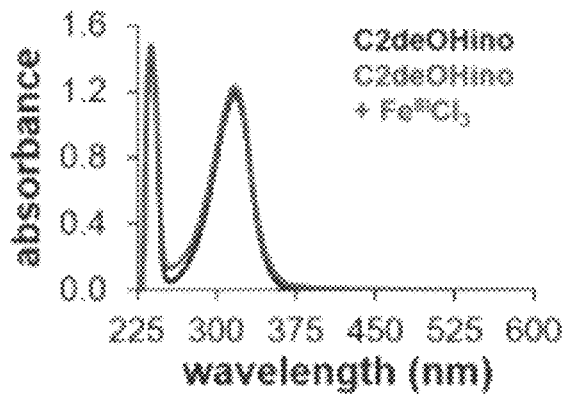
Figure 9C:
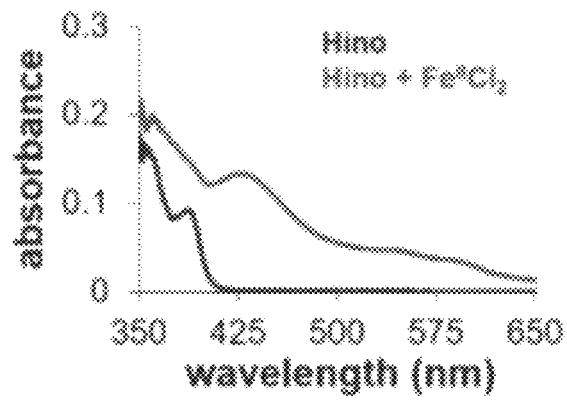
Figure 9D:
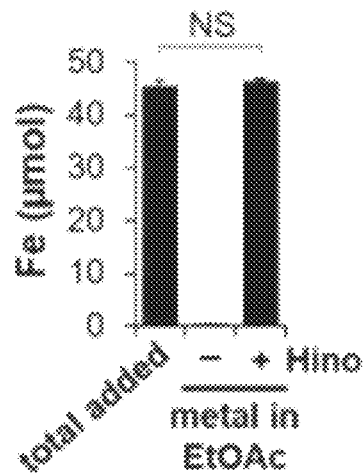
Figure 9E:
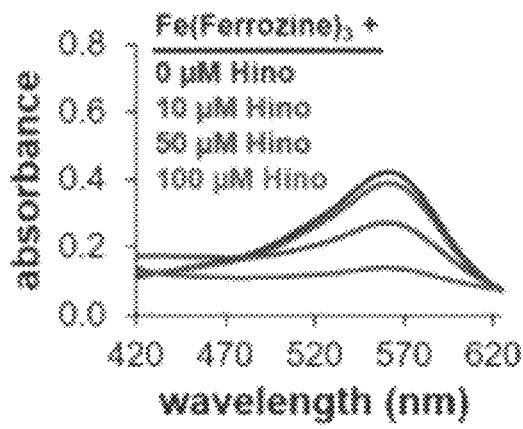
Figure 9F:
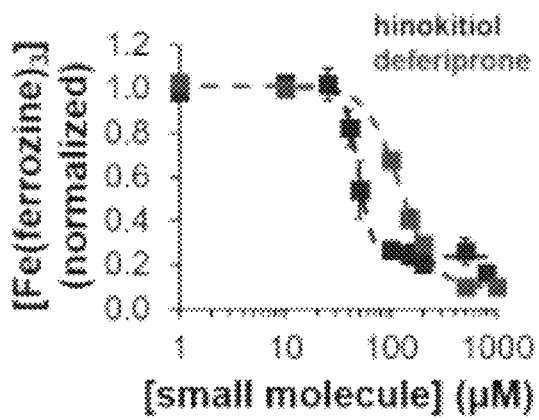
Figure 9G:
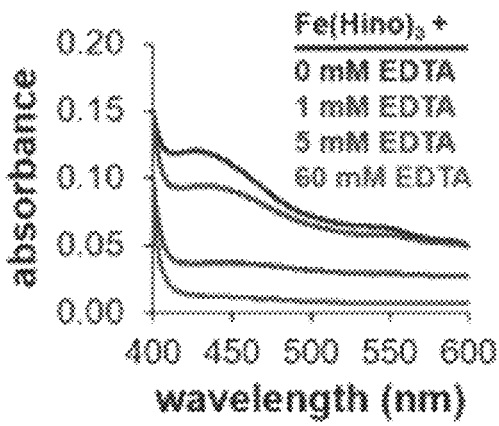
Figure 9H:
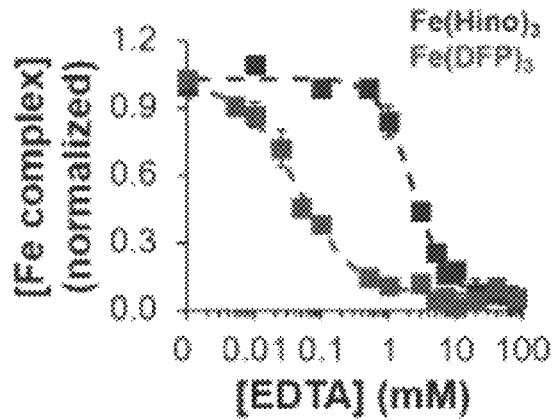
Figure 9I:
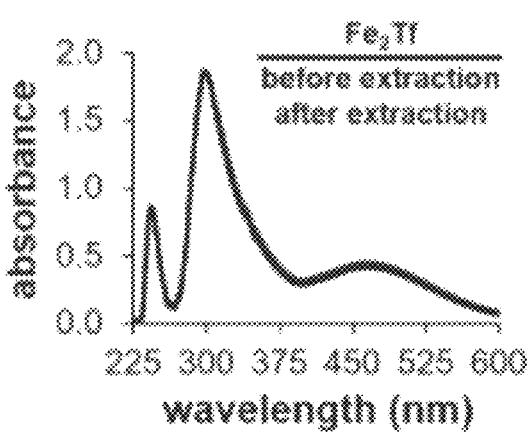
Figure 9J:
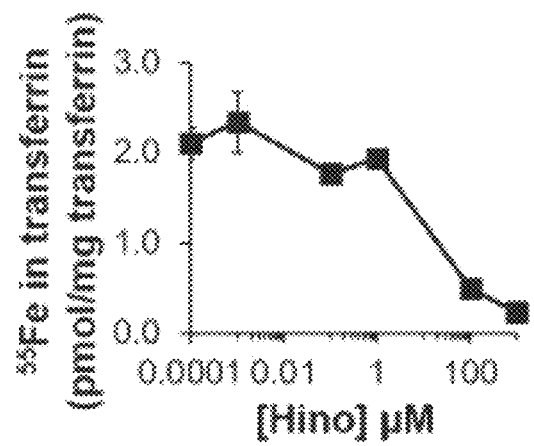
Figure 9K:
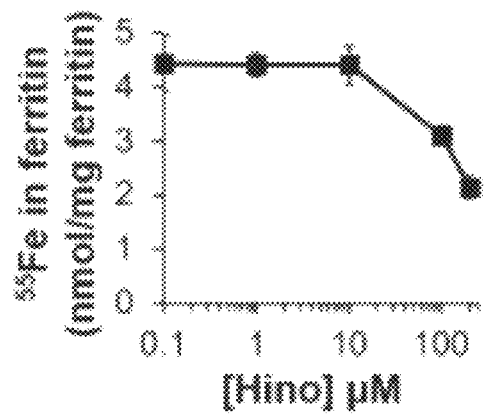
Figure 9L:
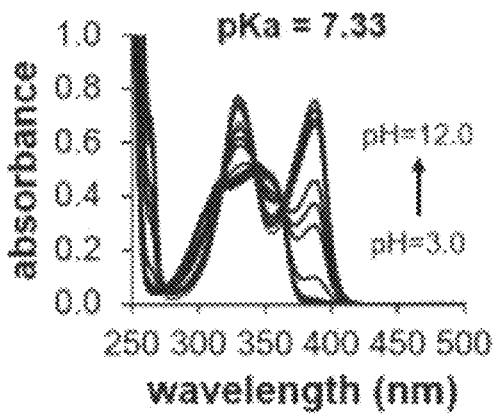
Figure 9M:
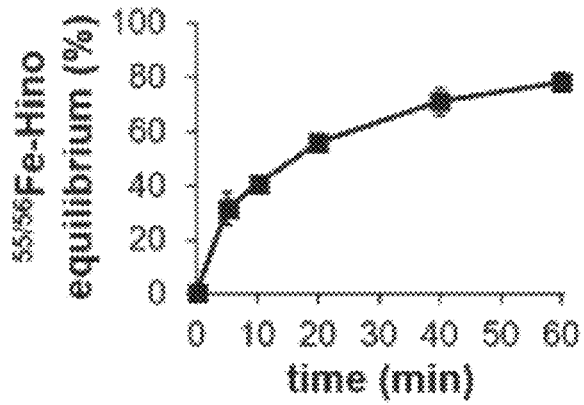
Figure 9N:
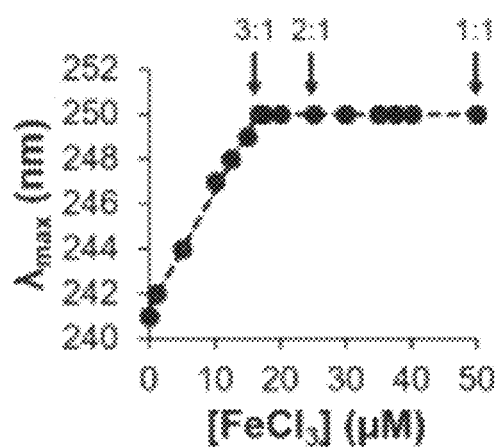
Figure 9O:
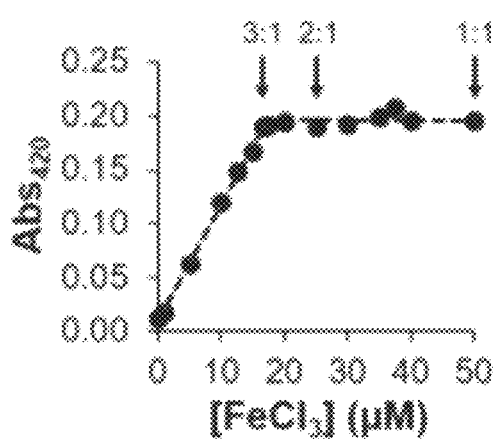
Figure 9P:
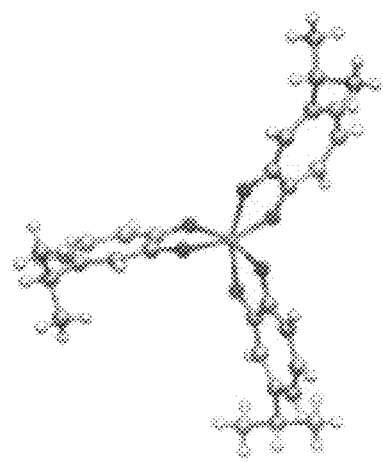

Determination of Small Molecule Iron Binding (FIG. 9A-C)

Small molecule iron (III) binding was determined by UV-Vis spectroscopy of small molecules (30 μM) before and after addition of $FeCl_3$ (10 μM) or iron (III) citrate (10 μM, Sigma F3388) in 10 mM MES/Tris buffer at pH=7.0. Iron (II) binding was determined by UV-Vis spectroscopy of small molecules (30 μM) and $FeCl_2$ (10 μM) in a 25 mM MES/Tris buffer at pH=7.0 containing 62.5 mM sodium ascorbate.

Titration of Hinokitiol with Iron (III) (FIG. 2B and FIG. 9N, O)

An iron (III) titration study was performed by addition of 50 μM hinokitiol and increasing equivalents of $FeCl_3$ (0, 1, 5, 10, 12.5, 15, 16.67, 17.5, 20, 25, 30, 35, 37.5, 40, and 50 μM) in 10 mM MES/Tris buffer at pH1=7.0. No precipitate was observed in all cases, and the solution changed to a brown colored solution with increasing equivalents of iron (III). As the amount of iron was increased, the λmax shifted from ~240 to 250 nm and the absorbance at 420 nm increased up to ~3:1 Hino:Fe.

Determination of Iron (II) and Iron (III) Binding Affinity with Small Molecules (FIG. 14E-H and Table S2)

The association constants of hinokitiol, deferiprone, tropolone, maltol, and/or EDTA with iron (1I) or iron (III) were determined through competition studies similar to previously reported (59). Specifically, the association constant for iron (II) was determined by a ferrozine competition assay (KA of ferrozine=$3.65\times10^{15}$) (60). $FeCl_2$ (25 μM) was pre-mixed with ferrozine (75 μM) in a 25 mM MES/Tris buffer at pH=7.0 containing 62.5 mM sodium ascorbate. Then increasing concentrations of small molecule (from 40X stocks in DMSO) were added to the indicated final concentrations. The solutions were allowed to equilibrate for 24 hours before reading of the absorbance at 562 nm. The association constants of hinokitiol, tropolone, and deferiprone for iron (III) was determined by an EDTA (KA=$1.7\times10^{24}$) competition assay (59), and a citrate (KA=$1\times10^{17}$) competition assay for maltol (61). Each chelator was mixed with $FeCl_3$ in a 3:1 ratio in 50 mM MES/Tris buffer at pH=7.0 containing 0.1 M KCl to form the corresponding iron complex. The λmax of the peak corresponding to the 3:1 chelator:iron complex was determined (~400-500 nm) for each complex. Then this Fe(chelator)$_3$ stock was added to a solution containing increasing concentrations of EDTA or citrate in 50 mM MES/Tris buffer at pH=7.0 containing 0.1 M KCl to give the indicated final concentrations of chelator (75 μM), $FeCl_3$ (25 μM), and the competitive chelator. The system was allowed to equilibrate overnight, and the absorbance corresponding to the Fe(chelator)$_3$ complex was determined. The EC50 values for each chelator were calculated by a nonlinear curve fit (Hill1) on OriginPro by plotting the absorbance vs. concentration of titrant, and the KA for each complex was determined from the equation: KA, ligand=(KA, competitor*[EC50])/[ligand] where the ligand is the molecule originally bound to iron, and the competitor is the competing chelator.

Figure 14I:
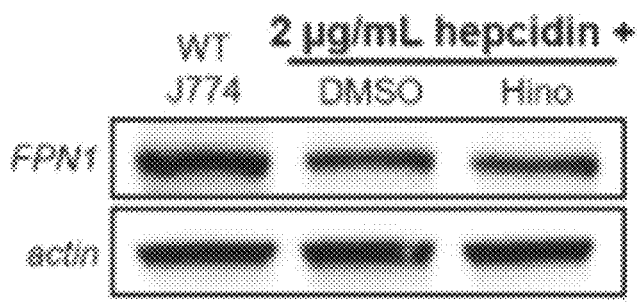
Figure 14J:
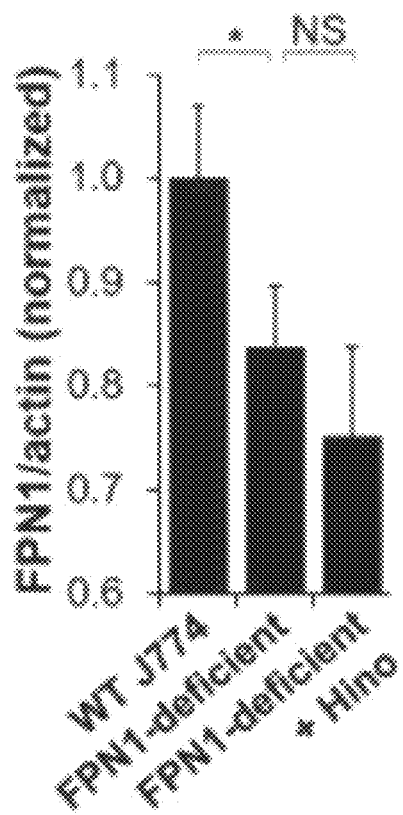
Figure 14K:
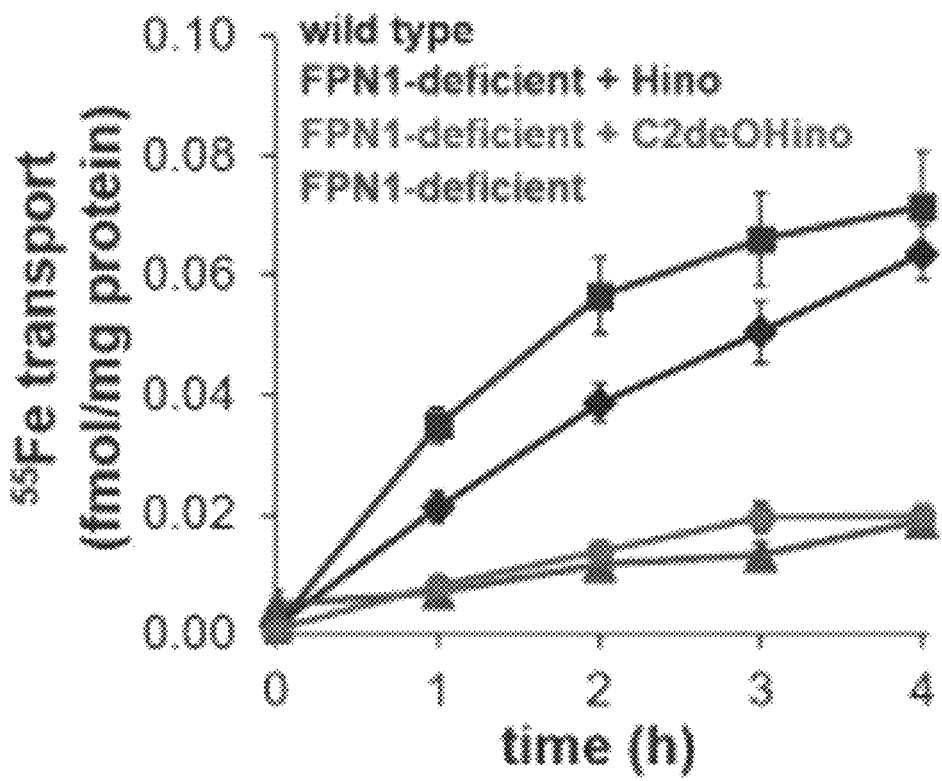
Figure 14L:
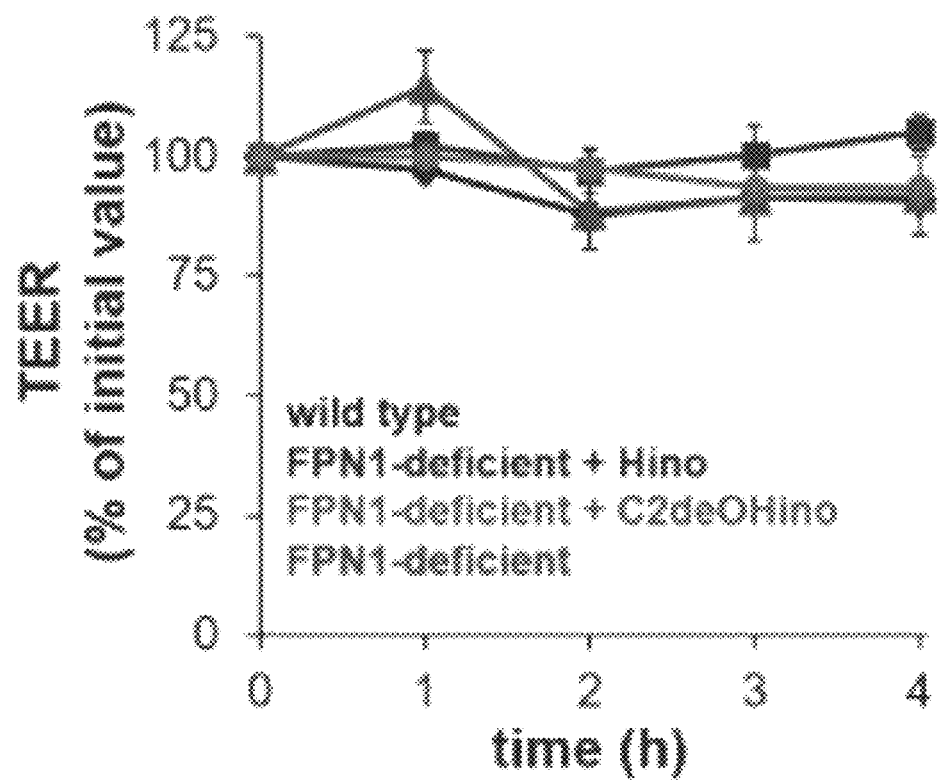
Figure 14M:
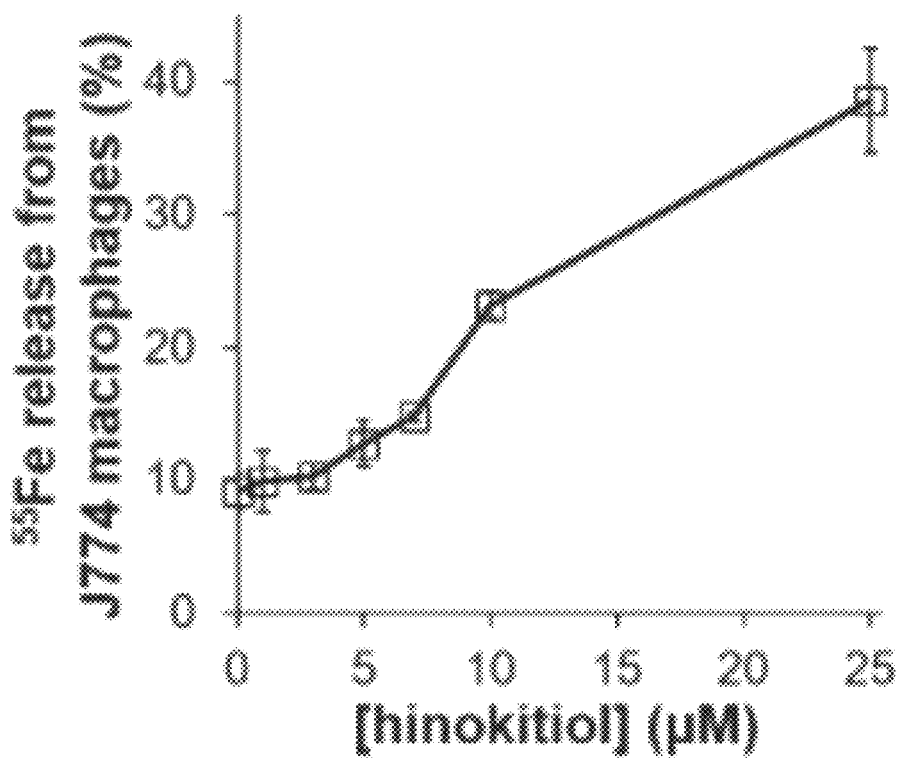

Removal of $^{55}Fe$ from Iron-Binding Proteins with Hinokitiol (FIG. 14I-K)

The capacity for hinokitiol to remove iron from transferrin was determined through a $^{55}Fe$ assay adapted from Cerami and coworkers (62). $^{55}Fe$ was loaded onto transferrin (Tf) similar to previously described in PBS buffer (63). Increasing hinokitiol doses (from 1000X stocks in DMSO) were added to a solution of $^{55}Fe2Tf$ (1 nM) in PBS buffer to give the final indicated concentrations. The solution was incubated at 37° C. for 3 hours. After incubation, any $^{55}Fe$ bound to hinokitiol was isolated by extraction of iron:hinokitiol complexes with EtOAc. The radioactive levels in the organic layer were determined after dilution in scintillation cocktail. No extraction of $^{55}Fe$ was observed in the absence of hinokitiol, and transferrin was not denatured from the extraction process as determined by UV-Vis spectroscopy of holo-transferrin before and after EtOAc extraction in PBS buffer.

Ferritin was loaded with $^{55}Fe$ by incubation of wild type Caco-2 monolayers and isolation of ferritin through immunoprecipitation as described below. The immunoprecipitated ferritin was diluted to 2.5 ng ferritin/mL (determined by ELISA as described below) in 50 mM MES/Tris buffer at pH=7.0, and increasing concentrations of hinokitiol were added (from 1000X stock in DMSO) to give the final indicated concentrations. The suspension was mixed at room temperature for 2 hours. After incubation, repeated centrifugations and rinses with PBS were performed to remove any $^{55}$Fe not bound to ferritin, and the radioactive levels remaining in the agar pellet were determined after dilution in scintillation cocktail and liquid scintillation counting.

Crystal Structure of Fe(Hino)$_3$ (FIG. 2E, FIG. 14P, and Table S8)

An x-ray quality crystal of synthesized Fe(Hino)$_3$ was obtained from a recrystallization of Fe(Hino)$_3$ (10 mg) in acetone (2 mL) and benzene (0.2 mL) in an uncapped 1 mL vial by allowing the solvent to slowly evaporate undisturbed overnight. X-Ray single crystal analysis was performed by the University of Illinois X-Ray facility.

Figure 15A:
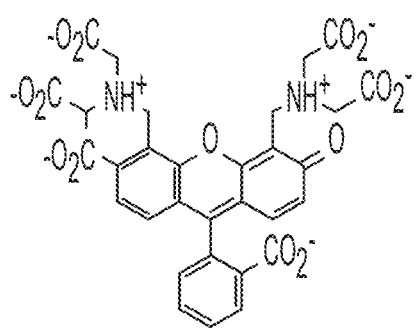
FIGS. 15A-15C show use of iron-sensitive fluorescent dyes to visualize intracellular iron levels. (A and B) Structures of turn-off probes (A) Calcein Green used to visualize cytosolic labile iron levels and (B) RPA used to visualize mitochondrial labile iron levels, respectively. Fluorescence quenching is observed after iron binding. (C) BSA-conjugated Oxyburst Green fluoresces after oxidation with H2O2 and labile Fe in the endosome.
Figure 15B:
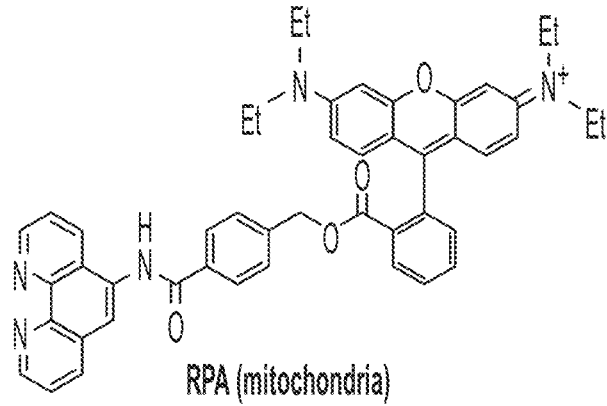
Figure 15C:
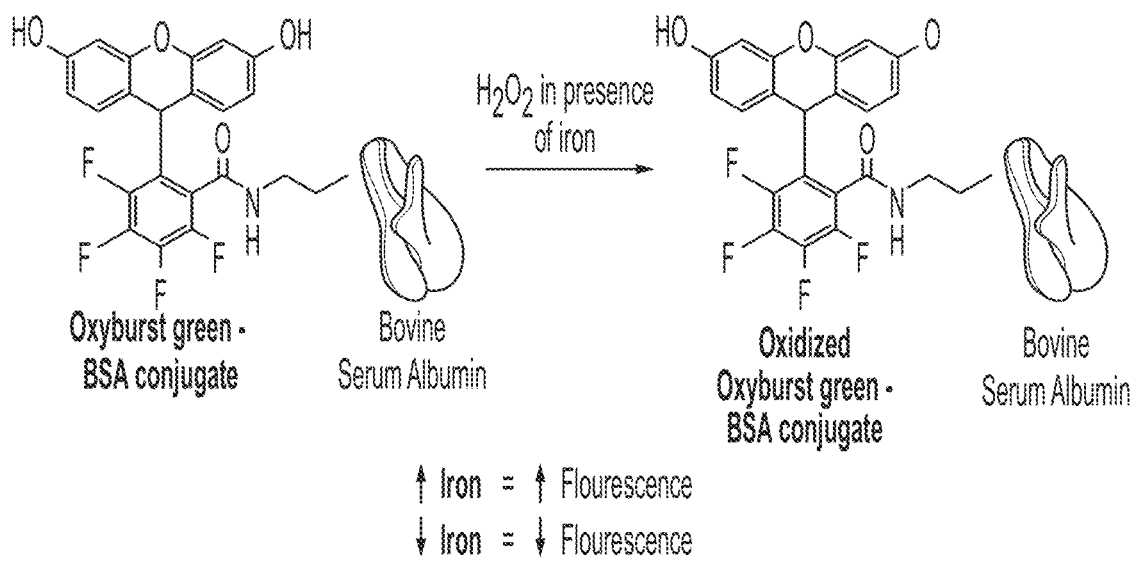
Figure 16A:
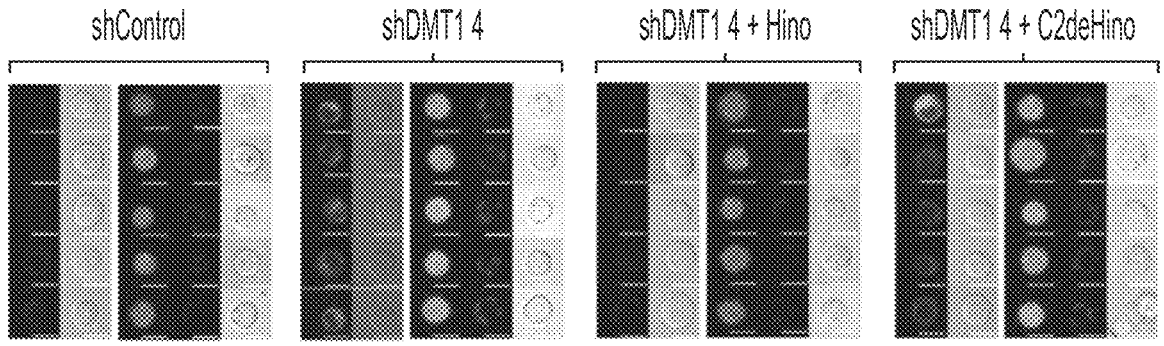
FIGS. 16A-16J show site-selective build-up of endosomal iron in DMT1-deficient MEL cells. (A) Representative confocal microscopy images of fluorescence from oxyburst green (green, left) localized in the endosome, calcein green (green, middle) in the cytosol, and RPA (red, right) in the mitochondria support a build-up of labile endosomal iron in DMT1-deficient MEL cells relative to shControl cells. Hinokitiol (1 µM) treatment decreases endosomal oxyburst green fluorescence and quenches calcein green and RPA fluorescence, suggesting hinokitiol-mediated release of labile iron from endosomes into the cytosol and subsequent mitochondrial utilization. C2deOHino (1 µM) has no effect. (B) ImageJ quantification of endosomal oxyburst green fluorescence. N≥40. (C and D) Flow cytometry of MEL cells stained with oxyburst green support hinokitiol releases iron from endosomes. N =6. (E) ImageJ quantification (N=23-67) and (F and G) flow cytometry analysis of calcein green fluorescence in the cytosol supports hinokitiol treatment to shDMT1 MEL cells increases cytosolic labile iron levels. N=6. (H) ImageJ quantification (N=23-67) and (I and J) flow cytometry analysis of RPA fluorescence in the mitochondria supports hinokitiol treatment to shDMT1 MEL cells increases mitochondrial labile iron levels. N=6. Scale bar=10 µm (A) (B, D, E, G, H, J) NS, not significant; * P≤0.05;  P≤0.01; * P≤0.001; **** P≤0.0001; Graphs depict means±SEM. (C, F, I) Representative graphs from three independent experiments.
Figure 16B:
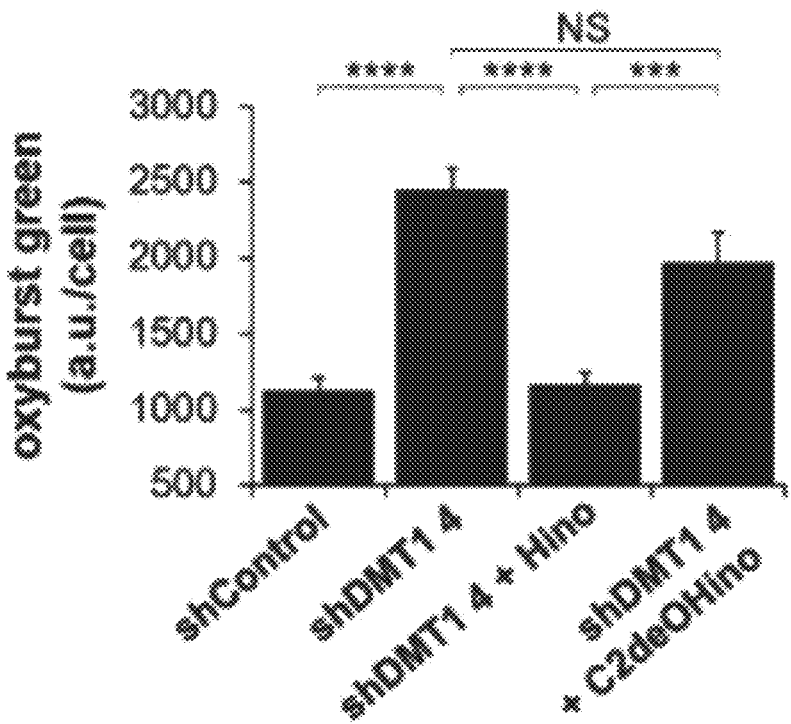

Determination of Hinokitiol Binding Selectivity by ICP-MS (FIG. 9D, FIG. 15A, B, and Table S2)

The binding selectivity for hinokitiol with multiple divalent metals was determined similar to previously described (32). Specifically, a 2 mM solution of hinokitiol in 10 mM MES/Tris buffer in 1:1 H2O:MeOH at pH=7.0 was mixed in equal volume with a solution containing 2 mM FeCl2, 2 mM MnCl2, 2 mM CoCl2, 2 mM NiCl2, 2 mM ZnCl2, and 2 mM CuCl2 in a 10 mM MES/Tris buffer in 1:1 H2O:MeOH at pH=7.0 to give a final concentration of 1 mM for each divalent metal and hinokitiol. The colored solution was allowed to incubate for 4 hours at room temperature. The solution was diluted in buffer, and extracted (×3) using 1:1 Hexanes:Ethyl Acetate. The organic layer was collected, dried by MgSO4, and filtered. The solvent was removed in vacuo, digested with 70% HNO3, and metal content was determined by ICP-MS analysis through the University of Illinois SCS Microanalysis Facility.

Control experiments were performed similar to those described above but in the absence of hinokitiol. No metal was detected in the organic layer by ICP-MS. Control experiments were also performed similar to those described above but using 60 mM hinokitiol. Metal content after extraction was compared to the initial metal content in the aqueous solution before extraction, and it was determined that the metal:hinokitiol complexes are extracted into the organic layer.

Figure 4F:
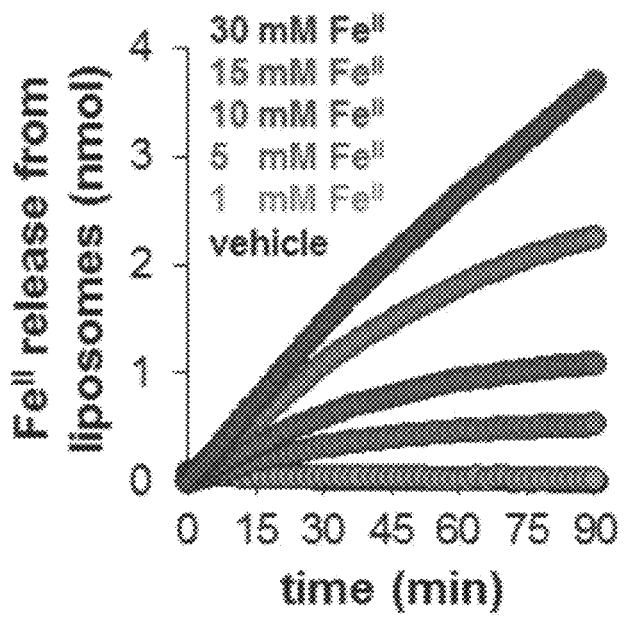
Figure 4G:
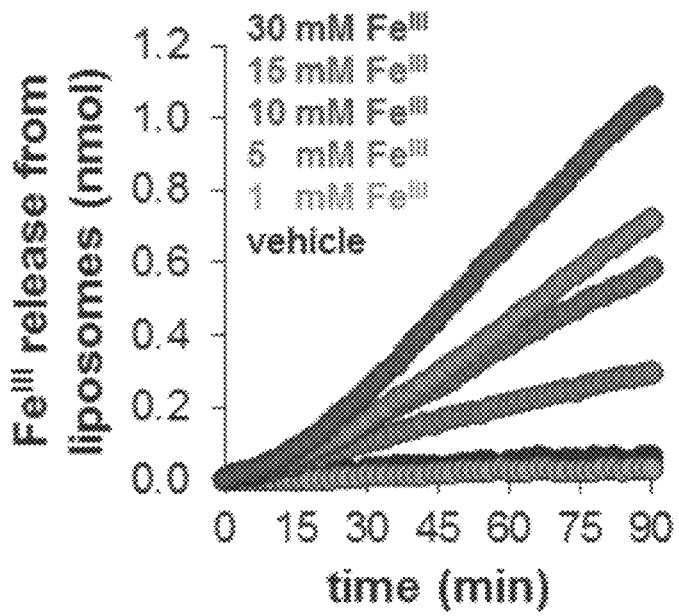
Figure 4H:
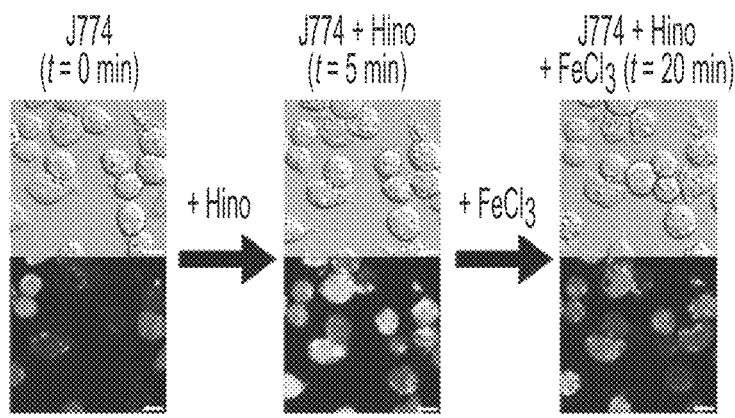
Figure 4I:
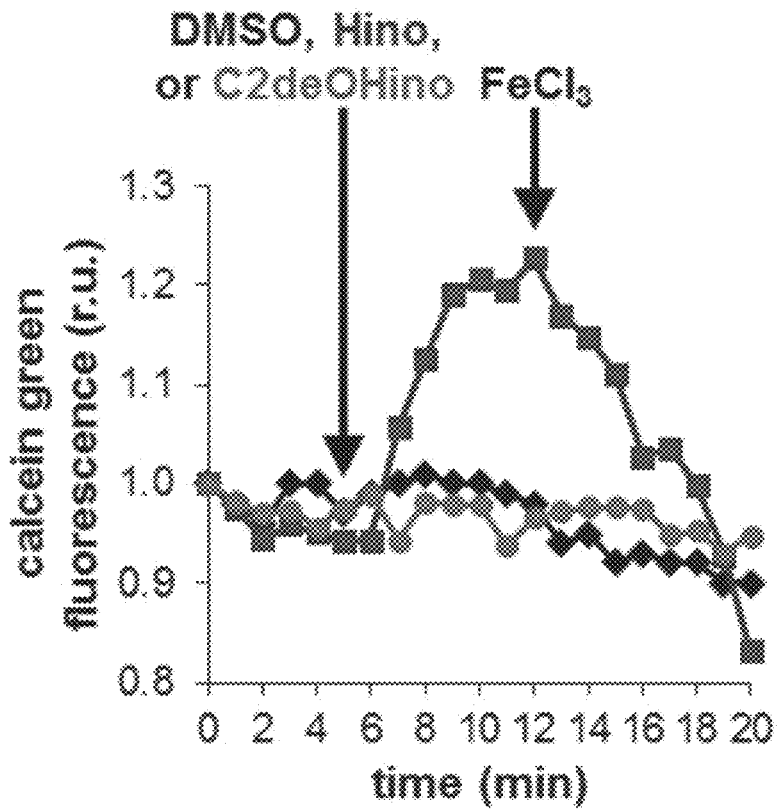

Determination of Iron Efflux from Liposomes Using Ferrozine (FIG. 2C, D, FIG. 4F, G, and FIG. S17A-D)

Iron (III) efflux from POPC liposomes was determined similar to previously reported (64). POPC liposomes were prepared as similarly reported (65) using 30 mM FeCl$_3$, 62.5 mM citrate at pH=7.0 in 25 mM Mes/Tris buffer. External iron was removed by size exclusion chromatography using Sephadex G-50 and eluting with external buffer. External buffer consisted of 62.5 mM ascorbate at pH=7.0 in 25 mM Mes/Tris buffer. The liposomes were diluted to 1 mM phosphorus in this buffer. Ferrozine (Sigma 160601) was added (100X stock in external buffer) to a final concentration of 500 µM. Liposomal suspension was then transferred to a 96-well plate, and either DMSO or 5 µM hinokitiol, C$_2$deOHino, deferiprone, or PIH (40X stock solution in DMSO) were added to initiate the experiment. The OD562 was determined every minute over the course of 2 hours using a plate-reader with continuous shaking at 30° C. to detect the relative amounts of external ferrozine-iron chelate at the indicated times. After 2 hours, liposomes were lysed with Triton-X to give 100% iron efflux. Hinokitiol dose- and temperature-dependently promoted iron (III) efflux from POPC liposomes while C$_2$deOHino showed no efflux up to 100 µM.

Iron (II) efflux was performed as described above, however, the internal buffer alternatively consisted of 30 mM FeSO$_4$, 62.5 mM ascorbate at pH=7.0 in 25 mM Mes/Tris buffer and Triton-X lysis was performed after 1 hour.

The rates of iron efflux with increasing concentrations of intraliposomal iron and/or hinokitiol were determined as described above using the indicated concentration of iron and hinokitiol. For the varying concentrations of iron, hinokitiol (10 µM) was added to the POPC liposomes, and the change in absorbance at 562 nm was determined over 2 hours. For the varying concentrations of hinokitiol, 30 mM intraliposomal iron was used as described above. The concentration of iron outside of liposomes was determined using the extinction coefficient for ferrozine-iron (27,900 M$^{-1}$ cm$^{-1}$) (66). This was used to determine the amount of iron released from liposomes at the indicated times using the total volume for each experiment. Rates of iron efflux were determined after one hour of hinokitiol treatment.

Determination of Metal Efflux from Liposomes Using PhenGreen (FIG. 15C-I and Table S2)

Hinokitiol-promoted release of different divalent metals from POPC liposomes was performed by tracking the quenching of PhenGreen (Fisher P14312) similar to previously reported (67, 68).

Liposomes were prepared as described above with an internal buffer consisting of either 10 mM ascorbate in a 5 mM MES/Tris buffer at pH=7.0 (for Fe$^{2+}$), 10 mM citrate in a 5 mM MES/Tris buffer at pH=7.0 (for Cu$^{2+}$), or a 5 mM MES/Tris buffer at pH=7.0 (for Mn$^{2+}$, Co$^{2+}$, Ni$^{2+}$, and Zn$^{2+}$). In all cases, liposomes were prepared using 5 mM of either FeCl2, MnCl2, CoCl2, NiCl2, ZnCl2, or CuCl2 added to the internal buffer. The external buffer was a 5 mM MES/Tris buffer at pH=7.0 containing 10 µM PhenGreen (from 1000X stock in DMSO). The liposome suspension was diluted to 1 mM of phosphorus. The liposome suspension was transferred to a 96-well plate, and either DMSO or 2 µM hinokitiol (from a 40X stock in DMSO) was added at t=2 min. The fluorescence was monitored with excitation at 500 nm and emission at 530 nm over 1 hour. After one hour, the liposomes were lysed with Triton-X and the fluorescence was recorded. In all cases, quenching of fluorescence was observed in the DMSO-treated liposomes after lysis, which reached similar levels to that for hinokitiol-treated liposomes before lysis (except for Mn$^{2+}$ where no efflux was observed in Hino-treated liposomes; fluorescence quenching was observed after lysis for Mn$^{2+}$). The DMSO-treated and hinokitiol-treated liposomes had similar fluorescence quenching levels after lysis. The total amount of metal efflux was determined using standard curves of fluorescence quenching in external buffer with 10 µM PhenGreen and known concentrations of each metal. The t1/2 values were calculated using an asymptotic fit in OriginPro. The t1/2 values indicate the time required to reach half of the maximum metal efflux for each metal.

Determination of Metal Selectivity in Yeast (FIG. 10J)

Figure 13H:
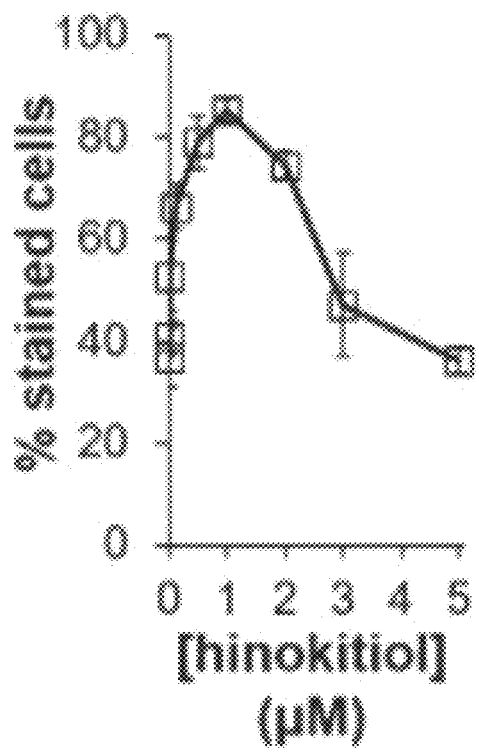

Hinokitiol-mediated changes in intracellular metal levels were determined using growth rescue conditions from FIG. 13H and an adaptation of the Fe uptake study in FIG. 1G. Specifically, wild type and fet3Δftr1Δ yeast were grown in YPD media overnight, rinsed, and incubated in SD media without FeCl$_3$ at 30° C. for 3 hours. Yeast were then resuspended at an OD600=0.50 in SD media (50 mM MES/Tris, pH=7.0) containing 100 µM FeCl$_3$ and either DMSO vehicle or 10 µM hinokitiol. After 2.5 hours of incubation, cells were centrifuged at 5° C., rinsed twice with cold 10 mM EDTA in 50 mM Tris/HCl buffer (pH=6.5), and once with cold metal-free water. Cells were then lyophilized for 48 hours. The lyophilized cells were digested with a 5:1 mixture of HNO3:HCl and then subjected to an automated sequential microwave digestion in a CEM Discover SP-D microwave digester. The resulting clear solution was diluted in metal-free water, and elemental analysis was performed by ICP-MS.

Exchangeability of Ferric Iron Bound to Hinokitiol (FIG. 14M)

The reversible exchange of ferric iron bound to hinokitiol was determined similar to previously described (69). Non-radioactive $FeCl_3$ (100 nM from a 1000X stock, referred to as $^{56}Fe$) was added to hinokitiol (100 nM from a 1000X stock) in 10 mM MES/Tris buffer at pH=7.0. The solution was equilibrated for 1 hour at 37° C., and then an equal amount of $^{55}FeCl_3$ (100 nM) was added. The solution was incubated at 37° C., and at the indicated time points an aliquot was taken and added to water. The iron-hinokitiol complex was immediately separated from unbound iron through extraction with ethyl acetate and the radioactive counts were determined by scintillation counting. Less than 2% of iron was found in the ethyl acetate layer in the absence of hinokitiol.

The percent equilibrium was then determined by normalizing the radioactive counts from the theoretical maximum $^{55}Fe$ found in the hinokitiol complex (1:1 $^{55}Fe$:$^{56}Fe$ at equilibrium).

Electrochemical Studies of Hinokitiol and Other Chelators (FIG. 2F, FIG. 1A-J, and Tables S2, 4-6)

Potentiostatic electrochemical methods were performed on a CH Instruments electrochemical workstation (model 760 C, Austin, TX) on a three-electrode cell. Hg working electrodes were fabricated by the electrodeposition of Hg on a Pt wire utilizing the procedure previously described by Barton et al. (70). All experiments were reported versus a Ag/AgCl reference electrode and utilized a graphite auxiliary electrode. The electrolyte was sparged with UHP argon before measurements. A positive pressure of argon was maintained throughout the experiments.

Unless otherwise indicated, experiments used a 0.1 M Tris buffer in H2O or 1:1 MeOH:H2O at pH=7.2 using HNO3 and KOH as titrant. Unless otherwise indicated, experiments used a 100 mV/s scan rate, 100 µM $Fe(NO_3)_3$, and 500 µM small molecule. All redox potentials are recorded versus a normal hydrogen electrode (NHE).

The estimated redox potential of $Fe(Hino)n$ was determined through extrapolation of the best-fit line of the determined redox potentials of $Fe(Hino)n$ as a function of the concentration of MeOH in the 0.1 M Tris buffer at pH=7.2.

Rate of Iron (III) Reduction (FIG. 11K, L)

The rate of iron (III) reduction in the absence or presence of hinokitiol was determined using ferrozine to quantify the concentration of iron (II) similar to previously described (71). Specifically, iron (III) or $Fe(Hino)_3$ was pre-mixed in a solution of H2O, and diluted into a 25 mM MES/Tris buffer at pH=7.0 containing 62.5 mM sodium ascorbate and ferrozine (3 mM) to a final concentration of 10 µM $FeCl_3$ and 30 µM hinokitiol. The absorbance at 562 nm, corresponding to $Fe(ferrozine)_3$, was determined at the indicated time points. The concentration of iron (II) was then calculated through the determined extinction coefficient of ferrozine-iron in this buffer ($\varepsilon$=19,200 $M^{-1}$ $cm^{-1}$).

Transfection of Caco-2 Cells and MEL Cells Against DMT1

Caco-2 cells were transfected as previously reported (36) using lipofectamine LTX (Invitrogen 15338-100) and Plus reagent (Invitrogen 11514-015) with 10 µg/well of either non-targeting control shRNA or four other shRNA constructs targeting human DMT1 (Qiagen KH05760N) 24 hours after seeding 2×10⁵ cells/well in 6-well plates (~30% confluent). The transfection agents were removed, and the cells were allowed to recover for 24 hours before treatment with Caco-2 Complete media containing 0.8 g/L G418. Cells were incubated in G418 media for ~2 weeks to promote selection of transfected cells while complete cell death was observed with non-transfected cells. Non-targeting control construct =5'-GGAATCTCATTCGATGCATAC-3'; shDMT1 construct (Clone 4)=5'-AACCTAT-TCTGGCCAGTTTGT-3'. MEL cells were transfected by electroporation (0.28 kV, 975 pF pulse) in 0.4 cm cuvette (Biorad 1652081) containing 400 µL of serum-free DMEM with 30 mM NaCl at 2×10⁷ cells/mL with 50 µg of either non-targeting control shRNA (Sigma, 5'-CAACAAGAT-GAAGAGCACCAA-3' using a CMV-neo vector) or five shRNA constructs targeting mouse DMT1 (Sigma, Clone 1-5: TRCN0000332748, TRCN0000306610, TRCN0000079533, TRCN0000079535, and TRCN0000079536). After transfection, cells were transferred to T25 flasks containing 10 mL of MEL Complete media, and allowed to grow for 6 days with re-seeding every 2 days at 10:1 dilution in fresh MEL Complete media. After this, cells were re-seeded at 1×10⁵ cells/mL in MEL Complete media containing 1 g/L G418, and cells were selected over the course of 2 weeks by re-seeding at 10:1 dilution into fresh G418 media every ~2 days until no cells were observed in T25 flasks originally containing non-electroporated wild type (DS19) MEL cells.

Mfrn1-deficient MEL cell lines were developed using CRISPR/Cas9 genome editing as previously described (72-74). Exons 2 and 4 of the Mfrn1 locus were targeted. The exon 2 targeting sequence was: 5'-GATGCTTGTATACCGGGCTT-3'; the exon 4 targeting sequence was: 5'-GAAGAACTCATAAACGGACC-3'. The primers used for documenting intragenic deletion of the Mfrn1 mouse locus were the following: Exon 4 (Fwd) 5'-GTTTGCCTCTGCGGTGTGATC-3'; Exon 2 (Fwd) 5'-GGAGGACGCTGTGGGGGGGGG-3'; Exon 2 (Rev) 5'-GTCCATCTTTTCTACAAGCC-3'.

qRT-PCR Conditions (FIG. 12A, FIG. 13A, FIG. 14A, and FIG. 22G, L)

Dmt1 mRNA levels were determined via qRT-PCR using SYBR Green (Agilent 600825) following manufacturer protocols after undergoing treatment as described below. For determination of Dmt1 mRNA levels in differentiated Caco-2 monolayers (21-28 days post seeding), mRNA was isolated using RNeasy Mini Kit (Qiagen 74104) according to manufacturer instructions. The threshold cycle (Ct) values of Dmt1 were normalized to internal control actin using primers against Dmt1 (Origene HP200584) and actin (Origene HP204660) using the Pfaffl Method and were then normalized to shControl levels.

For determination of relative Dmt1 mRNA levels in MEL clones, mRNA was isolated from MEL clones differentiated with 2% DMSO and 10 µM iron (III) citrate for 3 days using RNeasy Mini Kit (Qiagen 74104) according to manufacturer instructions. The Ct values of Dmt1 were normalized to internal control Hprt1 using primers against Dmt1 (Origene MP215650) and Hprt1 (Origene MP206455) using the Pfaffl Method and were then normalized to shControl levels.

Fpn1 and Fth1 mRNA levels in shDMT1 Caco-2 monolayers upon treatment with 25 µM $FeCl_3$ and increasing hinokitiol concentrations (0, 0.5, 1, 3, 5, 10, 25, and 50 µM) for four hours as described above were determined after isolation of mRNA as described above. The threshold cycle values were normalized to internal control actin using primers against Fpn1 (Origene HB210988) and Fth1 (Origene HP205786) using the Pfaffl Method and were then normalized to shDMT1 levels in the absence of hinokitiol.

Relative Mfrn1 mRNA levels were determined via qRT-PCR using TaqMan probes (Applied Biosystems) as previously described (75).

Western Blotting Conditions (FIG. 5A, G, FIG. 12B, C, FIG. 13B, C, J, FIG. 14G-J, FIG. 19D, F-K, N, O, and FIG. 22C-F, H-N)

Caco-2 monolayers, differentiated MEL cells, or J774 cells underwent treatment as described in rescue experiments before lysis with RIPA buffer (Thermo 89901) containing protease inhibitors (Thermo 88266). Protein concentrations were determined by a BCA kit (Thermo 23225) and diluted to 2 mg/mL in the same RIPA buffer. Relative protein levels were then determined through western blotting of 10 or 20 gg of protein lysate blocking for 2 hours at room temperature with 5% BSA and using primary antibodies consisting of either human anti-DMT1 (1:3,000 dilution, Santa Cruz sc-30120), mouse anti-DMT1 (1:1,000 dilution, Santa Cruz sc-166884), human anti-FTL1 (1:1,000 dilution, Santa Cruz sc-74513), human anti-FPN1 HRP conjugate (1:10,000 dilution, Novus Biologicals NBP1-21502H), mouse anti-globin a HRP conjugate (not heated at 100° C., 1:10,000 dilution, Lifespan Biosciences LS-C212172), human anti-TfR1 HRP conjugate (1:10,000 dilution, Abeam ab10250), human anti-IRP1 (1:1,000 dilution, Santa Cruz sc-14216), human anti-IRP2 (1:1,000 dilution, Santa Cruz sc-33682), human anti-Hif1α a HRP conjugate (1:1,000 dilution, Novus Biologicals NB100-105H), human anti-Hif2α HRP conjugate (1:1,000 dilution, Novus Biologicals NB100-122H), human anti-PCBP1 (1:1,000 dilution, Santa Cruz sc-393076), or human anti-actin HRP conjugate (1:10,000 dilution, Cell Signaling 5125S) in 5% BSA overnight at 5° C. before rinsing thoroughly with TBST and incubation (if non-HRP conjugated) with secondary antibody consisting of either goat anti-rabbit IgG HRP conjugate (1:5,000 dilution—DMT1, Cell Signaling 7074, in 5% milk), goat anti-mouse IgG1 HRP conjugate (1:1,000 dilution—PCBP1, 1:5,000 dilution—IRP2, 1:3,000 dilution—DMT1, Santa Cruz sc-2060, in 5% BSA), donkey anti-goat IgG HRP conjugate (1:1,000 dilution—IRP1, Santa Cruz sc-2020, in 5% BSA), or goat anti-mouse IgG2α HRP conjugate (1:10,000 dilution—FTL1, Santa Cruz sc-2061, in 5% BSA) at room temperature for two hours. Blots were thoroughly rinsed with TBST and imaged after addition of Femto Chemluminescence solution according to manufacturer instructions (Thermo Fisher 34095).

Figure 19E:
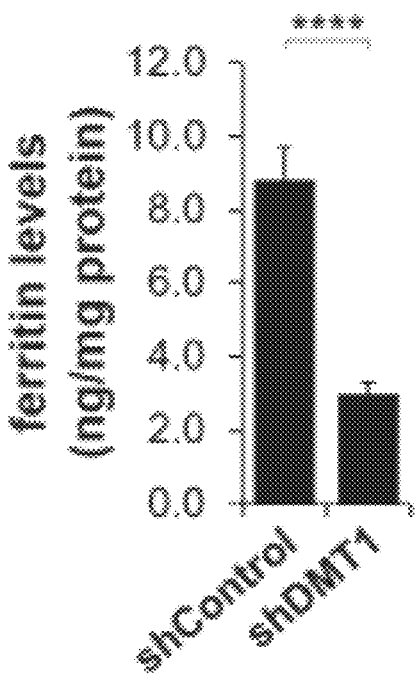
Figure 19F:
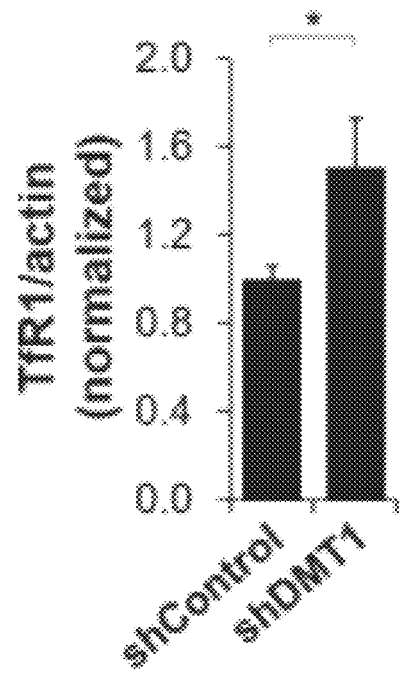
Figure 19G:
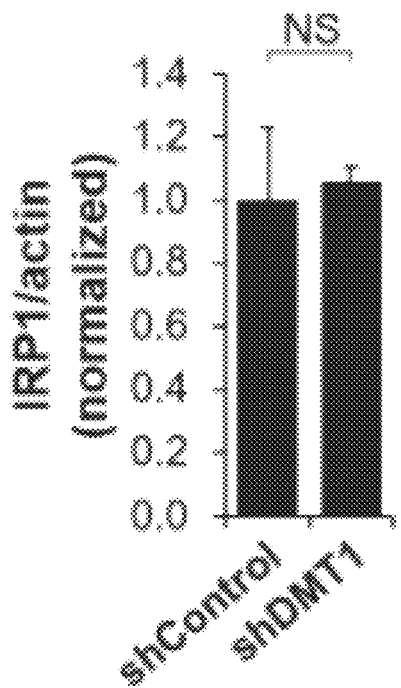
Figure 19H:
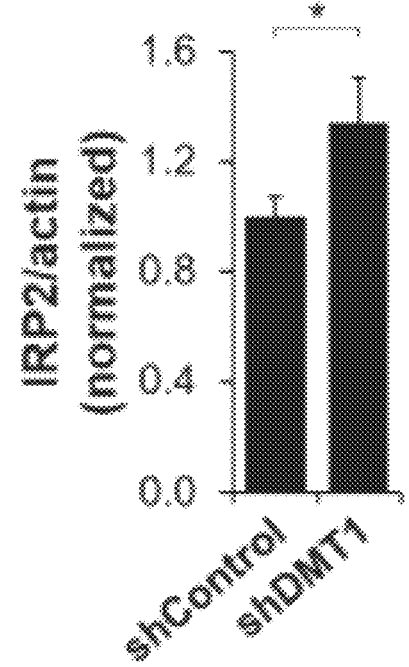
Figure 19I:
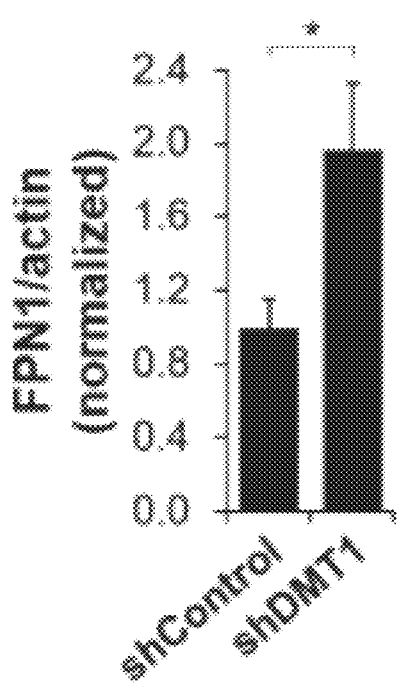
Figure 19J:
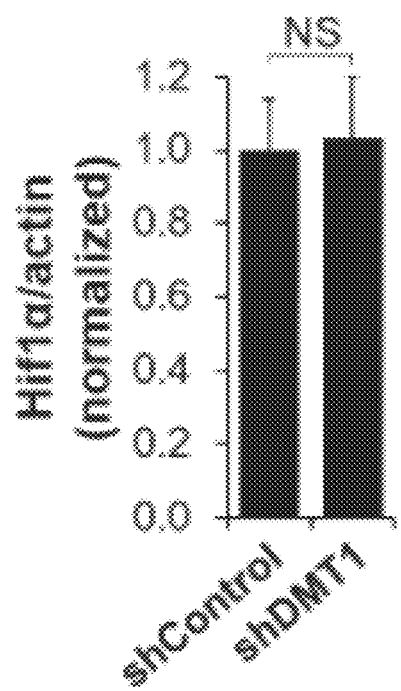
Figure 19K:
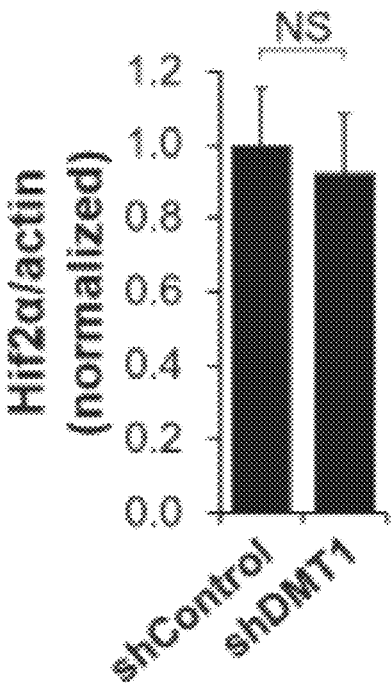
Figure 22A:
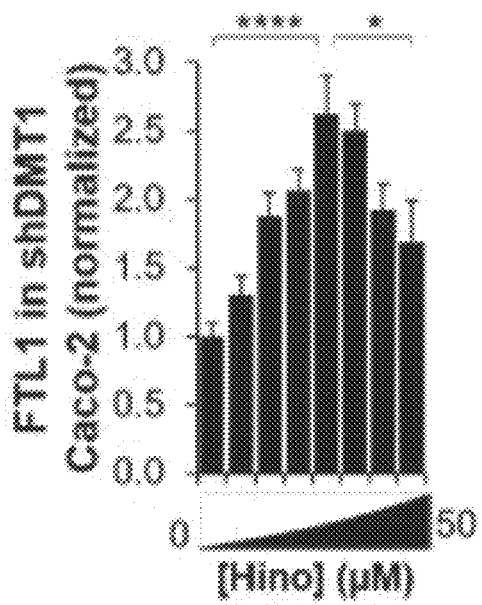
FIGS. 22A-22N show translational and transcriptional regulation of iron-related protein levels respond to hinokitiol-mediated iron uptake into Caco-2 epithelia. (A and B) Upon treatment of shDMT1 monolayers with FeCl$_3$ (25 µM) and hinokitiol (which increases intracellular iron) for four hours, (A) increased ferritin (5'-IRE) levels (N=6-21) and (B) increased 55Fe incorporation into immunoprecipitated ferritin was observed up to 5 µM hinokitiol. N=11-15. (C) Similarly, TfR1 (3'-IRE) levels decrease up to 5 µM hinokitiol. N =8. (D and E) As expected, (D) IRP1 levels did not change (N=14) while (E) decreased IRP2 protein levels were observed, consistent with hinokitiol-mediated increases in labile iron levels leading to translational regulation of ferritin and TfR1. N=12. (F and G) Consistent with Hif2α-mediated transcriptional regulation of FPN1, (F) decreased FPN1 protein (N=16) and (G) decreased Fpn1 mRNA levels were observed upon hinokitiol treatment up to 5 µM. N=9-12. (H and I) Hif1α and Hif2α levels respond to increases in labile iron up to 5 µM hinokitiol. N=4-13. (J) Presumably due to shRNA targeting DMT1, no translational regulation of DMT1 was observed up to 5 µM hinokitiol. N=6. (A-J) These effects were modestly reversed upon treatment with higher doses of hinokitiol up to 50 PM, possibly due to competitive chelation of labile iron with high hinokitiol doses. (K) IRE-independent protein levels of the iron chaperone PCBP1 (N=6) and (L) Hif2α-independent Fth1 mRNA levels did not change when treated with hinokitiol under identical conditions. N =16. (M and N) No changes were observed in FPN1 levels treated with hinokitiol in the absence of added iron, supporting the conclusion that the changes observed were due to translational and transcriptional responses to dynamic cellular iron status. N=6-8. (A-L) Experiments in shDMT1 Caco-2 monolayers used apical addition of hinokitiol (0, 0.5, 1, 3, 5, 10, 25, and 50 µM) in the presence of 25 µM apical FeCl$_3$ for 4 hours in the pH=5.5 apical buffer and pH=7.4 basolateral buffer as described previously. (M and N) Experiments utilized identical conditions using 500 nM Fe. (A-L, N) NS, not significant; * P≤0.05;  P≤0.01; * P≤0.001; **** P≤0.0001; Graphs depict means±SEM.

Determination of Ferritin Levels by ELISA (FIG. 19E and FIG. 22A)

Absolute ferritin protein levels in shControl and shDMT1 Caco-2 monolayer lysates were determined using a commercial sandwich ELISA kit (Abcam ab108837) according to manufacturer instructions.

For results found in FIG. 19E, protein lysate was isolated after treatment with 500 nM $FeCl_3$ as described below. For results found in FIG. 22A, Caco-2 monolayers were treated with 25 μM $FeCl_3$ and 0, 0.5, 1, 3, 5, 10, 25, or 50 μM hinokitiol as described below.

Figure 3B:
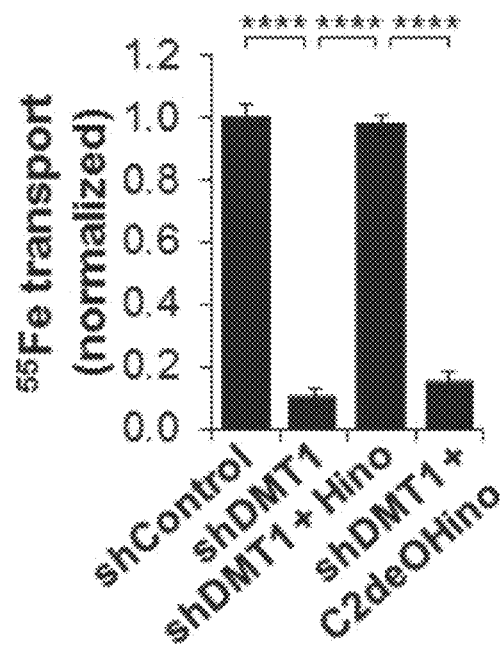
Figure 3C:
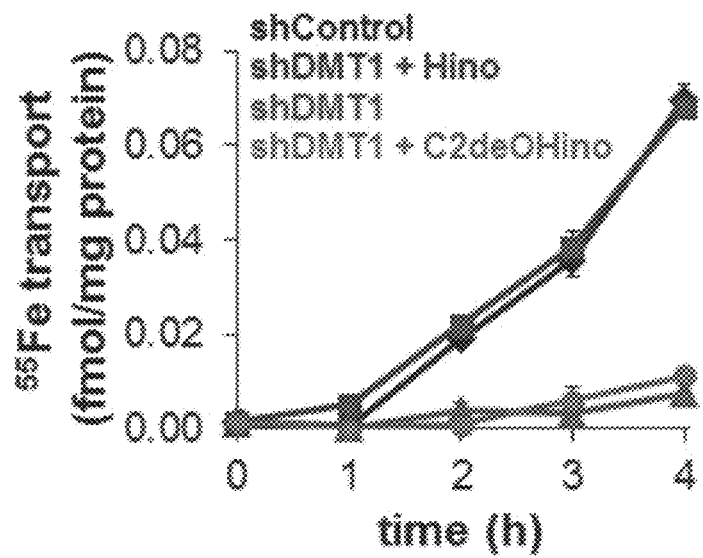
Figure 3D:
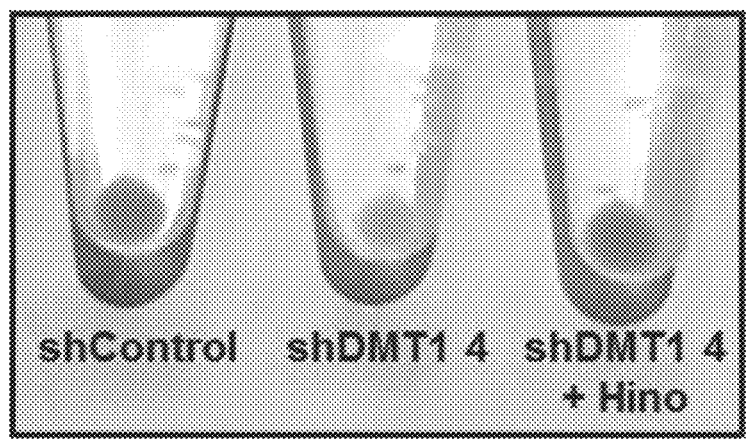
Figure 3E:
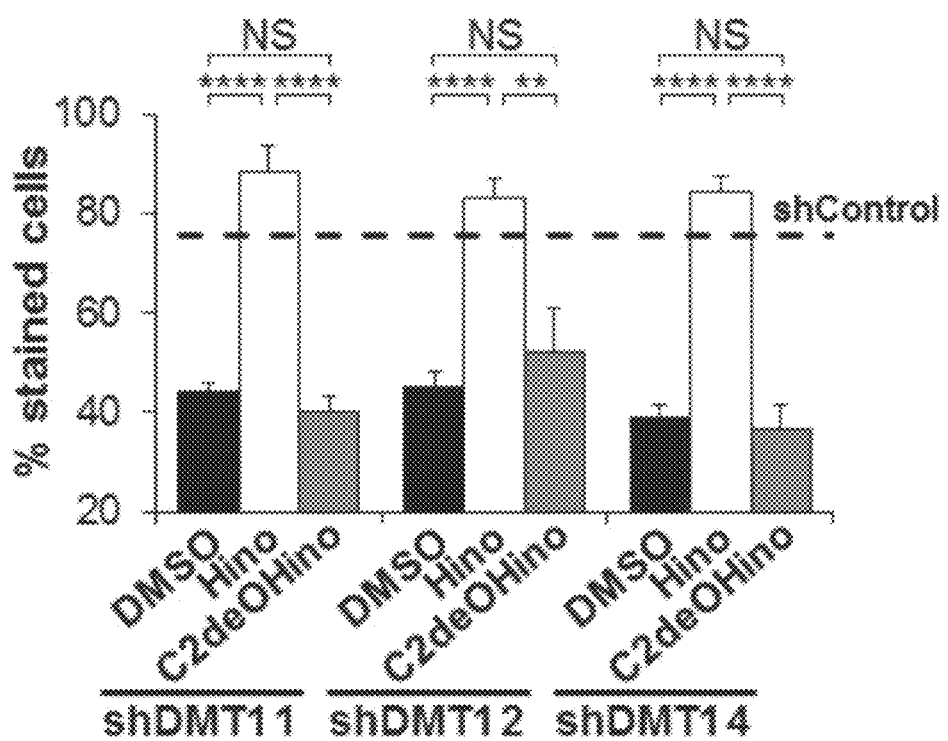
Figure 3F:
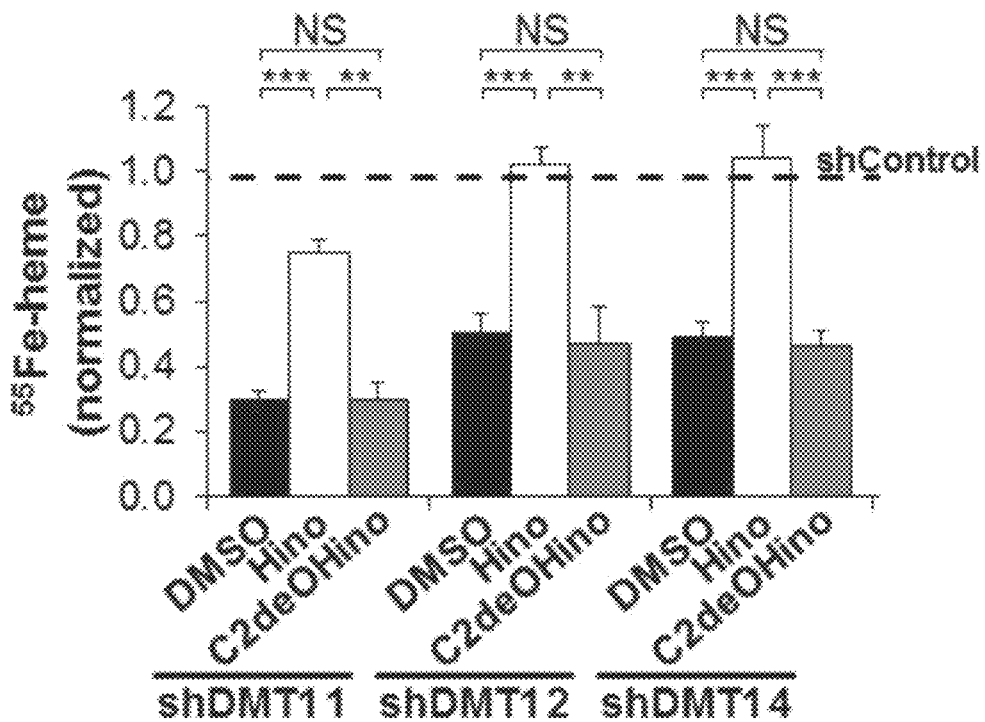
Figure 3G:
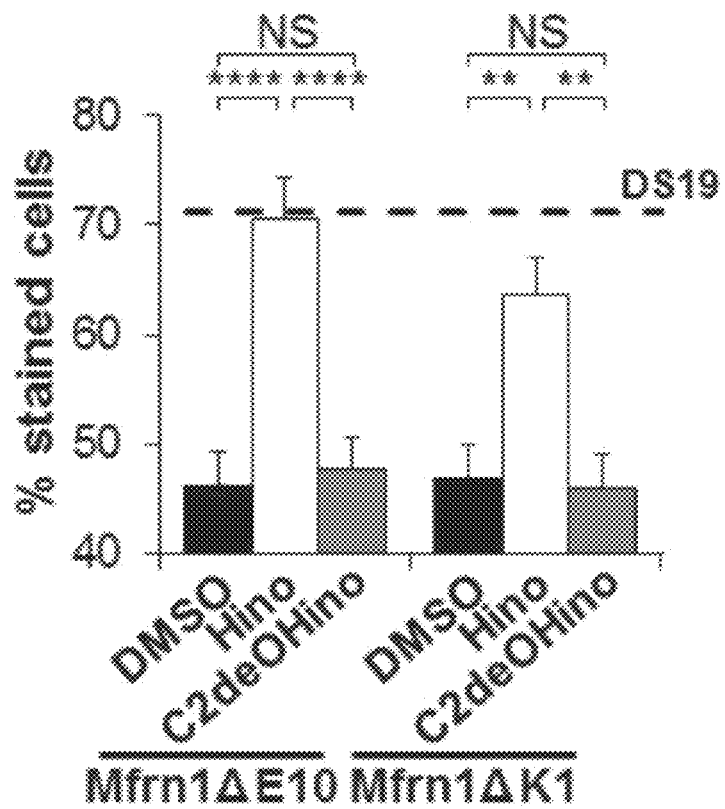
Figure 3H:
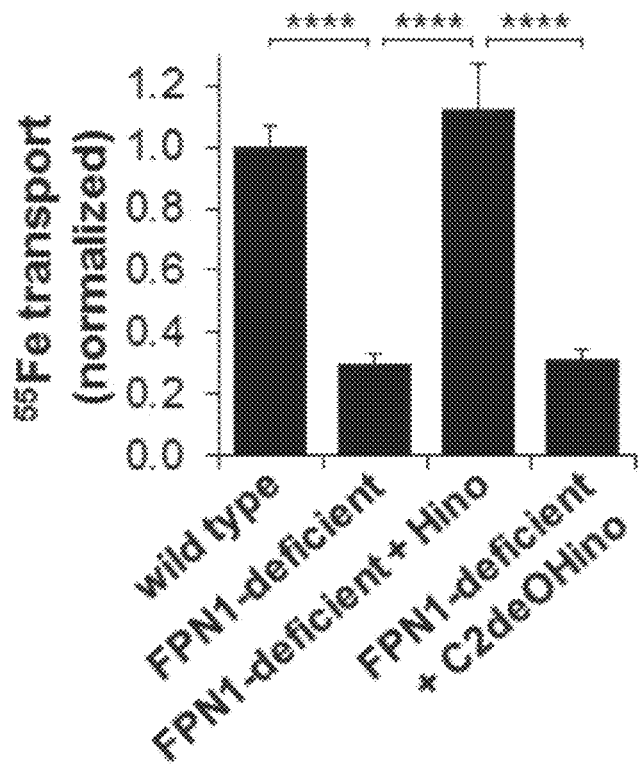
Figure 3I:
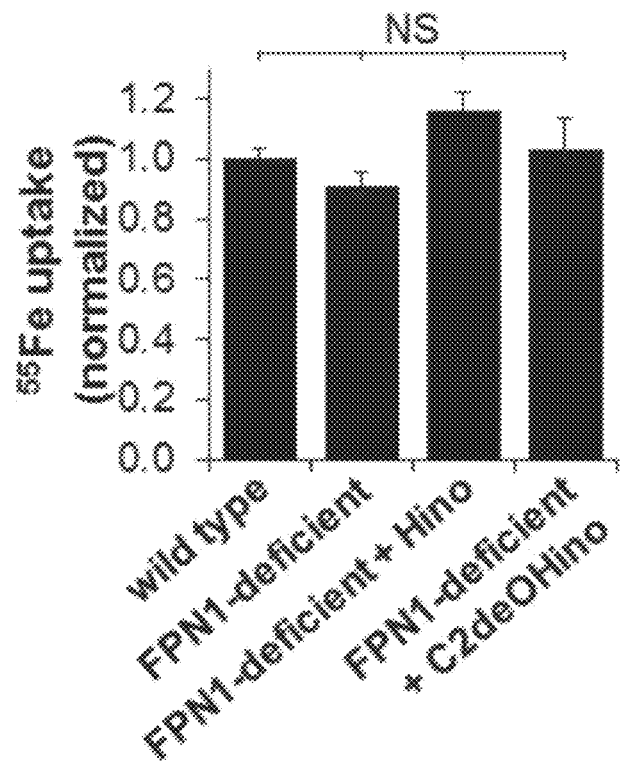

$^{55}Fe$ Uptake and Transport in Differentiated Caco-2 Monolayers (FIG. 3A-C, H, I, FIG. 5B, D-F, FIG. 12E-G, FIG. 14K, FIG. 19M, P, Q, FIG. 21, and FIG. 23A, D)

Media from differentiated Caco-2 monolayers (P25-50, 21-28 days post seeding) grown on PET inserts in 6-well plates was aspirated, and monolayers were rinsed with PBS. 2 mL of basolateral fluid (serum-free DMEM at pH=7.4 in 10 mM HEPES buffer) was added to the basolateralside, and 1 mL of apical fluid (serum-free DMEM at pH=5.5 in 10 mM MES buffer) containing 200 nM $^{55}FeCl_3$ or the indicated concentration of $FeCl_3$ and either DMSO vehicle, hinokitiol, $C_2$deOHino, deferiprone, PIH, SIH, or deferoxamine mesylate (Sigma D9533) (500 nM Hino/$C_2$deOHino for DMT1-deficiency, 1 μM Hino/$C_2$deOHino for FPN1-deficiency, or indicated concentration of small molecule from a 1000X stock in DMSO) was added to the apical side via addition on the wall of the membrane insert without disrupting the cell monolayer. The monolayers were then incubated for four hours at 37° C. unless otherwise noted. A 100 μL aliquot of the basolateral fluid was removed, diluted in scintillation cocktail, and radioactivity was determined on a liquid scintillation counter to quantify relative amounts of $^{55}Fe$ transport. To determine intracellular $^{55}Fe$, the basolateral and apical media was removed, and the monolayer was rinsed with PBS (×2). The cells were then lysed with 500 μL of 200 mM NaOH with nutator mixing overnight, and radioactivity was determined on a liquid scintillation counter after diluting the cell lysate in scintillation cocktail. All values were normalized to shControl monolayers unless otherwise noted. Absolute iron levels were determined through calibration of $^{55}Fe$ radioactivity levels with known standards and average mg of protein per membrane was determined by protein lysis with RIPA buffer containing protease inhibitors and quantified through a BCA kit according to manufacturer instructions.

Determination of $^{55}Fe$ transport as a function of pH (FIG. 12E) used the protocol described above except for the use of apical fluid containing either 10 mM PIPES (pH=6.5) or 10 mM HEPES (pH=7.4) in DMEM.

Determination of unidirectional uptake and transport (FIG. 5B and FIG. 19M) was determined as described above except for basolateral addition of $^{55}FeCl_3$ (200 nM) and basolateral addition of DMSO or hinokitiol (500 nM). An aliquot of the apical fluid was then taken to determine the basolateral to apical transport. Intracellular $^{55}Fe$ was determined as described above.

Determination of $^{55}Fe$ transport as a function of the concentration of iron and/or hinokitiol (FIG. 5E and FIG. 21) was performed as described above except for the use of the indicated concentration of iron (20:1 $^{56}Fe$:$^{55}Fe$ for each concentration) or hinokitiol (from a 1000X stock in DMSO). Experiments for the translational and transcriptional regulated changes in endogenous proteins upon addition of increasing hinokitiol concentrations (FIG. 5F-J, FIG. 21, and FIG. 22A-L) used 25 μM of non-radioactive $FeCl_3$ and the indicated concentration of hinokitiol (from a 1000X stock in DMSO).

Determination of ferroportin levels upon increasing hinokitiol concentrations in the absence of iron (FIG. 22M, N) used the procedure as described above containing 200 nM of non-radioactive $FeCl_3$.

Determination of $^{55}Fe$ transport after FPN1 knockdown (FIG. 5D and FIG. 19N-P) was determined as described above using 200 nM $^{55}FeCl_3$ after incubation of quercetin to knockdown FPN1 (40) as described below.

Figure 19L:
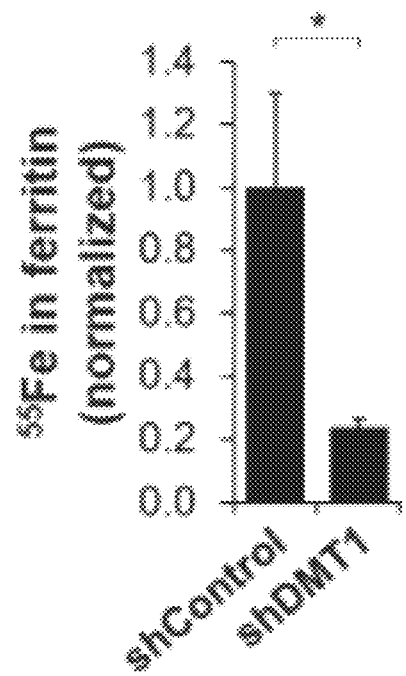
Figure 19M:
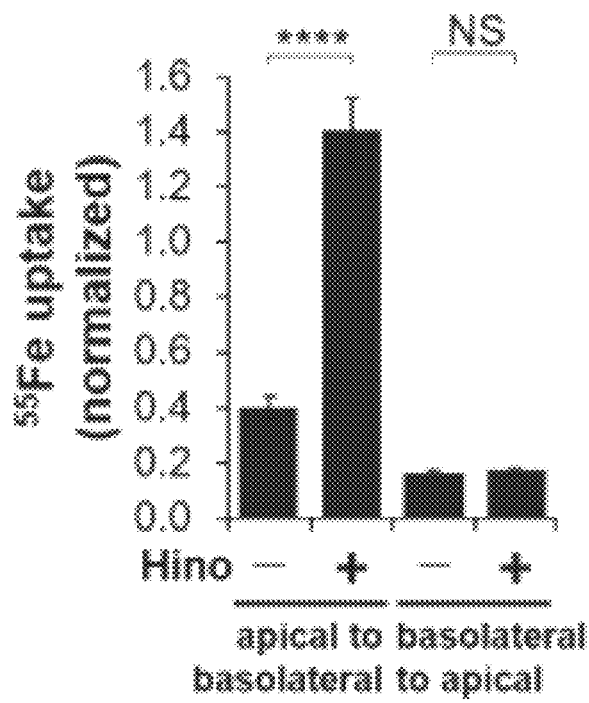
Figure 19N:
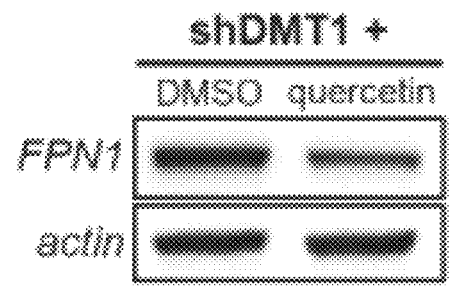
Figure 19O:
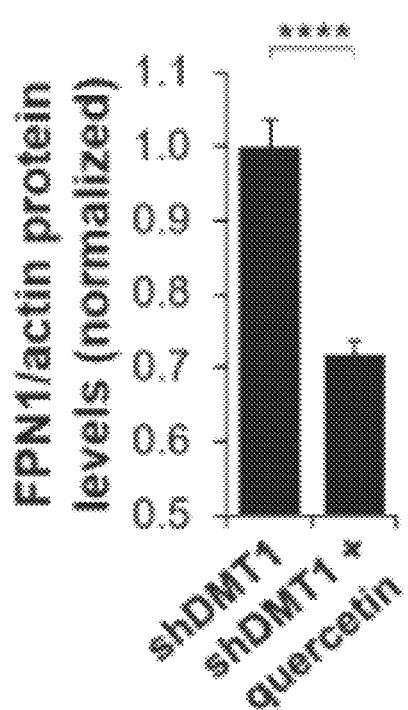
Figure 19P:
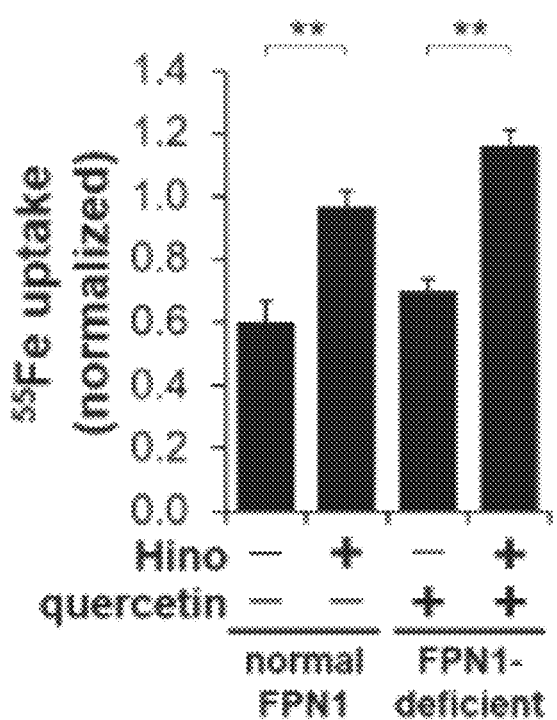
Figure 19Q:
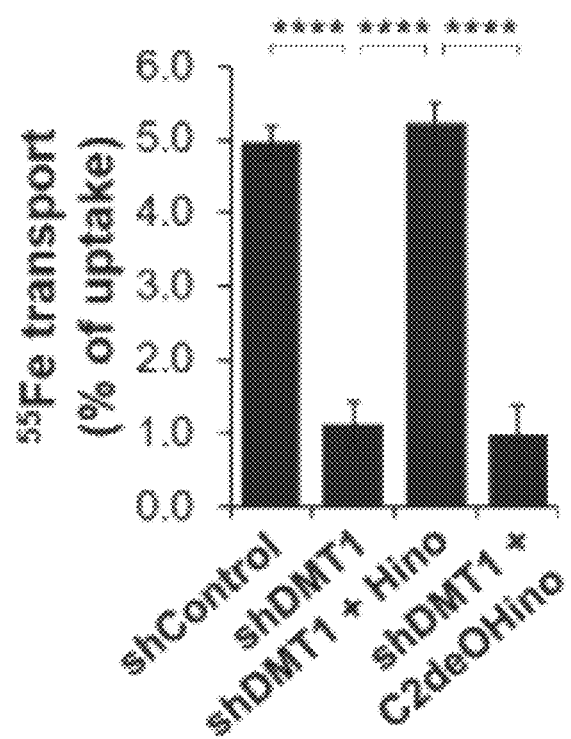
Figure 22B:
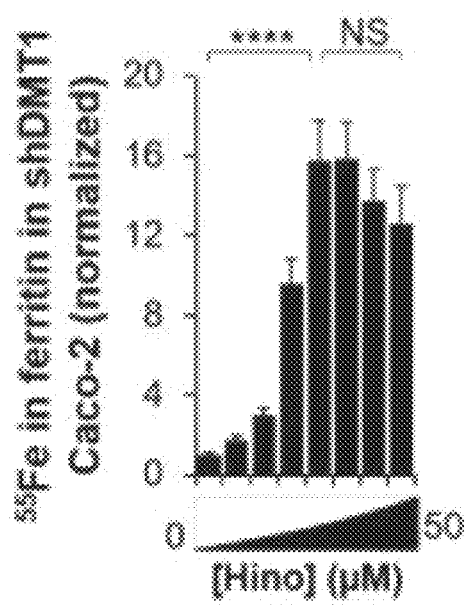
Figure 22C:
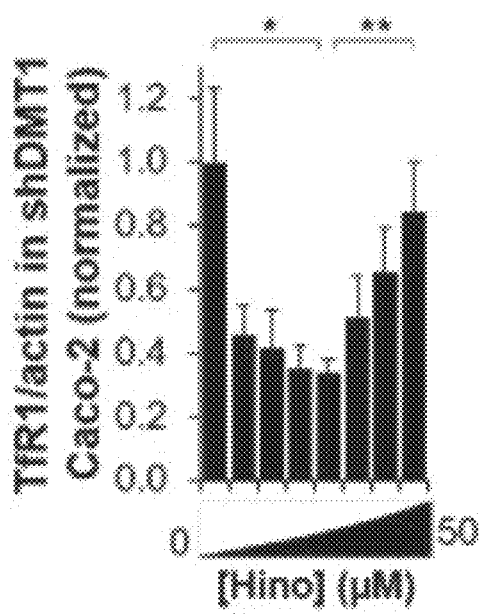
Figure 22D:
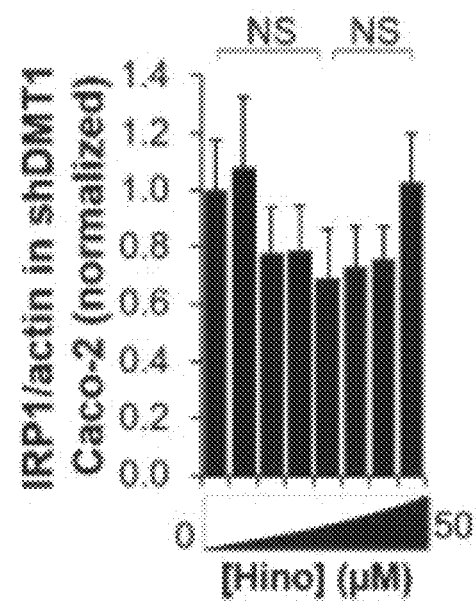
Figure 22E:
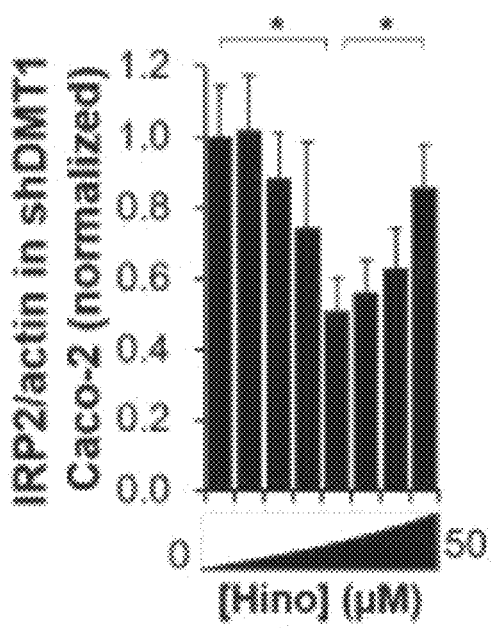
Figure 22F:
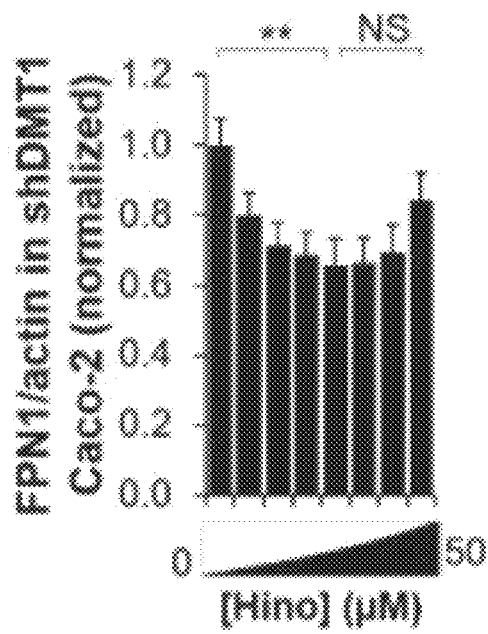
Figure 22G:
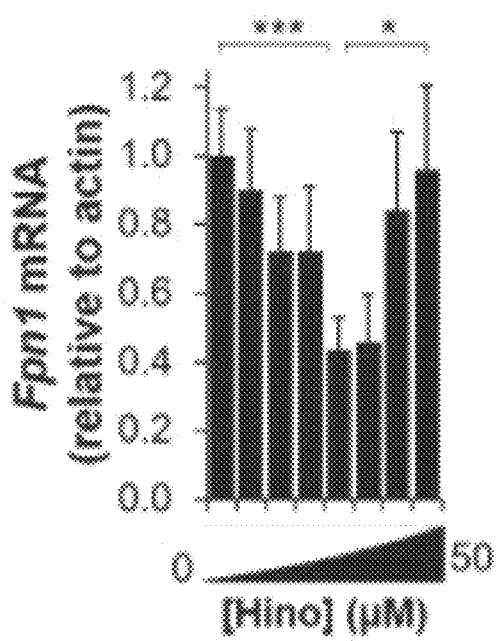
Figure 22H:
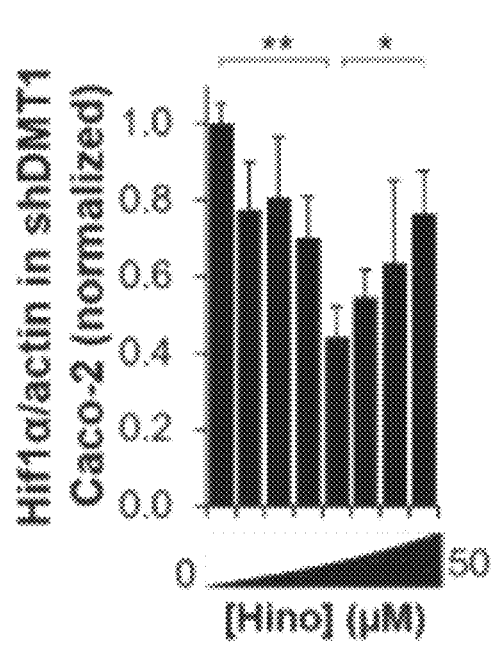
Figure 22I:
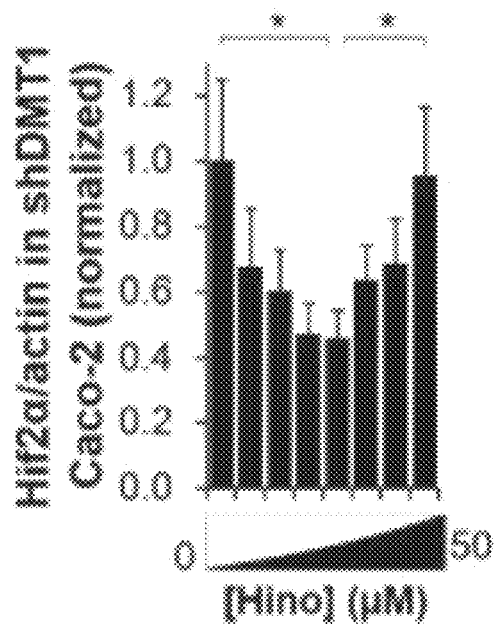
Figure 22J:
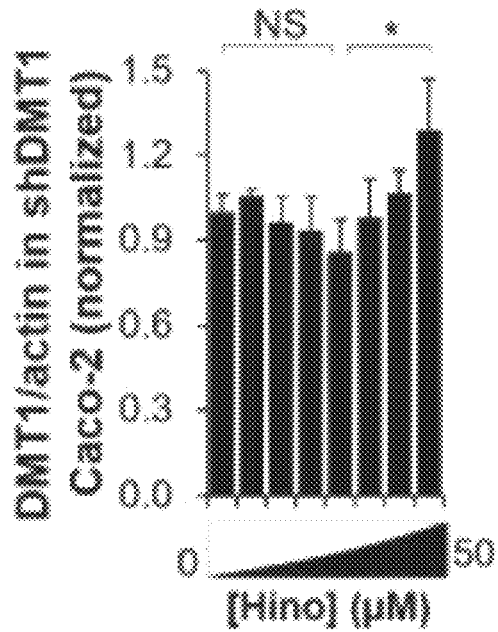
Figure 22K:
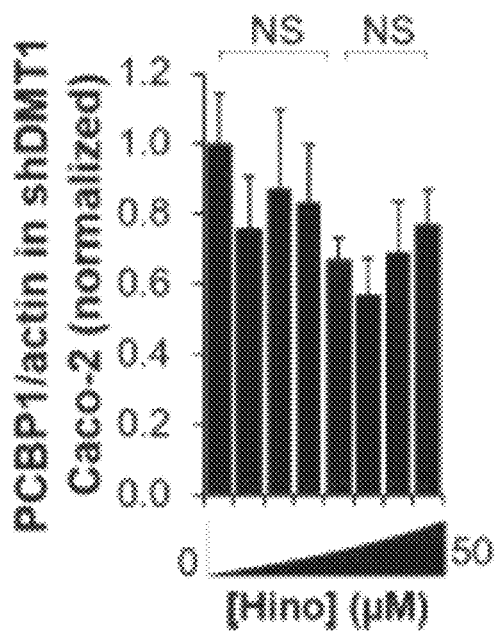
Figure 22L:
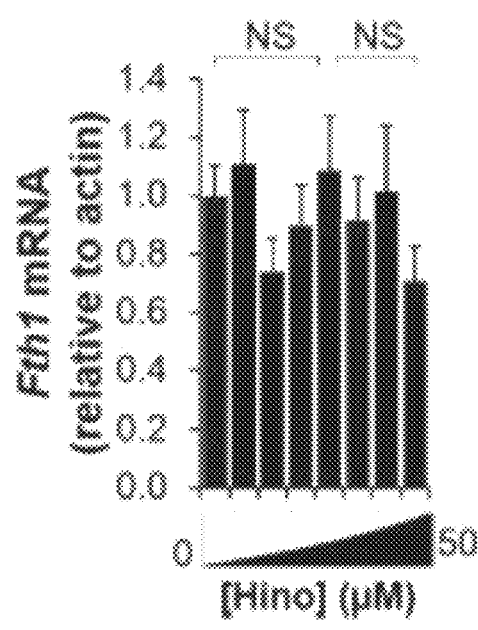
Figure 22M:
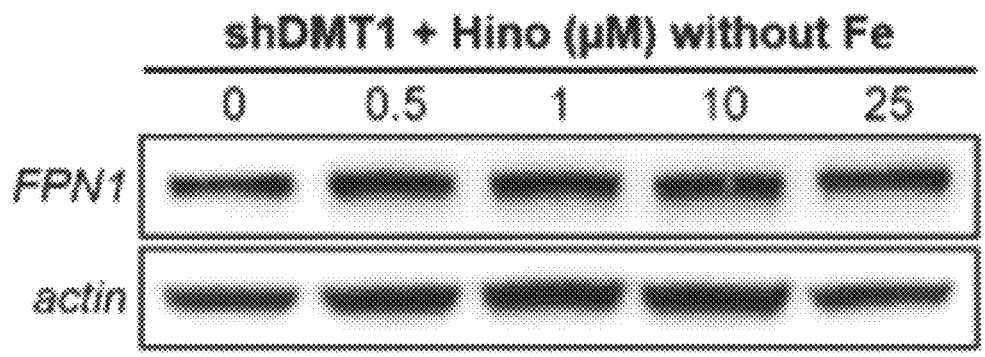
Figure 22N:
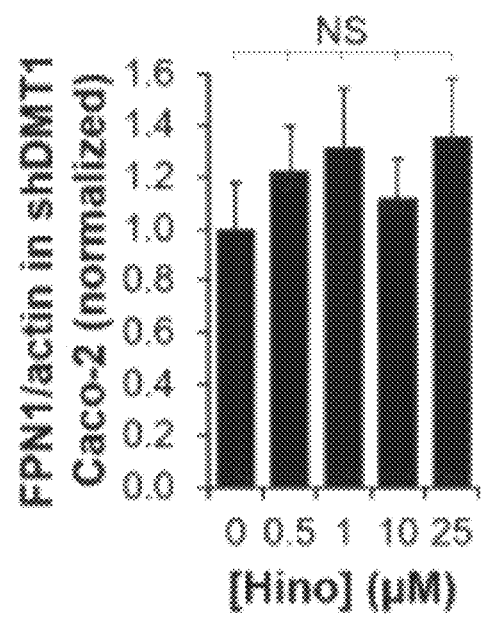
Figure 23D:
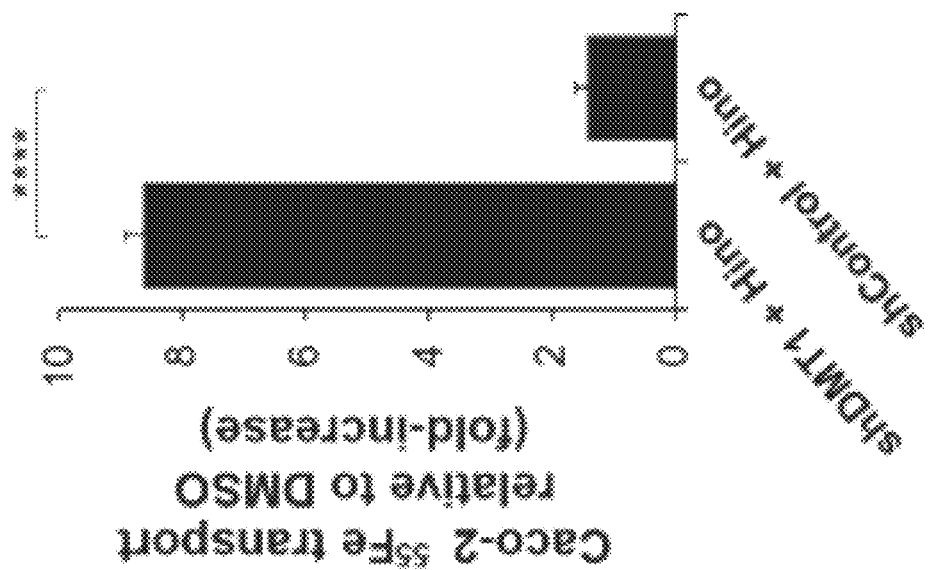
Figure 23E:
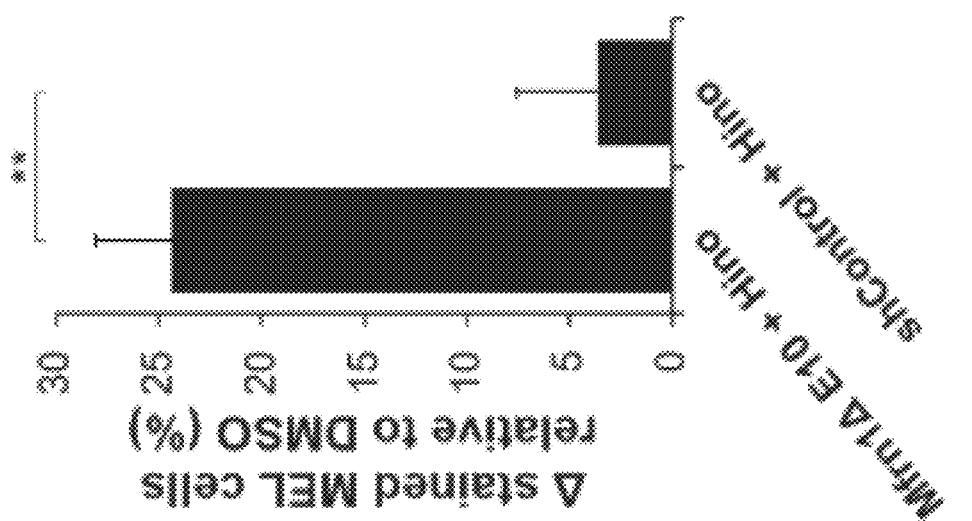
Figure 23F:
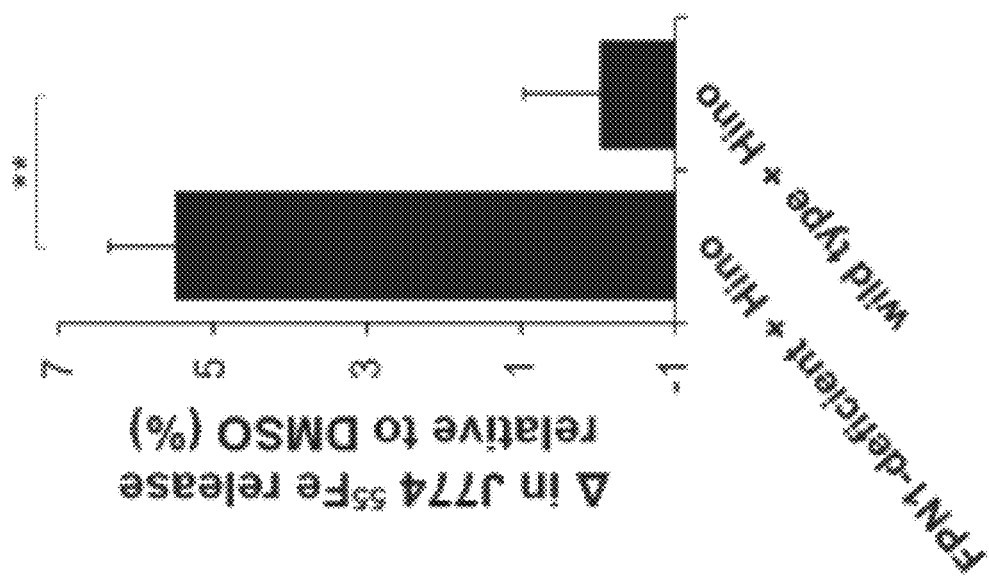

$^{55}Fe$ Immunoprecipitation of Ferritin in Caco-2 Monolayers (FIG. 5C, FIG. 19L, And FIG. 22B)

Immunoprecipitation of ferritin was performed using human anti-FTL1 (Santa Cruz sc-74513) and Protein G PLUS-Agarose beads (Santa Cruz sc-2002). Cell lysate was obtained from shControl and shDMT1 Caco-2 monolayers after apical treatment with DMSO or hinokitiol (500 nM for FIG. 19L and 0, 0.5, 1, 3, 5, 10, 25, or 50 μM for FIG. 22B) and $FeCl_3$ (200 nM of $^{55}Fe$ for FIG. 19L and 25 μM of 20:1 $^{56}Fe$:$^{55}Fe$) for four hours as described above. Cell lysate was incubated with primary antibody (1:100 dilution) at room temperature for 1 hour, then with the secondary antibody (1:10 dilution) at room temperature for 1 hour with constant mixing. Repeated centrifugations and PBS rinses were performed, and the radioactive levels in the agarose pellet were determined by dilution in scintillation fluid.

TEER determination in Caco-2 monolayers (FIG. 12D and FIG. 14L) To determine Caco-2 membrane integrity, transport studies were performed as described above, except for the use of non-radioactive iron instead of $^{55}FeCl_3$. At the indicated time points, the transepithelial electrical resistance (TEER) was determined with an epithelial voltohmmeter and compared to the TEER of the membrane at the beginning of the experiment.

WST-8 Toxicity in Cell Lines (Table S7)

Determination of small molecule-mediated toxicity in Caco-2, MEL, and/or J774 cells was performed according to manufacturer instructions using a WST-8 kit (Cayman Chemical 10010199) similar to previously reported (76) using a 1000× stock of the indicated small molecule in DMSO to give the indicated final concentration.

Differentiation of MEL Cells with DMSO (FIG. 3D) To perform differentiation experiments with MEL cells (39), the indicated MEL cells were diluted to 1×10$^5$ cells/mL in MEL Complete media containing 10 µM iron (III) citrate and 2% DMSO in the absence or presence of 1 µM hinokitiol or C$_2$deOHino (added from 1000X stock in DMSO) in 12-well plates. Cells were then incubated at 37° C. for 72 hours unless otherwise noted. Control experiments were performed under identical conditions in the absence of DMSO, and it was found that no differentiation was observed by o-dianisidine staining as described below.

Staining of Induced MEL Cells with Dianisidine (FIG. 3E, G, FIG. 13D, E, G, H, L, FIG. 14D, and FIG. 23B, E)

Hemoglobinized MEL cells were quantified three days after DMSO induction through o-dianisidine staining similar to previously reported (74). Cells were centrifuged three days after induction and rinsed with PBS. The cells were then suspended in a solution containing 7.5 mM o-dianisidine, 900 mM H2O2, and 150 mM acetic acid in water at ~1×10$^6$ cells/mL. Cells were then imaged on an AXIO Zoom V16 microscope to obtain color images. The number of stained cells were then quantified via ImageJ analysis and compared to the number of total cells in each image. To determine that hinokitiol requires DMSO induction for hemoglobinization, 2% DMSO was not added at the beginning of the experiment before a 72-hour incubation and o-dianisidine staining.

$^{55}$Fe Uptake in MEL Cells (FIG. 13F, K and FIG. 14B, E)

MEL cells were induced for differentiation as described above and incubated at 37° C. for 70 hours before addition of a saturated iron-transferrin ($^{55}$Fe2Tf) solution (40 nM final concentration from a 10 µM $^{55}$Fe2Tf stock). The cells were incubated for an additional two hours. After completion, the cells were counted with a hemocytometer, the media was removed after centrifugation, the cells were rinsed with PBS (×3), and the cell suspension was diluted in scintillation cocktail and radioactivity was determined. Radioactive levels were normalized per cell (counted by hemocytometer) relative to wild type (DS19) levels. $^{55}$Fe heme incorporation in MEL cells (FIG. 3F, FIG. 13K, and FIG. 14C, F) MEL cells were induced for differentiation as described above and incubated at 37° C. for 64 hours before addition of a saturated $^{55}$Fe2Tf solution (250 nM final concentration from a 10 µM $^{55}$Fe2Tf stock). The cells were incubated for an additional eight hours. After completion, the cells were counted with a hemocytometer, the media was removed after centrifugation, and the cells were rinsed with PBS (×3). The cells were then lysed with RIPA buffer, diluted with water, and heme was extracted using a 3:1 ethyl acetate:acetic acid solution. An aliquot of the organic extract was diluted in scintillation cocktail and radioactivity was determined. Radioactive levels were normalized per cell (counted by hemocytometer) relative to wild type (DS19) levels.

Figure 13I:
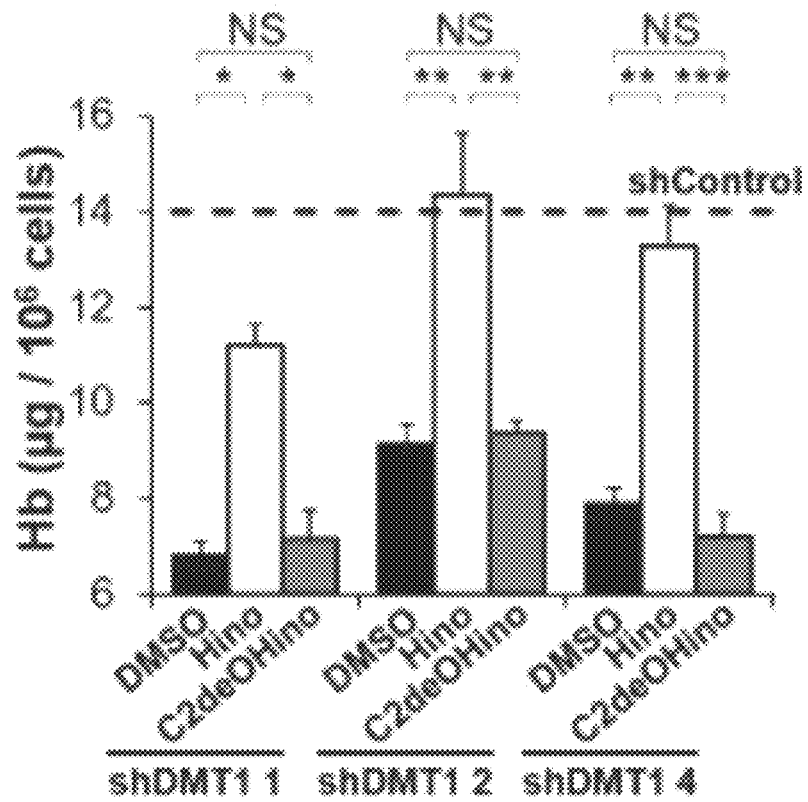
Figure 13J:
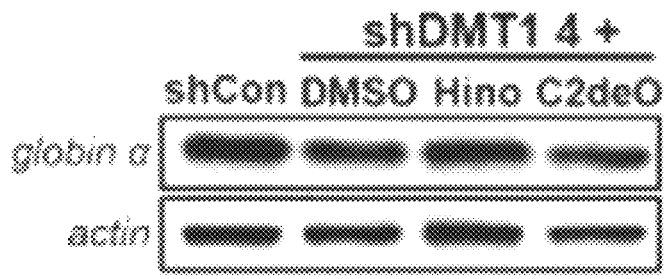
Figure 13K:
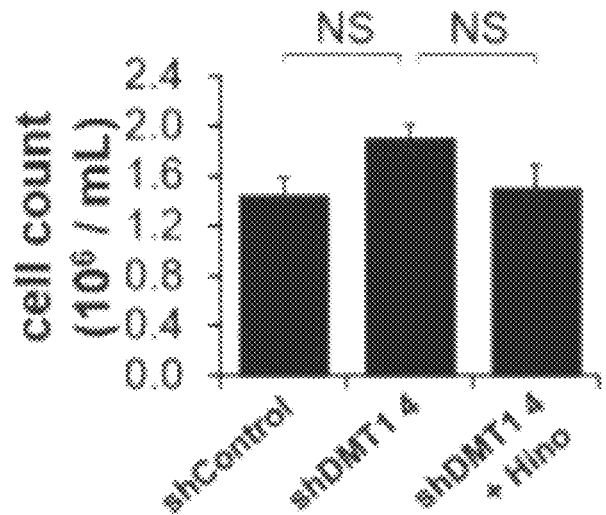
Figure 13L:
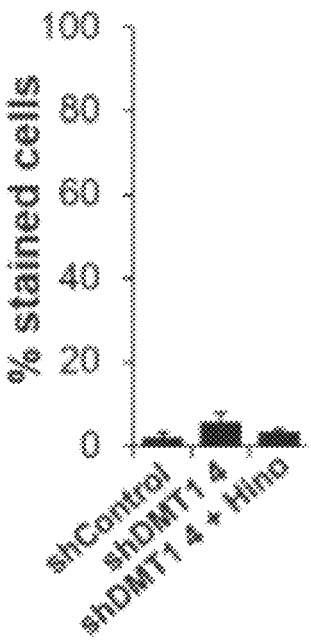

Determination of Hemoglobin Levels (FIG. 13I, J)

MEL cells were induced for differentiation as described above and incubated at 37° C. for 72 hours. After completion, the cells were counted with a hemocytometer, the media was removed after centrifugation, and cells were rinsed with PBS (×2). The cells were then lysed through repeated freeze/thaw cycles with water, and hemoglobin levels per 10$^6$ cells were determined as previously described (77) by determining the OD415 after centrifugation. Globin levels by western blot were determined after differentiation as described above. After incubation for 72 hours, cells were lysed and globin levels were determined by western blot as described above.

Knockdown of FPN1 in Caco-2 Cells and J774 Cells (FIG. 3H-K, FIG. 5D, FIG. 14G-M, and FIG. 19N-P)

To knockdown FPN1 levels in wild type Caco-2 cells, the differentiated epithelial monolayers were incubated with 150 µM quercetin (Sigma 337951) for 18 hours in Caco-2 Complete media containing G418 similar to previously described (40). To knockdown FPN1 levels in shControl and shDMT1 Caco-2 monolayers, incubation was performed as above except with 250 µM quercetin. After completion of the incubation, the apical and basolateral fluid was aspirated and rinsed with PBS before $^{55}$Fe transport and uptake were determined as described above.

To knockdown FPN1 levels in wild type J774 cells, the cells were incubated with 2 pg/mL mouse hepcidin (Peptides International PLP-3773-PI) for 1 hour in J774 Complete media similar to previously described (41) before $^{55}$Fe was loaded into J774 cells and $^{55}$Fe release was determined.

$^{55}$Fe Release from J774 Macrophages (FIG. 3J, K, FIG. 14M, and FIG. 23C, F)

J774 cells were grown in 12-well plates to ~80% confluency. The cells were then treated with vehicle or hepcidin in fresh J774 Complete media (1 mL) and incubated at 37° C. for 1 hour. After incubation, the media was aspirated, and then a $^{55}$Fe2Tf (50 nM) solution in J774 Complete media (1 mL) containing vehicle or hepcidin was added. The cells were incubated at 37° C. for 10 minutes, and the media was removed. The cells were rinsed with PBS (×2), and then rinsed with J774 Complete media (1 mL) for 10 minutes at 37° C. The media was aspirated, and J774 Complete media (1 mL) containing DMSO or small molecule (5 µM unless otherwise noted, 1000X dilution) was then added in the presence or absence of hepcidin. At the indicated times, aliquots (<100 µL) of the media were removed, diluted in scintillation cocktail, and radioactivity was determined by liquid scintillation counting. After completion of the experiment, the media was removed, the cells were rinsed with PBS, and the cells were lysed with 500 µL of 200 mM NaOH at 37° C. for 2 hours with continuous shaking (50 rpm). The cell lysate was diluted in scintillation cocktail and intracellular $^{55}$Fe levels were determined by liquid scintillation counting. The % $^{55}$Fe release was determined by the ratio of extracellular $^{55}$Fe to total (intracellular+ extracellular) $^{55}$Fe at the indicated times.

$^{55}$Fe Uptake into J774 Macrophages (FIG. 4D, E)

J774 cells were grown in 12-well plates to ~80% confluency. The cells were then treated with vehicle or hepcidin in serum-free DMEM media at pH=7.4 in 10 mM HEPES buffer (1 mL) containing 50 μM FeCl$_3$ (100:1 $^{56}$Fe:$^{55}$Fe). After four hours of incubation at 37° C., the cells were rinsed with PBS (×2), and lysed with 500 μL RIPA buffer containing protease inhibitors. The cell lysate was diluted in scintillation cocktail and intracellular $^{55}$Fe was determined by liquid scintillation counting and normalized to the total protein in each well.

Hinokitiol-promoted iron uptake as a function of extracellular iron (FIG. 4E) was performed similar to described above in wild type J774 macrophages using 1 μM hinokitiol (from 1000X stock in DMSO) and the indicated final concentration of FeCl$_3$ (20:1 $^{56}$Fe:$^{55}$Fe). At the indicated time, cells were rinsed with PBS (×2), and lysed with 200 mM NaOH. The cell lysate was diluted in scintillation cocktail and intracellular $^{55}$Fe was determined by liquid scintillation counting and normalized to the total protein in each well.

Live Cell Fluorescence Imaging of MEL Cells (FIG. 4A and FIG. 16A, B, E, H)

To visualize cytosolic and mitochondrial iron, confocal imaging of calcein green and RPA fluorescence was performed, respectively. MEL cells were induced for differentiation as described above. After 70 hours of incubation, iron (III) citrate (10 μM final concentration) was added. The cells were incubated for an additional 2 hours, and then were centrifuged and rinsed with PBS. The cells were then re-suspended in PBS containing 1 μM calcein green-AM (Thermo Fisher C34852) and 1 μM RPA (Axxora SQX-RPA.1). The cells were then incubated at 37° C. for 15 minutes. The cells were centrifuged, rinsed with PBS, and re-suspended in DMEM containing 10 μM Fe2Tf. The cells were then imaged within 10 minutes on a LSM710 microscope. Relative calcein green and RPA fluorescence per cell was determined by ImageJ analysis using >100 cells per experiment.

To visualize endosomal iron levels, confocal imaging of an oxyburst green-BSA conjugate (Thermo Fisher 013291) was performed. MEL cells were induced for differentiation as described above. After 70 hours, iron (III) citrate (10 μM final concentration) and an oxyburst green-BSA conjugate (200 μg/mL) were added. The cells were incubated for an additional 2 hours, and then were centrifuged and rinsed with PBS. The cells were then re-suspended in DMEM-HEPES buffer, and H2O2 (50 mM final concentration) was added. The cells were incubated at room temperature, and the oxyburst green fluorescence was then determined 10 minutes after addition of H2O2 on a LSM710 microscope. Relative oxyburst green fluorescence per cell was determined by ImageJ analysis using >100 cells per experiment.

Figure 16C:
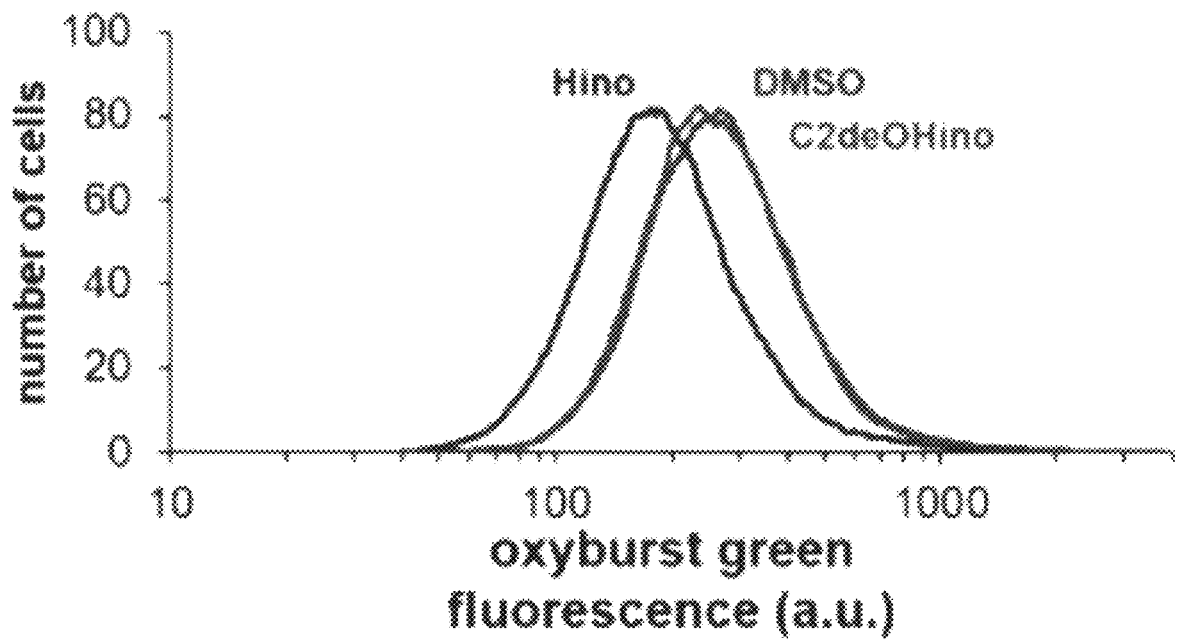
Figure 16D:
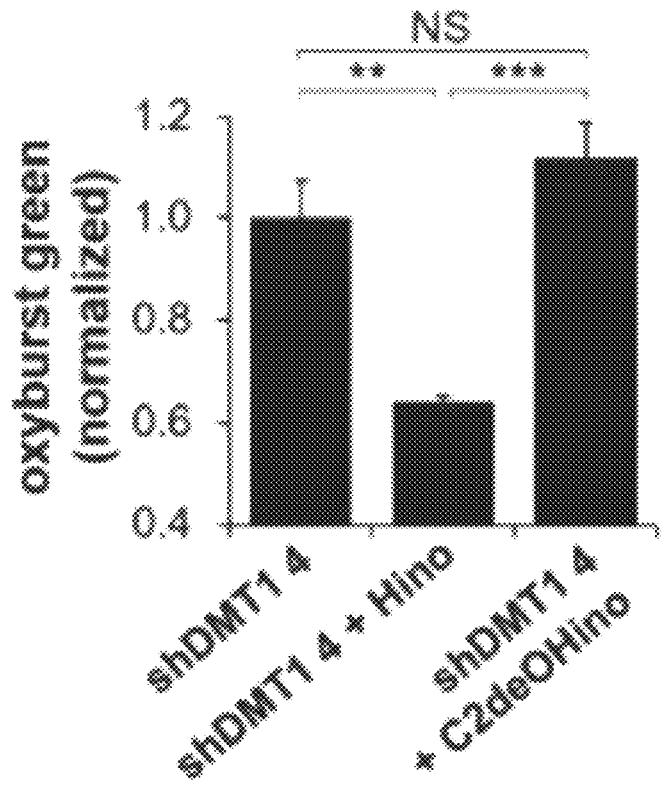
Figure 16E:
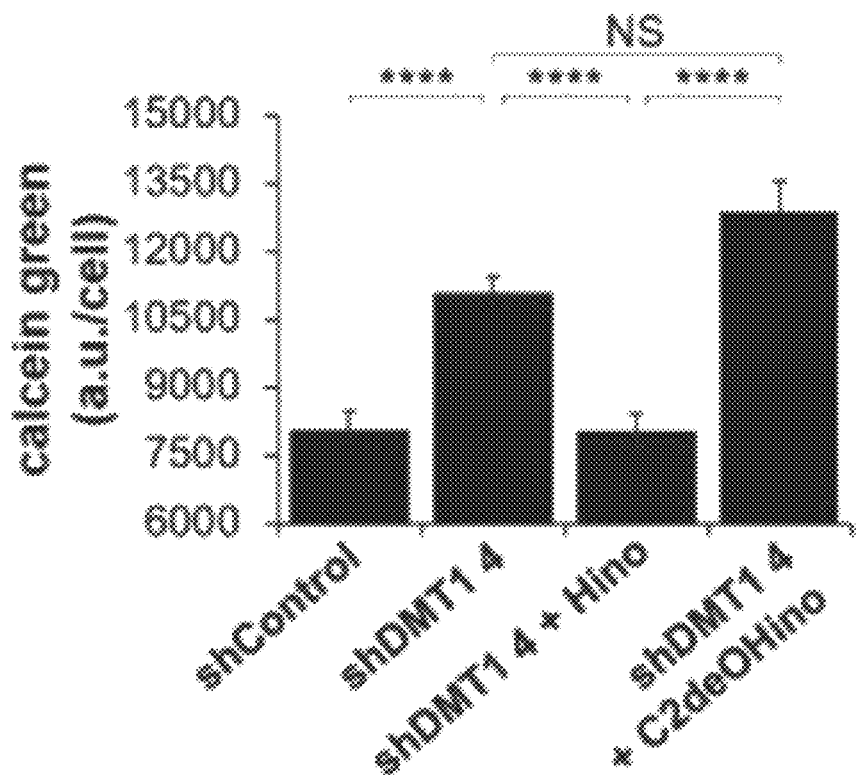
Figure 16F:
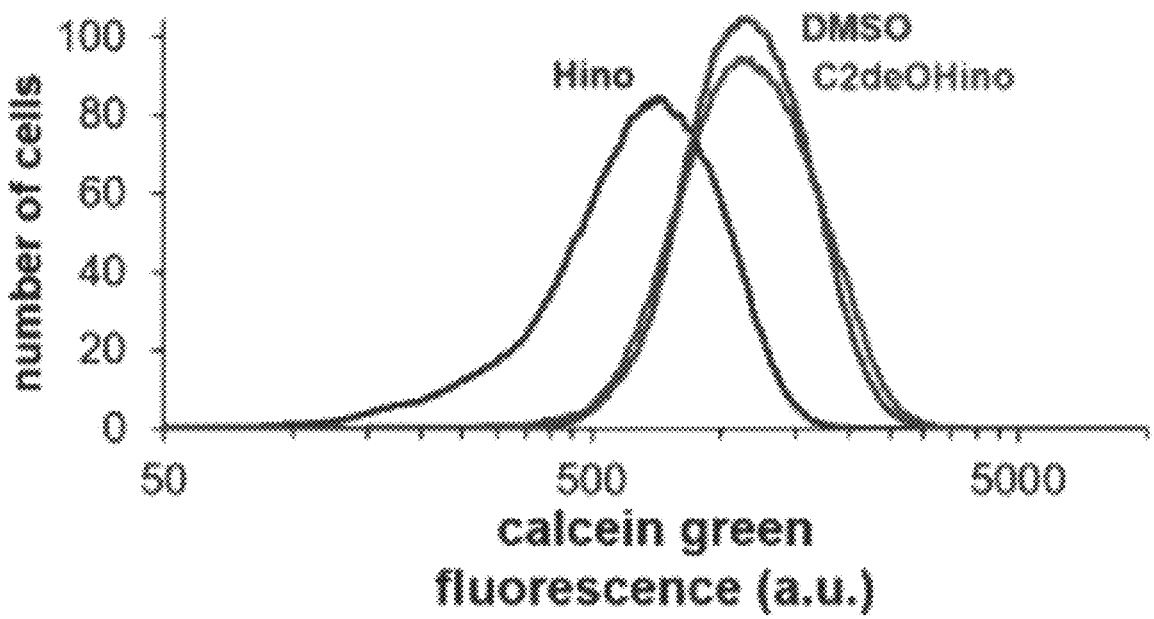
Figure 16G:
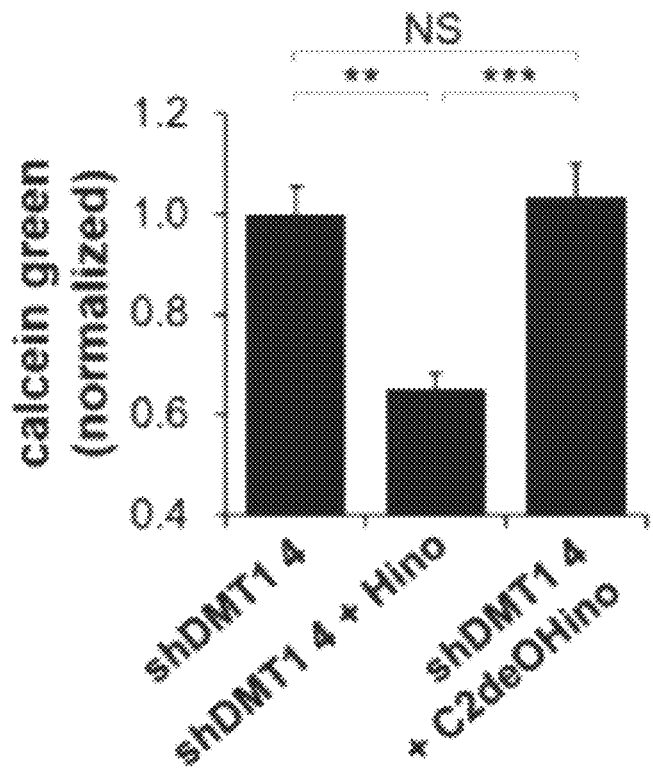
Figure 16H:
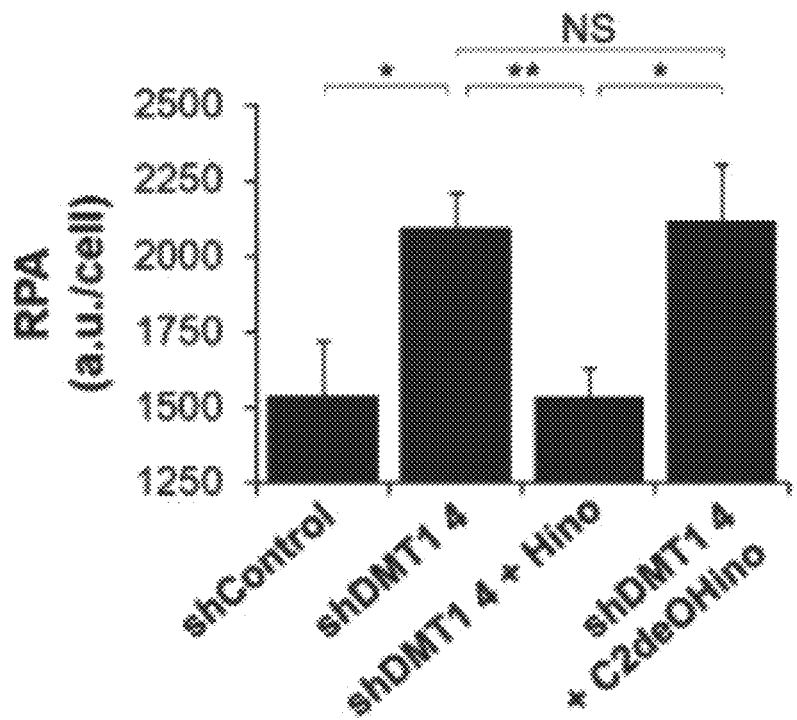
Figure 16I:
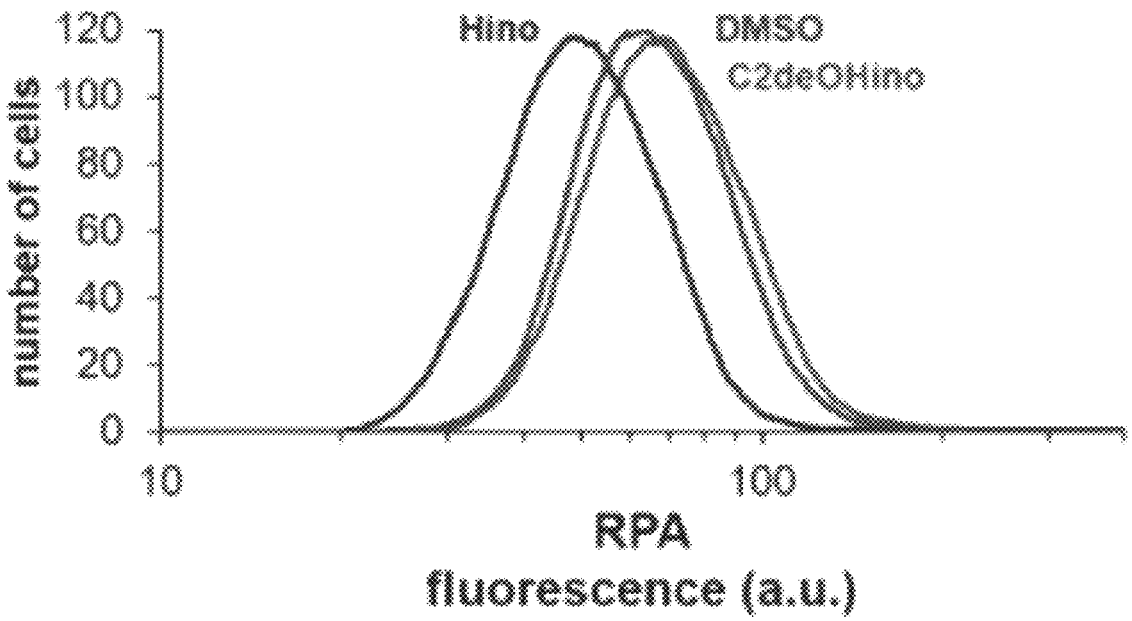
Figure 16J:
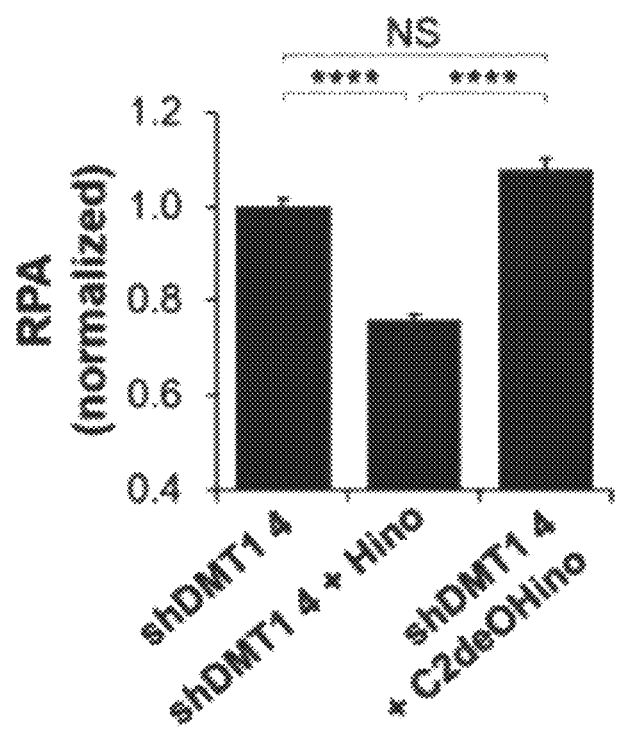

Flow Cytometry of MEL Cells (FIG. 16C, D, F, G, I, J)

To quantify median cellular calcein green and RPA fluorescence by flow cytometry, staining of cells was performed as described above except for the use of 0.1 μM calcein green-AM and 0.1 μM RPA. Calcein green and RPA fluorescence was then determined using a BD FACS Aria II Sorter at 37° C. counting >10,000 cells per experiment. Median fluorescence was then normalized to shDMT1 for each dye.

To quantify median cellular oxyburst green fluorescence by flow cytometry, staining of cells was performed as described above except for the use of 500 μg/mL oxyburst green-BSA conjugate, the use of 5 mM H2O2, and cells were incubated for 20 minutes at 37° C. after addition of H2O2 before fluorescence analysis using a BD LSR II flow cytometer counting 20,000 cells per experiment. Median fluorescence was then normalized to shDMT1 for each dye.

Figure 18A:
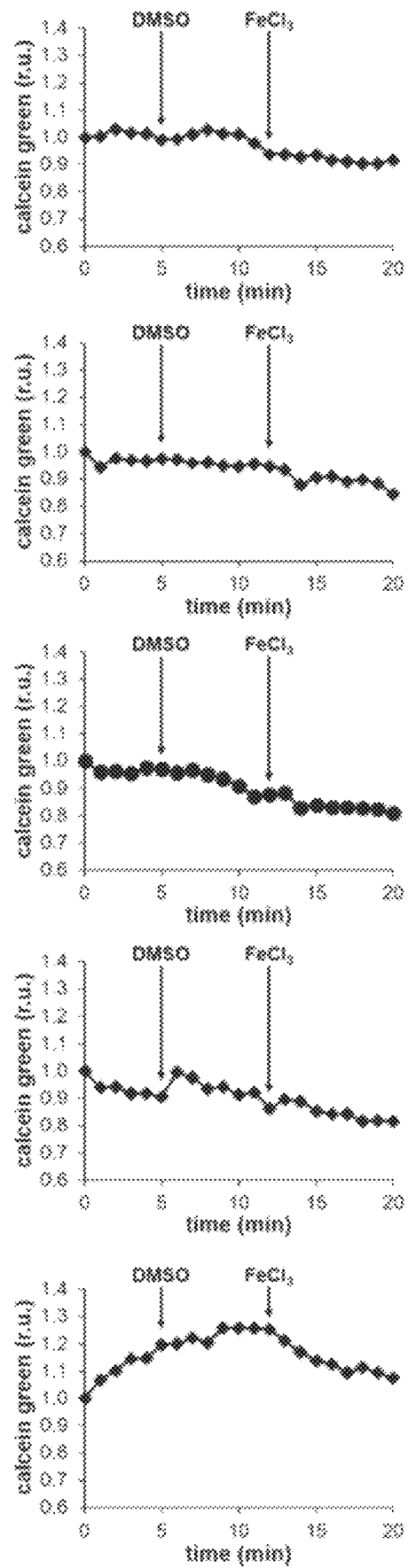
FIGS. 18A-18C show hinokitiol directionally transports iron as a function of transmembrane iron gradients. (A-C) Representative ImageJ quantification of calcein green fluorescence to detect changes in cytosolic labile iron levels over time. Wild type J774 cells were loaded with FeSO$_4$ (200 µM). At t=0 min the extracellular media was replaced for a low iron media (<500 nM) before addition of (A) DMSO, (B) 100 µM hinokitiol, or (C) 100 µM C$_2$deOHino at 5 minutes. An increase in calcein green fluorescence was observed in hinokitiol treated cells, consistent with hinokitiol-mediated release of iron from these cells. The gradient was then reversed by extracellular addition of FeCl$_3$ (100 µM) to the same cells at 12 minutes, and fluorescence quenching was alternatively observed in the hinokitiol treated cells. This data is consistent with initial hinokitiol-mediated release of iron from iron-loaded J774 cells, followed by hinokitiol-mediated iron uptake after addition of extracellular iron at t =12 min.
Figure 18B:
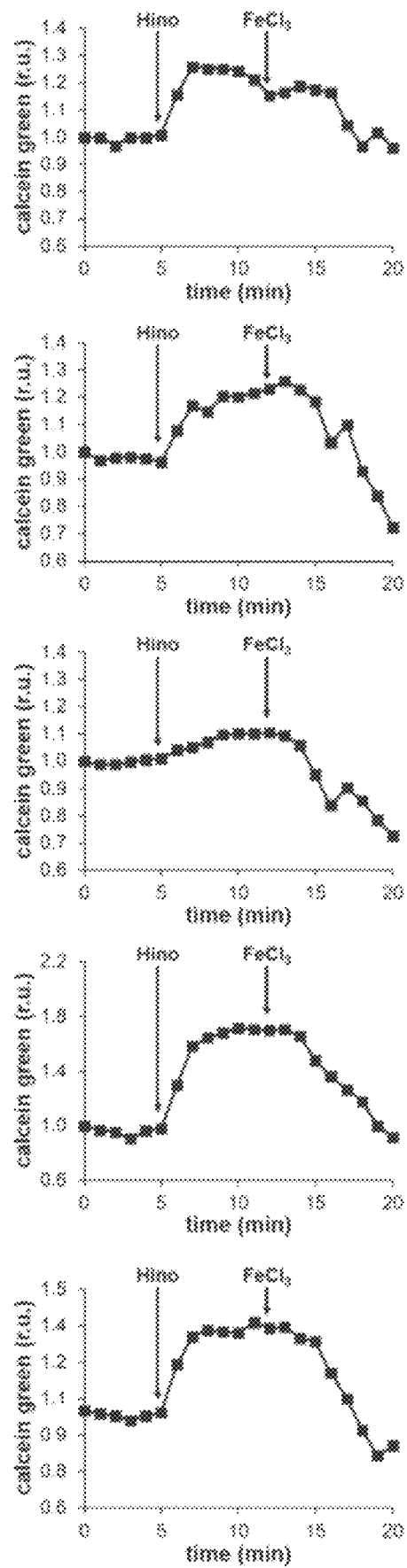
Figure 18C:
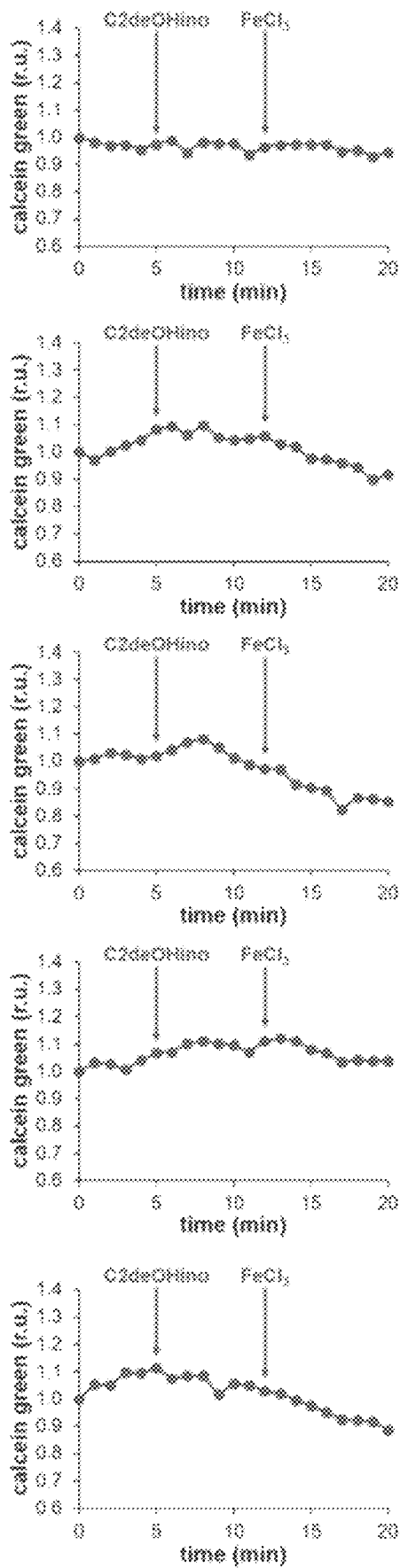

Temporal Imaging of Cytosolic Iron Levels in J774 Macrophages (FIG. 4B, C, H, I, FIG. 18A-C)

To assess for the capacity for hinokitiol to reversibly and autonomously transport iron across the plasma membrane through the creation of artificial iron gradients, J774 macrophages were grown in Ibidi dishes (Ibidi NC0723624) to ~80% confluency before incubation with J774 Complete media containing 5 mM ascorbic acid and 200 μM FeSO$_4$. The cells were incubated for 1.5 hours, media was aspirated, and the cells were rinsed with PBS. The cells were then incubated with calcein green-AM (1 μM) in DMEM for 20 minutes at 37° C. The media was aspirated and cells were rinsed (×2) with PBS before DMEM (pH=7.4 in 10 mM HEPES) and 1 mM probenecid (Sigma P8761) was added. Calcein green fluorescence was then imaged on a LSM880 microscope at 37° C. with 5% CO$_2$ at the indicated time points for 30 minutes. Hinokitiol (100 μM final concentration), C$_2$deOHino (100 μM final concentration), or DMSO (all from 1000X stocks in 50 μL DMEM) were added at 5 minutes, and a solution of FeCl$_3$ (100 μM final concentration, in 50 μL DMEM) was added at 12 minutes. Fluorescence in each image at each time point was analyzed by ImageJ analysis then normalized to the fluorescence at t=0 for each image using >100 cells per experiment.

Temporal live cell imaging of iron uptake in wild type and FPN1-deficient J774 cells was performed after staining of cells with calcein green as described above. The cells were then rinsed with PBS (×2), and incubated in J774 Complete media containing 200 μM FeSO4, 5 mM ascorbic acid, and 5 mM probenecid in the presence or absence of hepcidin. Calcein green fluorescence was obtained at the indicated time points, and fluorescence in each image at each time point was quantified by ImageJ analysis then normalized to the fluorescence at t=0 for each image using >100 cells per experiment.

Temporal Imaging of Cytosolic Iron with Calcein Green in Caco-2 Monolayers (FIG. 5H-J)

Temporal live cell imaging of labile iron levels in shDMT1 Caco-2 monolayers was performed after staining of Caco-2 monolayers with calcein green-AM (5 μM) in the apical and basolateral liquid for 30 minutes in pH=7.4 DMEM. After rinsing with PBS (×2 apically and basolaterally), monolayers were treated similar to Caco-2 transport experiments with a pH=7.4 HEPES buffer in DMEM (basolateral) and an apical fluid (pH=5.5 MES buffer in DMEM) containing 25 μM FeCl$_3$ and either 0, 0.5, 1, 3, 5, 10, 25, or 50 μM hinokitiol (from 1000×stocks in DMSO). Calcein green fluorescence was obtained at t=0 min and t=60 min, and the fluorescence in each image was quantified by ImageJ analysis. $^{59}$Fe gut absorption (FIG. 6A, B and FIG. 24A-C)

To characterize the effects of hinokitiol on the gastrointestinal absorption of iron in healthy (+/+) and ffe/+ mice, food was withheld for 4 hours (8 am to 12 Pm) prior to intragastric gavage. The mice were anesthetized with up to 2% isoflurane, and $^{59}$FeCl$_3$ was administered using a 20-gauge, 1.5-inch gavage needle. $^{59}$FeCl$_3$ (200 ρCi/kg body weight) was diluted in Tris-buffered saline containing 10 mM ascorbic acid in the presence or absence of 6 mM hinokitiol. Final volume administered was 1.5 mL/kg for each mouse, correcting for individual body weight. Blood was collected at 60, 120, and 240 min after administration to determine $^{59}$Fe levels. Mice were humanely sacrificed by isoflurane overdose after 6 hours and blood was collected by cardiac puncture. Radioactivity was quantified by gamma counting and calculated as the percentage of gavaged dose (±SEM). Experiments were performed with 4 genotyped-matched mice/day; preliminary analysis determined there were no gender effects on uptake of $^{59}$Fe after intragastric gavage; mixed genders were used in the experiments shown.

[59]Fe gastrointestinal absorption of iron in 3-5-month-old b/b rats was characterized similar to the procedure described above in the presence of either 6 mM hinokitiol or 6 mM C₂deOHino. To compare with the rate of normal iron uptake, age-matched sibling control (+/+ or +/b) Belgrade rats were tested by the same procedure except that $^{59}$Fe was administered without small molecule. Blood (50 µL) was taken from the tail vein at 15, 30, 60, 120, 180, 240, and 360 minutes post administration. Radioactivity was quantified by gamma counting and calculated as the percentage of gavaged dose (±SEM). Animals were humanely euthanized at 6 hours.

Figure 24D:
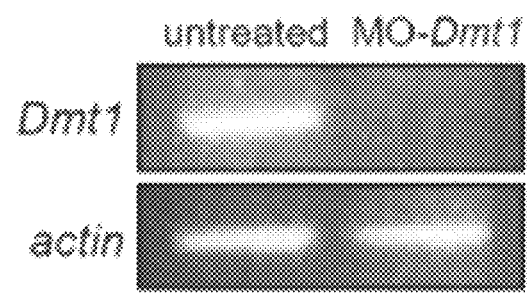
Figure 24E:
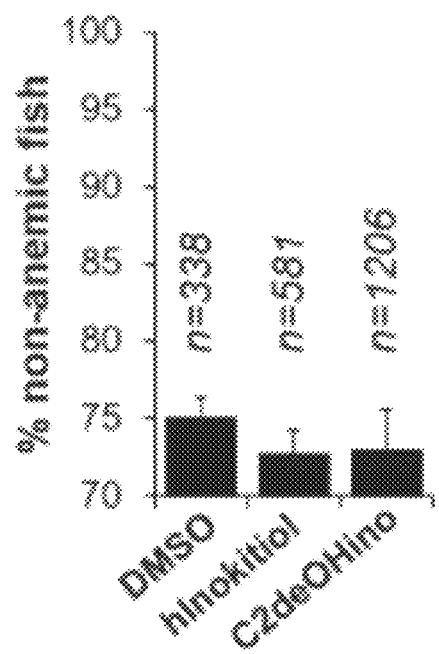
Figure 25A:
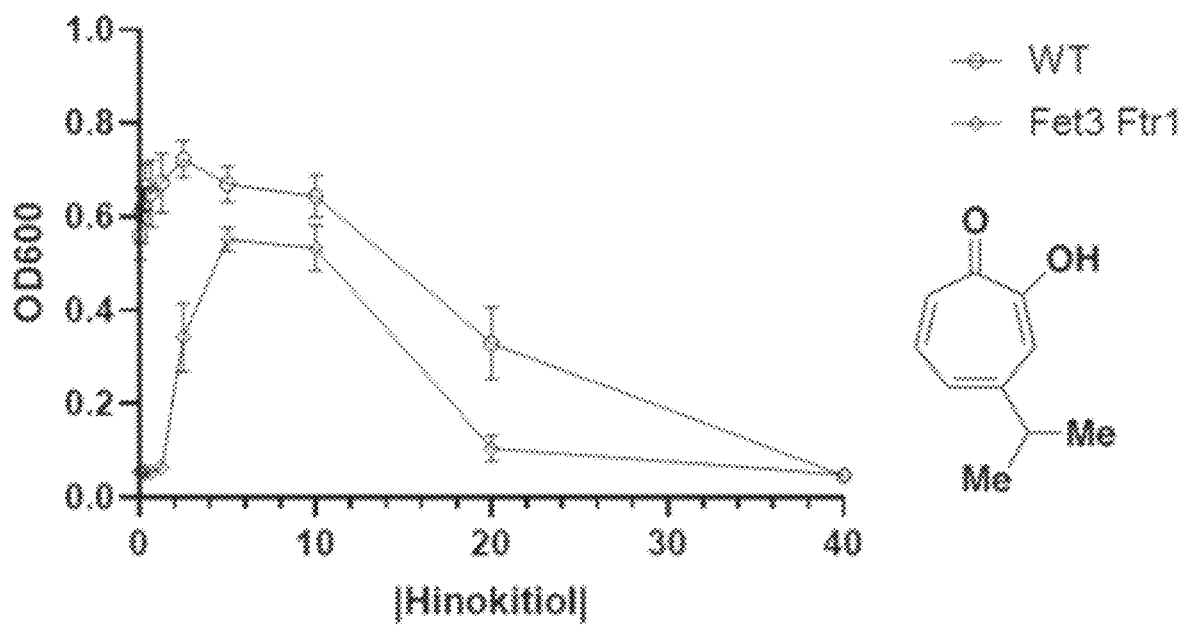
FIGS. 25A-25D show the results of structure-activity relationship studies identifying a window for the optimum size of the hydrocarbon substituent on the tropolone ring for activity replacing missing protein iron transporter function. (A) Hinokitiol rescues growth of iron transporter-deficient yeast (Fet3Ftr1) at low concentrations, and kills wild-type yeast (WT) only at high concentrations. (B) Tropolone shows rescue of Fet3Ftr1 yeast, but only at higher concentrations, and does not show toxicity to either wild type yeast or rescued Fet3Ftr1 yeast. (C) C2deOHino, which does not bind or transport iron, has no biological activity in either yeast strain. (D) 4-isopentyl tropolone, a synthesized derivative with an extended alkyl chain (5 carbons, two methylenes inserted into the hino side chain), shows no rescue of Fet3Ftr1 yeast, and is the most toxic to wide type yeast.
Figure 25B:
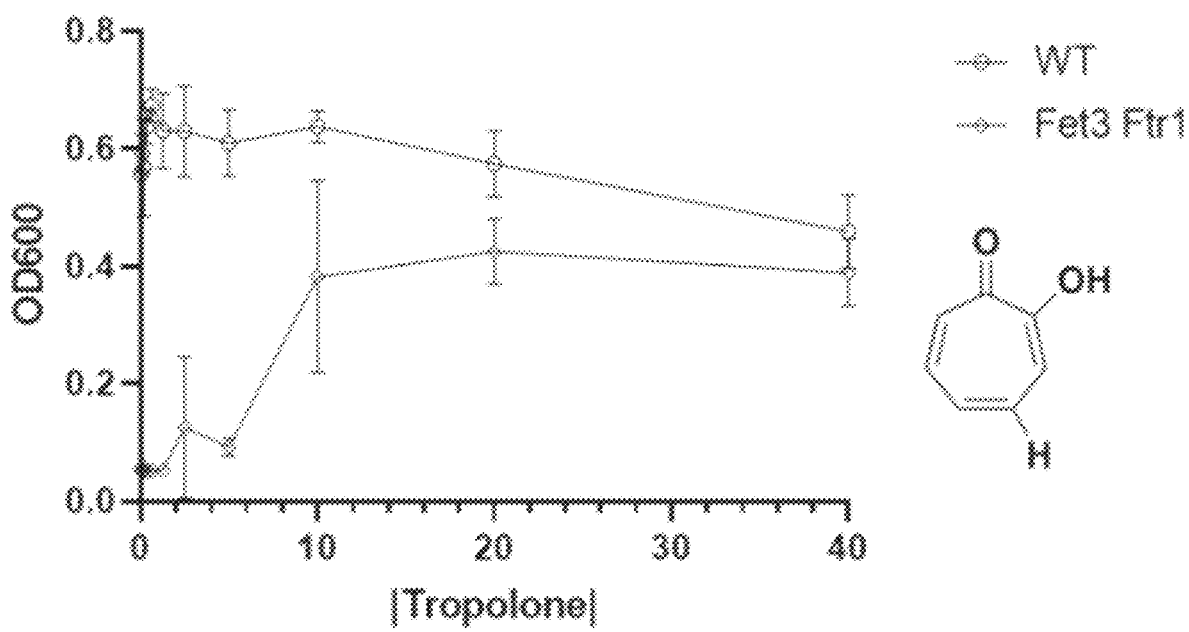
Figure 25C:
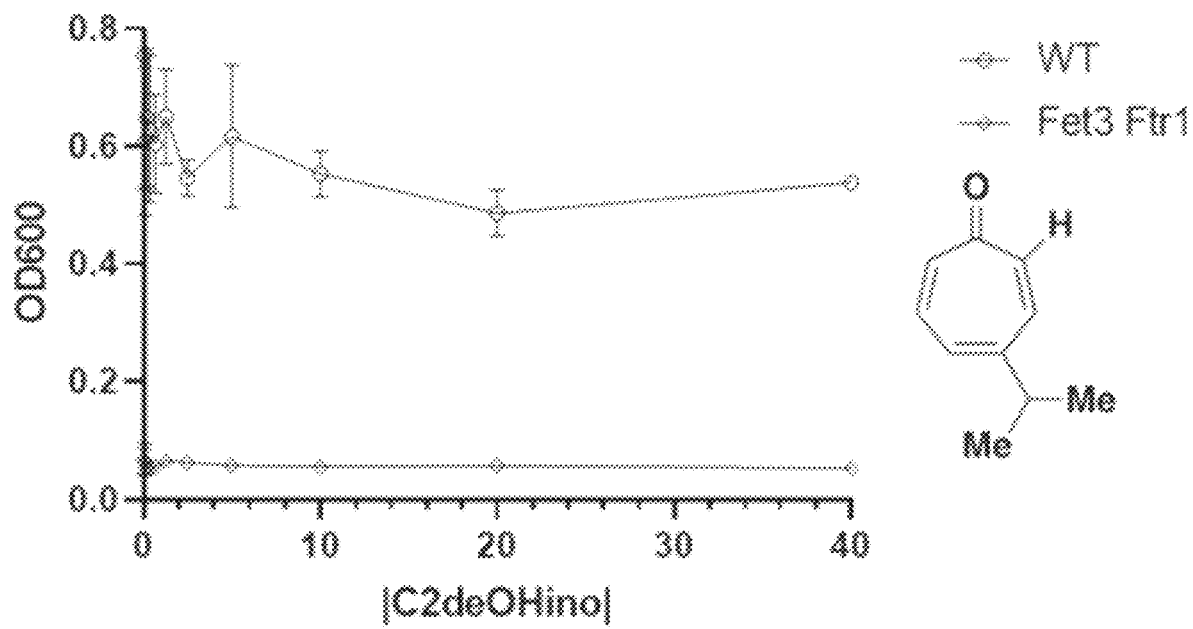
Figure 25D:
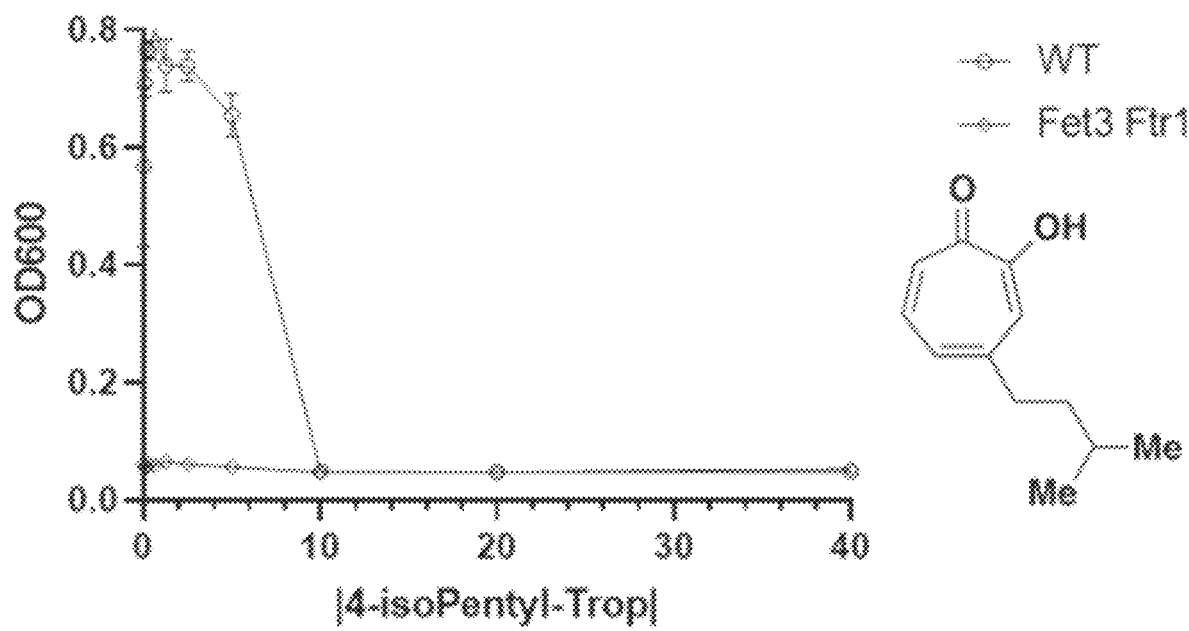

Knockdown in Morphant Zebrafish (FIG. 6C, E and FIG. 24D)

The morpholinos (MOs) were purchased from GeneTools, LLC (Philomath, OR). The sequences of the MO used were as follows: dmt1 MO: 5'-GAGTGT-GAAACGTGACGCACCCCTT-3'; mfrn1 MO: 5'-TAAGTTGCATTACCTTGACTGAATC-3'. Zebrafish embryos at the 1-cell stage were injected with MOs as previously described (72, 78). o-dianisidine staining for hemoglobinized cells in embryos was as previously described (79). Quantification by flow cytometry using fluorescently labeled erythrocytes from the transgenic Tg(globinLCR:eGFP) line (50) was performed as previously described (72, 75). Semi-quantitative RT-PCR of dmt1 mRNA in morphants was performed using custom designed probes as previously described (80). The sequences of the dmt1 primers are as follows: 5'-CT-GAACCTGCGCTGGTCCC-3' (Fwd); 5'-TCCGT-TAGCGAAGTCGTGCATG-3' (Rev). The sequences of the control actb primers were as follows: 5'-GTTGGTATGGGACAGAAAGACAG-3' (Fwd); 5'-ACCAGAGGCATACAGGGACAG-3' (Rev).

Restored Hemoglobinization in Transporter-Deficient Zebrafish (FIG. 6C-F and FIG. 24E)

Either mutant or morphant embryos were allowed to develop to >24 hours post fertilization (hpf), then dechorionated with pronase as previously described (81). The dechorionated embryos or morphants were then incubated in the presence of 1 µM hinokitiol (or vehicle) and 10 µM iron (III) citrate for an additional forty-eight hours. Vehicle treated embryos were exposed to 0.01 mM DMSO. C₂deOHino (1 µM) with iron (III) citrate (10 µM) was used as a negative control. Control and either mutant or morphant embryos at ~72 hpf were either (a) directly stained by o-dianisidine (79) or (b) mechanically homogenized as previously described for flow cytometry (75, 78).

Figure 6G:
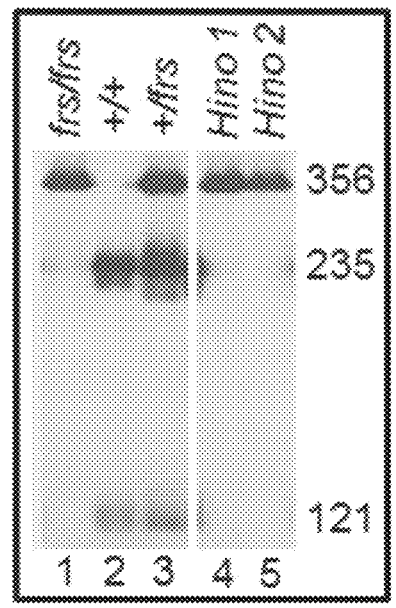
Figure 6H:
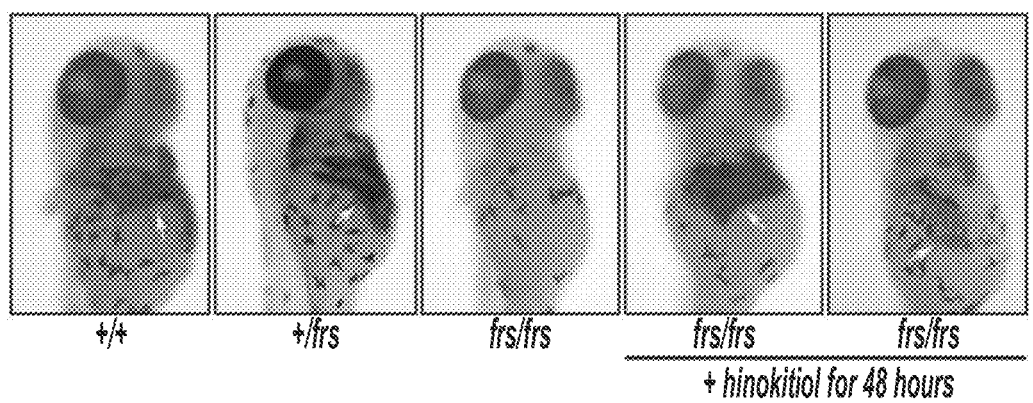

Genotyping and Imaging of Mutant Zebrafish from Heterozygous Cross (FIG. 6G, H)

Genotyping of the hinokitiol-rescuedfrstq223 embryos were performed as previously described (10).

Synthesis and Characterization of Small Molecules

Materials

Commercial reagents were purchased from Sigma-Aldrich and were used without further purification unless otherwise noted. Solvents were purified via passage through packed columns as described by Pangborn and coworkers (82). All water was deionized prior to use.

General Experimental Procedures

Unless otherwise noted, reactions were performed in flame-dried round-bottomed or modified Schlenk flasks fitted with rubber septa under a positive pressure of argon. Organic solutions were concentrated via rotary evaporation under reduced pressure with a bath temperature of 20-35° C. unless otherwise noted. Reactions were monitored by analytical thin layer chromatography (TLC) using the indicated solvent on E. Merck silica gel 60 F254 plates (0.25 mm). Compounds were visualized by exposure to a UV lamp (λ=254 nm or 366 nm), and/or a solution of KMnO₄ stain, followed by heating using a Varitemp heat gun. Flash column chromatography was performed using Merck silica gel grade 9385 60 Å (230-240 mesh). Preparative HPLC purification was performed using an Agilent 1260 Infinity series preparative HPLC with a SunFire 5 µm C18 column (Waters Corporation).

Structural Analysis

1H NMR, $^{13}$C NMR, and $^{19}$F NMR were recorded at 20° C. on Unity Inova 500NB, Varian XR500, or Unity 500 instruments. Chemical shifts (δ) are reported in parts per million (ppm) downfield from tetramethylsilane and referenced to residual protium in the NMR solvent (CHCl3, δ=7.26; DMSO-d6, δ=2.50). Data are reported as follows: chemical shift, multiplicity (s=singlet, d=doublet, t=triplet, m=multiplet, app=apparent), coupling constant (J) in Hertz (Hz), and integration. $^{13}$C NMR are referenced to carbon resonances in the NMR solvent (CDCl3, δ=77.16; DMSO-d6, δ=39.52). $^{19}$F NMR are referenced to fluorine resonance in an external standard (CFCl3, δ=0.00)

Iron (III) Hinokitiol Complex

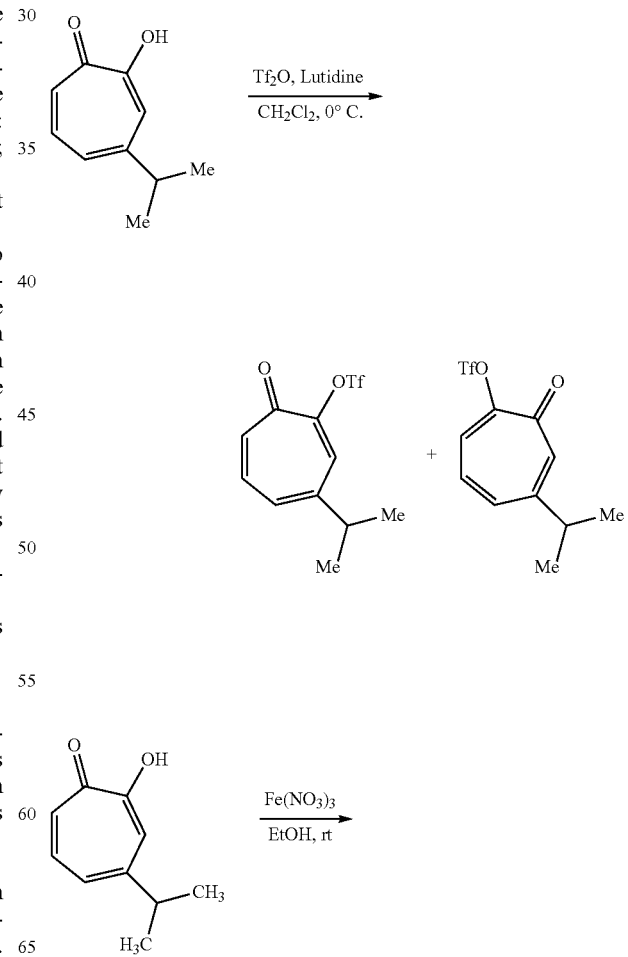

-continued

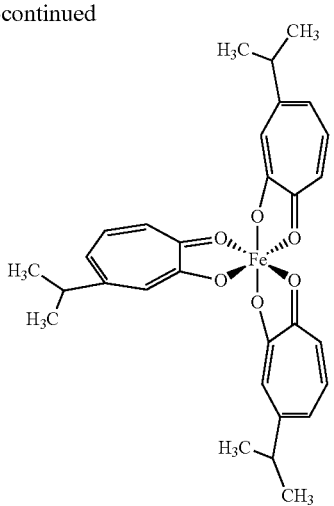

To a flame-dried 20-mL vial equipped with a stir bar was added iron (III) nitrate nonahydrate (819.8 mg, 2.03 mmol) followed by hinokitiol (1.0092 g, 6.15 mmol). Then ethanol (10 mL) was added. The reaction was vigorously stirred for 2 hours to give a purple colored suspension. The product was collected via filtration and recrystallized in acetone to yield the product as a purple solid (959.9 mg, 1.76 mmol, 86.7% yield).

HRMS (ESI+)
Calculated for $C_{30}H_{34}O_6Fe$ (M+H)+:546.1705; Observed:546.1703
Elemental Analysis
Calculated [C]: 66.06%; Observed [C]: 65.88%
Calculated [H]: 6.10%; Observed [H]: 6.21%
Calculated [Fe]: 10.24%; Observed [Fe]: 10.19%

Triflation of Hinokitiol

To an oven-dried 300 mL round-bottomed flask equipped with a stir bar was added hinokitiol (3.014 g, 18.27 mmol) followed by anhydrous CH2Cl2 (200 mL). The system was put under nitrogen, and freshly distilled lutidine (2.54 mL, 21.92 mmol) was added via syringe. The system was cooled to 0° C. in an ice/water bath before triflic anhydride (3.38 mL, 20.10 mmol) was added dropwise via syringe. The solution was stirred for 15 minutes at 0° C., then allowed to warm to room temperature and stirred for an additional 3 hours. After completion, the reaction was quenched with a saturated aqueous $NH_4Cl$ solution. The product was extracted in $CH_2Cl_2$, washed with $CuSO_4$, washed with brine, and dried over anhydrous MgSO4. The product was filtered and solvent removed by rotary evaporation. The product was then purified as an inseparable mixture of the C-2 and C-7 isomers by flash column chromatography (3:1 Hexane:EtOAc) to yield a slightly colored oil (4.819 g, 16.27 mmol, 88.6% yield as a 53:47 mixture of the C-2 and C-7 isomers).

TLC (1:1 Hex:EtOAc)
Rf=0.68, visualized by UV (254 nm) and KMnO4 stain
1H NMR (500 MHz, CDCl3)
δ 7.34-7.24 (m, 5H), 7.14 (dt, J=11.5, 0.7 Hz, 1H), 7.08 (dt, J=8.6, 0.6 Hz, 1H), 6.99 (dd, J=11.4, 9.4 Hz, 1H), 2.91-2.80 (app. m, 2H), 1.26 (d, J=6.8 Hz, 6H), 1.26 (d, J=6.8 Hz, 6H) 13C NMR (126 MHz, CDCl3)
δ 178.0, 177.7, 158.7, 155.9, 152.3, 139.0, 138.2, 137.9, 137.8, 131.9, 129.9, 129.3, 127.6, 38.8, 38.2, 22.9, 2.8
19F NMR (470.2 MHz, CDCl3)
δ-74.76,-74.84

HRMS (ESI+)
Calculated for $C_{11}H_{12}F_3O_4S$ (M+H)*: 297.0408; Observed: 297.0408

Hydrogenolysis of Hinokitiol-Triflate

Sodium acetate (1.11 g, 13.4 mmol), the triflated hinokitiol (2.00 g, 6.76 mmol), 10 wt % palladium on carbon (71.8 mg) and methanol (75 mL) were added to a flame-dried 200 mL round-bottomed flask containing a stir bar. The suspension was degassed with $N_2$, then put under a H2 atmosphere without bubbling H2 through the solution. The reaction was stirred and analyzed by TLC ($Et_2O$) for 30 minutes. After completion, $N_2$ was bubbled through the system, and the black suspension was filtered over celite. The methanol was removed by rotary evaporation, and the product was extracted in diethyl ether and washed with brine. After drying with anhydrous MgSO4, the solvent was removed by rotary evaporation to yield a slightly colored oil. The product was purified by preparative HPLC (283 nm, 20% MeCN in H2O) to yield C2-deoxyhinokitiol and C7-deoxyhinokitiol as clear oils (C2deOHino: 325 mg, 2.21 mmol, 32.4% yield; C7deOHino: 204 mg, 1.38 mmol, 20.4% yield).

TLC ($Et_2O$)
Rf=0.49, visualized by UV (254 nm) and KMnO4 stain
1H NMR (500 MHz, CDCl3)
δ C2: 7.10-6.97 (m, 3H), 6.91 (ddd, J=12.0, 2.6, 0.8 Hz, 1H), 6.81 (ddd, J=8.7, 1.5, 0.7 Hz, 1H), 2.73 (heptet, J=6.8 Hz, 1H), 1.19 (d, J=6.9 Hz, 6H)
δ C7: 7.09-7.01 (m, 3H), 6.93-6.92 (m, 2H), 2.74 (heptet, J=6.8 Hz, 1H), 1.21 (d, J=6.9 Hz, 6H)
13C NMR (126 MHz, CDCl3)
δ C2: 188.0, 156.2, 141.9, 140.1, 138.1, 137.2, 130.5, 38.1, 23.0
δ C7: 188.0, 157.4, 141.9, 138.7, 137.1, 136.1, 133.8, 38.4, 22.9
HRMS (ESI+)
Calculated for C10H13O (M+H)+: 149.0966; Observed: 149.0973

Synthesis of Salicylaldehyde Isonicotinoyl Hydrazone

Isonicotinic hydrazide (198 mg, 1.4 mmol) was added to a flame-dried 7 mL vial containing a stir bar and EtOH (3 mL). Salicylaldehyde (175 mg, 1.4 mmol) was then added dropwise via syringe. The solution was stirred at 75° C. under $N_2$ for 6 hours. The solution was cooled to 0° C., and the solid was collected by vacuum filtration. The product was rinsed with cold EtOH, and recrystallized in EtOH to yield a white solid after vacuum filtration (237 mg, 1.0 mmol, 69% yield, >95% pure). Characterization matched that to previously reported (83).

TLC (EtOAc)
Rf=0.38, visualized by UV (254 nm) and KMnO4 stain
1H NMR (500 MHz, DMSO-d6)
δ 11.08 (s, 1H), 8.80 (dd, J=4.5, 1.7 Hz, 2H), 8.68 (s, 1H), 7.85 (dd, J=4.4, 1.7 Hz, 2H), 7.61 (dd, J=7.7, 1.7 Hz, 1H), 7.32 (ddd, J=8.2, 7.2, 1.7 Hz, 1H), 6.97-6.90 (m, 2H),–1.76 (s, 1H)
13C NMR (126 MHz, DMSO-d6)
δ 161.4, 157.5, 150.4, 149.0, 140.0, 131.8, 129.3, 121.6, 119.5, 118.7, 116.5
HRMS (ESI+)
Calculated for $C13H12N_3O_2$ (M+H)+: 242.0930; Observed:242.0924

Definition of Ion-Transport Proteins

As used herein, "ion-transport proteins" is taken to mean proteins used by the cell to transport ions across membranes, and we further bifurcate these into "active ion-transport proteins" and "passive ion-transport proteins". With the phrase "active ion-transport proteins" we mean to define those that transport ions against their electrochemical gradient by coupling the 'uphill' transport process to an energy source such as ATP (primary active) or the 'downhill' movement of another ion or substrate molecule (secondary active). These active ion-transport proteins are often alternatively referred to as "pumps" or "exchangers". With the phrase "passive ion-transport proteins" we mean to describe protein ion channels and other ion-transport proteins that are passive, simply catalyzing the downhill movement of ions. These passive ion-transport proteins are often alternatively referred to as "channels" and/or "(passive) transporters".

Tables

TABLE 1

Disorders of iron absorption, homeostasis, and metabolism. Noninclusive list of hereditary diseases in humans that are associated with defective iron absorption, homeostasis, and metabolism. These diseases can broadly be separated into three categories: (i) Diseases of defective iron absorption, (ii) Diseases of iron-related proteins associated with aberrant tissue iron levels, and (iii) Secondary disorders associated with aberrant tissue iron levels. In addition to other effects, these diseases are associated with abnormal levels of iron in certain subcellular compartments, cells, or tissues, in which a small molecule iron transporter may be helpful in ameliorating the effects of the abnormal iron homeostasis.

| Mendelian Disease | Gene Affected | Sites of aberrant iron levels | Reference |
|---|---|---|---|
| DISEASES OF DEFECTIVE IRON ABSORPTION | | | |
| Hypochromic, Microcytic Anemia | DMT1 | Decreased iron absorption; decreased iron in entrocytes; increased iron in endosomes; increased hepatic iron | 6, 86 |
| Erythropoietic Protoporphyria | Mfrn1 | Predicted decrease of iron in mitochondrial matrix; predicted increase of iron in intermembrane space | 87 |
| Ferroportin Disease | FPN1 | Increased iron in enterocytes: increased iron in Kupffer cells | 88, 89 |
| Iron Refractor Iron Deficiency Anemia | TMPRSS6 | Increased iron in enterocytes; increased iron in Kupffer cells | 89 |
| Hemochromatosis | DcytB | Predicted decrease of iron absorption | 90 |
| Inflammatory Bowel Disease | Multiple | Increased iron in enterocytes; increased iron Kupffer cells | 8, 9 |
| Rheumatoid Arthritis | HLA | Increased iron in enterocytes; increased iron Kupffer cells | 8, 9 |
| DISEASES OF IRON-RELATED PROTEINS ASSOCIATED WITH ABERRANT TISSUE IRON LEVELS | | | |
| Hemochromatosos Type 1-3 | HFE3, HFE2, HAMP, TfR2 | Increased iron abssorption; inclased hepatic and cardiac iron | 6-8 89, 90 |
| Friedreich's Ataxia | Frataxin | Increased iron in mitochondria | 6, 8, 91 |
| Erytrhopoietic Protoporphyria | Ferrochelatase | Increased iron in mitochondria | 92 |
| Aceruloplasminemia | Ceruloplasmin | Increased iron in hepatocytes, brain, and pancreas | 6-8, 89, 90 |
| Neuroferritinopathy | FTL1 | Increased iron in basal ganglia of brain | 91, 93, 94 |
| Congenital Hypochromic Anemia | STEAP3 | Predicted increase of endosomal iron; increased hepatic iron | 95 |
| FTH1-Related iron Overload | FTH1 | Increased iron in liver, spleen; increased serum iron | 96 |
| Hepatic Iron-Overload Insulin-Resistance Syndrome | HFE | Increased FPN1; increased iron in hepatocytes | 91, 97 |
| SECONDARY DISORDERS ASSOCIATED WITH ABERRANT TISSUE IRON LEVELS | | | |
| Wilson's Disease | ATP7B | Increased iron in liver | 8 |
| Menkes Disease | ATP7A | Increased iron in liver; increased iron deposition in the brain | 8 |
| Familial Porphyria Cutanea Tarda | UROD | Increased iron absorption; increased hepatic iron | 8 |
| Beta-thalassemia | HBB | Increased iron in liver and pancreas | 98 |
| Sideroblastic Anemia | Glutaredoxin-5 | Increased iron in the mitochondria | 99 |
| X-Linked Sideroblatic Anemia with Ataxia | ABC7 | Increased iron in the mitochondria | 8 |
| Huntington's Disease | HTT | Increased iron in basal ganglia of brain | 8, 93 |
| MPAN Disease | c19orf12 | Increased iron deposition in the brain | 93 |
| PKAN Disease | PANK2 | Increased iron deposition in the brain | 8, 93 |
| Kufor-Rakeb Syndrome | ATPC13A2 | Increased iron deposition in the brain | 93 |
| PLAN Disease | PLA2G6 | Increased iron deposition in the brain | 93 |
| BPAN Disease | WDR45 | Increased iron deposition in the brain | 93 |
| Woodhouse-Sakati Syndrome | DCAF17 | Increased iron deposition in the brain | 93 |
| Amyotrophic Lateral Sclerosis | SOD1 | Increased iron deposition in the brain | 100 |
| Congenital Dyserythropoietic Anemia Type I-IV | CDAN1, SEC23B KIF23, KLF1 | Increased serum iron | 8 |
| Congenital Sideroblastic Anemia | SLC25A38 | Increased serum iron; increased iron in cytoplasm | 101 |
| X-Linked Sideroblastic Anemia | Alas2 | Increased iron in liver, heart, pancreas, and brain | 8 |
| Sickle Cell Disease | HBB | Increased river and serum iron | 102 |
| Myelodysplastic Syndrome | Multiple | Increased liver and serum iron | 103 |

TABLE 2

Physical characteristics of iron chelators. Binding affinities and redox potentials of hinokitiol and other chelators was determined through competition assays and cyclic voltammetry, respectively. Hinokitiol binds iron (II) and iron (III) stronger than many other iron chelators, including deferiprone. The iron:hinokitiol complex is soluble in non-polar solvents as determined by its octanol-water partition coefficient. Values represent means.

| Small Molecule | $K_A$ for iron (II) | $K_A$ for iron (III) | $pFe^{III}$ | $E^0$ (mV vs. N.H.E.) 1:1 MeOH:H$_2$O | $E^0$ (mV vs. N.H.E.) Aqueous | logP Fe$^{III}$ Complex |
|---|---|---|---|---|---|---|
| Hinokitiol | $5.1 \times 10^{15}$ | $5.8 \times 10^{25}$ | 23.7† | −211 | −361¶ | 1.71 |
| Deferiprone | $2.1 \times 10^{15}$ | $1.2 \times 10^{24}$ | 22$^+$ (21)§ | −410 | −420 (−423)# | −1.32 |
| Tropolene | $2.3 \times 10^{15}$ | $1.1 \times 10^{24}$ | 22$^+$ | 38 | 39 (0)** | −0.03 |
| Maltol | $7.8 \times 10^{13}$ | $3.9 \times 10^{17}$ | 15.4± (15)§ | 8 | 41 (40)*** | 0.01 |
| EDTA | $1.2 \times 10^{15}$ | $(1.7 \times 10^{24})$* | (22)‖ | 139 | 131 (137)**** | — |

Literature values indicated in parenthesis
‖Reference 104 Literature values not run under identical conditions
¶Estimated from MeOH standard curve (see FIG. §6H)
*Reference 60
Reference 107
†Estimated from known pFe of EDTA (pFe = 22.2): Ref 104
**Reference 71
±Estimated from known pFe of Citrate (pFe = 14.8): Ref 105
***Reference 108
§Reference 106
****Reference 109

TABLE 3

Selectivity of hinokitiol binding and transport. Hinokitiol binds and transports many other divalent metals, as determined by ICP-MS analysis of organic-soluble hinokitiol:metal complexes after extraction and by determination of the rates of metal efflux from liposomes. The selectivity for binding and transport in biological systems is likely high for iron due to the high metallomic abundance of labile iron over other metals inside of cells (see References 33 and 34).

| Divalent Metal | Extracted Metal (μmol) 10:1* Hino:Metals | Extracted Metal (μmol) 1:1$^+$ Hino:Metals | $t_{1/2}$ (s) | Labile [Metal] (M)± |
|---|---|---|---|---|
| Fe$^{II}$ | 46 ± 0.4 | 4.80 ± 0.61 | 1054 ± 88 | $10^{-5}$ |
| Mn$^{II}$ | 37 ± 0.8 | 0.0003 ± 0.0001 | ND | $10^{-7}$ |
| Co$^{II}$ | 41 ± 0.3 | 0.001 ± 0.000 | 219 ± 3 | $10^{-10}$ |
| Ni$^{II}$ | 35 ± 0.3 | ND | 432 ± 64 | $10^{-10}$ |
| Zn$^{II}$ | 38 ± 0.2 | 0.0015 ± 0.0006 | 164 ± 1 | $10^{-11}$ |
| Cu$^{II}$ | 46 ± 0.2 | 45.15 ± 6.46 | 13 ± 13 | $10^{-15}$ |

*60 mM Hino and 1 mM of each metal in 10 mM Mes/Tris in 1:1 MeOH:H$_2$O at pH = 7.0
$^+$1 mM Hino and 1 mM of each metal in 10 mM Mes/Tris in 1:1 MeOH:H$_2$O at pH = 7.0
±Estimated cytosolic labile metal found inside of cells: Reference 33 and 34
ND = Not Determined;
Values represent means of at least three independent experiments.

TABLE S4

Standard redox potentials of hinokitiol:iron complexes at different Hino:Fe ratios. Two different redox waves were observed in the cyclic voltammogram (CV) of hinokitiol. The redox potential decreased with increasing hinokitiol concentrations. CVs were obtained with a 100 mV/s scan rate with a Hg electrode, Ag/AgCl reference, and graphite auxiliary using a 0.1M Tris buffer in 1:1 MeOH:H$_2$O at pH = 7.2 and 100 μM Fe(NO$_3$)$_3$.

| Hino:Fe | $E^0_1$ (mV vs. NHE) | $E^0_2$ (mV vs. NHE) |
|---|---|---|
| 1:1 | ND* | −340 |
| 2:1 | −156 | −367 |
| 3:1 | −192 | −384 |
| 4:1 | −209 | −388 |
| 5:1 | −211 | −390 |

*No oxidative wave was observed
ND = Not Determined;
Values represent means of three independent experiments.

TABLE 5

Standard redox potentials of hinokitiol:iron complexes at different pHs. The redox potential of the redox wave corresponding to the one electron redox process ($E^0_1$) was determined at various pHs. The redox potential increases with decreasing pH, possibly due to increased speciation to the 2:1 or 1:1 hinokitiol:iron complexes. CVs were obtained with a 100 mV/s scan rate with a Hg electrode, Ag/AgCl reference, and a graphite auxiliary using a 0.1M Tris buffer in 1:1 MeOH:H$_2$O at the indicated pH using 500 μM hinokitiol and 100 μM Fe(NO$_3$)$_3$.

| pH | $E_{1, red}$ (mV vs. NHE) | $E_{1, ox}$ (mV vs. NHE) | $E^0_1$ (mV vs. NHE) |
|---|---|---|---|
| 5 | −209 | ND* | ND* |
| 6 | −241 | −116 | −181 |
| 7 | −263 | −143 | −203 |
| 8 | −260 | −163 | −212 |
| 9 | −311 | −143 | −227 |
| 10 | −397 | −187 | −293 |

*No oxidative wave observed
ND = Not Determined;
Values represent means of 1-3 independent experiments.

TABLE 6

Redox potentials of different iron complexes in relation to NADP$^+$. The redox potentials were obtained by cyclic voltammetry for a number of different iron:chelator complexes. CVs were obtained with a 100 mV/s scan rate with a Hg electrode, Ag/AgCl reference, and a graphite auxiliary using a 0.1M Tris buffer in 1:1 MeOH:H$_2$O at pH = 7.2 using 500 μM small molecule and 100 μM Fe(NO$_3$)$_3$. Values represent means of 1-3 independent experiments.

| | Chemical Species | $E^0$ (mV vs. N.H.E.) 1:1 MeOH:H$_2$O | Aqueous | literature† |
|---|---|---|---|---|
| Primarily Reduced | Fe$^{III}$(H$_2$O)$_6$ | — | — | 770‡ |
| | Fe$^{III}$(EDTA) | 139 | 181 | 137§ |
| | NADP$^+$ | — | — | 108 |
| | Fe$^{III}$(Tropolone)$_3$ | 49 | 38 | 0‖ |

TABLE 6-continued

Redox potentials of different iron complexes in relation to NADP$^+$. The redox potentials were obtained by cyclic voltammetry for a number of different iron:chelator complexes. CVs were obtained with a 100 mV/s scan rate with a Hg electrode, Ag/AgCl reference, and a graphite auxiliary using a 0.1M Tris buffer in 1:1 MeOH:H$_2$O at pH = 7.2 using 500 μM small molecule and 100 μM Fe(NO$_3$)$_3$. Values represent means of 1-3 independent experiments.

| | | $E^0$ (mV vs. N.H.E.) | | |
|---|---|---|---|---|
| | Chemical Species | 1:1 MeOH:H$_2$O | Aqueous | literature[†] |
| Primarily Oxidized | Fe$^{III}$(Maltol)$_3$ | 8 | 41 | 40[¶] |
| | Fe$^{III}$(Hino)$_3$ | −211 | −361[*] | — |
| | Fe$^{III}$(Deferiprone)$_3$ | −410 | −420 | −423[‡] |

[*]Estimated from MeOH concentration study (see FIG. S6H)
[§]Determined from a Fe(EDTA)/Br$_2$ redox (see FIG. S6H) cell; Reference 109
[†]Literature values not run under identical conditions to the obtained values
[∥]Not determined from cyclic voltammetry; Reference 71
[‡]Reference 107
[¶]Reference 108

TABLE 7

Evaluation of small molecule toxicity. Hinokitiol, C2deOHino, deferiprone, and PIH EC$_{90}$ values in different cell types as determined by a WST-8 assay after >24 hours of small molecule treatment. Values represent means of three independent experiments.

| Wild Type Cell Line | Toxicity (μM)[*] | | | |
|---|---|---|---|---|
| | Hino | C2deOHino | deferiprone | PIH |
| Caco-2 | >100 | >100 | >100 | 31 |
| MEL | 24 | — | — | — |
| J774 | >100 | — | — | — |

[*]Determined from WST-8 assay after ≥24 hours of incubation

TABLE 8

Figure 30:
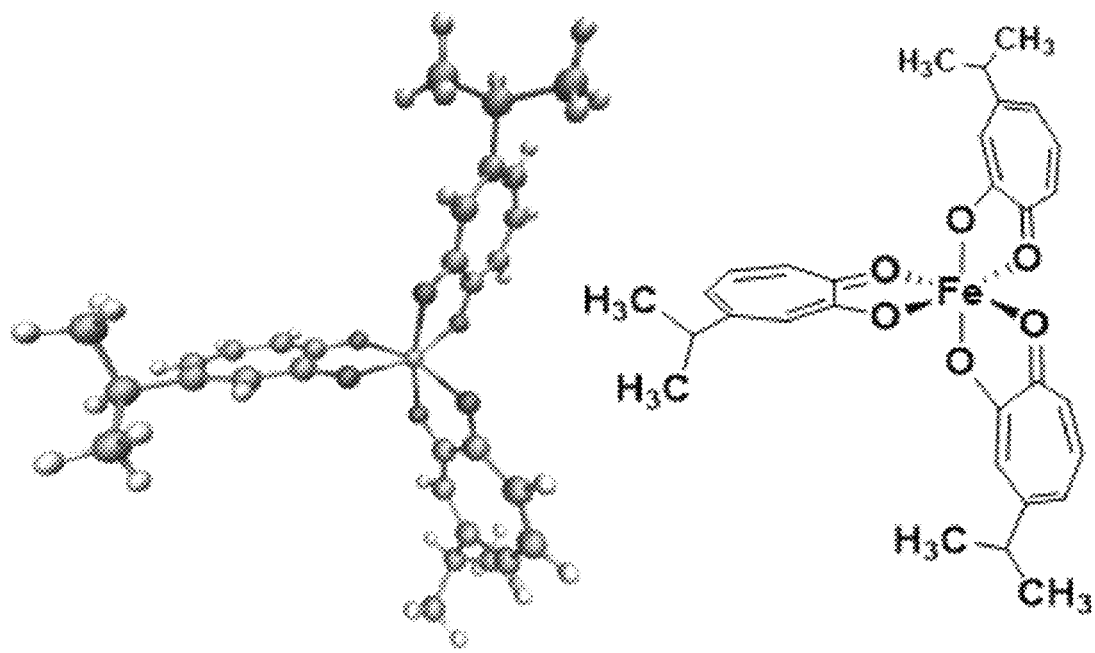
FIG. 30 shows the X-ray crystal structure of $Fe(Hino)_3$.

Crystal data and structure refinement for Fe (Hino)$_3$ (cm63dsa). The X-ray crystal structure of Fe (Hino)$_3$ is shown in FIG. 30.

| | |
|---|---|
| Identification code | cm63dsa |
| Empirical formula | C30 H33 Fe O6 |
| Formula weight | 545.41 |
| Temperature | 176 (2) K |
| Wavelength | 0.71073 Å |
| Crystal system | Triclinic |
| Space group | P-1 |
| Unit cell dimensions | a = 10.6129 (19) Å  a = 87.546 (5)°. |
| | b = 14.274 (2) Å  b = 82.397 (5)°. |
| | c = 18.757 (3) Å  g = 77.118 (5)°. |
| Volume | 2745.4 (8) Å$^3$ |
| Z | 4 |
| Density (calculated) | 1.320 Mg/m$^3$ |
| Absorption coefficient | 0.590 mm$^{-1}$ |
| F (000) | 1148 |
| Crystal size | 0.485 × 0.176 × 0.144 mm$^3$ |
| Theta range for data collection | 1.10 to 26.24°. |
| Index ranges | −13 <= h <= 13, −17 <= k <= 17, −23 <= l <= 23 |
| Reflections collected | 10932 |
| Independent reflections | 10932 [R (int) = 0.0346] |
| Completeness to theta = 26.24° | 98.7 % |
| Absorption correction | Integration |
| Max. and min. transmission | 0.9480 and 0.9064 |
| Refinement method | Full-matrix least-squares on F2 |
| Data/restraints/parameters | 10932/1927/1097 |
| Goodness-of-fit on F2 | 1.045 |
| Final R indices [I > 2sigma(I)] | R1 = 0.0525, wR2 = 0.1512 |
| R indices (all data) | R1 = 0.0646, wR2 = 0.1642 |
| Largest diff. peak and hole | 1.755 and −0.639 e.Å$^{-3}$ |

BIBLIOGRAPHY

1. E. Gouaux, R. MacKinnon, *Science* 310, 1461-1465 (2005).
2. M. W. Hentze, M. U. Muckenthaler, B. Galy, C. Camaschella, *Cell* 142, 24-38 (2010).
3. V. Shah et al., *Science* 351, 503-507 (2016).
4. F. Yi et al., *Science* 352, aaf2669 (2016).
5. P. Imbrici et al., *Front. Pharmacol.* 7, eCollection (2016).
6. N. C. Andrews, *Nat. Rev. Genet.* 1, 208-217 (2000).
7. N. C. Andrews, *N. Engl. J. Med.* 341, 1986-1995 (1999).
8. P. T. Lieu, M. Heiskala, P. A. Peterson, Y. Yang, *Mol. Aspects Med.* 22, 1-87 (2001).
9. G. Weiss, L. T. Goodnough, *N. Engl. J. Med.* 352, 1011-1023 (2005).
10. G. C. Shaw et al., *Nature* 440, 96-100 (2006).
11. J. Chung et al., *J. Biol. Chem.* 289, 7835-7843 (2014).
12. A. Donovan et al., *Nature* 403, 776-781 (2000).
13. A. T. McKie et al., *Mol. Cell* 5, 299-309 (2000).
14. I. E. Zohn et al., *Blood* 109, 4174-4180 (2007).
15. Y. A. Seo, M. Wessling-Resnick, *FASEB J.* 29, 2726-2733 (2015).
16. Y. S. Sohn, W. Breuer, A. Munnich, Z. I. Cabantchik, *Blood* 111, 1690-1699 (2008).
17. H. C. Hatcher, R. N. Singh, F. M. Torti, S. V. Torti, *Future Med. Chem.* 1, 1643-1670 (2009).
18. X. P. Huang, M. Spino, J. J. Thiessen, *Pharm. Res.* 23, 280-290 (2006).
19. J. L. Buss, M. Hermes-Lima, P. Ponka, *Adv. Exp. Med. Biol.* 509, 205-229 (2002).
20. A. G. Cioffi, J. Hou, A. S. Grillo, K. A. Diaz, M. D. Burke, *J. Am. Chem. Soc.* 137, 10096-10099 (2015).
21. M. R. Bleackley, R. T. A. MacGillivray, *Biometals* 24, 785-809 (2011).
22. T. Nozoe, *Bull. Chem. Soc. Japan* 11, 295-298 (1936).
23. B. E. Bryant, W. C. Fernelius, *J. Am. Chem. Soc.* 76, 1696-1697 (2002).
24. M. C. Barret, M. F. Mahon, K. C. Molloy, J. W. Steed, P. Wright, *Inorg. Chem.* 40, 4384-4388 (2001).
25. K. Nomiya et al., *J. Inorg. Biochem.* 98, 46-60 (2004).
26. K. Nomiya et al., *Inorg. Chim. Acta.* 362, 43-55 (2009).
27. C. Meck, M. P. D'Erasmo, D. R. Hirsch, R. P. Murelli, *MedChemComm* 5, 842-852 (2014).
28. Y. Ido et al., *Cell Prolif.* 32, 63-73 (1999).
29. K. Murakami, Y. Ohara, M. Haneda, R. Tsubouchi, M. Yoshino, *Basic Clin. Pharmacol. Toxicol.* 97, 392-394 (2005).
30. M. J. Lee, J. W. Kim, E. G. Yang, *Biochem. Biophys. Res. Commun.* 396, 370-375 (2010).
31. G. Bohme, P. Schonfeld, U. Kuster, W. Kunz, H. Lyr, *Acta Biol. Med. Ger.* 39, 1153-1163 (1980).
32. G. Ghssein et al., *Science* 352, 1105-1109 (2016).
33. L. A. Finney, T. V. O'Halloran, *Science* 300, 931-936 (2003).
34. L. A. Ba, M. Doering, T. Burkholz, C. Jacob, *Metallomics* 1, 292-311 (2009).
35. M. S. Cyert, C. C. Philpott, *Genetics* 193, 677-713 (2013).
36. A. Espinoza et al., *Biol. Trace Elem. Res.* 146, 281-286 (2012).
37. I. Hubatsch, E. G. E. Ragnarsson, P. Artursson, *Nat. Protoc.* 2, 2111-2119 (2007).
38. M. Tabuchi, T. Yoshiomori, K. Yamaguchi, T. Yoshida, F. Kishi, *J. Biol. Chem.* 275, 22220-22228 (2000).
39. C. Friend, W. Scher, J. G. Holland, T. Sato, *Proc. Natl. Acad. Sci. U.S.A.* 68, 378-382 (1971).
40. M. Lesjak et al., *PLoS One* 9, e102900 (2014).

41. M. D. Knutson, M. Oukka, L. M. Koss, F. Aydemir, M. Wessling-Resnick, *Proc. Natl. Acad. Sci. U.S.A.* 102, 1324-1328 (2005).
42. B. P. Esposito, W. Breuer, Z. I. Cabantchik, *Biochem. Soc. Trans.* 30, 729-732 (2002).
43. Y. S. Sohn et al., *Haematologica* 97, 670-678 (2012).
44. M. Arredondo, A. Orellana, M. A. Garate, M. T. Nunez, *Am. J. Physiol.* 273, G275-280 (1997).
45. D. L. Zhang, R. M. Hughes, H. Ollivierre-Wilson, M. C. Ghosh, T. A. Rouault, *Cell Metab.* 9, 461-473 (2009).
46. N. Imai et al., *J. Toxicol. Sci.* 31, 357-370 (2006).
47. T. Veuthey, M. Wessiling-Resnick, Front. *Pharmacol.* 5, 1-82 (2014).
48. S. Avagyan, L. I. Zon, *Hum. Gene Ther.* 27, 287-294 (2016).
49. A. Donovan et al., *Blood* 100, 4655-4659 (2002).
50. J. J. Ganis et al., *Dev. Biol.* 366, 185-194 (2012).
51. A. Brownlie et al., *Nat. Genet.* 20, 244-250 (1998).
52. C. Miller, *Nature* 440, 484-489 (2006).
53. E. Y. Kwok, S. Severance, D. J. Kosman, *Biochemistry* 45, 6317-6327 (2006).
54. C.-W. Yun, J. S. Tiedeman, R. E. Moore, C. C. Philpott, *J. Biol. Chem.* 275, 16354-16359 (2000).
55. Y. A. Seo, J. A. Elkhader, M. Wessling-Resnick, *Biometals* 29, 147-155 (2016).
56. S. Severance, S. Chakraborty, D. J. Kosman, *Biochem. J.* 380, 487-496 (2004).
57. J. C. Dearden, G. M. Bresnen, *Quantitative structure-activity relationships* 7, 133-144 (2016).
58. A. Andres et al., *Eur. J. Pharm. Sci.* 76, 181-191 (2015).
59. S. R. Park et al., *Nat. Commun.* 7, 1-11 (2016).
60. L. E. Gentry, M. A. Thacker, R. Doughty, R. Timkovich, L. S. Busenlehner, *Biochemistry* 52, 6085-6096 (2013).
61. H. Katoh, N. Hagino, T. Ogawa, *Plant Cell Physiol.* 42, 823-827 (2001).
62. G. P. White, A. Jacobs, R. W. Grady, A. Cerami, *Blood* 48, 923-929 (1976).
63. D. Vyoral, J. Petrak, *Biochim. Biophys. Acta.* 1403, 179-188 (1998).
64. C. Y. Li, J. A. Watkins, J. Glass, *J. Biol. Chem.* 269, 10242-10246 (1994).
65. S. A. Davis et al., *J. Am. Chem. Soc.* 137, 15102-15104 (2015).
66. B. S. Berlett, R. L. Levine, P. B. Chock, M. Chevion, E. R. Stadtman, *Proc. Nat. Acad. Sci., U.S.A.* 98, 451-456 (2001).
67. A. C. Ming, A. Shawki, C. L. Cunningham, B. Mackenzie, *J. Biol. Chem.* 287, 30485-30496 (2012).
68. I. A. Ehrnstorfer, E. R. Geertsma, E. Pardon, J. Steyaert, R. Dutzler, *Nat. Struct. Mol. Biol.* 21, 990-996 (2014).
69. W. Lovenberg, B. B. Buchanan, J. C. Rabinowitz, *J. Biol. Chem* 238, 3899-3913 (1963).
70. Z. J. Barton, J. Rodriguez-Lopez, *Anal. Chem.* 86, 10660-10667 (2014).
71. P. N. Diouf et al., *Appl. Environ. Microbiol.* 68, 4377-4382 (2002).
72. J. Chung et al., *Sci. Signal* 8, ra34 (2015).
73. M. C. Canver et cd., *J. Biol. Chem.* 289, 21312-21324 (2014).
74. Y. Y. Yien et al., *J. Clin. Invest.* 124, 4294-4304 (2014).
75. G. Hildick-Smith et al., *Am. J. Hum. Genet.* 93, 906-914 (2013).
76. B. C. Wilcock, M. M. Endo, B. E. Uno, M. D. Burke, *J. Am. Chem. Soc.* 135, 8488-8491 (2013).
77. M. Foresti, I. Paoletti, F. Mele, G. Geraci, *Mutat. Res.* 374, 269-275 (1997).
78. J. D. Cooney et al., *Dev. Biol.* 373, 431-441 (2013).
79. J. D. Amigo et al., *Blood* 114, 4654-4663 (2009).
80. R. Nilsson et al., *Cell Metab.* 10, 119-130 (2009).
81. J. R. Kardon et al., *Cell* 161, 858-867 (2015).
82. A. B. Pangborn, M. A. Giardello, R. H. Grubbs, R. K. Rosen, F. J. Timmers, *Organometallics* 15, 1518-1520 (1996).
83. P. A. Provencher, J. A. Love, *J. Org. Chem.* 80, 9603-9609 (2015).
84. D. C. Gadsby, *Nat. Rev. Mol. Cell Biol.* 10, 344-352 (2009).
85. A. J. Bard, L. R. Faulkner, Ed. *Electrochemical Methods: Fundamentals and Applications*. D. Harris, E. Swain, C. Robey, E. Aiello (John Wiley & Sons, Inc. New York, N.Y., 2' Ed., 2001).
86. A. Iolascon et al., *J. Pediatr.* 152, 136-139 (2008).
87. Y. Want et al., *Exp. HematoL* 39, 784-793 (2011).
88. A. Pietrangelo, Blood Cells Mol. Dis. 32, 131-138 (2004).
89. P. Brissot, E. Bardou-Jacquet, A. M. Jouanolle, O. Loréal, *Trends Mol. Med.* 17, 707-713 (2011).
90. C. N. Roy, N. C. Andrews, *Hum. Mol. Genet.* 10, 2181-2186 (2001).
91. S. Sheth, G. M. Brittenham, *Annu. Rev. Med.* 51, 443-464 (2000).
92. L. Gouya et al., *Blood* 93, 2015-2110 (1999).
93. A. Gregory, S. Hayflick, In *Neurodegeneration with Brain Iron Accumulation Disorders Overview*. (University of Washington, Seattle, Wash., 2014).
94. G. Papanikolaou, K. Pantopoulos, *Toxicol. Appl. Pharmacol.* 202, 199-211 (2005). 95. B. Grandchamp et al., *Blood* 118, 6660-6666 (2011).
96. J. Kato et al., *Am. J. Hum. Genet.* 69, 191-197 (2001).
97. M. H. Mendler et al., *Gastroenterology* 117, 1155-1163 (1999).
98. S. Gardenghi et al., *Blood* 109, 5027-5035 (2007).
99. H. Ye et al., *J. Clin. Invest.* 120, 1749-1761 (2010). 100. A. Gajowiak, A. Styś, R. R. Starzyński, R. Staroń, P. Lipiński, Postepy Hig. Med. Dosw. 70, 709-721 (2016).
101. D. L. Guernsey et al., *Nat. Genet.* 41, 651-653 (2009).
102. R. Raghupathy, D. Manwani, J. A. Little, *Adv. Hematol.* 2010, 1-9 (2010).
103. N. Shenoy, N. Vallumsetla, E. Rachmilewitz, A. Verma, Y. Ginzburg, *Blood* 124, 873-881 (2014).
104. R. C. Hider, Y. Ma, In *Metal Chelation in Medicine*. R. Crichton, R. J. Ward, R. C. Hider, (The Royal Society of Chemistry, Cambridge, UK, 2017) Chapter 2: 24-55.
105. J. Burgess, M. Rangel, *Adv. Inorg. Chem.* 60, 167-243 (2008).
106. T. Franza, D. Expert, In *Iron Uptake and Homeostasis in Microorganisms*. P. Cornelis, S. C. Andrews (Caister Academic Press, Norfolk, UK, 1, 2010) Chapter 6: 101-116.
107. M. Merkofer, R. Kissner, R. C. Hider, W. H. Koppenol, *Helv. Chim. Acta* 87, 3021-3034 (2004).
108. S. A. Kazmi, S. Amin, *J. Chem. Soc.* Pak. 30, 824-828 (2008).
109. Y. H. Wen et al., *J. Electrochem. Soc.* 153, A929-A934 (2006).

Example 2: Synthesis of Hinokitiol Derivatives—β-Substituted Bromide

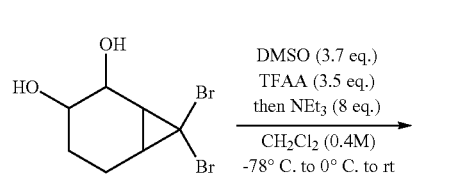

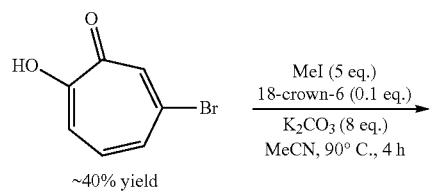

~40% yield

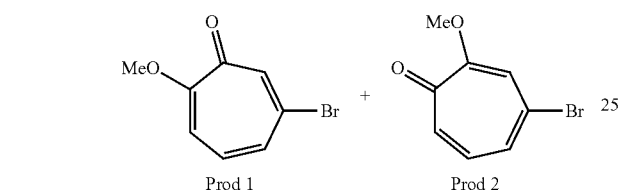

Prod 1     Prod 2

90% yield
60:40 mixture

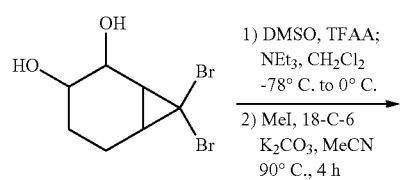

ASG.317C
28% yield over 2 steps

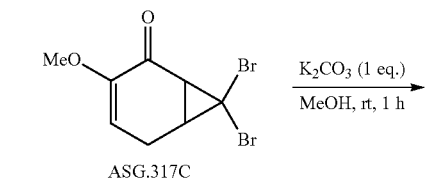

180 mg, 97% yield

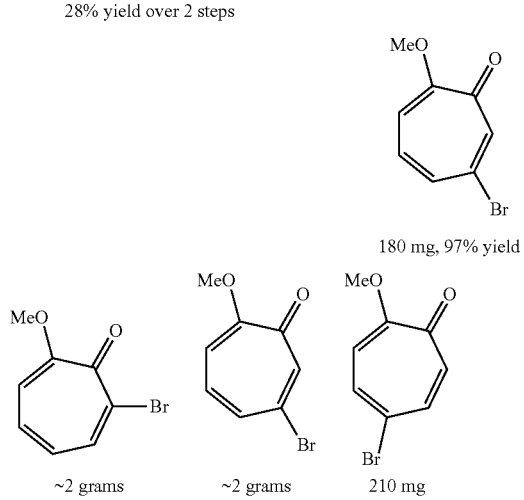

~2 grams     ~2 grams     210 mg

Can make ~15 derivatives with 200 mg of bromide

Example 3: Synthesis of Hinokitiol Derivatives –100 mg Scale Reaction

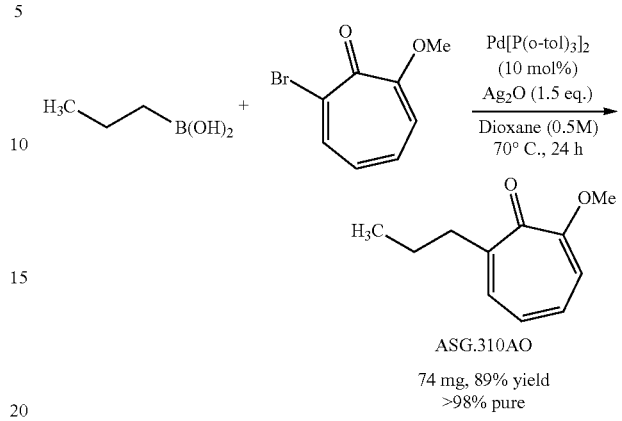

ASG.310AO
74 mg, 89% yield
>98% pure

Example 4: Modular Four-Step Total Synthesis of Hinokitiol

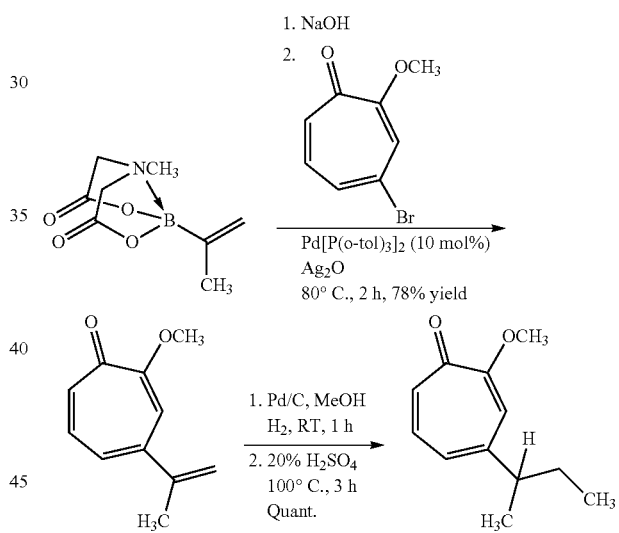

Alternative bornates:

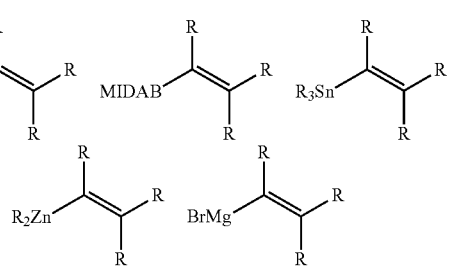

wherein R is independently $C_{1-20}$-alkyl, $C_{2-20}$-alkenyl, $C_{3-9}$-cycloalkyl, aryl, or heteroaryl, each of which is unsubstituted or substituted with a substituent selected from the group consisting of halo, $NO_2$, CN, $C_{1-6}$-haloalkyl, and $C_{1-6}$-alkoxy.

Example 5: Synthesis of Hinokitiol Derivatives Primary Boronic Acids
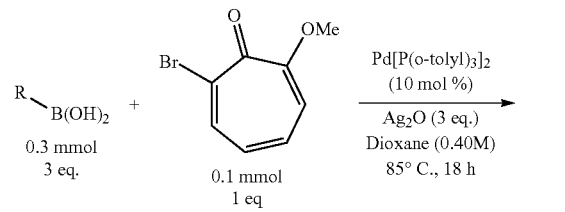
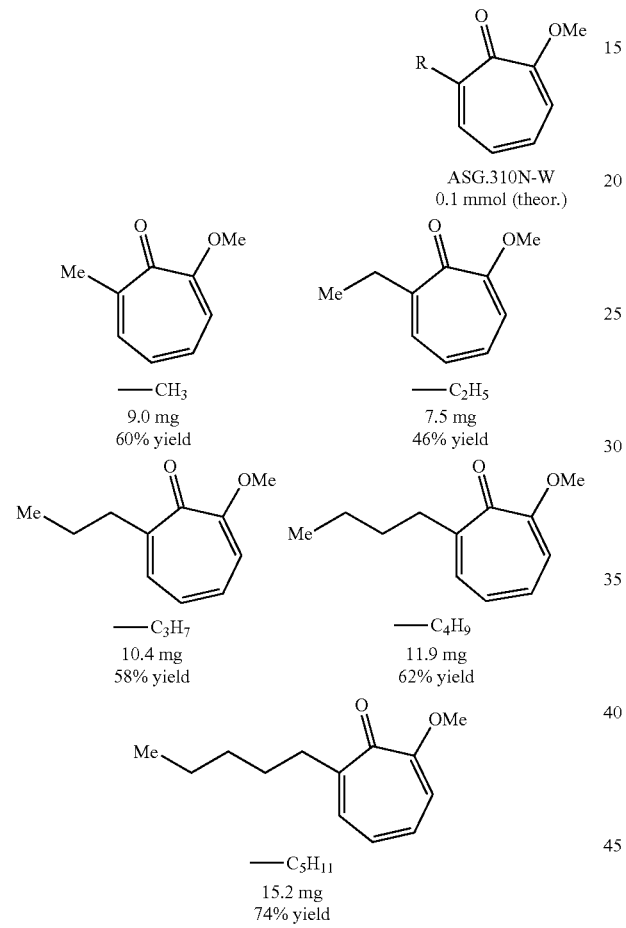
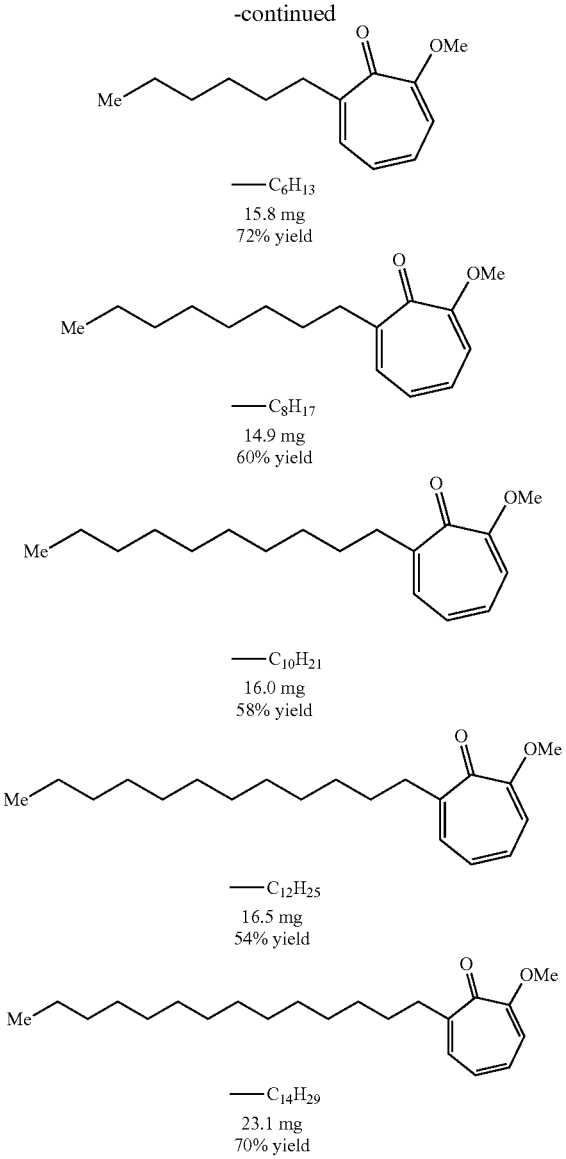
Example 6: Synthesis of Hinokitiol Derivatives—Testing Lipophilicity
| #C's | $H_a$ | $H_b$ | $H_c$ | $H_d$ | C1 | C2 | C3 | C4 | C5 | C6 | C7 |
|---|---|---|---|---|---|---|---|---|---|---|---|
| 0 | 6.74 | 7.08 | 6.87 | 7.22 | 180.6 | 165.5 | 137.0 | 136.8 | 132.9 | 128.0 | 112.5 |
| 1 | 6.74 | 6.99 | 6.79 | 7.42 | 180.0 | 164.5 | 146.6 | 136.1 | 130.8 | 127.2 | 112.4 |
| 2 | 6.71 | 6.98 | 6.82 | 7.35 | 179.7 | 163.9 | 151.7 | 135.1 | 130.7 | 127.3 | 112.1 |
| 3 | 6.70 | 6.96 | 6.80 | 7.34 | 179.7 | 163.9 | 150.2 | 135.9 | 130.7 | 127.2 | 112.1 |
| 4 | 6.70 | 6.96 | 6.79 | 7.35 | 179.7 | 163.9 | 150.5 | 135.8 | 130.7 | 127.2 | 112.1 |
| 5 | 6.71 | 6.97 | 6.80 | 7.35 | 179.6 | 163.9 | 150.5 | 135.9 | 130.7 | 127.2 | 112.2 |
| 6 | 6.70 | 6.96 | 6.79 | 7.34 | 179.6 | 163.9 | 150.5 | 135.3 | 130.7 | 127.2 | 112.1 |
| 8 | 6.71 | 6.97 | 6.80 | 7.35 | 179.6 | 163.9 | 150.6 | 135.8 | 130.7 | 127.2 | 112.2 |

| #C's | $H_a$ | $H_b$ | $H_c$ | $H_d$ | C1 | C2 | C3 | C4 | C5 | C6 | C7 |
|---|---|---|---|---|---|---|---|---|---|---|---|
| 10 | 6.71 | 6.97 | 6.80 | 7.35 | 179.7 | 163.9 | 150.6 | 135.9 | 130.7 | 127.2 | 112.2 |
| 12 | 6.70 | 6.96 | 6.80 | 7.35 | 179.7 | 163.9 | 150.6 | 135.8 | 130.7 | 127.2 | 112.1 |
| 14 | 6.70 | 6.96 | 6.80 | 7.34 | 179.6 | 163.9 | 150.6 | 135.8 | 130.7 | 127.2 | 112.2 |
Example 7: Synthesis of Hinokitiol Derivatives
Example 8: Synthesis of Hinokitiol Derivatives
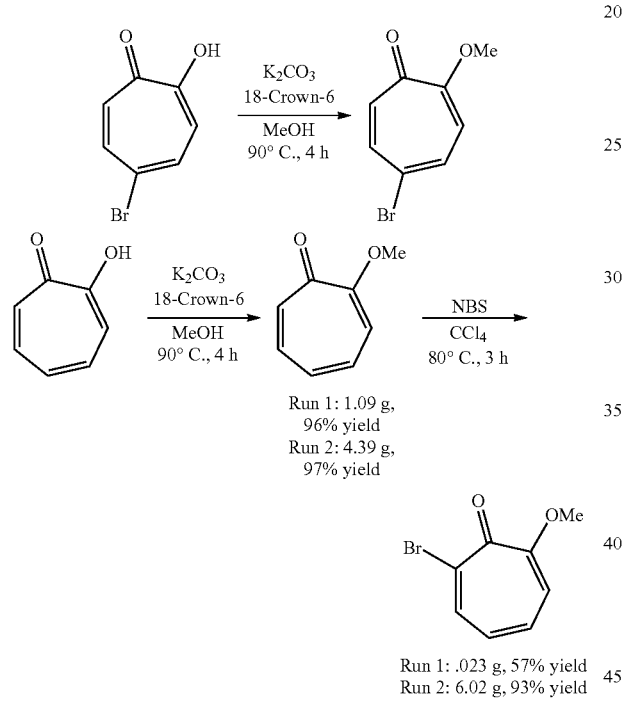
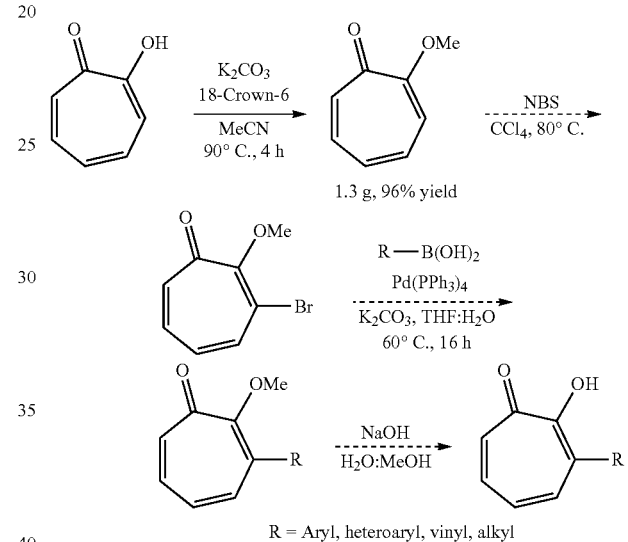
Example 9: Synthesis of 3-Bromo, 4-Bromo, and 5-Bromotropolone
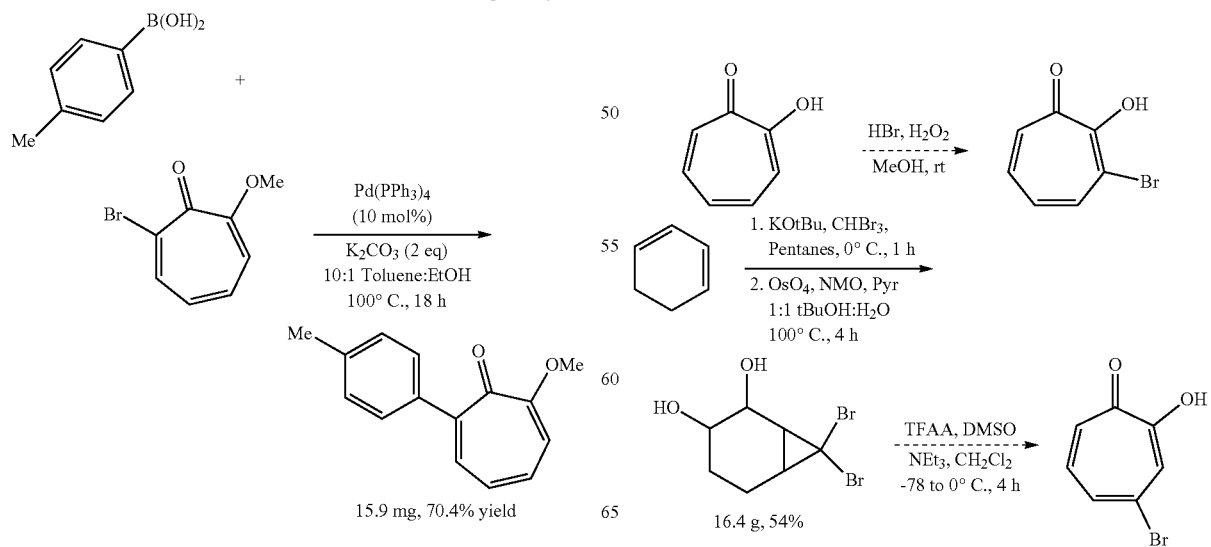

 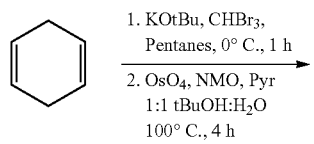
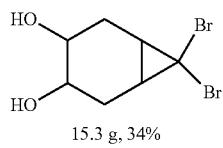 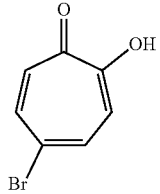
15.3 g, 34%
Run 1: 1.2 eq. HBr, 1.05 eq. H$_2$O$_2$, 20 h
Run 2: 2.2 eq. HBr, 2.0 eq. H$_2$O$_2$, 20 h
Run 1: ND
Run 2: ND
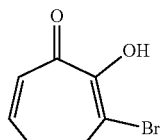 + 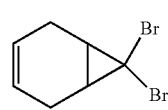
Run 1: 2.08 g
Run 2: 1.95 g
Run 1: 2.67 g
Run 2: 2.50 g
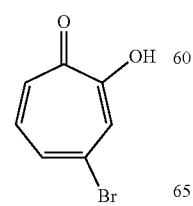
16.4 g, 54%
 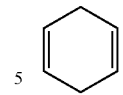
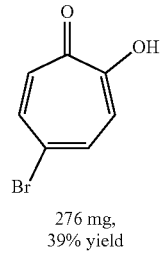
15.3 g, 34%
276 mg, 39% yield
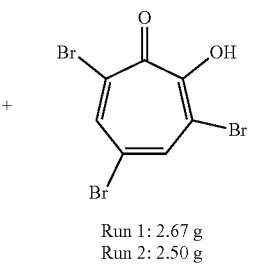
Run 1 (10 g SM) = 7.42 g, 22.6% yield
Run 2 (25 g SM) = 33.54 g, 51.9% yield
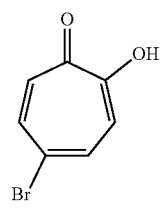
Run 1 (1 g SM) = 472 mg, 41% yield
Run 2 (4 g SM) = 1.64 g, 49% yield
276 mg, 39% yield
Purification Procedure:
1) 2M HCl, CH$_2$Cl$_2$
2) Florisil column, 10% MeOH:CH$_2$Cl$_2$ eluent
3) Concentrate, dissolve in CH$_2$Cl$_2$, remove florisil
4) Extract with CH$_2$Cl$_2$ and 2M HCl to protonate
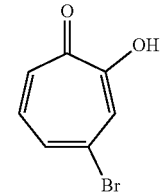
44.2 g, 67.5% yield Example 10: Cross-Couplings of BromoTropolones
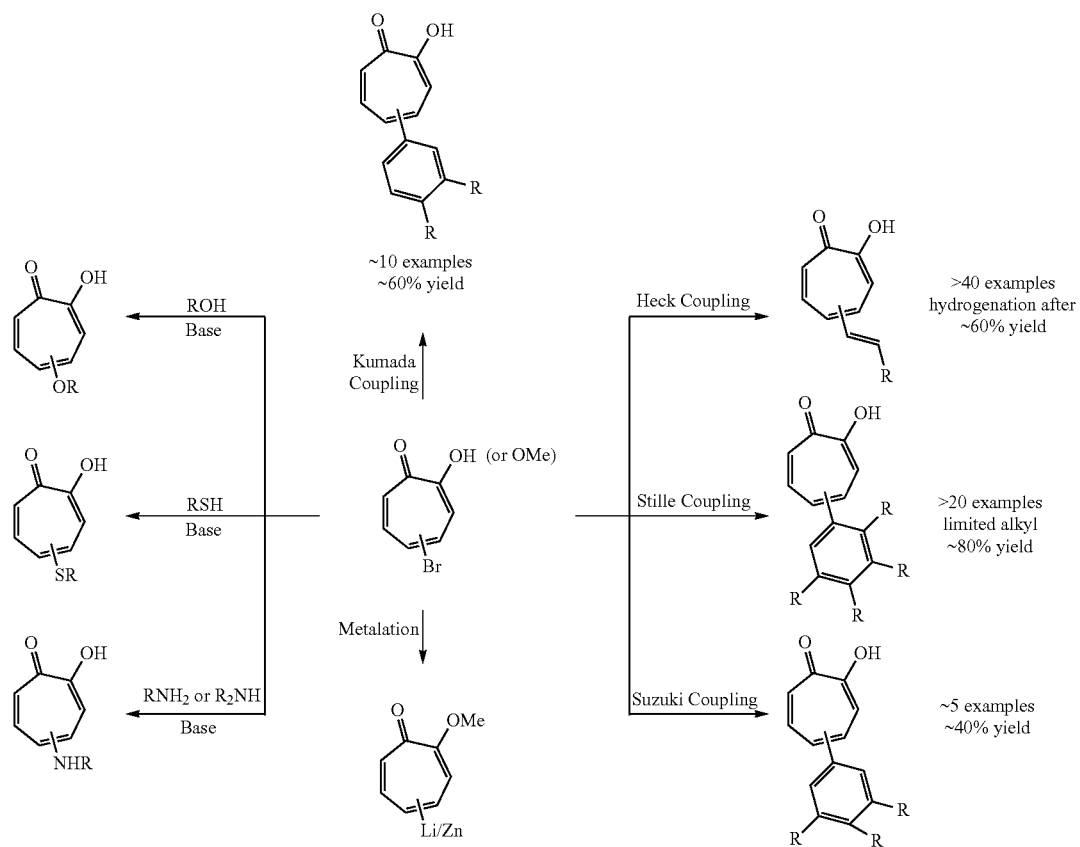
Example 11: Synthesis of Hinoitiol Derivatives—β-Substituted Bromide
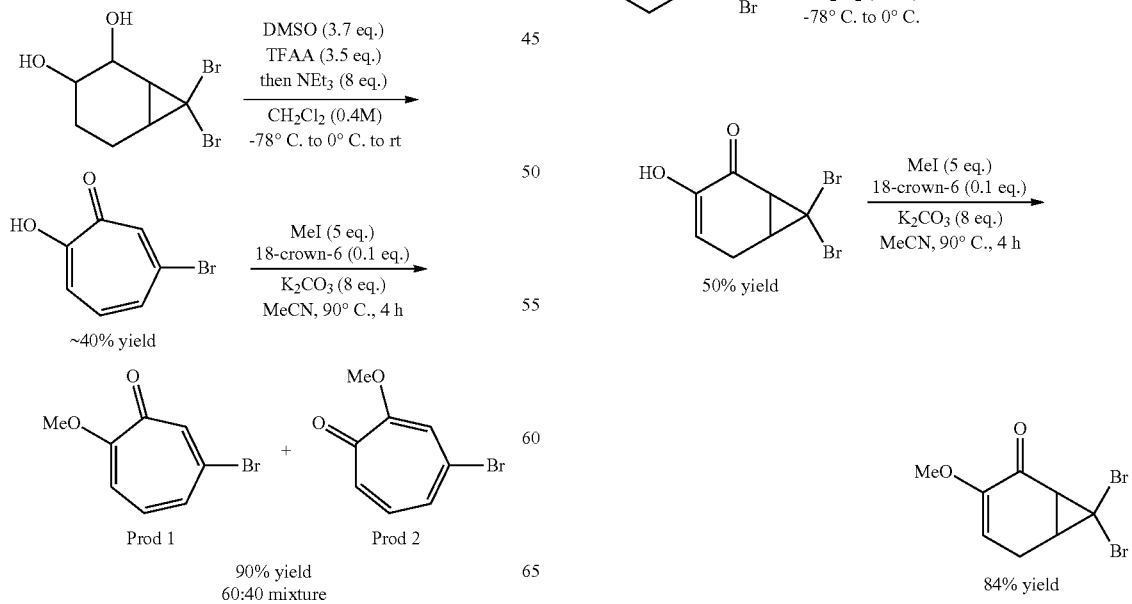

Example 12: Synthesis of Hinokitiol Derivatives—Secondary Boronic Acids

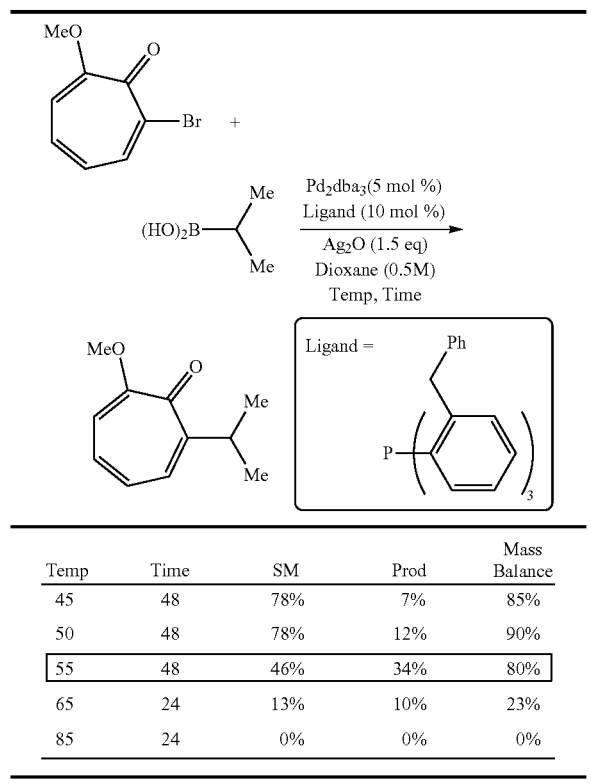

| Temp | Time | SM | Prod | Mass Balance |
|------|------|-----|------|--------------|
| 45 | 48 | 78% | 7% | 85% |
| 50 | 48 | 78% | 12% | 90% |
| 55 | 48 | 46% | 34% | 80% |
| 65 | 24 | 13% | 10% | 23% |
| 85 | 24 | 0% | 0% | 0% |

Example 13: Restored fetΔftr1Δ Growth with Hinokitiol Derivatives

Figure 31:
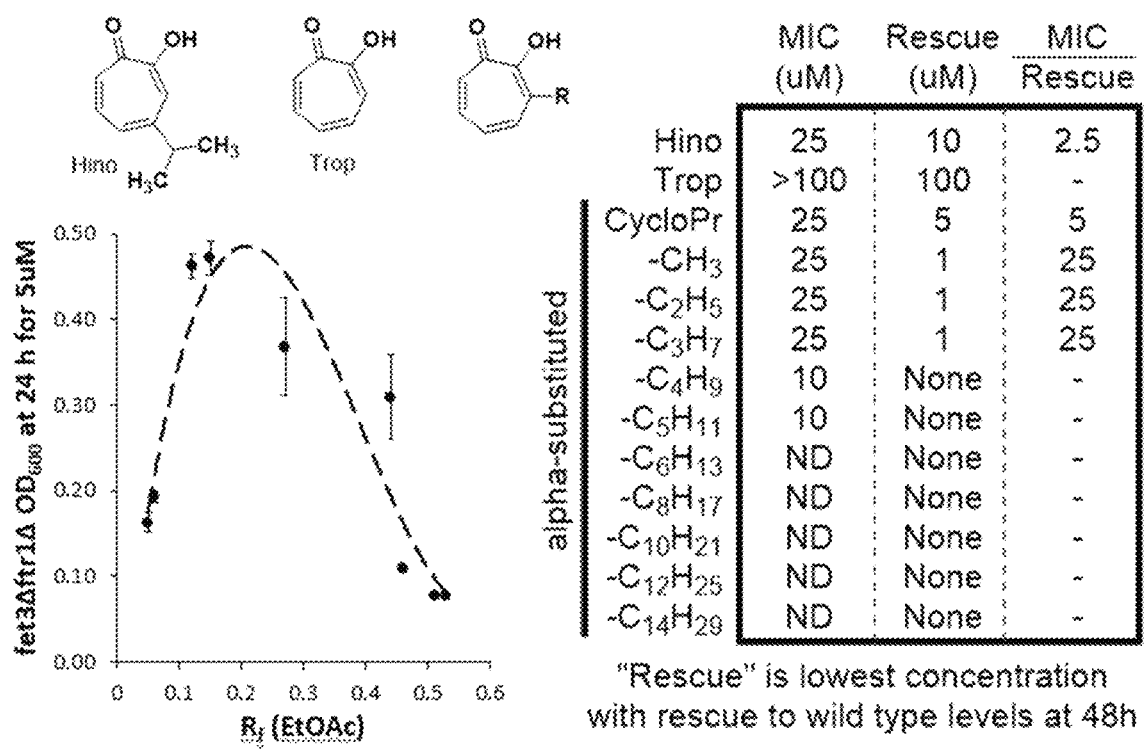
FIG. 31 shows the results of a structure-activity relationship study of hinokitiol, tropolone, and various alpha-substituted tropolone derivatives for restoring fet3Δftr1Δ growth.

The results of a structure-activity relationship study of hinokitiol, tropolone, and various alpha-substituted tropolone derivatives for restoring fet3Δftr1Δ growth is shown in FIG. 31.

Example 14: Structure-Activity Relationship Study of Hinokitiol Derivatives in Restoring fetΔftr1Δ Growth This study identifies an optimum window for the size of the hydrocarbon substituent on the tropolone ring for optimized activity. If the side chain becomes too long, specifically more than 4 carbons, there is a major loss in capacity to replace missing protein iron transporter function. This data set adds strong evidence for the boundedness of the optimum window for hydrocarbon substituents (i.e., 1-4 carbons appears to be optimal). (FIG. 25A-25D)

Example 15: Hinokitiol Releases Iron from the Liver of FPN-Deficient Mice

Figure 26D:
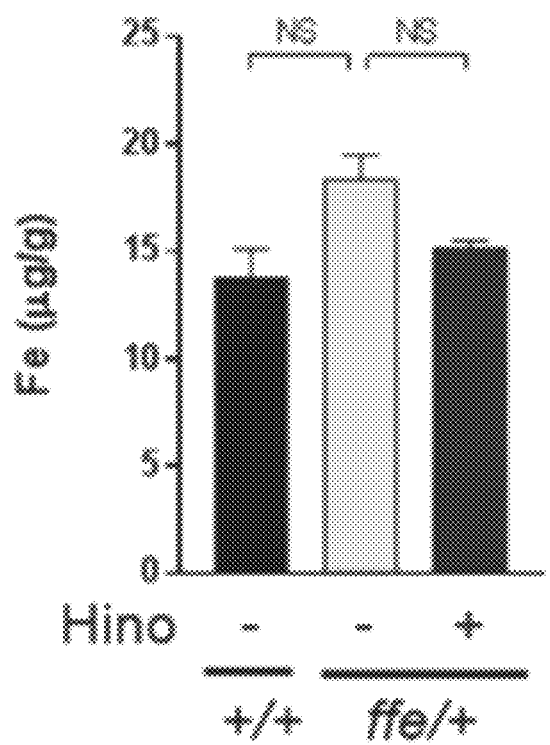
Figure 26E:
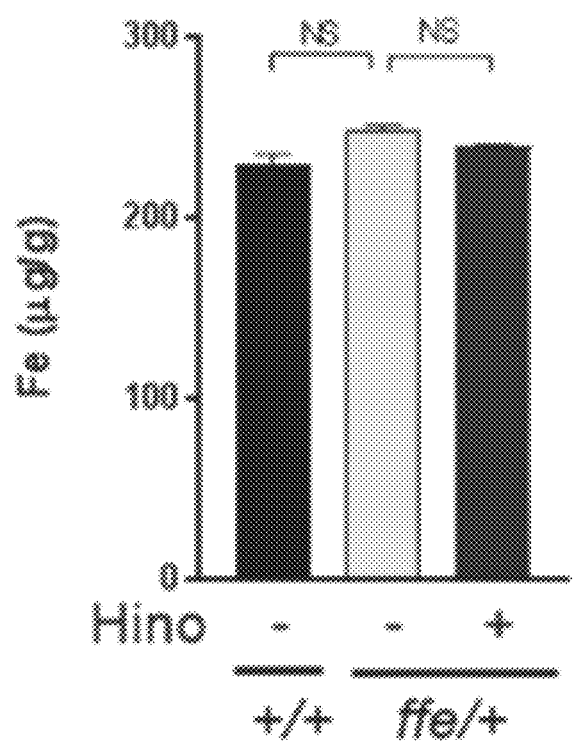

To characterize the effects of hinokitiol on iron mobilization and distribution in flatiron mice, hinokitiol was administered with increasing doses (1-50 mg/kg) via intraperitoneal (IP) injection. Mice were euthanized 4 hours post-administration, and blood and a range of tissues were collected. A dose-dependent decrease in liver non-heme iron was observed. Total iron in a variety of tissues including liver and spleen was further measured by inductively coupled plasma mass spectrometry (ICP-MS). Data show that treatment of flatiron mice with hinokitiol (at 10 mg/kg) releases iron from the liver (FIG. 26B). These data demonstrate that hinokitiol releases iron from the liver of FPN-deficient mice. Other tissues yielded data suggestive of reductions in non-heme iron (FIGS. 26C-26E).

Figure 27A:
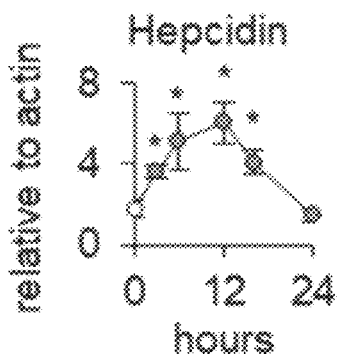
FIGS. 27A-27E show hinokitiol efficacy in a model of acute anemia of inflammation (AI). Mice (male; C57BL/6; 7-week-old; n=8-10) were administered turpentine oil (TO) (5 mL/kg) or saline, and euthanized 3, 6, 12, 16, 24 h post injection. (A) Hepcidin mRNA measured by qPCR. (B) Proteins quantified by Western blot analysis. (C) Tissue and serum non-heme iron measured by bathophenanthroline colorimetric assay. (D) Hematocrit measured by centrifugation of heparinized capillaries. (E) Mice given compounds indicated once daily for 3 days. On the third day, mice injected with saline or TO, and euthanized 16 h post-injection.
Figure 27B:
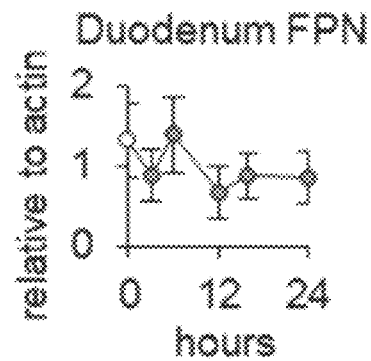
Figure 27C:
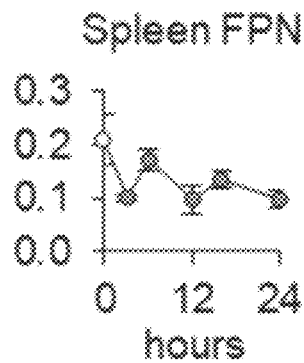
Figure 27C:
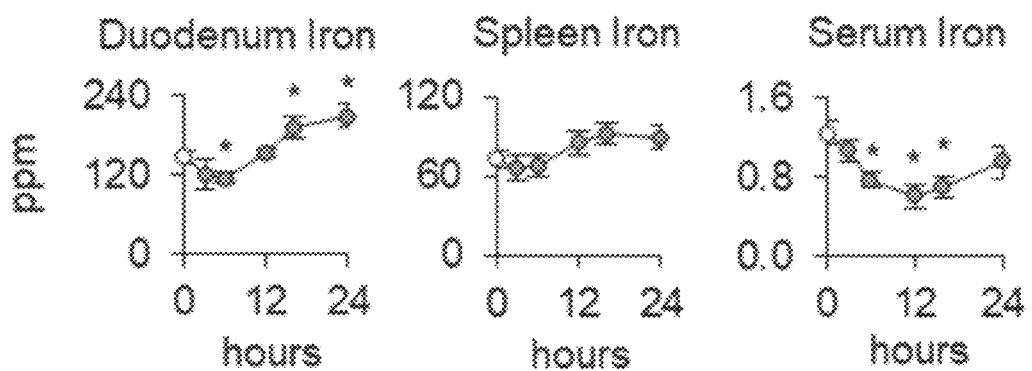
Figure 27D:
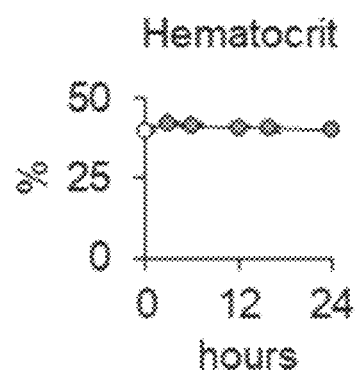
Figure 27E:
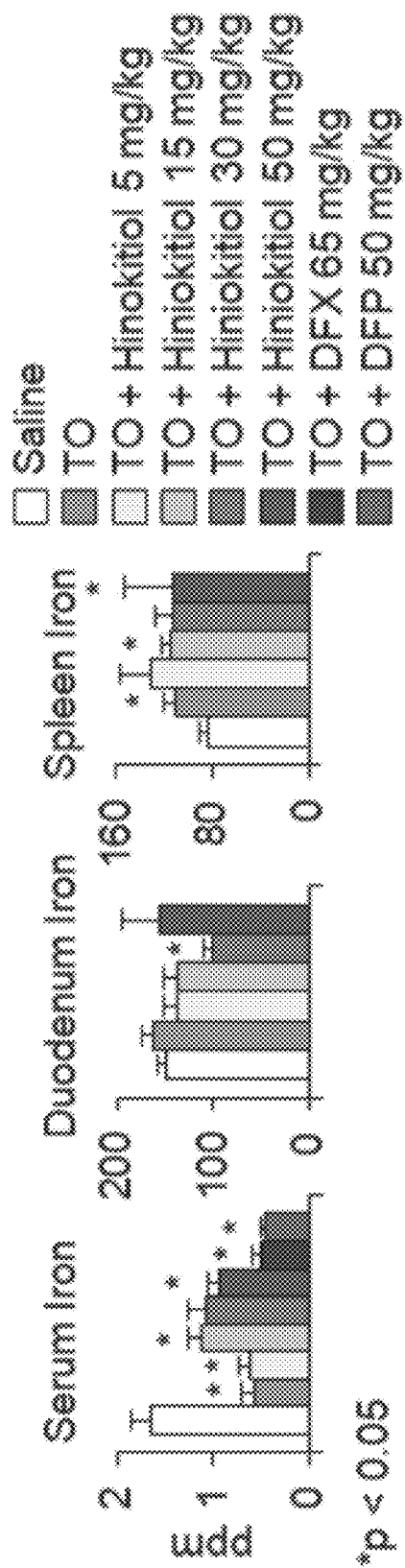

Example 16: Hypoferremia Induced by Turpentine Oil Injection Was Mitigated by Hinokitiol Treatment Injection of turpentine oil (TO) is a common method to induce inflammation in mice. A single dose of TO rapidly increased hepcidin mRNA levels in the liver (FIG. 27A) with concomitant down-regulation of FPN protein levels in the duodenum and spleen (FIG. 27B). As a result, iron buildup occurred in the duodenum and spleen. Moreover, serum iron decreased (FIG. 27C) without affecting hematocrit values (FIG. 27D). Hypoferremia induced by TO injection was mitigated by hinokitiol treatment, while other FDA-approved drugs failed to provide that effect (FIG. 27E).

Example 17: An Animal Model of Chronic AI Using TO

Figure 28A:
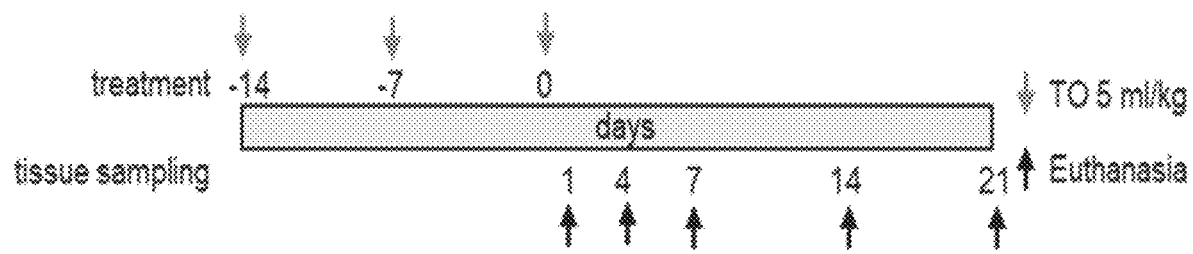
FIGS. 28A-28E show development of an animal model of chronic anemia of inflammation (AI). (A) Mice ($C_{57}BL/6$; 8-week old; n=3-6) were injected with saline or turpentine oil (TO) every week for up to 3 injections, and euthanized at 1, 4, 7, 14, and 21 days post last injection. (B) Hepcidin mRNA was measured by qPCR, and serum non-heme iron was measured by colorimetric assay using bathophenanthroline. (C) Protein levels were measured by Western Blot analysis. (D) Tissue non-heme iron levels were measured using bathophenanthroline. (E) Hemoglobin levels were measured by colorimetric assay using Drakbin's reagent and hematocrit through centrifugation of capillary tubes.
Figure 28B:
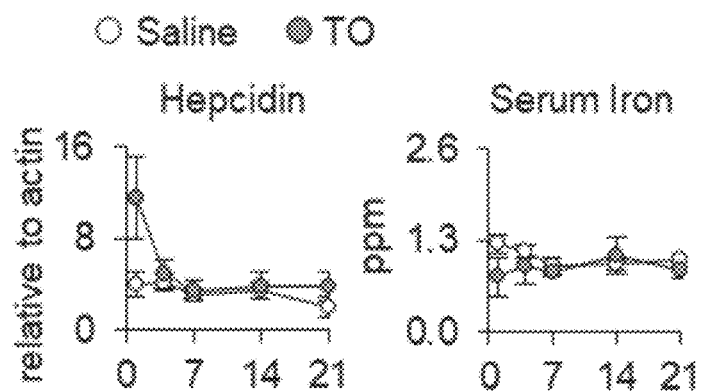
Figure 28C:
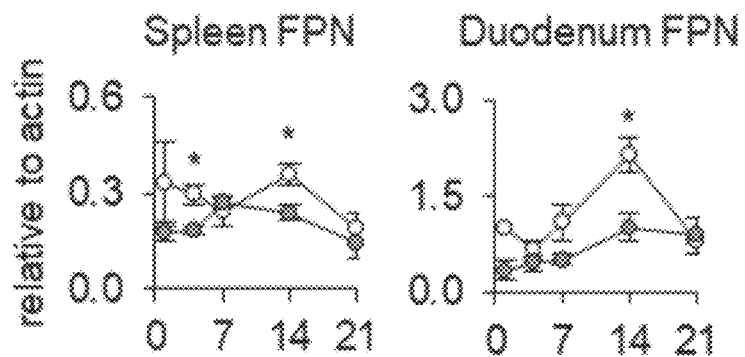
Figure 28D:
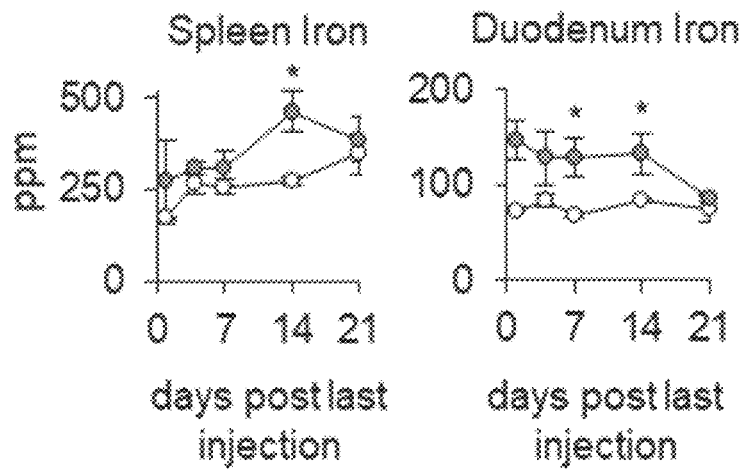
Figure 28E:
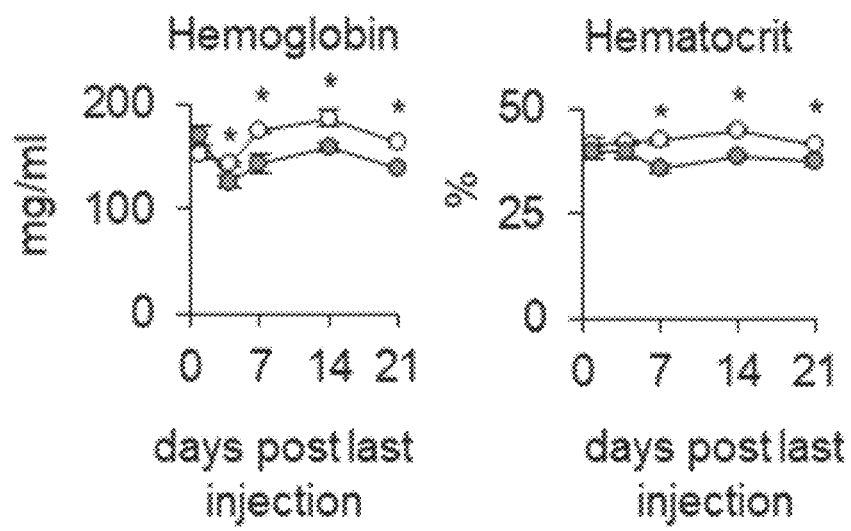

Since chronic AI is clinically relevant, an animal model of chronic AI using TO was developed and optimized. We found the best model to be a weekly injection of TO for 3 weeks in C57BL/6 mice (FIG. 28A). Upon chronic inflammation, upregulation of liver hepcidin disappeared 4 days after the last injection, and serum iron returned to the baseline levels (FIG. 28B). However, the FPN downregulation (FIG. 28C) and tissue iron buildup in spleen and duodenum (FIG. 28D) persisted for at least two weeks. Importantly, anemia was developed (FIG. 28E).

Figure 29A:
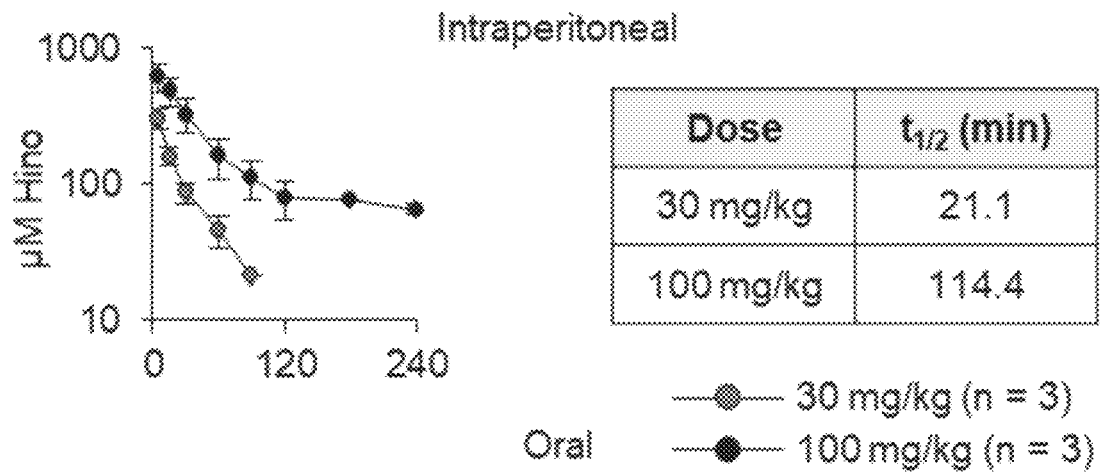
FIGS. 29A-29B show single-dose in vivo pharmacokinetics of hinokitiol in mice. Mice were mixed C57BL/6 and 129/Sv background (2-3 mo. old) were administered various concentrations of hinokitiol (30 or 100 mg Hino/kg body weight) by two different routes (A) intraperitoneal injection and (B) oral gavage. Plasma samples were collected at various timepoints (5-360 minutes) for drug measurement by HPLC.
Figure 29B:
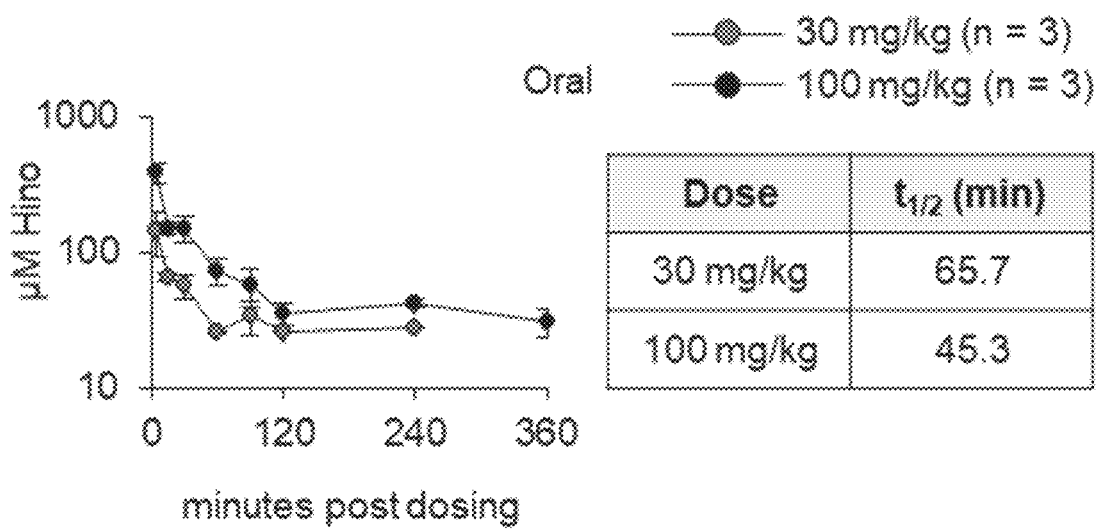

Example 18: Structure-Activity Relationship Study of Hinokitiol Derivatives in Restoring fetΔftr1Δ Growth In addition to evaluating the pharmacodynamics (effect) of hinokitiol in AI, the pharmacokinetics of hinokitiol were characterized to guide the optimal dose scheme for treatment. Single dose by intraperitoneal injection (FIG. 29A) and oral gavage administration (FIG. 29B) demonstrated a rapid disposition of hinokitiol. Hinokitiol exhibited dose-dependent pharmacokinetics; increased half-life was observed at a higher dose (100 mg/kg), likely due to saturation of hinokitiol metabolism.

INCORPORATION BY REFERENCE

All of the US patents and US and PCT published patent applications mentioned herein are hereby incorporated by reference in their entirety. In case of conflict, the present application, including any definitions herein, will control.

EQUIVALENTS

While specific embodiments of the subject invention have been discussed, the above specification is illustrative and not restrictive. Many variations of the invention will become apparent to those skilled in the art upon review of this specification and the claims below. The full scope of the invention should be determined by reference to the claims, along with their full scope of equivalents, and the specification, along with such variations.

We claim:

1. A compound having a structure according to Formula (I):

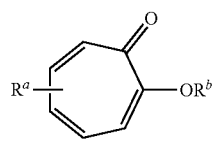

or a salt thereof; wherein $R^a$ is selected from the group consisting of

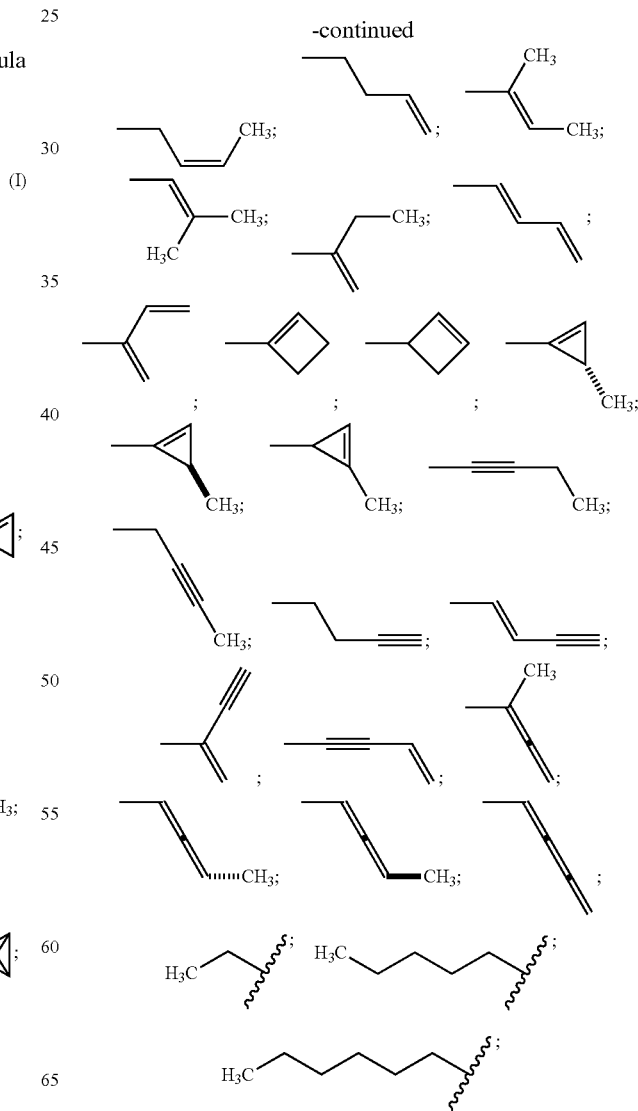

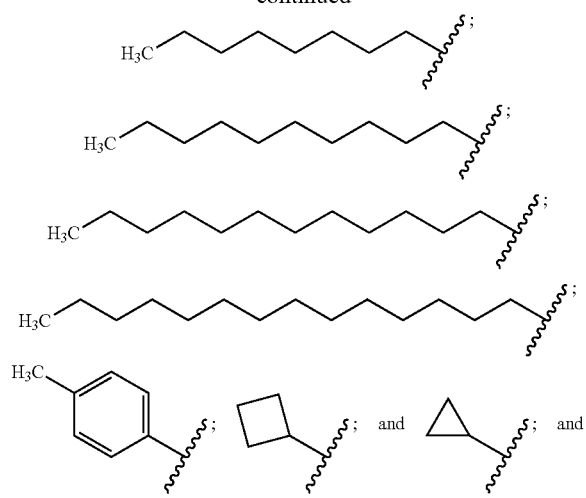
Rb is hydrogen or methyl;
provided that if $R^a$ is
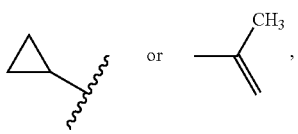
then $R^b$ is methyl.
2. The compound of claim 1, wherein $R^a$ is selected from the group consisting of:
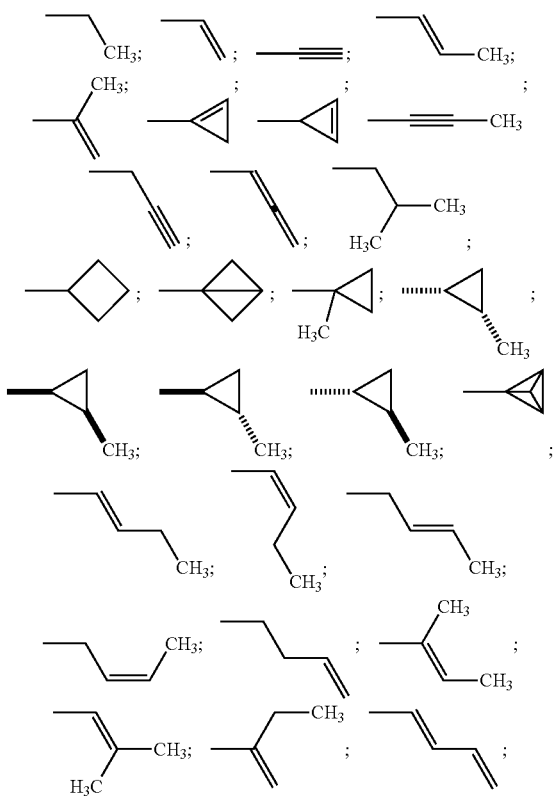
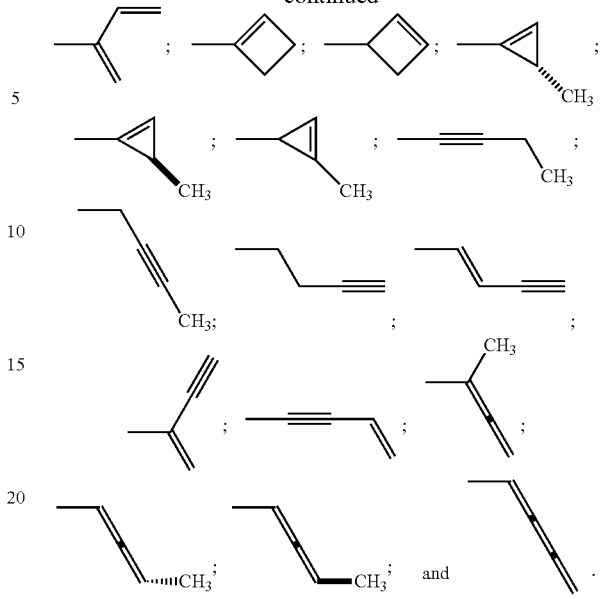
3. The compound of claim 1, wherein $R^a$ is selected from the group consisting of:
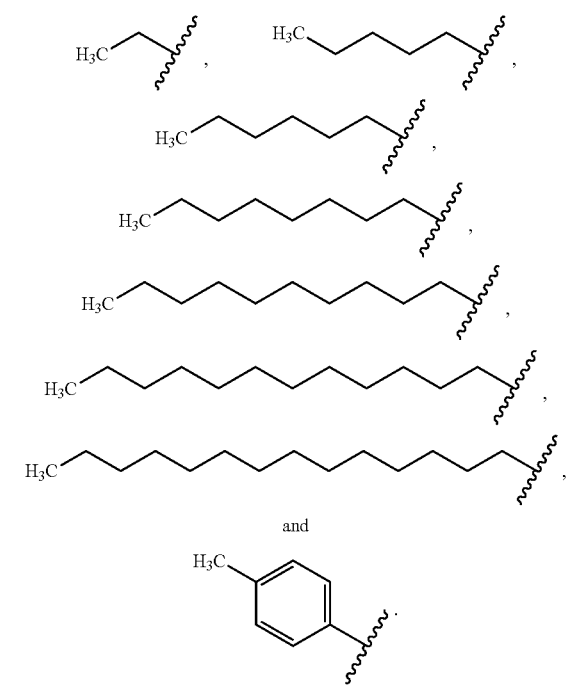
4. The compound of claim 1, wherein $R^a$ is selected from the group consisting of:
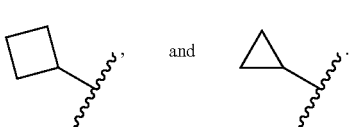

5. A compound selected from:
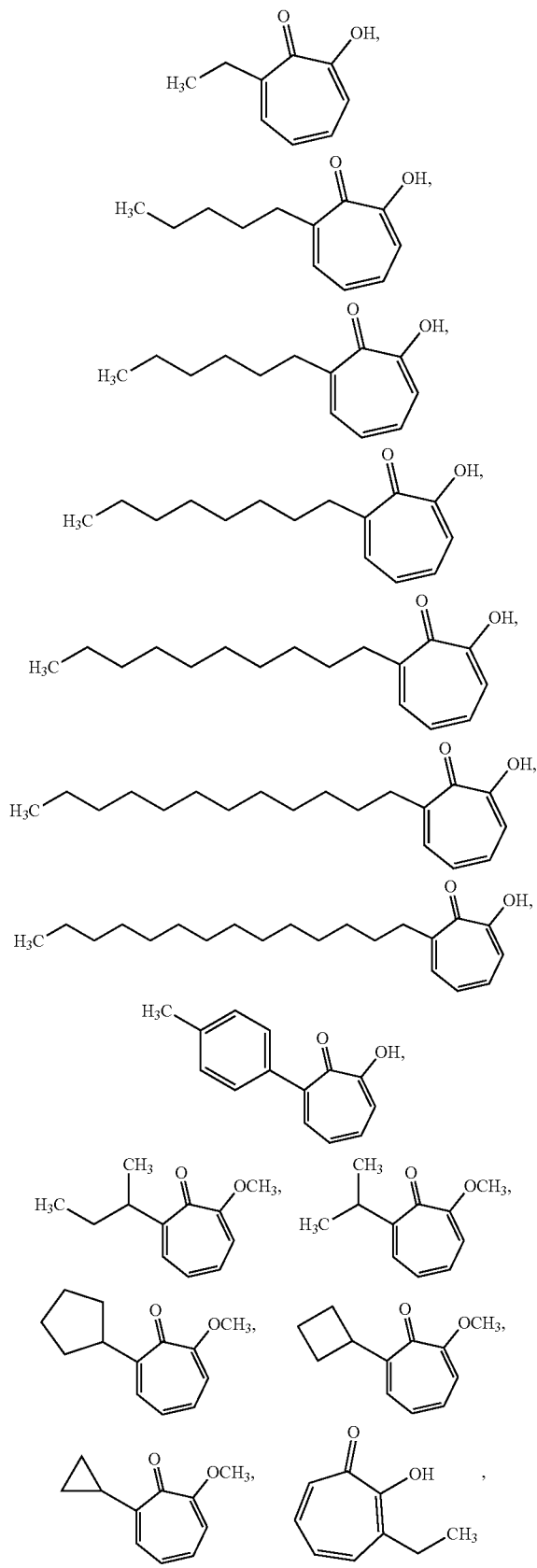
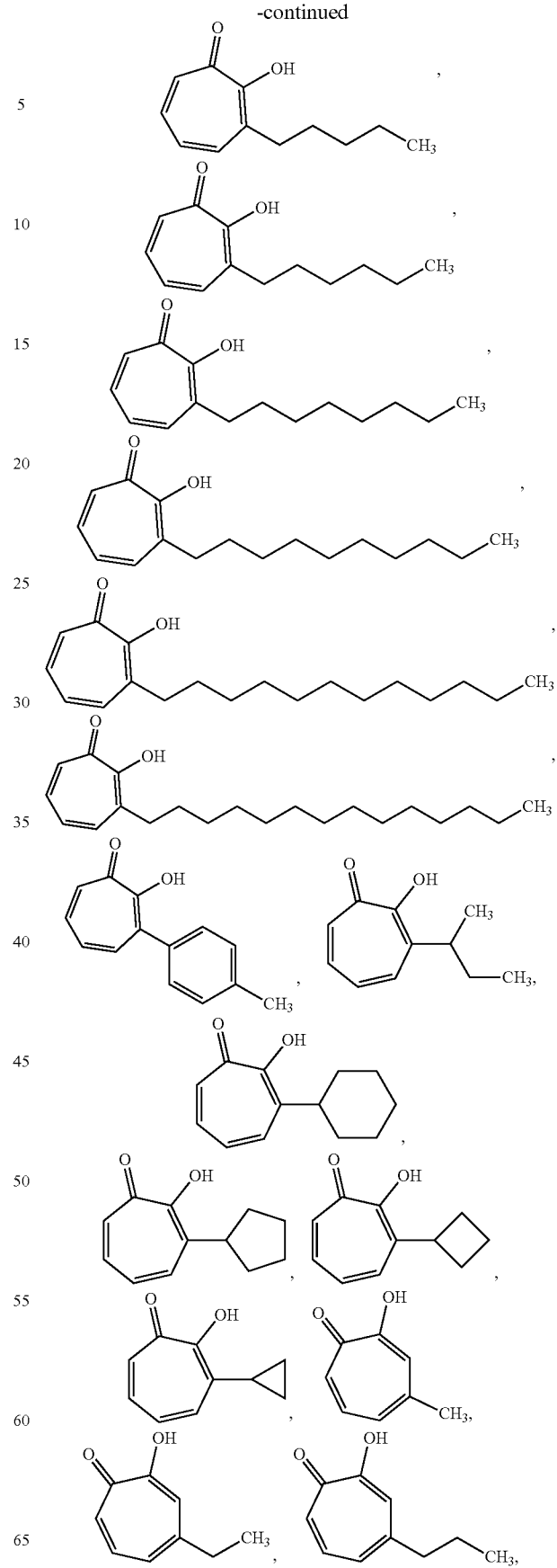

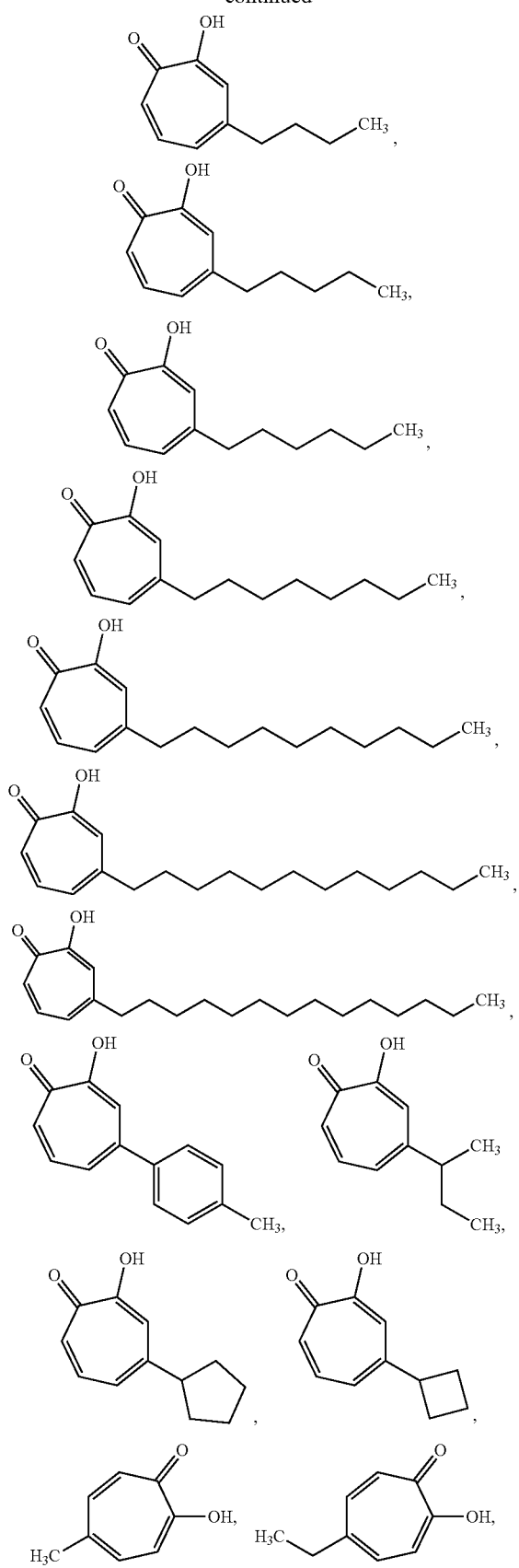
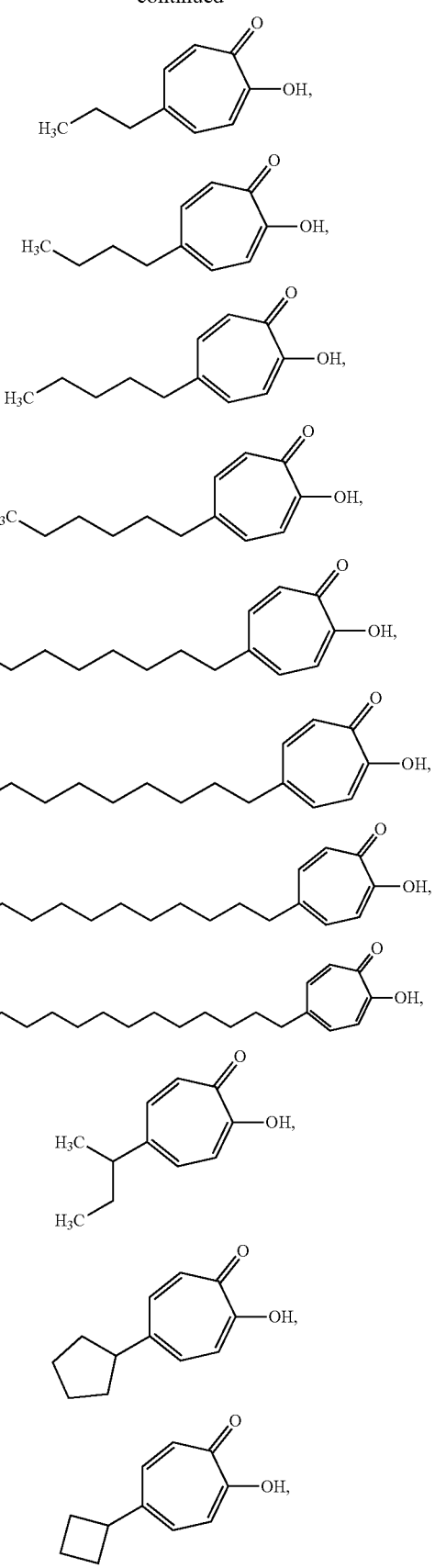

-continued
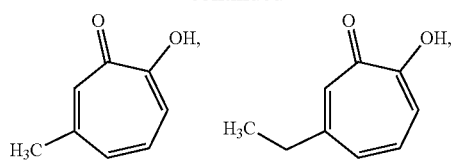
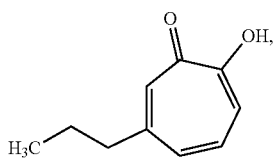
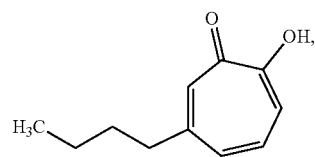
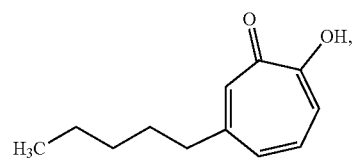
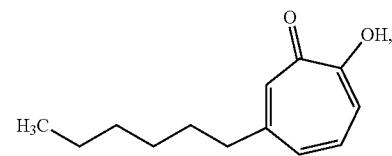
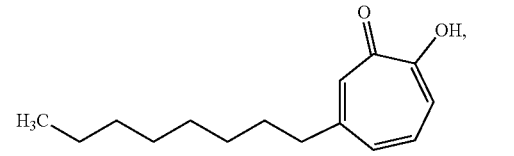
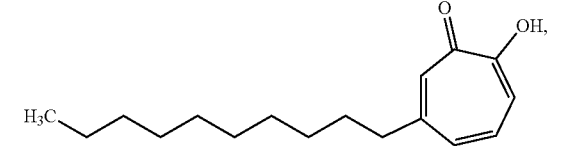
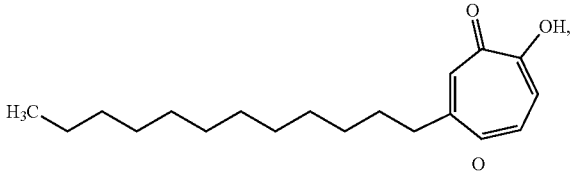
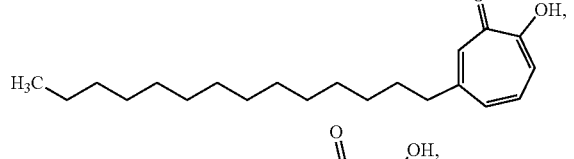
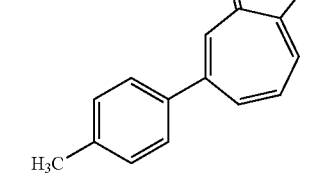
-continued
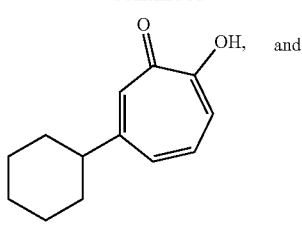
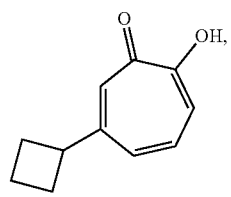
or a salt thereof.
6. The compound of claim 5, wherein the compound is selected from:
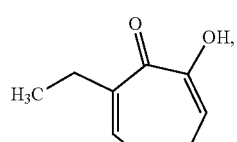
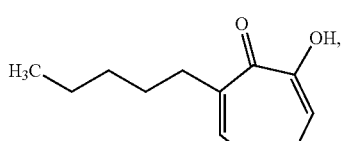
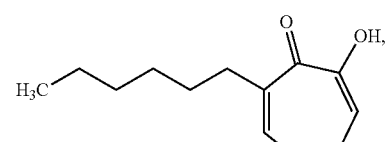
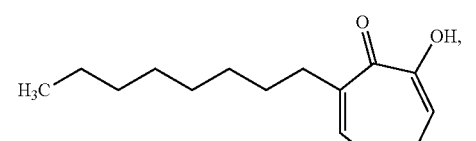
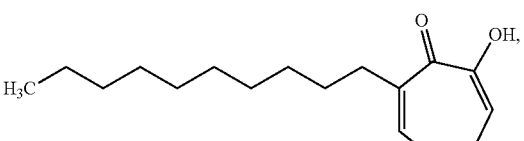
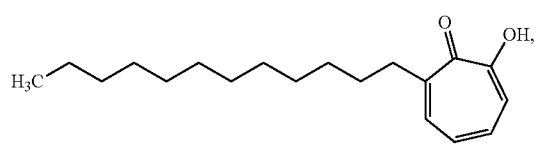
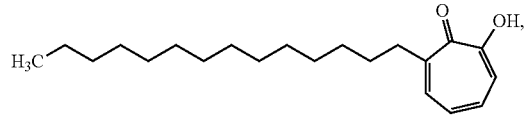

-continued
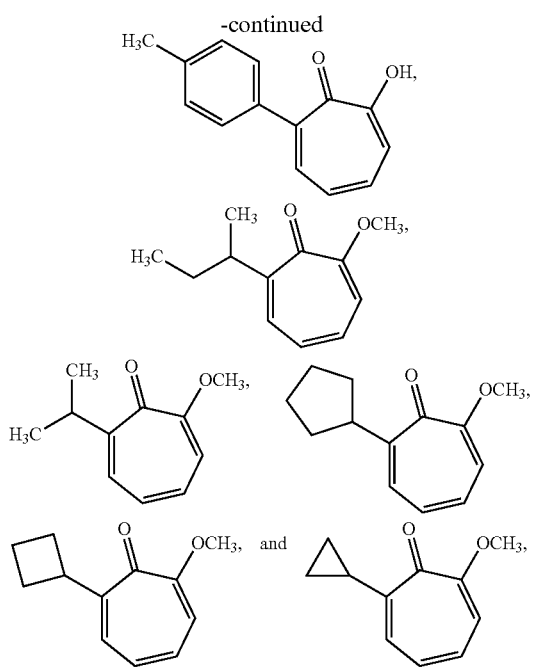
or a salt thereof.
7. The compound of claim 5, wherein the compound is selected from:
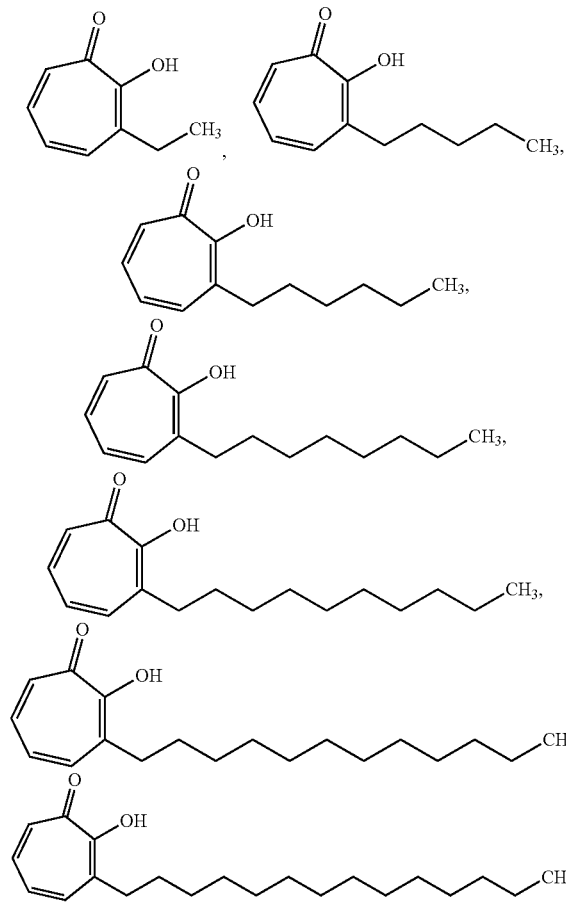
-continued
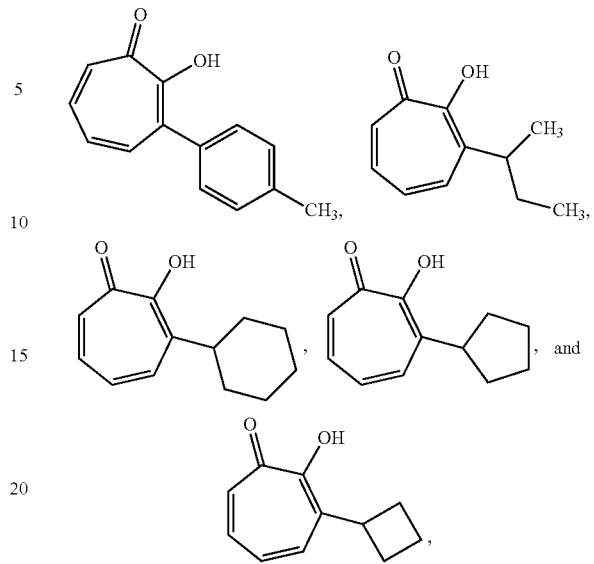
or a salt thereof.
8. The compound of claim 5, wherein the compound is selected from:
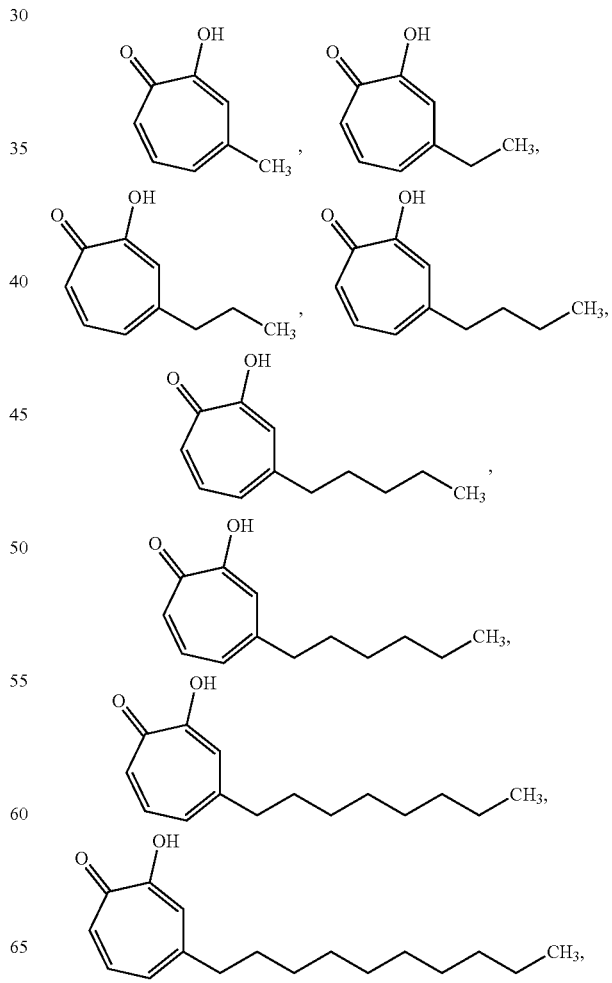

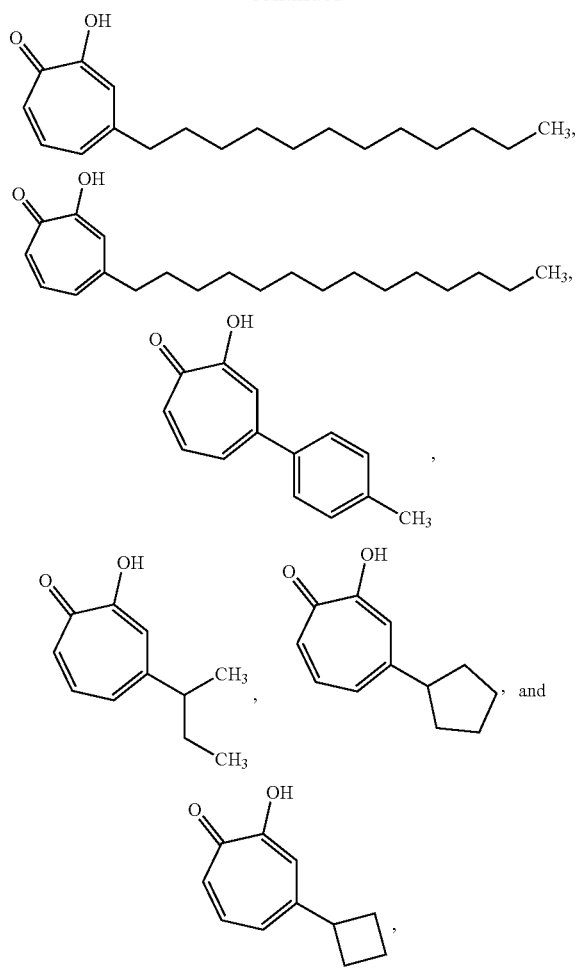
or a salt thereof.
9. The compound of claim 5, wherein the compound is selected from:
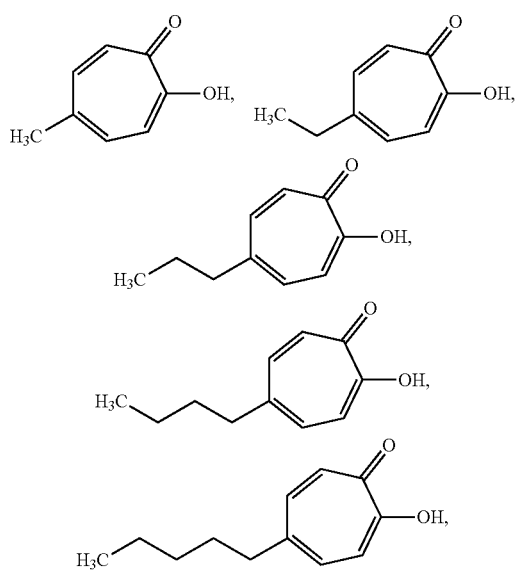
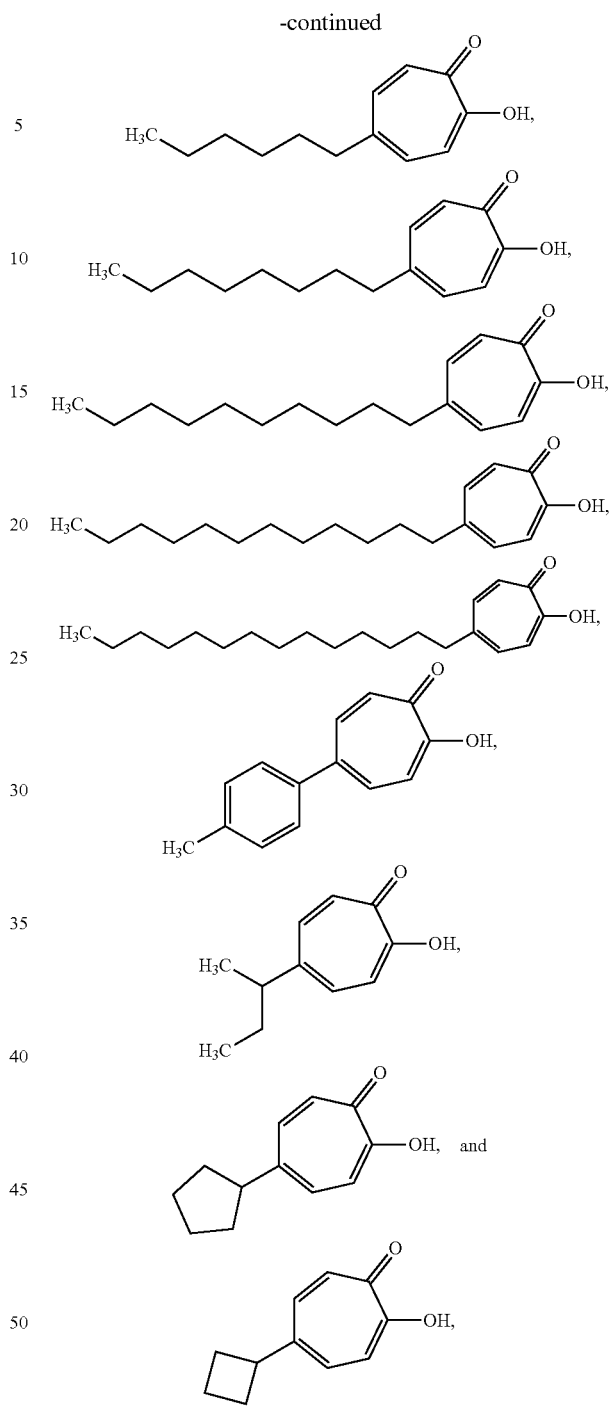
or a salt thereof.
10. The compound of claim 5, wherein the compound is selected from:
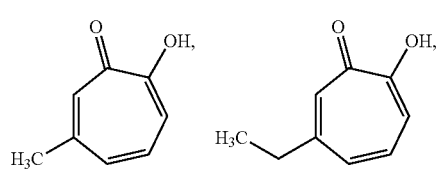

-continued
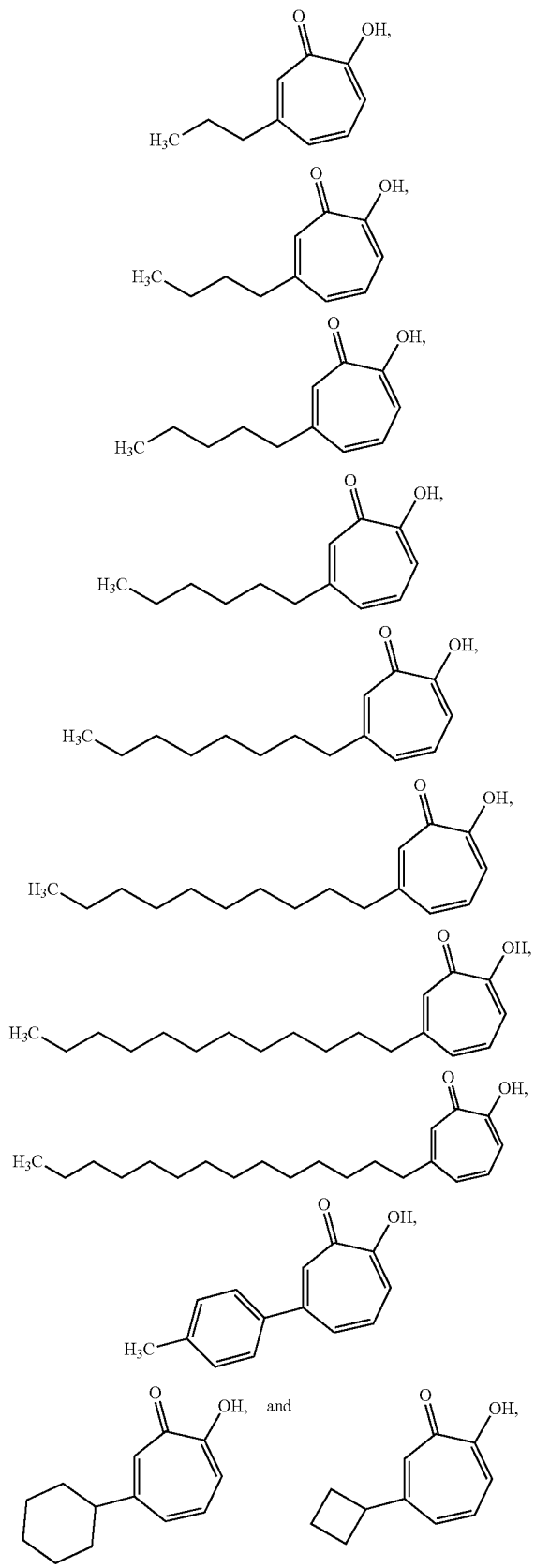
or a salt thereof.
11. A compound selected from the group consisting of:
(a)
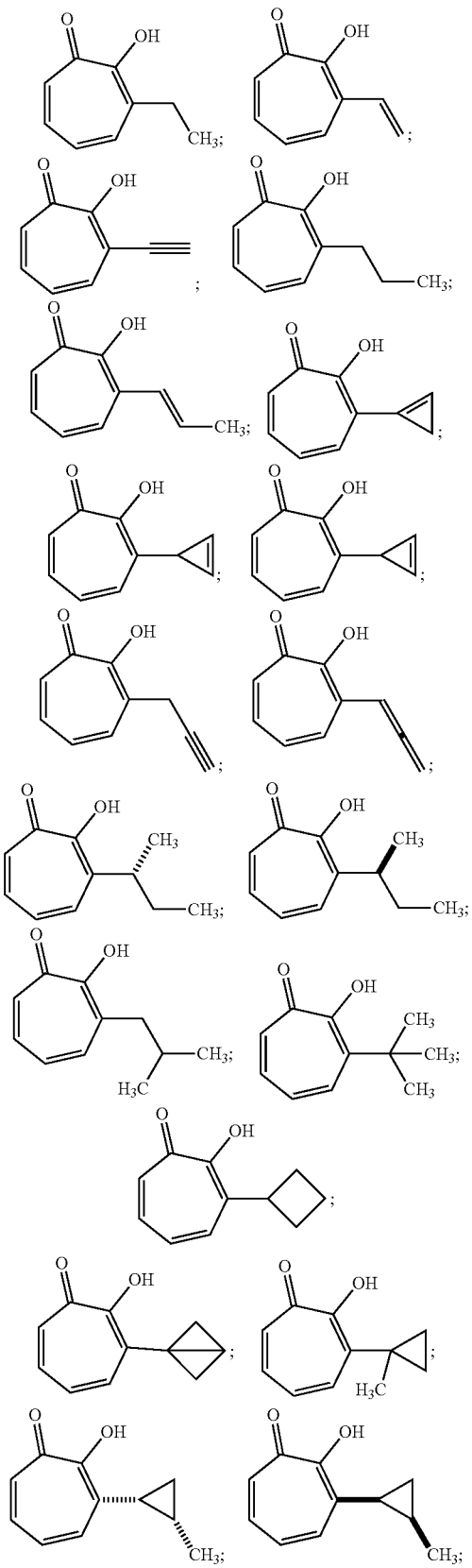

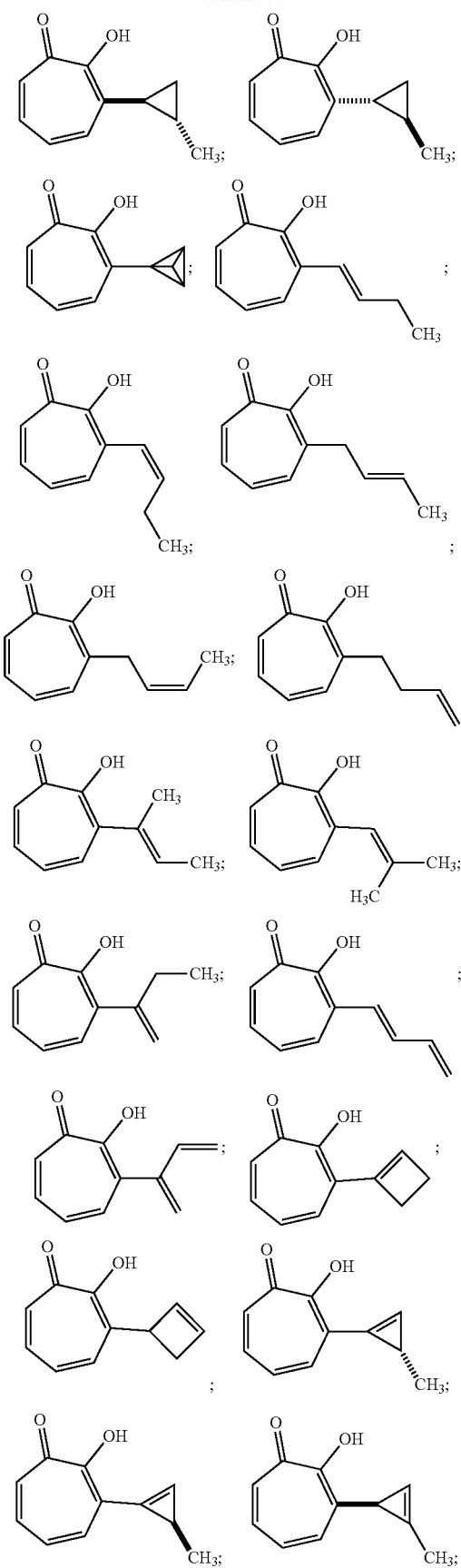
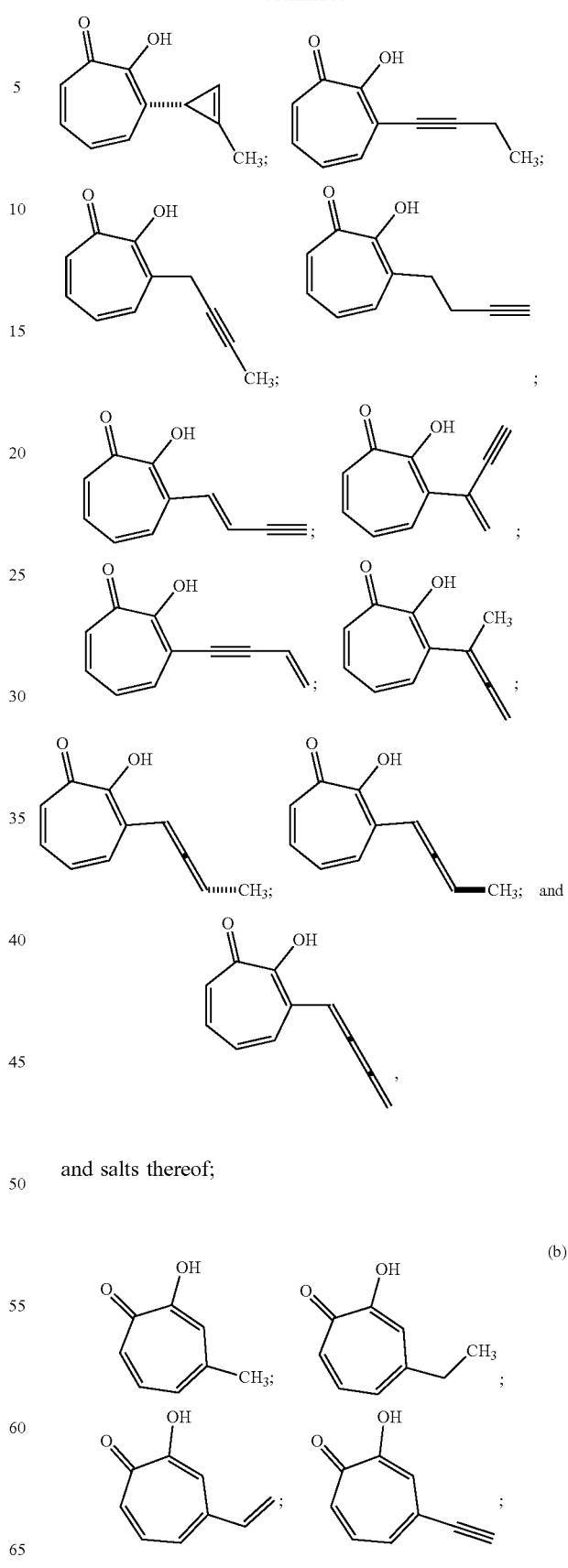
and salts thereof;

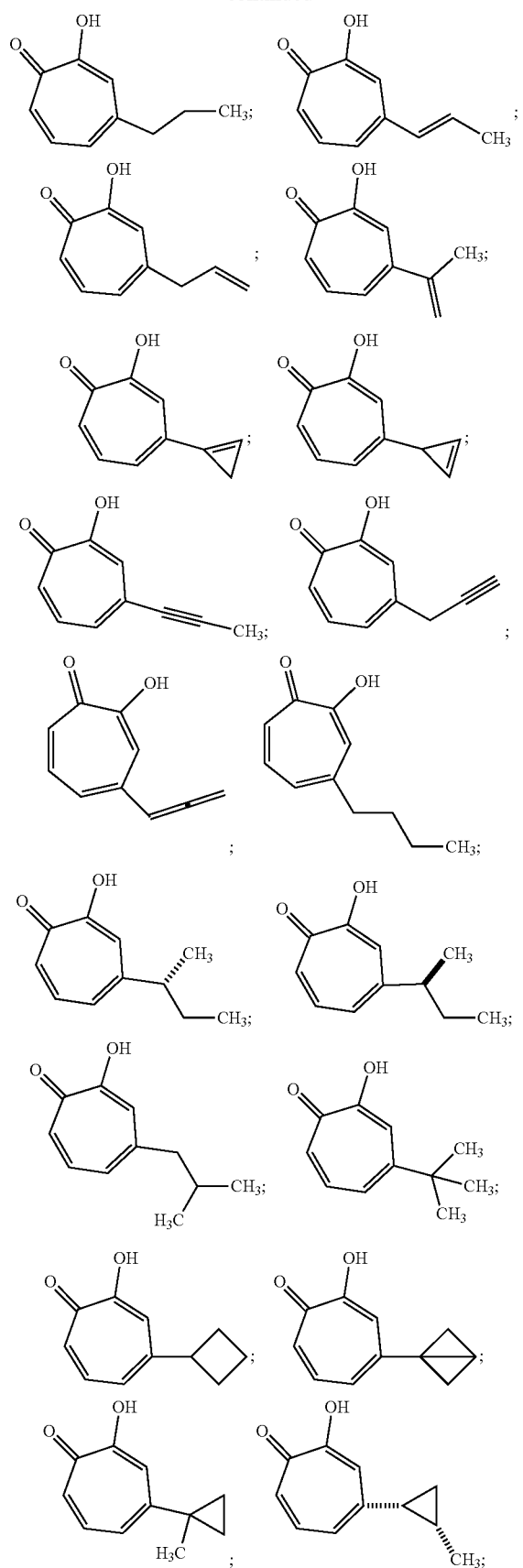
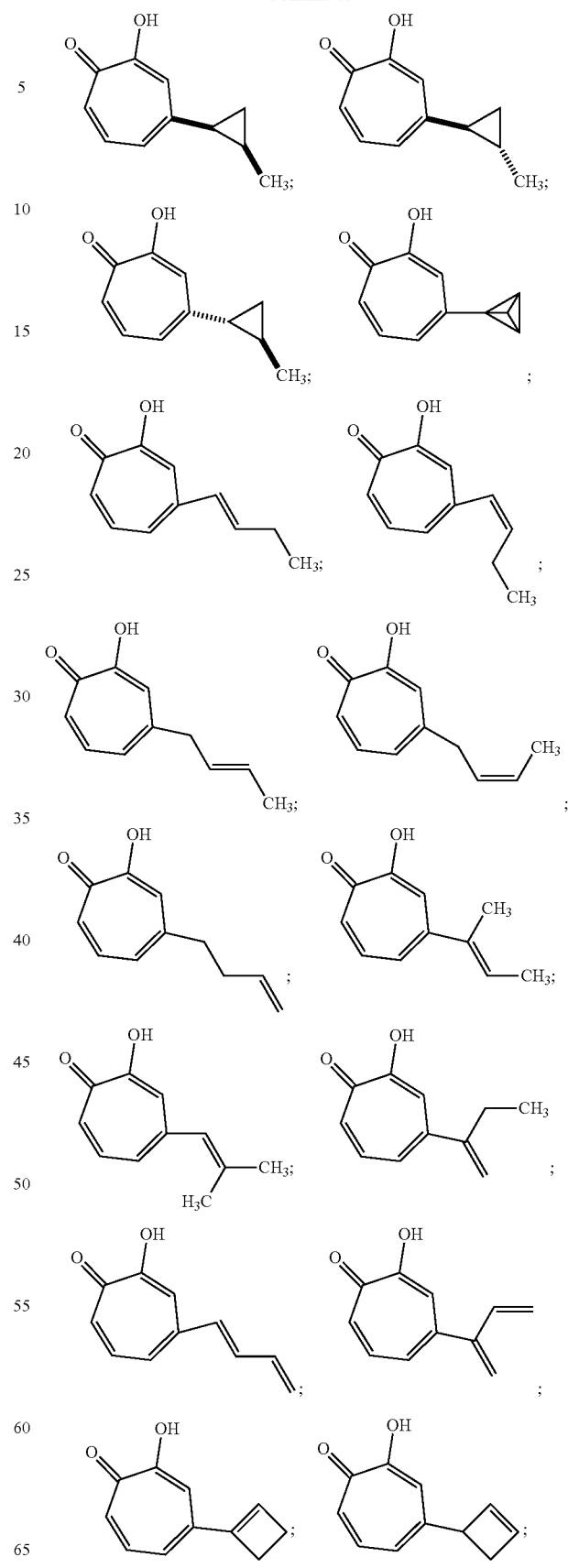

297
-continued
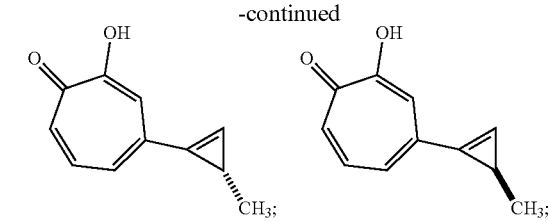
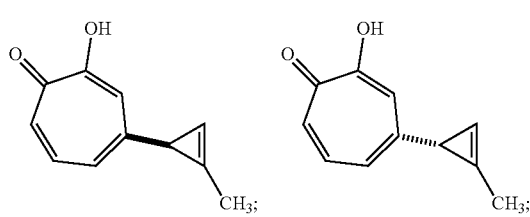
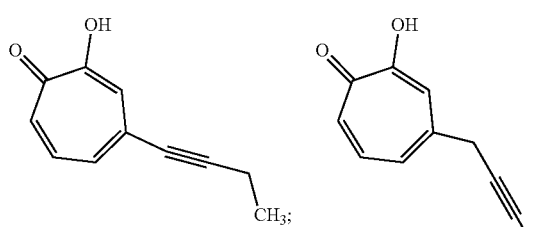
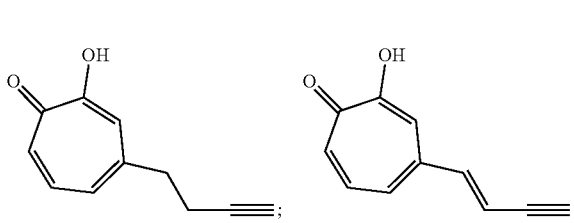
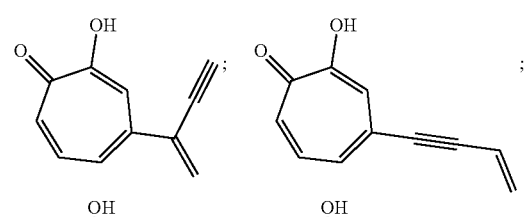
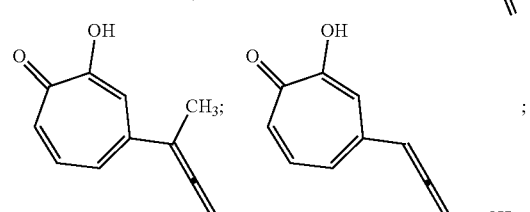
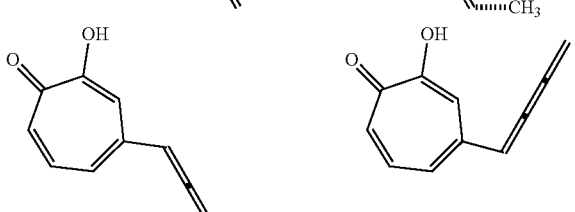
CH₃; and
298
and salts thereof; and
(c)
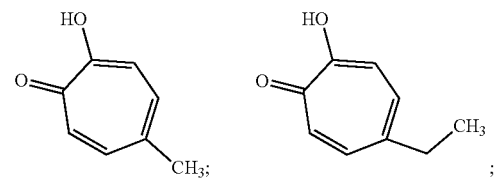
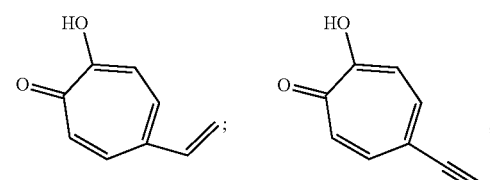
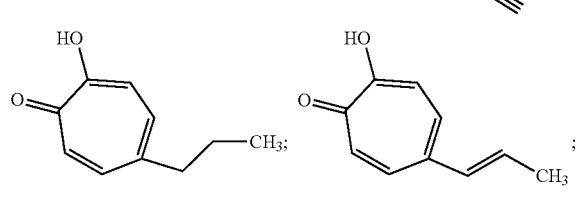
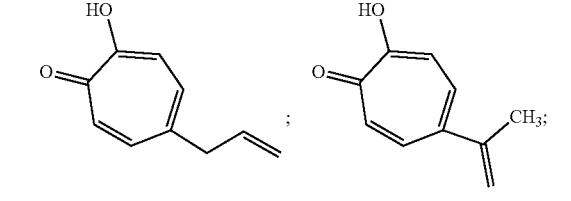
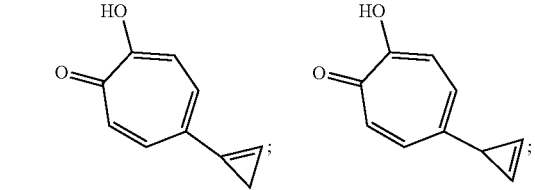
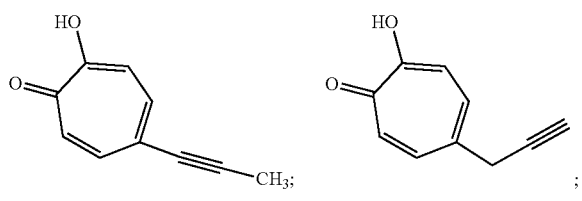
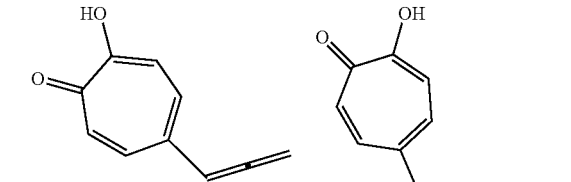
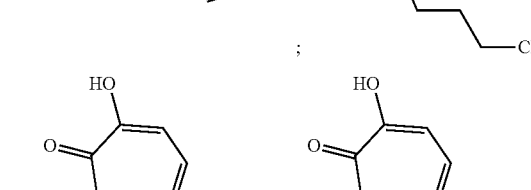
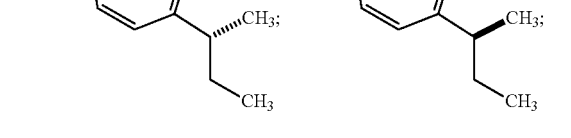

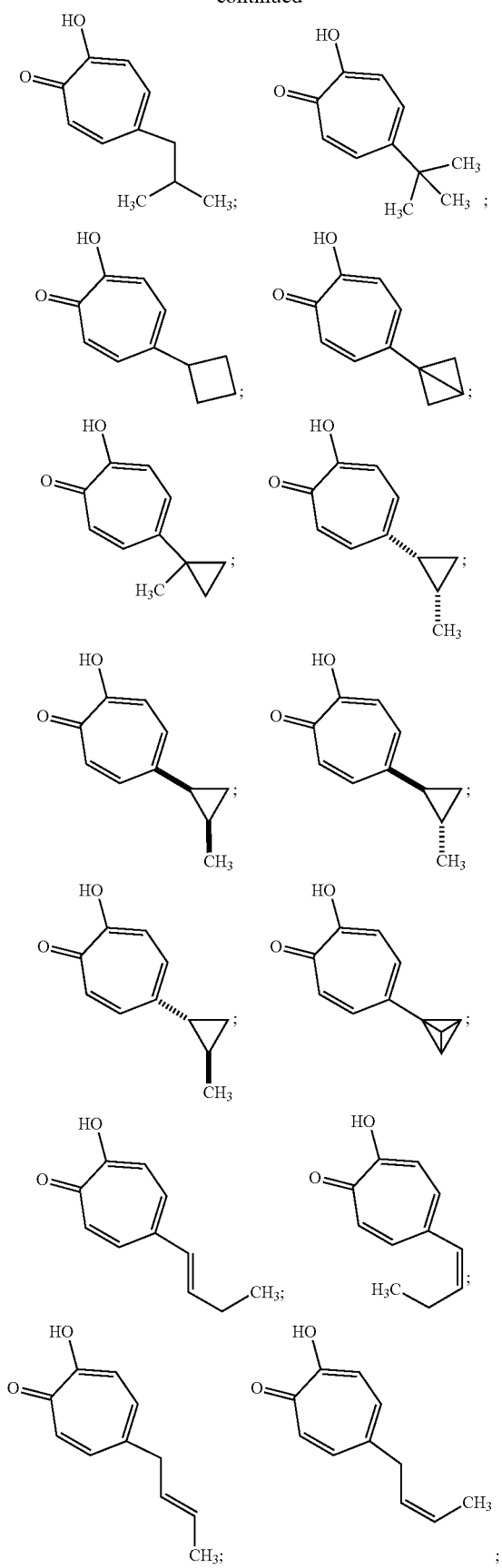
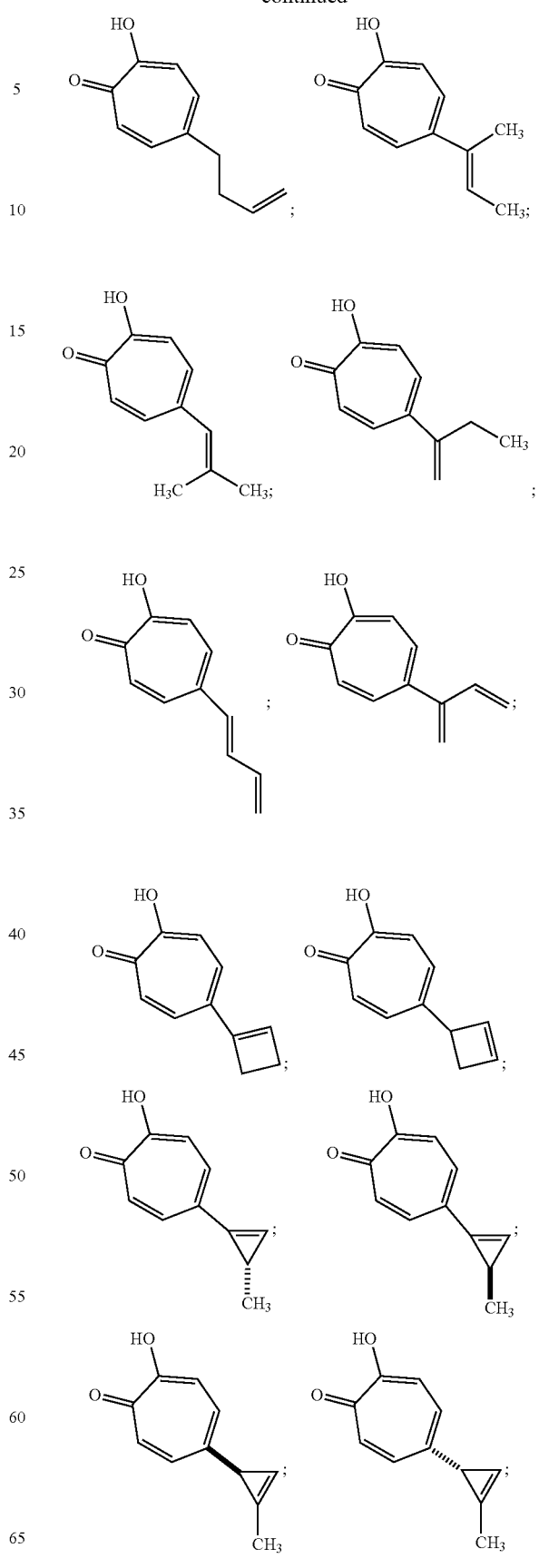

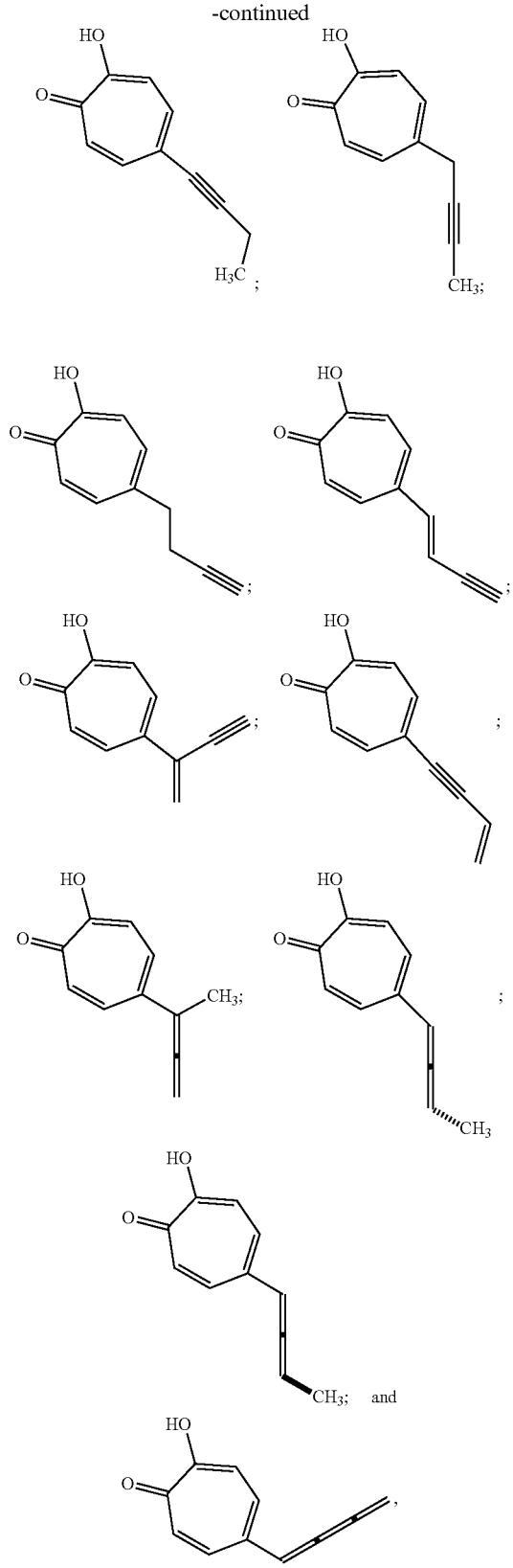
and salts thereof.
12. The compound of claim 11, selected from the group consisting of:

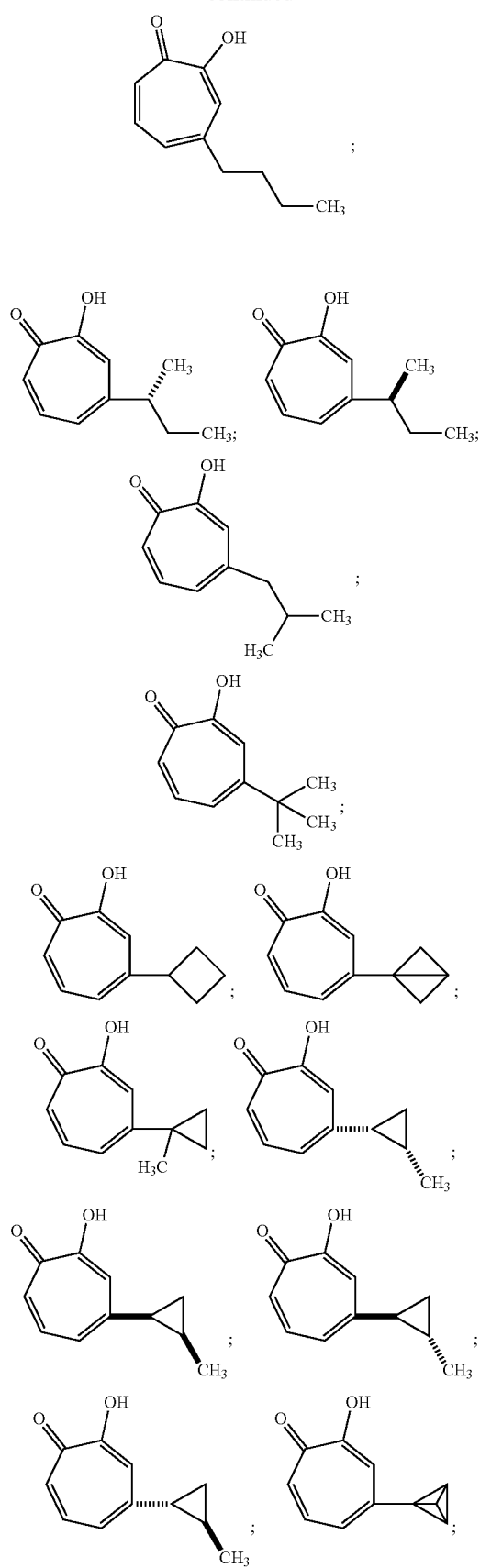
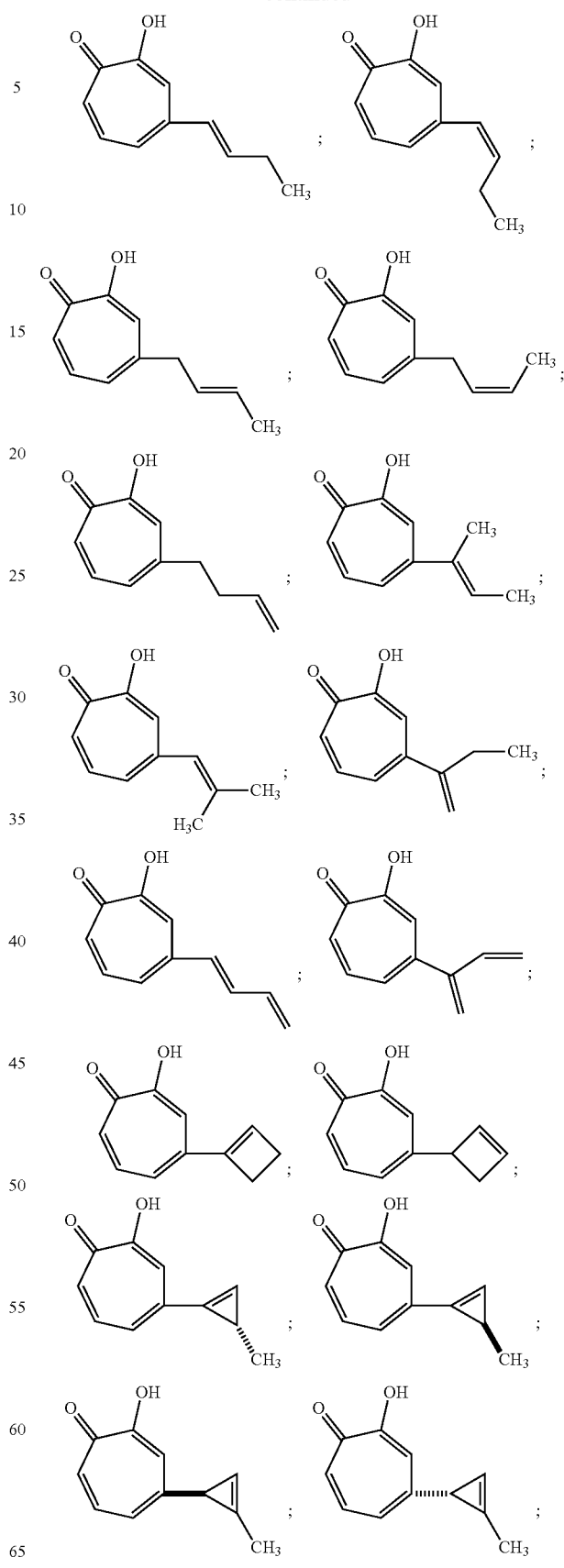

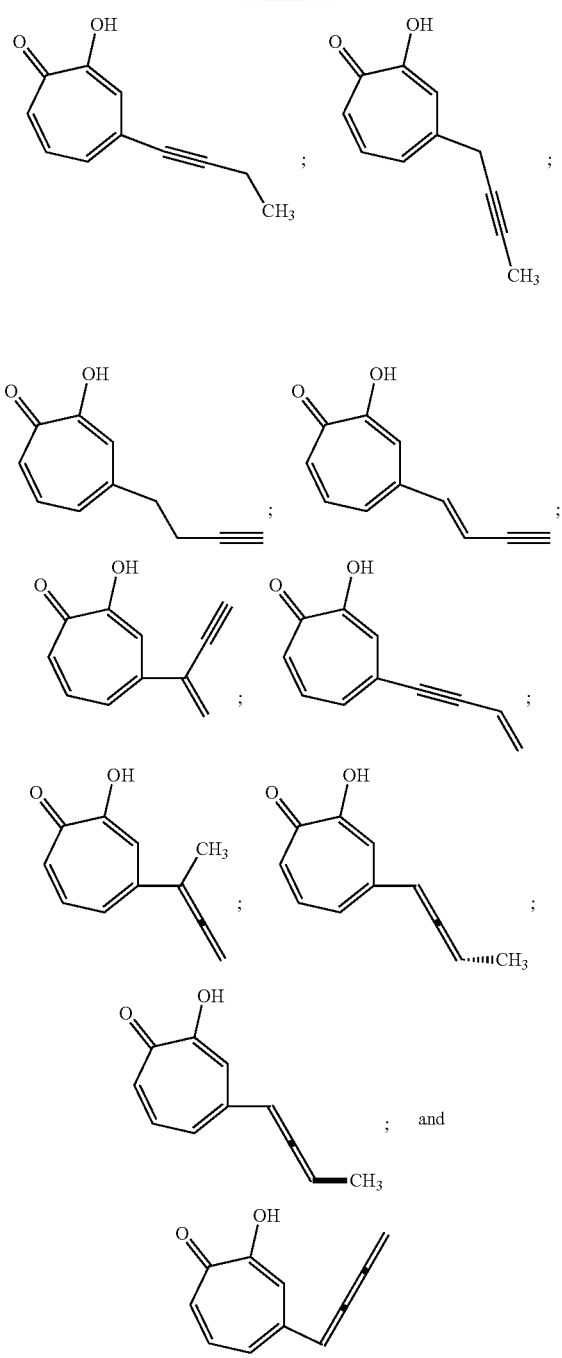
and salts thereof.
13. The compound of claim 11, selected from the group consisting of:
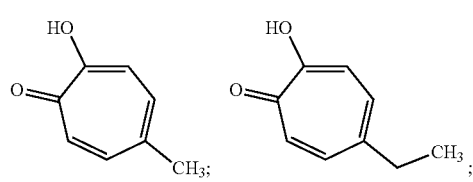
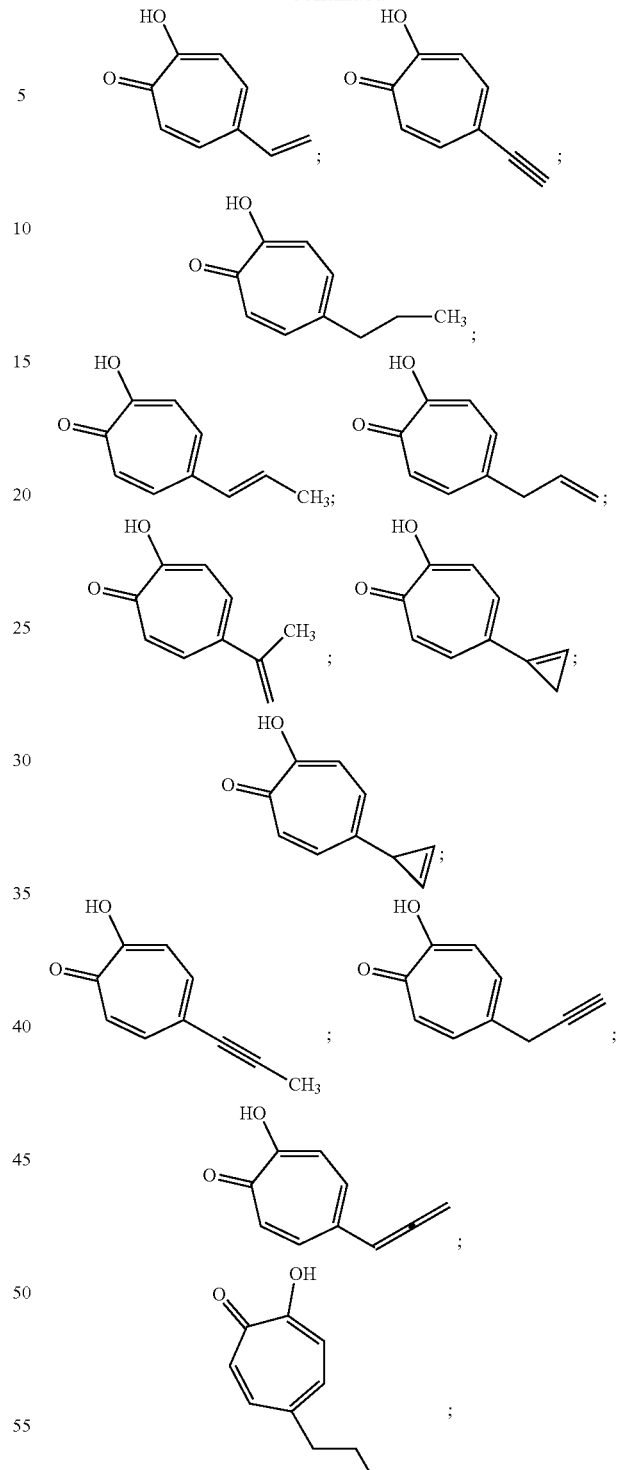
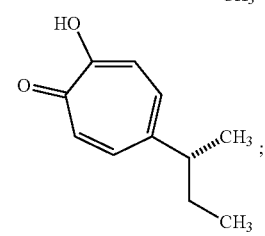

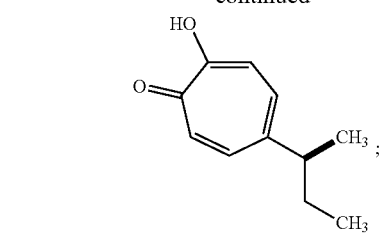
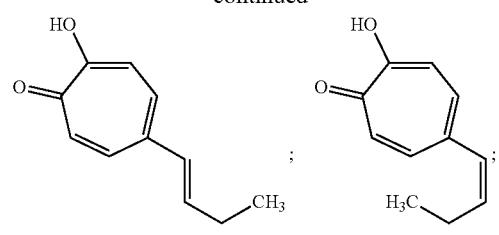
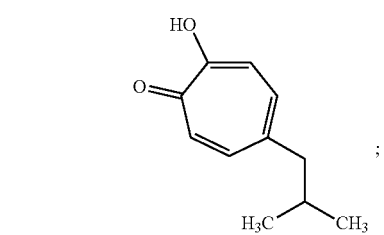
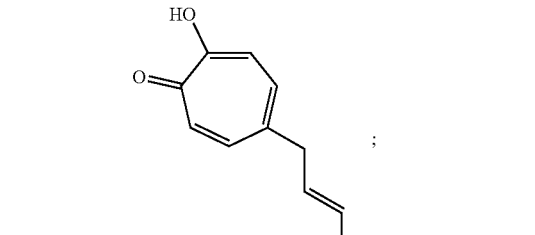
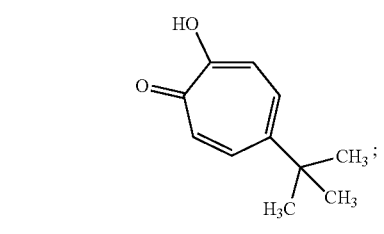
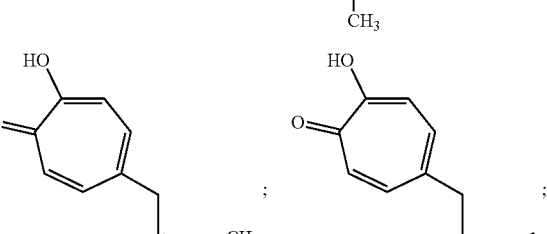
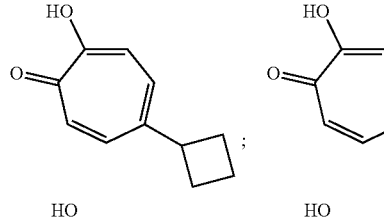
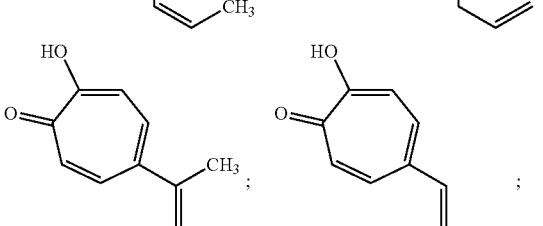
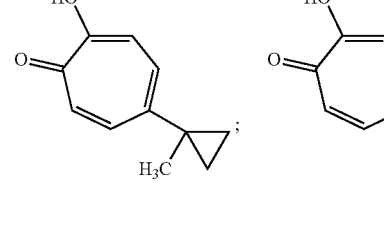
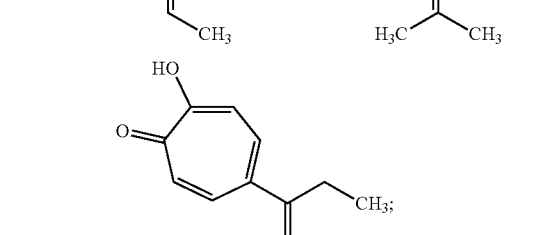
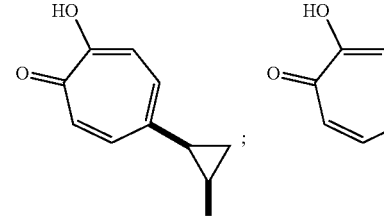
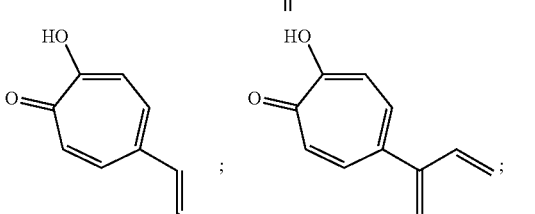
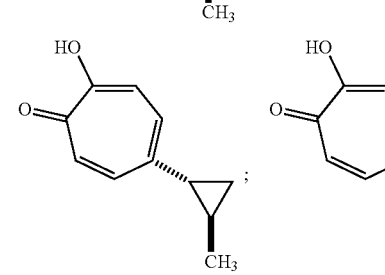
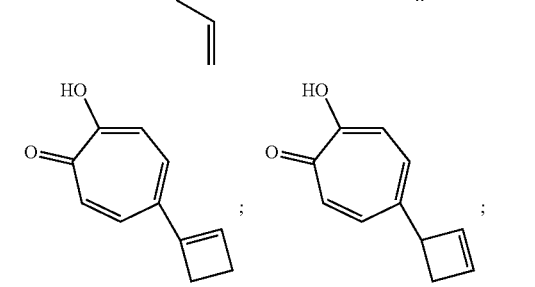

-continued

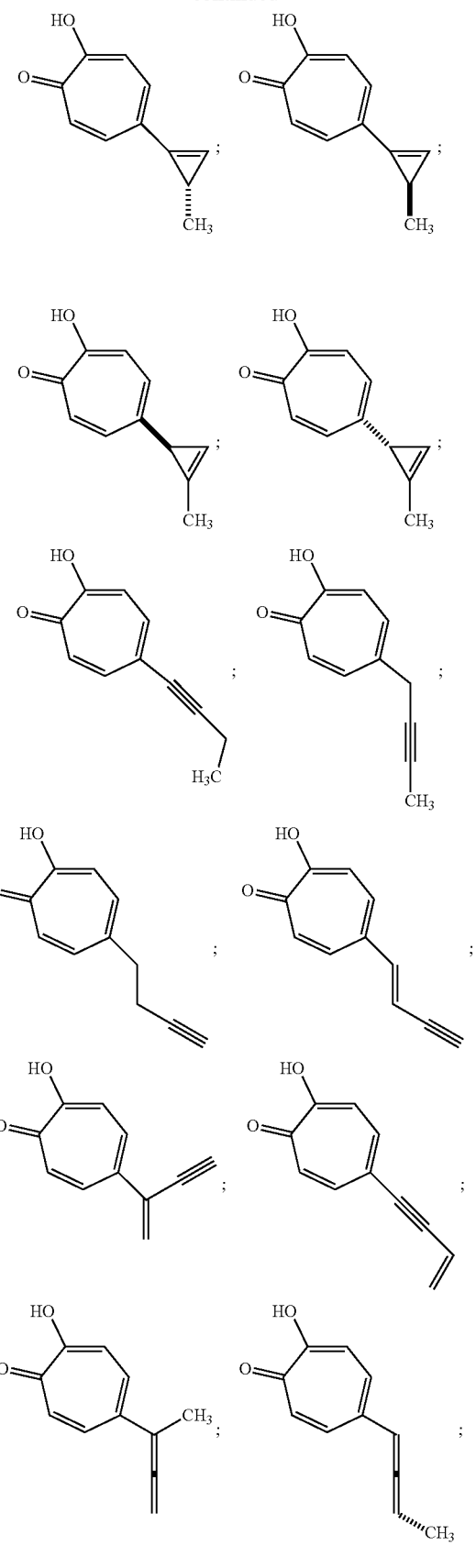

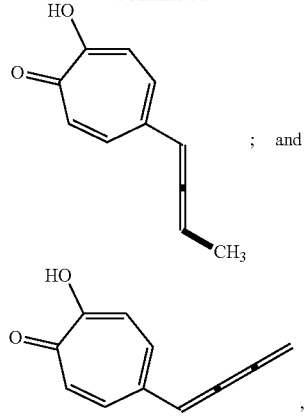

and salts thereof.

14. A pharmaceutical composition, comprising a compound of claim 1, or a salt thereof; and a pharmaceutically acceptable carrier or excipient.

15. A method of treating a disease or condition characterized by a deficiency of or a defect in an iron transporter, comprising administering to a subject in need thereof a therapeutically effective amount of a compound selected from the group consisting of tropolone and a compound of claim 1.

16. The method of claim 15, wherein the disease or condition characterized by a deficiency of or defect in an iron transporter is hypochromic, microcytic anemia.

17. A method of increasing (a) transepithelial iron transport, (b) physiology, (c) hemoglobinization, or (d) iron release, comprising administering to a subject in need thereof an effective amount of a compound selected from the group consisting of tropolone and a compound of claim 1.

18. The method of claim 15, further comprising administering an effective amount of one or more additional compounds selected from the group consisting of amphotericin B (AmB), calcimycin, nonactin, deferiprone, purpurogallin, and maltol.

19. The compound of claim 1, wherein $R^b$ is hydrogen.

20. The compound of claim 1, wherein $R^b$ is methyl.

21. The compound of claim 1, provided that if $R^a$ is

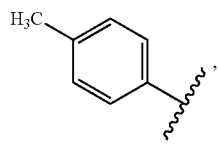

then $R^b$ is methyl.

22. The compound of claim 1, wherein $R^a$ is selected from the group consisting of

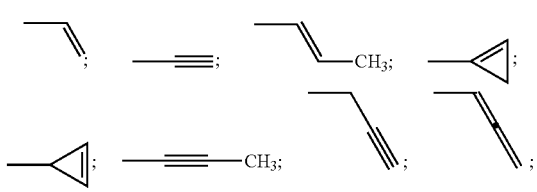

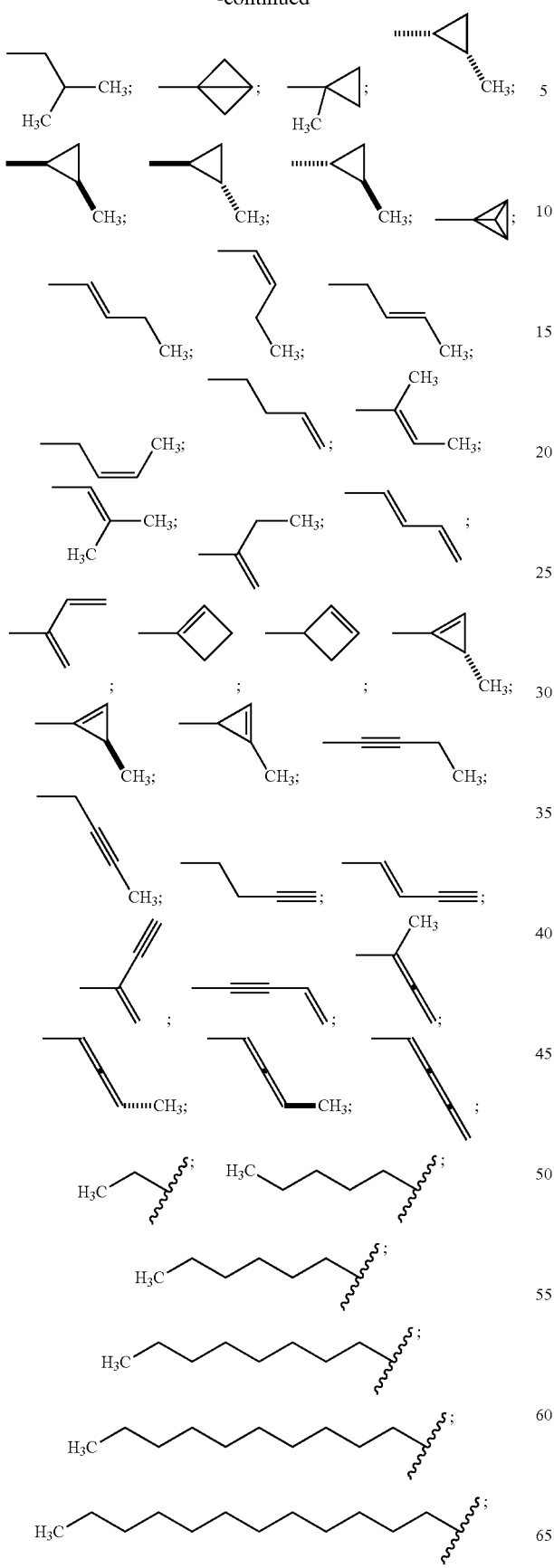
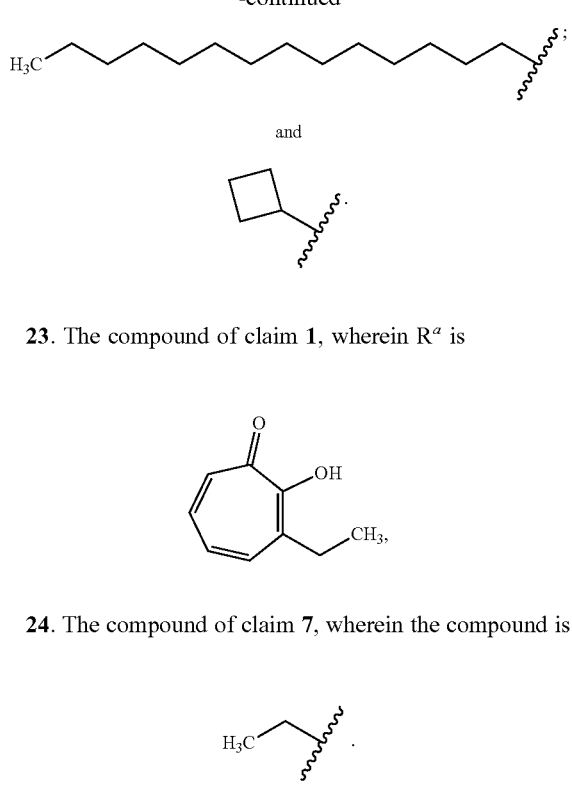
23. The compound of claim 1, wherein $R^a$ is
24. The compound of claim 7, wherein the compound is:
or a salt thereof.
25. The compound of claim 11, or a salt thereof, selected from the group consisting of:
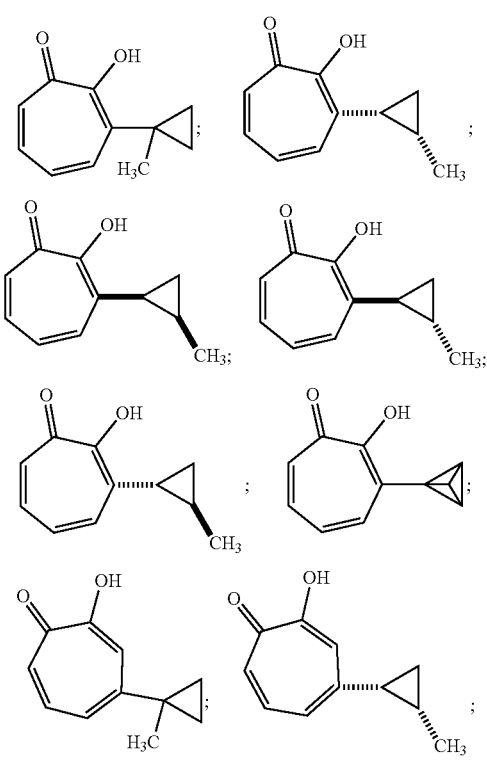

313
-continued
314
-continued
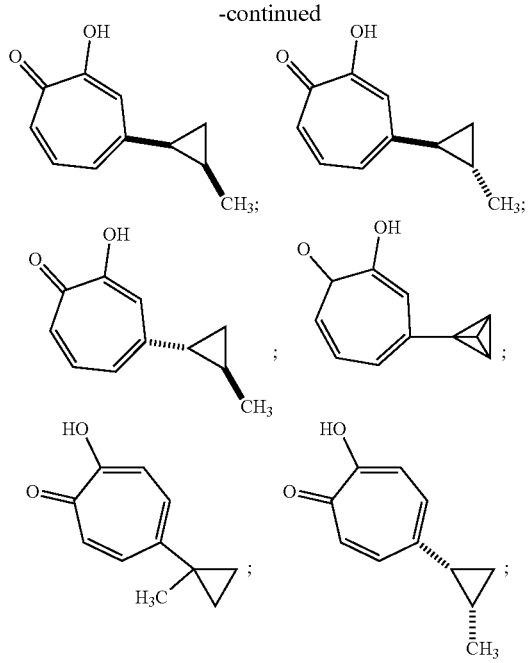
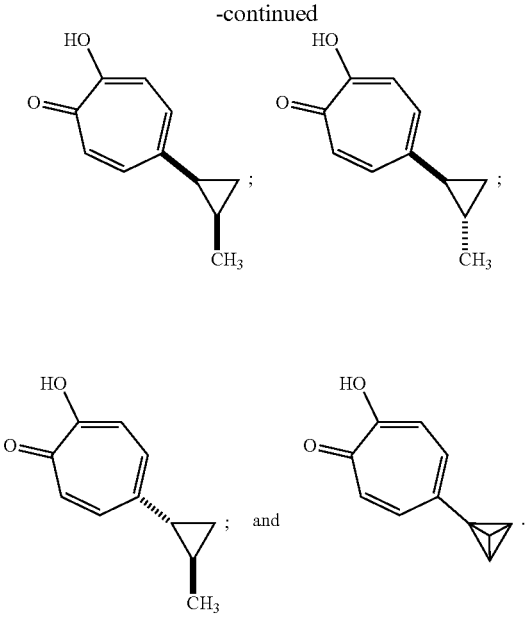
* * * * *

SEQUENCE LISTING

<160> NUMBER OF SEQ ID NOS: 14

<210> SEQ ID NO 1
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1
ggaatctcat tcgatgcata c                                              21

<210> SEQ ID NO 2
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 2
aacctattct ggccagtttg t                                              21

<210> SEQ ID NO 3
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 3
caacaagatg aagagcacca a                                              21

<210> SEQ ID NO 4
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 4
gatgcttgta taccgggctt                                                20

<210> SEQ ID NO 5
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 5
gaagaactca taaacggacc                                                20

<210> SEQ ID NO 6
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
gtttgcctct gcggtgtgat c                                              21

<210> SEQ ID NO 7
<211> LENGTH: 21
<212> TYPE: DNA
<213> ORGANISM: Artificial Sequence
<220> FEATURE:
<223> OTHER INFORMATION: Description of Artificial Sequence: Synthetic
     primer

<400> SEQUENCE: 7
ggaggacgct gtgggggggg g                                              21

<210> SEQ ID NO 8
<211> LENGTH: 20
<212> TYPE: DNA
<213> ORGANISM: Artificial Sequence
<220> FEATURE:
<223> OTHER INFORMATION: Description of Artificial Sequence: Synthetic
     primer

<400> SEQUENCE: 8
gtccatcttt tctacaagcc                                                20

<210> SEQ ID NO 9
<211> LENGTH: 25
<212> TYPE: DNA
<213> ORGANISM: Artificial Sequence
<220> FEATURE:
<223> OTHER INFORMATION: Description of Artificial Sequence: Synthetic
     oligonucleotide

<400> SEQUENCE: 9
gagtgtgaaa cgtgacgcac ccctt                                          25

<210> SEQ ID NO 10
<211> LENGTH: 25
<212> TYPE: DNA
<213> ORGANISM: Artificial Sequence
<220> FEATURE:
<223> OTHER INFORMATION: Description of Artificial Sequence: Synthetic
     oligonucleotide

<400> SEQUENCE: 10
taagttgcat taccttgact gaatc                                          25

<210> SEQ ID NO 11
<211> LENGTH: 19
<212> TYPE: DNA
<213> ORGANISM: Artificial Sequence
<220> FEATURE:
<223> OTHER INFORMATION: Description of Artificial Sequence: Synthetic
     primer

<400> SEQUENCE: 11
ctgaacctgc gctggtccc                                                 19

<210> SEQ ID NO 12
<211> LENGTH: 22
<212> TYPE: DNA
<213> ORGANISM: Artificial Sequence
<220> FEATURE:
<223> OTHER INFORMATION: Description of Artificial Sequence: Synthetic
     primer

<400> SEQUENCE: 12
tccgttagcg aagtcgtgca tg                                             22

```
<210> SEQ ID NO 13
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
gttggtatgg gacagaaaga cag                                              23

<210> SEQ ID NO 14
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
accagaggca tacagggaca g                                                21
```